US012163952B2

(12) United States Patent
Christin et al.

(10) Patent No.: US 12,163,952 B2
(45) Date of Patent: Dec. 10, 2024

(54) DETERMINING TOXICITY RISK IN CAR T-CELL THERAPY

(71) Applicant: Juno Therapeutics, Inc., Seattle, WA (US)

(72) Inventors: Brian Christin, Seattle, WA (US); Michael Gerard Covington, Seattle, WA (US); Kedar Himanshu Dave, Seattle, WA (US); Richard James Getto, Jr., Seattle, WA (US); Tom Kowski, Seattle, WA (US); Ryan P. Larson, Seattle, WA (US); Christopher Glen Ramsborg, Seattle, WA (US); Nikolaus Sebastian Trede, Seattle, WA (US); Clinton Weber, Seattle, WA (US); James Boyd Whitmore, Seattle, WA (US); Nathan Yee, Seattle, WA (US); Pascal Beauchesne, Seattle, WA (US); Travis Beckett, Seattle, WA (US); Samuel Charles Blackman, Seattle, WA (US); Nathaniel Chartrand, Seattle, WA (US); Mel Davis-Pickett, Seattle, WA (US); Mark Gilbert, Seattle, WA (US); Nathaniel Lambert, Seattle, WA (US); He Li, Seattle, WA (US); Mary Mallaney, Seattle, WA (US); Kathryn Lindsay Pollock, Seattle, WA (US); Valerie Odegard, Seattle, WA (US); Jeff Smith, Seattle, WA (US); Claire Sutherland, Seattle, WA (US); Andrew W. Walker, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 1349 days.

(21) Appl. No.: 16/488,935

(22) PCT Filed: Feb. 27, 2018

(86) PCT No.: PCT/US2018/020054

§ 371 (c)(1),
(2) Date: Aug. 26, 2019

(87) PCT Pub. No.: WO2018/157171

PCT Pub. Date: Aug. 30, 2018

(65) Prior Publication Data

US 2020/0191774 A1 Jun. 18, 2020

Related U.S. Application Data

(60) Provisional application No. 62/464,371, filed on Feb. 27, 2017, provisional application No. 62/465,817, filed on Mar. 1, 2017, provisional application No. 62/470,180, filed on Mar. 10, 2017, provisional application No. 62/527,002, filed on Jun. 29, 2017, provisional application No. 62/580,416, filed on Nov.

(Continued)

(51) Int. Cl.

| | |
|---|---|
| ***G01N 33/50*** | (2006.01) |
| ***A61K 35/17*** | (2015.01) |
| ***A61K 39/00*** | (2006.01) |
| ***C12N 5/0783*** | (2010.01) |
| ***G01N 33/68*** | (2006.01) |

(52) U.S. Cl.

CPC ...... *G01N 33/5091* (2013.01); *A61K 39/4611* (2023.05); *A61K 39/4631* (2023.05); *A61K 39/464412* (2023.05); *C12N 5/0636* (2013.01); *G01N 33/6869* (2013.01); *A61K 2239/28* (2023.05); *A61K 2239/31* (2023.05); *A61K 2239/48* (2023.05); *C12N 2510/00* (2013.01); *G01N 2800/28* (2013.01); *G01N 2800/42* (2013.01)

(58) Field of Classification Search

None

See application file for complete search history.

(56) References Cited

U.S. PATENT DOCUMENTS

| | | | |
|---|---|---|---|
| 4,452,773 | A | 6/1984 | Molday |
| 4,690,915 | A | 9/1987 | Rosenberg |

(Continued)

FOREIGN PATENT DOCUMENTS

| | | |
|---|---|---|
| EP | 0452342 | 10/1991 |
| EP | 2537416 | 12/2012 |

(Continued)

OTHER PUBLICATIONS

US 8,252,592 B2, 08/2012, Sadelain (withdrawn)

(Continued)

*Primary Examiner* — Christina M Borgeest

(74) *Attorney, Agent, or Firm* — MORRISON & FOERSTER LLP

(57) ABSTRACT

Provided herein are methods, compositions and articles of manufacture for use in connection with cell therapy involving the administration of one or more doses of a therapeutic T cell composition. The cells of the T cell composition express recombinant receptors such as chimeric receptors, e.g. chimeric antigen receptors (CARs) or other transgenic receptors such as T cell receptors (TCRs). Features of the provided embodiments, including the numbers of cells or units of cells administered and/or the potency of administered cells, provide various advantages, such as lower risk of toxicity in subjects administered the T cell compositions.

28 Claims, 67 Drawing Sheets

Specification includes a Sequence Listing.

Related U.S. Application Data

1, 2017, provisional application No. 62/584,740, filed on Nov. 10, 2017, provisional application No. 62/596,703, filed on Dec. 8, 2017.

(56) References Cited

U.S. PATENT DOCUMENTS

| | | | |
|---|---|---|---|
| 4,795,698 | A | 1/1989 | Owen |
| 5,200,084 | A | 4/1993 | Liberti |
| 5,219,740 | A | 6/1993 | Miller |
| 5,591,827 | A | 1/1997 | Brankenhoff et al. |
| 6,040,177 | A | 3/2000 | Riddell |
| 6,123,655 | A | 9/2000 | Fell |
| 6,207,453 | B1 | 3/2001 | Maass |
| 6,410,319 | B1 | 6/2002 | Raubitschek |
| 6,451,995 | B1 | 9/2002 | Cheung |
| 6,733,433 | B1 | 5/2004 | Fell |
| 7,070,995 | B2 | 7/2006 | Jensen |
| 7,265,209 | B2 | 9/2007 | Jensen |
| 7,354,762 | B2 | 4/2008 | Jensen |
| 7,446,179 | B2 | 11/2008 | Jensen |
| 7,446,190 | B2 | 11/2008 | Sadelain |
| 7,446,191 | B2 | 11/2008 | Jensen |
| 8,324,353 | B2 | 12/2012 | Jensen |
| 8,389,282 | B2 | 3/2013 | Sadelain |
| 8,399,645 | B2 | 3/2013 | Campana |
| 8,497,118 | B2 | 7/2013 | Jensen |
| 8,562,991 | B2 | 10/2013 | Igawa et al. |
| 8,709,797 | B2 | 4/2014 | Woods |
| 8,802,374 | B2 | 8/2014 | Jensen |
| 8,822,647 | B2 | 9/2014 | Jensen |
| 8,911,993 | B2 | 12/2014 | June |
| 8,936,905 | B2 | 1/2015 | Woods et al. |
| 9,233,125 | B2 | 1/2016 | Davila et al. |
| 9,565,854 | B2 | 2/2017 | Woods |
| 11,413,310 | B2 | 8/2022 | Albertson et al. |
| 11,564,946 | B2 | 1/2023 | Albertson et al. |
| 11,815,514 | B2 | 11/2023 | Li et al. |
| 11,944,647 | B2 | 4/2024 | Albertson et al. |
| 2002/0131960 | A1 | 9/2002 | Sadelain |
| 2002/0150914 | A1 | 10/2002 | Andersen et al. |
| 2003/0170238 | A1 | 9/2003 | Gruenberg |
| 2003/0223994 | A1 | 12/2003 | Hoogenboom et al. |
| 2004/0191260 | A1 | 9/2004 | Reiter et al. |
| 2006/0034850 | A1 | 2/2006 | Weidanz et al. |
| 2007/0116690 | A1 | 5/2007 | Yang et al. |
| 2008/0171951 | A1 | 7/2008 | Fell |
| 2009/0226474 | A1 | 9/2009 | Weidanz et al. |
| 2009/0304679 | A1 | 12/2009 | Weidanz |
| 2011/0003380 | A1 | 1/2011 | Miltenyi |
| 2011/0045999 | A1 | 2/2011 | Willman et al. |
| 2011/0306622 | A1 | 12/2011 | Lannutti et al. |
| 2013/0149337 | A1 | 6/2013 | Cooper |
| 2013/0287748 | A1 | 10/2013 | June |
| 2014/0271635 | A1 | 9/2014 | Brogdon |
| 2014/0294841 | A1 | 10/2014 | Scheinberg et al. |
| 2014/0314795 | A1 | 10/2014 | Riddell |
| 2015/0283178 | A1 | 10/2015 | June et al. |
| 2016/0046724 | A1 | 2/2016 | Brogdon et al. |
| 2016/0122782 | A1 | 5/2016 | Crisman et al. |
| 2016/0184330 | A1 | 6/2016 | Sordillo et al. |
| 2016/0185861 | A1 | 6/2016 | Bedoya et al. |
| 2016/0206656 | A1 | 7/2016 | Gilbert et al. |
| 2016/0362472 | A1 | 12/2016 | Bitter et al. |
| 2019/0277858 | A1 | 9/2019 | Li et al. |
| 2019/0336504 | A1 | 11/2019 | Gill et al. |
| 2020/0078400 | A1 | 3/2020 | Li et al. |
| 2020/0147136 | A1 | 5/2020 | Albertson et al. |
| 2020/0352998 | A1 | 11/2020 | Albertson et al. |
| 2021/0071258 | A1 | 3/2021 | DuBose et al. |
| 2022/0088070 | A1 | 3/2022 | Albertson et al. |
| 2023/0149458 | A1 | 5/2023 | Albertson et al. |
| 2023/0172988 | A1 | 6/2023 | Albertson et al. |
| 2024/0103012 | A1 | 3/2024 | Li et al. |
| 2024/0115612 | A1 | 4/2024 | Albertson et al. |

FOREIGN PATENT DOCUMENTS

| | | |
|---|---|---|
| RU | 2423525 | 7/2011 |
| WO | WO 1992/008796 | 5/1992 |
| WO | WO 1994/028143 | 12/1994 |
| WO | WO 1996/013593 | 5/1996 |
| WO | WO 1996/018105 | 6/1996 |
| WO | WO 1999/018129 | 4/1999 |
| WO | WO 1999/060120 | 11/1999 |
| WO | WO 2000/0014257 | 3/2000 |
| WO | WO 2000/038762 | 7/2000 |
| WO | WO 2003/020763 | 3/2003 |
| WO | WO 2003/068201 | 8/2003 |
| WO | WO 2004/033685 | 4/2004 |
| WO | WO 2006/000830 | 1/2006 |
| WO | WO 2009/072003 | 6/2009 |
| WO | WO 2010/033140 | 3/2010 |
| WO | WO 2011/044186 | 4/2011 |
| WO | WO 2011/119773 | 9/2011 |
| WO | WO 2012/062596 | 5/2012 |
| WO | WO 2012/062904 | 5/2012 |
| WO | WO 2012/129514 | 9/2012 |
| WO | WO 2013/071154 | 5/2013 |
| WO | WO 2013/090419 | 6/2013 |
| WO | WO 2013/123061 | 8/2013 |
| WO | WO 2013/126726 | 8/2013 |
| WO | WO 2013/166321 | 11/2013 |
| WO | WO 2014/011984 | 1/2014 |
| WO | WO 2014/031687 | 2/2014 |
| WO | WO 2014/055668 | 4/2014 |
| WO | WO 2015/136298 | 9/2015 |
| WO | WO 2015/157384 | 10/2015 |
| WO | WO 2015/164675 | 10/2015 |
| WO | WO 2016/019300 | 2/2016 |
| WO | WO 2016/028896 | 2/2016 |
| WO | WO 2016/030414 | 3/2016 |
| WO | WO 2016/033570 | 3/2016 |
| WO | WO 2016/057705 | 4/2016 |
| WO | WO 2016/064929 | 4/2016 |
| WO | WO 2016/073602 | 5/2016 |
| WO | WO 2016/132366 | 8/2016 |
| WO | WO 2016/164731 | 10/2016 |
| WO | WO 2016/172606 | 10/2016 |
| WO | WO 2016/191755 | 12/2016 |
| WO | WO 2016/191756 | 12/2016 |
| WO | WO 2017/015427 | 1/2017 |
| WO | WO 2017/019848 | 2/2017 |
| WO | WO 2017/040930 | 3/2017 |
| WO | WO 2017/049166 | 3/2017 |
| WO | WO 2017/053889 | 3/2017 |
| WO | WO 2017/058850 | 4/2017 |
| WO | WO 2017/096331 | 6/2017 |
| WO | WO 2017/165571 | 9/2017 |
| WO | WO 2017/214207 | 12/2017 |
| WO | WO 2018/102787 | 6/2018 |
| WO | WO 2018/148567 | 8/2018 |
| WO | WO 2018/223101 | 12/2018 |
| WO | WO 2019/046832 | 3/2019 |
| WO | WO 2019/089848 | 5/2019 |
| WO | WO 2019/109053 | 6/2019 |
| WO | WO 2020/113194 | 6/2020 |

OTHER PUBLICATIONS

Bishnoi et al., PLoS ONE 10(2): e0117282. doi:10.1371/journal.pone.0117282 (Year: 2015).*

Kochenderfer, J. N. & Rosenberg, (2013) S. A. Nat. Rev. Clin. Oncol. 10, 267-276 (Year: 2013).*

Bergamaschi et al., Blood. 2012; 120(1): e1-e8 (Year: 2012).*

Erin Kimbrel and Robert Lanza, Nature Reviews Drug Discovery, 2020; 19: 463-479 (Year: 2020).*

Santomasso et al., Am Soc Clin Oncol Educ Book, 2019; 39: 433-444 (Year: 2019).*

Tao et al., Mol Biol Rep (2012) 39:4201-4205 (Year: 2012).*

"JCAR015 in ALL: A Root-Cause Investigation," Cancer Discov. (2018) 8(1):4-5.

(56) References Cited

OTHER PUBLICATIONS

"Database accession No. P20963.2," version 211. Retrieved from UNIPROT, https://www.uniprot.org/uniprot/P20963. Retrieved on Dec. 18, 2019.
Abramson et al., "CR rates in relapsed/refractory (R/R) aggressive B-NHL treated with the CD19-directed CAR T-cell product JCAR017 (TRANSCEND NHL 001), " J. Clin. Oncol. (2017) 35 (15): 7513 Abstract.
Abramson et al., "High Durable CR Rates in Relapsed/Refractory (R/R) Aggressive B-NHL Treated with the CD19-Directed CAR T Cell Product JCAR 017 (TRANSCEND NHL001): Defined Composition Allows for Dose-Finding and Definition of Pivotal Cohort," Blood (2017) 130:581 Abstract.
Abramson et al., "High Durable CR Rates in Relapsed/Refractory (R/R) Aggressive B-NHL Treated with the CD19-Directed CAR T Cell Product JCAR 017 (TRANSCEND NHL001): Defined Composition Allows for Dose-Finding and Definition of Pivotal Cohort," oral presentation on Dec. 9, 2017 at ASH 2017.
Abramson et al., "TRANSCEND NHL 001: Immunotherapy with the CD19-directed CAR T-cell Product JCAR017 Results in High Complete Response Rates in Relapsed or Refractory B-Cell Non-Hodgkin Lymphoma," Blood (2016) 128:4192 Abstract.
Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.
Annaloro et al., "Severe fludarabine neurotoxicity after reduced intensity conditioning regimen to allogeneic hematopoietic stem cell transplantation: a case report," Clin. Case Rep. (2015) 3(7):650-55.
Barret, D.M. et al. (2014, e-pub. Nov. 20, 2013). "Chimeric Antigen Receptor Therapy for Cancer," Annu Rev Med. (2014);65:333-347.
Baum, C. et al. (Jun. 2006, e-pub. Apr. 24, 2006). "Retrovirus Vectors: Toward the Plentivirus?", Molecular Therapy 13(6)1050-1063.
Behrends et al., "Network organization of the human autophagy system," Nature. (2010) 466(7302): 68-76.
Bhojwani et al., "Methotrexate-induced neurotoxicity and leukoencephalopathy in childhood acute lymphoblastic leukemia," J. Clin. Oncol (2014) 32(9):949-59.
Bishop et al, "Long-term outcomes of adults with acute lymphoblastic leukemia after autologous or unrelated donor bone marrow transplantation: a comparative analysis by the National Marrow Donor Program and Center for International Blood and Marrow Transplant Research," Bone Marrow Transplant (2008) 41(7):635-42.
Blincyto (blinatumomab) prescribing information. Thousand Oaks, CA: Amgen Inc. 2014.
Bonifant et al., "Toxicity and management in CAR T-cell therapy," Mol. Ther. Oncolytics (2016) 3:16011.
Boris-Lawrie, K.A. et al. (Feb. 1993). "Recent advances in retrovirus vector technology", *Curr Opin Genet Dev.* 3(1):102-109.
Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.
Brentjens et al., "CD19-targeted T cells rapidly induce molecular remissions in adults with chemotherapy-refractory acute lymphoblastic leukemia," Sci Transl Med. (2013) 5(177):177ra38.
Brentjens et al., "Safety and persistence of adoptively transferred autologous CD19-targeted T cells in patients with relapsed or chemotherapy refractory B-cell leukemias," Blood (2011) 118(18):4817-4828.
Brudno et al, "T Cells Expressing a Novel Fully-Human Anti-CD19 Chimeric Antigen Receptor Induce Remissions of Advanced Lymphoma in a First-in-Humans Clinical Trial," A50. Blood (2016) 128 (22): 999.
Brudno et al., "Toxicities of chimeric antigen receptor T cells: recognition and management," Blood (2016) 127(26):3321-3330.
Brunstein et al., "Alternative donor transplantation after reduced intensity conditioning: results of parallel phase 2 trials using partially HLA-mismatched related bone marrow or unrelated double umbilical cord blood grafts," Blood (2011) 118(2):282-88.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.
Carceller et al., "Response Assessment in Paediatric Phase I Trials According to RECIST Guidelines: Survival Outcomes, Patterns of Progression and Relevance of Changes in Tumour Measurements," Pediatr Blood Cancer. (2016) 63(8):1400-1406.
Carlens et al., "Ex vivo T lymphocyte expansion for retroviral transduction: influence of serum-free media on variations in cell expansion rates and lymphocyte subset distribution," Exp Hematol (2000) 28(10): 1137-46.
Carvalho Da Fonseca et al., "The impact of microglial activation on blood-brain barrier in brain diseases," Front. Cell. Neurosci. (2014) 8:362.
Cavalieri et al., "Human T lymphocytes transduced by lentiviral vectors in the absence of TCR activation maintain an intact immune competence," Blood (2003) 102(2): 497-505.
Challita et al., "Multiple modifications in cis elements of the long terminal repeat of retroviral vectors lead to increased expression and decreased DNA methylation in embryonic carcinoma cells," J Virol. (1995) 69(2): 748-55.
Cheadle et al., "Chimeric antigen receptors for T-cell based therapy," Methods Mol Biol. (2012);907:645-66.
Chervin et al., "Engineering higher affinity T cell receptors using a T cell display system," (2008) J Immunol Methods, 339, 175-84.
Cheson et al., "Neurotoxicity of purine analogs: a review," J. Clin. Oncol. (1994) 12(10):2216-28.
Chicaybam et al., "An efficient low cost method for gene transfer to T lymphocytes," PLoS ONE (2013) 8(3): e60298.
Cho et al., "Human mammalian cell sorting using a highly integrated micro-fabricated fluorescence-activated cell sorter (microFACS)," Lab Chip (2010) 10: 1567-1573.
Chong et al., "Chimeric Antigen Receptor Modified T Cells Directed Against CD19 (CTL019) in Patients with Poor Prognosis, Relapsed or Refractory CD19+ Follicular Lymphoma: Prolonged Remissions Relative to Antecedent Therapy," Blood (2016) 128(22):1100.
Chothia et al. "The outline structure of the T-cell alpha beta receptor," (1988) EMBO J. 7:3745.
Clackson et al. "Making antibody fragments using phage display libraries," Nature (1991) 352:624-628.
Clinical Trial Study Record No. NCT02535364. First posted Aug. 28, 2015. Updated Jul. 19, 2018. Accessed Nov. 19, 2019.
Clinical Trial Study Record No. NCT01044069. First posted Jan. 7, 2010. Updated Feb. 4, 2019. Accessed Jun. 5, 2018.
Cohen et al. "Recombinant antibodies with MHC-restricted, peptide-specific, T-cell receptor-like specificity: new tools to study antigen presentation and TCR-peptide-MHC interactions," (2003) J Mol. Recogn. 16:324-332.
Common Terminology for Adverse Events (CTCAE) Version 4, U.S. Department of Health and Human Services, Published: May 28, 2009 (v4.03: Jun. 14, 2010).
Cooper et al., "T-cell clones can be rendered specific for CD19: toward the selective augmentation of the graft-versus-B-lineage leukemia effect," Blood (2003) 101:1637-1644.
Dantzer et al., "From inflammation to sickness and depression: when the immune system subjugates the brain," Nat. Rev. Neurosci. (2009) 9(1):46-55.
Davila et al., "CD19 CAR-targeted T cells induce long-term remission and B Cell Aplasia in an immunocompetent mouse model of B cell acute lymphoblastic leukemia," PLoS ONE (2013) 8(4): e61338.
Davila et al., "Efficacy and toxicity management of 19-28z CAR T cell therapy in B cell acute lymphoblastic leukemia," Sci Transl Med (2014) 6:224ra25.
De Felipe, "Skipping the co-expression problem: the new 2A "CHYSEL" technology," Genet Vaccines Ther Sep. 13, 2004;2(1):13.
De Felipe, "Targeting of proteins derived from self-processing polyproteins containing multiple signal sequences," Traffic (2004) 5(8):616-626.

(56) References Cited

OTHER PUBLICATIONS

De Loecker et al., "Effects of Cell Concentration on Viability and Metabolic Activity during Cryopreservation," Crybiology (1998) 37(2):103-9.
DeAngelo et al., "Clinical Outcomes for the Phase 2, Single-Arm, Multicenter Trial of JCAR015 in Adult B-ALL (Rocket Study)," Journal for Immuno Therapy of Cancer (2017) 5:86.
Dobber et al., "The in vivo effects of neutralizing antibodies against IFN-gamma, IL-4, or IL-10 on the humoral immune response in young and aged mice," Cell Immunol (1995) 160(2):185-192.
Dutcher et al., "High dose interleukin-2 (Aldesleukin)—expert consensus on best management practices—2014," Journal for ImmunoTherapy of Cancer (2014) 2:26.
Eisenhauer et al., "New response evaluation criteria in solid tumours: Revised RECIST guideline (version 1.1)," Eur J Cancer (2009) 45:228-247.
Fedorov et al., "PD-1- and CTLA-4-based inhibitory chimeric antigen receptors (iCARs) divert off-target immunotherapy responses," Sci. Transl. Medicine (2013) 5(215).
Feuerstein et al., "A method for the production of cryopreserved aliquots of antigen-preloaded, mature dendritic cells ready for clinical use," J. Immunol. Methods (2000) 245(1-2): 15-29.
Fludarabine Phosphate for Injection prescribing information. Schaumburg, IL: Sagent Pharmaceuticals. 2014.
Frecha, C. et al. (Oct. 2010, e-pub. Aug. 24, 2010). "Advances in the Field of Lentivector-based Transduction of T and B Lymphocytes for Gene Therapy", Molecular Therapy 18(10):1748-1757.
Frey, "Optimizing Chimeric Antigen Receptor (CAR) T Cell Therapy for Adult Patients with Relapsed or Refractory Acute Lymphoblastic Leukemia," J. Clin. Oncol. (2016) 34(15 supp):7002.
Gardner et al., "CD19 CAR T Cell Products of Defined CD4:CD8 Composition and Transgene Expression Show Prolonged Persistence and Durable MRD-Negative Remission in Pediatric and Young Adult B-Cell ALL," Blood (2016)128:219.
Gardner et al., "CD19 CAR T Cell Products of Defined CD4:CD8 Composition and Transgene Expression Show Prolonged Persistence and Durable MRD-Negative Remission in Pediatric and Young Adult B-Cell ALL," Oral presentation presented at ASH Dec. 3, 2016, 2016.
Gardner et al., "Intent-to-treat leukemia remission by CD19 CAR T cells of defined formulation and dose in children and young adults," Blood (2017) 129(25):3322-31.
Garfall et al., "Posterior Reversible Encephalopathy Syndrome (PRES) after Infusion of Anti-Bcma CAR T cells (CART-BCMA) for Multiple Myeloma: Successful Treatment with Cyclophosphamide," Blood Dec. 2016; 128(22):5702.
Gilbert et al., "Severe Neurotoxicity in the Phase 2 Trial of JCAR015 in Adult B-ALL (Rocket Study): Analysis of Patient, Protocol and Product Attributes," Oral presentation presented at Society for Immunotherapy of Cancer on Nov. 9, 2017.
Glick et al., "Autophagy: cellular and molecular mechanisms," J. Pathol. (2010) 221(1):3-12.
Godin et al., "Microfluidics and photonics for Bio-System-on-a-Chip: a review of advancements in technology towards a microfluidic flow cytometry chip," J Biophoton. (2008) 1(5):355-376.
Gokbuget et al., "Adult patients with acute lymphoblastic leukemia and molecular failure display a poor prognosis and are candidates for stem cell transplantation and targeted therapies," Blood (2012) 120(9):1868-1876.
Gokbuget et al., "Blinatumomab vs historical standard therapy of adult relapsed/refractory acute lymphoblastic leukemia," Blood Cancer J (2016) 6(9):e473.
Gong et al., "An Antagonist of Monocyte Chemoattractant Protein 1 (MCP-1) Inhibits Arthritis in the MRL-Ipr Mouse Model," J Exp Med (1997) 186(1):131-137.
Grupp et al., "Analysis of a Global Registration Trial of the Efficacy and Safety of CTL019 in Pediatric and Young Adults with Relapsed/Refractory Acute Lymphoblastic Leukemia (ALL)," Blood (2016) 128(22):221.
Grupp et al., "Chimeric antigen receptor-modified T cells for acute lymphoid leukemia," N. Engl. J. Med. (2013) 368:1509-1518.
Hackett, P.B. et al. (Apr. 2010, e-pub. Jan. 26, 2010). "A Transposon and Transposase System for Human Application", Mol. Ther. 18(4):674-683.
Hannum et al., "Interleukin-1 receptor antagonist activity of a human interleukin-1 inhibitor," Nature (1990) 343:336-340.
Harvey et al., "Development and Validation of a Highly Sensitive and Specific Gene Expression Classifier to Prospectively Screen and Identify B-Precursor Acute Lymphoblastic Leukemia (ALL) Patients With a Philadelphia Chromosome-Like ("Ph-like' or "BCR-ABL /-Like') Signature for Therapeutic Targeting and Clinical Intervention," Blood (2013) 122: 826.
Harvey et al., "Rearrangement of CRLF2 is associated with mutation of JAK kinases, alteration of IKZF1, Hispanic/Latino ethnicity, and a poor outcome in pediatric B-progenitor acute lymphoblastic leukemia," Blood. (2010) 115(26): 5312-5321.
Heipel et al., "Pharmacokinetic, Pharmacodynamic and Blood Analytes Associated with Clinical response and Safety in Relapsed/Refractory Aggressive B-NHL Patients Treated with JCAR017," Blood (2017) 130 (Suppl 1):2835.
Henig et al., "Hematopoietic stem cell transplantation—50 years of evolution and future perspectives," Rambam Maimonides Med J (2014) 5(4):e0028.
Hermans et al., "The VITAL assay: a versatile fluorometric technique for assessing CTL- and NKT-mediated cytotoxicity against multiple targets in vitro and in vivo," J. Immunological Methods (2004) 285(1): 25-40.
Holler et al., "In vitro evolution of a T cell receptor with high affinity for peptide/MHC," PNAS (2000) 97(10):5387-5392.
Holler et al., "TCRs with high affinity for foreign pMHC show self-reactivity," Nat Immunol (2003) 4(1):55-62.
Hollyman et al, "Manufacturing validation of biologically functional T cells targeted to CD19 antigen for autologous adoptive cell therapy," J Immunother (2009) 32(2):169-180.
Hu et al., "Predominant cerebral cytokine release syndrome in CD19-directed chimeric antigen receptor-modified T cell therapy," J Hematol Oncol (2016) 9(1):70.
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin. Cancer Res. (2013) 19:3153.
Hunter et al., "Neutralizing anti-IL-10 antibody blocks the protective effect of tapeworm infection in a murine model of chemically induced colitis," J Immunol (2005) 174(11):7368-7375.
Janeway et al., Immunobiology: The Immune System in Health and Disease, 3rd Ed., Current Biology Publications (1997), p. 4:33.
Johnston, et al., "Biolistic transformation: microbes to mice," Nature (1990) 346: 776-777.
Jores et al., "Resolution of hypervariable regions in T-cell receptor beta chains by a modified Wu-Kabat index of amino acid diversity.," PNAS (1990) 87(23):9138-9142.
Kantarjian et al., "Blinatumomab versus Chemotherapy for Advanced Acute Lymphoblastic Leukemia," N Engl J Med (2017) 376(9):836-847.
Kantarjian et al., "Inotuzumab Ozogamicin versus Standard Therapy for Acute Lymphoblastic Leukemia," N Engl J Med (2016) 375(8):740-753.
Kawamura et al., "Effects of angiopoietin-1 on hemorrhagic transformation and cerebral edema after tissue plasminogen activator treatment for ischemic stroke in rats," PLoS One (2014) 9(6):e98639.
Kindt, T.J. et al. (2007). "Antigens and Antibodies," Chapter 4 in Kuby Immunology 6th Ed., W.H. Freeman and Co., p. 91.
Klaver et al.,"Adoptive T-cell therapy: A need for standard immune monitoring," (2015) Immunotherapy 7(5)513-33.
Klebanoff et al., "Sorting through subsets: which T-cell populations mediate highly effective adoptive immunotherapy?," J Immunother. (2012) 35(9): 651-660.
Kochenderfer et al., "Anti-CD19 CAR T Cells Administered after Low-Dose Chemotherapy Can Induce Remissions of Chemotherapy-Refractory Diffuse Large B-Cell Lymphoma," Blood (2014) 124(21):550.

(56) References Cited

OTHER PUBLICATIONS

Kochenderfer et al., "B-cell depletion and remissions of malignancy along with cytokine-associated toxicity in a clinical trial of anti-CD19 chimeric-antigen-receptor-transduced T cells," Blood (2012) 119 : 2709-2720.
Kochenderfer et al., "Chemotherapy-refractory diffuse large B-cell lymphoma and indolent B-cell malignancies can be effectively treated with autologous T cells expressing an anti-CD19 chimeric antigen receptor," J Clin Oncol (2015) 33(6):540-549.
Kochenderfer et al., "Construction and preclinical evaluation of an anti-CD19 chimeric antigen receptor," J. Immunotherapy (2009) 32(7): 689-702.
Kochenderfer, "Anti-CD19 chimeric antigen receptor T cells preceded by low-dose chemotherapy to induce remissions of advanced lymphoma," J. Clin. Oncol. (2017) 34:18 suppl.
Koste et al., "T-cell receptor transfer into human T cells with ecotropic retroviral vectors," Gene Therapy (2014) 21: 533-538.
Kotb et al., "Bacterial pyrogenic exotoxins as superantigens," Clinical Microbiology Reviews (1995) 8:411-426.
Kranick et al, "Aphasia as a Complication of CD19-Targeted Chimeric Antigen Receptor Immunotherapy," Annual Meeting of the American Academy of Neurology 2014; Philadelphia, PA.
Kurucz et al., "A bacterially expressed single-chain Fv construct from the 2B4 T-cell receptor," PNAS (1993) 90(9):3830-3834.
Lee et al,, "Current concepts in the diagnosis and management of cytokine release syndrome," Blood. (2014) 124(2):188-95.
Lee et al., "Long-Term Outcomes Following CD19 CAR T Cell Therapy for B-ALL Are Superior in Patients Receiving a Fludarabine/Cyclophosphamide Preparative Regimen and Post-CAR Hematopoietic Stem Cell Transplantation," Blood (2016) 128(22):218.
Lee et al., "T cells expressing CD19 chimeric antigen receptors for acute lymphoblastic leukaemia in children and yound adults: a phase 1 dose escalation trial," The Lancet (2015) 385(9967): 517-528.
Lefranc et al., "IMGT unique numbering for immunoglobulin and T cell receptor variable domains and Ig superfamily V-like domains," Dev Comp Immunol (2003) 27(1):55-77.
Li, JJ et al., "Thrombin induces the release of angiopoietin-1 from platelets," Thromb Haemost (2001) 85(2):204-206.
Li, Y. et al. (Mar. 2005, e-pub Feb. 20, 2005). "Directed evolution of human T-cell receptors with picomolar affinities by phage display", Nat Biotechnol. 23(3):349-354.
Lim et al. "The Molecular Engineering of an Anti-Idiotypic Antibody for Pharmacokinetic Analysis of a Fully Human Anti-Infective. "PloS one 10.12 (2015): e0145381.
Ling et al. (1987). Leucocyte typing III. 302.
Liu et al., "Inclusion of Strep-Tag II in design of antigen receptors for T cell immunotherapy," Nat Biotechnol. (2016) 34(4): 430-434.
Locke et al., "Primary Results from ZUMA-1: A Pivotal Trial of Axicabtagene Ciloleucel (Axi-cel; KTE-C19) in Patients with Refractory Aggressive Non-Hodgkin Lymphoma (NHL)," Cancer Research (2017) 77(13):Abstract CT019.
Locke et al., "Immune Signatures of Cytokine Release Syndrome and Neurologic Events in a Multicenter Registrational Trial (ZUMA-1) in Subjects with Refractory Non-Hodgkin Lymphoma Treated with Axicabtagene Ciloleucel (KTE-C19)," Cancer Research (2017) 77(13): Abstract CT020.
Locke et al., "Product characteristics associated with in vivo expansion of anti-CD19 CAR T cells in patients treated with axicabtagene ciloleucel (axi-cel)," J. Clin. Oncol. (2017) 35 (No. 15_suppl):3023.
Lupton S. D. et al., "Dominant positive and negative selection using a hygromycin phosphotransferase-thymidine kinase fusion gene," Mol. and Cell Biol. (1991) 11:6.
Luznik et al, "HLA-haploidentical bone marrow transplantation for hematologic malignancies using nonmyeloablative conditioning and high-dose, posttransplantation cyclophosphamide," Biol Blood Marrow Transplant (2008) 14(6):641-650.
Maloney et al., "Preliminary Safety Profile of the CD19-Directed Defined Composition CAR T Cell Product JCAR017 in Relapsed/Refractory Aggressive B-NHL Patients: Potential for Outpatient Administration," Blood (2017) 130 (Suppl 1):1552.
Manuri et al., "piggyBac transposon/transposase system to generate CD19-specific T cells for the treatment of B-lineage malignancies," Hum Gene Ther (2010) 21(4): 427-437.
Martinez-Lopez et al. Prognostic value of deep sequencing method for minimal residual disease detection in multiple myeloma. Blood. 2014;123(20):3073-3079.
Maude et al, "Efficacy of Humanized CD19-Targeted Chimeric Antigen Receptor (CAR)-Modified T Cells in Children and Young Adults with Relapsed/Refractory Acute Lymphoblastic Leukemia," Blood (2016) 128(22):217.
Maude et al., "Chimeric Antigen Receptor T Cells for Sustained Remissions in Leukemia," N Engl J Med. (2014) 371(16): 1507-1517.
Maude et al., "Efficacy and Safety of CTL019 in the First US Phase II Multicenter Trial in Pediatric Relapsed/Refractory Acute Lymphoblastic Leukemia: Results of an Interim Analysis," Blood (2016) 128(22):2801.
Maus et al., "Antibody-modified T cells: CARs take the front seat for hematologic malignancies," Blood (2014) 123(17):2625-2635.
Miller et al., "Improved retroviral vectors for gene transfer and expression," BioTechniques (1989) 7:980-990.
Miller et al., "Retrovirus packaging cells," Human Gene Therapy (1990) 1:5-14.
Monsky et al. "Semi-Automated Volumetric Quantification of Tumor Necrosis in Soft Tissue Sarcoma Using Contrast Enhanced MRI," Anticancer Res. (2012) 32(11):4951-4961.
Mullen et al., "Transfer of the bacterial gene for cytosine deaminase to mammalian cells confers lethal sensitivity to 5-fluorocytosine: a negative selection system," Proc. Natl. Acad. Sci. USA (1992) 89:33.
O'Brien et al., "High-dose vincristine sulfate liposome injection for advanced, relapsed, and refractory adult Philadelphia chromosome-negative acute lymphoblastic leukemia," J Clin Oncol (2013) 31(6):676-683.
O'Brien et al., "Outcome of adults with acute lymphocytic leukemia after second salvage therapy," Cancer (2008) 113(11):3186-3191.
Ozmen et al., "Mouse soluble IFN gamma receptor as IFN gamma inhibitor. Distribution, antigenicity, and activity after injection in mice," J Immunol (1993) 150(7):2698-2705.
Parizel et al., "Cerebral complications of murine monoclonal CD3 antibody (OKT3): CT and MR findings," AJNR Am J Neuroradiol (1997) 18(10):1935-1938.
Park et al., "Baseline and early post-treatment clinical and laboratory factors associated with severe neurotoxicity following 19-28z CAR T cells in adult patients with relapsed B-ALL," Annual Meeting of the American Society of Clinical Oncology (2017), Chicago, IL.Oncology 35(15):suppl. 7024.
Park et al., "CD-19-targeted CAR T-cell therapeutics for hematologic malignancies: interpreting clinical outcomes to date," Blood (2016) 127(26):3312-3320.
Park et al., "Impact of disease burden on long-term outcome of 19-28z CAR modified T cells in adult patients with relapsed B-ALL," J. Clin. Oncol. (2016) 34(No. 15_suppl):7003.
Park et al., "Treating cancer with genetically engineered T cells," Trends Biotechnol. (2011) 29(11): 550-557.
Perez-Andreu et al., "Inherited GATA3 variants are associated with Ph-like childhood acute lymphoblastic leukemia and risk of relapse," Nat Genet. (2013) 45(12): 1494-1498.
Ponticelli et al., "Neurological complications in kidney transplant recipients," J Nephrol (2005) 18(5):521-528.
Porter et al., "Chimeric antigen receptor T cells persist and induce sustained remissions in relapsed refractory chronic lymphocytic leukemia," Sc.i Trans. Med. (2015) 7(303): 303ra139.
Porter et al., "Randomized, Phase II Dose Optimization Study of Chimeric Antigen Receptor Modified T Cells Directed Against CD19 (CTL019) in Patients With Relapsed, Refractory CLL," Blood. Nov. 2013;122(21):873.
Portolano et al., "Lack of promiscuity in autoantigen-specific H and L chain combinations as revealed by human H and L chain "roulette"," J. Immunol. (1993) 150:880-887.

(56) References Cited

OTHER PUBLICATIONS

Ramsborg et al., "JCAR017 Is a Defined Composition CAR T Cell Product with Product and Process Controls That Deliver Precise Doses of CD4 and CD8 Car T Cell to Patients with NHL," Blood (2017) 130 (Suppl 1):4471.
Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington," Human Gene Therapy (1992) 3:319-338.
Roberts et al., "Genetic alterations activating kinase and cytokine receptor signaling in high-risk acute lymphoblastic leukemia," Cancer Cell. (2012) 22(2):153-66.
Roberts et al., "High Frequency and Poor Outcome of Philadelphia Chromosome-Like Acute Lymphoblastic Leukemia in Adults," J Clin Oncol. (2017) 35(4): 394-401.
Roberts et al., "Targetable kinase-activating lesions in Ph-like acute lymphoblastic leukemia," N Engl J Med.( 2014) 371(11):1005-15.
Rosenberg, et al., "Cell transfer immunotherapy for metastatic solid cancer—what clinicians need to know," Nat Rev Clin Oncol. (2011) 8(10):577-85).
Sadelain et al., "The basic principles of chimeric antigen receptor design," Cancer Discov. (2013) 3(4): 388-398.
Santomasso et al., "Biomarkers associated with neurotoxicity in adult patients with relapsed or refractory B-ALL (R/R B-ALL) treated with CD19 CAR T cells," J. Clin. Oncol. (2017) 35 (Supp. 15):3019.
Scarpa et al., "Characterization of recombinant helper retroviruses from Moloney-based vectors in ecotropic and amphotropic packaging cell lines," Virology (1991) 180:849-852.
Schlueter et al. "Specificity and Binding Properties of a Single-chain T Cell Receptor," J. Mol. Biol. (1996) 256(5):859.
Schuler et al. SYFPEITHI, Database for Searching and T-Cell Epitope Prediction. in Immunoinformatics Methods in Molecular Biology, vol. 409(1): 75-93 2007.
Schuster et al., "Treatment with Chimeric Antigen Receptor Modified T Cells Directed Against CD19 (CTL019) Results in Durable Remissions in Patients with Relapsed or Refractory Diffuse Large B Cell Lymphomas of Germinal Center and Non-Germinal Center Origin, "Double Hit" Diffuse Large B Cell Lymphomas, and Transformed Follicular to Diffuse Large B Cell Lymphomas," Blood (2016) 128(22):3026.
Sentman "Challenges of creating effective chimeric antigen receptors for cancer therapy," (2013) Immunotherapy, 5(8):783-785.
Shah et al., "High Rates of Minimal Residual Disease-Negative (MRD-) Complete Responses (CR) in Adult and Pediatric and Patients With Relapsed/Refractory Acute Lymphoblastic Leukemia (R/R ALL) Treated With KTE-C19 (Anti-CD19 Chimeric Antigen Receptor [CAR] T Cells): Preliminary Results of the ZUMA-3 and ZUMA-4 Trials," Blood (2016) 12(22):2803.
Shahrara et al., "Inhibition of Monocyte Chemoattractant Protein-1 Ameliorates Rat Adjuvant-Induced Arthritis," J Imunol (2008) 180:3447-3456.
Sharma et al., "Efficient sleeping beauty DNA transposition from DNA minicircles," Molec Ther Nucl Acids (2013) 2, e74.
Siddiqi et al., "Patient Characteristics and Pre-Infusion Biomakers of Inflammation Correlate with Clinical Outcomes after Treatment with the Defined Composition, CD19-Targeted CAR T Cell Product, JCAR017," ASH 2017 Oral Presentation, presented Dec. 9, 2017.
Siddiqi et al., "Patient Characteristics and Pre-Infusion Biomakers of Inflammation Correlate with Clinical Outcomes after Treatment with the Defined Composition, CD19-Targeted Car T Cell Product, JCAR017," ASH 2017. Abstract 193.
Singh et al., "ProPred: prediction of HLA-DR binding sites," Bioinformatics 17(12):1236-1237 2001.
Soo Hoo et al., "Characterization of a single-chain T-cell receptor expressed in *Escherichia coli*," Proc Natl Acad Sci U S A. (1992) 89(10):4759-63.
Sugita et al., "HLA-Haploidentical Peripheral Blood Stem Cell Transplantation with Post-Transplant Cyclophosphamide after Busulfan-Containing Reduced-Intensity Conditioning," Biol Blood Marrow Transplant (2015) 21(9):1646-1652.
Swanson et al., "Predicting Clinical Response and Safety of JCAR017 in B-NHL Patients: Potential Importance of Tumor Microenvironment Biomarkers and CAR T-Cell Tumor Infiltration," Blood (2017) 130 (Suppl 1):194.
Swanson et al., "Predicting Clinical Response and Safety of JCAR017 in B-NHL Patients: Potential Importance of Tumor Microenvironment Biomarkers and CAR T-Cell Tumor Infiltration," oral presentation presented on Dec. 11, 2017 at ASH 2017.
Takeshita and Ransohoff, "Inflammatory cell trafficking across the blood-brain barrier: chemokine regulation and in vitro models," Immunol. Rev. (2012) 248(1):228-39.
Tamada et al., "Redirecting gene-modified T cells toward various cancer types using tagged antibodies," Clin Cancer Res. (2012) 18(23): 6436-45.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
Thurston et al., "Angiopoietin-1 protects the adult vasculature against plasma leakage," Nat Med (2000) 6(4):460-463.
Trede and Hasskarl, "Ensuring safety for patients throughout the lifecycle of an ATMP: Case study," Oral presentation presented at European Biopharmaceutical Enterprises on Dec. 5, 2017.
Tsukahara et al., "CD19 target-engineered T-cells accumulate at tumor lesions in human B-cell lymphoma xenograft mouse models," Biochem Biophys Res Commun (2013) 438(1): 84-9.
Turtle et al, "High rates of Durable Complete Response in ALL, NHL and CLL after Immunotherapy with Optimized Lymphodepletion and Defined Composition CD19 CAR-T cells (JCAR014)," ASH 2016 Oral Presentation. Presented Jun. 4, 2016.
Turtle et al., "Biomarkers of Cytokine Release Syndrome and Neurotoxicity after CD19 CAR-T Cells and Mitigation of Toxicity by Cell Dose," Blood (2016) 128(22):1852.
Turtle et al., "CD19 CAR-T Cells (JCAR014) are Highly effective in Ibrutinib-Refractory High-Risk CLL," ASH oral presentation abstract 56, presented Dec. 3, 2016.
Turtle et al., "CD19 CAR-T Cells Are Highly Effective in Ibrutinib-Refractory Chronic Lymphocytic Leukemia," Blood (2016) 128(22): 56.
Turtle et al., "CD19 CAR-T cells of defined CD4+:CD8+ composition in adult B cell ALL patients," J. Clin. Invest. (2016) 126(6):2123-38.
Turtle et al., "Endothelial Activation and Blood-Brain Barrier Disruption in Neurotoxicity after CD19 CAR-T Cell Immunotherapy," Blood (2017) 130(Supp. 1):805.
Turtle et al., "Endothelial Activation and Blood-Brain Barrier Disruption in Neurotoxicity after CD19 CAR-T Cell Immunotherapy," Oral presentation presented at ASH 2017.
Turtle et al., "Engineered T cells for anti-cancer therapy," Curr. Opin. Immunol. (2012) 24(5): 633-39.
Urbanska et al., "A Universal Strategy for Adoptive Immunotherapy of Cancer through Use of a Novel T-cell Antigen Receptor," Cancer Res (2012) 72: 1844-1852.
Van Tendeloo et al., "High-level transgene expression in primary human T lymphocytes and adult bone marrow CD34+ cells via electroporation-mediated gene delivery," Gene Therapy (2000) 7(16): 1431-1437).
Varatharaj and Galea, "The blood-brain barrier in systemic inflammation," Brain Behav. Immun. (2017) 60:1-12.
Verhoeyen et al., "Lentiviral vector gene transfer into human T cells," Methods Mol Biol. (2009) 506: 97-114.
Wang et al., "Phenotypic and functional attributes of lentivirus-modified CD19-specific human CD8+ central memory T cells manufactured at clinical scale," J Immunother. (2012) 35(9):689-701.
Wigler et al., "Transfer of purified herpes virus thymidine kinase gene to cultured mouse cells," Cell (1997) 11: 223-232.

(56) References Cited

OTHER PUBLICATIONS

Wu et al., "Adoptive T-cell therapy using autologous tumor-infiltrating lymphocytes for metastatic melanoma: current status and future outlook," Cancer (2012) 18(2): 160-75.
Wulfing et al., "Correctly Folded T-cell Receptor Fragments in the Periplasm of *Escherichia coli*: Influence of Folding Catalysts," J. Mol. Biol. (1994) 242(5): 655-669.
Xu et al., "Cytokine release syndrome in cancer immunotherapy with chimeric antigen receptor engineered T cells," Cancer Letters (2014) 343:172-78.
Yap et al., "Diagnostic evaluation of RNA sequencing for the detection of genetic abnormalities associated with Ph-like acute lymphoblastic leukemia (ALL)," Leuk Lymphoma (2017) 58(4):950-958.
Zuurbier et al., "Clinical Course of Cerebral Venous Thrombosis in Adult Acute Lymphoblastic Leukemia," J Stroke Cerebrovasc Dis (2015) 24(7):1679-1684.
"Affymetrix GeneChip Human Genome U133 Array Set HG-U133A", GEO,,Mar. 11, 2002 (Mar. 11, 2002), XP002254749.
Bacher et al., "Gene expression profiling for diagnosis and therapy in acute leukaemia and other haematologic malignancies," Cancer Treat Rev. (2010) 36(8):637-646.
Egbelakin et al., "Increased risk of vincristine neurotoxicity associated with low CYP3A5 expression genotype in children with acute lymphoblastic leukemia," Pediatr Blood Cancer (2011) 56(3): 361-367.
Imai et al. "Chimeric receptors with 4-1BB signaling capacity provoke potent cytotoxicity against acute lymphoblastic leukemia." *Leukemia* (2004) 18.4 : 676-684.
King et al., "Biomarkers for Predicting Toxicity and Response in Adult Acute Lymphoblastic Leukemia (ALL) Patients Treated with Blinatumomab," Blood (2017) 130 Abs 3883.
Lacey et al., "Biomarker Profiling Differentiates Sepsis from Cytokine Release Syndrome in Chimeric Antigen Receptor T-Cell Therapy for Acute Lymphoblastic Leukemia (ALL)," Blood (2016) 128(22): 2812-2812.
Maus et al., "T cells expressing chimeric antigen receptors can cause anaphylaxis in humans," Cancer Immunol Res. Jul. 2013;1(1):26-31.
Teachey et al., "Biomarkers Accurately Predict Cytokine Release Syndrome (CRS) after Chimeric Antigen Receptor (CAR) T Cell Therapy for Acute Lymphoblastic Leukemia (ALL)," Blood (2015) 126(23):1334.
Zuo et al., "A pathway-based gene signature correlates with therapeutic response in adult patients with Philadelphia chromosome-positive acute lymphoblastic leukemia", Mod Pathol. (2010) 23(11): 1524-1534.
U.S. Appl. No. 18/067,672, filed Dec. 16, 2022, by Albertson et al. (Copy not provided). (Copy not submitted herewith pursuant to the waiver of 37 C.F. R. § 1.98(a)(2)(iii) issued by the Office on Sep. 21, 2004).
Aagaard et al., "RNAi therapeutics: principles, prospects and challenges," Adv Drug Deliv Rev. (2007) 59(2-3):75-86.
Abramson et al., "High durable CR rates and preliminary safety profile for JCAR017 in R/R aggressive b-NHL (TRANSCEND NHL 001 Study): A defined composition CD19-directed CAR T-cell product with potential for outpatient administration," Journal of Clinical Oncology. (2018) 36:5_suppl. 120-120.
Abramson et al., "Updated safety and long term clinical outcomes in TRANSCEND NHL 001, pivotal trial of lisocabtagene maraleucel (JCAR017) in R/R aggressive NHL," J Clin Oncol (2018) 36(15):7505.
Avdic et al., "Human Cytomegalovirus-Encoded Human Interleukin-10 (IL-10) Homolog Amplifies Its Immunomodulatory Potential by Upregulating Human IL-10 in Monocytes," J Virol. (2016) 90(8): 3819-3827.
Batlevi et al., "Novel immunotherapies in lymphoid malignancies," Nat Rev Clin Oncol. Jan. 2016;13(1):25-40.
Bork et al., "Powers and pitfalls in sequence analysis: the 70% hurdle," Genome Res. (2000) 10(4):398-400.
Bowie et al., "Deciphering the message in protein sequences: tolerance to amino acid substitutions," Science. (1990) 247(4948): 1306-10.
Brandl et al., "The effect of dexamethasone on polyclonal T cell activation and redirected target cell lysis as induced by a CD19/CD3-bispecific single-chain antibody construct," Cancer Immunol Immunother. (2007) 56(10):1551-63.
Brown et al., "Tolerance of single, but not multiple, amino acid replacements in antibody VH CDR 2: a means of minimizing B cell wastage from somatic hypermutation?" J Immunol. (1996) 156(9):3285-91.
Burgess et al., "Possible dissociation of the heparin-binding and mitogenic activities of heparin-binding (acidic fibroblast) growth factor-1 from its receptor-binding activities by site-directed mutagenesis of a single lysine residue," J Cell Biol. (1990) 111(5 Pt 1):2129-38.
Chen et al., "Anti-CD19 Chimeric Antigen Receptor T Cells Improve Responses to Chemotherapy-Refractory Mantle Cell Lymphoma: A Case Report," Blood. (2016) 128(22): 5393.
Clark et al., "Discovery and development of Janus kinase (JAK) inhibitors for inflammatory diseases," J Med Chem. (2014) 57(12):5023-38.
Davila et al., "CD19-Targeted T Cells for Hematologic Malignancies: Clinical Experience to Date," Cancer J (Dec. 2015) 21(6):470-474.
Dick et al., "Use of LDH and autoimmune side effects to predict response to ipilimumab treatment," Immunotherapy (2016) 8(9):1033-1044.
Franke et al., "Antibodies against CD20 or B-cell receptor induce similar transcription patterns in human lymphoma cell lines," PLoS One.(2011) 6(2): e16596.
Frey et al., "Cytokine release syndrome with novel therapeutics for acute lymphoblastic leukemia," Hematology Am Soc Hematol Educ Program (Dec. 2016) 2016(1):567-572.
Ghobadi, "Chimeric antigen receptor T cell therapy for non-Hodgkin lyphoma," Curr Res Transl Med (2018) 66(2):43-49.
Grupp et al., "CD19-Redirected Chimeric Antigen Receptor T (CART19) Cells Induce a Cytokine Release Syndrome (CRS) and Induction of Treatable Macrophage Activation Syndrome (MAS) That Can Be Managed by the IL-6 Antagonist Tocilizumab (toc).," Blood. (2012) 120 (21): 2604.
Guido et al., "Virtual screening and its integration with modern drug design technologies," Curr Med Chem. (2008) 15(1):37-46.
Johnson et al., "Imaging for Staging and Response Assessment in Lymphoma," Radiology (Aug. 2015) 276(2):323-338.
Law et al., "What does it take to bind CAR?," Mol Ther. (2005) 12(4):599-609.
Larson et al., "Abstract 960: Defined cell composition and precise control over JCAR017 dose enables identification of relationships between chimeric antigen receptor T cell product attributes, pharmacokinetics, and clinical endpoints in NHL," Cancer Res (2018) 78(13 Suppl.): Abstract nr 960.
Lazar et al., "Transforming growth factor alpha: mutation of aspartic acid 47 and leucine 48 results in different biological activities," Mol Cell Biol. (1988) 8(3):1247-52.
Liu et al., "Overall survival of cancer patients with serum lactate dehydrogenase greater than 1000 IU/L," Tumour Biol. (2016) 37(10):14083-14088.
Maude et al., "Managing Cytokine Release Syndrome Associated With Novel T Cell-Engaging Therapies," Cancer J (2014) 20(2): 119-122.
Mount et al., "Cell-based therapy technology classifications and translational challenges," Philos Trans R Soc Lond B Biol Sci. (2015) 370(1680): 20150017.
Neelapu et al., "Chimeric antigen receptor T-cell therapy—assessment and management of toxicities," Nat Rev Clin Oncol (2018) 15(1):47-62.
Porz et al., "Fully Automated Enhanced Tumor Compartmentalization: Man vs. Machine Reloaded," PLoS One. (2016) 11(11): e0165302.
Rossi, J.F., How to increase the efficiency of effector cells in cancer immunotherapy? Immunologiya Gemopoeza [in Russian], 2015, vol. 13, No. 2, p. 6-29 (English translation included), Abstract only.

(56) References Cited

OTHER PUBLICATIONS

Ruella et al., "Kinase inhibitor ibrutinib to prevent cytokine-release syndrome after anti-CD19 chimeric antigen receptor T cells for B-cell neoplasms," Leukemia (Sep. 2016) 31(1): 246-248.
Shevchenko E.K. et al., Prospects for increasing the effectiveness of gene and cell therapy for cardiovascular diseases: genetically modified cells, Cell transplantology and tissue engineering [in Russian], 2010, vol. 5, No. 2, pp. 19-28.
Shimabukuro-Vornhagen et al., "Cytokine release syndrome," J Immunother Cancer. (2018) 6(1):56.
Siebert et al., "Monitoring cytokine profiles during immunotherapy," Immunotherapy. (2010) 2(6):799-816.
Sommermeyer et al., "Chimeric antigen receptor-modified T cells derived from defined CD8+ and Cd4+ subsets confer superior antitumor reactivity in vivo," Leukemia (Feb. 2016) 30(2): 492-500.
Tateishi et al., "Prognostic significance of metabolic tumor burden by positron emission tomography/computed tomography in patients with relapsed/refractory diffuse large B-cell lymphoma," Cancer Sci. (2015) 106(2):186-93.
Tirkes et al. "Response criteria in oncologic imaging: review of traditional and new criteria." *Radiographics* 33.5 (2013): 1323-1341.
Turtle et al. "Addition of fludarabine to cyclophosphamide lymphodepletion improves in vivo expansion of CD19 chimeric antigen receptor-modified T cells and clinical outcome in adults with B cell acute lymphoblastic leukemia." Blood 126.23 (2015): 3773.
Turtle et al., "Immunotherapy of non-Hodgkin's lymphoma with a defined ratio of CD8+ and CD4+ CD19-specific chimeric antigen receptor-modified T cells," Sci Transl Med (Sep. 2016) 8(355):355ra116.
Vajdos et al., "Comprehensive functional maps of the antigen-binding site of an anti-ErbB2 antibody obtained with shotgun scanning mutagenesis," J Mol Biol. (2002);320(2):415-28.
Walliman et al., "Steroids in Molecular Recognition," Chem Rev. Aug. 5, 1997;97(5):1567-1608. (42 pgs).
Wang et al., "Effective response and delayed toxicities of refractory advanced diffuse large B-cell lymphoma treated by CD20-directed chimeric antigen receptor-modified T cells," Clin Immunol. (2014) 155(2):160-75.
Warzocha et al., "Antisense strategy: biological utility and prospects in the treatment of hematological malignancies," Leuk Lymphoma. (1997) 24(3-4):267-81.
Yu et al., "Serum lactate dehydrogenase predicts prognosis and correlates with systemic inflammatory response in patients with advanced pancreatic cancer after gemcitabine-based chemotherapy," Scientific Reports (2017) 7(1):45194.
Christiansen et al., "Elevate serum levels of soluble ICAM-1 in non-Hodgkins lymphomas correlate with tumour burden, disease activity and other prognostic markers," Br J Haematology (1996) pp. 639-646.
Mazur et al., "Influence of cell concentration on the contribution of unfrozen fraction and salt concentration to the survival of slowly frozen human erythrocytes," Cryobiology (1985) 22(6):509-36.
Morozova et al., Prospects of genetic programming of T-cells in adoptive immunotherapy of malignant neoplasms, Sechenovsky Vestnik, 2016, No. 3 (25), p. 23-28.(Including English abstract), Abstract only.
Tang et al., "Opportunities and Challenges of Chimeric Antigen Receptor Modified T Cell Immunotherapy," PLA Journal of Medicine (2015) 27(1):12-25.(Including English translation).
WANG Appendix Supplementary Data (2014), 3 pages.
Sheth et al., "Taming the beast: CRS and ICANS after CAR T-cell therapy for ALL," Bone Marrow Transplant (Mar. 2021) 56(3):552-566.
Tang et al., "The global landscape of cancer cell therapy," Nat Rev Drug Discov (2018) 17(7):465-466.
Yan et al., "Characteristics and Risk Factors of Cytokine Release Syndrome in Chimeric Antigen Receptor T Cell Treatment," Front Immunol (Feb. 23, 2021) 12:611366, 8 pages.
Zhu et al., "Anti-CD19 chimeric antigen receptor T-cell therapy for adult Philadelphia chromosome-positive acute lymphoblastic leukemia,"Two case reports. Medicine (Baltimore). (2016) 95(51):e5676.
Hay et al., "Kinetics and biomarkers of severe cytokine release syndrome after CD19 chimeric antigen receptor-modified T-cell therapy," Blood (2017) 130(21):2295-2306 and Supplemental Data.
Wang et al., "Biomarkers of cytokine release syndrome and neurotoxicity related to CAR-T cell therapy," Biomarker Res. (Jan. 22, 2018) 6:4, 10 pages.

* cited by examiner

DETERMINING TOXICITY RISK IN CAR T-CELL THERAPY

CROSS-REFERENCE TO RELATED APPLICATIONS

The application is a National Stage application under 35 U.S.C. § 371 of International Application No. PCT/US2018/020054, filed on Feb. 27, 2018 which claims the benefit of priority to U.S. provisional patent applications: 62/464,371, filed Feb. 27, 2017, entitled "COMPOSITIONS, ARTICLES OF MANUFACTURE AND METHODS RELATED TO DOSING IN CELL THERAPY"; 62/465,817, filed Mar. 1, 2017, entitled "COMPOSITIONS, ARTICLES OF MANUFACTURE AND METHODS RELATED TO DOSING IN CELL THERAPY"; 62/470,180, filed Mar. 10, 2017, entitled "COMPOSITIONS, ARTICLES OF MANUFACTURE AND METHODS RELATED TO DOSING IN CELL THERAPY"; 62/527,002, filed Jun. 29, 2017, entitled "COMPOSITIONS, ARTICLES OF MANUFACTURE AND METHODS RELATED TO DOSING IN CELL THERAPY"; 62/580,416, filed Nov. 1, 2017, entitled "COMPOSITIONS, ARTICLES OF MANUFACTURE AND METHODS RELATED TO DOSING IN CELL THERAPY"; 62/584,740, filed Nov. 10, 2017, entitled "COMPOSITIONS, ARTICLES OF MANUFACTURE AND METHODS RELATED TO DOSING IN CELL THERAPY"; and 62/596,703, filed December 8, entitled "COMPOSITIONS, ARTICLES OF MANUFACTURE AND METHODS RELATED TO DOSING IN CELL THERAPY" the contents of which is hereby incorporated by reference in their entirety for all purposes.

INCORPORATION BY REFERENCE OF SEQUENCE LISTING

The present application is being filed along with a Sequence Listing in electronic format. The Sequence Listing is provided as a file entitled 735042009300SeqList.TXT, created Aug. 25, 2019, which is 37,881 bytes in size. The information in the electronic format of the Sequence Listing is incorporated by reference in its entirety.

FIELD

The present disclosure relates to cell therapy involving the administration of one or more doses of a therapeutic T cell composition, and methods, compositions and articles of manufacture for use in the same. The cells of the T cell composition express recombinant receptors such as chimeric receptors, e.g. chimeric antigen receptors (CARs) or other transgenic receptors such as T cell receptors (TCRs). Features of the embodiments of the present disclosure, including the numbers of cells or units of cells administered and/or the potency of administered cells, provide various advantages, such as lower risk of toxicity in subjects administered the T cell compositions.

BACKGROUND

Various cell therapy methods are available for treating diseases and conditions. Improved methods are needed, for example, to reduce the risk of toxicity of such methods. For example, improved methods are needed to reduce the risk of toxicity to cell therapies, while maintaining efficacy of the administered cells in the subject. Provided are compositions, articles of manufacture, methods and uses that meet such needs.

SUMMARY

Provided herein are embodiments related to cell therapies, such as adoptive cell therapies, including those useful in predicting, reducing, preventing, ameliorating, or one or more unwanted or adverse effects or toxicities, or risk thereof, that may be associated with such therapies, such as toxicities, including severe toxicities, including severe or fatal neurotoxicity including toxicities associated with or involving cerebral edema. Among such provided embodiments are articles of manufacture, compositions such as compositions containing one or more unit dose of cells and methods and uses such as those that relate to or are for adoptive cellular immunotherapies such as engineered T cell therapies including CAR-T cell therapies.

Among the provided embodiments are articles of manufacture, such as those comprising: (a) a container comprising a unit dose of a therapeutic T cell composition comprising T cells comprising a recombinant receptor, which optionally is a chimeric antigen receptor (CAR), that specifically binds to an antigen, wherein the unit dose contains a target number of reference units (RU) within a given range, wherein RU in a given composition is defined by the formula RU=A×B, wherein: A is the number of cells, or multiple, fraction or transformation thereof, of a phenotype present in the given composition or is the average or weighted average of the number of cells, or multiple, fraction or transformation thereof, of two or more phenotypes in the given composition; and B is the value of a parameter, or a fraction or multiple or transformation thereof, that indicates or correlates with the degree of a recombinant receptor-dependent, optionally CAR-dependent, activity in the given composition; and (b) instructions for administering the composition, optionally one or more unit doses thereof, to a subject, optionally a subject having or suspected of having a disease or condition.

Also provided is an article of manufacture, comprising: (a) a container comprising a unit dose of a therapeutic T cell composition, the therapeutic T cell composition comprising T cells comprising a recombinant receptor, which optionally is a chimeric antigen receptor (CAR), that specifically binds to an antigen, wherein: the unit dose contains at or about (i) a target number of total recombinant receptor-expressing cells or a target number of total CD3+ recombinant receptor-expressing cells or a target number of total CD8+ recombinant receptor-expressing cells, or (ii) a target number of reference units (RU) within a given range, which target number of reference RUs is at or below a threshold number of RUs, wherein the unit dose does not contain greater than the threshold number of RUs, wherein the number of RU in a given composition is defined by the formula: RU=A×B, wherein A is the number of cells, or multiple or transformation thereof, of a phenotype present in the given composition or is the average or weighted average of the number of cells, or multiple, fraction or transformation thereof, of two or more phenotypes in the given composition; and B is the value of a parameter, or a multiple, or transformation thereof, that indicates or correlates with the degree of a recombinant receptor-dependent, optionally CAR-dependent, activity in the given T cell composition; and (b) instructions for administering the composition, optionally one or more unit doses thereof, to a subject, optionally a subject having or suspected of having a disease or condition.

Also provided is an article of manufacture, comprising: (a) a container comprising a unit dose of a therapeutic T cell composition comprising T cells expressing a chimeric antigen receptor (CAR) that specifically binds to an antigen, wherein the unit dose contains a target dose of the therapeutic T cell composition, wherein: (i) if the value of a parameter that indicates or correlates with the degree of recombinant receptor-dependent activity of the composition is at or greater than a threshold value, the target dose is a first number (or is within a first range of numbers) of cells of a given phenotype of the composition; (ii) if the value of the parameter is less than the threshold value, the target dose is a second number (or is within a second range of numbers) of cells of a given phenotype of the composition wherein the first number (or first range) is lower than the second number (or second range); and (b) instructions for administering the composition, optionally one or more unit doses thereof, to a subject, optionally a subject having or suspected of having a disease or condition.

Also provided is an article of manufacture, comprising: (a) a container comprising a unit dose of a therapeutic T cell composition, the therapeutic T cell composition comprising T cells comprising a recombinant receptor, which optionally is a chimeric antigen receptor (CAR), that specifically binds to an antigen, wherein: the unit dose contains a target dose of the therapeutic T cell composition; and the therapeutic T cell composition is above a lower specification limit (LSL) and below an upper specification limit (USL) for B, wherein B is the value of a parameter that indicates or correlates with the degree of recombinant receptor-dependent activity of the composition; and (b) instructions for administering the composition, optionally one or more unit doses thereof, to a subject, optionally a subject having or suspected of having a disease or condition.

Provided herein is a method of treatment, the method comprising administering to a subject having a disease or condition a unit dose of a T cell composition comprising cells comprising a recombinant receptor, optionally a chimeric antigen receptor (CAR), that specifically binds to an antigen associated with the disease or condition, wherein the unit dose contains a target number of reference units (RU) within a given range, wherein RU in a given composition is defined by the formula RU=A×B, wherein: A is the number of cells, or multiple, fraction or transformation thereof, of a phenotype present in the given composition or is the average or weighted average of the number of cells, or multiple, fraction or transformation thereof, of two or more phenotypes in the given composition; and B is the value of a parameter, or a multiple or transformation thereof, that indicates or correlates with the degree of a recombinant receptor-dependent, optionally CAR-dependent, activity in the given composition.

Also provided is a method of treatment, the method comprising administering to a subject having a disease or condition a unit dose of a T cell composition comprising cells comprising a recombinant receptor, optionally a chimeric antigen receptor (CAR), that specifically binds to an antigen associated with the disease or condition, wherein the unit dose contains at or about (i) a target number of total recombinant receptor-expressing cells or a target number of total CD8+ recombinant receptor-expressing cells or (ii) a target number of reference units (RU) within a given range, which target number is at or below a threshold number of RUs, wherein the unit dose does not contain greater than the threshold number of RUs, wherein the number of RU in a given composition is defined by the formula: RU=A×B, wherein A is the number of cells, or multiple or transformation thereof, of a phenotype present in the given composition or is the average or weighted average of the number of cells, or multiple, fraction or transformation thereof, of two or more phenotypes in the given composition; and B is the value of a parameter, or a multiple, or transformation thereof, that indicates or correlates with the degree of a recombinant receptor-dependent, optionally CAR-dependent, activity in the given T cell composition.

In particular embodiments, A is the total number of T cells, total number of CD3+ cells, total number of CD4+ or CD8+ cells, total number of CD3+CAR+ cells, total number of CD8+CAR+ cells, total number of CD4+CAR+, or total number of live or viable cells of any of the foregoing, or a multiple or transformed value thereof. In some embodiments, A is the total number of CD3+ cells, total number of CD8+, total number of CD3+CAR+ cells, total number of CD8+CAR+ cells, or total number of live or viable cells of any of the foregoing, or a multiple or transformed value thereof. In certain embodiments, A is the total number of apoptotic marker negative (−) cells that are CD3+ CAR+ cells, total number of apoptotic marker negative (−) cells that are CD4+ CAR+, total number of apoptotic marker negative (−) cells that are CD8+ CAR+ cells, or a multiple or transformed value thereof, wherein the apoptotic marker is Annexin V or active Caspase 3. In particular embodiments, A is the total number of apoptotic marker—CD3+ CAR+ cells or the total number of apoptotic marker—CD8+ CAR+ cells, optionally wherein the apoptotic marker is Annexin V or active Caspase 3.

Also provided is a method of treatment, the method comprising administering to a subject having a disease or condition a unit dose of a T cell composition comprising cells comprising a recombinant receptor, optionally a chimeric antigen receptor (CAR), that specifically binds to an antigen associated with the disease or condition, wherein the unit dose contains target dose of the therapeutic T cell composition: (i) if the value of a parameter that indicates or correlates with the degree of recombinant receptor-dependent, optionally CAR-dependent, activity of the composition is at or greater than a threshold value, the target dose is a first number (or is within a first range of numbers) of cells of a given phenotype of the composition; (ii) if the value of the parameter is less than the threshold value, the target dose is a second number (or is within a second range of numbers) of cells of a given phenotype of the composition wherein the first number (or first range) is lower than the second number (or second range).

Also provided is a method of assaying a therapeutic composition comprising a unit dose of a T cell composition, the method comprising: (a) assaying a sample from a T cell composition comprising T cells derived from a subject having a disease or condition and transduced with a nucleic acid encoding a recombinant receptor, optionally a chimeric antigen receptor (CAR), that specifically binds to an antigen associated with a disease or condition, wherein the assay determines B for the cell composition, wherein B is the value of a parameter, or a multiple or transformation thereof, that indicates or correlates with the degree of a recombinant receptor-dependent activity in the given composition; and (b) assessing potency of the cell composition based on B and/or assessing whether the composition is above a lower specification limit (LSL) for B or below an upper specification limit (USL) for B.

Also provided is a method of assaying a therapeutic T composition, the method comprising assessing a sample from a T cell composition comprising T cells comprising a recombinant receptor that specifically binds to an antigen associated with a disease or condition for potency of the cell composition based on B and/or assessing whether the composition is above a lower specification limit (LSL) for B or below an upper specification limit (USL) for B.

Also provided is a method of assessing a risk of toxicity to a therapeutic T cell composition, the method comprising: (a) assessing a sample from a T cell composition having been administered to a subject for reference units (RU) within a given range, the T cell composition comprising T cells comprising a recombinant receptor that specifically binds to an antigen associated with a disease or condition, wherein RU in a given composition is defined by the formula: RU=A×B, wherein: A is the number of cells, or multiple, fraction or transformation thereof, of cells of a phenotype present in the given composition or is the average or weighted average of the number of cells, or multiple, fraction or transformation thereof, of two or more phenotypes in the given composition; and B is the value of a parameter, or a fraction or multiple or transformation thereof, that indicates or correlates with the degree of a recombinant receptor-dependent, optionally CAR-dependent, activity in the given composition; and (b) comparing the RUs to a reference safety number of RUs, wherein the comparison indicates whether the subject is or is not at risk for developing an adverse event, optionally a severe adverse event, optionally severe neurotoxicity at or above grade 4 or grade 5 or at least prolonged grade 3 neurotoxicity.

Also provided is a method of producing a therapeutic composition comprising a unit dose of a T cell composition, the method comprising: (a) assaying a T cell composition comprising T cells derived from a subject having a disease or condition and transduced with a nucleic acid encoding a recombinant receptor, optionally a chimeric antigen receptor (CAR), that specifically binds to an antigen associated with a disease or condition, wherein the assay determines B for the cell composition, wherein B is the value of a parameter, or a multiple or transformation thereof, that indicates or correlates with the degree of a recombinant receptor-dependent, optionally CAR-dependent, activity in the given composition; and (b) filling a container with all or a portion of the composition and optionally another solution to achieve a unit dose of the T cell composition, wherein the unit dose contains a target number of reference units (RU) of the T cell composition, wherein RU in a given composition is defined by the formula: RU=A×B, wherein A is the number of cells, or multiple, fraction or transformation thereof, of a phenotype present in the given composition or is the average or weighted average of the number of cells, or multiple, fraction or transformation thereof, of two or more phenotypes in the given composition.

Also provided is a method of producing a therapeutic composition comprising a unit dose of a T cell composition, the method comprising filling a container with all or a portion of a T cell composition comprising T cells comprising a recombinant receptor that specifically binds an antigen associated with a disease or condition, and optionally another solution, to achieve a unit dose of the T cell composition, wherein the unit dose contains a target number of reference units (RU) of the T cell composition, wherein RU in a given composition is defined by the formula: RU=A×B, wherein A is the number of cells, or multiple, fraction or transformation thereof, of a phenotype present in the given composition or is the average or weighted average of the number of cells, or multiple, fraction or transformation thereof, of two or more phenotypes in the given composition; and B is the value of a parameter, or a multiple or transformation thereof, that indicates or correlates with the degree of a recombinant receptor-dependent, optionally CAR-dependent, activity in the given composition.

Also provided is a method of producing therapeutic T cell composition for cell therapy, the method comprising filling a container with all or a portion of a composition comprising T cells to a concentration of between about 10 million cells and about 70 million cells per mL, inclusive, and optionally another solution.

Provided is a unit dose of a therapeutic T cell composition comprising a number of cells comprising a recombinant receptor, optionally a chimeric antigen receptor (CAR), specific for an antigen associated with or expressed by a disease or condition, wherein the number of cells is between and between about $5.0\times10^6$ and $2.25\times10^7$, $\mathbf{5.0\times10^6}$ and $2.0\times10^7$, $5.0\times10^6$ and $1.5\times10^7$, $5.0\times10^6$ and $1.0\times10^7$, $5.0\times10^6$ and $7.5\times10^6$, $7.5\times10^6$ and $2.25\times10^7$, $7.5\times10^6$ and $2.0\times10^7$, $7.5\times10^6$ and $1.5\times10^7$, $7.5\times10^6$ and $1.0\times10^7$, $1.0\times10^7$ and $2.25\times10^7$, $1.0\times10^7$ and $2.0\times10^7$, $1.0\times10^7$ and $1.5\times10^7$, $1.5\times10^7$ and $2.25\times10^7$, $1.5\times10^7$ and $2.0\times10^7$, $2.0\times10^7$ and $2.25\times10^7$ recombinant-receptor expressing cells, each inclusive, optionally recombinant-receptor expressing cells that are CD8+ or that are apoptotic marker negative (−) and CD8+, optionally wherein the apoptotic marker is Annexin V or active Caspase 3.

Provided herein is a method of determining if a subject is at risk of toxicity, comprising assaying the number of recombinant receptor-expressing cells in the blood of a subject, said subject having been previously administered a dose of the recombinant receptor-expressing cells, wherein the subject is at risk of development of a toxicity if: (i) no more than four days after initiation of the administration the number of recombinant receptor-expressing cells in the blood of the subject is at least at or about 2 recombinant receptor-expressing cells per microliter; (ii) no more than five or six days after initiation of the administration the number of recombinant receptor-expressing cells in the blood of the subject is at least at or about 5 recombinant receptor-expressing cells per microliter or is at least at or about 10 recombinant receptor-expressing cells per microliter; or (iii) no more than seven days after initiation of the administration the number of recombinant receptor-expressing cells in the blood of the subject is at least at or about 15 recombinant receptor-expressing cells per microliter.

Also provided is method of determining if a subject is at risk of toxicity, comprising: (a) administering to a subject having a disease or condition a dose of cells expressing a recombinant receptor; and (b) after administering the cells, assaying the number of recombinant receptor-expressing cells in the blood of a subject, wherein the subject is at risk of development of a toxicity if: (i) no more than four days after initiation of the administration the number of recombinant receptor-expressing cells in the blood of the subject is at least at or about 2 recombinant receptor-expressing cells per microliter; (ii) no more than five or six days after initiation of the administration the number of recombinant receptor-expressing cells in the blood of the subject is at least at or about 5 recombinant receptor-expressing cells per microliter or is at least at or about 10 recombinant receptor-expressing cells per microliter; or (iii) no more than seven days after initiation of the administration the number of recombinant receptor-expressing cells in the blood of the subject is at least at or about 15 recombinant receptor-expressing cells per microliter.

Also provided is a method for assessing a stimulatory reagent for use in producing a therapeutic T cell composition, the method comprising: (i) assessing a T cell composition produced using a stimulatory reagent for a recombinant receptor-dependent activity or a phenotype; and (ii) comparing the recombinant receptor-dependent activity or the phenotype, to the same activity or phenotype produced from a control composition or compared to a standard unit for the recombinant receptor-dependent activity or phenotype, wherein the stimulatory agent is determined suitable for release for use in a method for producing a therapeutic T cell composition if the recombinant receptor-dependent activity or phenotype of the cell composition produced using the stimulatory reagent varies by no more than 40% or no more than 30% or no more than 20% or no more than 10% or no more than 5% from the same activity produced by the control composition or from the standard unit.

In some of any such embodiments, the extent or level of a recombinant receptor-dependent activity or a phenotype of a therapeutic T cell composition, in certain aspects, represent attributes or properties particular to the therapeutic compositions and/or the production thereof that are associated with a risk of developing an adverse side effect following administration of the therapeutic T cell composition to a subject. In some aspects, such risks are greater in or occur at a higher incidence in certain subjects having one or more risk factors, such as in (i) subjects having received fewer prior therapies, optionally less than two prior therapies, prior to initiation of administration of the therapeutic T cell composition, (ii) subjects of a young age, optionally less than 30 years, (iii) subjects in which the ratio of CD4:CD8 in an apheresis sample from the subject is below a certain threshold, optionally below 1:1 or below 1.5:1 or below 0.5:1 or lower, such as wherein the dose administered is based on total T cells or total T cells expressing an engineered or recombinant receptor such as a CAR, e.g., without specifying number or ratio of CD4+ or CD8+ T cells in dose; (iv) subjects having a weight greater than the average weight among the group of subjects treated; (v) subjects with a platelet count less than or about less than 120,000; (vi) subjects having a B cell leukemia, optionally acute lymphocytic leukemia (ALL); (vii) subjects having a high disease burden prior to, such as immediately prior to or within one month prior to, initiation of administration of the therapeutic T cell composition, optionally as determined based on percent of bone marrow blasts greater than or equal to 5%, sum of product diameter (SPD), or levels of lactate dehydrogenase; or (viii) subjects not exhibiting a Philadelphia chromosome (Ph+) and/or Ph chromosome-like (Ph-like) molecular subtype of acute lymphoblastic leukemia (ALL); (ix) subjects having received a bridging chemotherapy prior to initiation of administration of the therapeutic T cell composition; (x) subjects having been preconditioned with a lymphodepleting therapy, optionally comprising the administration of fludarabine and/or cyclophosphamide, prior to initiation of administration of the therapeutic T cell composition; and/or (xi) subjects in which the level, amount or concentration of interleukin-15 (IL-15) in a blood sample prior to initiation of administration of the therapeutic T cell composition is greater than a threshold value. In some embodiments, provided embodiments, such as provided methods, articles of manufacture, compositions, doses and dosing strategies, account for such attributes or properties, such as in connection with dosing a subject, and thereby prevent, ameliorate or reduce the risk or likelihood of a subject developing an adverse event or toxicity, such as severe neurotoxicity or grade 3 or higher or prolonged grade 3, grade 4 or grade 5 neurotoxicity, following administration of the therapeutic T cell composition.

In some of any such embodiments, exemplary attributes include numbers or frequencies of (or numbers/kg of) viable cells, and/or cells of various phenotypes, in individual doses administered to individual subjects. Exemplary such phenotypes included expression of one or more surface markers, as assessed by flow cytometry. For example, in some aspects, phenotypes include CD3+, CD8+, CD4+, and/or CAR+. Also among the phenotypes are viability and those associated with or indicative of or considered to indicate functional, healthy or biologically active cells. In certain aspects, such phenotypes include negative or low presence or expression of markers indicative of apoptosis, of apoptotic cells or of various, e.g., early or late, stages of one or more death or apoptotic pathway entry (e.g. Annexin V, Caspase 3). In particular aspects, such markers include the ability of cells to produce cytokines or other factors in a non-CAR antigen-specific manner, such as in an intracellular cytokine staining (ICS) in response to PMA/ionomycin and/or FOXP3. In some aspects, markers and phenotypes include those associated with one or more of T cell activation, exhaustion, stem-like properties, naïve T cells, longevity, T cells subsets, memory phenotype(s) and phenotypes of one or more T-memory subsets such as one or more of $T_{CM}$, $T_{EM}$, and $T_{SCM}$.

In some of any such embodiments, therapeutic cell composition-related attributes include total number of CD8+ CAR+ T cells in the dose administered, total number or frequency (e.g., among CD8+CAR+ T cells) of CD8+CAR+ T cells in the dose administered that were observed to be negative for a factor indicative of apoptosis, such as surface staining with Annexin V (Annexin V−) or caspase 3 cleavage (indicating non-apoptotic cells). In particular examples, therapeutic cell composition-related attributes include total number of CD3+CAR+ T cells in the dose administered, total number or frequency (e.g., among CD3+CAR+ T cells) of CD3+CAR+ T cells in the dose administered that were observed to be negative for a factor indicative of apoptosis, such as surface staining with Annexin V (Annexin V−) or caspase 3 cleavage (indicating non-apoptotic cells).

In some of any such embodiments, exemplary parameters are properties particular to the therapeutic compositions and/or the production thereof, including viable cell concentration (VCC), fold expansion of the cells between inoculation and harvest of the drug product; and vector copy number (VCN) in the administered dose. Also among the exemplary parameters are those generally associated with or indicative of function or activity or other features or capabilities of cells in the compositions. Among these are various attributes associated with outcomes of cell stimulation, including various indications of proliferation and activation or activity, including those induced in a TCR and/or CAR-induced or dependent manner. Exemplary such parameters related to function or activity were measures or levels (such as amount or concentration or level thereof per cell) of production of one or more factors (such as various cytokines) by cells in the composition, in response to CAR antigen-specific or other stimulation.

In some of any such embodiments, parameters indicative of CAR-targeted antigen-specific activities and functions (such as CAR-antigen-dependent cytokine secretion and cytotoxicity) of the compositions are assessed in co-culture assays. Cells of the therapeutic composition being assessed are incubated in the presence of CD19-expressing target cells. For cytokine assays, accumulated amounts (pg/mL) of the cytokine(s) (e.g. IL-2, IFN-gamma, TNF-alpha, IL-6, sCD137, MIP1b, MIP1a, IL-10, IL-4, IL-13, IL-5 or GM-CSF) may be assessed following incubation of target cells and an amount of the various compositions including the same number of transduced or CAR+ cells, in the same volume, such as for a period of approximately 22-24 hours.

Such assays provided a measure of antigen-specific cytokine secretion per CAR+ cell in the dose. In other assays, cytolytic activity against CD19-expressing target cells was assessed after incubation with the T cells.

In some of any such embodiments, measures of activity or functional effect in response to a non-CAR antigen-specific stimulus are assessed, such as cytokine or other factor production following stimulation with anti-CD3/anti-CD28, e.g., coated on magnetic beads. In such assays, cultures including fewer CAR+ cells among the T cells in the culture may exhibit a higher relative level of the measure.

In some of any such embodiments, relationships with respect to vector copy number (per cell or per genome) are considered surrogate indicators of cell fitness and/or multiple variables that associated with relative representation of engineered or not engineered cells in the composition and/or density of total cells in the composition. For example, in some embodiments, cells from blood samples that are generally less healthy at the start of the process have a lower likelihood of survival during the transduction phase and/or cell death during transduction can improve transduction efficiency. Thus, in certain cases, higher copy numbers of a viral vector per composition, such as one introduced via lentiviral or gammaretroviral vector transduction, may indicate compositions in which a larger percentage of cells were unhealthy at the start of the process and in particular aspects may have had properties that correlated, e.g., inversely, with neurotoxicity. In some embodiments, higher frequency of transduction can result in a composition that has a higher frequency of engineered (e.g., CAR+) cells during cryopreservation, storage and thaw. In certain aspects, when dose is based on numbers of engineered cells (or subtype thereof, e.g., CAR+CD3+), such compositions with higher frequency of engineered cells can include lower overall cell densities, which in particular embodiments correlates with reduced levels or frequency of biologically active or non-apoptotic cells.

In some of any such embodiments, various measures of number(s) or normalized numbers of cells that are negative for surface staining for markers of apoptosis (including Annexin V), in the doses administered to the subject (or frequency of such apoptotic marker-negative cells among cells of the product such as among CAR+CD3+ or CAR+ CD8+) correlate or are associated with an adverse event, such as a toxicity, e.g. neurotoxicity. In some aspects, Annexin V and caspase 3 were generally observed to be similar. Whereas such parameters may also be considered to relate to function or potency of a CAR-T cell composition, and thus may be expected to relate to efficacy, these variables generally do not significantly correlate with treatment response outcome, such as whether or not the subject achieved a complete response or no response.

In some of any such embodiments, a combination of attributes or parameters of the therapeutic CAR-T cell composition (e.g., antigen specific activity and/or viability), subject factors and/or characteristics (e.g., age, weight, and/or disease), and other treatments (e.g., number of prior treatments) are associated with the risk of developing fatal neurotoxicity, e.g., following treatment with a CAR-T cell composition.

In some of any such embodiments, cerebral edema is correlated and/or associated with early and rapid expansions of CAR T cells and/or with a rise in the level of IL-15, an inflammation biomarker and CAR-T growth factor. In some aspects, the dose and function of CD8+CAR+ cells, together with subject characteristics and/or factors, drive, correlate to, and/or are associated with early and/or rapid CAR-T cell expansion.

In some of any such embodiments, the subject characteristics and/or factors are or include young age (e.g., less than 30 years of age), prior treatment (e.g., with two or fewer prior regimens), intensive bridging chemotherapy, and/or the use of high intensity fludarabine/cyclophosphamide, such as for lymphodepletion.

In some of any such embodiments, cerebral edema, e.g., cerebral edema associated with and/or following CAR-T cell therapy, is associated with endothelial damage and complete blood brain barrier (BBB) breakdown. In certain aspects, the cerebral edema is not associated with CAR T cell infiltration of the brain, central nervous system (CNS) leukemia, or prior CNS leukemia therapies.

In some of any such embodiments, identifying high-risk patients before or prior to treatment, e.g., with a CAR-T cell therapy, is key to potentially managing and mitigating risk, e.g., risk or likelihood of toxicity such as neurotoxicity or cerebral edema. In particular aspects, the risk of fatal neurotoxicity may be mitigated, reduced, and/or decreased by minimizing variability of CAR-T cell compositions, e.g., minimizing variability among cell compositions for a parameter such as viability, CD4+/CD8+ ratio, and activity. In certain aspects, the use of a defined composition product, e.g., CAR-T cell compositions with defined parameters, can reduce variability in dose and function.

In some of any such embodiments, the provided methods, articles of manufacture, compositions, doses and dosing strategies are advantageous in that they take into account and, where relevant, adjust or correct for, potential sources of variability, including those deriving from change in reagents and/or patient-to-patient variability. For example, in certain embodiments, it can be advantageous to produce engineered T cells by a process that involves the use of a T cell stimulation/expansion reagent (or lot thereof) that has been verified by a release assay to be below or within an acceptable range of variance as compared to a threshold level of a parameter, e.g., specific activity with respect to such a parameter of the therapeutic composition (such as measure of the amount or relative amount of the reagent necessary to induce a particular degree of the antigen-specific activity in the final T cell composition produced by T cell engineering process, for example, as compared to a control reagent or standard unit with respect to such assay). In particular embodiments, the provided embodiments involve cell doses in which the cells have been produced by a process involving a release assay to confirm that any variability in such a specific activity parameter (e.g., antigen-specific inflammatory cytokine measure) is within an acceptable range and/or below an upper specification limit. In some embodiments, the provided processes include such a release assay. In certain embodiments, the production of the cell compositions is carried out using reagents and/or processes in which variance of such parameters is within an acceptable range. In particular embodiments, the provided methods, compositions and articles of manufacture are advantageous in that they use dosing and/or cell production strategies that mitigate risk associated with potential variance in such specific activity parameters, e.g., by minimizing variability in a second parameter that, together with the specific activity parameter, correlate with risk of toxicity. For example, by minimizing the variance in frequency of biologically active or healthy cells (e.g., non-apoptotic cells) produced by a process, impacts in changes of specific activity-related parameters on safety can be minimized. In some embodiments, a dose or dosing strategy that includes feature(s) related to the number or frequency of biologically active or non-apoptotic cells, such as biologically active or non-apoptotic engineered cells or engineered CD8+ cells, reduces risk associated with variance in antigen-specific activity parameters. In certain aspects, this is achieved by doses that include an upper limit of such cells and/or that define dose based upon reference units, e.g., based on a formula taking into account the number of biologically active cells.

In particular embodiments, the use of a process with reduced variability in frequency of such biologically active cells among engineered cells, reduces the risk that certain patients (e.g., those having cells less prone to apoptosis or that are more healthy) will inadvertently be given a higher dose than intended of biologically active cells, when dosing based on engineered T cell numbers as a whole. Processes such as this one with a greater degree of control over phenotype and function further have been observed to reduce the degree of variability in the ability of cells produced by the process to make inflammatory cytokines in an antigen-specific manner. The results in the study above are consistent with an interpretation that, particularly when combined with numbers of biologically active engineered cells, a dosing strategy taking into account such cell-specific activity parameters (e.g., such that a specific target range of such activity—or no more than a threshold—is represented in a given dose), can be used to provide a dose capable of achieving a desired clinical or therapeutic outcome, while still within a safety margin or reducing the risk of unwanted toxicity, e.g., neurotoxicity.

In some embodiments, the use of a process that yields consistently higher frequencies of biologically active engineered cells, permits the use of cell doses that are far lower (from the perspective of numbers of engineered, e.g., CAR+, cells), as compared to other dosing strategies, in which a higher frequency of engineered cells are positive for apoptotic markers or otherwise are less healthy. For example, based on observations herein, and considering the observation that available dosing strategies generally have not taken to account frequency of apoptotic cells, in certain embodiments, numbers of engineered (e.g., CAR+) T cells (e.g., engineered CD8+ and/or CD4+ cells), are as low as 5, 10, 11, 12, 13, 14, 15, 16, 17, 18, 19, 20, 30, 40 or 50 million cells.

In some of any such embodiments, the provided embodiment includes assessing or determining the number of cells, or multiple or fraction or transformation thereof, of a given phenotype present in the given composition. In some embodiments, A is the average or weighted average of the number of cells, or multiple, fraction or transformation thereof, of two or more phenotypes in the give composition. In certain embodiments, the target number of units is less than a threshold number of units, which optionally is a safety number of reference units, wherein, the safety number of reference units is, with respect to a group of subjects analyzed following treatment with a therapeutic T cell composition comprising the T cells expressing the recombinant receptor, optionally the CAR, the lowest number of reference units of the therapy administered to a subject among those subjects in the group that went on to develop an adverse event. In particular embodiments, the adverse event is a severe adverse event, optionally severe neurotoxicity, optionally at or above grade 4 or grade 5 or at least prolonged grade 3 neurotoxicity.

In some embodiments, the target number of reference units is less than the safety number of reference units by an amount corresponding to a safety factor and/or by an amount within a range of 1.5- to 3-fold, optionally about 2-fold, or by an amount that is a multiple of a standard deviation of a group of subjects that did not develop the adverse event, optionally grade 0-2 neurotoxicity, optionally wherein the multiple is within a range of 1.5- to 3-fold. In certain embodiments, the target number of reference units is at or above a reference efficacy number of reference units, wherein the reference efficacy number is, with respect to a group of subjects analyzed following treatment with a therapeutic T cell composition comprising the recombinant receptor, optionally the CAR, a number of units of the therapy administered to one or more subjects among the group that exhibited a desired therapeutic outcome, optionally a partial response or a complete response (CR).

In particular embodiments, A is the average or weighted average of the number of cells, or multiple, fraction or transformation thereof, of two or more phenotypes in the given composition. In some embodiments: the target number is the target number of recombinant-receptor expressing cells that are CD3+ that are apoptotic marker negative (−) and CD3+, optionally wherein the apoptotic marker is Annexin V or active Caspase 3; or the target number is the target number of recombinant-receptor expressing cells that are CD8+ that are apoptotic marker negative (−) and CD8+, optionally wherein the apoptotic marker is Annexin V or active Caspase 3.

In certain embodiments, the target number of cells in (i) is: between and between about $5.0\times10^6$ and $2.25\times10^7$, $5.0\times10^6$ and $2.0\times10^7$, $5.0\times10^6$ and $1.5\times10^7$, $5.0\times10^6$ and $1.0\times10^7$, $5.0\times10^6$ and $7.5\times10^6$, $7.5\times10^6$ and $2.25\times10^7$, $7.5\times10^6$ and $2.0\times10^7$, $7.5\times10^6$ and $1.5\times10^7$, $7.5\times10^6$ and $1.0\times10^7$, $1.0\times10^7$ and $2.25\times10^7$, $1.0\times10^7$ and $2.0\times10^7$, $1.0\times10^7$ and $1.5\times10^7$, $1.5\times10^7$ and $2.25\times10^7$, $1.5\times10^7$ and $2.0\times10^7$, $2.0\times10^7$ and $2.25\times10^7$ recombinant-receptor expressing cells, each inclusive, optionally recombinant-receptor expressing cells that are CD3+ or CD8+ or that are apoptotic marker negative (−) and CD8+, optionally wherein the apoptotic marker is Annexin V or active Caspase 3.

In particular embodiments, the target number of cells in (i) is: between at least or at least about $5\times10^6$, $6\times10^6$, $7\times10^6$, $8\times10^6$, $9\times10^6$, $10\times10^6$ and about $15\times10^6$ recombinant-receptor expressing cells, each inclusive, optionally recombinant-receptor expressing cells that are CD8+ or that are apoptotic marker negative (−) and CD8+, optionally wherein the apoptotic marker is Annexin V or active Caspase 3; between at least or at least about $5.55\times10^6$, $6.66\times10^6$, $7.77\times10^6$, $8.99\times10^6$, $1.0\times10^7$, $1.1\times10^7$ and about $1.67\times10^7$ recombinant-receptor expressing cells, each inclusive, optionally recombinant-receptor expressing cells that are CD8+ or that are apoptotic marker negative (−) and CD8+, optionally wherein the apoptotic marker is Annexin V or active Caspase 3; between at least or at least about $6.25\times10^6$, $7.5\times10^6$, $8.75\times10^6$, $1.0\times10^7$, $1.13\times10^7$, $1.25\times10^7$ and about $1.9\times10^7$ recombinant-receptor expressing cells, each inclusive, optionally recombinant-receptor expressing cells that are CD8+ or that are apoptotic marker negative (−) and CD8+, optionally wherein the apoptotic marker is Annexin V or active Caspase 3; between at least or at least about $7.14\times10^6$, $8.5\times10^6$, $1.0\times10^7$, $1.14\times10^7$, $1.29\times10^7$, $1.42\times10^7$ and about $2.14\times10^7$ recombinant-receptor expressing cells, each inclusive, optionally recombinant-receptor expressing cells that are CD8+ or that are apoptotic marker negative (−) and CD8+, optionally wherein the apoptotic marker is Annexin V or active Caspase 3.

In some embodiments, the target number of cells in (i) is between at least or at least about $5\times10^6$, $6\times10^6$, $7\times10^6$, $8\times10^6$, $9\times10^6$, $10\times10^6$ and about $15\times10^6$ recombinant-receptor expressing cells that are apoptotic marker negative (−) and CD8+, each inclusive, optionally wherein the apoptotic marker is Annexin V or active Caspase 3. In certain embodiments, the target number of cells in (i) is between at least or at least about $6.25\times10^6$, $7.5\times10^6$, $8.75\times10^6$, $1.0\times10^7$, $1.13\times10^7$, $1.25\times10^7$ and about $1.9\times10^7$ recombinant-receptor expressing cells that are CD8+, each inclusive.

In particular embodiments, the target reference number of RUs is less than a threshold number of units or is less than a reference safety number of RUs, wherein the reference safety number of RUs is, with respect to a group of subjects analyzed following treatment with a therapeutic T cell composition comprising the T cells expressing the recombinant receptor, optionally the CAR, the lowest number of reference units of the therapy administered to a subject among those subjects in the group that went on to develop an adverse event.

In some embodiments, A is the number of cells of a phenotype present in the given composition and B is the value of a parameter that indicates or correlates with the degree of recombinant receptor-dependent activity in the given composition. In certain embodiments, A and/or B is a transformation of the number or value, respectively, wherein the transformation comprises a logarithmic transformation, power transformation or logit transformation. In particular embodiments, A is a number of cells of a phenotype present in the given composition and B is a multiple or transformation of the value of the parameter that indicates or correlates with the degree of CAR-dependent activity in the given T cell composition, optionally wherein B is a logarithmic transformation of the value.

In some embodiments, the logarithmic transformation is a common log($\log_{10}(x)$), a natural log ($\ln(x)$) or a binary log($\log_2(x)$). In certain embodiments, is the number of viable cells in the composition and/or is the number of cells that are not apoptotic, do not exhibit a factor indicative of early apoptosis or of apoptosis, are not in the early stages of apoptosis, or are not in the late stages of apoptosis, and/or is the number of cells of a particular differentiation state, and/or is the number of cells having a memory/stem-like attribute or is a multiple or transformation thereof.

In particular embodiments, the phenotype comprises positive expression of a surface marker that is one or more of CD3, CD4 or CD8 and/or comprises positive expression of the recombinant receptor, optionally the CAR, or a surrogate marker for expression of the recombinant receptor. In some embodiments, the phenotype is CD3+ CAR, CD4+/CAR+, CD8+/CAR+. In certain embodiments, the phenotype comprises absence of a factor indicative of apoptosis or one or more steps in an apoptotic cascade or pathway, optionally expression of a marker of apoptosis. In particular embodiments, the phenotype comprises negative expression of a marker of apoptosis, optionally a marker of early apoptosis or late apoptosis. In some embodiments, the marker of apoptosis is surface phosphatidylserine and/or is detected with Annexin V, or is an active or proform of a caspase, optionally an active or proform of Caspase 3. In certain embodiments, the phenotype comprises Annexin-.

In particular embodiments, the phenotype comprises an indicator of production of one or a combination of cytokines, optionally non-specific to the antigen or the recombinant receptor and/or that is polyclonally produced, wherein the one or more cytokines is IL-2, IL-13, IL-17, IFN-gamma or TNF-alpha. In some embodiments, the indicator of production is measured in an assay, optionally an intracellular cytokine staining assay, comprising incubating a sample of the T cell composition with a polyclonal agent, an antigen-specific agent or an agent that binds the recombinant receptor, optionally CAR. In certain embodiments, the agent is or comprises PMA and ionomycin or is or comprises a T cell receptor or T cell receptor complex agonist. In particular embodiments, the phenotype comprises negative expression of an activation marker, wherein the activation marker is selected from among CD25, CD127, LAG3, Ki67 and combinations thereof.

In some embodiments, the phenotype comprises negative expression of an exhaustion marker, wherein the exhaustion maker is a PD1 or FOXP3 gene product or a combination thereof. In certain embodiments, the phenotype comprises a naïve phenotype or a memory phenotype, optionally wherein the memory phenotype comprises a T effector memory phenotype, a T central memory phenotype, or a T effector memory phenotype expressing CD45RA (Temra).

In some embodiments, the threshold value of the recombinant receptor-dependent activity is less than a reference safety value, wherein the reference safety value is, with respect to a group of subjects analyzed following treatment with a therapeutic T cell composition comprising T cells expressing the recombinant receptor, optionally the CAR, the lowest value of the CAR-dependent activity of the therapeutic composition administered to a subject among those subjects in the group that went on to develop an adverse event. In certain embodiments, the measure is in an assay involving culture or incubation for a fixed time, optionally 24 hours, of a given composition or sample thereof in the presence of the antigen, cells expressing the antigen and/or agent that specifically binds to the recombinant receptor, optionally the CAR. In particular embodiments, the assay is an ELISA.

In some embodiments, the measure of the factor is: (i) concentration, relative concentration, amount, or relative amount of the factor; or (ii) amount or relative amount of the factor per unit of input cells of the given composition, or (iii) amount or relative amount of the factor per unit of input cells of the given composition per unit of time, optionally one hour; or (iv) a level indicative of any of (i)-(iii). In certain embodiments, the one or more factors is one or a combination of soluble factors, optionally one or a combination of cytokines, chemokines or soluble receptors, optionally soluble costimulatory receptors. In particular embodiments, the one or more factors is one of or a combination of a pro-inflammatory cytokines, Th2 cytokines and Th17 cytokines. In some embodiments, the one or more factors is one of or a combination of IL-2, IFN-gamma, TNF-alpha, IL4, IL-5, IL-10, IL-13, GM-CSF, sCD137, MIP1a and M1Pb. In certain embodiments, the one or more factors is one of or a combination of IL-2, IFN-gamma, TNF-alpha and IL-10. In particular embodiments, the one or more factors is a combination of any of two or more of the foregoing soluble factors and the parameter is an arithmetic mean or geometric mean of the measure of the two or more factors.

In some embodiments, the parameter is an arithmetic mean or geometric mean of a measure, optionally amount or concentration, of at least two of TNF-alpha, IFN-gamma and IL-2 or of TNF-alpha, IFN-gamma and IL-2. In certain embodiments, the parameter is the normalized value of the measure, wherein normalization is as compared to a reference measure of the factor. In particular embodiments, the reference measure is the average of the measure among a plurality, optionally at least 10, at least 15, at least 20, of reference therapeutic T cell compositions comprising the chimeric antigen receptor (CAR) in which: (i) each of the reference therapeutic T cell compositions has been observed or determined to result in an acceptable safety profile following administration to a subject, optionally wherein the subject has a disease or condition expressing or associated with the antigen; and/or (ii) each of the reference therapeutic T cell compositions has been observed or determined to result in a desired efficacy following administration to a subject, optionally wherein the subject has a disease or condition expressing or associated with the antigen. In some embodiments, the acceptable safety profile is absence of observed grade 2 or higher or absence of grade 3 or higher, neurotoxicity. In certain embodiments, the acceptable safety profile is the absence of observed grade 3 or higher neurotoxicity.

In particular embodiments, the efficacy is a partial response or is a complete response (CR). In some embodiments, the reference measure is the measure, by the same assay, of the factor in a reference T cell composition produced by the same method as the therapeutic T cell composition but not expressing the recombinant receptor, optionally the CAR, not specifically recognizing the antigen and/or not expressing any recombinant receptor, optionally any CAR. In certain embodiments, the parameter is normalized to control for patient-specific variation of the measure of the one or more factors.

In particular embodiments, the parameter is a normalized value of the measure of the factor, compared to the same measure in the same assay, of a control factor, wherein the level of the control factor in a therapeutic T cell composition is known not to, or has been observed not to, indicate or correlate or significantly correlate with an adverse event or toxicity outcome or likelihood or risk thereof, wherein the adverse event or toxicity outcome optionally is severe neurotoxicity. In some embodiments, the control factor is a factor that is not statistically correlated and/or does not correlate to development of the adverse event among a plurality of subjects that went on to develop the adverse event following administration of the T cell composition, optionally the control factor is or comprises one of or a combination of IL-5, IL-13, GM-CSF, and IL-6, optionally wherein the measure of the control factor is an arithmetic mean or geometric mean of two or more of the foregoing.

In certain embodiments, the parameter does not comprise cytolytic activity or a measure thereof. In particular embodiments, the parameter does not comprise recombinant receptor-dependent or antigen-specific cytolytic activity or a measure thereof. In some embodiments, the phenotype is CD8+CAR+ cells or apoptotic marker-CD8+CAR+ cells, optionally wherein the apoptotic marker is Annexin V or active Caspase 3; and the parameter is a measure of a pro-inflammatory cytokine, which optionally is one of or a combination of TNF-alpha, IL-2, and IFN-gamma, or is a normalized value thereof.

In certain embodiments, the adverse event is grade 4 or 5 neurotoxicity and the threshold number of units: is or is about $1.75\times10^7$ if A is apoptotic marker negative (−) and CD8+CAR+ and B is TNF-alpha or a normalized value thereof; is or is about $2.19\times10^7$ if A is CD8+CAR+ and B is TNF-alpha or a normalized value thereof; is or is about $1.25\times10^7$ if A is apoptotic marker negative (−) CD8+CAR+ and if B is IFN-gamma or a normalized value thereof; is or is about $1.56\times10^7$ if A is CD8+CAR+ and B is IFN-gamma or a normalized value thereof; is or is about $1.5\times10^7$ if A is apoptotic marker negative (−) CD8+CAR+ and if B is IL-2 or a normalized value thereof; is or is about $1.88\times10^7$ if A is CD8+CAR+ and B is IL-2 or a normalized value thereof; is or is about $1.5\times10^7$ if A is apoptotic marker negative (−) CD8+CAR+ and if B is TNF-alpha and IFN-gamma or a normalized value thereof; is or is about $1.88\times10^7$ if A is CD8+CAR+ and B is TNF-alpha and IFN-gamma or a normalized value thereof; is or is about $2.0\times10^7$ if A is apoptotic marker negative (−) CD8+CAR+ and if B is TNF-alpha and IL-2 or a normalized value thereof; is or is about $2.5\times10^7$ if A is CD8+CAR+ and B is TNF-alpha and IL-2 or a normalized value thereof; is or is about $1.25\times10^7$ if A is apoptotic marker negative (−) CD8+CAR+ and if B is IFN-gamma and IL-2 or a normalized value thereof; is or is about $1.56\times10^7$ if A is CD8+CAR+ and B is IFN-gamma and IL-2 or a normalized value thereof; is or is about $1.75\times10^7$ if A is apoptotic marker negative (−) CD8+CAR+ and if B is TNF-alpha, IFN-gamma and IL-2 or a normalized value thereof; is or is about $2.19\times10^7$ if A is CD8+CAR+ and B is TNF-alpha, IFN-gamma and IL-2 or a normalized value thereof, optionally wherein the apoptotic marker is Annexin V or active Caspase 3.

In particular embodiments, the adverse event is grade 4 or 5 neurotoxicity and the given range of the target reference units: is between or about between $2.0\times10^5$ and $1.75\times10^7$, inclusive, if A is apoptotic marker negative (−) and CD8+ CAR+ and B is TNF-alpha or a normalized value thereof; is between or about between $2.5\times10^5$ and $2.19\times10^7$, inclusive, if A is CD8+CAR+ and B is TNF-alpha or a normalized value thereof; is between or about between $4\times10^5$ and $1.25\times10^7$, inclusive, if A is apoptotic marker negative (−) CD8+CAR+ and if B is IFN-gamma or a normalized value thereof; is between or about between $5\times10^6$ and $1.56\times10^7$, inclusive, if A is CD8+CAR+ and B is IFN-gamma or a normalized value thereof; is between or about between $2.0\times10^5$ and $1.5\times10^7$ if A is apoptotic marker negative (−) CD8+CAR+ and if B is IL-2 or a normalized value thereof; is between or about between $2.5\times10^5$ and $1.88\times10^7$, inclusive, if A is CD8+CAR+ and B is IL-2 or a normalized value thereof; is between or about between $3.0\times10^5$ and $1.5\times10^7$, inclusive, if A is apoptotic marker negative (−) CD8+CAR+ and if B is TNF-alpha and IFN-gamma or a normalized value thereof; is between or about between $3.75\times10^5$ and $1.88\times10^7$, inclusive, if A is CD8+CAR+ and B is TNF-alpha and IFN-gamma or a normalized value thereof; is between or about between $3.0\times10^5$ and $2.0\times10^7$, inclusive, if A is apoptotic marker negative (−) CD8+CAR+ and if B is TNF-alpha and IL-2 or a normalized value thereof; is between or about between $3.75\times10^5$ and $2.5\times10^7$, inclusive, if A is CD8+CAR+ and B is TNF-alpha and IL-2 or a normalized value thereof; is between or about between $4.0\times10^5$ and $1.25\times10^7$, inclusive, if A is apoptotic marker negative (−) CD8+CAR+ and if B is IFN-gamma and IL-2 or a normalized value thereof; is between or about between $5.0\times10^5$ and $1.56\times10^7$, inclusive, if A is CD8+CAR+ and if B is IFN-gamma and IL-2 or a normalized value thereof; is between or about between $4.0\times10^5$ and $1.75\times10^7$, inclusive, if A is apoptotic marker negative (−) CD8+CAR+ and if B is TNF-alpha, IFN-gamma and IL-2 or a normalized value thereof; is between or about between $5.0\times10^5$ and $2.19\times10^7$, inclusive, if A is CD8+CAR+ and B is TNF-alpha, IFN-gamma and IL-2 or a normalized value thereof, optionally wherein the apoptotic marker is Annexin V or active Caspase 3.

In some embodiments, the adverse event is at least prolonged grade 3 neurotoxicity and the threshold number of units: is or is about $1.0\times10^6$ if A is apoptotic marker negative (−) and CD8+CAR+ and B is TNF-alpha or a normalized value thereof; is or is about $1.25\times10^6$ if A is CD8+CAR+ and B is TNF-alpha or a normalized value thereof; is or is about $2.0\times10^6$ if A is apoptotic marker negative (−) CD8+CAR+ and if B is IFN-gamma or a normalized value thereof; is or is about $2.5\times10^6$ if A is CD8+CAR+ and B is IFN-gamma or a normalized value thereof; is or is about $3.0\times10^6$ if A is apoptotic marker negative (−) CD8+CAR+ and if B is IL-2 or a normalized value thereof; is or is about $3.75\times10^6$ if A is CD8+CAR+ and B is IL-2 or a normalized value thereof; is or is about $1.5\times10^6$ if A is apoptotic marker negative (−) CD8+CAR+ and if B is TNF-alpha and IFN-gamma or a normalized value thereof; is or is about $1.88\times10^6$ if A is CD8+CAR+ and B is TNF-alpha and IFN-gamma or a normalized value thereof; is or is about $2.5\times10^6$ if A is apoptotic marker negative (−) CD8+CAR+ and if B is TNF-alpha and IL-2 or a normalized value thereof; is or is about $3.12\times10^6$ if A is CD8+CAR+ and B is TNF-alpha and IL-2; or a normalized value thereof is or is about $3.0\times10^6$ if A is apoptotic marker negative (−) CD8+CAR+ and if B is IFN-gamma and IL-2 or a normalized value thereof; is or is about $3.75\times10^6$ if A is CD8+CAR+ and B is IFN-gamma and IL-2 or a normalized value thereof; is or is about $2.0\times10^6$ if A is apoptotic marker negative (−) CD8+CAR+ and if B is TNF-alpha, IFN-gamma and IL-2 or a normalized value thereof; is or is about $2.5\times10^6$ if A is CD8+CAR+ and B is TNF-alpha, IFN-gamma and IL-2 or a normalized value thereof, optionally wherein the apoptotic marker is Annexin V or active Caspase 3.

In certain embodiments, the adverse event is at least prolonged grade 3 and the given range of the target reference units: is between or about between $3.0\times10^5$ and $1.0\times10^6$, inclusive, if A is apoptotic marker negative (−) and CD8+CAR+ and B is TNF-alpha or a normalized value thereof; is between or about between $3.75\times10^5$ and $1.25\times10^6$, inclusive, if A is CD8+CAR+ and B is TNF-alpha or a normalized value thereof; is between or about between $4\times10^5$ and $2.0\times10^6$, inclusive, if A is apoptotic marker negative (−) CD8+CAR+ and if B is IFN-gamma or a normalized value thereof; is between or about between $5\times10^6$ and $2.5\times10^6$, inclusive, if A is CD8+CAR+ and B is IFN-gamma or a normalized value thereof; is between or about between $2.0\times10^5$ and $3.0\times10^6$, inclusive, if A is apoptotic marker negative (−) CD8+CAR+ and if B is IL-2 or a normalized value thereof; is between or about between $2.5\times10^5$ and $3.75\times10^6$, inclusive, if A is CD8+CAR+ and B is IL-2 or a normalized value thereof; is between or about between $3.0\times10^5$ and $1.5\times10^6$, inclusive, if A is apoptotic marker negative (−) CD8+CAR+ and if B is TNF-alpha and IFN-gamma or a normalized value thereof; is between or about between $3.75\times10^5$ and $1.88\times10^6$, inclusive, if A is CD8+CAR+ and B is TNF-alpha and IFN-gamma or a normalized value thereof; is between or about between $3.0\times10^5$ and $2.5\times10^6$, inclusive, if A is apoptotic marker negative (−) CD8+CAR+ and if B is TNF-alpha and IL-2 or a normalized value thereof; is between or about between $3.75\times10^5$ and $3.12\times10^6$, inclusive, if A is CD8+CAR+ and B is TNF-alpha and IL-2 or a normalized value thereof; is between or about between $4.0\times10^5$, inclusive, and $3.0\times10^6$ if A is apoptotic marker negative (−) CD8+CAR+ and if B is IFN-gamma and IL-2 or a normalized value thereof; is between or about between $5.0\times10^5$ and $3.75\times10^6$, inclusive, if A is CD8+CAR+ and B is IFN-gamma and IL-2 or a normalized value thereof; is between or about between $4.0\times10^5$ and $2.0\times10^6$, inclusive, if A is apoptotic marker negative (−) CD8+CAR+ and if B is TNF-alpha, IFN-gamma and IL-2 or a normalized value thereof; is between or about between $5.0\times10^5$ and $2.5\times10^6$, inclusive, if A is CD8+CAR+ and B is TNF-alpha, IFN-gamma and IL-2 or a normalized value thereof, optionally wherein the apoptotic marker is Annexin V or active Caspase 3.

In particular embodiments, the therapeutic T cell composition comprises between about 10 million cells per mL and about 70 million cells per mL or between about 10 million viable cells per mL and about 70 million viable cells per mL, each inclusive. In some embodiments, the therapeutic T cell composition comprises between about 15 million cells or viable cells per mL and about 60 million cells or viable cells per mL, each inclusive. In certain embodiments, the T cell composition comprises greater than 10 million cells or viable cells per mL. In particular embodiments, the therapeutic T cell composition comprises greater than 15 million cells or greater than 15 million cells per mL. In some embodiments, the composition further comprises a cryoprotectant and/or the article further includes instructions for thawing the composition prior to administration to the subject.

In certain embodiments, the disease or condition is a cancer, optionally a myeloma, lymphoma or leukemia. In particular embodiments, the disease or condition is a B cell malignancy, optionally a B cell malignancy is selected from the group consisting of acute lymphoblastic leukemia (ALL), adult ALL, chronic lymphoblastic leukemia (CLL), non-Hodgkin lymphoma (NHL), and Diffuse Large B-Cell Lymphoma (DLBCL). In some embodiments, the antigen is avβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In particular embodiments, the article further contains information indicating that the container contains the target number of units. In some embodiments, the container is a first container and the article further comprises additional containers, wherein each of the additional containers comprises a unit dose comprising the target number of units of the T cell composition. In certain embodiments, the additional containers comprise between about 10 million cells or viable cells per mL and about 70 million cells or viable cells per mL, between about 15 million cells or viable cells and about 60 million cells or viable cells per mL, each inclusive, greater than 10 million cells or viable cells per mL, greater than 15 million cells or viable cells per mL, or a combination thereof. In particular embodiments, the unit dose contains no more than $15\times10^6$ number of CD8+CAR+ cells that are negative for detection with Annexin V or for the active or proform of Caspase 3. In some embodiments, the unit dose further comprises a number of CD4+ cells positive for the CAR, wherein the number is at a ratio of CD8+CAR+ cells of or about 1:1.

In certain embodiments, the T cell composition is produced by a process in which: the frequency, (1) among CAR+ cells in the composition, (2) among CAR+CD3+ cells in the composition, and/or (3) among CAR+CD8+ cells in the composition, of a cell of a phenotype that indicates a features of biologically active cells and/or of the absence of apoptosis or early or late stages of apoptosis varies by no more than 40%, or no more than 30%, or no more than 20% or no more than 10% or no more than 5% from an average of said frequency in a plurality of T cell compositions produced by the process and/or varies from such average by no more than one standard deviation; or the frequency, (1) among CAR+ cells in the composition, (2) among CAR+ CD3+ cells in the composition, and/or (3) among CAR+ CD8+ cells in the composition, in the composition, of cell of a phenotype that indicates the absence of apoptosis or early or late stage of apoptosis, varies by no more than 40% or no more than 20% or no more than 10% among a plurality of T cell compositions produced by the process.

In particular embodiments, the process comprises: (a) incubating a population of cells comprising T cells with an agent comprising a nucleic acid molecule encoding the recombinant receptor under conditions to introduce the nucleic acid encoding the recombinant receptor into cells in the population; and (b) stimulating the cells, prior to, during and/or subsequent to said incubation, wherein stimulating comprises incubating the cells in the presence of a stimulating condition that induces a primary signal, signaling, stimulation, activation and/or expansion of the cells. In some embodiments, the process further comprises, prior to (a), isolating the population of cells from a biological sample. In certain embodiments, the isolating comprises, selecting cells based on surface expression of CD3 or based on surface expression of one or both of CD4 and CD8, optionally by positive or negative selection.

In some embodiments, the biological sample is or comprises a whole blood sample, a buffy coat sample, a peripheral blood mononuclear cells (PBMC) sample, an unfractionated T cell sample, a lymphocyte sample, a white blood cell sample, an apheresis product, or a leukapheresis product.

In certain embodiments, the stimulating condition comprises incubation with a stimulatory reagent capable of activating one or more intracellular signaling domains of one or more components of a TCR complex and/or one or more intracellular signaling domains of one or more costimulatory molecules.

In particular embodiments, the stimulatory reagent comprises a primary agent that specifically binds to a member of a TCR complex and a secondary agent that specifically binds to a T cell costimulatory molecule. In some embodiments, the primary agent specifically binds to CD3 and/or the costimulatory molecule is selected from the group consisting of CD28, CD137 (4-1-BB), OX40, or ICOS. In certain embodiments, the primary and secondary agents comprise antibodies and/or are present on the surface of a solid support, optionally a bead.

In particular embodiments: the stimulatory reagent is one in which it has been determined that a recombinant receptor-dependent activity or an antigen-specific activity, optionally recombinant receptor-dependent or antigen-specific dependent production or accumulation of a proinflammatory cytokine, varies by no more than 40%, or no more than 30%, or no more than 20% or no more than 10% or no more than 5% from an average of a measure of the production or accumulation of the proinflammatory cytokine among a plurality of T cell compositions produced by the process using the stimulatory reagent and/or varies from such average by no more than one standard deviation; and/or the stimulatory reagent is one in which it has been determined that a recombinant receptor-dependent activity or an antigen-specific activity, optionally recombinant receptor-dependent or antigen-specific dependent production or accumulation of a proinflammatory cytokine, varies by no more than 40%, or no more than 30%, or no more than 20% or no more than 10% or no more than 5% among a plurality of T cell compositions produced by the process; and/or the stimulatory reagent is one in which it has been determined that a recombinant receptor-dependent activity or an antigen-specific activity, optionally recombinant receptor-dependent or antigen-specific dependent production or accumulation of a proinflammatory cytokine, of a cell composition produced using the stimulatory reagent varies by no more than 40%, no more than 30%, no more than 20% or no more than 10% or no more than 5% from a control composition, wherein the control composition and cell composition are produced using the same process, including from the same population of cells, except the control composition is carried out in the presence of a control stimulatory reagent or standard unit for the recombinant receptor-dependent activity. In some embodiments, the control stimulatory reagent, when employed in the process, is known to produce a T cell composition in which the recombinant receptor-dependent activity or antigen-specific activity is within an acceptable range of variance.

In certain embodiments, a container is filled with all or a portion of the T cell composition, and optionally another solution, to a concentration between about 10 million cells and about 70 million cells per mL, inclusive. In particular embodiments, the container is filled with another solution and the solution comprises a cryoprotectant, optionally DMSO. In some embodiments, the concentration is between about 15 and about 60 million cells per mL, inclusive. In certain embodiments, the concentration is greater than 10 million cells per mL. In particular embodiments, the concentration is greater than 15 million cells per mL. In some embodiments, the concentration of DMSO is or is about or is no more than 7.5%. In certain embodiments, the concentration is greater than 60 million cells per m. In particular embodiments, the concentration of DMSO is greater than 7.5%, optionally between or about between 7.5% and 9.0%, inclusive.

In some embodiments, the filling is carried out in an automated fashion, optionally in a closed system. In certain embodiments, the adjusted unit dose is less than, optionally less than 1.5-fold, less than 2-fold, less than 3-fold, less than 4-fold, the average unit dose of a group of subjects treated with a therapeutic T cell composition comprising the T cells expressing the recombinant receptor, optionally the CAR. In particular embodiments, a sample of the T cell composition, optionally a cryopreserved sample is assessed after administration of the T cell composition to the subject. In some embodiments, if B is above the USL, the subject is determined to be at risk of toxicity. In certain embodiments, if B is above the USL, a subject administered the composition is monitored and/or is treated with an agent to ameliorate or reduce the likelihood of a toxicity outcome or cytokine release syndrome following administration of the cell composition and optionally prior to the development of a sign or symptom of the toxicity outcome.

Figure 3A:
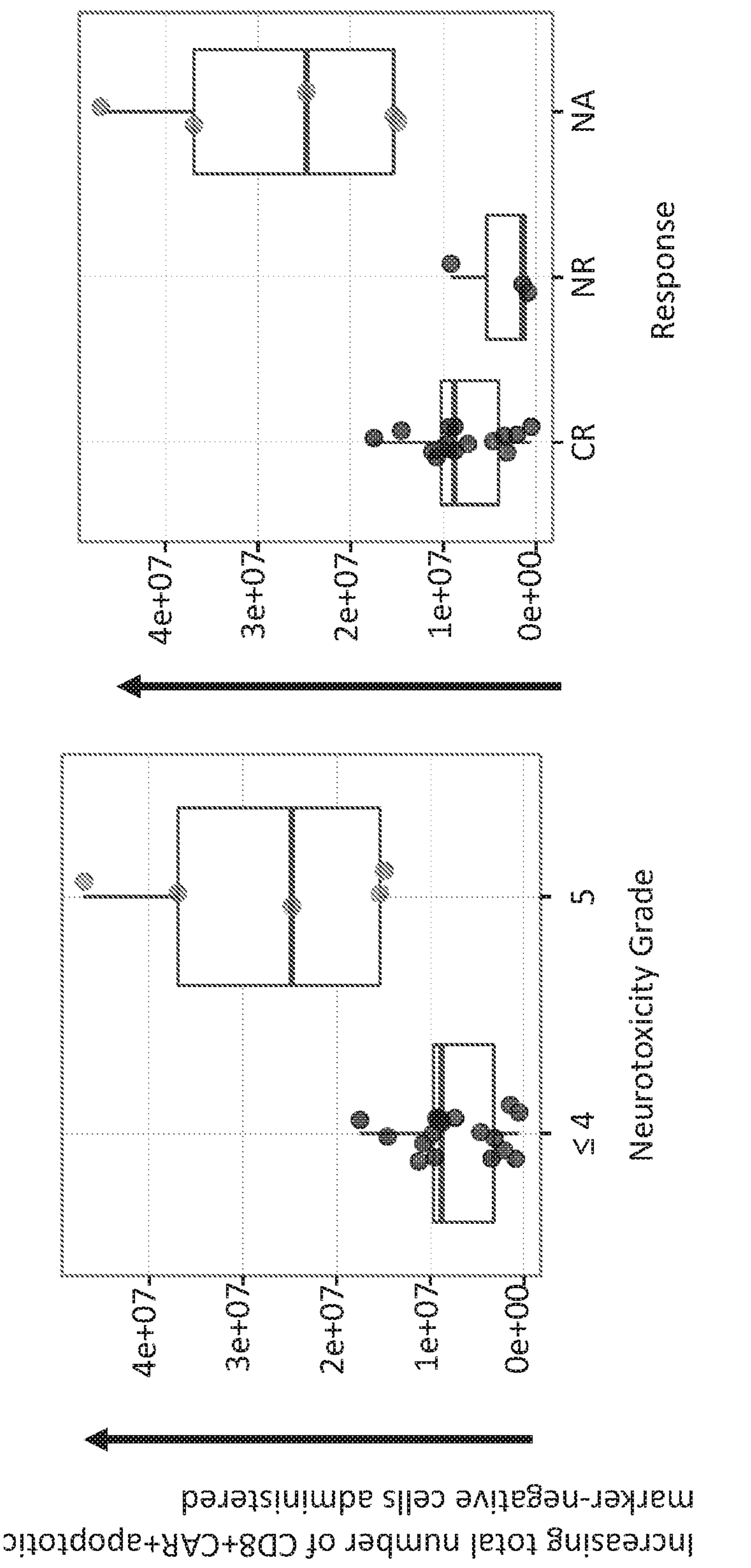
FIGS. 3A to 3V shows box plots quantifying different parameters of cell compositions containing cells that express an anti-CD19 CAR. The box plots on the left compare measurements of cell compositions derived from subjects who developed grade 4 or less neurotoxicity with measurements of cell compositions derived from subjects who developed grade 5 neurotoxicity. The box plots on the right compare measurements of cell compositions derived from subjects who experienced a complete response (CR) with measurements of cell compositions derived from subjects who experienced no response (NR). Measurements of cell compositions derived from subjects whose response is not available are also shown in this plot (NA).

The box plots of FIG. 3A show the measurements of total number of CD8+CAR+apoptotic marker-negative cells administered to the subjects.

Figure 3B:
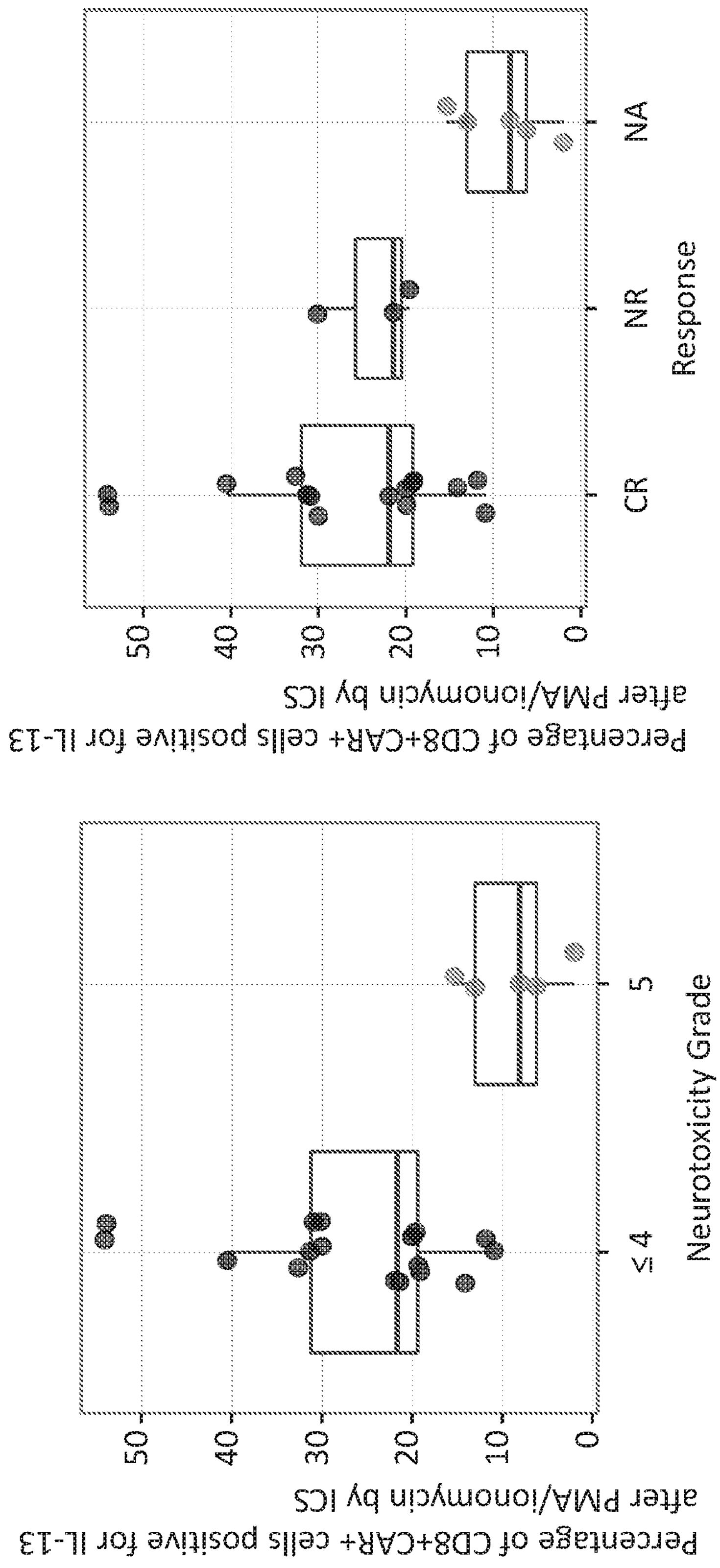

The box plots of FIG. 3B show percentage of CD8+CAR+ cells positive for IL-13 after PMA/ionomycin by internal cytokine staining (ICS) in administered doses.

Figure 3C:
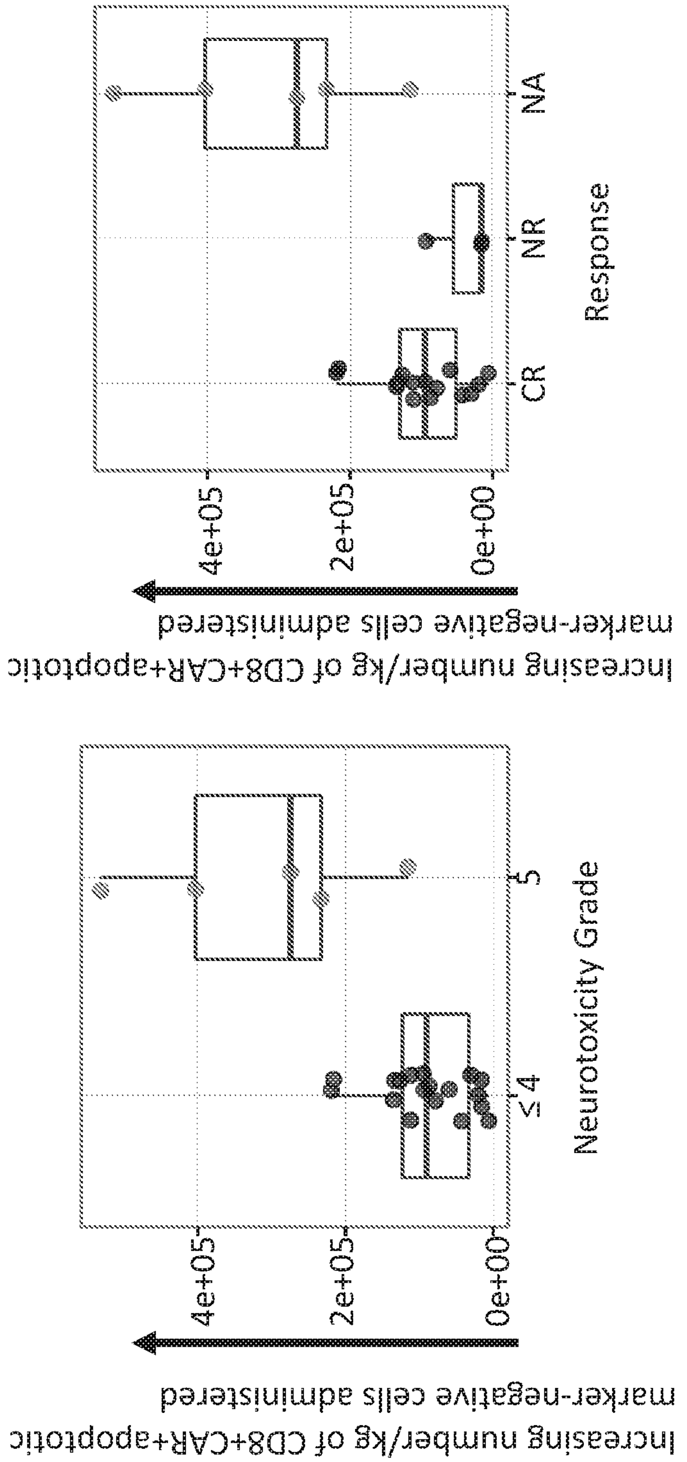

The box plots of FIG. 3C show the number/kg of CD8+ CAR+apoptotic marker (Annexin V−)-negative cells administered.

Figure 3D:
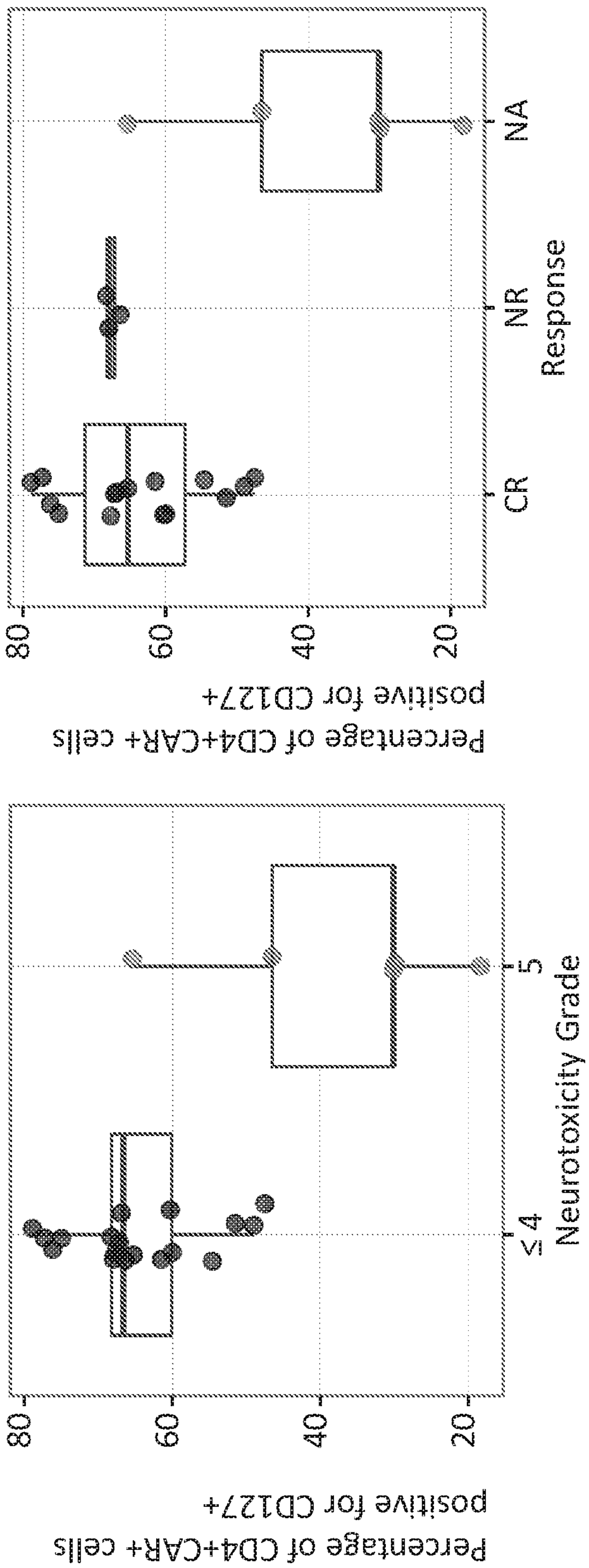

The box plots of FIG. 3D show the percentage of CD4+ CAR+ cells positive for CD127+.

Figure 3E:
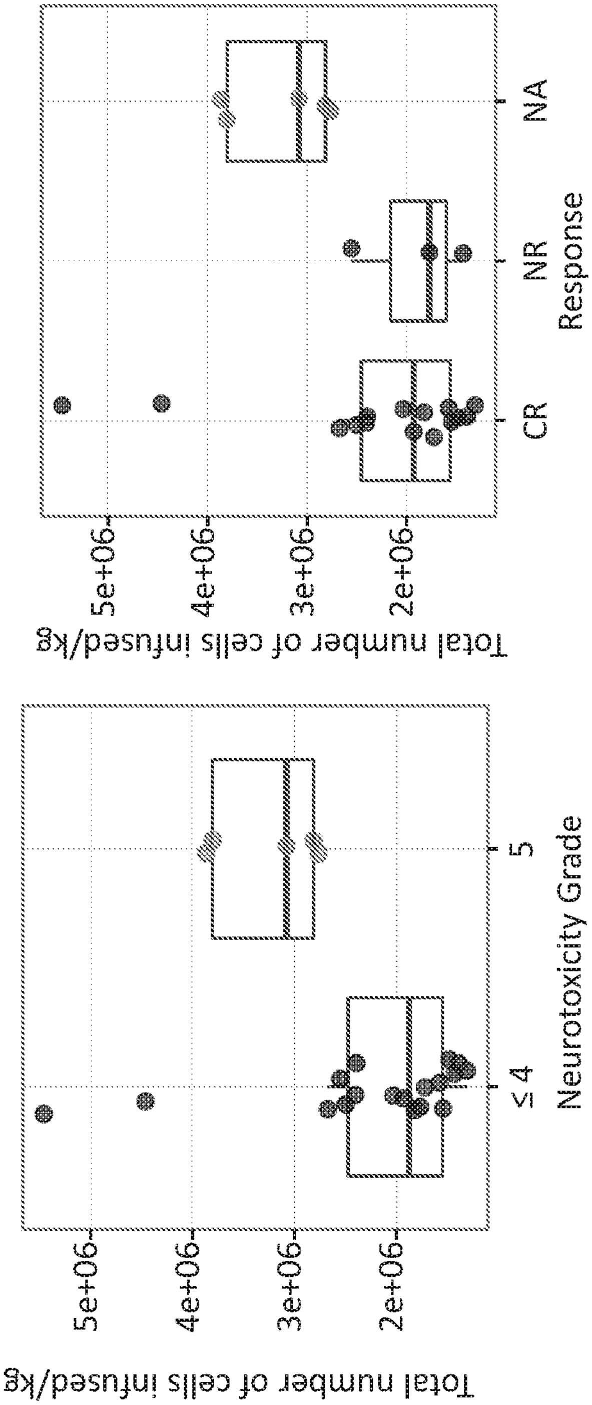

The box plots of FIG. 3E show the total number of cells infused/kg.

Figure 3F:
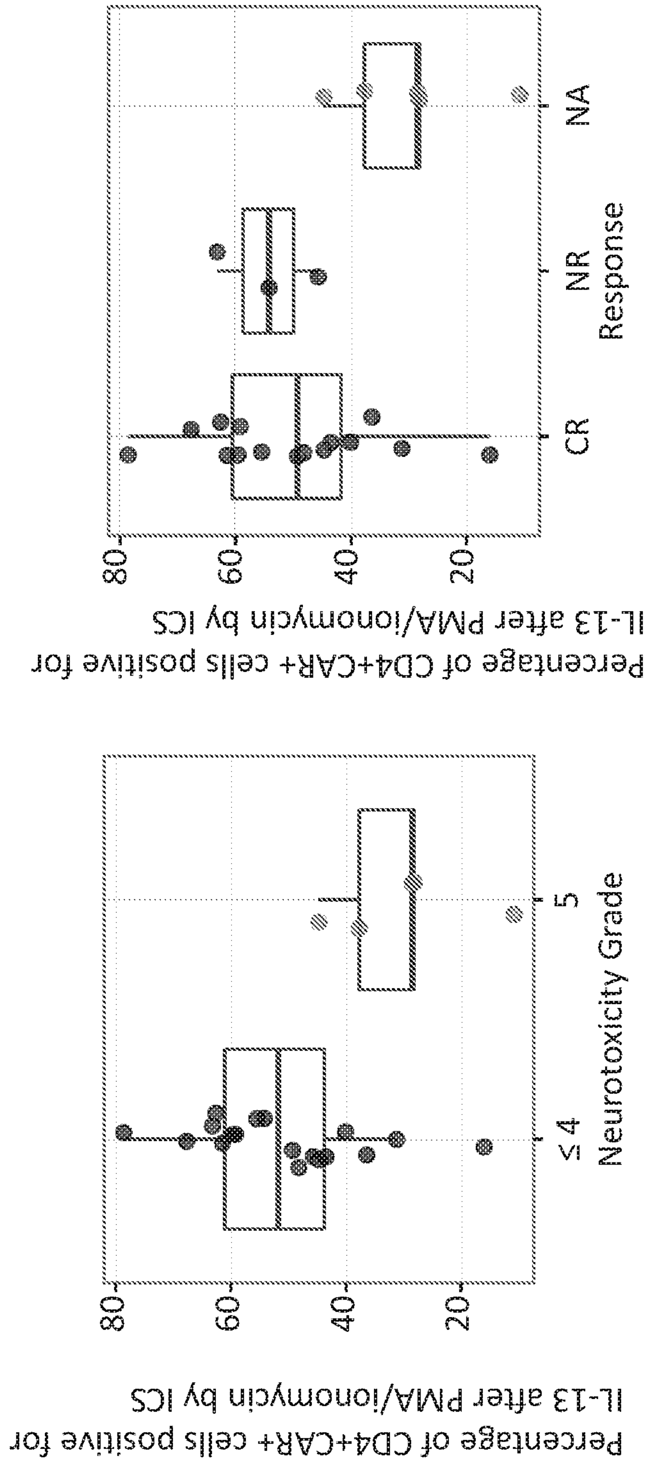

The box plots of FIG. 3F show percentage of CD4+CAR+ cells positive for IL-13 after PMA/ionomycin by ICS.

Figure 3G:
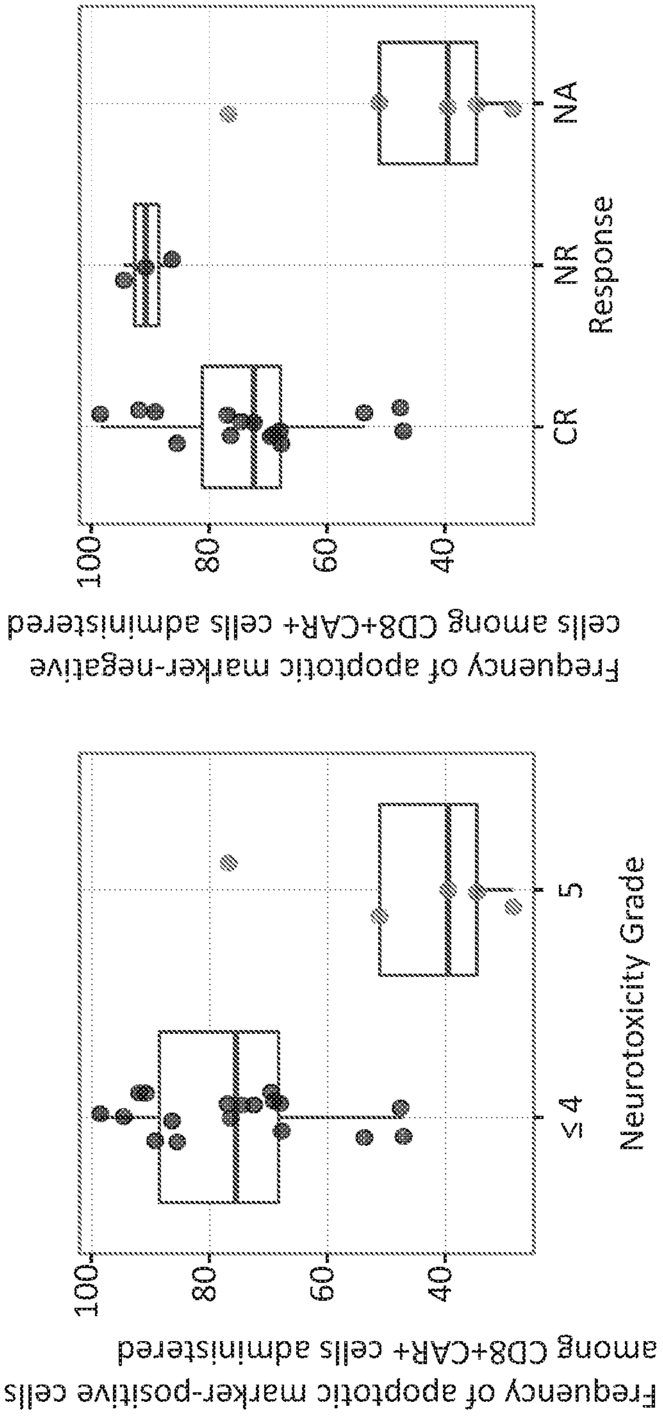

The box plots of FIG. 3G show frequency of apoptotic marker (Annexin V) positive cells among CD8+CAR+ cells administered.

Figure 3H:
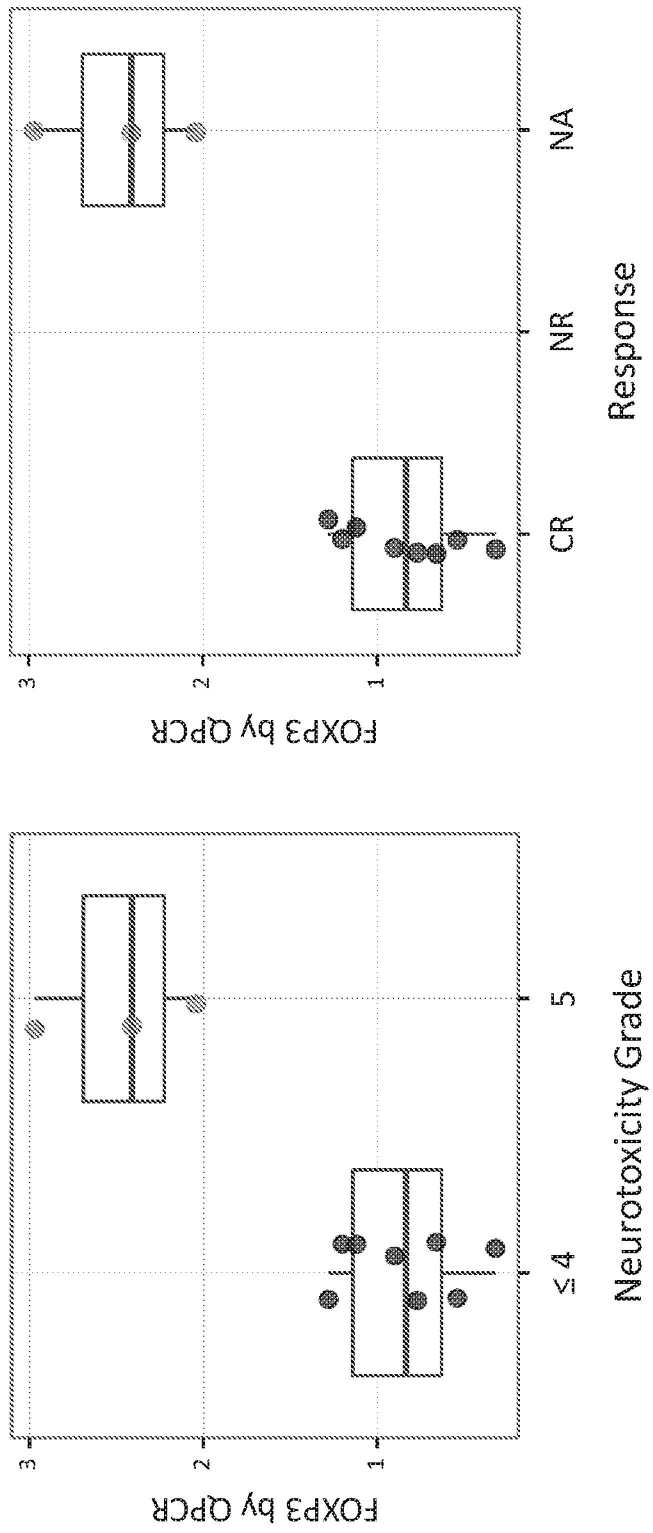

The box plots of FIG. 3H show levels of FOXP3 by QPCR.

Figure 3I:
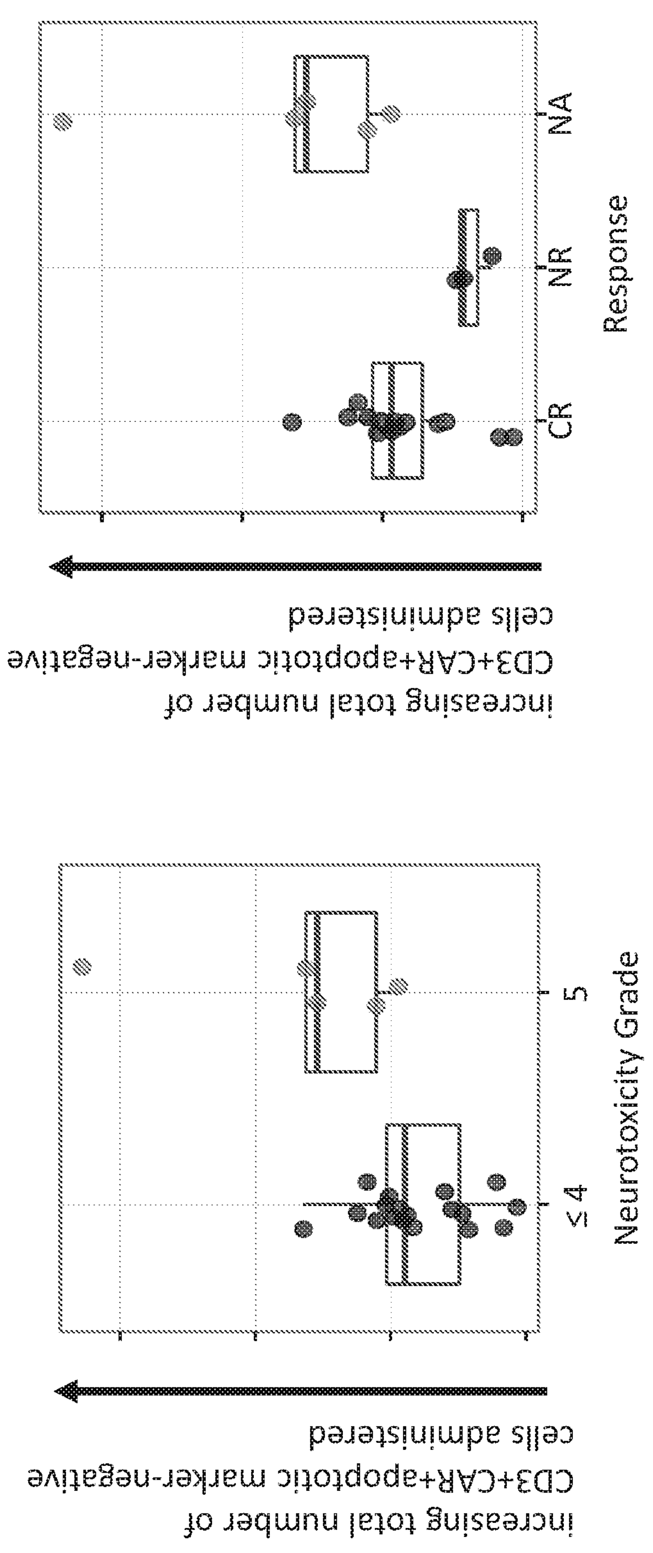

The box plots of FIG. 3I show total number of CD3+ CAR+apoptotic marker (Annexin V)-negative cells administered.

Figure 3J:
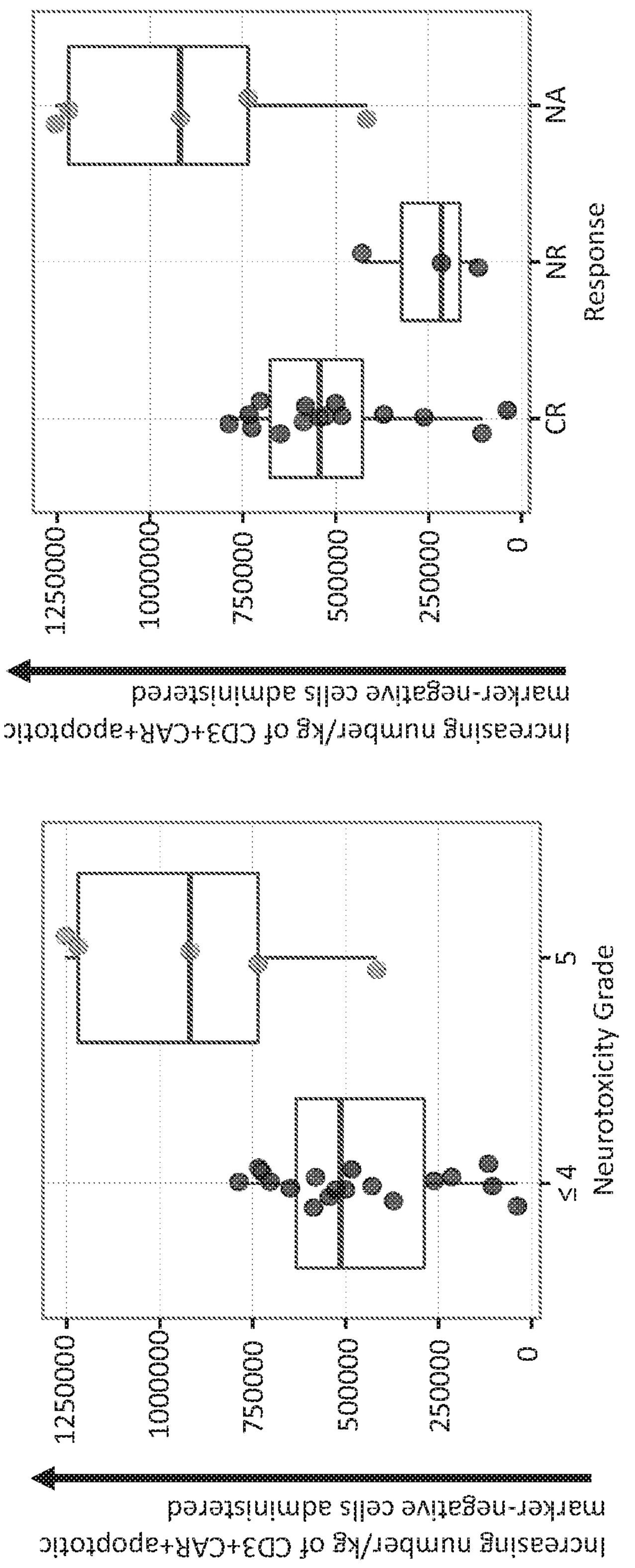

The box plots of FIG. 3J show the number/kg of CD3+ CAR+ apoptotic marker (Annexin V−)-negative cells administered.

Figure 3K:
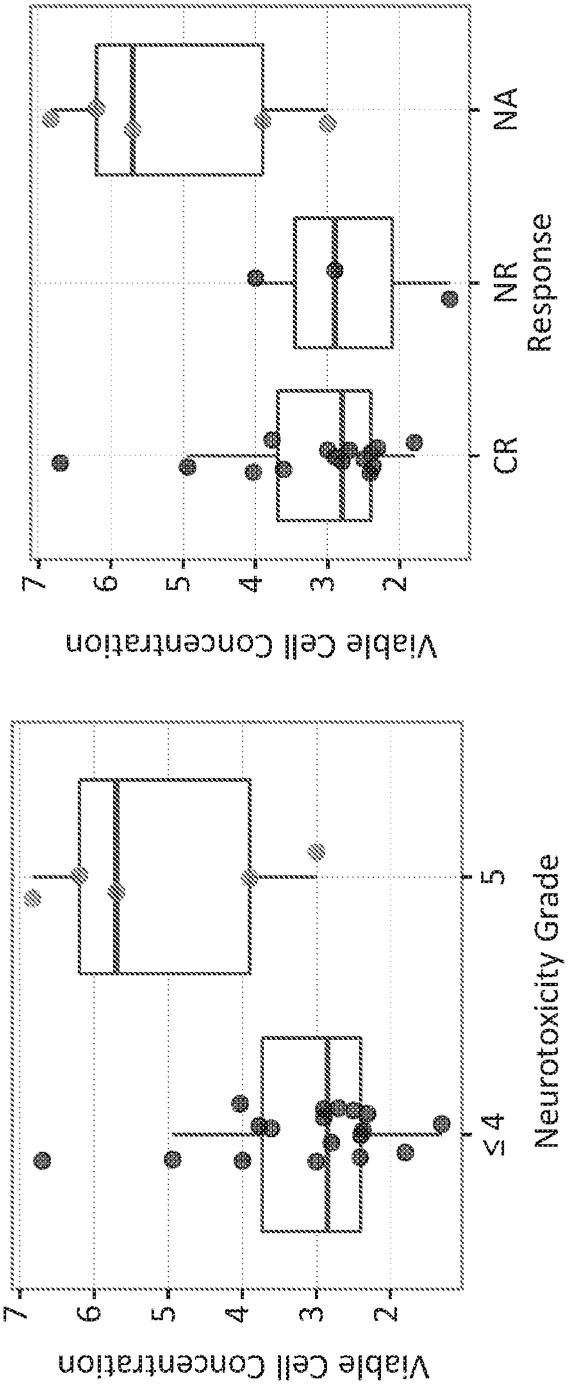

The box plots of FIG. 3K show viable cell concentration of the cryopreserved drug product (CDP).

Figure 3L:
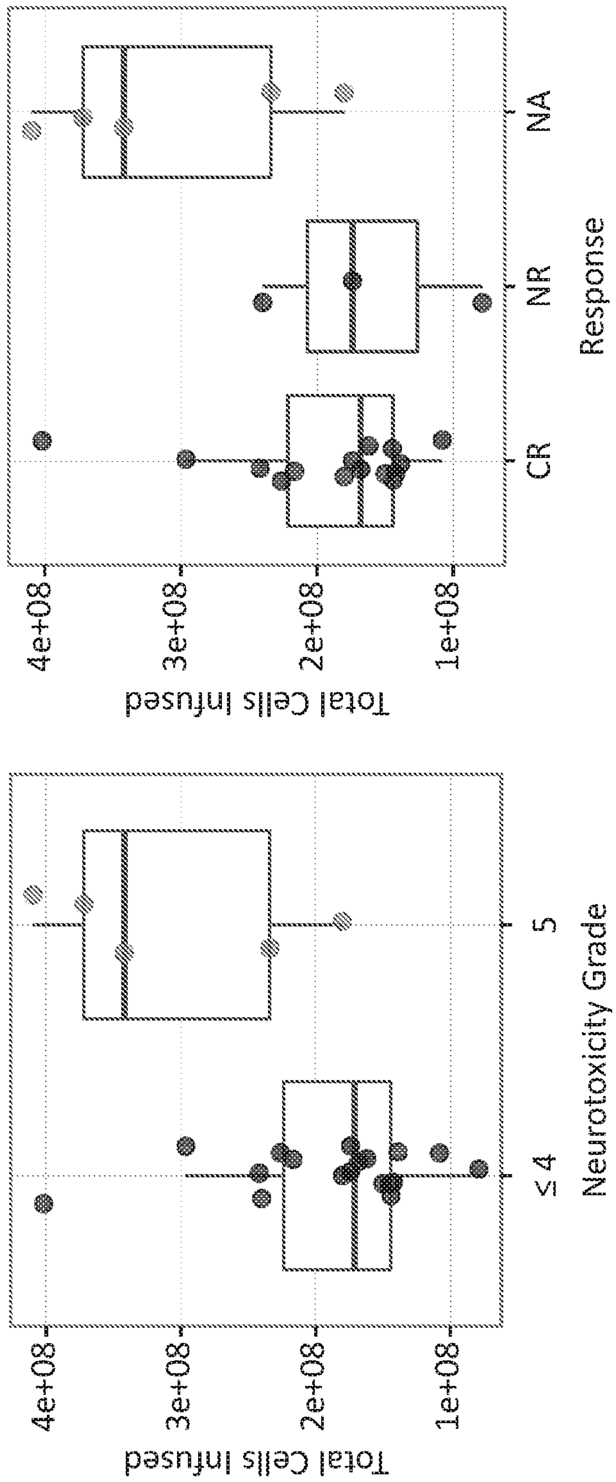

The box plots of FIG. 3L show the total cells infused.

Figure 3M:
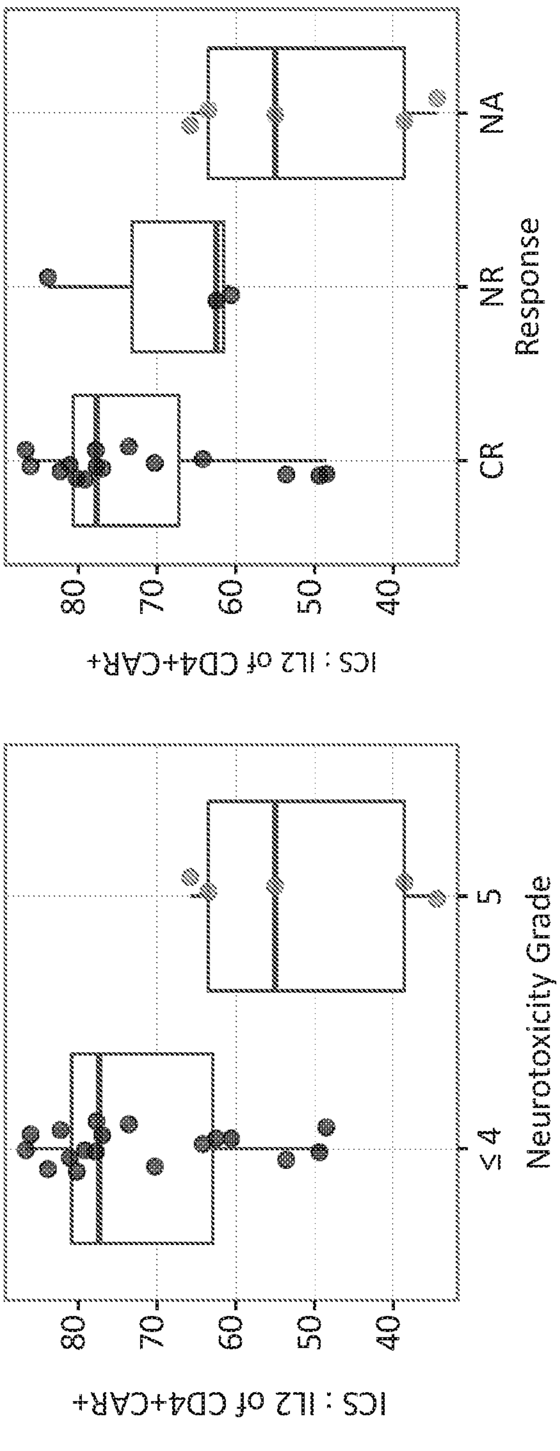

The box plots of FIG. 3M show ICS of IL2 in CD4+ CAR+ cells.

Figure 3N:
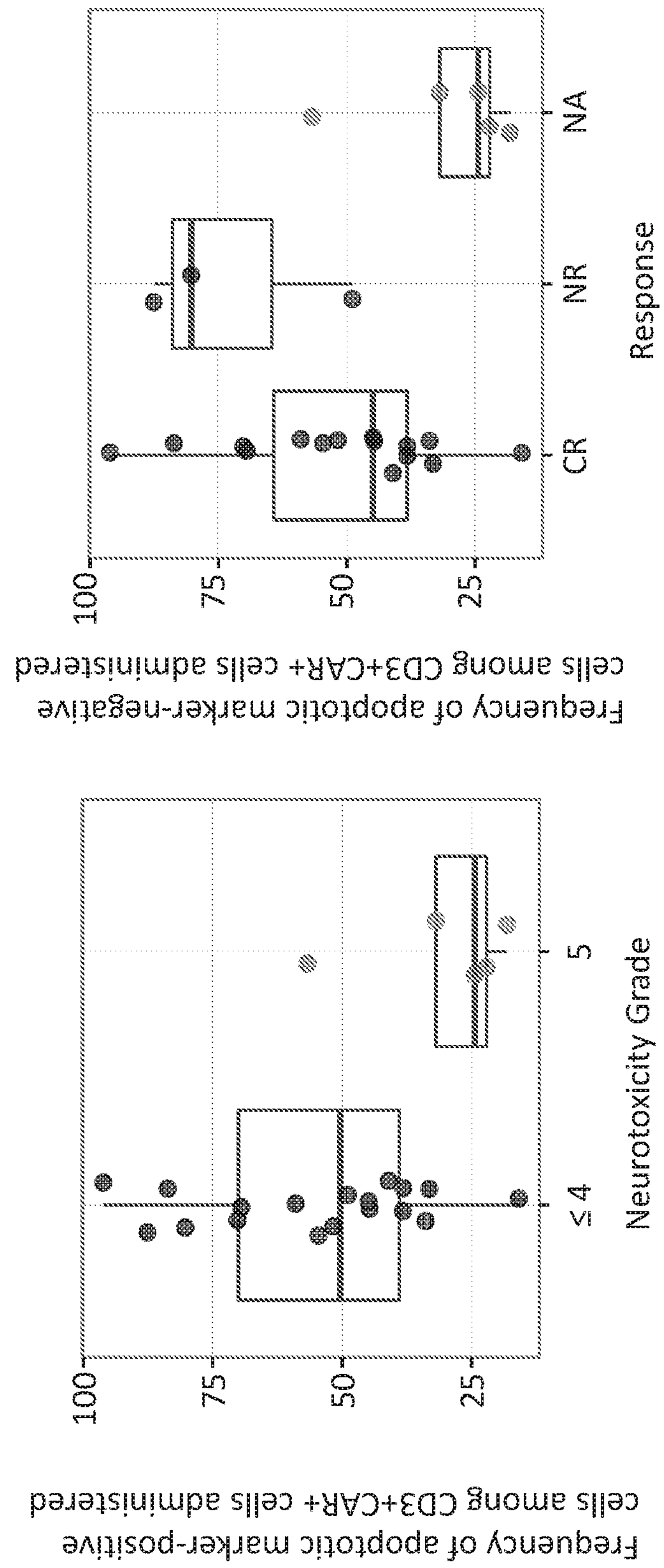
Figure 3O:
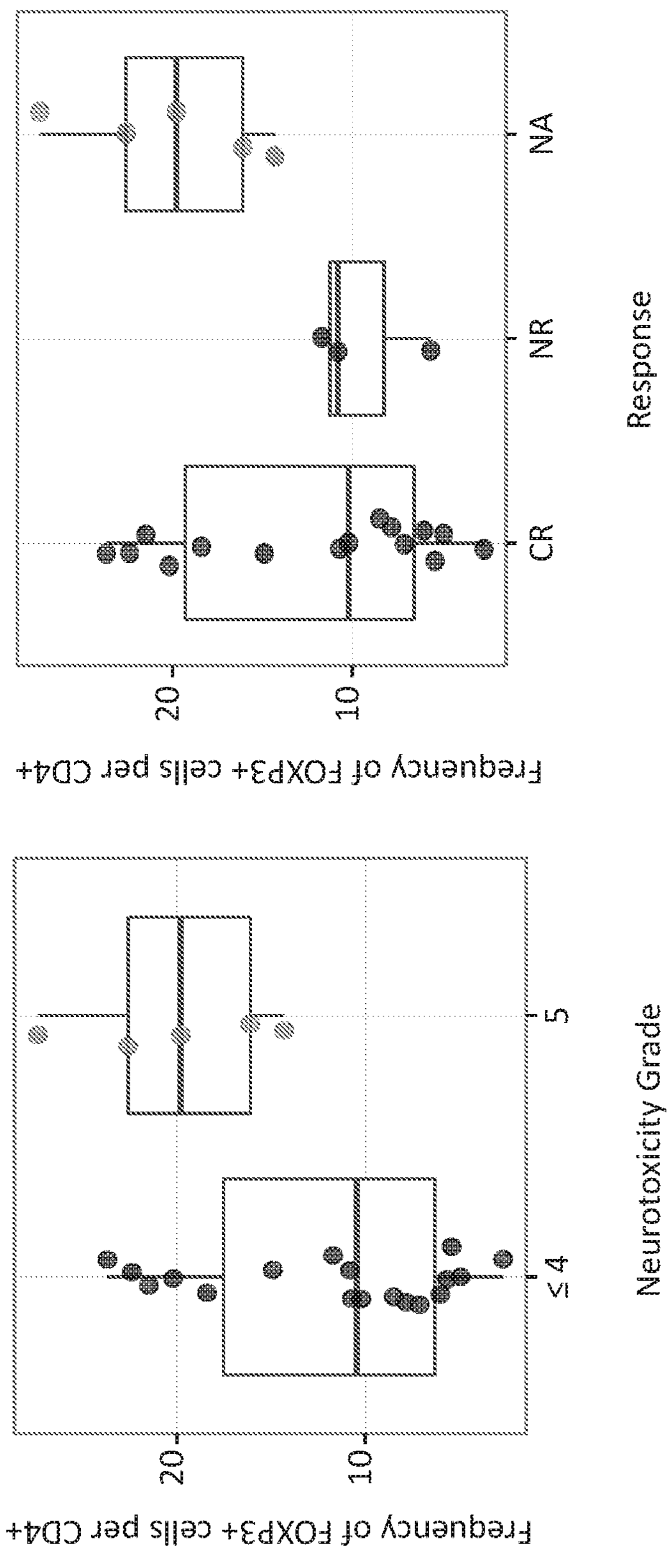

The box plots of FIG. 3N show frequency of apoptotic marker (Annexin V)-positive cells among CD3+CAR+ cells administered.

The box plots of FIG. 30 show the frequency of FOXP3+ cells per CD4+ cells.

Figure 3P:
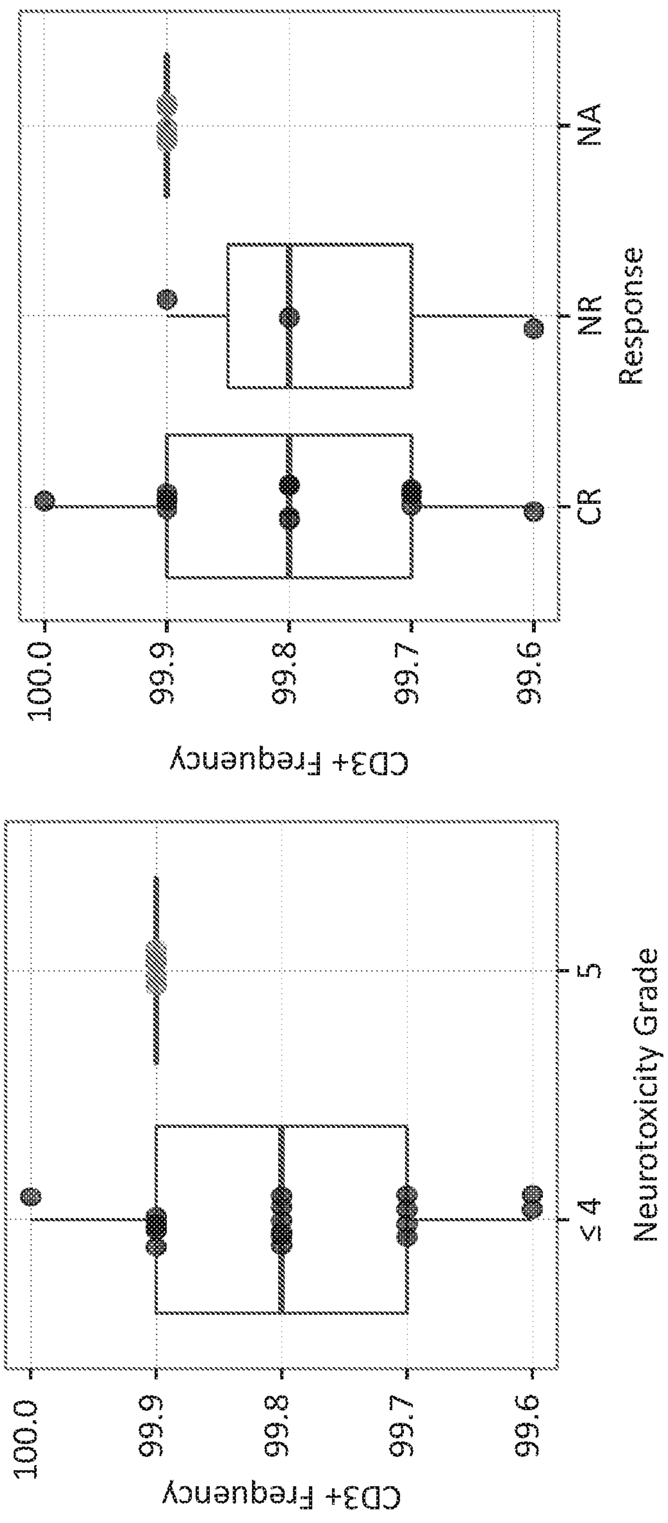

The box plots of FIG. 3P show the frequency of CD3+ cells.

Figure 3Q:
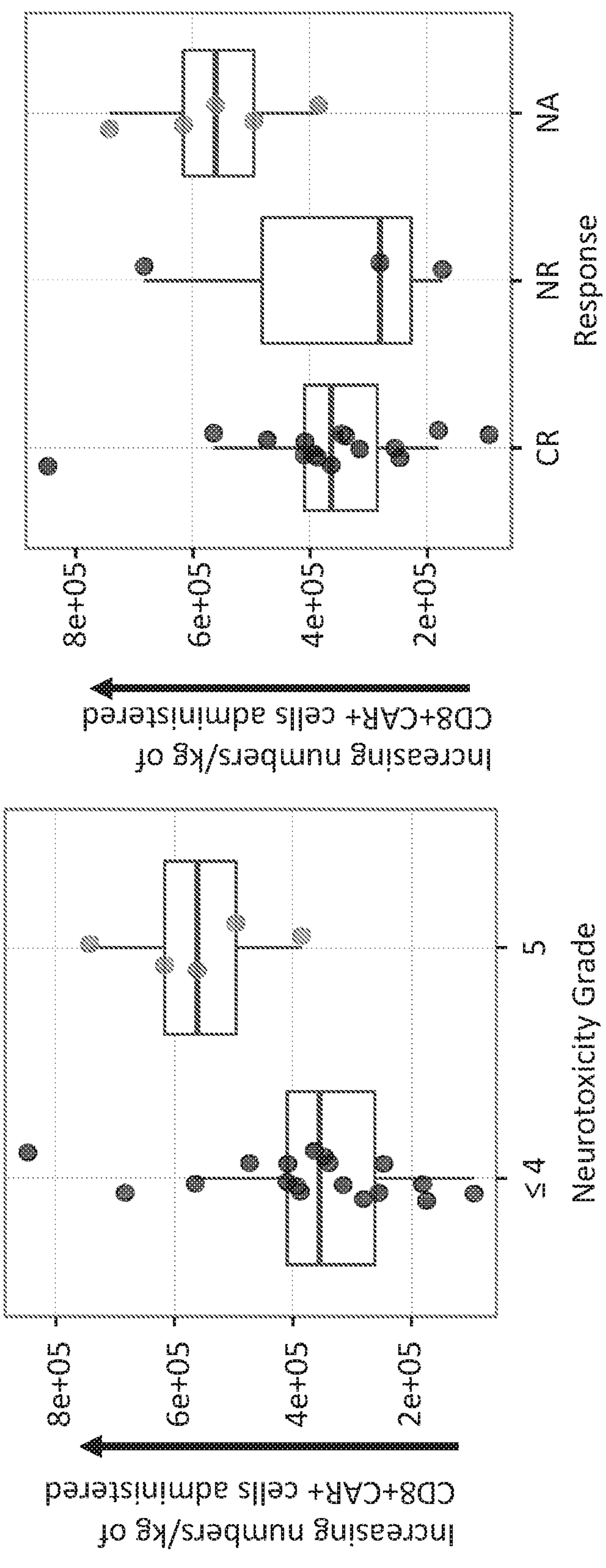

The box plots of FIG. 3Q show numbers/kg of CD8+ CAR+ cells administered.

Figure 3R:
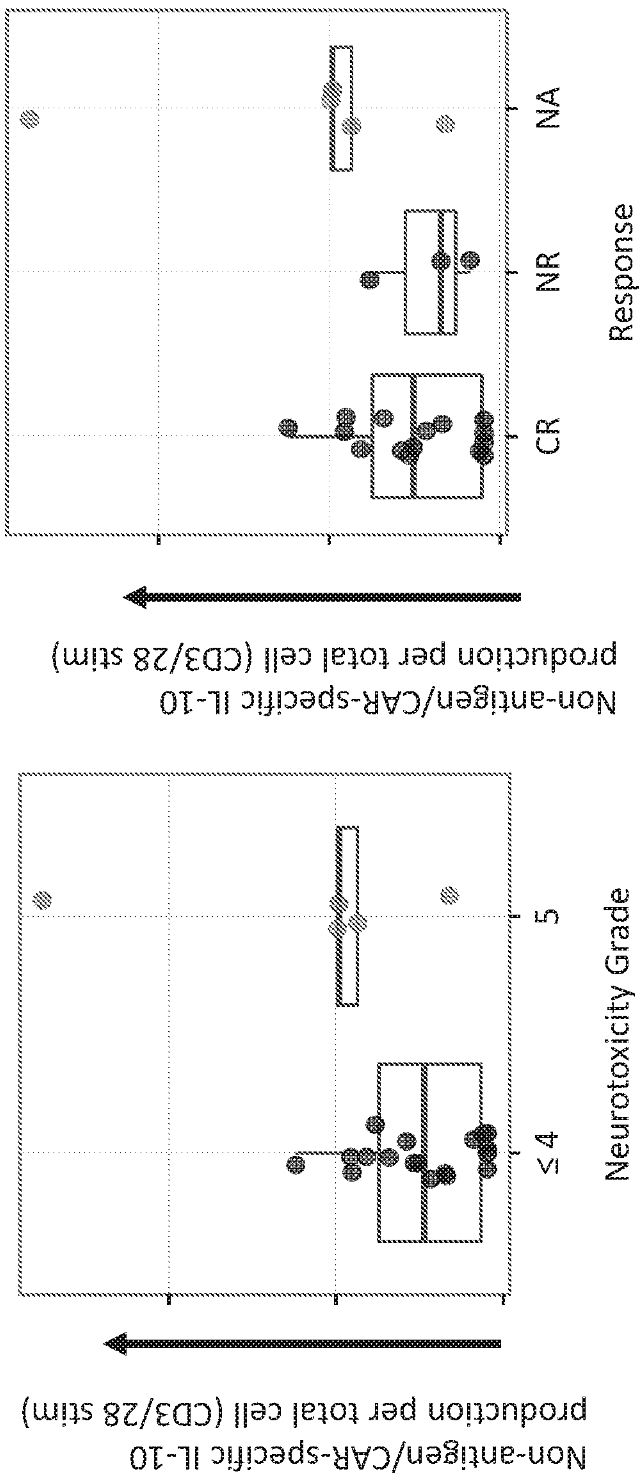

The box plots of FIG. 3R show non-antigen/CAR-specific IL-10 production per total cell (CD3/28 stim).

Figure 3S:
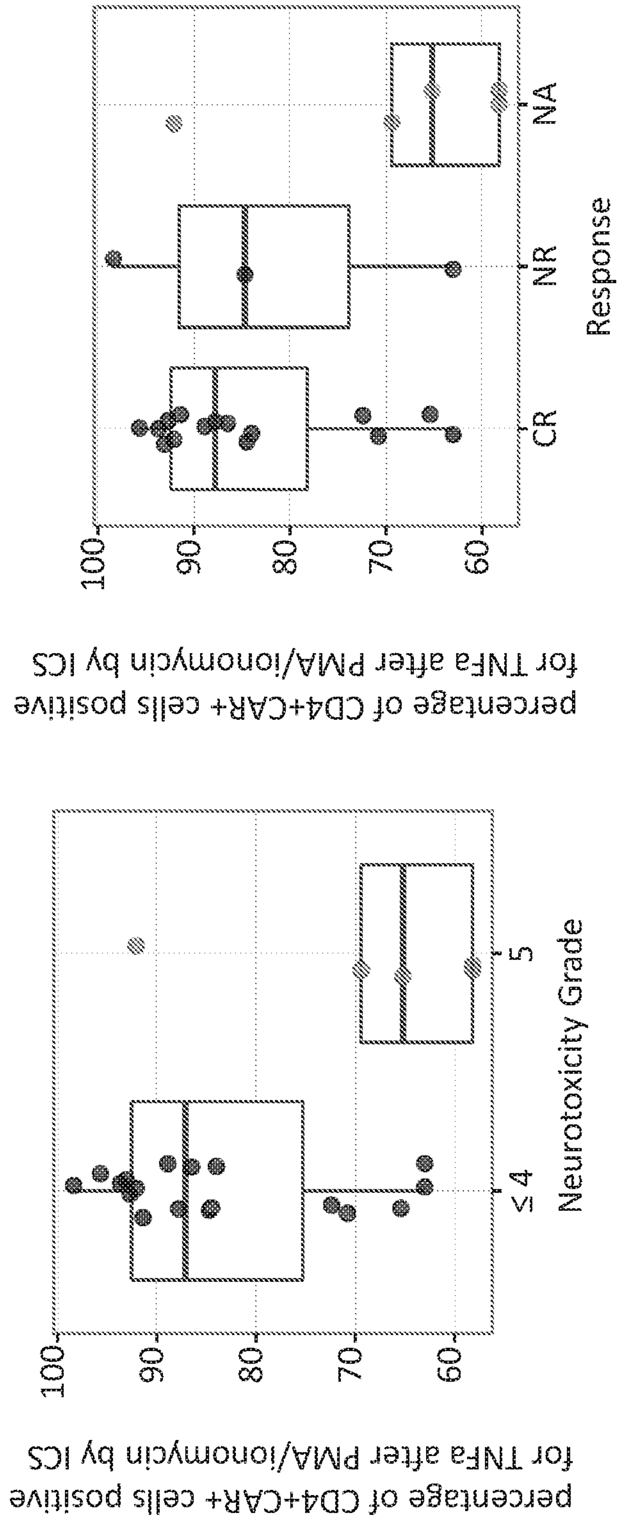

The box plots of FIG. 3S show ICS of TNF alpha of CD4+CAR+ cells.

Figure 3T:
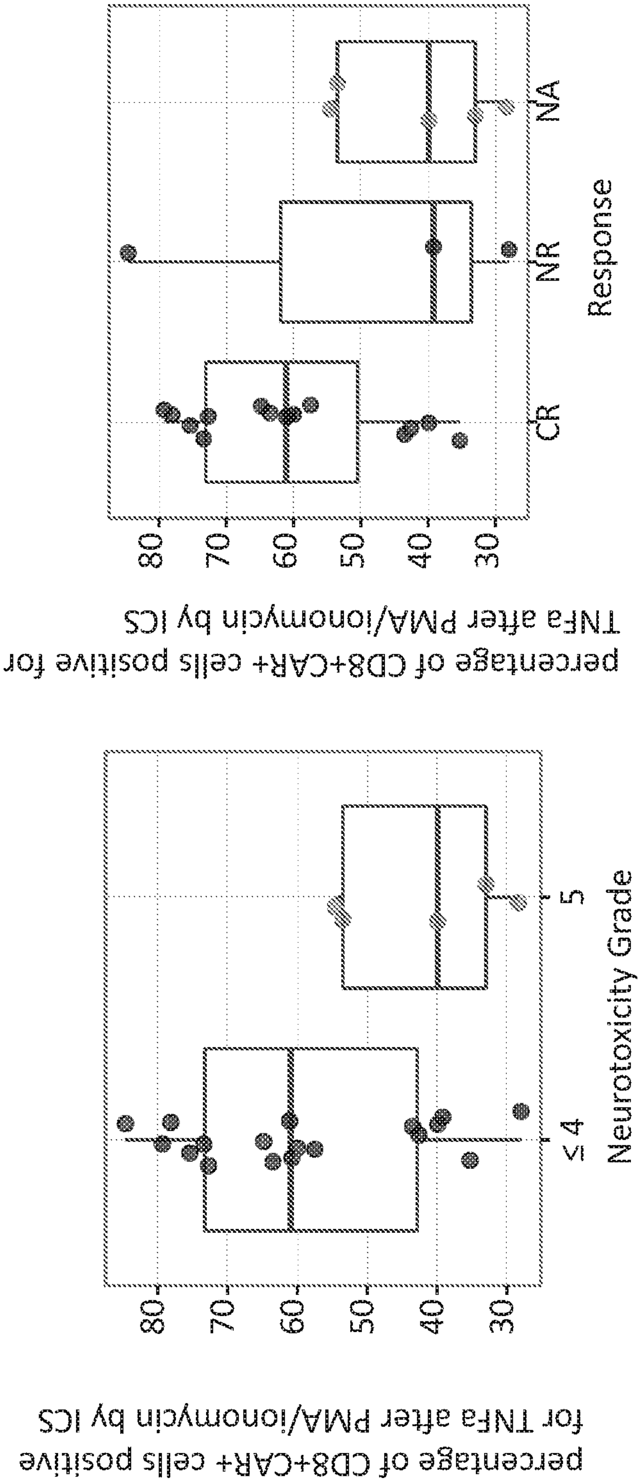

The box plots of FIG. 3T show ICS of TNF alpha of CD8+CAR+ cells.

Figure 3U:
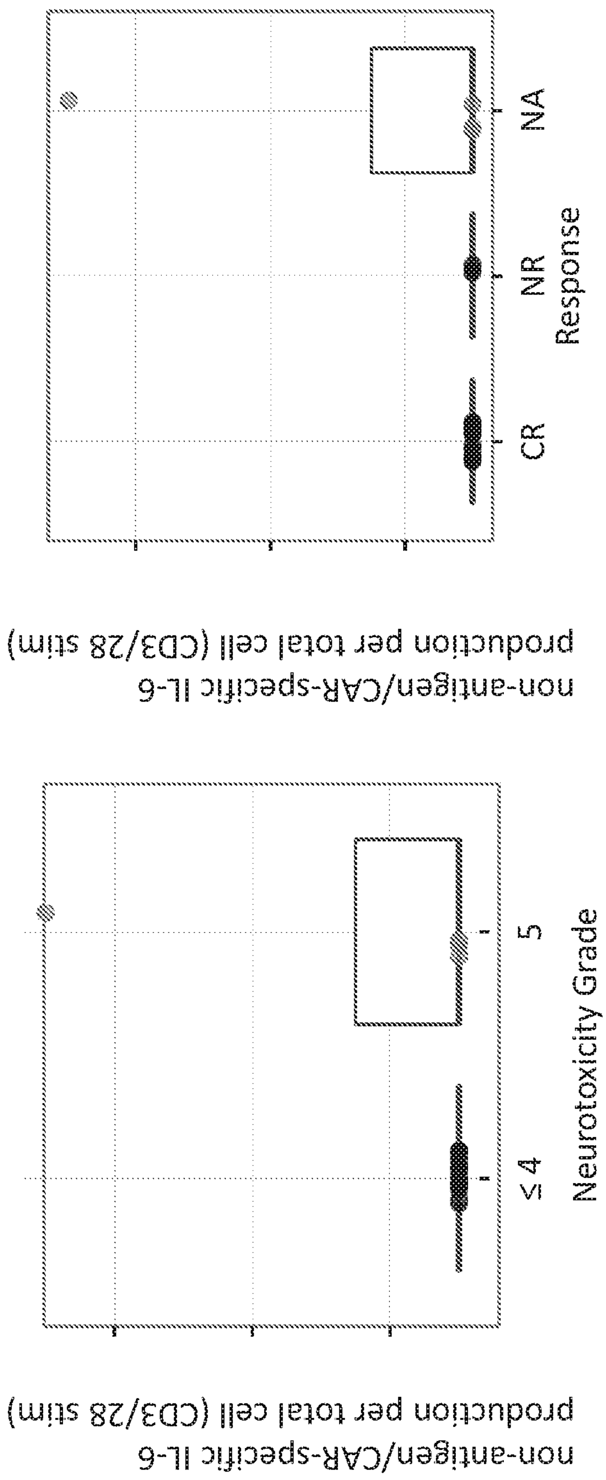

The box plots of FIG. 3U show non-antigen/CAR-specific IL-6 production per total cell (CD3/28 stim).

Figure 3V:
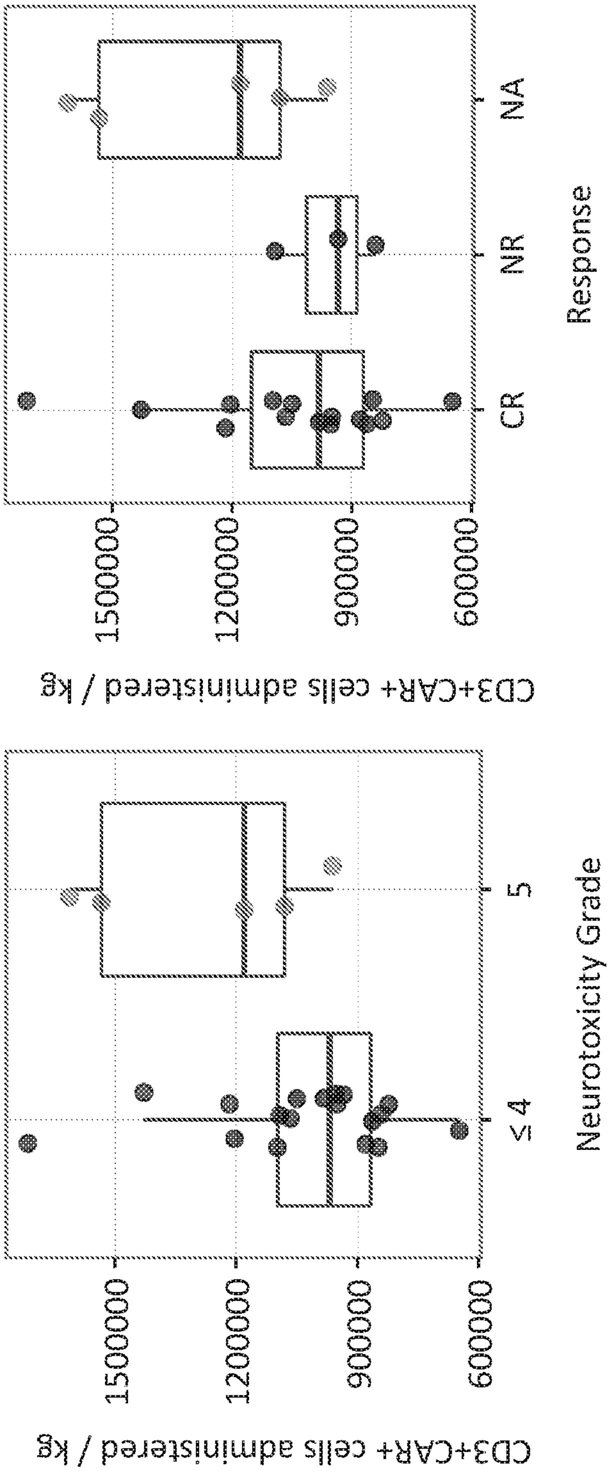

The box plots of FIG. 3V show the number of CD3+ CAR+ cells administered/kg.

Figure 4:
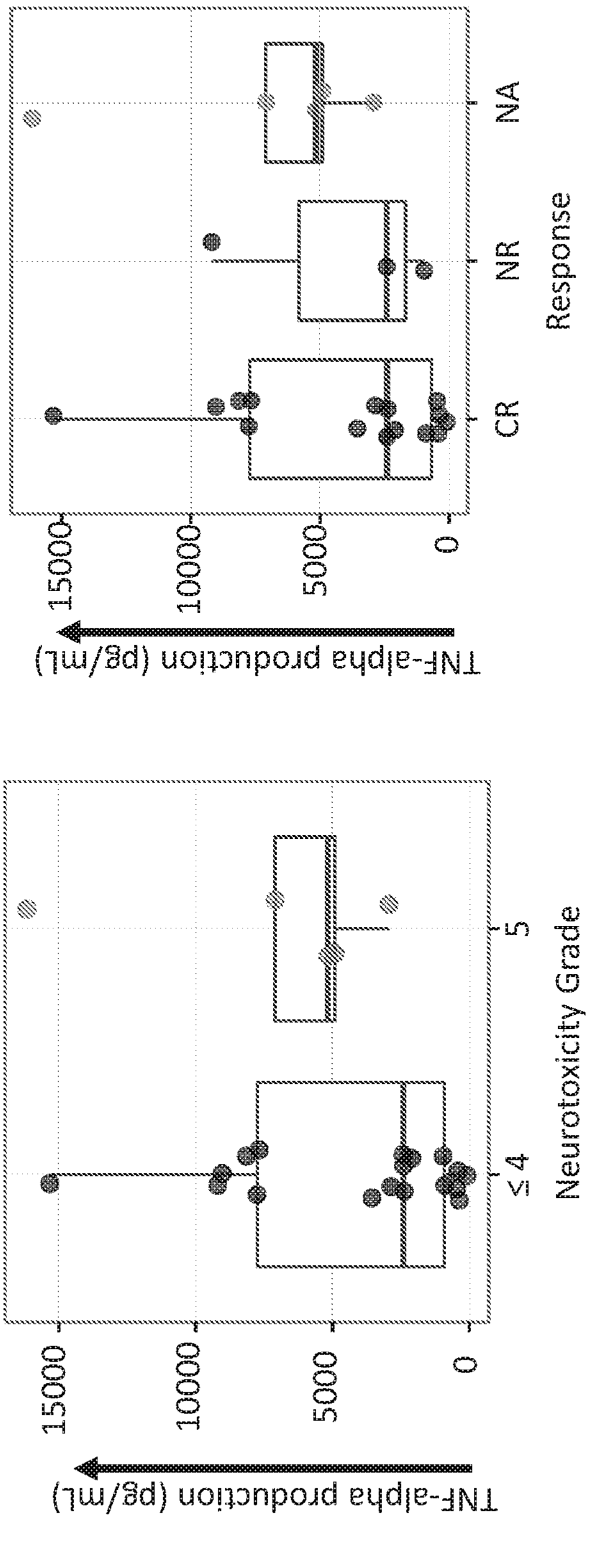

FIG. 4 shows box plots quantifying TNF-alpha production following stimulus with CD19 by cell compositions containing cells that express an anti-CD19 CAR. The box plot on the left compares measurements of cell compositions derived from subjects who developed grade 4 or less neurotoxicity with measurements of cell compositions derived from subjects who developed grade 5 neurotoxicity. The box plots on the right compare measurements of cell compositions derived from subjects who experienced a CR with measurements of cell compositions derived from subjects who experienced NR. Measurements of cell compositions derived from subjects whose response is not available are also shown in this plot (NA).

Figure 5A:
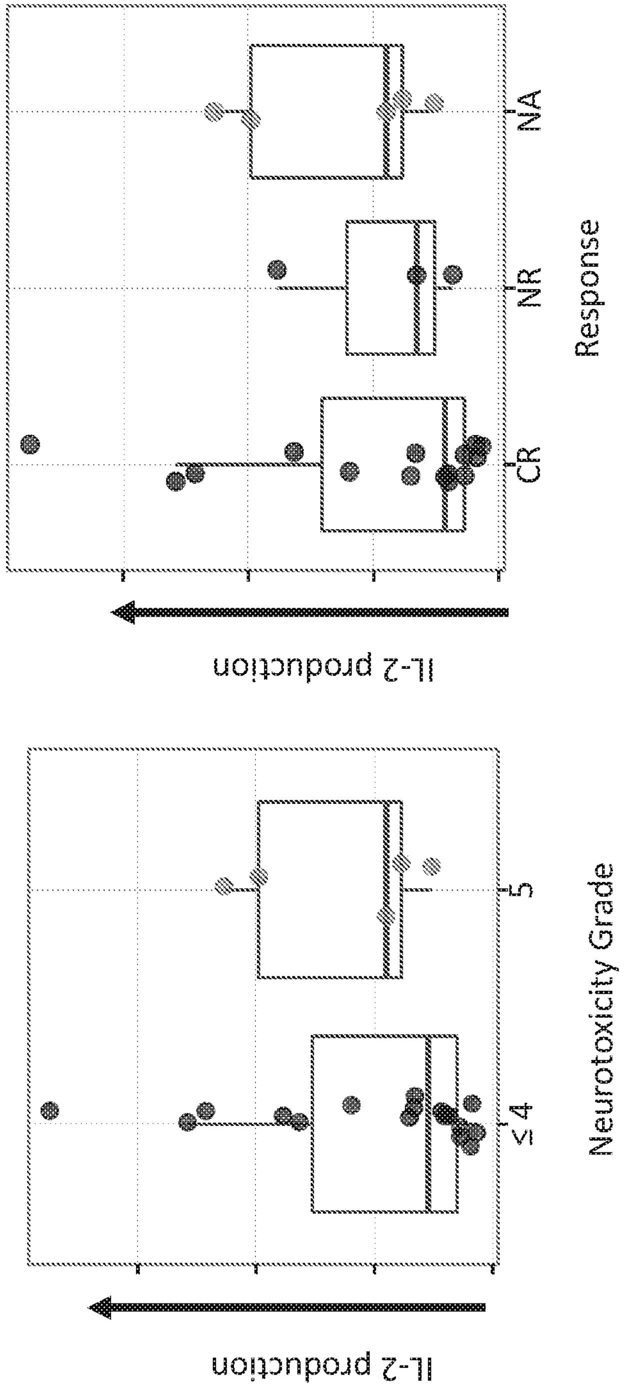
Figure 5B:
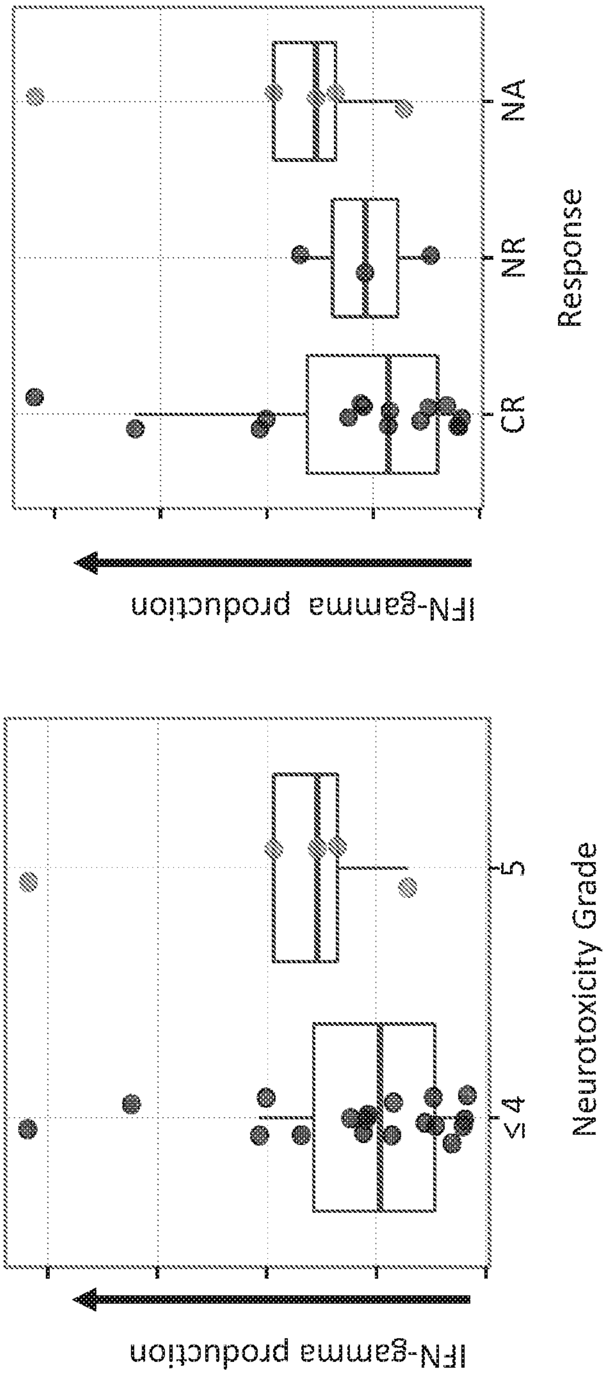

FIGS. 5A-B show box plots quantifying cytokine production following stimulus with CD19 by cell compositions containing cells that express an anti-CD19 CAR. The box plot on the left compares measurements of cell compositions derived from subjects who developed grade 4 or less neurotoxicity with measurements of cell compositions derived from subjects who developed grade 5 neurotoxicity. The box plots on the right compare measurements of cell compositions derived from subjects who experienced a CR with measurements of cell compositions derived from subjects who experienced NR. Measurements of cell compositions derived from subjects whose response is not available are also shown in this plot (NA).

The box plots of FIG. 5A show antigen stimulated IL-2 production.

The box plots of FIG. 5B show antigen stimulated IFN gamma production.

Figure 6A:
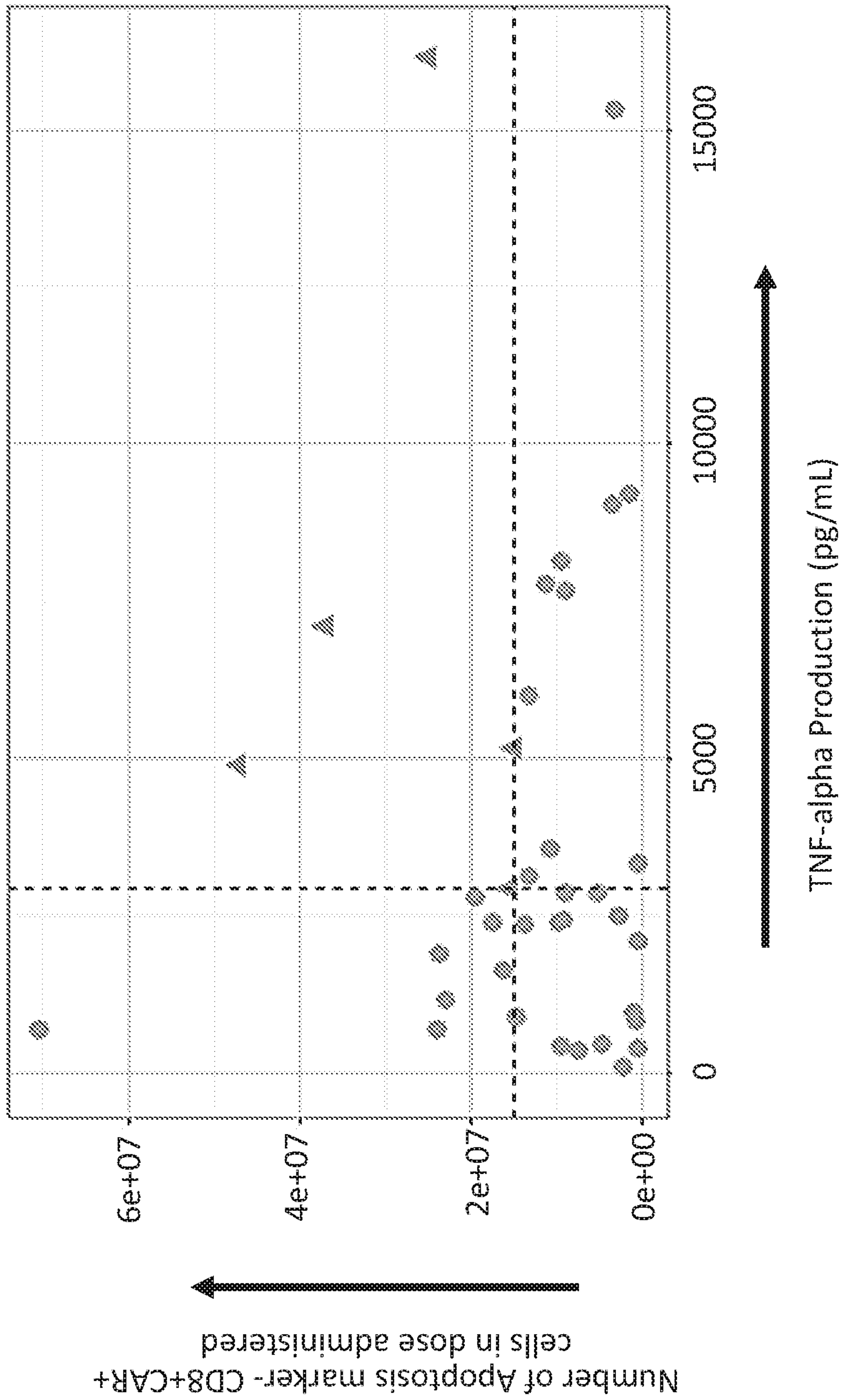
Figure 6B:
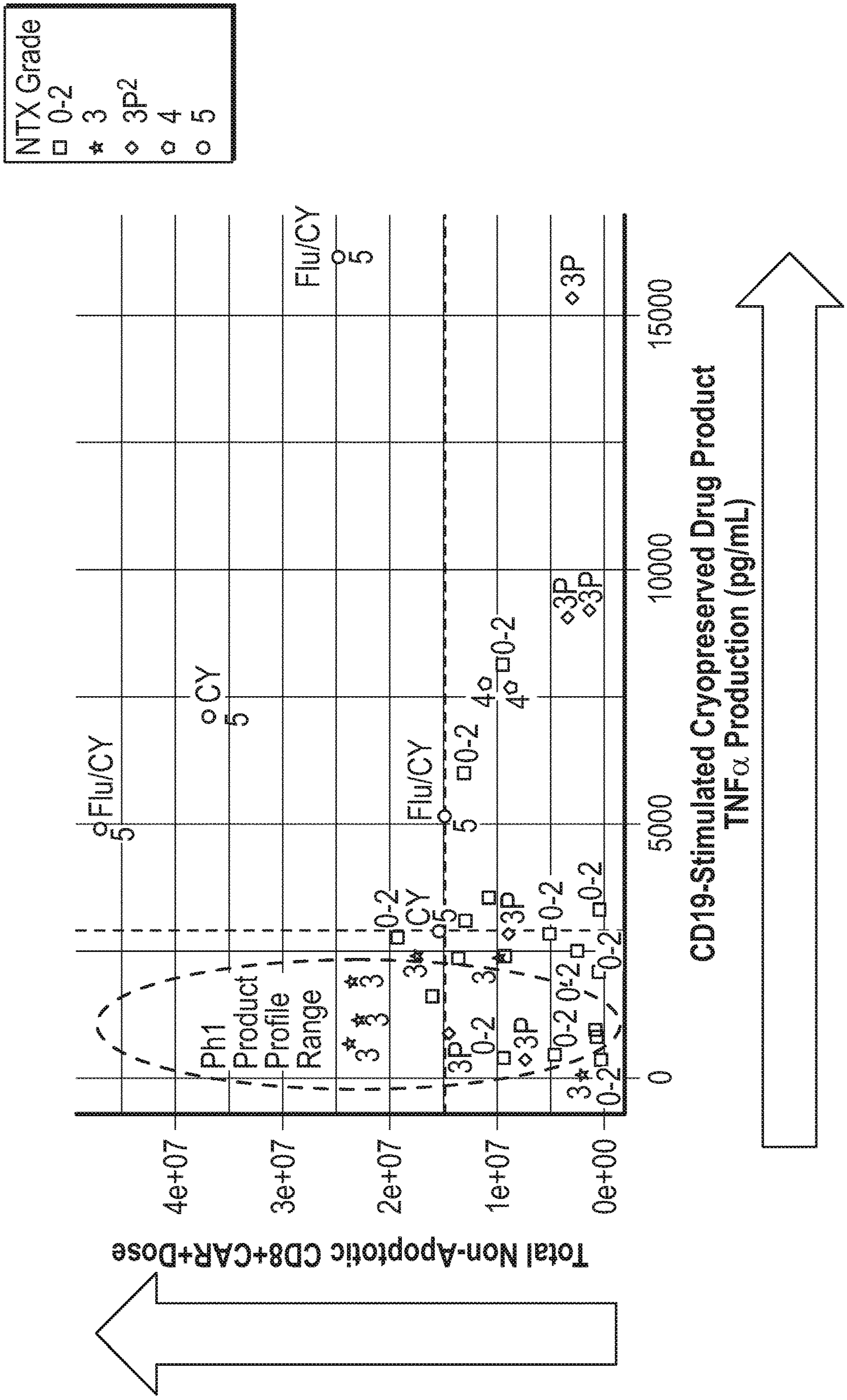

FIGS. 6A and 6B show two dimensional scatter plots of number of Apoptosis marker—(Annexin V−) CD8+CAR+ cells in dose administered and antigen stimulated TNF alpha production. Data points from cell compositions derived from subjects who developed grade 4 or less (circles) or grade 5 neurotoxicity (triangles) are shown in FIG. 6A. Data points from cell compositions derived from subjects who developed grade 0-2, 3, prolonged 3 (3p), 4, and 5 neurotoxicity are shown in FIG. 6B. In FIG. 6B, data points associated with subjects who developed grade 5 neurotoxicity and received lymphodepleting chemotherapy with cyclophosphamide (CY) or fludarabine and cyclophosphamide (Flu/CY) are shown. The oval indicates the range for these parameters for a majority of 11 exemplary cell compositions assessed from a clinical study in which no subjects exhibited grade 5 neurotoxicity or cerebral edema.

Figure 7:
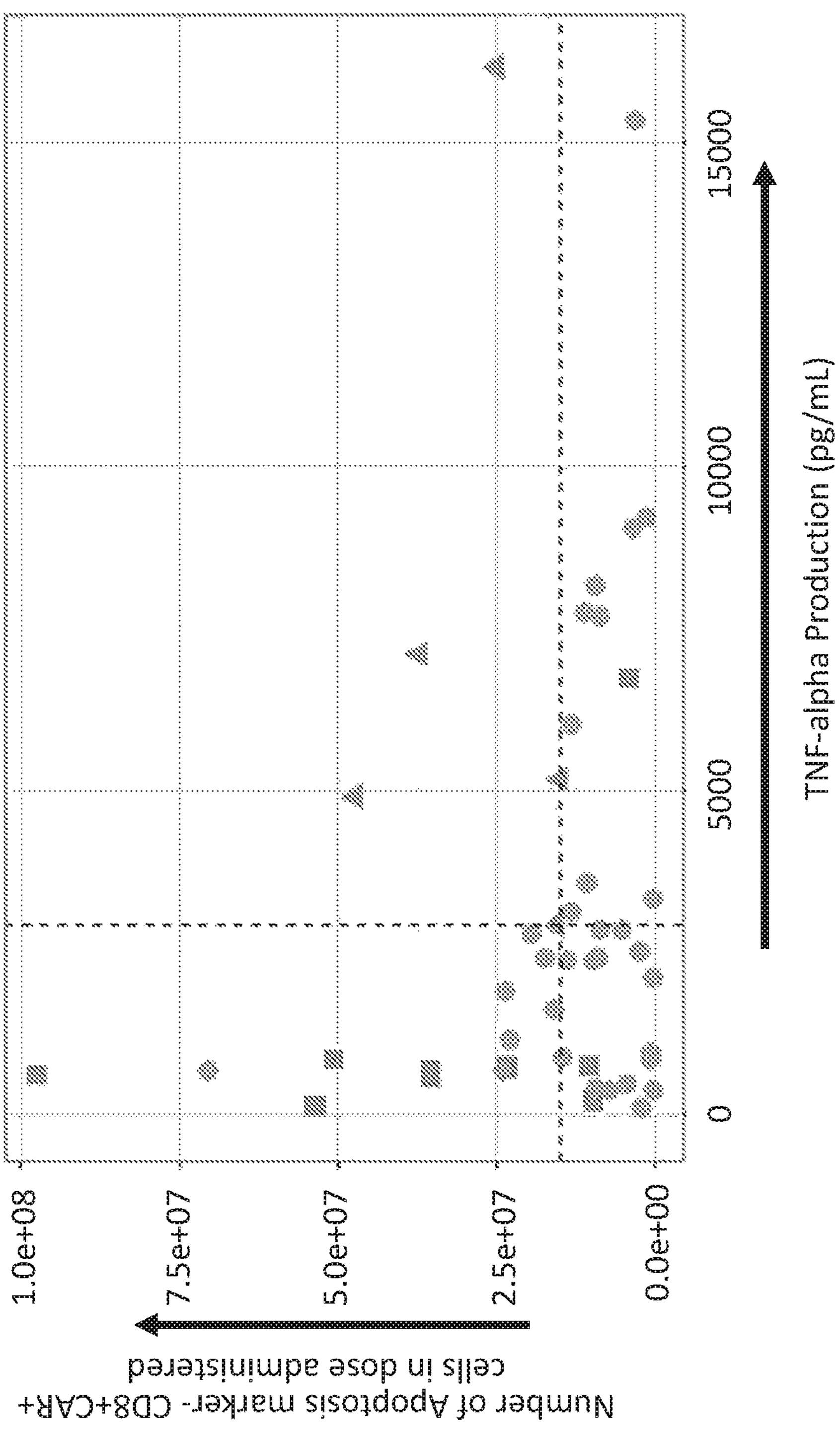

FIG. 7 shows a two dimensional scatter plot of number of Apoptosis marker-(Annexin V−) CD8+CAR+ cells in dose administered and antigen stimulated TNF alpha production. Data points from cell compositions derived from subjects who developed grade 4 or less (squares and circles) or grade 5 neurotoxicity (triangles) are shown. Cell compositions that were derived from subjects of an additional clinical study are shown (squares).

Figure 8:
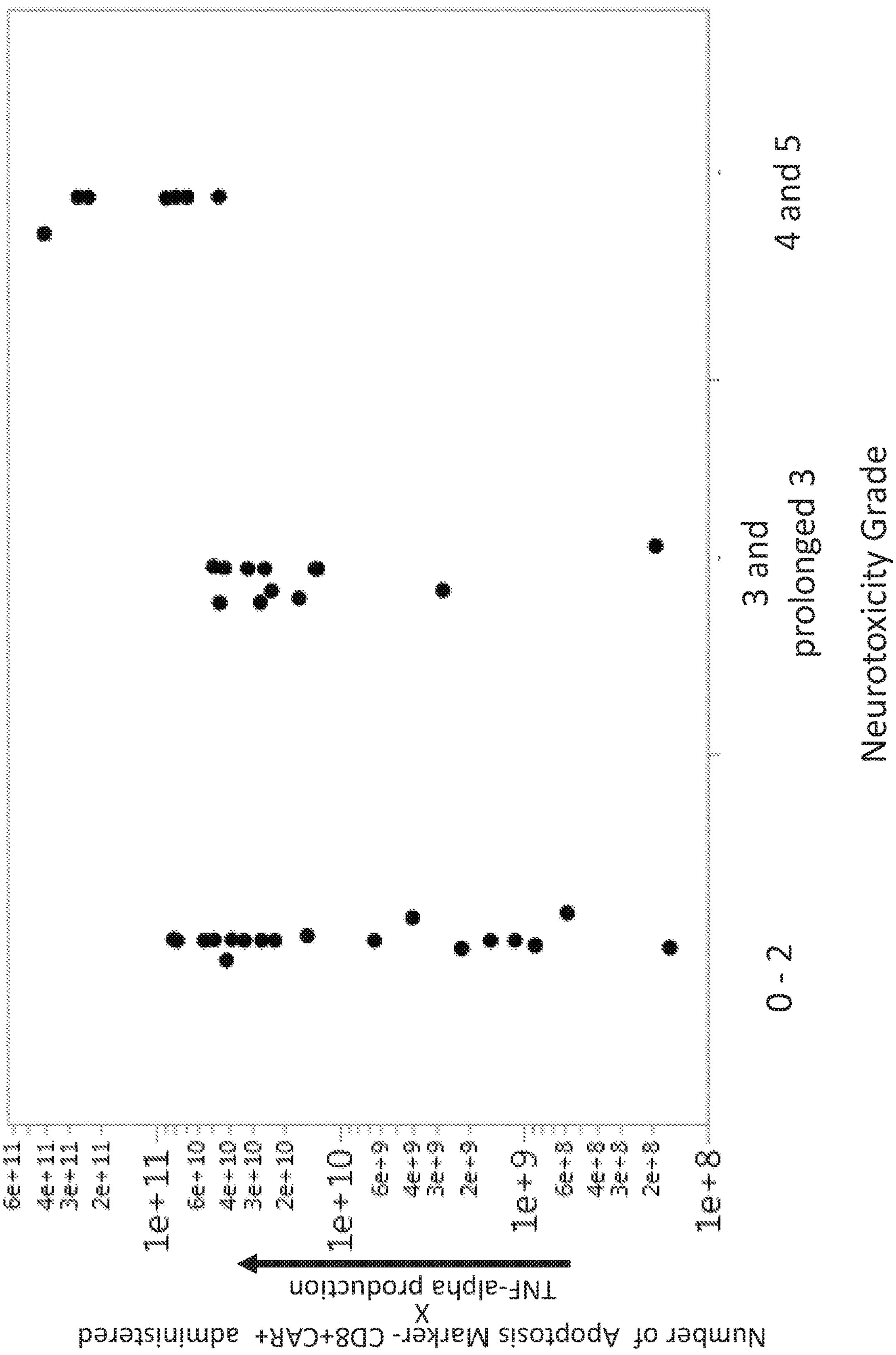

FIG. 8 shows a graph displaying individual data points of the number of apoptosis marker (Annexin V)−CD8+CAR+ cells administered x TNF-alpha production for subjects who developed different grades of neurotoxicity.

Figure 9:
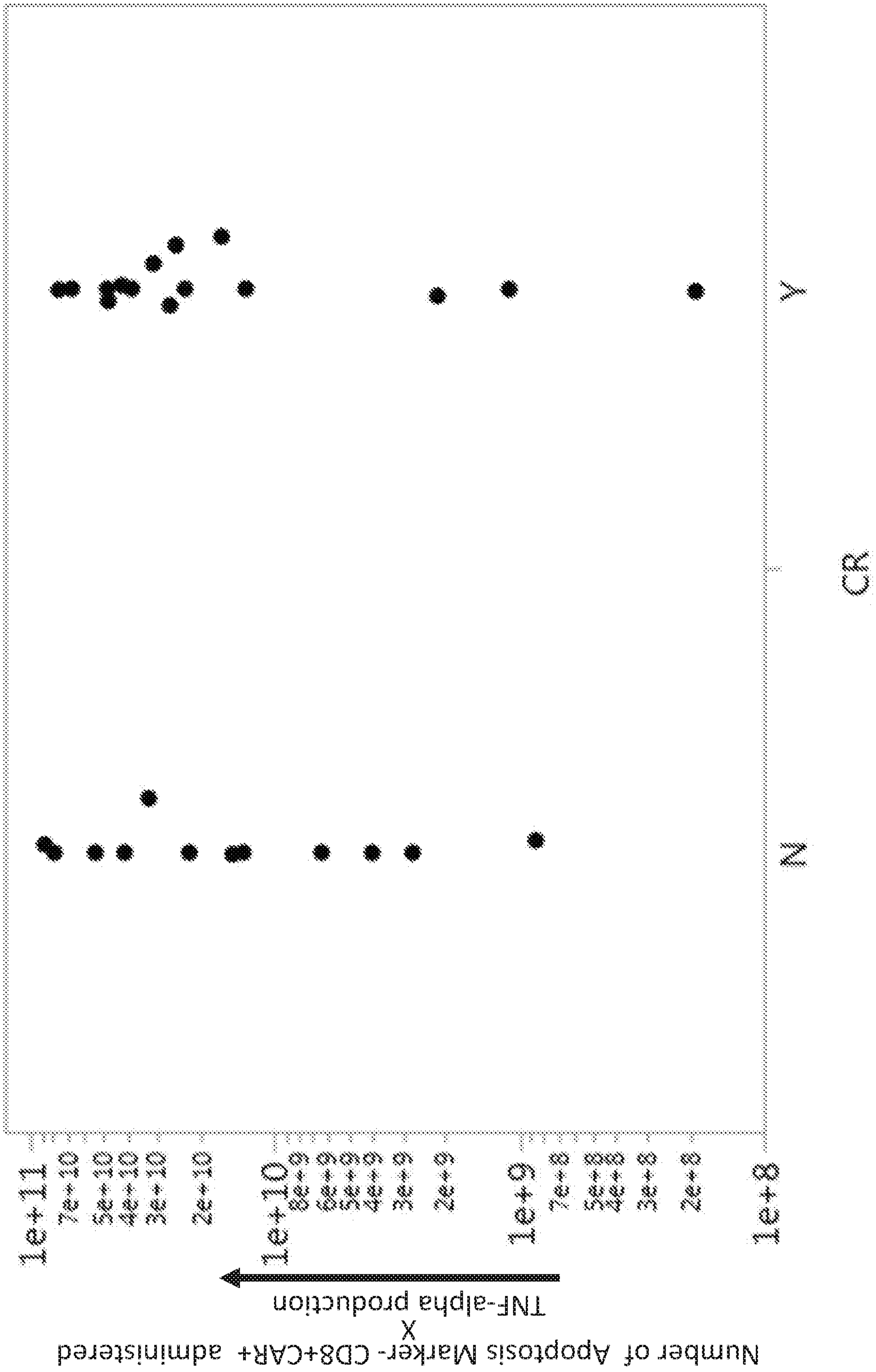

FIG. 9 shows a graph displaying individual data points of the number of apoptosis marker-(Annexin V−) CD8+CAR+ cells administered x TNF-alpha production for subjects with different responses.

Figure 10:
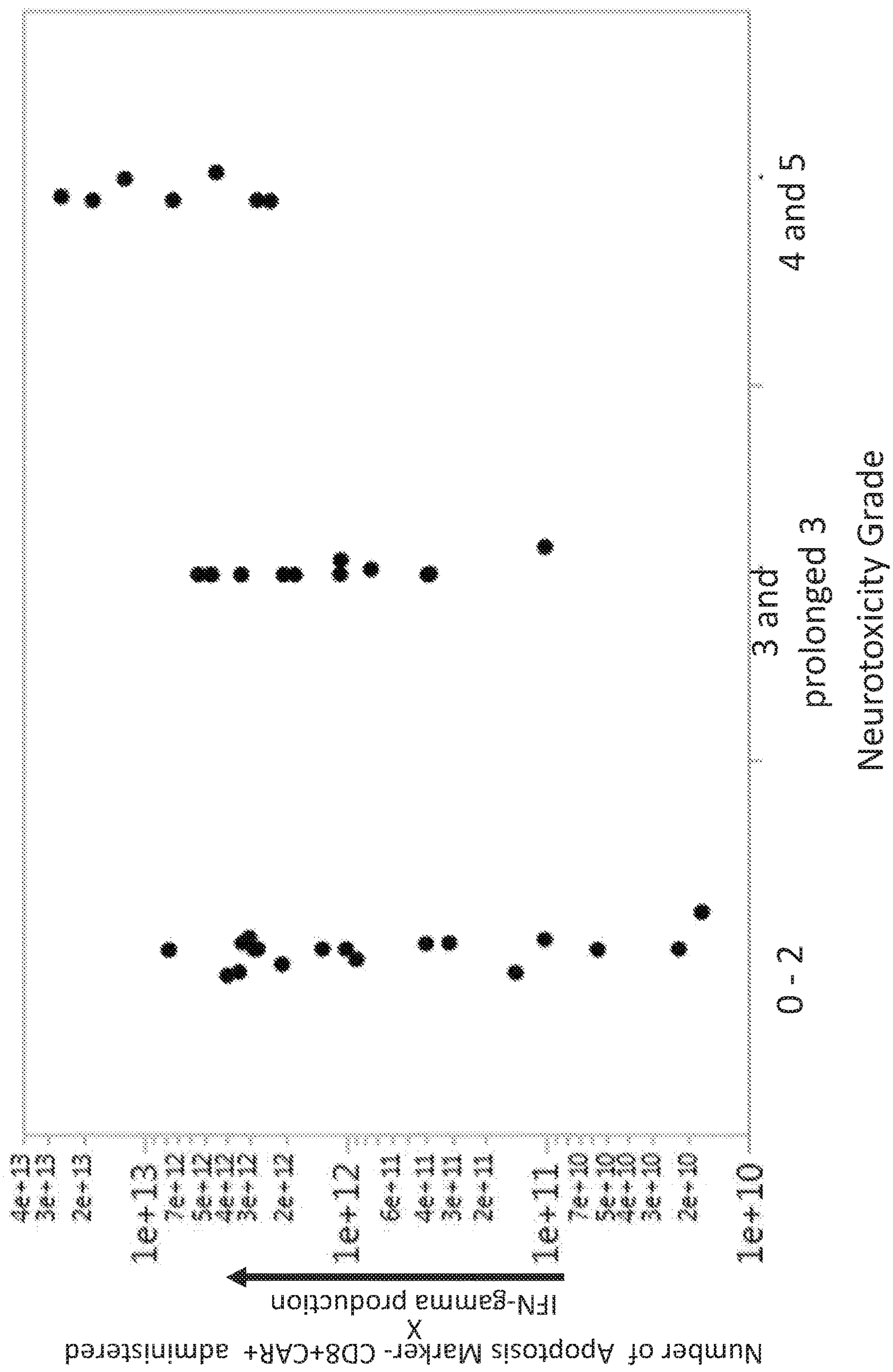

FIG. 10 shows a graph displaying individual data points of the number of apoptosis marker-(Annexin V−) CD8+ CAR+ cells administered x IFN gamma production for subjects who developed different grades of neurotoxicity.

Figure 11:
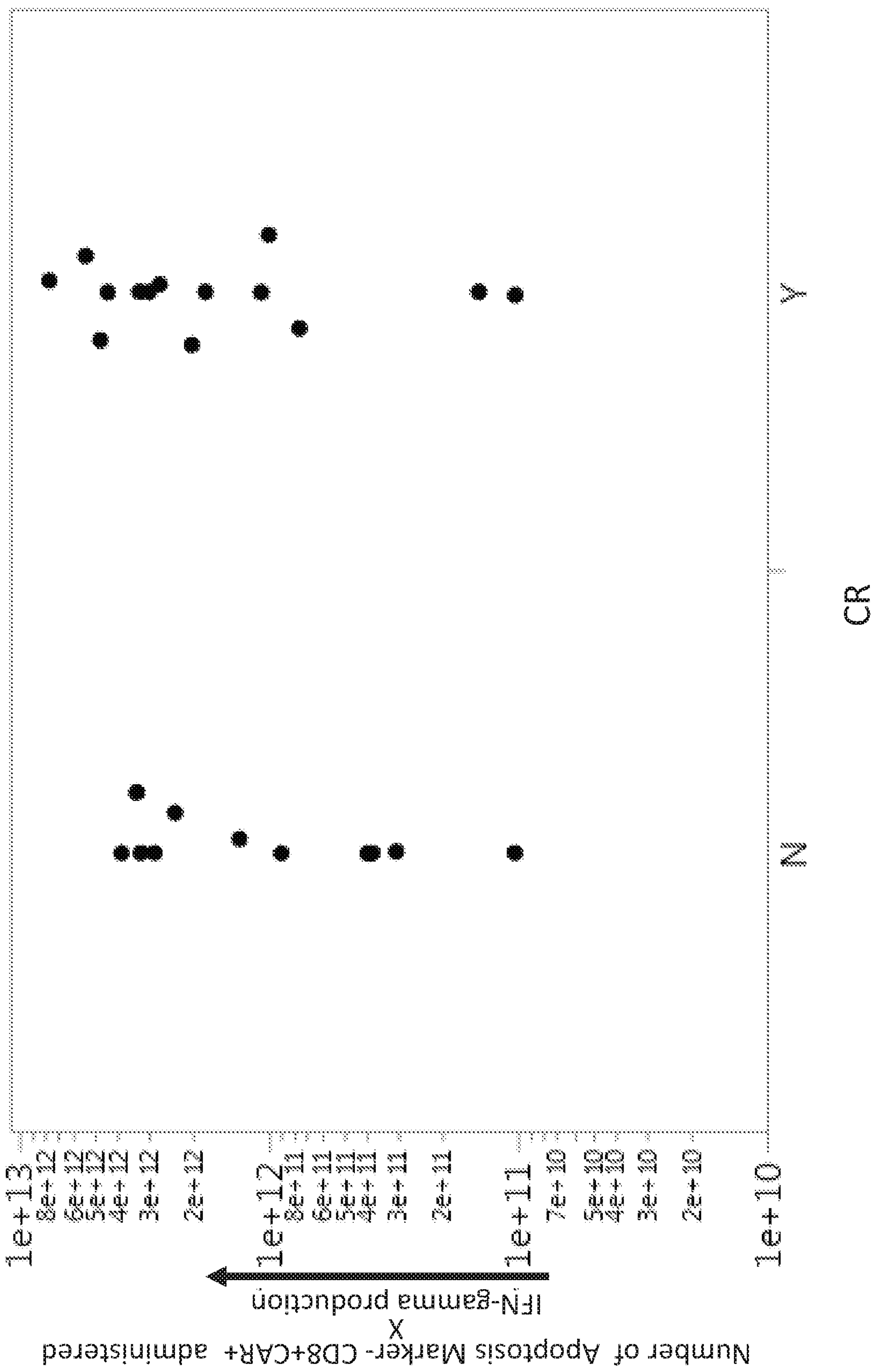

FIG. 11 shows a graph displaying individual data points of the number of apoptosis marker-(Annexin V−) CD8+ CAR+ cells administered x IFN gamma production for subjects with different clinical responses.

Figure 12:
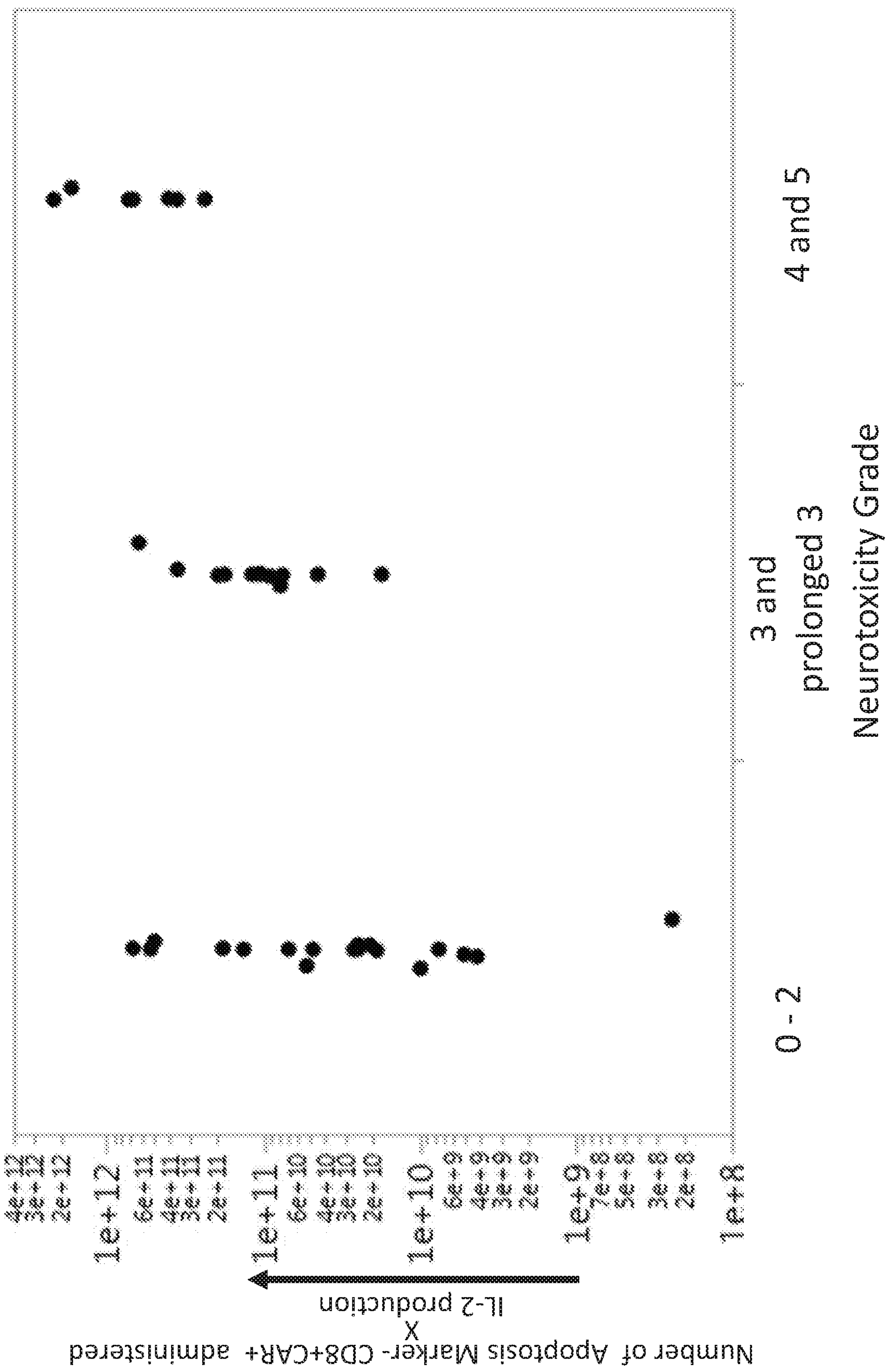

FIG. 12 shows a graph displaying individual data points of the number of apoptosis Marker-(Annexin V−) CD8+ CAR+ cells administered x IL-2 production for subjects who developed different grades of neurotoxicity.

Figure 13:
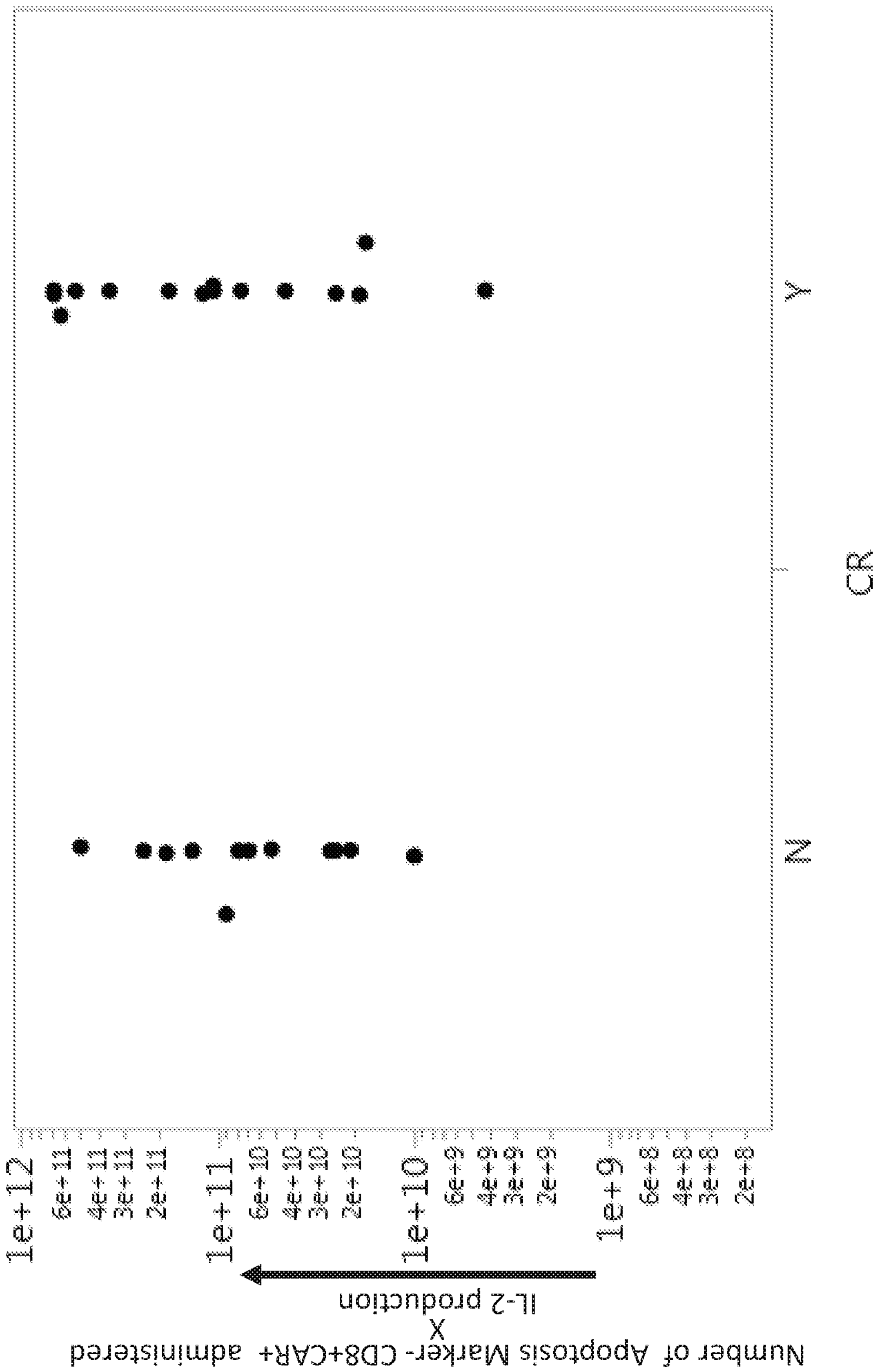

FIG. 13 shows a graph displaying individual data points of the number of apoptosis marker-(Annexin V−) CD8+ CAR+ cells administered x IL-2 production for subjects with different clinical responses.

Figure 14A:
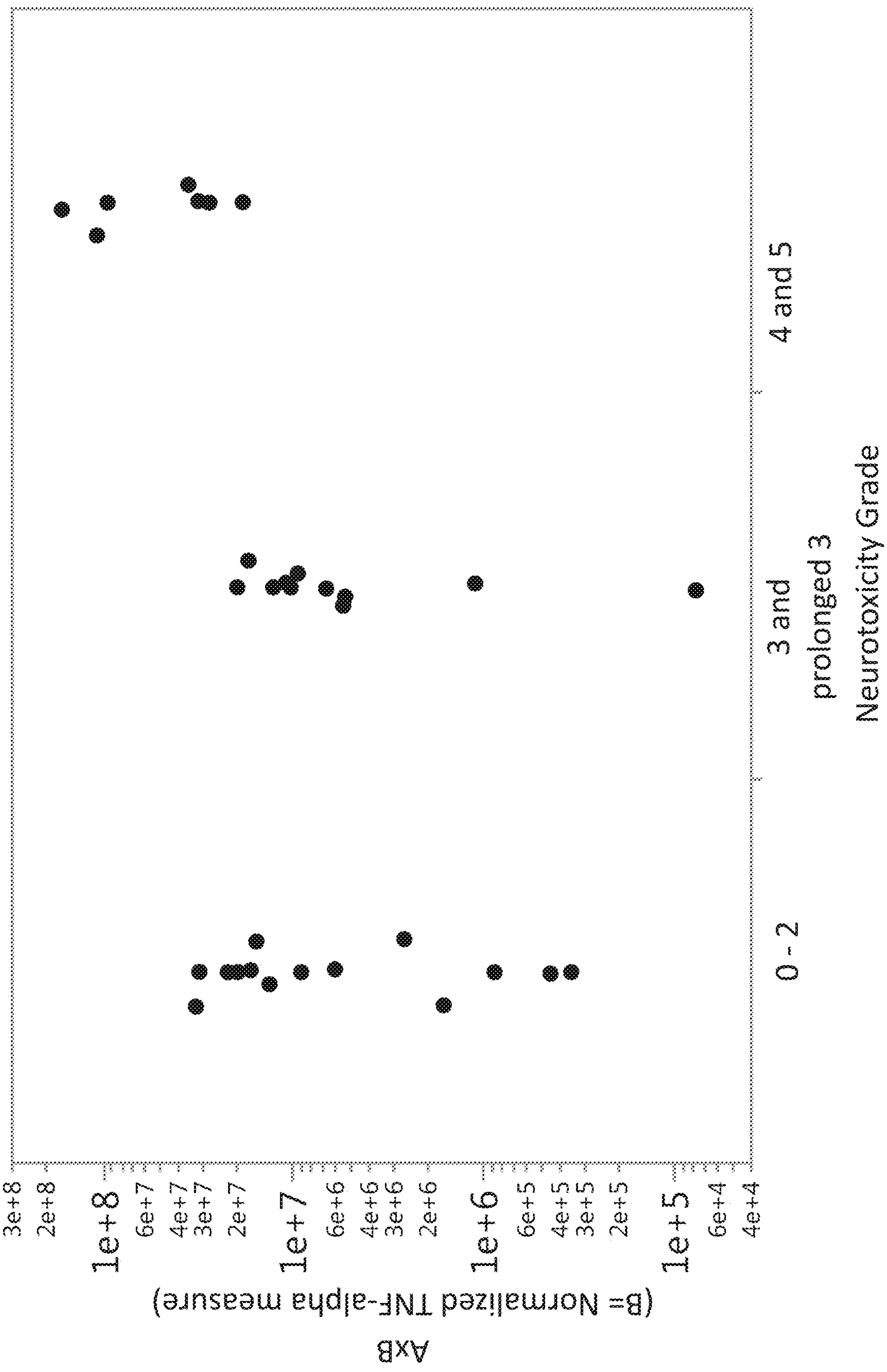
Figure 14B:
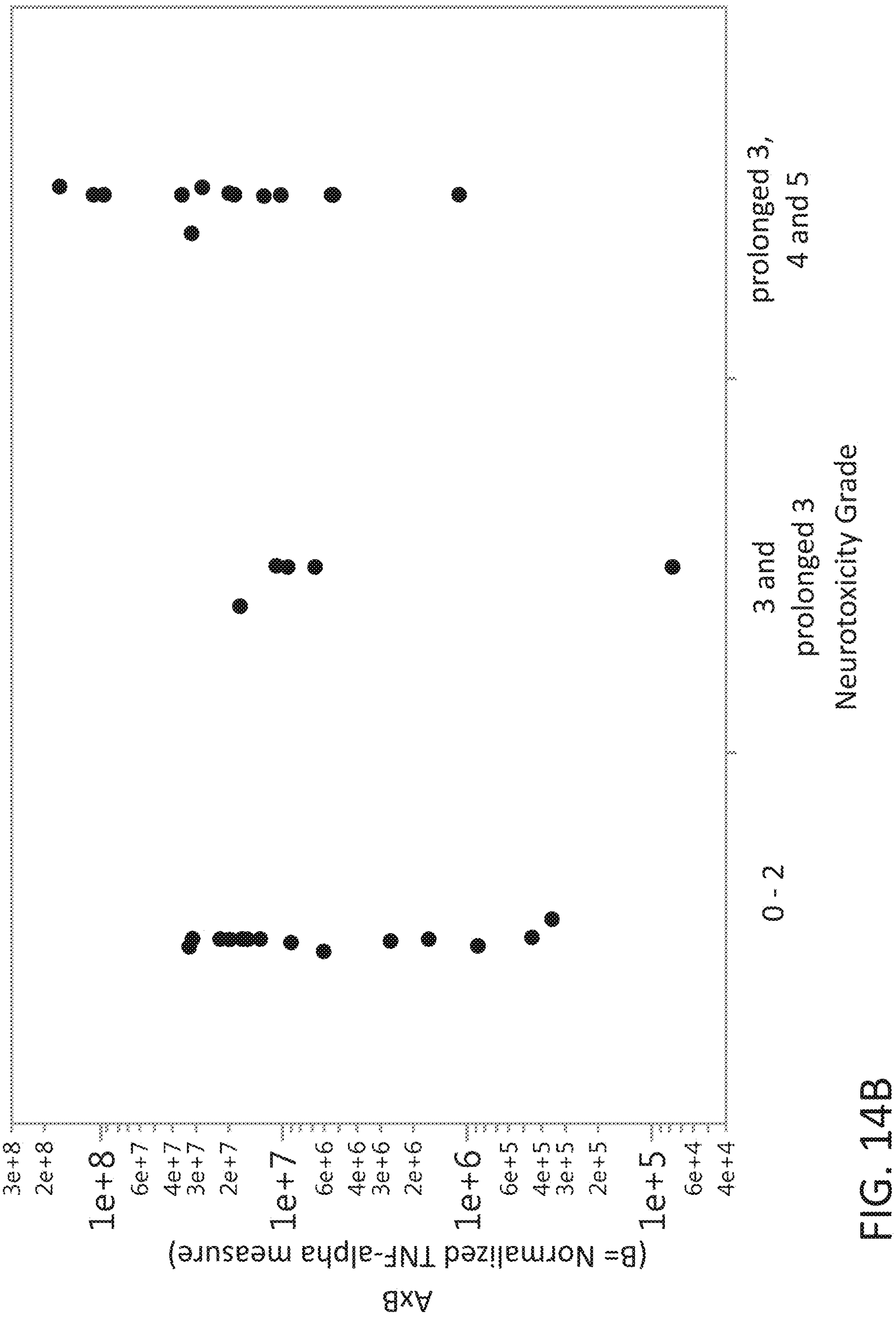
Figure 14C:
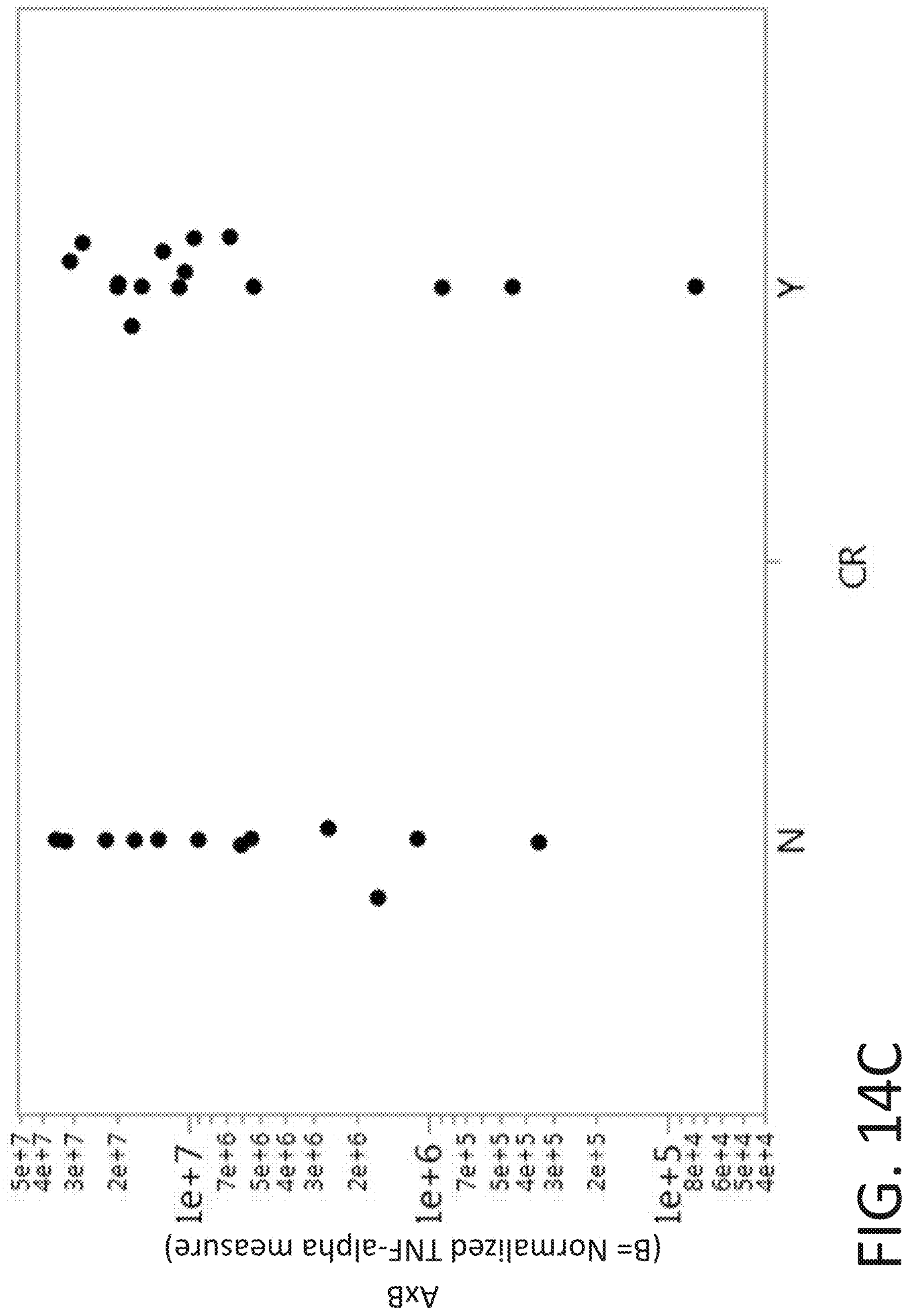

FIGS. 14A-C show graphs displaying individual data points of the number of apoptosis marker-(Annexin V−) CD8+CAR+ cells administered (A) x normalized TNF-alpha production (B) for subjects who developed different grades of neurotoxicity (FIG. 14A-B) or for subjects with different responses (FIG. 14C).

Figure 15A:
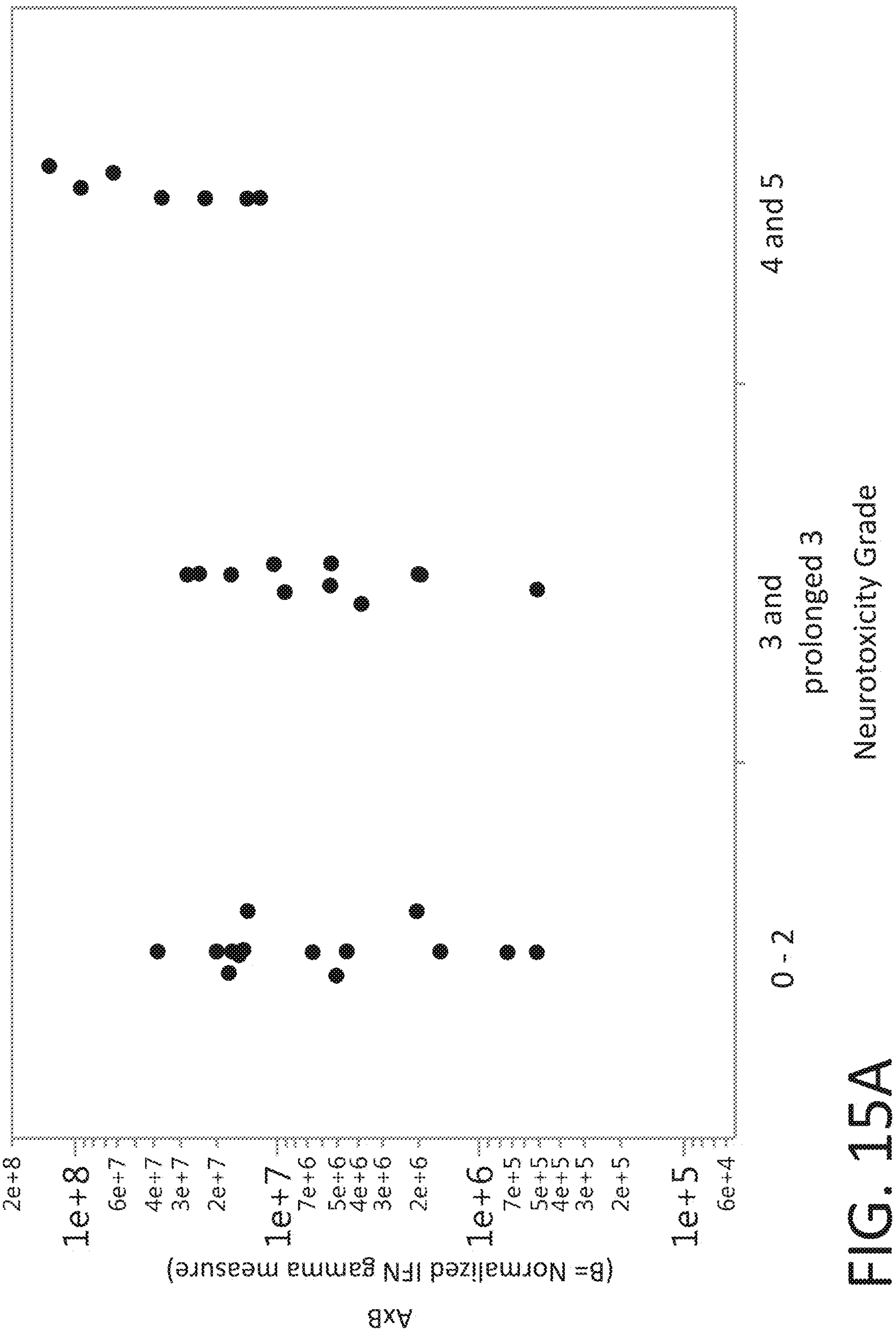
Figure 15B:
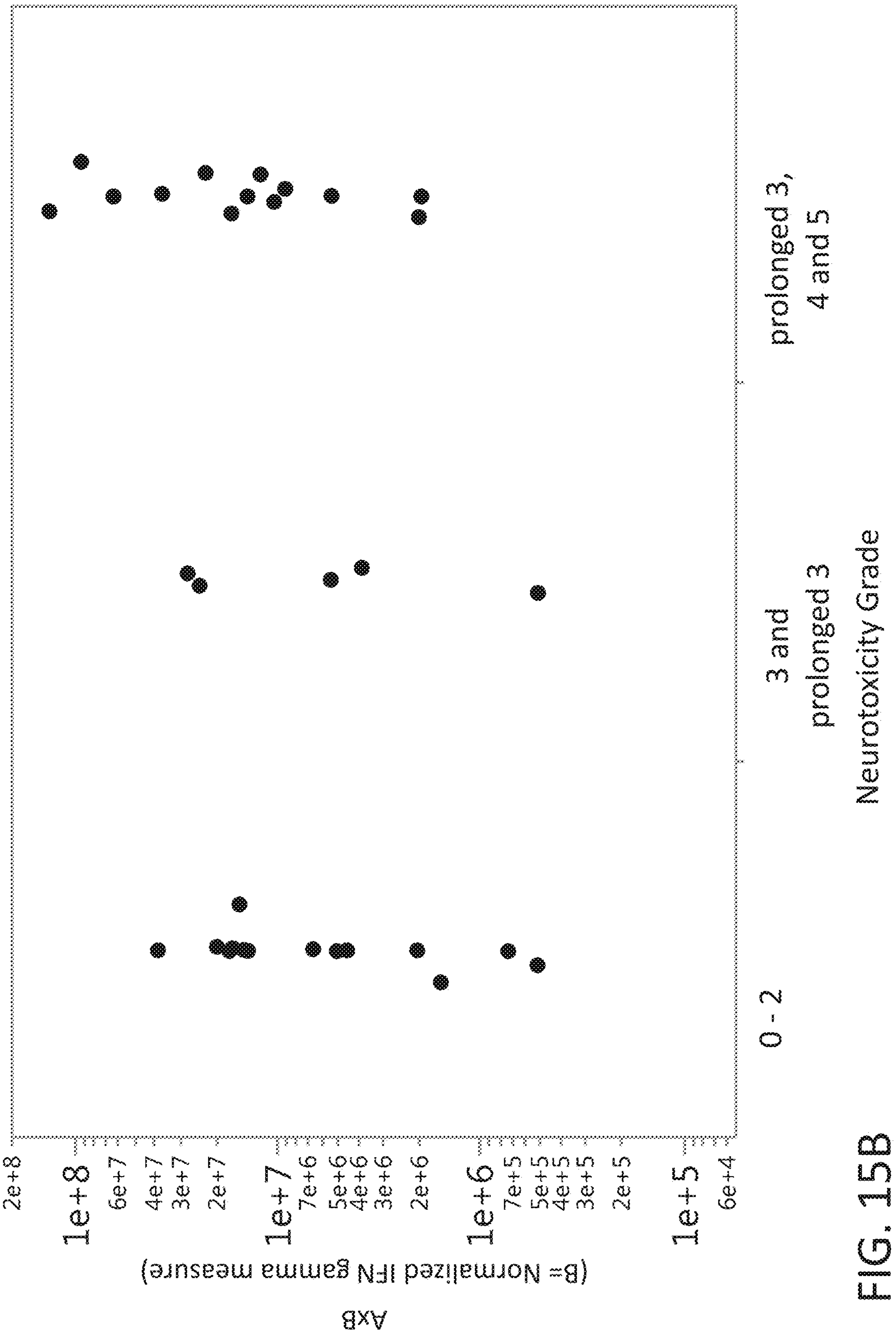
Figure 15C:
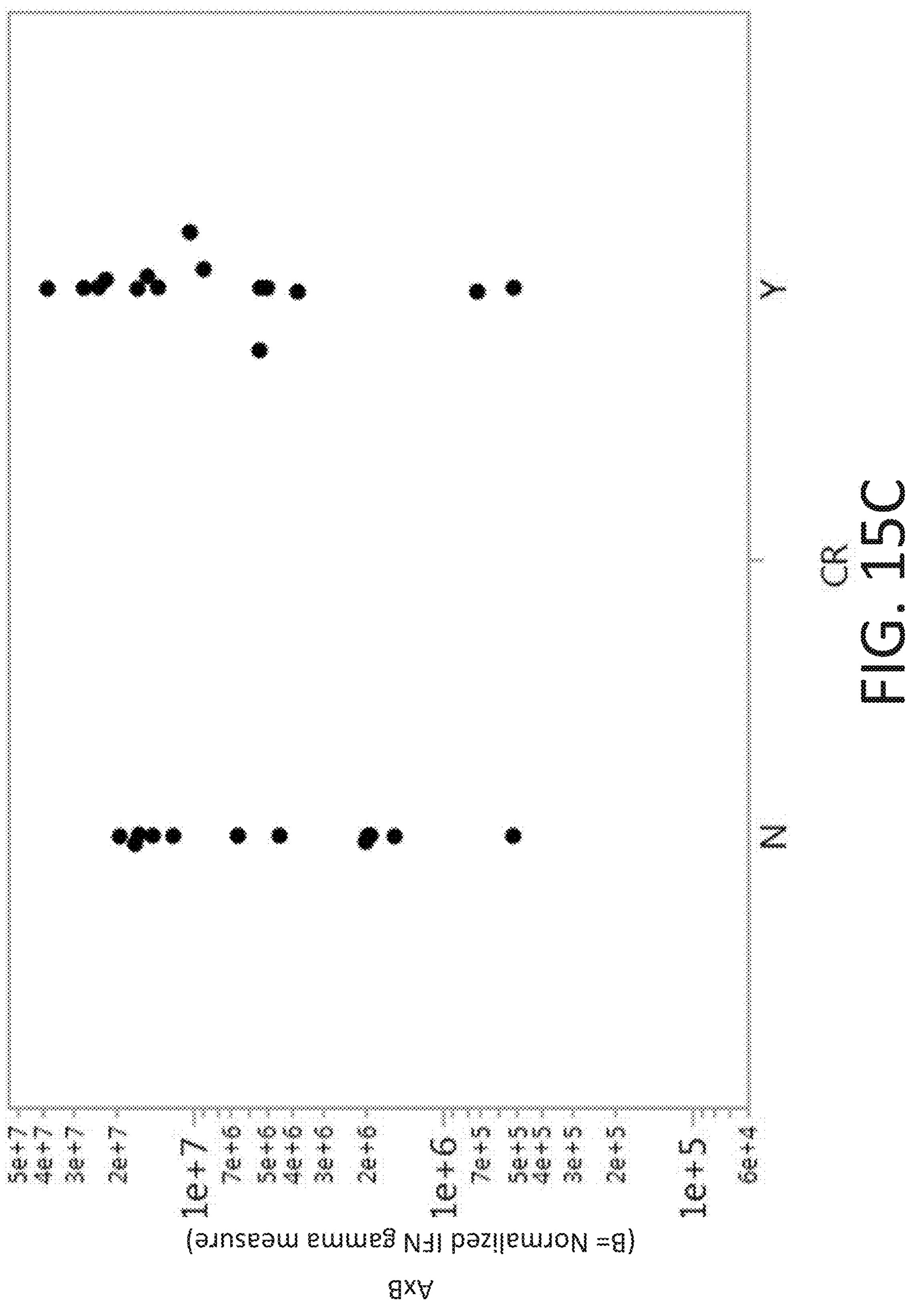

FIGS. 15A-C show a graph displaying individual data points of the number of apoptosis marker-(Annexin V−) CD8+CAR+ cells administered (A) x normalized IFN-gamma production (B) for subjects who developed different grades of neurotoxicity (FIG. 15A-B) or for subjects with different responses (FIG. 15C).

Figure 16A:
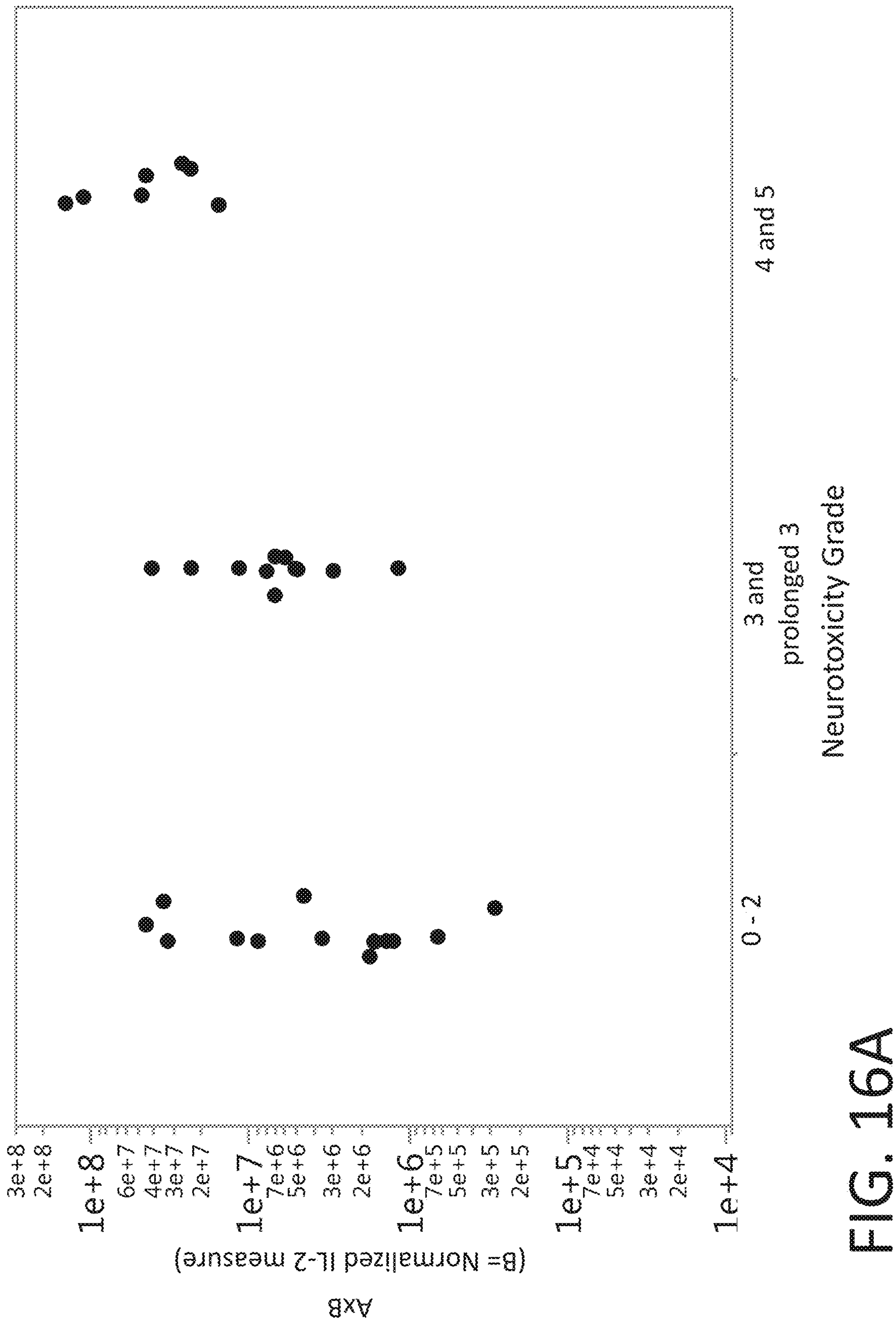
Figure 16B:
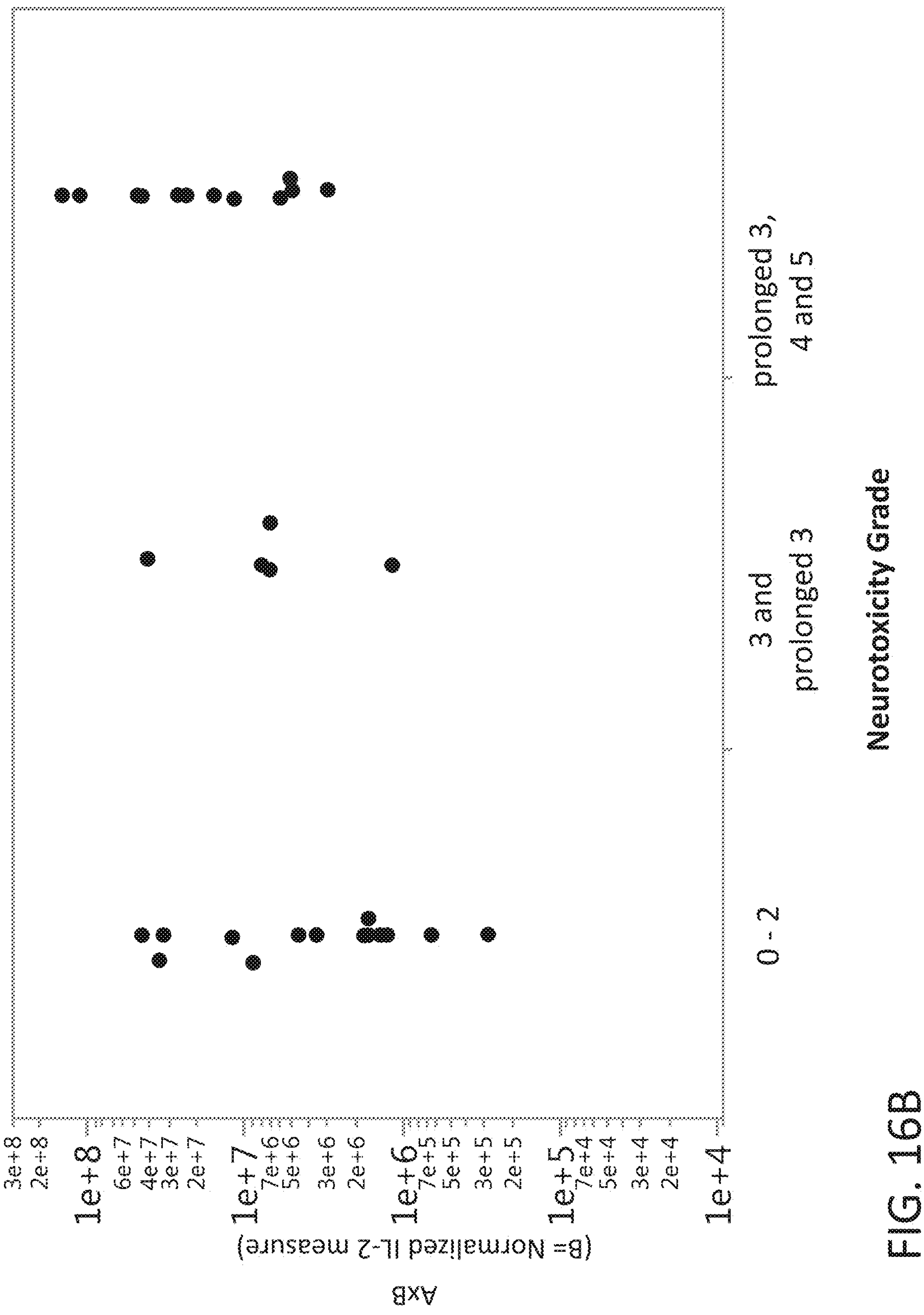
Figure 16C:
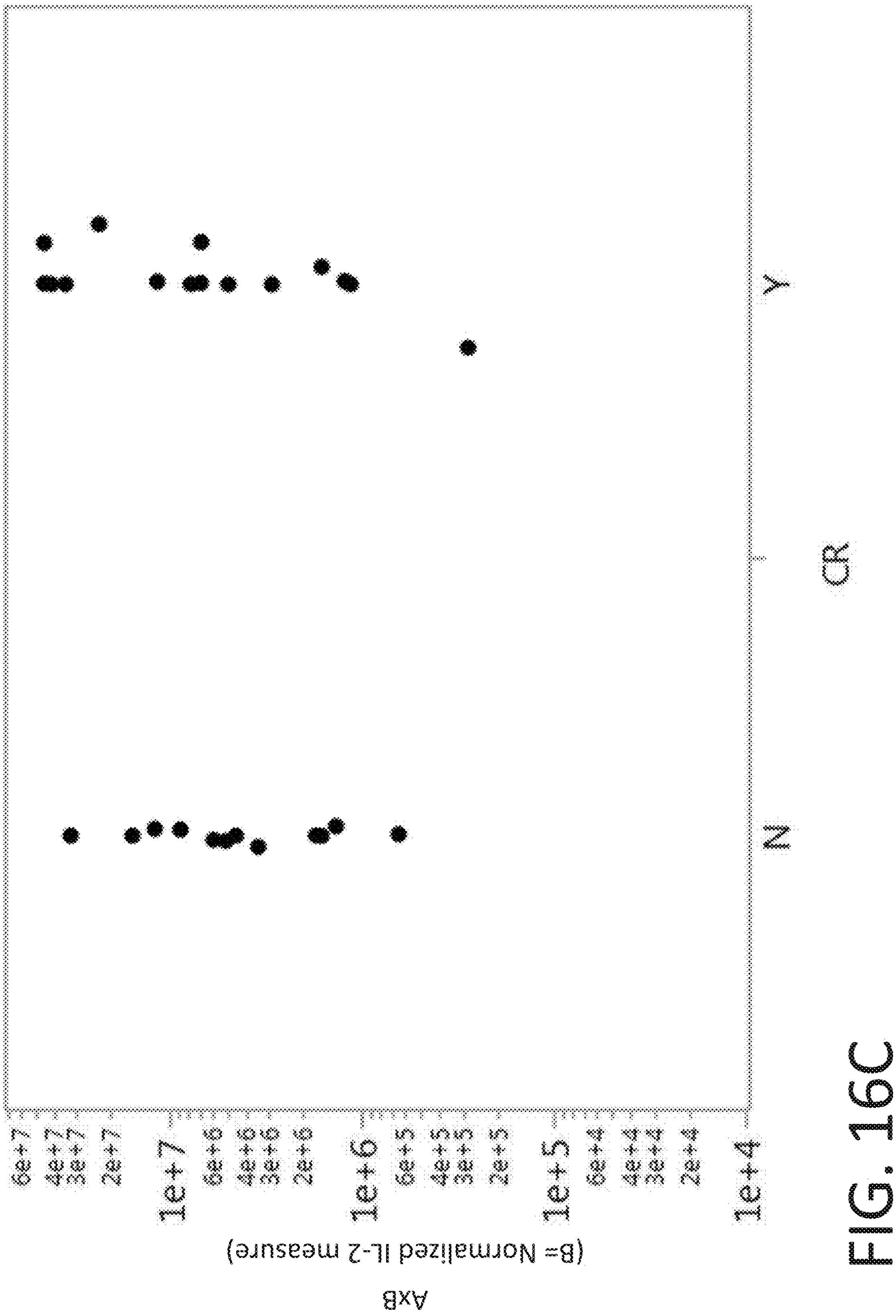

FIGS. 16A-C show a graph displaying individual data points of the number of apoptosis marker-(Annexin V−) CD8+CAR+ cells administered (A) x normalized IL-2 production (B) for subjects who developed different grades of neurotoxicity (FIG. 16A-B) or for subjects with different responses (FIG. 16C).

Figure 17A:
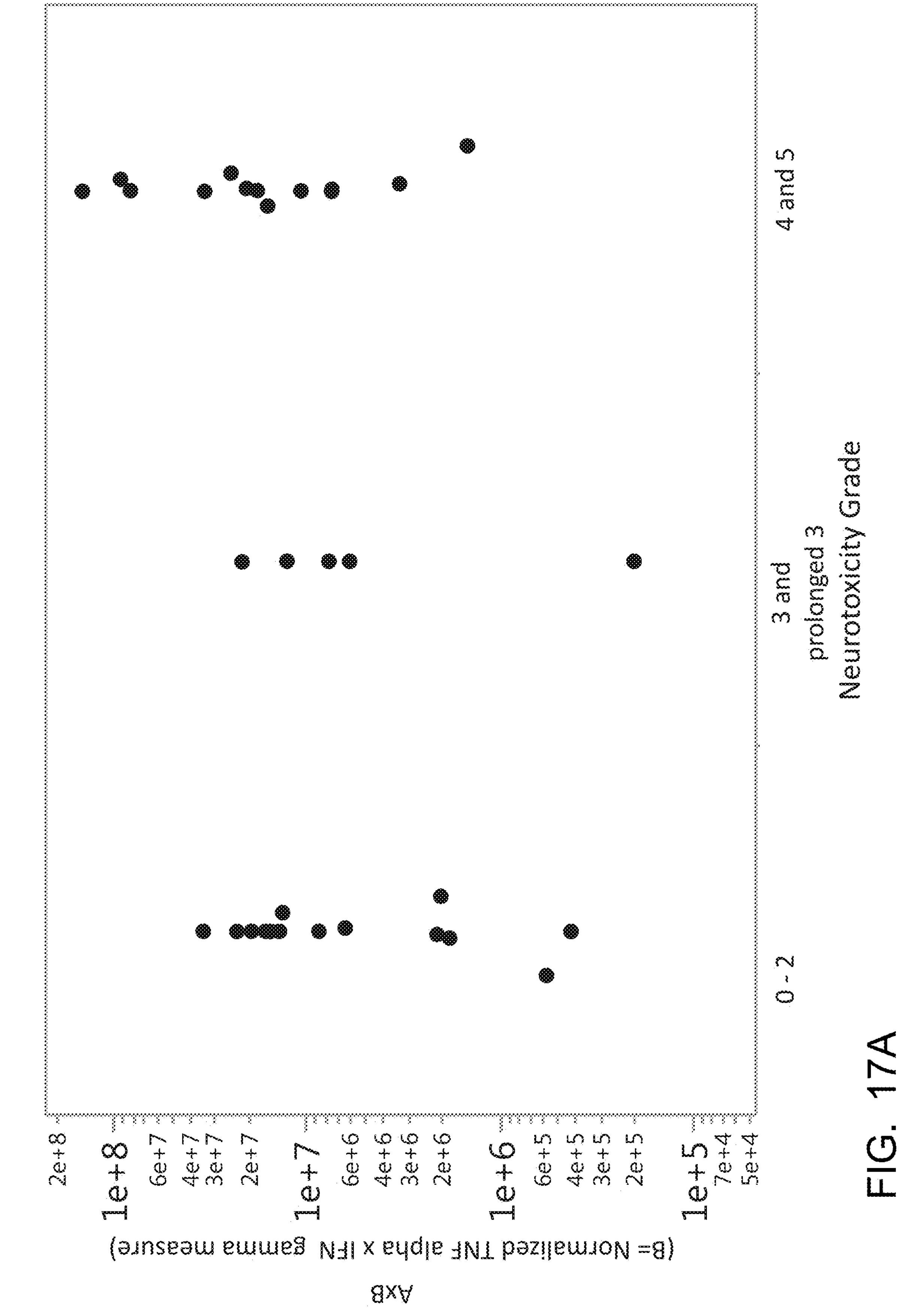
Figure 17B:
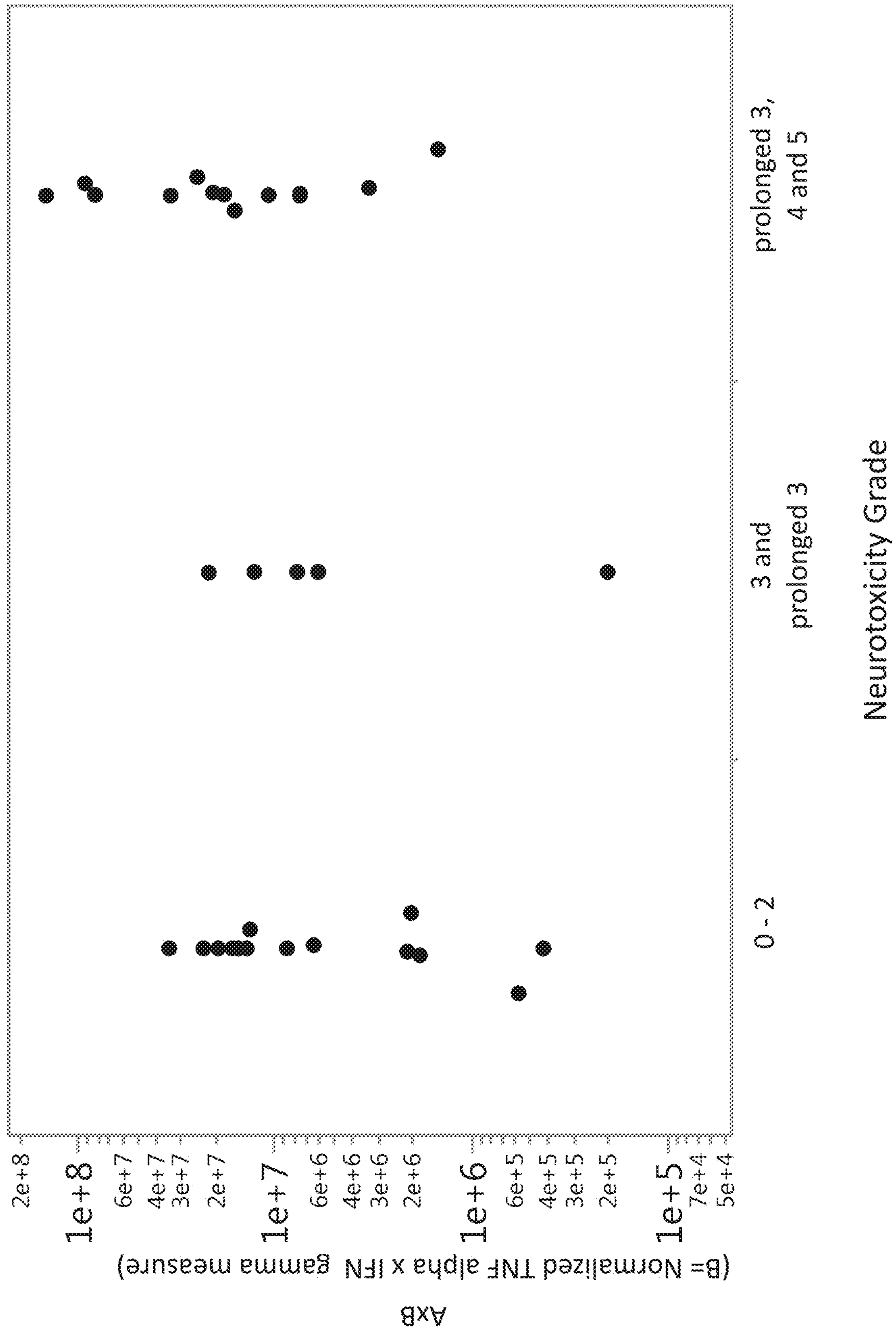
Figure 17C:
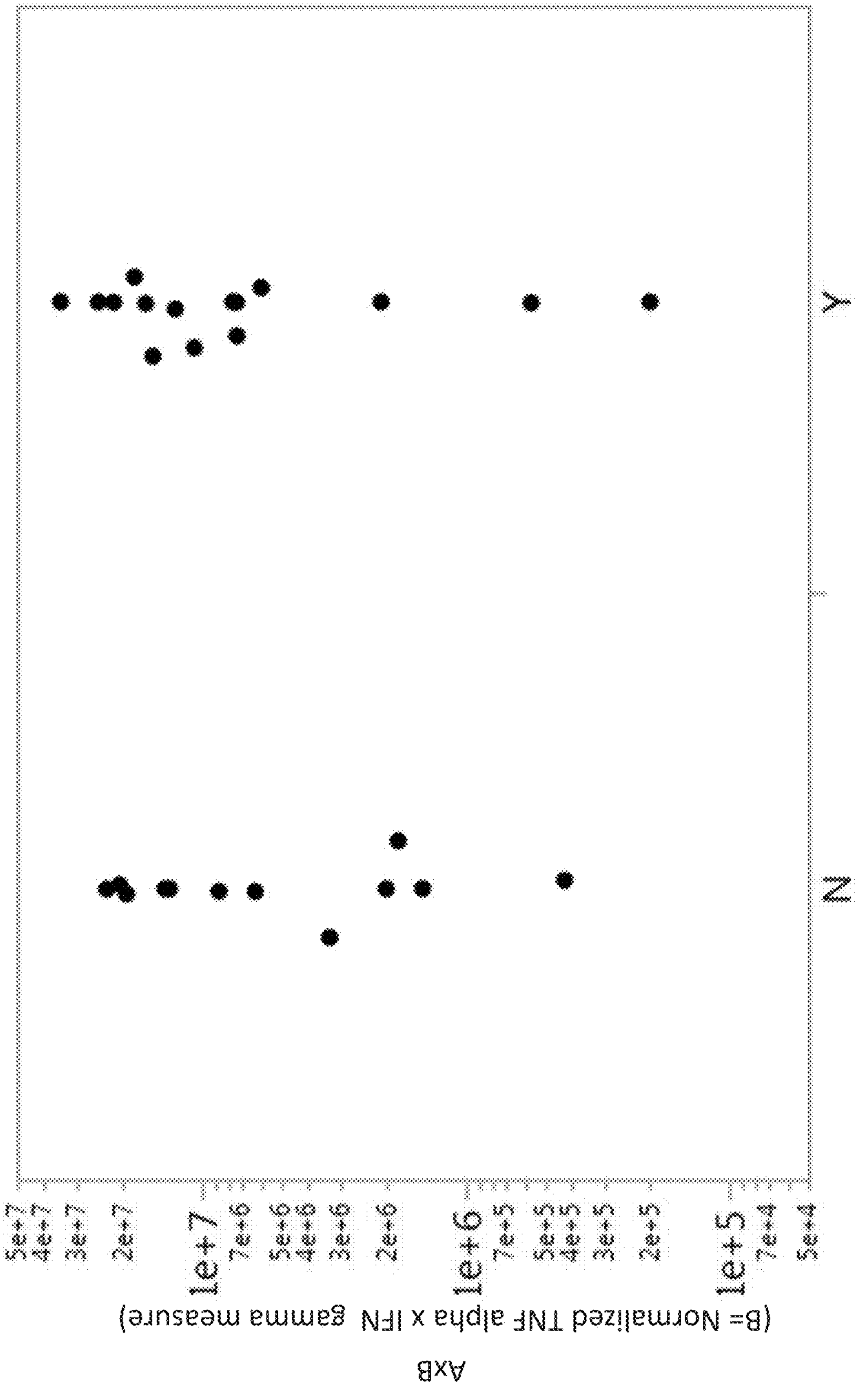

FIGS. 17A-C show a graph displaying individual data points of the number of apoptosis marker-(Annexin V)-CD8+CAR+ cells administered (A) x normalized TNF alpha and IFN gamma production (B) for subjects who developed different grades of neurotoxicity (FIG. 17A-B) or for subjects with different responses (FIG. 17C).

Figure 18A:
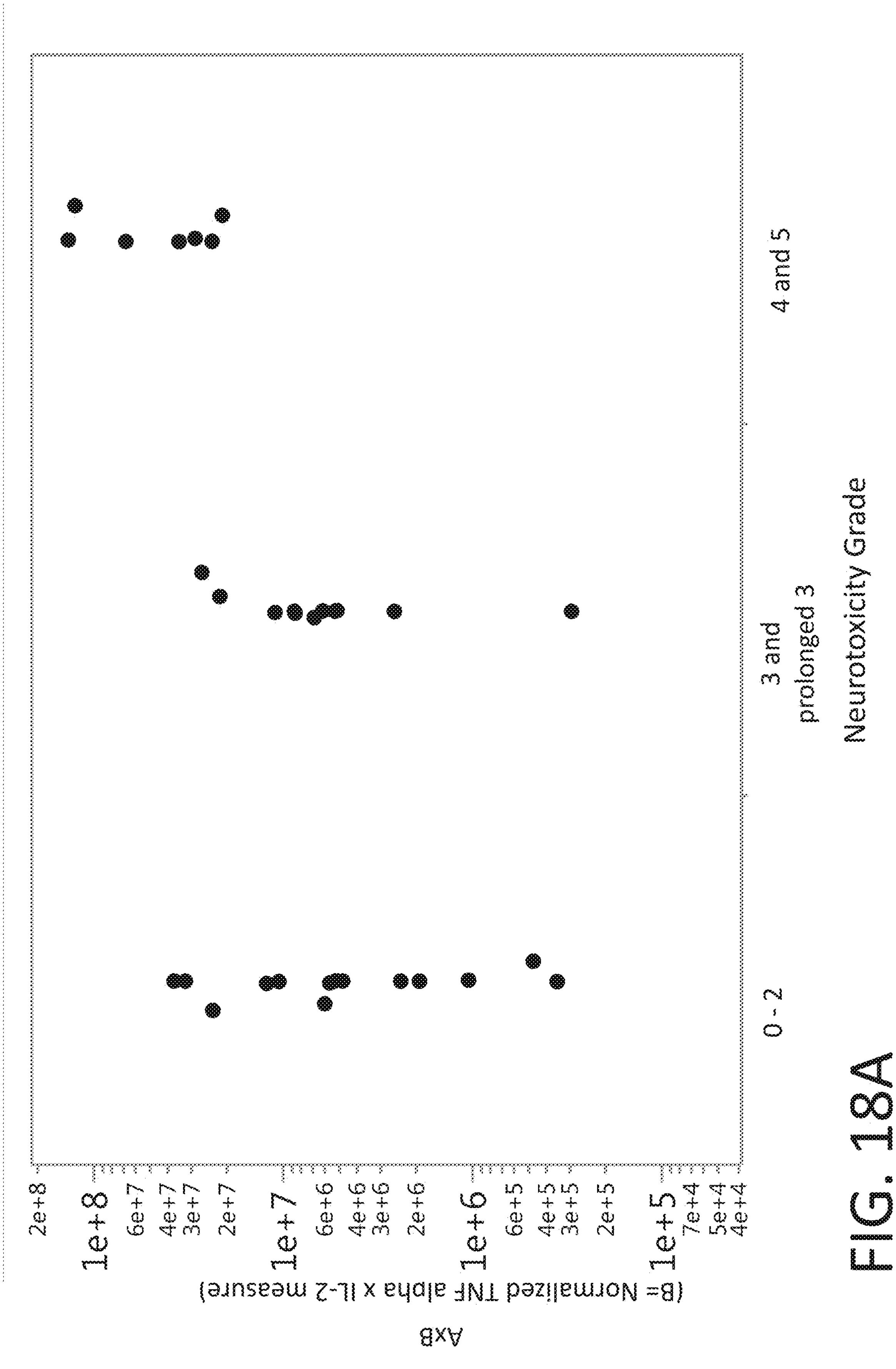
Figure 18B:
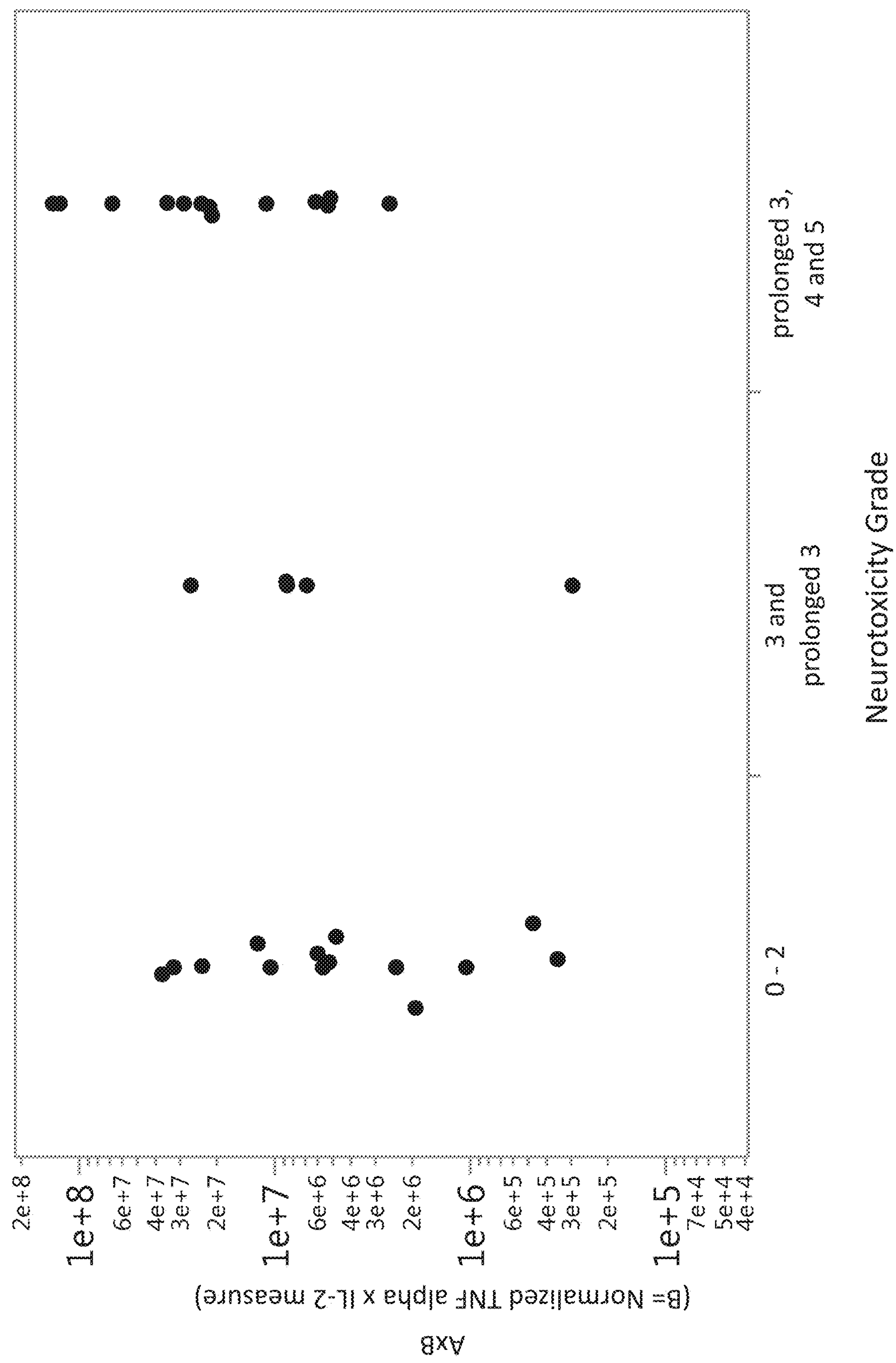
Figure 18C:
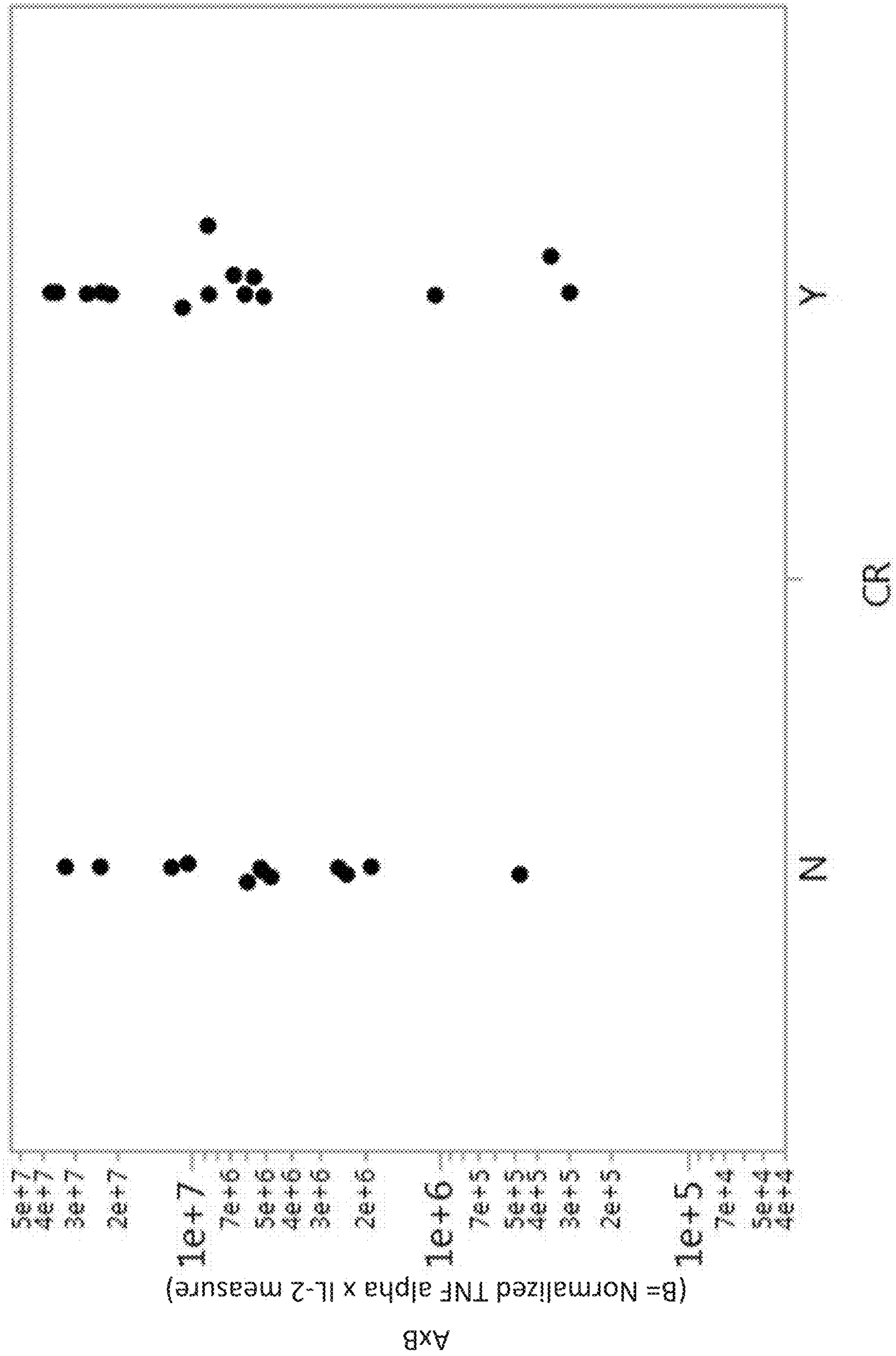

FIGS. 18A-C show a graph displaying individual data points of the number of apoptosis marker-(Annexin V−) CD8+CAR+ cells administered (A) x normalized TNF alpha and IL-2 production (B) for subjects who developed different grades of neurotoxicity (FIG. 18A-B) or for subjects with different responses (FIG. 18C).

Figure 19A:
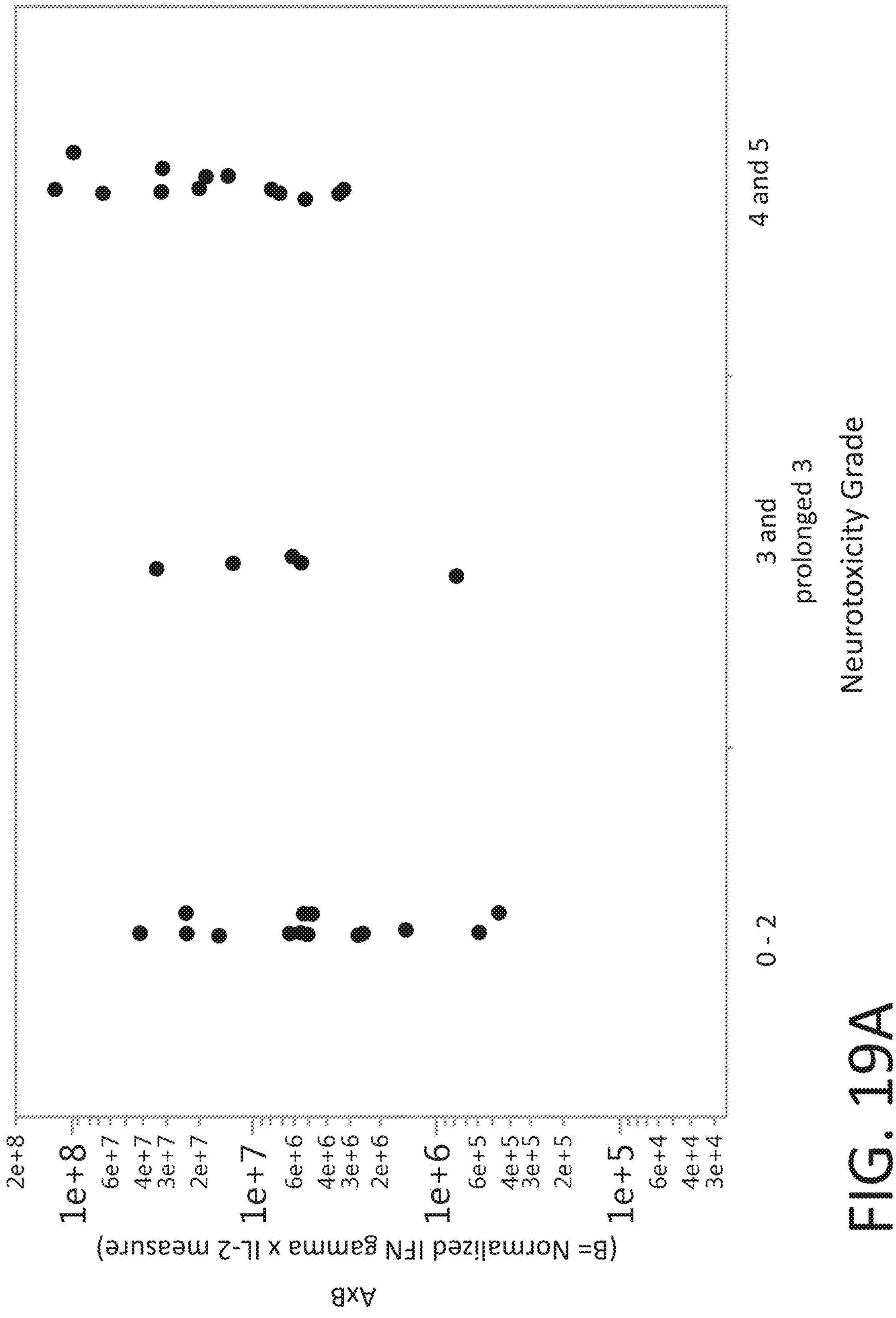
Figure 19B:
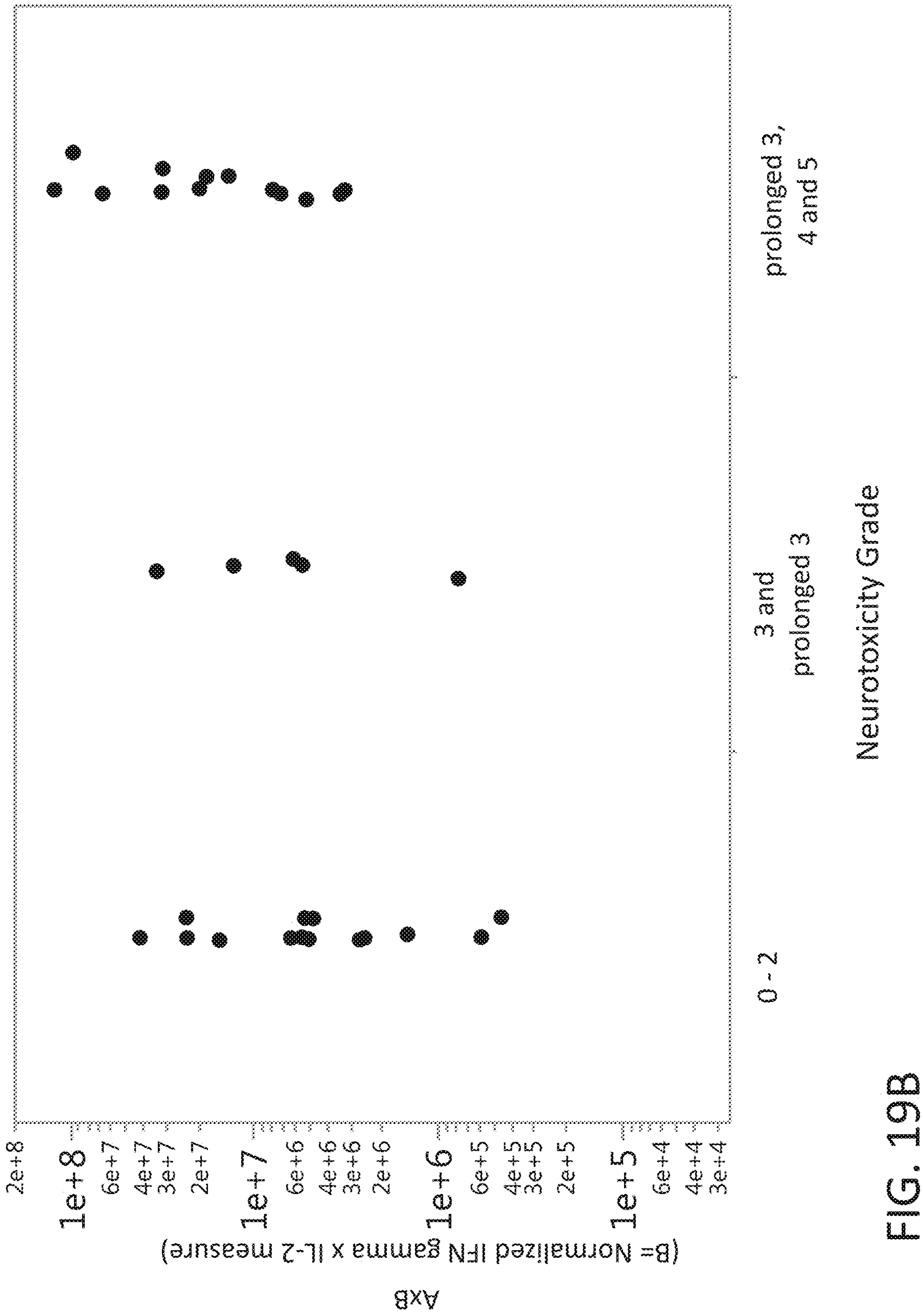
Figure 19C:
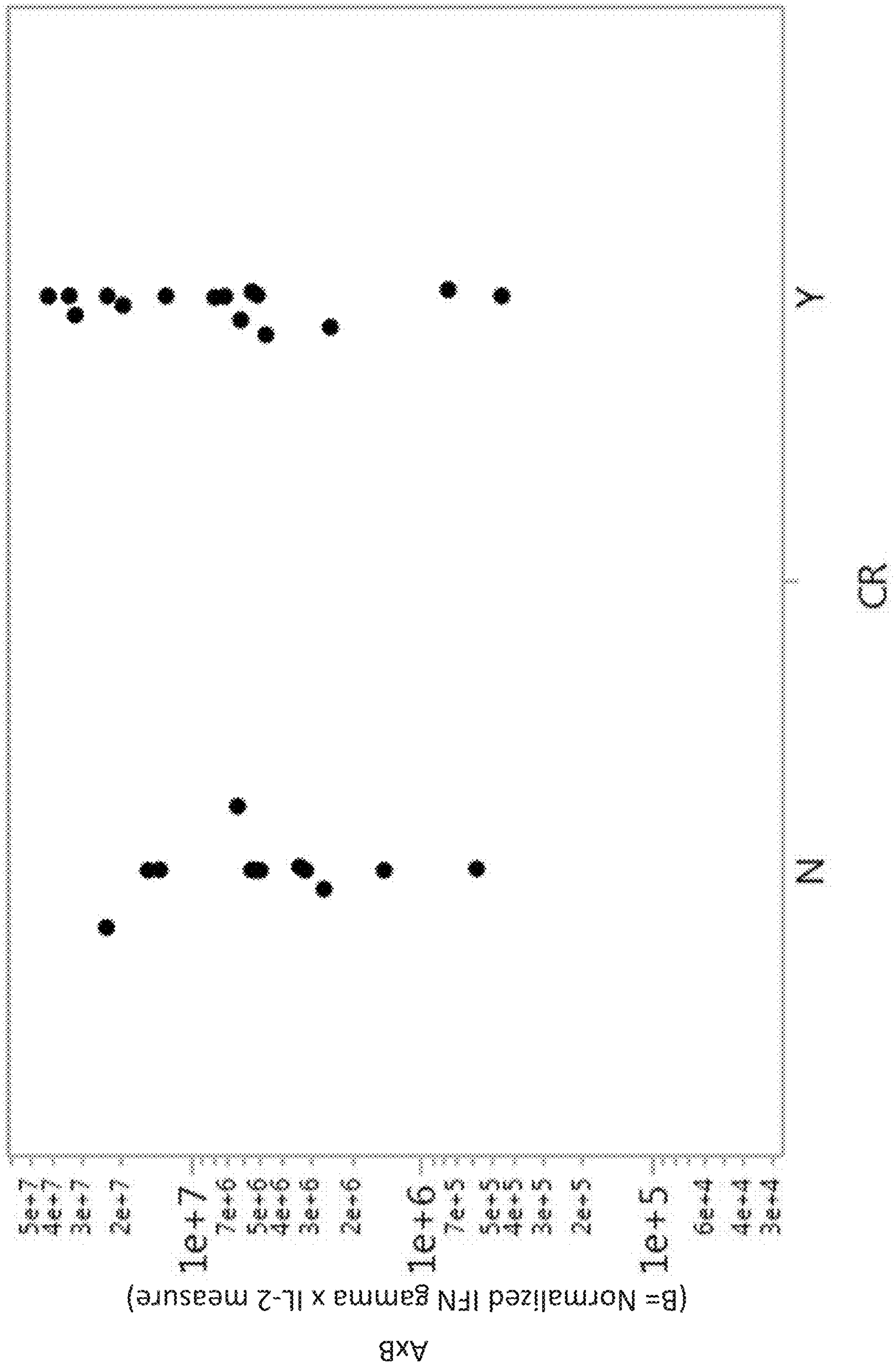

FIGS. 19A-C show a graph displaying individual data points of the number of apoptosis marker-(Annexin-) CD8+ CAR+ cells administered (A) x normalized IFN gamma and IL-2 production (B) for subjects who developed different grades of neurotoxicity (FIG. 19A-B) or for subjects with different responses (FIG. 19C).

Figure 20A:
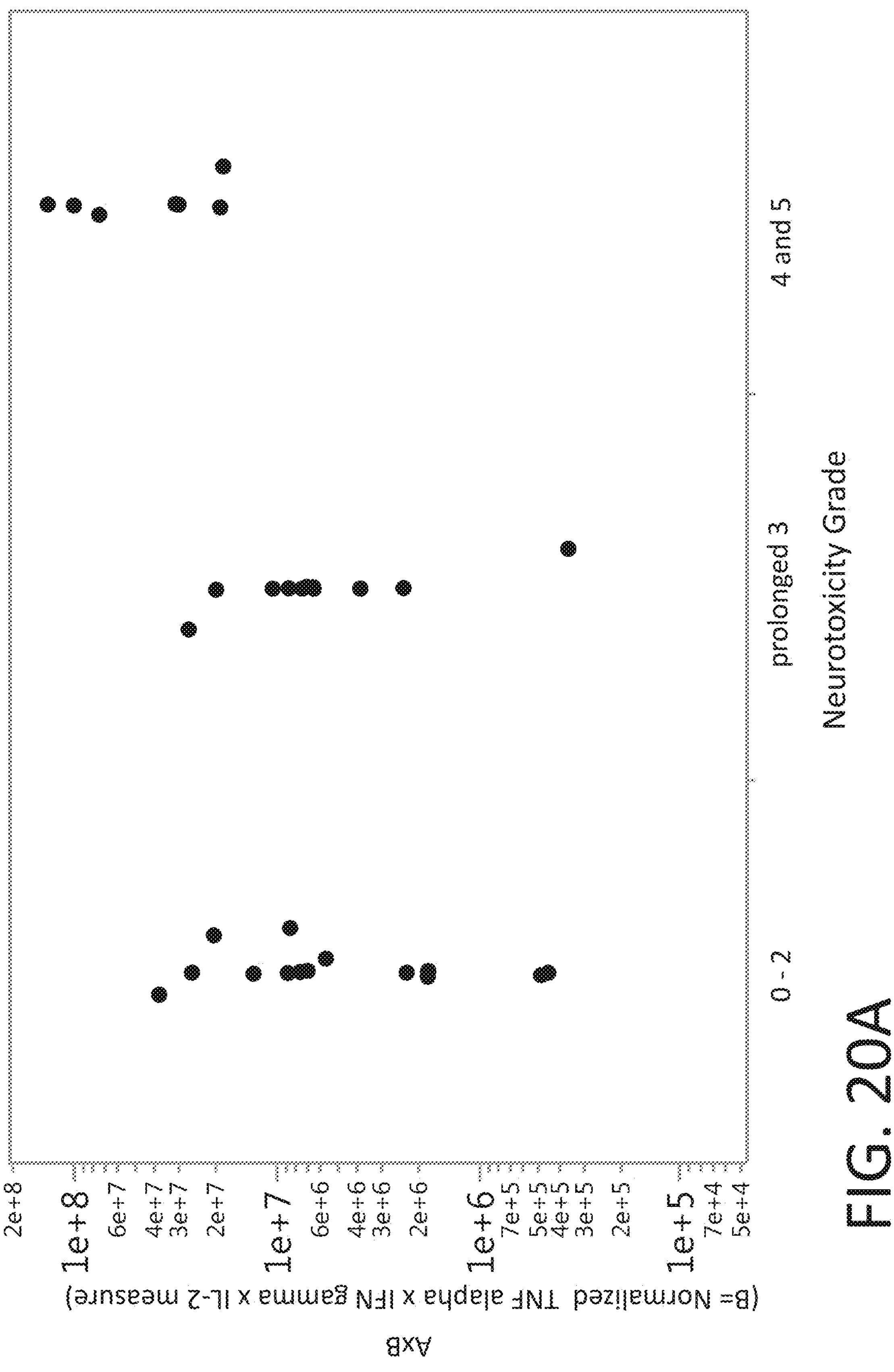
Figure 20B:
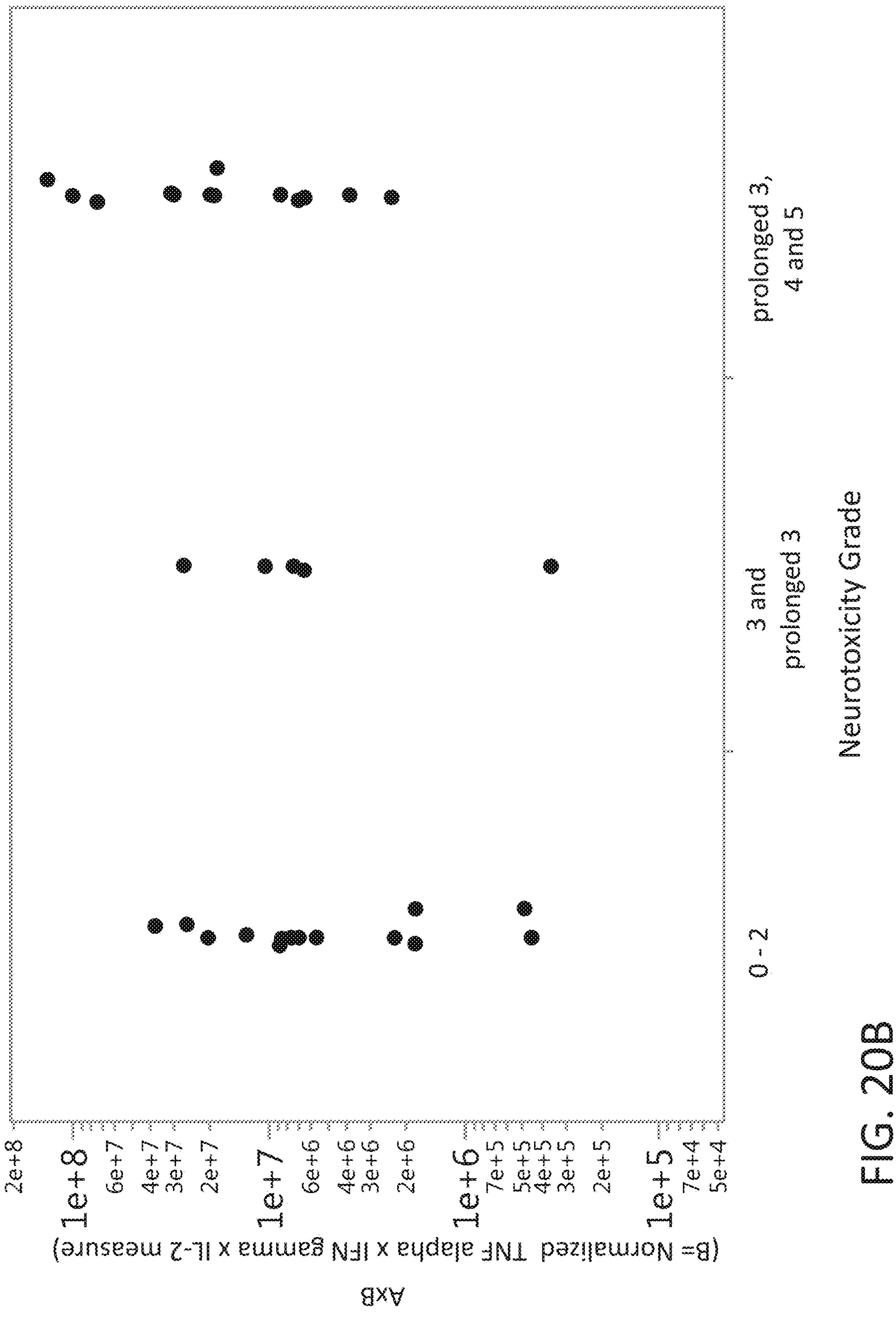
Figure 20C:
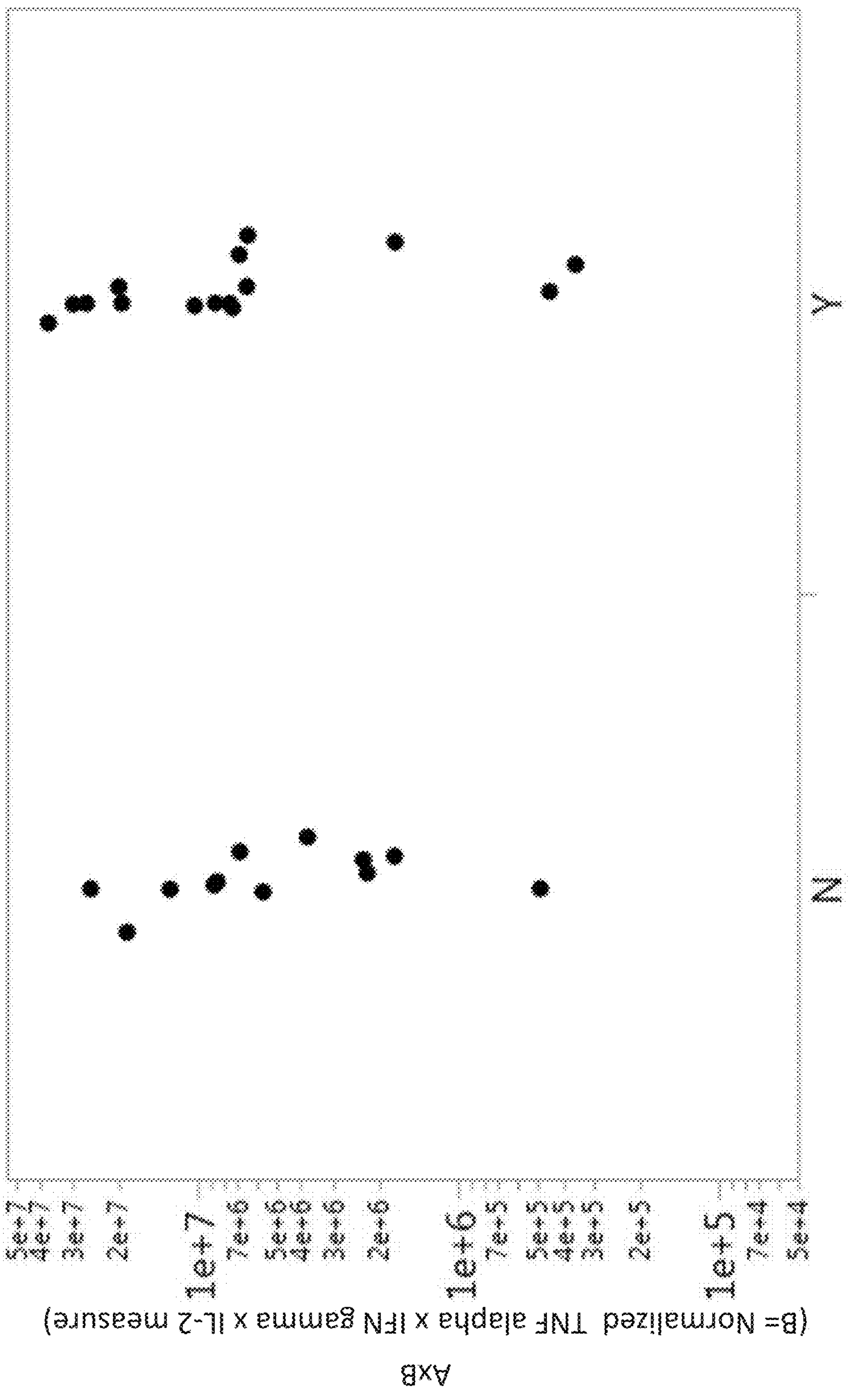

FIGS. 20A-C show a graph displaying individual data points of the number of apoptosis marker-(Annexin-) CD8+ CAR+ cells administered (A) x normalized TNF alpha, IFN gamma, and IL-2 production (B) for subjects who developed different grades of neurotoxicity (FIG. 20A-B) or for subjects with different responses (FIG. 20C).

Figure 21A:
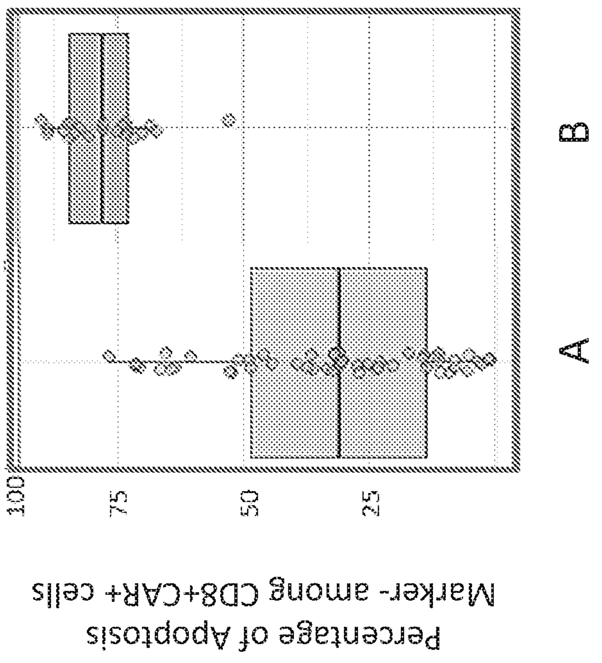
Figure 21B:
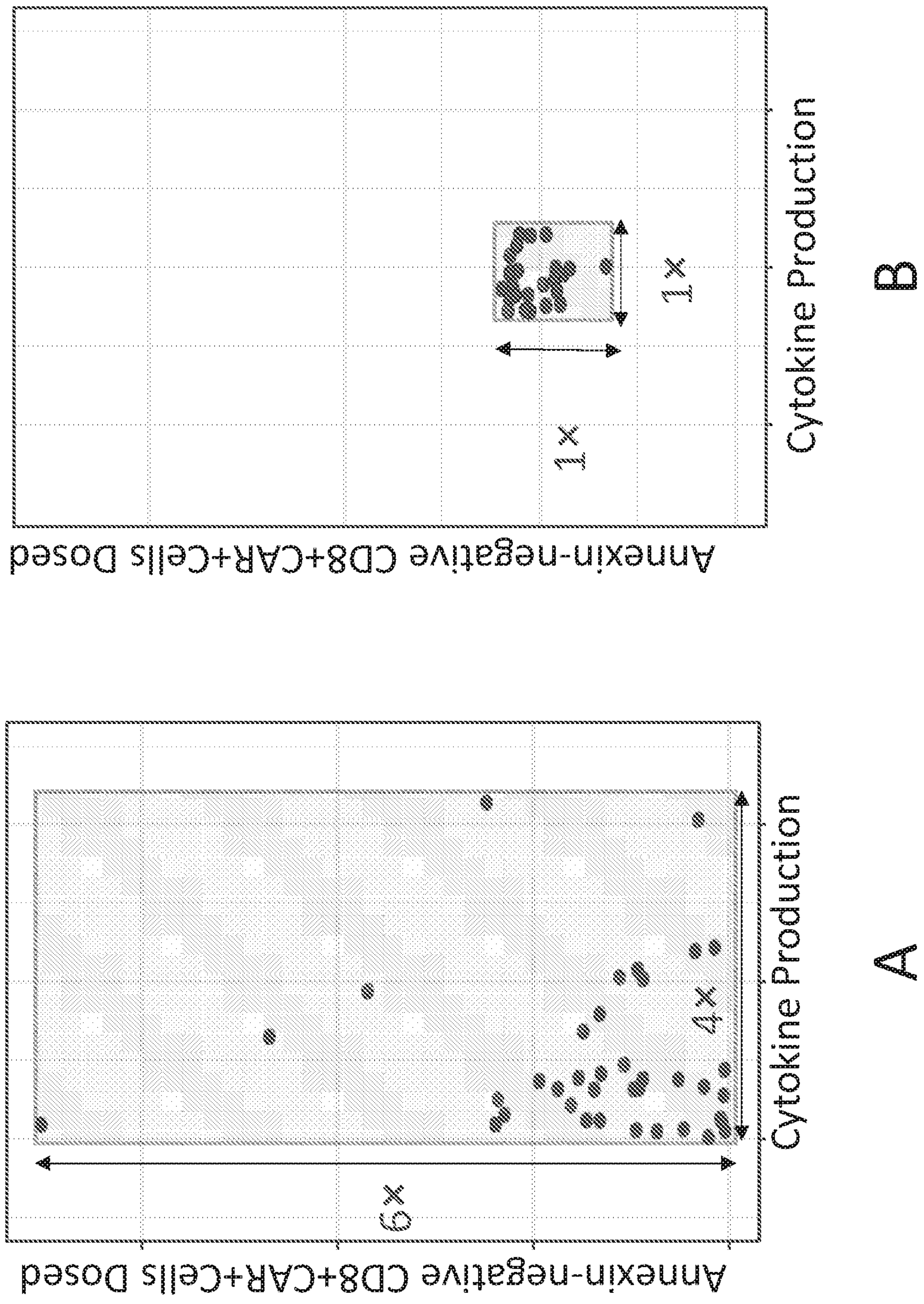

FIGS. 21A and 21B show graphs displaying phenotypes of cells from compositions containing anti-CD19 CAR+ cells that were produced by the process described in Example 1 (A) and the alternative process described in Example 2 (B). FIG. 21A shows a box plot displaying the percentage of apoptosis marker-(Annexin V−) cells among CD8+CAR+ cells.

FIG. 21B shows a graph displaying the values of individual cell compositions for Annexin-negative CD8+CAR+ cells dosed and cytokine production for cell compositions produced by an exemplary process A and an exemplary process B. Shaded boxes indicate the observed distributions.

Figure 22:
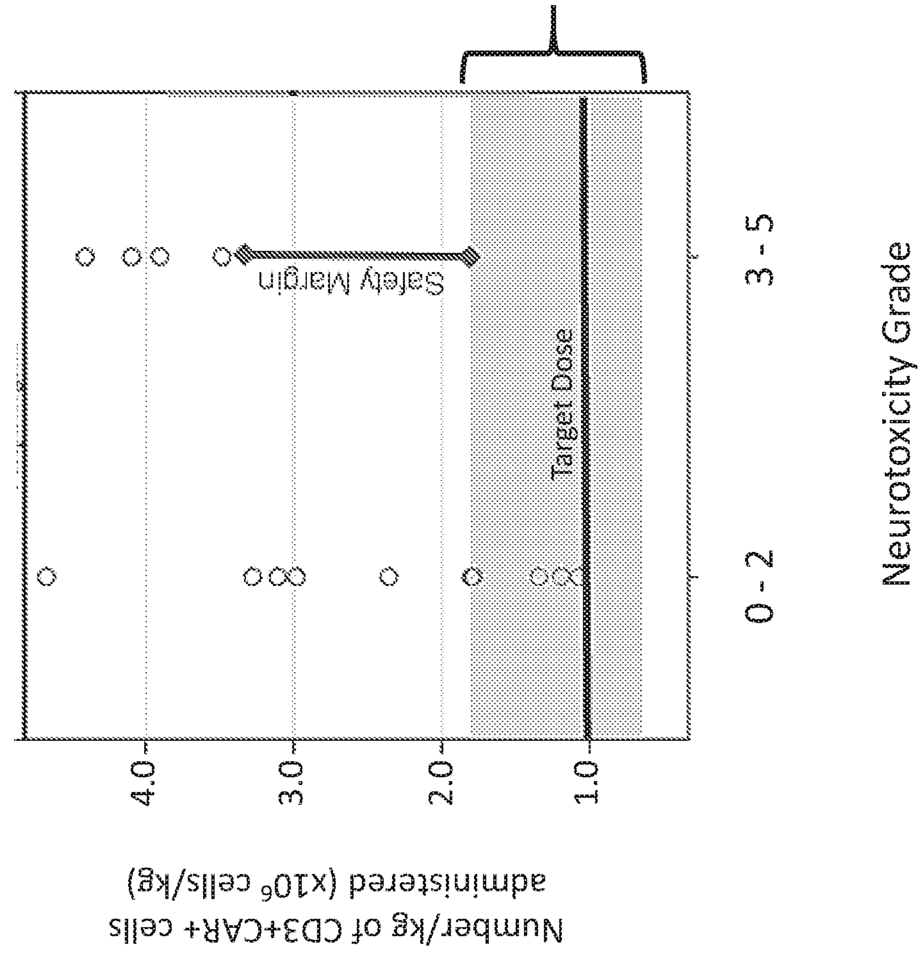

FIG. 22 shows individual data points of the number/kg of CD3+CAR+ cells administered ($\times10^6$ cells/kg) to subjects who developed grade 0-2 or grade 3-5 neurotoxicity.

Figure 23A:
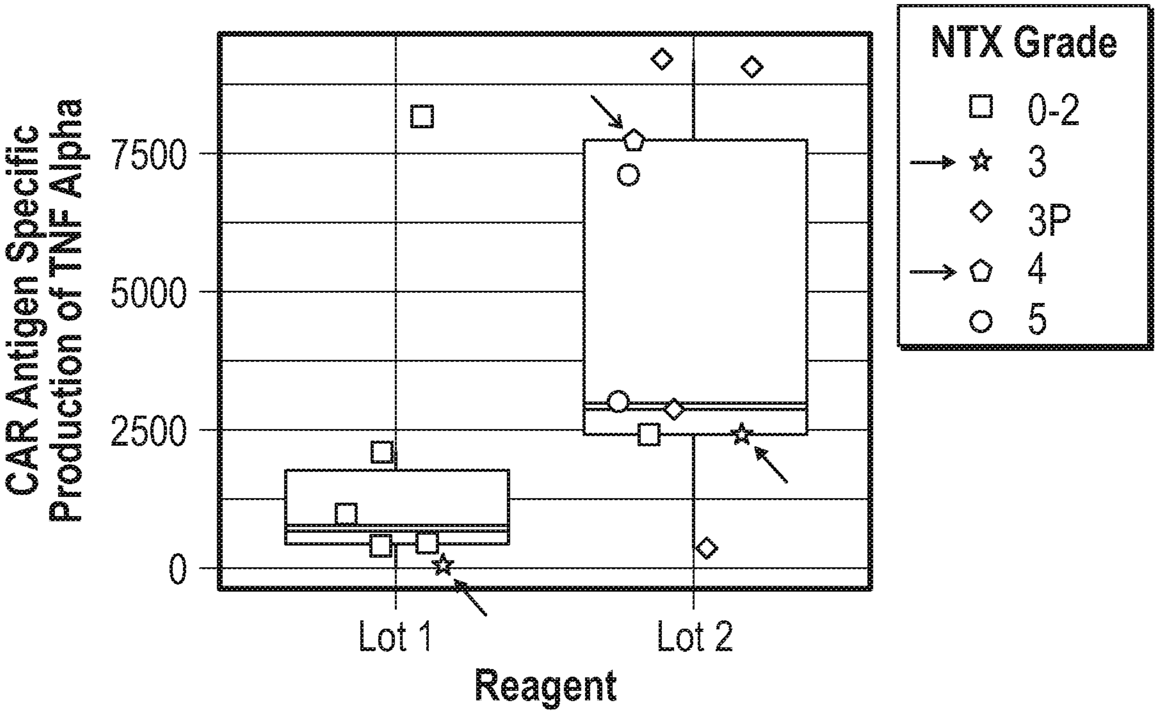
Figure 23B:
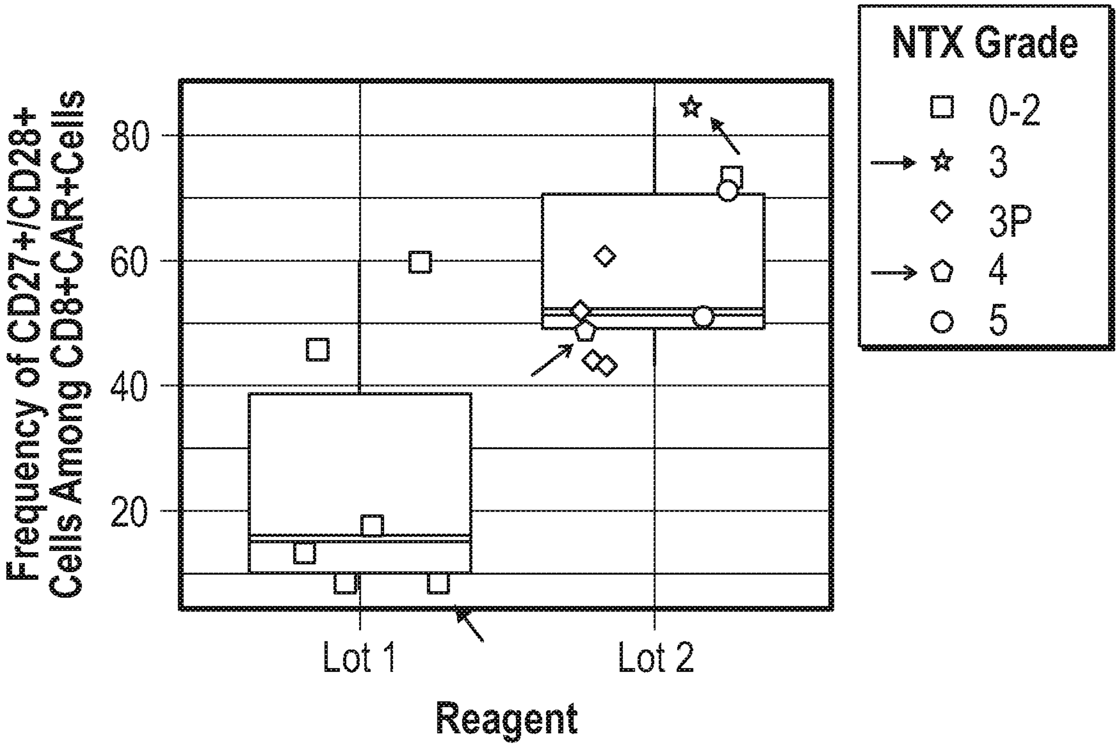
Figure 23C:
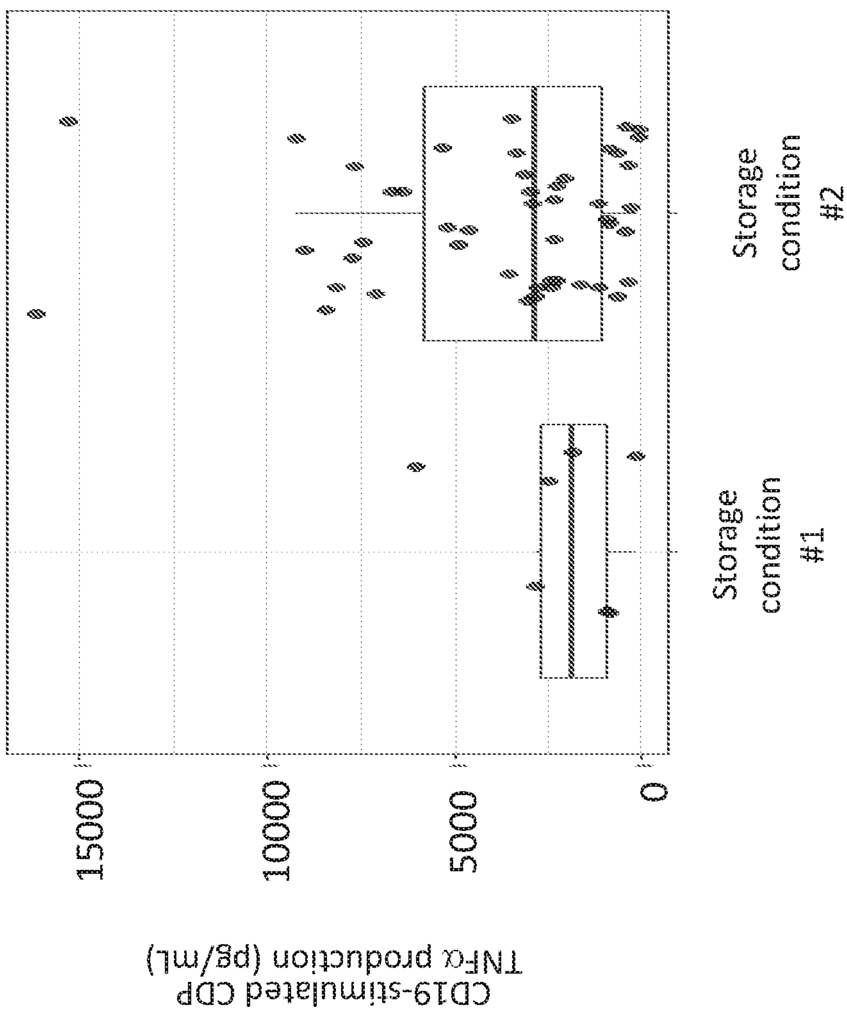

FIGS. 23A-C show box plots comparing T cell compositions containing cells that express an anti-CD19 CAR. FIGS. 23A and 23B show box plots comparing T cell compositions containing that were treated with the same reagent from different lots during production. FIG. 23A quantifies TNF-alpha production following stimulus with CD19 by cell. FIG. 23B displays the frequency of CD27+/CD28+ cells among CD8+CAR+ cells. Data points from T cell compositions associated with a neurotoxicity grade of 0-2 (square), 3 (star with arrow), prolonged 3 (3p; diamond), 4 (pentagon with arrow), and 5 (circle) are shown. FIG. 23C shows TNF-alpha production following stimulus with CD19 expressing cells in T cell compositions containing cells that express an anti-CD19 CAR that were generated with the same media that was stored under different conditions.

Figure 24:
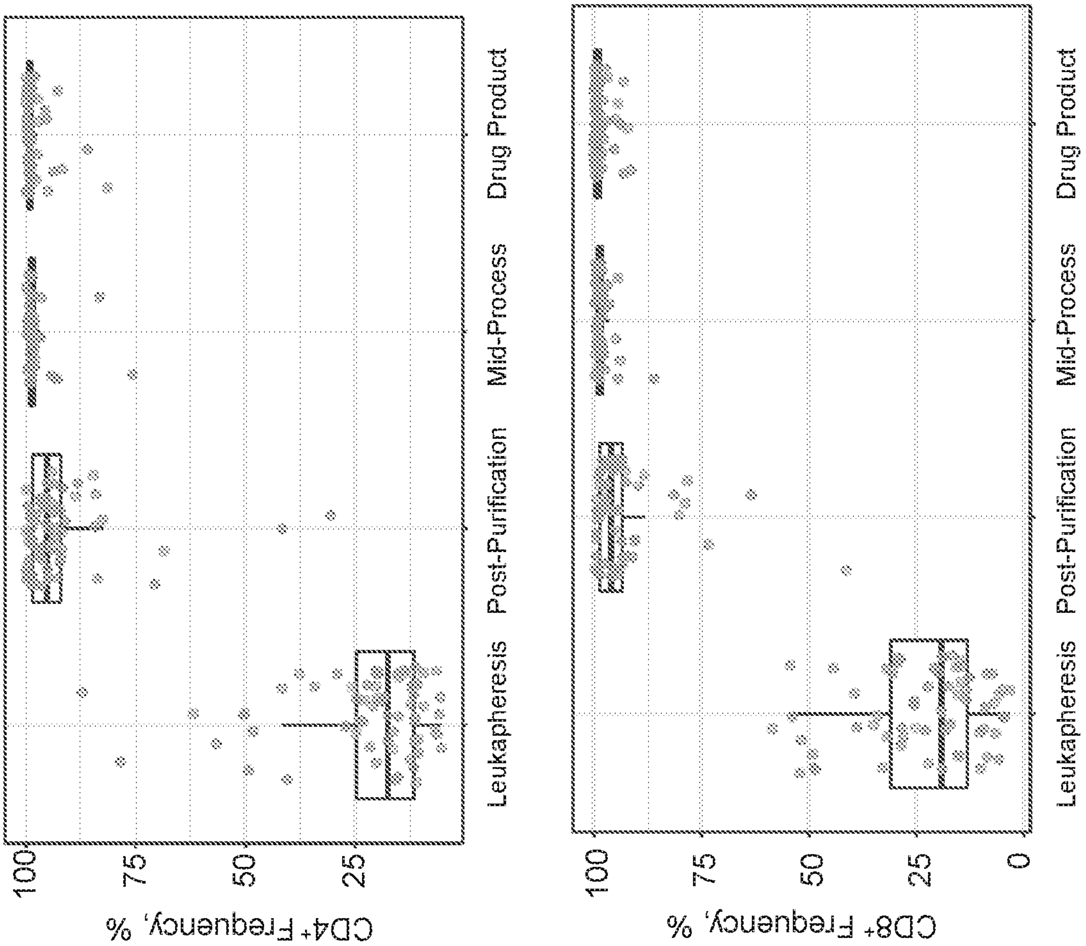

FIG. 24 shows box plots displaying the T cell purity of T cell compositions enriched for CD4+ and CD8+ cells at different stages of the process for generating engineered cell compositions containing CAR T cells that is described in Example 8. The frequency (% of total leukocytes) of CD4+ and CD8+ cells in the compositions are shown.

Figure 25:
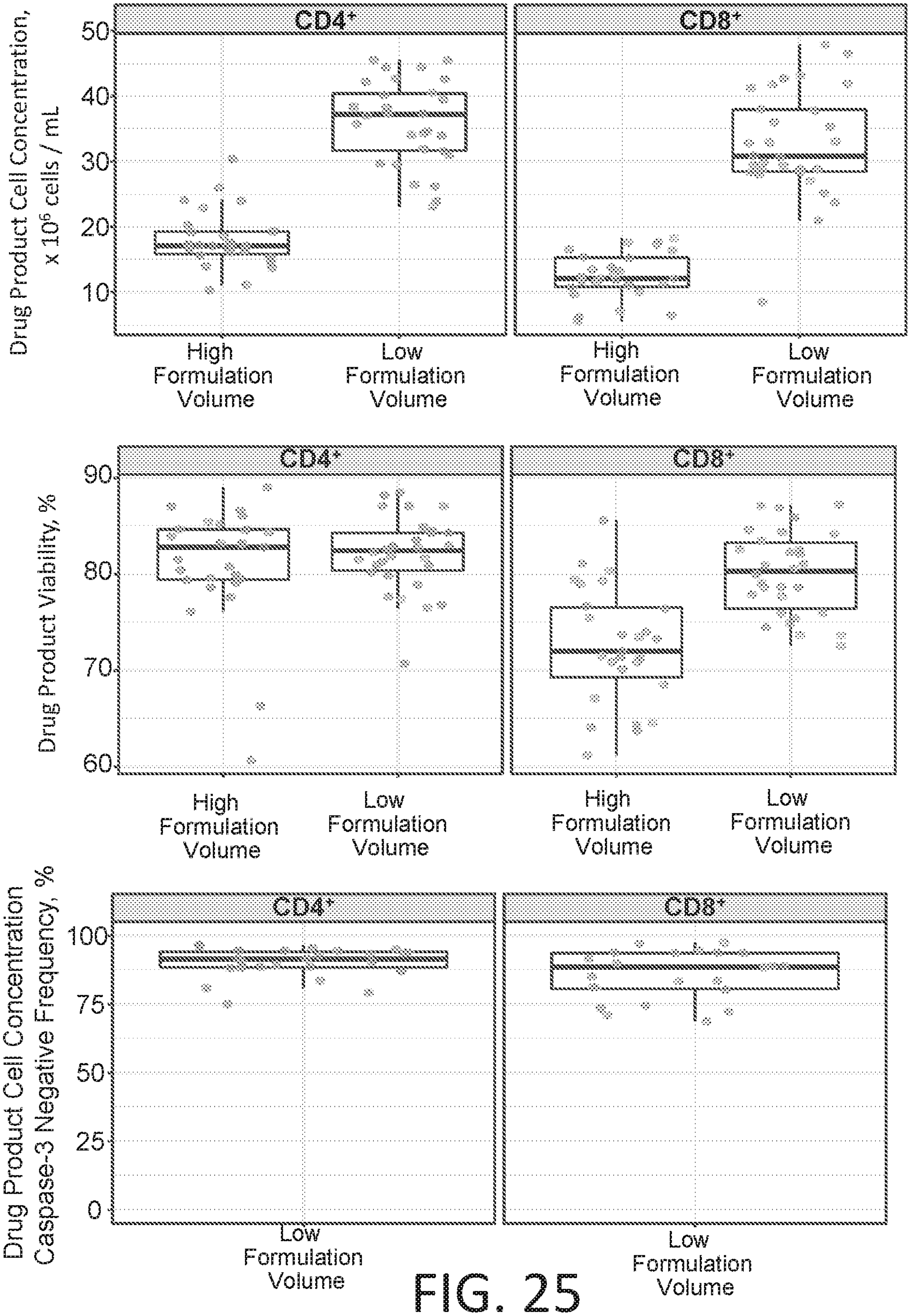

FIG. 25 shows a graph depicting the levels of CD3+ T cells in individual doses at dose level 1 (DL1) and dose level 2 (DL2).

Figure 26:
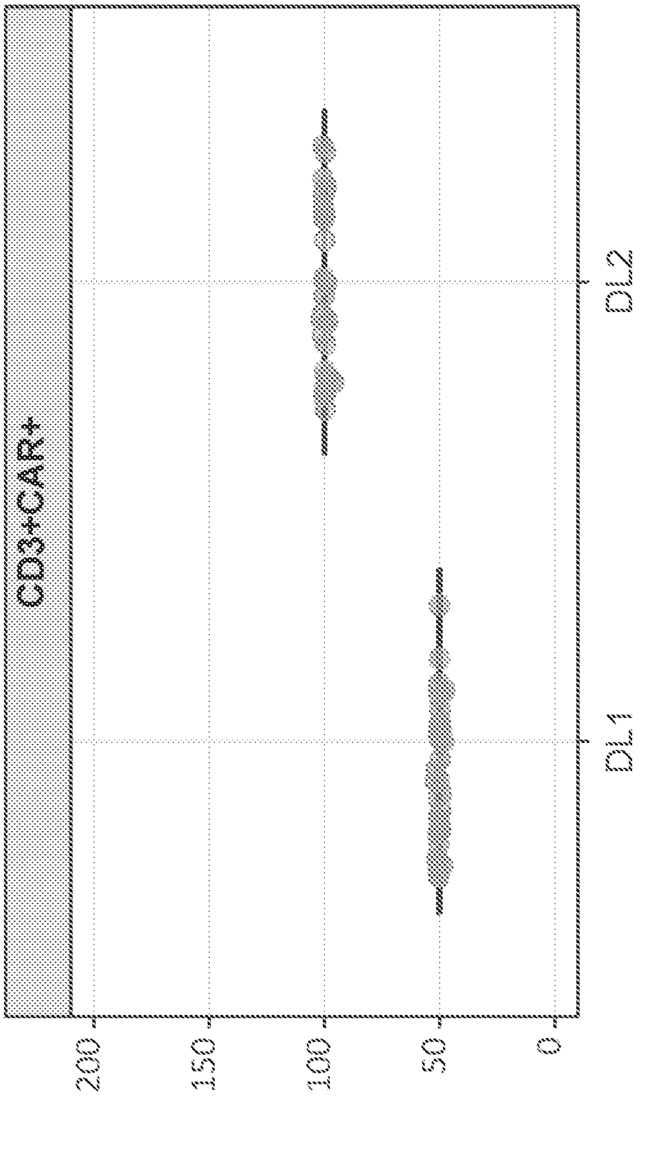

FIG. 26 shows box plots displaying the concentration, viability, and frequency of caspase-3 negative CD4+ and CD8+ T cells of therapeutic cell compositions containing CAR-T cells in a high or low formulation volume.

Figure 27:
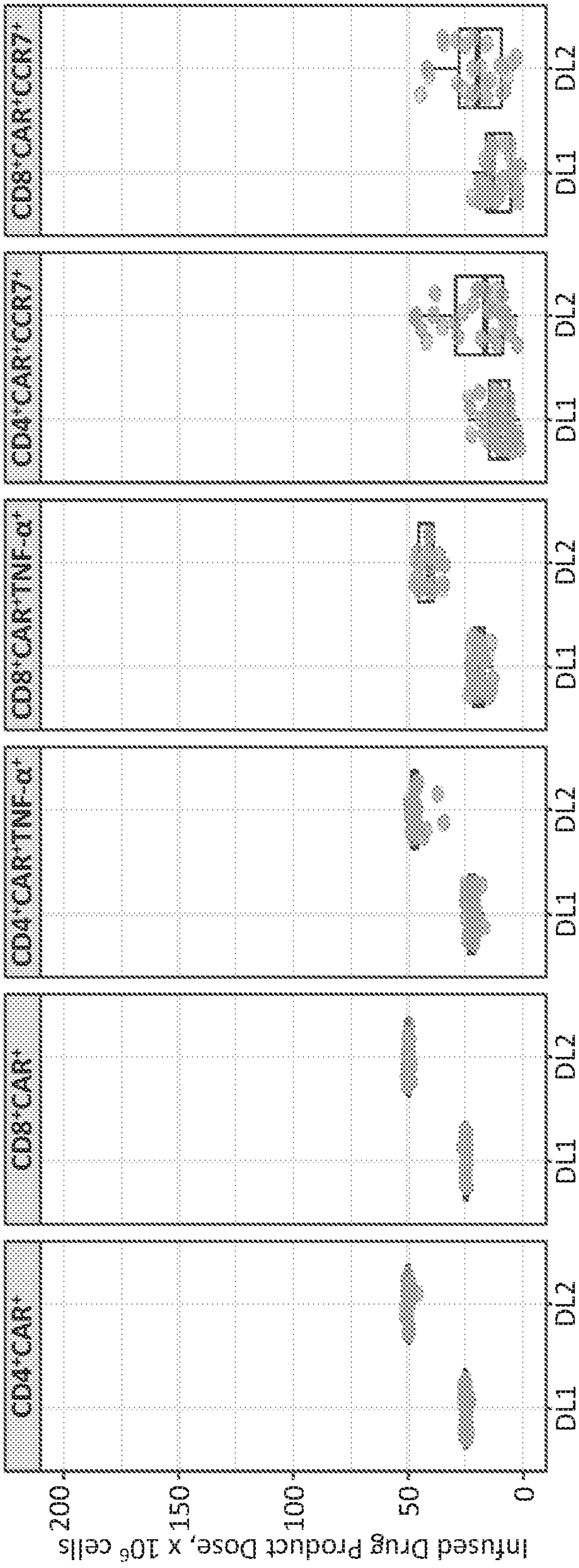

FIG. 27 shows graphs displaying the controlled dose, T cell phenotypes, and cell specific function of individual therapeutic cell composition containing CAR T cells that were infused. Data points of the amounts of CD4+CAR+, CD8+CAR+, CD4+CAR+TNF-α, CD8+CAR+TNF-α, CD4+CAR+CCR7+, CD8+CAR+CCR7+ infused into individual subjects are shown.

Figure 28:
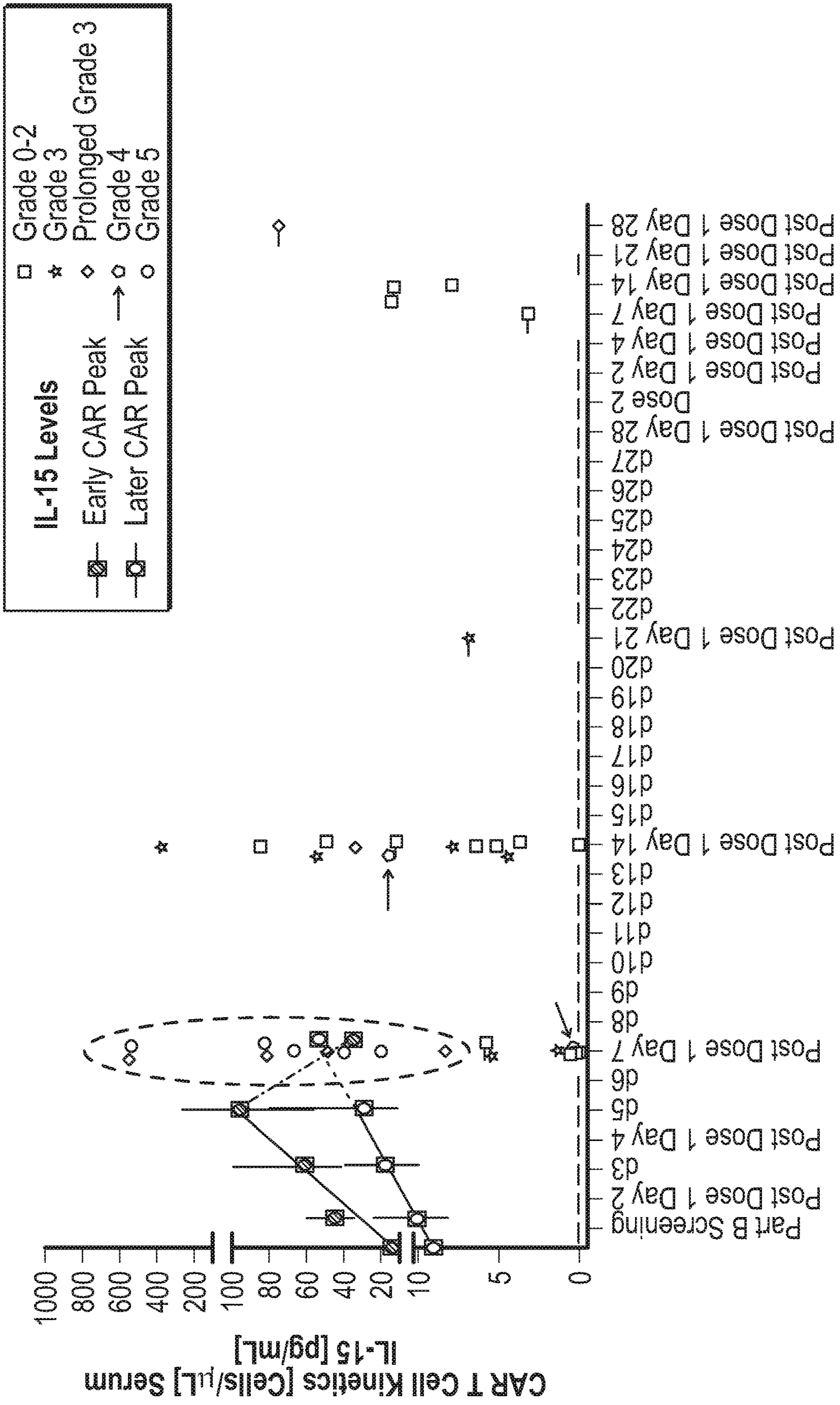

FIG. 28 shows a graph displaying (i) for each of a number of individual subjects, individual non-boxed dots indicate maximum PK measure (number of CAR+ T cells/μL of blood (PK measure) at peak (on an individual subject-by-subject basis, the time-point at which the highest number of CAR+ T cells was measured, among the time-points at which CAR+ T cell numbers were assessed following treatment of the subject with anti-CD19 CAR-expressing T cell compositions) (with dots also indicating the highest grade of neurotoxicity observed for each subject: grade 0-2 (square), grade 3 (star), prolonged grade 3 (diamond), grade 4 (pentagon with arrow), or grade 5 (circle) neurotoxicity, and (ii) median levels, for those of such patients deemed to have had an early or late CAR+ T cell peak (indicated by upper and lower lines with boxed dots with range bars, respectively) of IL-15 (picograms/mL) in serum at various indicated time points prior to and following administration of such T cell compositions. The oval indicates subjects in which early, rapid expansion of CAR-T cells was observed, as compared to other subjects.

DETAILED DESCRIPTION

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. DOSES AND DOSE DETERMINATION IN THERAPEUTIC T CELL COMPOSITIONS TO REDUCE RISK OF TOXICITY

Provided herein are methods, compositions, and articles of manufacture for use in connection with cell therapy, such as engineered T cell therapy for the treatment of diseases and conditions, including various tumors. The provided embodiments relate to therapeutic T cell compositions containing engineered T cells such as those engineered to express recombinant proteins such as expressing recombinant receptors designed to recognize and/or specifically bind to molecules associated with the disease or condition and result in a response, such as an immune response against such molecules upon binding to such molecules. The receptors may include chimeric receptors, e.g., chimeric antigen receptors (CARs), and other transgenic antigen receptors including transgenic T cell receptors (TCRs).

The provided embodiments in some aspects relate to aspects in which certain parameters related to function or activity of the therapeutic T cell composition, e.g. antigen-specific or recombinant receptor-dependent activity, may predict risk of the likelihood of developing an adverse event or toxicity, such as severe neurotoxicity, in a subject administered the T cell composition and/or may provide information about the potency of the therapeutic T cell composition. Aspects of the provided embodiments also relate to administering or providing a unit dose containing a number of units, such as a target number of units, that is a function of the number of cells of a certain phenotype, such as a phenotype indicative of biologically active cells or a cell population, and the function or activity of cells present in the therapeutic T cell composition, e.g., antigen-specific or recombinant receptor-dependent activity, including for use in connection with dosing of the therapeutic T cell composition. In some aspects, the provided methods can ameliorate or reduce the risk of toxicity in a subject administered a dose of the therapeutic T cell composition, while ensuring potency of the T cell composition. Also provided are articles of manufacture containing the cells and designed for administration following such dosing regimens.

In some embodiments, the provided methods, doses, unit doses, compositions, and articles of manufacture are based on observations that it can be advantageous to take into account certain parameters and combinations thereof when determining appropriate dose of cell therapy and/or releasing cell compositions for therapy. In certain available methods, doses are based on numbers of particular cell types, such as those engineered to exhibit a particular activity, such as those positive for an engineered receptor. For example, in certain available methods and doses, dose is based upon an observed or suspected relationship between the number (or number per patient weight) of viable engineered T cells, or of a subset thereof, such as of viable, cytotoxic (e.g., CD8+) engineered T cells. In various contexts, such numbers can have a relationship with efficacy and/or safety outcomes, such as response and/or risk of toxicities such as neurotoxicity (NTx), cerebral edema and CRS. Provided herein are embodiments based on the observation that nonetheless, such metrics in some contexts do not consistently adequately predict the risk of toxicities, e.g., of severe neurotoxicity or cerebral edema, particularly without taking into account other variables. Accordingly, approaches for defining dose and evaluating product for release that rely on such metrics alone may not be entirely satisfactory. For example, such approaches may in some contexts fail to define an appropriate safety margin and/or therapeutic window, for safe and effective cell therapy. Provided herein are methods (including treatment, dosing, dose-determination and release assay methods), and doses and therapeutic compositions that address such shortcomings.

In some aspects, it is found herein that certain product specific attributes and clinical or patient specific factors can impact risk, relative risk or probability of developing a toxicity following administration of a cell therapy. In some cases, variability in such product-specific and/or patient-specific attributes can result in variability in attributes of doses of therapeutic cell compositions administered to different individuals within a group of subjects and/or to outcomes observed in such different individuals following such administration. In some aspects, such variability is observed despite certain similarities in the doses administered to the various individual subjects, such as where the dose or composition administered contains cells engineered to express the same engineered receptor, such as chimeric antigen receptor, containing or transduced or transfected with the same vector; in some aspects, the different doses or compositions administered to the different subjects include or contain or consist of the same number (or number per weight or other characteristic of a subject) of cells (or cells of a particular phenotype). In some aspects, controlling variability of one or more attributes of the cell composition can minimize such risks and/or minimize such variability in attributes of doses or outcomes. In some aspects, minimizing or controlling variability such as degree of variance in (or increasing consistency in) one or more product or composition attributes across subjects to which a particular therapy is administered, can minimize the impact of variability in outcome or dose attributes among patients with variability in patient-specific factors or clinical factors that would otherwise impact such outcome or dose attributes. For example, in some aspects, reducing variability in product or composition attribute(s) can reduce variability in, or can reduce, risk or likelihood of a subject or population of subjects developing a treatment-related toxicity such as neurotoxicity or cerebral edema or grade thereof, such as without reducing or substantially reducing likelihood of achieving a particular response or clinical outcome. In some cases, reducing variability account for clinical or patient specific factors may minimize risk of developing a toxicity, such as a neurotoxicity or cerebral edema, following administration of a cell therapy.

In some aspects, variability among unit doses of a cell composition can be due to one or more aspects of manufacturing processes employed in the generation or manufacture of an engineered cell therapy. In some cases, changes to raw materials or handling or storage thereof may impact variables observed herein to impact risk of toxicity and/or outcomes. In some aspects, lot-to-lot variability or storage/handling of raw materials and/or the use of different raw materials among processes carried out across a number of subjects, may impact, such as by increasing the variability of or increasing or decreasing, certain aspects of the generated cell compositions, such as aspects that, if varied, may result in variability in toxicity risk or clinical outcomes among subjects administered cell therapies, particularly among such subjects differing in certain patient-specific attributes. In some embodiments, provided are approaches involving the assessment, testing for, and/or controlling for potential impact on or variability in one or more such product attributes or risks or likelihoods, as a result of a (such as any or all) raw material(s), lot(s), reagent(s) or storage or handling thereof, or change thereto. In some embodiments, such approaches include assays such as those carried out prior to the use of such raw material, lot, storage or handling, in production of a cell composition to be administered to a subject or before such administration. In some aspects, the assays assess the impact of the raw material, lot, change, or handling or storage method, on one or more attributes in a cell composition such as those observed herein to impact risk of toxicity or outcome or to exacerbate the impact of patient-to-patient variability in such outcomes. In some aspects, the assays assess whether an acceptably low degree of variance in, compared to another material, lot, or storage or handling method, or an acceptably low impact, on such one or more attributes. In some aspects, the raw material, lot, or method for storage or handling, is released for use in manufacturing of the cell therapy to be administered to the patient— or such cell therapy is administered to the patient—if, such as only if or only after, the assay confirms that such variance or impact is within the acceptable range or value or limit. In some of any such embodiments, such parameters assessed may include number or percentage of biologically active cells, non-apoptotic cells, healthy cells, cells of a particular potency (or number or percentage of biologically active, non-apoptotic, or healthy or potent cells of a given phenotype) and/or a metric indicative of potency, such as potency per cell, of the composition. In some embodiments, determining that variability in one or more such attribute is below a certain level with a new raw material or lot or storage or handling method, can mitigate risk of toxicity or reduction in response following implementation of such new raw material or lot or storage or handling method. In some embodiments, among such provided methods are methods that assay a composition prior to release of product and/or adjust the dosing strategy based on such parameters.

In some embodiments, one or more risks or outcomes such as risk of toxicity or appropriate dose may be dependent on or vary with one or more treatment- or patient-specific variable. For example, among the exemplary clinical and patient attributes that can correlate in some embodiments with risk of certain toxicities, including neurotoxicity or cerebral edema or grade thereof, include patient health or age (e.g., whether the patient was greater than or less than or equal to 30 years of age), prior treatment history, including numbers of prior treatments and/or whether a patient has received a lymphodepleting and/or holding chemotherapy prior to treatment, such as one including fludarabine. In particular, among such patient or clinical attributes that may increase the risk, relative risk and/or probability of developing a toxicity following administration of a dose of cells of a cell therapy (e.g. CAR-T cell therapy), include, for example, fewer prior therapies, such as two or fewer prior therapies, young age, e.g. younger than 30 years of age, the ratio of CD4+ to CD8+ T cell in a patient apheresis sample or the number of cells administered to a subject due to weight-based dosing of cells, e.g. more cells administered to subjects with a greater weight. Such attributes may impact the resulting attributes of an engineered cell composition generated from the subject and/or impact patient factors at infusion that may contribute to a risk of developing toxicity following administration of a cell therapy (e.g. CAR T cells). Provided are approaches that decrease variability in outcomes and/or risk in toxicities among patients with variability in one or more such patient-specific or treatment attributes. Also provided are approaches that take into account such patient- or treatment-specific attributes in determining or formulating or administering a dose of the cell therapy to a patient or patients.

In some embodiments, the provided approaches such as administration methods and doses include (or include administering) fewer cells or fewer biologically active or potent cells (or engineered cells) in a dose administered to a subject that is healthier, is younger, e.g. younger than 30 years of age, has had fewer prior therapies, e.g. two or fewer prior therapies, or has had a certain prior treatment such as a lymphodepleting therapy or chemotherapy, such as one including fludarabine, and/or transplant. In other embodiments, attributes of the process or dosing approach account for variability in such patient-specific factors, e.g., such that such patient-specific factors do not result in or do not result in substantial variability in toxicity or other risk. In some embodiments, the provided methods implement flat dosing, e.g. total number of CAR+ cells, total number of CAR+ CD8+ T cells and/or CAR+/CD4+ T cells, such as to administer a precise or fixed dose of such cell type(s) to each of a group of subjects treated, including subjects of variable weight. In some aspects, the patient-specific variables are relevant to dosing if the therapy is autologous, such that properties of the patient's cells will be relevant to the health or function or fitness of cells in the composition.

In some aspects, certain patient or clinical factors can amplify expansion of administered cells of a cell therapy within a subject to which the therapy is administered, which, in some cases, can impact, such as increase, or be associated with or associated with an increased, risk, relative risk or probability of developing a toxicity, e.g. neurotoxicity, following administration of a cell therapy. In some embodiments, patient or clinical factors that are associated with a risk of developing a toxicity, such as neurotoxity or cerebral edema, include the disease type (e.g. ALL); disease burden (e.g. as determined by a volumetric measure or presence of an inflammatory marker); whether the subject has received a prior bridging chemotherapy or a lymphodepleting therapy, such as involving fludarabine (Flu) or cyclophosphamide and fludarabine (CY/Flu); peak early recombinant receptor (e.g. CAR)-T cell expansion in the blood, such as within 2, 3, 4, 5, 6, or 7 days following initiation of administration of the cell therapy; and/or the presence of peak levels of IL-15, such as greater than or equal to 30 pg/mL, in the blood or serum, such as within 2, 3, 4, 5, 6 or 7 days following initiation of administration of the cell therapy. In some embodiments, the provided approaches, such as provided processes and/or dosing strategies such as approaches for controlling dose and/or variability can minimize or reduce such risks and/or minimize impact of patient or clinical factors on such risks or outcome. Among such approaches are those in which such factors are taken into account in adjusting or determining dose to such subjects and those in which attributes of the process or dosing are used that minimize impact of such factors on risk of toxicity or outcome.

In some embodiments, the provided compositions, doses and methods are advantageous in that they limit variability, in the dose of cells administered to individual subjects, in factors observed to correlate with adverse events such as toxicities such as neurotoxicities, including severe forms of neurotoxicity and/or cerebral edema. Such variability is limited or reduced in some aspects by a dose or dose-determination approach that accounts or corrects for such variability, for example, dosing based on numbers of cells or phenotype of cells that exhibit a property known to correlate to an adverse event. In some aspects, variability is limited through the use of a release assay that accounts for such variability. In some embodiments, in addition to numbers of engineered T cells, dose and/or product release is further based on one or more of a combination of important metrics. Such metrics in some aspects include parameters indicative of the degree to which viable cells are biologically active or healthy (e.g., not programmed for death), which in some aspects is determined based on the absence of detectable apoptotic marker, and/or based on relatively low levels of intracellular production of certain factors, as compared to dying or apoptotic cells. In some aspects, the metrics include frequency of engineered CD8+ cells, as opposed to considering only numbers of engineered T cells as a whole and/or the ratio of CD4:CD8 cells among the engineered cells. In some aspects, the metrics include parameters indicative of the degree of antigen- or cell-specific activity present in the composition, such as measures of the degree to which cells in the composition are capable of exerting certain activities or functions, such as secretion of certain factors (such as pro-inflammatory cytokines) in response to antigen- or cell-specific stimulation.

In some embodiments, dose is based upon the number of biologically active engineered T cells; in some aspects, biologically active refers to a property of cells not programmed to undergo cell death, e.g., a property of non-apoptotic cells or cells not showing indications of entry into an apoptotic pathway. In some aspects, dose is based upon number of biologically active engineered CD8+ T cells, and/or, where dose is based upon total numbers of biologically active engineered T cells, an upper limit or threshold number of biologically active CD8+ engineered T cells is also specified.

In some embodiments, ensuring that a unit dose encompasses a relatively consistent number of biologically active engineered cells is achieved in part by a cell production process that exhibits a variance in such biologically active population that is low or below an acceptable or threshold variance, among compositions produced by the process, including those derived from samples from a number of different subjects, such as those having different characteristics, such as subjects of different ages, numbers and/or types of prior therapies, and indication and subtype or severity or grade thereof. In some aspects, such processes generate a frequency of such biologically active population that varies by no more than 20% or no more than 10% or no more than 5% from an average of said frequency in a plurality of T cell compositions produced by the process and/or varies from such average by no more than one standard deviation or varies by no more than 20%, or no more than 10%, or no more than 5% among a plurality of T cell compositions produced by the process among such various samples and patients. In some such aspects, dose is based on number (or number per patient weight or height or blood volume) of engineered T cells or CD8+ engineered T cells, taking into account the expected frequency of biologically active or non-apoptotic cells among such cells, and/or the variance in such frequency across a cell compositions engineered from a representative population of subjects. In some aspects, the number of the population of cells in the dose is selected to provide an adequate safety margin, e.g., to be below a threshold value, taking into account such variance and frequency.

In some embodiments, dose and/or product release is further based upon a metric indicative of potency, e.g., particular measure of antigen- or cell-specific activity that provides information regarding risk of an adverse event or toxicity. In some aspects, such metric is or includes a parameter observed or described herein to correlate to risk of an adverse event such as severe or a particular grade (e.g., grade 3, prolonged grade 3, grade 4 and/or grade 5) neurotoxicity or cerebral edema. In some aspects, the parameter is indicative of engineered cell- or antigen-specific release of an inflammatory cytokine, and/or of one or a combination of TNFa, IFNg, IL-2, and IL-10.

In some embodiments, the approach further accounts for variability (e.g., among cells engineered from different subjects and/or the use of different raw materials such as activation reagents in the process). For example, in some embodiments, the parameter indicative of cell-specific activity or potency is normalized against a similar measure, which may vary among such subjects or processes, but does not predict the adverse outcome. For example, the parameter indicative of the cell-specific activity (e.g., measure of antigen-specific secretion of a pro-inflammatory cytokine) may in some aspects be normalized against or relative to another parameter, such as antigen- or cell-specific release of a factor that does not correlate with or predict the unwanted outcome, such as severe or grade (e.g., grade 3, prolonged grade 3, grade 4 and/or grade 5) neurotoxicity or cerebral edema. For example, it is observed that in some embodiments, secretion of cytokines such as IL-5, IL-13, GM-CSF, and IL-6 does not correlate with or predict the unwanted outcome. In response to cell-specific antigen, while it may vary among cells engineered from different subjects (e.g., patient-to-patient variability), variability in this parameter does not generally correlate with or predict risk of the unwanted outcome such as severe or grade (e.g., grade 3, prolonged grade 3, grade 4 and/or grade 5) neurotoxicity or cerebral edema. In some embodiments, secretion of one or more of such cytokines can serve as a control factor, such as an arithmetic mean or geometric mean of a measure of two or more IL-5, IL-13, GM-CSF, and IL-6.

In some aspects, currently available methods are not satisfactory to characterize both the safety and efficacy of a therapeutic T cell composition. For example, in some cases current methods utilize a lower threshold release parameter (for example, measuring interferon-gamma release of a therapeutic T cell composition), which does not include an upper safety limit. In some cases, a therapeutic T cell composition will not be released for further use as a therapy unless the lower threshold is met; for example, if the therapeutic T cell composition does not release above a threshold amount of cytokine in a defined assay, the composition will not be released for infusion into a patient. In some aspects, such parameters may include cytokine release, cytotoxic granule release, and determination of T cell activation state (for example, a certain percentage of cells expressing one or more activation markers). In some aspects, currently utilized parameters include lower limits of percentages of CAR+ cells and/or cells exhibiting a specific phenotype. In some methods, it is possible that while efficacy may be controlled by ensuring that a therapeutic T cell composition has a minimum activity (i.e. releases a minimal amount of cytokine and/or performs at a certain level in a cytotoxicity assay) or phenotype, whether or not the composition is safe to administer is not determined using an upper limit of similar parameters.

The provided embodiments are based on findings that certain phenotypes and/or parameters associated with function or activity of a therapeutic T cell composition are associated with a risk of developing a toxicity, e.g. severe neurotoxicity, in a subject administered the T cell composition. In some aspects, it is found that fitness of cells that are administered is a feature that correlates with a risk of toxicity. In some embodiments, the number or dose of cells administered to a subject that have a phenotype indicating biological activity, such as cells that do not have an apoptotic phenotype and/or that have a phenotype that does not exhibit a parameter indicative of apoptosis (e.g. a parameter indicative of early or late apoptosis, such as detected by Annexin V) and/or that produce certain cytokines (e.g. proinflammatory cytokines), can correlate with a risk of toxicity. In some aspects, subjects receiving a higher total number of cells, such as based on total CD3+CAR+ cells or CD8+CAR+ cells or a subset thereof, may be at a greater risk of developing a severe toxicity than a subject receiving a smaller total number of such cells. In some cases, certain dosing regimens that do not take into account the number of total cells with such features and/or in which there is a high degree of variability in the phenotype or function of cells administered among a group of treated subjects can, in certain aspects, result in an overall risk of toxicity developing in treated subjects.

In some aspects, it is found that a lower total dose of administered cells that exhibit such a phenotype may be desirable, for example, to ameliorate or minimize the risk of toxicity. Yet, although such features of the cells can impact risk of toxicity in a subject administered the cells, administering too few of such cells can reduce efficacy of the therapeutic composition. To account for efficacy, it is common among dosing methods to set a lower limit of potency of a cell composition, such as based on cytolytic activity, production of a cytokine or other factor associated with a therapeutic T cell composition, for example to ensure enough cells are administered to a subject to achieve an effect. The studies described herein, however, demonstrate that dosing methods that administer a dose of cells, including a fixed dose of cells, in which only a lower level of potency or function has been met may be putting a subject at risk of toxicity if such cells exhibit a high level of antigen-specific activity or function.

Based on the findings herein, methods, compositions and articles of manufacture are provided in which a unit dose of cells is based on two functions, (A) the number of cells of a certain phenotype, such as a phenotype indicative of biological activity and (B) the value of a parameter that indicates or correlates with the recombinant receptor-dependent activity and/or antigen-specific activity in the composition. Exemplary variables that are found herein to be an indicator of A or B are described elsewhere herein, including in the Examples. In some embodiments, the function B, such as antigen-specific cytokine, e.g. proinflammatory cytokine, production or accumulation, is one that often can differ and/or can be variable among T cell compositions generated from cells derived from subjects, including patient-specific risk factors, for example, due to the particular disease or condition of the subject, the age of the subject, the weight of the subject, prior treatments, and other factors that may alter or impact one or more functional attributes of the T cells.

In some embodiments, it is found that B is an indicator of safety of a therapeutic T cell composition. In some cases, if B is too high, a lower dose of cells should be administered to reduce or minimize a risk of toxicity, such as severe neurotoxicity. In some cases, if B is below a threshold level or limit, there may be a greater window on the dose that can be administered, such that a target dose of cells can be administered to a subject without a known risk of developing a toxicity or adverse event, such as a severe toxicity. In some aspects, controlling or adjusting the number of total cells or total cells of a particular phenotype (e.g. CD3+CAR+ or CD8+CAR+ or Annexin V−CD8+CAR+) in a therapeutic T cell composition that is administered can standardize or regulate the total units of activity of administered T cell compositions among subjects treated, thereby accounting for functional or activity differences of B among T cells across T cell composition derived from a group of subjects that may otherwise have led to a risk of developing a toxicity, e.g. severe toxicity, in some subjects.

In some embodiments, B, which is a value of a parameter of a recombinant receptor-dependent (e.g. CAR-dependent), such as antigen-specific activity, can provide for a potency control for a T cell composition. In some aspects, a potency assay based on T cell function of B can offer advantages over existing methods. First, in some aspects, existing potency assays for cell compositions rely on features that correlate to efficacy of the cells, e.g. cytolytic activity and/or IFN-gamma production, as opposed to safety. Moreover, such potency assays often have only a lower limit or level of potency within the assay.

Based on the findings herein, among the provided embodiments are potency assays, such as those in which there is a lower specification limit (LSL) and/or an upper specification limit (USL). In some aspects, the USL is based on a parameter B. In some aspects, the USL provides for a safety check of the T cell composition, for example in connection with a release assay prior to administering the composition to a subject. As indicated above, various clinical criteria and other patient-specific features can influence the degree or extent of function of engineered cells. Likewise, in some cases, the overall process, including reagents, used in connection with manufacturing or engineering a cell composition and/or in freezing cells produced by a cell process also can lead to variability of B among a plurality of T cell compositions produced using the same process. In some cases, it is found that freezing cells below a density of less than $15\times10^6$ cells/mL can lead to increased variability and/or reduced potency of a T cell composition. In some embodiments, the provided methods are particularly advantageous for assessing cell compositions in which the variability of cells having a certain phenotype, such as a phenotype A described below, including a phenotype indicative of biological activity e.g. Annexin V−CD8+CAR+, varies or is likely to vary by more than 20%, more than 30%, more than 40%, more than 50% or more among a plurality of T cell compositions produced by the process or from an average of the frequency of the phenotype in a plurality of T cell compositions produced by the process and/or varies or is likely to vary from such average by no more than one standard deviation.

In some embodiments of the provided methods and doses, cells are produced by a process designed to minimize variability in factors such as those observed herein to correlate (alone or in combination) with risk for neurotoxicity. In some aspects of such embodiments, dosing may be based on a total number or relative number of engineered cells or engineered T cell or T cell population, without increasing the risk of toxicity that may be present when cells are produced using a process in which such parameters are more variable. In some aspects, such processes include the use of lentiviral vectors, defined ratios of subsets of T cells such as CD4 and/or CD8 cells. In some aspects, they include engineering of cells including a CAR with a 41BB-derived costimulatory domain as opposed to a CD28 domain. In some aspects, the process includes controlled ratios of T cell subsets, cytokines and reagents to allow for control of phenotype, function and metabolic state) and/or controlled and relatively higher total cell density during cryopreservation (such as between 10 and between 60 or between 15 and 60 million cells per mL, each inclusive), storage and/or thawing of sample prior to administration. In some aspects a process is used in which metabolic and functional properties of T cells are more easily controlled. In some embodiments, such processes are used to provide consistent doses of biologically active cells, even in the context of patient-specific variables which may affect cell health.

Among the embodiments are those in which processes produce higher frequencies of biologically active or healthy cells among CD8+CAR+ cells, as measured by negativity for various apoptotic markers among samples generated using the process. In some aspects, there is a lower degree of variance in this parameter among samples produced by the process from different subjects. As observed herein, number of such cells can correlate with grade 5 neurotoxicity and cerebral edema, whereas CD3+CAR+ viable cells (not accounting for apoptotic state vs biologically active cells) may not always predict toxicity or clearly define a safety boundary with respect to this risk.

In some embodiments, the use of a process with reduced variability in frequency of such biologically active cells among engineered cells, reduces the risk that certain patients, such as those that have certain patient-specific risk factors as described (e.g., those having cells less prone to apoptosis or that are more healthy) will inadvertently be given a higher dose than intended of biologically active cells, when dosing based on engineered T cell numbers as a whole. Processes with a greater degree of control over phenotype and function further have been observed to reduce the degree of variability in the ability of cells produced by the process to make inflammatory cytokines in an antigen-specific manner. The results herein are consistent with an interpretation that, particularly when combined with numbers of biologically active engineered cells, a dosing strategy taking into account such cell-specific activity parameters (e.g., such that a specific target range of such activity—or no more than a threshold—is represented in a given dose), can be used to provide a dose capable of achieving a desired clinical or therapeutic outcome, while still within a safety margin or reducing the risk of unwanted toxicity, e.g., neurotoxicity.

In some embodiments, the use of a process that yields consistently higher frequencies of biologically active engineered cells, permits the use of cell doses that are far lower (from the perspective of numbers of engineered, e.g., CAR+, cells), as compared to other dosing strategies, in which a higher frequency of engineered cells are positive for apoptotic markers or otherwise are less healthy. For example, based on observations herein, and considering the observation that available dosing strategies generally have not taken into account frequency of apoptotic cells, in some embodiments, numbers of engineered (e.g., CAR+) T cells (e.g., engineered CD8+ and/or CD4+ cells), are as low as 5, 10, 11, 12, 13, 14, 15, 16, 17, 18, 19, 20, 30, 40 or 50 million cells.

The provided methods provide a release assay that can monitor or assess cell compositions to determine, if the composition is administered to a subject, whether it is likely to correlate with a risk of developing a toxicity, such as severe neurotoxicity. In some embodiments, a T cell composition is recommended not to be administered to a subject and/or the unit dose to be administered to a subject is altered or adjusted if B is above the USL. If B is below the USL, a product may be released for treatment. In some embodiments, assessing whether B is above a LSL and/or below an USL also can provide information about whether a subject previously administered a T cell composition is at risk for developing a toxicity, such as a severe toxicity. In some embodiments, assessment of a sample of a T cell composition administered to a subject is carried out post facto for B. In some embodiments, a subject administered a T cell composition is determined to be at risk for developing a toxicity, such as severe neurotoxicity, if B is at or above the USL. In such embodiments, a subject administered the composition is monitored and/or is treated with an agent to ameliorate or reduce the likelihood of a toxicity outcome, such as neurotoxicity or cytokine release syndrome, following administration of the cell composition and optionally prior to the development of a sign or symptom of the toxicity outcome.

In some aspects, the provided embodiments are based on observations that the efficacy of adoptive cell therapy may be limited by the development of toxicity in the subject to whom such cells are administered, which toxicity in some cases can be severe. For example, in some cases, administering a dose of cells expressing a recombinant receptor, e.g. a CAR, can result in toxicity or risk thereof, such as CRS or neurotoxicity. In some cases, while a higher dose of such cells can increase the efficacy of the treatment, for example, by increasing exposure to the cells such as by promoting expansion and/or persistence, they may also result in an even greater risk of developing a toxicity or a more severe toxicity. Also, in some cases, subjects with a higher disease burden also may be at a greater risk for developing a toxicity or a more severe toxicity.

Certain available methods for treating or ameliorating toxicity may not always be entirely satisfactory. Many such approaches focus, for example, on targeting downstream effects of toxicity, such as by cytokine blockade, and/or delivering agents such as high-dose steroids which can also eliminate or impair the function of administered cells. Additionally, such approaches often involve administration of such interventions only upon detection of physical signs or symptoms of toxicity, which in general involve signs or symptoms of moderate or severe toxicity (e.g. moderate or severe CRS). Many of these other approaches also do not prevent other forms of toxicity such as neurotoxicity, which can be associated with adoptive cell therapy. In some cases, this is at a time where such symptoms are severe, and that therefore may require even harsher or more extreme treatments (e.g. higher dosages or an increased frequency of administration) to ameliorate or treat the toxicity.

The use of certain alternative approaches does not provide satisfactory solutions to such issues. In some cases, such agents and therapies (e.g. steroids) are themselves associated with toxic side effects. Such side effects may be even greater at the higher dose or frequency in which is it necessary to administer or treat with the agent or therapy in order to treat or ameliorate the severity of the toxicity that can result from cell therapy. In addition, in some cases, it is believed that an agent or therapy for treating a toxicity may limit the efficacy of the cell therapy, such as the efficacy of the chimeric receptor (e.g. CAR) expressed on cells provided as part of the cell therapy (Sentman (2013) Immunotherapy, 5:10).

The provided embodiments offer advantages in dealing with or addressing the risk of toxicity, such as severe neurotoxicity, in subjects administered a therapeutic T cell composition. In some embodiments, the likelihood of a subject developing a toxicity, such as a severe neurotoxicity, is reduced or prevented by the provided embodiments in which the safety features of the composition is assessed and/or adjusted by the dosing of the subject. In some embodiments, the likelihood of a subject developing a toxicity, such as a severe toxicity, is reduced or prevented by monitoring or assessing the safety of a therapeutic T cell composition prior to release for administration to a subject and/or by administering a unit dose of cells containing no more than a target dose of cells or at or no more than a target number of reference units (RUs) of cells.

In some embodiments, the provided embodiments are designed to or include features that result in a lower degree of or a lower degree of risk of toxicity, a toxic outcome or symptom, toxicity-promoting profile, factor or property, such as a symptom or outcome associated with or indicative of cytokine release syndrome (CRS) or neurotoxicity, for example, compared to other methods in which the therapeutic T cell composition has not been assessed in an assay for safety control and/or in which the therapeutic T composition has not been administered to a subject in accord with the provided dosing formula taking into account A and B and/or dosing at a target number of RUs, such as less than a threshold number of RUs, or dosing at a target number of cells or a number of cells within a given target range, of the therapeutic T cell composition.

Toxicity and Toxic Outcome

In some aspects, the toxic outcome of a therapy, such as a cell therapy, is or is associated with or indicative of cytokine release syndrome (CRS) or severe CRS (sCRS). CRS, e.g., sCRS, can occur in some cases following adoptive T cell therapy and administration to subjects of other biological products. See Davila et al., Sci Transl Med 6, 224ra25 (2014); Brentjens et al., Sci. Transl. Med. 5, 177ra38 (2013); Grupp et al., N. Engl. J. Med. 368, 1509-1518 (2013); and Kochenderfer et al., Blood 119, 2709-2720 (2012); Xu et al., Cancer Letters 343 (2014) 172-78.

Typically, CRS is caused by an exaggerated systemic immune response mediated by, for example, T cells, B cells, NK cells, monocytes, and/or macrophages. Such cells may release a large amount of inflammatory mediators such as cytokines and chemokines. Cytokines may trigger an acute inflammatory response and/or induce endothelial organ damage, which may result in microvascular leakage, heart failure, or death. Severe, life-threatening CRS can lead to pulmonary infiltration and lung injury, renal failure, or disseminated intravascular coagulation. Other severe, life-threatening toxicities can include cardiac toxicity, respiratory distress, neurologic toxicity and/or hepatic failure.

Outcomes, signs and symptoms of CRS are known and include those described herein. In some embodiments, where a particular dosage regimen or administration effects or does not effect a given CRS-associated outcome, sign, or symptom, particular outcomes, signs, and symptoms and/or quantities or degrees thereof may be specified.

In the context of administering CAR-expressing cells, CRS, such as severe CRS, typically occurs 6-20 days after infusion of cells that express a CAR. See Xu et al., Cancer Letters 343 (2014) 172-78. In some cases, CRS occurs less than 6 days or more than 20 days after CAR T cell infusion. The incidence and timing of CRS may be related to baseline cytokine levels or tumor burden at the time of infusion. Commonly, CRS involves elevated serum levels of interferon (IFN)-γ, tumor necrosis factor (TNF)-α, and/or interleukin (IL)-2. Other cytokines that may be rapidly induced in CRS are IL-1β, IL-6, IL-8, and IL-10.

CRS criteria that appear to correlate with the onset of CRS to predict which patients are more likely to be at risk for developing sCRS have been developed (see Davilla et al. Science translational medicine. 2014; 6 (224): 224ra25). Factors include fevers, hypoxia, hypotension, neurologic changes, elevated serum levels of inflammatory cytokines, such as a set of seven cytokines (IFNγ, IL-5, IL-6, IL-10, Flt-3L, fractalkine, and GM-CSF) whose treatment-induced elevation can correlate well with both pretreatment tumor burden and sCRS symptoms. Other guidelines on the diagnosis and management of CRS are known (see e.g., Lee et al, Blood. 2014; 124 (2): 188-95). In some embodiments, the criteria reflective of CRS grade are those detailed in Table 1 below.

TABLE 1

Exemplary Grading Criteria for CRS

| Grade | Description of Symptoms |
|---|---|
| 1<br>Mild | Not life-threatening, require only symptomatic treatment such asantipyretics and anti-emetics (e.g., fever, nausea, fatigue, headache, myalgias,malaise) |
| 2<br>Moderate | Require and respond to moderate intervention:<br>Oxygen requirement < 40%, or<br>Hypotension responsive to fluids or low dose of a single vasopressor, or<br>Grade 2 organ toxicity (by CTCAE v4.0) |
| 3<br>Severe | Require and respond to aggressive intervention:<br>Oxygen requirement ≥ 40%, or<br>Hypotension requiring high dose of a single vasopressor (e.g., norepinephrine ≥ 20 μg/kg/min, dopamine ≥ 10 μg/kg/min, phenylephrine ≥ 200 μg/kg/min, or epinephrine ≥ 10 μg/kg/min), or<br>Hypotension requiring multiple vasopressors (e.g., vasopressin + one of the above agents, or combination vasopressors equivalent to ≥20 μg/kg/min |

TABLE 1-continued

| Exemplary Grading Criteria for CRS | |
|---|---|
| Grade | Description of Symptoms |
| | norepinephrine), or<br>Grade 3 organ toxicity or Grade 4 transaminitis (by CTCAE v4.0) |
| 4<br>Life-threatening | Life-threatening:<br>Requirement for ventilator support, or<br>Grade 4 organ toxicity (excluding transaminitis) |
| 5<br>Fatal | Death |

In some embodiments, a subject is deemed to develop "severe CRS" ("sCRS") in response to or secondary to administration of a cell therapy or dose of cells thereof, if, following administration, the subject displays: (1) fever of at least 38 degrees Celsius for at least three days; (2) cytokine elevation that includes either (a) a max fold change of at least 75 for at least two of the following group of seven cytokines compared to the level immediately following the administration: interferon gamma (IFNγ), GM-CSF, IL-6, IL-10, Flt-3L, fracktalkine, and IL-5 and/or (b) a max fold change of at least 250 for at least one of the following group of seven cytokines compared to the level immediately following the administration: interferon gamma (IFNγ), GM-CSF, IL-6, IL-10, Flt-3L, fracktalkine, and IL-5; and (c) at least one clinical sign of toxicity such as hypotension (requiring at least one intravenous vasoactive pressor) or hypoxia (PO2<90%) or one or more neurologic disorder(s) (including mental status changes, obtundation, and/or seizures). In some embodiments, severe CRS includes CRS with a grade of 3 or greater, such as set forth in Table 1.

In some embodiments, outcomes associated with severe CRS or grade 3 CRS or greater, such as grade 4 or greater, such as set forth in Table 1. In some embodiments, these include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines, such as a max fold change, e.g., of at least at or about 75, compared to pre-treatment levels of at least two cytokines (e.g., at least two of the group consisting of interferon gamma (IFNγ), GM-CSF, IL-6, IL-10, Flt-3L, fracktalkine, and IL-5, and/or tumor necrosis factor alpha (TNFα)), or a max fold change, e.g., of at least at or about 250 of at least one of such cytokines; and/or at least one clinical sign of toxicity, such as hypotension (e.g., as measured by at least one intravenous vasoactive pressor); hypoxia (e.g., plasma oxygen (PO2) levels of less than at or about 90%); and/or one or more neurologic disorders (including mental status changes, obtundation, and seizures). In some embodiments, severe CRS includes CRS that requires management or care in the intensive care unit (ICU).

In some embodiments, severe CRS encompasses a combination of (1) persistent fever (fever of at least 38 degrees Celsius for at least three days) and (2) a serum level of CRP of at least at or about 20 mg/dL. In some embodiments, severe CRS encompasses hypotension requiring the use of two or more vasopressors or respiratory failure requiring mechanical ventilation. In some embodiments, the dosage of vasopressors is increased in a second or subsequent administration.

In some embodiments, severe CRS or grade 3 CRS encompasses an increase in alanine aminotransferase, an increase in aspartate aminotransferase, chills, febrile neutropenia, headache, left ventricular dysfunction, encephalopathy, hydrocephalus, and/or tremor.

In some aspects, the toxic outcome of a therapy, such as a cell therapy, is or is associated with or indicative of neurotoxicity or severe neurotoxicity. In some embodiments, symptoms associated with a clinical risk of neurotoxicity include confusion, delirium, expressive aphasia, obtundation, myoclonus, lethargy, altered mental status, convulsions, seizure-like activity, seizures (optionally as confirmed by electroencephalogram [EEG]), elevated levels of beta amyloid (AB), elevated levels of glutamate, and elevated levels of oxygen radicals. In some embodiments, neurotoxicity is graded based on severity (e.g., using a Grade 1-5 scale (see, e.g., Guido Cavaletti & Paola Marmiroli *Nature Reviews Neurology* 6, 657-666 (December 2010); National Cancer Institute-Common Toxicity Criteria version 4.03 (NCI-CTCAE v4.03).

In some instances, neurologic symptoms may be the earliest symptoms of sCRS. In some embodiments, neurologic symptoms are seen to begin 5 to 7 days after cell therapy infusion. In some embodiments, duration of neurologic changes may range from 3 to 19 days. In some cases, recovery of neurologic changes occurs after other symptoms of sCRS have resolved. In some embodiments, time or degree of resolution of neurologic changes is not hastened by treatment with anti-IL-6 and/or steroid(s).

In some embodiments, a subject is deemed to develop "severe neurotoxicity" in response to or secondary to administration of a cell therapy or dose of cells thereof, if, following administration, the subject displays symptoms that limit self-care (e.g. bathing, dressing and undressing, feeding, using the toilet, taking medications) from among: 1) symptoms of peripheral motor neuropathy, including inflammation or degeneration of the peripheral motor nerves; 2) symptoms of peripheral sensory neuropathy, including inflammation or degeneration of the peripheral sensory nerves, dysesthesia, such as distortion of sensory perception, resulting in an abnormal and unpleasant sensation, neuralgia, such as intense painful sensation along a nerve or a group of nerves, and/or paresthesia, such as functional disturbances of sensory neurons resulting in abnormal cutaneous sensations of tingling, numbness, pressure, cold and warmth in the absence of stimulus. In some embodiments, severe neurotoxicity includes neurotoxicity with a grade of 3 or greater, such as set forth in Table 2. In some embodiments, a severe neurotoxicity is deemed to be a prolonged grade 3 if symptoms or grade 3 neurotoxicity last for 10 days or longer. In some embodiments, a toxicity, such as a neurotoxicity, such as a grade 3 or 4 neurotoxicity, is deemed to be a prolonged neurotoxicity (e.g., prolonged grade 3 neurotoxicity) if symptoms of a given grade, such as grade 3 or higher, neurotoxicity, are or have been present for at least 10 days or at least about 10 days or at least 11 days or at least about 11 days or at least 10-11 days or about 10-11 days. Prolonged grade 3 neurotoxicity generally is associated with grade 3 neurotoxicity that persist for greater than or greater than an average of 9 days, 8 days, or 1 week. In some aspects, non-prolonged grade 3 neurotoxicity generally is associated with symptoms of grade 3 neurotoxicity that do not persist for greater than or greater than an average of 9 days, 8 days, or 1 week or in some cases less such as 6, 5, 4, or 3 days.

TABLE 2

| Exemplary Grading Criteria for neurotoxicity | |
|---|---|
| Grade | Description of Symptoms |
| 1 Asymptomatic or Mild | Mild or asymptomatic symptoms |
| 2 Moderate | Presence of symptoms that limit instrumental activities of daily living (ADL), such as preparing meals, shopping for groceries or clothes, using the telephone, managing money |
| 3 Severe | Presence of symptoms that limit self-care ADL, such as bathing, dressing and undressing, feeding self, using the toilet, taking medications |
| 4 Life-threatening | Symptoms that are life-threatening, requiring urgent intervention |
| 5 Fatal | Death |

In some embodiments, the provided embodiments, including methods of treatment, uses, articles of manufacture, unit doses, lead to reduced symptoms associated with neurotoxicity following cell therapy compared to other embodiments or methods. For example, subjects treated according to the provided methods may have reduced symptoms of neurotoxicity, such as limb weakness or numbness, loss of memory, vision, and/or intellect, uncontrollable obsessive and/or compulsive behaviors, delusions, headache, cognitive and behavioral problems including loss of motor control, cognitive deterioration, and autonomic nervous system dysfunction, and sexual dysfunction, compared to subjects treated by other methods. In some embodiments, subjects treated according to the provided methods may have reduced symptoms associated with peripheral motor neuropathy, peripheral sensory neuropathy, dysesthesia, neuralgia or paresthesia.

In some embodiments, the methods reduce outcomes associated with neurotoxicity including damages to the nervous system and/or brain, such as the death of neurons. In some aspects, the methods reduce the level of factors associated with neurotoxicity such as beta amyloid (AB), glutamate, and oxygen radicals.

In some embodiments, subjects administered one or more unit doses of a provided therapeutic T cell composition, or a therapeutic T cell composition that is released for administration according to the provided methods and/or who are dosed in accord with the provided methods are at a reduced likelihood of developing a severe adverse event, such as at least a prolonged grade 3 neurotoxicity, such as a grade 4 or grade 5 neurotoxicity. In some aspects, subjects treated according to the provided embodiments do not develop a neurotoxicity or develop a grade of neurotoxicity that is less severe than if the subject had been treated by other methods or with other therapeutic T cell compositions, including therapeutic T cell compositions not assessed in accord with the provided methods.

II. ATTRIBUTES OF CELL COMPOSITIONS

The provided methods herein relate to attributes of cells in a therapeutic T cell composition. In some embodiments, the attributes, alone or in combination, correlate with a risk of developing an adverse event or toxicity, such as a severe toxicity, such as at least a prolonged grade 3 toxicity or a grade 4 or grade 5 toxicity. In some embodiments, the attribute is a phenotype of cells in the composition, also referred to as "A" herein, including a phenotype indicative of biological activity of cells or a cell population. In some embodiments, the attribute is a recombinant receptor-dependent activity, such as an antigen-specific activity, also referred to as "B" herein. In some embodiments, attribute A and/or B of cells in a T cell composition is considered in connection with the provided methods. In some aspects, a function of an attribute A and B is considered in connection with determining a target number of reference units (RUs), such as in connection with providing or administering a unit dose of a therapeutic T cell composition. In some aspects, a threshold value of attribute B, or a lower specification level (LSL) and upper specification level (USL) of B, is used to assess or determine safety or likelihood of safety of a therapeutic T cell composition, such as in connection with a potency assay or release assay. Various exemplary methods in which attributes A and/B are considered or assessed are provided.

A. Phenotypes of Cell Compositions

In some embodiments, the phenotype "A" is the presence or absence of one or more specific molecules, including surface molecules and/or molecules that may accumulate or be produced by the cells or a subpopulation of cells within a T cell composition. In some embodiments, the phenotype, directly or inversely, indicates or is indicative of a biological activity of the cells or of a population of cells within the T cell composition. In some embodiments, phenotype may include cell activity, such as production of a factor in response to a stimulus. In certain embodiments, assessment of a cell composition is performed to identify, detect, or quantify a phenotype of the cell composition. In particular embodiments, a measurement of a cell composition is performed to identify, detect, or quantify the presence, absence, degree of expression or level of a specific molecule In some embodiments, the phenotype is indicative of viability of a cell. In some embodiments, the phenotype is indicative of absence of apoptosis, absence of early stages of apoptosis or absence of late stages of apoptosis. In some embodiments, the phenotype is the absence of a factor indicative of absence of apoptosis, early apoptosis or late stages or apoptosis. In some embodiments, the phenotype is a phenotype of a sub-population or subset of T cells, such as recombinant receptor-expressing T cells (e.g. CAR+ T cells) or CD8+ T cells, naïve T cells or certain sub-population of memory T cells or T cells that exhibit memory stem-like attributes. In some embodiments, the phenotype is a phenotype of cells that are not activated and/or that lack or are reduced for or low for expression of one or more activation marker. In some embodiments, the phenotype is a phenotype of cells that are not exhausted and/or that lack or are reduced for or low for expression of one or more exhaustion markers.

In some embodiments, the phenotype is indicated by the presence, absence, or level of expression in a cell of one or more specific molecules, such as certain surface markers indicative of the phenotype, e.g., surface proteins, intracellular markers indicative of the phenotype, or nucleic acids indicative of the phenotype or other molecules or factors indicative of the phenotype. In some embodiments, the phenotype is or comprises a positive or negative expression of the one or more of specific molecules. In some embodiments, the specific molecules include, but are not limited to, a surface marker, e.g., a membrane glycoprotein or a receptor, a marker associated with apoptosis or viability, or a specific molecule that indicates the status of an immune cells, e.g., a marker associated with activation, exhaustion, or a mature or naïve phenotype. In some embodiments, any known method for assessing or measuring, counting, and/or quantifying cells based on specific molecules can be used to determine the number of cells of the phenotype.

In some embodiments, a phenotype is or includes a positive or negative expression of one or more specific molecules in a cell. In some embodiments, the positive expression is indicated by a detectable amount of the specific molecule in the cell. In certain embodiments, the detectable amount is any detected amount of the specific molecule in the cell. In particular embodiments, the detectable amount is an amount greater than a background, e.g., background staining, signal, etc., in the cell. In certain embodiments, the positive expression is an amount of the specific molecule that is greater than a threshold, e.g., a predetermined threshold. Likewise, in particular embodiments, a cell with negative expression of a specific molecule may be any cell not determined to have positive expression, or is a cell that lacks a detectable amount of the specific molecule or a detectable amount of the specific molecule above background. In some embodiments, the cell has negative expression of a specific molecule if the amount of the specific molecule is below the threshold. One of skill in the art will understand how to define a threshold to define positive and/or negative expression for a specific molecule as a matter of routine skill, and that the thresholds may be defined according to specific parameters, for example but not limited to the assay or method of detection, the identity of the specific molecule, reagents used for detection, and instrumentation.

Examples of methods that can be used to detect a specific molecule and/or analyze a phenotype of the cells include, but are not limited to, biochemical analysis; immunochemical analysis; image analysis; cytomorphological analysis; molecule analysis such as PCR, sequencing, determination of DNA methylation; proteomics analysis such as determination of protein glycosylation and/or phosphorylation pattern; genomics analysis; epigenomics analysis; transcriptomics analysis; and any combination thereof. In some embodiments, molecular features of the phenotype analyzed by image analysis, PCR (including the standard and all variants of PCR), microarray (including, but not limited to DNA microarray, MMchips for microRNA, protein microarray, cellular microarray, antibody microarray, and carbohydrate array), sequencing, biomarker detection, or methods for determining DNA methylation or protein glycosylation pattern. In particular embodiments, the specific molecule is a polypeptide, i.e. a protein. In some embodiments, the specific molecule is a polynucleotide.

In some embodiments, positive or negative expression of a specific molecule is determined by incubating cells with one or more antibodies or other binding agent that specifically bind to one or more surface markers expressed or expressed (marker+) at a relatively higher level (markerhigh) on the positively or negatively selected cells, respectively. In particular embodiments, the positive or negative expression is determined by flow cytometry, immunohistochemistry, or any other suitable method for detecting specific markers.

In particular embodiments, expression of a specific molecule is assessed with flow cytometry. Flow cytometry is a laser- or impedance-based, biophysical technology employed in cell counting, cell sorting, biomarker detection and protein engineering, by suspending cells in a stream of fluid and passing them by an electronic detection apparatus. It allows simultaneous multiparametric analysis of the physical and chemical characteristics of up to thousands of particles per second.

The data generated by flow-cytometers can be plotted in a single dimension, to produce a histogram, or in two-dimensional dot plots or even in three dimensions. The regions on these plots can be sequentially separated, based on fluorescence intensity, by creating a series of subset extractions, termed "gates." Specific gating protocols exist for diagnostic and clinical purposes especially in relation to immunology. Plots are often made on logarithmic scales. Because different fluorescent dyes' emission spectra overlap, signals at the detectors have to be compensated electronically as well as computationally. Data accumulated using the flow cytometer can be analyzed using software, e.g., JMP (statistical software), WinMDI, [10] Flowing Software, and web-based Cytobank [12]), Cellcion, FCS Express, FlowJo, FACSDiva, CytoPaint (aka Paint-A-Gate), VenturiOne, CellQuest Pro, Infinicyt or Cytospec.

Flow Cytometry is a standard technique in the art and one of skill would readily understand how to design or tailor protocols to detect one or more specific molecules and analyze the data to determine the expression of one or more specific molecules in a population of cells. Standard protocols and techniques for flow cytometry are found in Loyd "Flow Cytometry in Microbiology; Practical Flow Cytometry by Howard M. Shapiro; Flow Cytometry for Biotechnology by Larry A. Sklar, Handbook of Flow Cytometry Methods by J. Paul Robinson, et al., Current Protocols in Cytometry, Wiley-Liss Pub, Flow Cytometry in Clinical Diagnosis, v4, (Carey, McCoy, and Keren, eds), ASCP Press, 2007, Ormerod, M. G. (ed.) (2000) Flow Cytometry-A practical approach. 3rd edition. Oxford University Press, Oxford, UK, Ormerod, M. G. (1999) Flow Cytometry. 2nd edition. BIOS Scientific Publishers, Oxford., and Flow Cytometry-A basic introduction. Michael G. Ormerod, 2008.

In some embodiments, cells are sorted by phenotype for further analysis. In some embodiments, cells of different phenotypes within the same cell composition are sorted by Fluorescence-activated cell sorting (FACS). FACS is a specialized type of flow cytometry that allows for sorting a heterogeneous mixture of cells into two or more containers, one cell at a time, based upon the specific light scattering and fluorescent characteristics of each cell. It is a useful scientific instrument as it provides fast, objective and quantitative recording of fluorescent signals from individual cells as well as physical separation of cells of particular interest.

In some embodiments, the phenotype includes the number of total T cells or the number of total CD3+ T cells. In particular embodiments, a cell T composition, e.g., a therapeutic T cell composition that contains cells that express a recombinant receptor or a CAR, may include one or more different subtypes of T cells. In some embodiments, the phenotype is or includes the identity of a T cell subtype. Different populations or subtypes of T cells include, but are not limited to effector T cells, helper T cells, memory T cells, Regulatory T cells, CD4+ T cells, and CD8+ T cells. In certain embodiments, a T cell sub-type may be identified by detecting the presence or absence of a specific molecule. In certain embodiments, the specific molecule is a surface marker that can be used to identify a T cell subtype.

In some embodiments, the phenotype is positive or high level expression of one or more specific molecule that are surface markers, e.g., CD3, CD4, CD8, CD28, CD62L, CCR7, CD27, CD127, CD45RA, and/or CD45RO. In certain embodiments, the phenotype is surface marker of T cells or of a subpopulation or subset of T cells, such as based on positive surface marker expression of one or more surface markers, e.g., CD3+, CD4+, CD8+, $CD28^+$, $CD62L^+$, $CCR7^+$, $CD27^+$, $CD127^+$, $CD4^+$, $CD8^+$, $CD45RA^+$, and/or $CD45RO^+$.

In certain embodiments, the surface marker indicates expression of a recombinant receptor, e.g., a CAR. In particular embodiments, the surface marker is expression of the recombinant receptor, e.g. CAR, which, in some aspects, can be determined using an antibody, such as an anti-idiotype antibody. In some embodiments, the surface marker that indicates expression of the recombinant receptor is a surrogate marker. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same polynucleotide that encodes the recombinant receptor that is used for transduction. A non-limiting example of a surrogate marker includes, but is not limited to, a truncated EGFR (EGFRt), a truncated HER2 (tHER2) or a prostate-specific membrane antigen (PSMA) or modified form thereof. In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR). In certain embodiments, a cell that has a detectable amount of CAR has a phenotype that is or includes CAR+. In particular embodiments, a cell that has a detectable amount of a surrogate marker has a phenotype that is or includes CAR+.

In certain embodiments, the phenotype comprises expression, e.g. surface expression, of one or more of the surface markers CD3, CD4, CD8, and/or a recombinant receptor (e.g. CAR) or its surrogate marker indicating or correlating to expression of a recombinant receptor (e.g. CAR).

In particular embodiments, the phenotype is identified by the expression of one or more specific molecules that are surface markers. In certain embodiments, the phenotype is or includes positive or negative expression of CD3, CD4, CD8, and/or a recombinant receptor, e.g. a CAR. In certain embodiments, the recombinant receptor is a CAR. In particular embodiments the phenotype comprises CD3+/CAR+, CD4+/CAR+, and/or CD8+/CAR+.

In some embodiments, the phenotype is viability. In certain embodiments, the phenotype is the positive expression of a marker that indicates that the cell undergoes normal functional cellular processes and/or has not undergone or is not under the process of undergoing necrosis or programmed cell death. In some embodiments, viability can be assessed by the redox potential of the cell, the integrity of the cell membrane, or the activity or function of mitochondria. In some embodiments, viability is the absence of a specific molecule associated with cell death, or the absence of the indication of cell death in an assay.

In some embodiments, the phenotype is or comprises cell viability. In certain embodiments, the viability of cells can be detected, measured, and/or assessed by a number of means that are routine in the art. Non-limiting examples of such viability assays include, but are not limited to, dye uptake assays (e.g., calcein AM assays), XTT cell viability assays, and dye exclusion assays (e.g., trypan blue, Eosin, or propidium dye exclusion assays). Viability assays are useful for determining the number or percentage (e.g., frequency) of viable cells in a cell dose, a cell composition, and/or a cell sample. In particular embodiments, the phenotype comprises cell viability along with other features, e.g., recombinant receptor expression.

In certain embodiments, the phenotype is or includes cell viability, viable CD3+, viable CD4+, viable CD8+, viable CD3+/CAR+, viable CD4+/CAR+, viable CD8+/CAR+, or a combination thereof.

In particular embodiments, the phenotype is or includes an absence of apoptosis and/or an indication the cell is undergoing the apoptotic process. Apoptosis is a process of programmed cell death that includes a series of stereotyped morphological and biochemical events that lead to characteristic cell changes and death. These changes include blebbing, cell shrinkage, nuclear fragmentation, chromatin condensation, chromosomal DNA fragmentation, and global mRNA decay. Apoptosis is a well characterized process, and specific molecules associated with various stages are well known in the art.

In some embodiments, the phenotype is the absence of an early stage of apoptosis, and/or an absence of an indicator and/or a specific molecule associated with an early stage of apoptosis. In the early stages of apoptosis, changes in the cellular and mitochondrial membrane become apparent. Biochemical changes are also apparent in the cytoplasm and nucleus of the cell. For example, the early stages of apoptosis can be indicated by activation of certain caspases, e.g., 2, 8, 9, and 10. In particular embodiments, the phenotype is the absence of a late stage of apoptosis, and/or an absence of an indicator and/or a specific molecule associated with a late stage of apoptosis. The middle to late stages of apoptosis are characterized by further loss of membrane integrity, chromatin condensation and DNA fragmentation, include biochemical events such as activation of caspases 3, 6, and 7.

In particular embodiments, the phenotype is negative expression of one or more factors associated with programmed cell death. In certain embodiments, the phenotype is the negative expression of one or more factors associated with apoptosis, including pro-apoptotic factors known to initiate apoptosis, e.g., members of the death receptor pathway, activated members of the mitochondrial (intrinsic) pathway, such as Bcl-2 family members, e.g., Bax, Bad, and Bid, and caspases. In some embodiments, the phenotype is a negative or low amount of a marker of apoptosis. In certain embodiments, the phenotype is the negative expression of a marker of apoptosis. In certain embodiments, the phenotype is the absence of an indicator, e.g., an Annexin V molecule, that will preferentially bind to cells undergoing apoptosis when incubated with or contacted to a cell composition. In some embodiments, the phenotype is or includes the expression of one or more markers that are indicative of an apoptotic state in the cell.

In some embodiments, the phenotype is the negative (or low) expression of a specific molecule that is a marker for apoptosis. Various apoptosis markers are known to those of ordinary skill in the art and include, but are not limited to, an increase in activity of one or more caspases i.e. an activated caspase, an increase in PARP cleavage, activation and/or translocation of Bcl-2 family proteins, members of the cell death pathway, e.g., Fas and FADD, presence of nuclear shrinkage (e.g., monitored by microscope) and presence of chromosome DNA fragmentation (e.g., presence of chromosome DNA ladder) or with apoptosis assays that include TUNEL staining, and Annexin V staining.

Caspases are enzymes that cleave proteins after an aspartic acid residue, the term is derived from "cysteine-aspartic acid proteases." Caspases are involved in apoptosis, thus activation of caspases, such as caspase-3 is indicative of an increase or revival of apoptosis. In certain embodiments, caspase activation can be detected by methods known to the person of ordinary skill. In some embodiments, an antibody that binds specifically to an activated caspase (i.e., binds specifically to the cleaved polypeptide) can be used to detect caspase activation. In another example, a fluorochrome inhibitor of caspase activity (FLICA) assay can be utilized to detect caspase-3 activation by detecting hydrolysis of acetyl Asp-Glu-Val-Asp 7-amido-4-methylcoumarin (Ac-DEVD-AMC) by caspase-3 (i.e., detecting release of the fluorescent 7-amino-4-methylcoumarin (AMC)). FLICA assays can be used to determine caspase activation by a detecting the product of a substrate processed by multiple caspases (e.g., FAM-VAD-FMK FLICA). Other techniques include The CASPASE-GLO® caspase assays (PROMEGA) that use luminogenic caspase-8 tetrapeptide substrate (Z-LETD-aminoluciferin), the caspase-9 tetrapeptide substrate (Z-LEHD-aminoluciferin), the caspase-3/7 substrate (Z-DEVD-aminoluciferin), the caspase-6 substrate (Z-VEID-aminoluciferin), or the caspase-2 substrate (Z-VDVAD-aminoluciferin).

In certain embodiments, the phenotype is or includes negative expression of active caspase-1, active caspase-2, active caspase-3, active caspase-7, active caspase-8, active caspase-9, active caspase-10 and/or active caspase-13 in a cell. In particular embodiments, the phenotype is or includes active caspase 3-. In some embodiments, the proform (zymogen cleaved) form of a caspase, such as any above, also is a marker indicating the presence of apoptosis. In some embodiments, the phenotype is or includes the absence of or negative expression of a proform of a caspase, such as the proform of caspase-3.

In some embodiments, the marker of apoptosis is cleaved the Poly ADP-ribose polymerase 1 (PARP). PARP is cleaved by caspase during early stages of apoptosis. Thus, detection of a cleaved PARP peptide is a marker for apoptosis. In particular embodiments, the phenotype is or includes positive or negative expression of cleaved PARP.

In some embodiments, the marker of apoptosis is a reagent that detects a feature in a cell that is associated with apoptosis. In certain embodiments, the reagent is an annexin V molecule. During the early stages of apoptosis the lipid phosphatidylserine (PS) translocates from the inner to the outer leaflet of the plasma membrane. PS is normally restricted to the internal membrane in healthy and/or non-apoptotic cells. Annexin V is a protein that preferentially binds phosphatidylserine (PS) with high affinity. When conjugated to a fluorescent tag or other reporter, Annexin V can be used to rapidly detect this early cell surface indicator of apoptosis. In some embodiments, the presence of PS on the outer membrane will persist into the late stages of apoptosis. Thus in some embodiments, annexin V staining is an indication of both early and late stages of apoptosis. In certain embodiments, an Annexin, e.g. Annexin V, is tagged with a detectable label and incubated with, exposed to, and/or contacted to cells of a cell composition to detect cells that are undergoing apoptosis, for example by flow cytometry. In some embodiments, fluorescence tagged annexins, e.g., annexin V, are used to stain cells for flow cytometry analysis, for example with the annexin-V/7-AAD assay. Alternative protocols suitable for apoptosis detection with annexin include techniques and assays that utilize radiolabeled annexin V. In certain embodiments, the phenotype is or includes negative staining by annexin, e.g. annexin V−. In particular embodiments, the phenotype is or includes the absence of PS on the outer plasma membrane. In certain embodiments, the phenotype is or includes-cells that are not bound by annexin e.g. annexin V. In certain embodiments, the cell that lacks detectable PS on the outer membrane is annexin V−. In particular embodiments, the cell that is not bound by annexin V− in an assay, e.g., flow cytometry after incubation with labeled annexin V, is annexin V−.

In particular embodiments, the phenotype is annexin V−, annexin V−CD3+, annexin V−CD4+, annexin V−CD8+, annexin V−CD3+/CAR+, annexin V−CD4+/CAR+, annexin V−CD8+/CAR+, activated caspase 3−, activated caspase 3−/CD3+, activated caspase 3−/CD4+, activated caspase 3−/CD8+, activated caspase 3−/CD3+/CAR+, activated caspase 3−/CD4+/CAR+, activated caspase 3−/CD8+/CAR+, or a combination thereof.

Particular embodiments contemplate that cells positive for expression of a marker for apoptosis are undergoing programmed cell death, show reduced or no immune function, and have diminished capabilities if any to undergo activation, expansion, and/or bind to an antigen to initiate, perform, or contribute to an immune response or activity. In particular embodiments, the phenotype is defined by negative expression for an activated caspase and/or negative staining with annexin V.

In certain embodiments, the phenotype is or includes activated caspase 3-(caspase 3−) and/or annexin V−.

In certain embodiments, the phenotype is the negative expression of one or more factors associated with inflammatory cell death. In some embodiments, the inflammatory cell death is pyroptosis. In particular embodiments, pyroptosis occurs or may potentially occur in virally infected and/or transduced cells, e.g., virally infected and/or transduced CD4+ and/or CD8+ T cells. In some embodiments, pyroptosis is or may be associated with one or more of cell lysis, cell swelling, pore formation, DNA fragmentation, and/or caspase-1 activation. In certain embodiments, pyroptosis does not result in membrane blebbing, caspase-3 activation, and/or cytochrome-C release.

In some embodiments, the one or more factors associated with pyroptosis is or includes pattern recognition receptors, inflammasomes, active caspase-1, active IL-1b, and/or active IL-18. In some embodiments, the one or more factors is or includes activated and/or ligated pattern receptors. In particular embodiments, the one or more factors is or includes activated and/or ligated TLR, NOD-like receptors, RIG-I, MDA5, and/or STING. In some embodiments, the one or more factors is or includes active IL-1b. In particular embodiments, the one or more factors is or includes active IL-18. In certain embodiments, the one or more factors is or includes active caspase-1.

In certain embodiments, the phenotype is or includes activated caspase-1-(caspase-1-). In some embodiments, the phenotype is or includes active IL-1b-. In particular embodiments, the phenotype is or includes active IL-18-.

In particular embodiments, the inflammatory cell death is or includes necroptosis. In certain embodiments, the phenotype is the negative expression of one or more factors associated necroptosis. In some embodiments, necroptosis is a programmed necrotic cell death driven by activation of the RIP kinase family. In some embodiments, necroptosis occurs or may occur following binding and/or activation of TNF family of receptors and/or following the engagement of pattern recognition receptors (i.e. viral components binding RIG-I/MDA5 or related pathways). In some embodiments, production of TNFα during viral infection leads to stimulation of its receptor TNFR1, activation of the TNFR-associated death protein TRADD which in turn activates RIPKIto recruit RIPK3 to form a necrosome. In some embodiments, the formation of the necrosome results in the phosphorylation of MLKL and oligomerization of MLKL which allows MLKL to insert into and permeabilize plasma membranes and organelles. In some embodiments, the integration of MLKL leads to the inflammatory phenotype and release of damage-associated molecular patterns (DAMPs), which elicit immune responses.

In some embodiments, the one or more factors associated with necroptosis is activated and/or ligated pattern recognition receptors, e.g., activated and/or ligated RIG-I/MDA5, activated TNFR1, TRADD, a necrosome, and/or phosphorylated and/or oligomerized MLKL. In some embodiments, the one or more factors associated with necroptosis is or includes activated RIP kinase, e.g., RIPK1, RIPK2, RIPK3, RIPK4, and/or RIPK5. In some embodiments, the one or more factors is activated RIPK1 and/or RIPK3. In some embodiments, the phenotype is or includes activated RIPK1−, activated RIPK3−, phosphorylated MLKL−, and/or oligomerized MLKL−.

In particular embodiments, the phenotype is the negative expression of one or more factors associated autophagy. In some embodiments, autophagy is or includes cell intrinsic catabolic mechanism that occurs and/or may occur under certain cell culture conditions, e.g., conditions where critical nutrients are limited and/or in response to certain cytokines. In some embodiments, autophagy occurs independent of caspase activity.

In some embodiments, the autophagy is macro-autophagy, micro-autophagy, and/or chaperone-mediated autophagy. In some embodiments, one or more factors associated with autophagy marker include AMPK, ULK1, ULK2 and/or other Atg family members (e.g., ATG16L), PIK3C3, BECN1, Vps34, Beclin-1, MAPILC3A,B,C, GABARAP, GABARAPL1, GABARAPL2, UVRAG, IRGM, CLN3, Parkin, p62, and LAMP2 and/or other known factors such as described in Behrends, Nature. 2010 Jul. 1; 466 (7302): 68-76 and Glick et al. J Pathol. 2010 May; 221 (1): 3−12. In some embodiments, the phenotype is AMPK−, ULK1−, ULK2−, PIK3C3−, BECN1−, Vps34−, Beclin−1−, MAPILC3A−, MAPILC3B−, MAPILC3C−, GABARAP−, GABARAPL1−, GABARAPL2−, UVRAG−, IRGM−, CLN3−, Parkin−, p62−, and/or LAMP2−.

Among the phenotypes are the expression or surface expression of one or more markers generally associated with one or more sub-types or subpopulations of T cells, or phenotypes thereof. T cell subtypes and subpopulations may include CD4+ and/or of CD8+ T cells and subtypes thereof that may include naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), $T_{EMRA}$ cells or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the phenotype is or includes a phenotype of a memory T cell or memory T cell subset. Memory T cells are antigen-specific T cells that have previously been exposed to their cognate antigen. Memory T cells persist long-term after an infection has resolved. Memory T cells quickly expand to large numbers of effector T cells upon re-exposure to their cognate antigen, thus providing the immune system with "memory" against past infections. Memory T cells comprise three subtypes: central memory T cells ($T_{CM}$ cells) and two types of effector memory T cells ($T_{EM}$ cells and $T_{EMRA}$ cells). In some embodiments the phenotype is or includes a phenotype of a memory T cell (or one or more markers associated therewith), such as a $T_{CM}$ cell, a $T_{EM}$ cell, or a $T_{EMRA}$ cell, a memory stem T cell ($T_{SCM}$) cell, or a combination thereof. In particular embodiments, the phenotype is or includes the expression of one or more specific molecules that is a marker for memory and/or memory T cells or subtypes thereof.

In particular embodiments, the phenotype is or includes the expression of one or more specific molecules that is a marker for naïve T cells. Naïve T cells include fresh T cells that have been produced in the bone marrow and are able to respond to newly encountered pathogens containing antigens the immune system has not processed before. After stimulation by their cognate antigen, a portion activated naive T-cells will develop into memory cells.

In some embodiments, the phenotype is or includes a memory T cell or a naive T cell. In certain embodiments, the phenotype is the positive or negative expression of one or more specific molecules that are markers for memory. In some embodiments, the memory marker is a specific molecule that may be used to define a memory T cell population.

In some embodiments, the phenotype is or includes a phenotype of or one or more marker associated with a non-memory T cell or sub-type thereof; in some aspects, it is or includes a phenotype or marker(s) associated with a naïve cell. In some embodiments, the phenotype is CCR7+/CD27+/CD28+/CD45RA+. In certain embodiments, the phenotype is or includes CCR7+/CD45RA+. In some embodiments, the phenotype is or includes a phenotype of a central memory T cell. In particular embodiments, the phenotype is or includes CCR7+/CD27+/CD28+/CD45RA". In some embodiments, the phenotype is or includes an effector memory cell. In some embodiments, the phenotype is or includes CCR7/CD27+/CD28+/CD45RA". In certain embodiments, the phenotype is or includes that of a $T_{EMRA}$ cell or a $T_{SCM}$ cell. In certain embodiments, the phenotype is or includes CD45RA+. In particular embodiments, the phenotype is or includes CCR7−/CD27/CD28−/CD45RA+. In some embodiments, the phenotype is or includes one of CD27+/CD28+, CD27/CD28+, CD27+/CD28", or CD27−/CD28−.

In some embodiments the phenotype is or includes any of the foregoing phenotypic properties and further includes the expression of a recombinant receptor, such as phenotype associated with a memory T cell or memory subtype and that expresses a CAR, or a phenotype associated with a naïve cell that expresses a CAR. In certain embodiments, the phenotype is or includes that of a central memory T cell or stem central memory T cell that expresses a CAR. In particular embodiments, the phenotype is or includes that of an effector memory cell that expresses a CAR. In some embodiments, the phenotype is or includes that of a $T_{EMRA}$ cell that expresses a CAR. In particular embodiments, the phenotype is or includes CAR$^+$/CCR7$^+$/CD27$^+$/CD28$^+$/CD45RA$^-$; CAR$^+$/CCR7$^-$/CD27$^+$/CD28$^+$/CD45RA$^-$; CAR$^+$/CCR7$^-$/CD27$^-$/CD28$^-$/CD45RA$^+$; CAR$^+$/CD27$^+$/CD28$^+$; CAR$^+$/CD27$^-$/CD28$^+$; CAR$^+$/CD27$^+$/CD28$^-$; or CAR$^+$/CD27$^-$/CD28$^-$.

In certain embodiments, the phenotype is or includes a phenotype of a T cell that is negative for a marker of apoptosis. In certain embodiments, the phenotype is or includes a naïve cell that is negative for a marker of apoptosis. In some embodiments, the marker of apoptosis is activated caspase 3. In some embodiments, the marker of apoptosis is positive staining by annexin V.

In particular embodiments, the phenotype is or includes that of a memory T cell or subtype thereof that is negative for a marker of apoptosis that expresses a CAR. In particular embodiments, the phenotype is or includes that of a memory T cell or particular subtype that is negative for marker of apoptosis that expresses a CAR. In certain embodiments, the phenotype is or includes a naïve cell that is negative for a marker of apoptosis that expresses a CAR. In certain embodiments, the phenotype is or includes that of a central memory T cell or $T_{SCM}$ Cell or naïve cell that is negative for a marker of apoptosis that expresses a CAR. In particular embodiments, the phenotype is or includes that of an effector memory cell that is negative for a marker of apoptosis that expresses a CAR. In certain embodiments, the phenotype is or includes annexin $V^-/CAR^+/CCR7^+/CD27^+/CD28^+/CD45RA^-$; annexin $V^-/CAR^+/CCR7^-/CD27^+/CD28^+/CD45RA^-$; annexin $V^-/CAR^+/CCR7^-/CD27^-/CD28^-/CD45RA^+$; annexin $V^-/CAR^+/CD27^+/CD28^+$; annexin $V^-/CAR^+/CD27^-/CD28^+$; annexin $V^-/CAR^+/CD27^+/CD28^-$; or annexin $V^-/CAR^+/CD27^-/CD28^-$. In certain embodiments, the phenotype is or includes activated caspase $3^-/CAR^+/CCR7^+/CD27^+/CD28^+/CD45RA^-$; activated caspase $3^-/CAR^+/CCR7^-/CD27^+/CD28^+/CD45RA^-$; activated caspase $3^-/CAR^+/CCR7^-/CD27^-/CD28^-/CD45RA^+$; activated caspase $3^-/CAR^+/CD27^+/CD28^+$; activated caspase $3^-/CAR^+/CD27^-/CD28^+$; activated caspase $3^-/CAR^+/CD27^+/CD28^-$; or activated caspase $3^-/CAR^+/CD27^-/CD28^-$.

In some embodiments, the phenotype is or includes positive or negative expression a marker of exhaustion. T cell exhaustion is a state of T cell dysfunction that arises during many chronic infections and cancer. It is defined by poor effector function, sustained expression of inhibitory receptors and a transcriptional state distinct from that of functional effector or memory T cells. Exhaustion prevents optimal control of infection and tumors. In certain embodiments, the phenotype is or includes positive or negative expression of a specific molecule that is associated with exhaustion. In certain embodiments, the specific molecule is any molecule that is associated with exhaustion or a quality associated with exhaustion, e.g., poor effector function or inhibitory receptor expression. In particular embodiments, the phenotype is positive or negative expression of an immune checkpoint inhibitor. In particular embodiments, marker of exhaustion is CTLA-4, FOXP3, PD-1, TIGIT, LAB-3, 2B4, BTLA, TIM3, VISTA, or CD96, or a combination thereof. In certain embodiments, the phenotype is the positive or negative expression of CTLA-4, FOXP3, PD-1, TIGIT, LAB-3, 2B4, BTLA, TIM3, VISTA, or CD96, or a combination thereof. In particular embodiments, the phenotype is positive or negative expression of PD1 and/or FOXP3.

In certain embodiments, the phenotype is the negative expression of a specific molecule that is associated with T cell activation. In some embodiments, the phenotype is or includes the negative expression of one or more of a specific molecule that is an activation marker. T cell activation refers to the elicitation of an immune response by a T cell, upon stimulation of the latter by an antigen presenting cell (APC). This interactive pathway explains the main stimulatory signals that trigger T cell activation as well as their downstream pathways. In general, T cell activation requires two simultaneous signals. The first is binding of the T cell receptor complex (TCR) to a major histocompatibility complex (MHC) molecule carrying a peptide antigen. The second is provided by the binding of the co-stimulatory receptor CD28 to proteins in the surface of the APC, such as B7-2 or B7-1. In certain embodiments, the specific molecule is associated with TCR activation, e.g., is activated, altered, or expressed as a result of T cell activation. In some embodiments, the specific molecule is associated with activation of a CD28 receptor, e.g., a molecule that is activated, altered, or expressed as a result of T cell activation.

In some embodiments, the phenotype is or includes positive or negative expression a marker of exhaustion. T cell exhaustion is a state of T cell dysfunction that arises during many chronic infections and cancer. It is defined by poor effector function, sustained expression of inhibitory receptors and a transcriptional state distinct from that of functional effector or memory T cells. Exhaustion prevents optimal control of infection and tumors. In certain embodiments, the phenotype is or includes positive or negative expression of a specific molecule that is associated with exhaustion. In certain embodiments, the specific molecule is any molecule that is associated with exhaustion or a quality associated with exhaustion, e.g., poor effector function or inhibitory receptor expression. In particular embodiments, the phenotype is positive or negative expression of an immune checkpoint inhibitor. In particular embodiments, marker of exhaustion is CTLA-4, FOXP3, PD-1, TIGIT, LAB-3, 2B4, BTLA, TIM3, VISTA, or CD96, or a combination thereof. In certain embodiments, the phenotype is the positive or negative expression of CTLA-4, FOXP3, PD-1, TIGIT, LAB-3, 2B4, BTLA, TIM3, VISTA, or CD96, or a combination thereof. In particular embodiments, the phenotype is positive or negative expression of PD1 and/or FOXP3.

In some embodiments, the phenotype is or includes positive or negative expression of an exhaustion marker in a CD3+ cell that expresses a recombinant receptor or a CAR. In particular embodiments, the phenotype is or includes positive or negative expression of an exhaustion marker in a CD4+ cell that expresses a recombinant receptor or a CAR. In some embodiments, the phenotype is or includes positive or negative expression of an exhaustion marker and CD3+ and positive expression of a recombinant receptor or a CAR. In particular embodiments, the phenotype is or includes positive or negative expression of an exhaustion marker in a CD4+ cell that expresses a recombinant receptor or a CAR. In some embodiments, the phenotype is or includes positive or negative expression of an exhaustion marker in a CD8+ cell that expresses a recombinant receptor or a CAR. In particular embodiments, the exhaustion marker is one or more of CTLA-4, FOXP3, PD-1, TIGIT, LAB-3, 2B4, BTLA, TIM3, VISTA, or CD96. In particular embodiments, the exhaustion marker is PD1 and/or FOXP3.

In particular embodiments, the phenotype is or includes PD1−/CD3+, PD1−/CD4+, PD1−/CD8+, PD1−/CD3+/CAR+, PD1−/CD4+/CAR+, PD1−/CD8+/CAR+, PD1−/annexin V−, PD1−/annexin V−/CD3+, PD1−/annexin V−/CD4+, PD1−/annexin V−/CD8+, PD1−/annexin V/−CD3+/CAR+, PD1−/annexin V−/CD4+/CAR+, PD1−/annexin V−/CD8+/CAR+, PD1−/activated caspase 3−, PD1−/activated caspase 3−/CD3+, PD1−/activated caspase 3-/CD4+, PD1−/activated caspase 3−/CD8+, PD1−/activated caspase 3−/CD3+/CAR+, PD1−/activated caspase 3−/CD4+/CAR+, PD1−/activated caspase 3−/CD8+/CAR+, or a combination thereof.

In certain embodiments, the phenotype is or includes FOXP3−/CD3+, FOXP3−CD4+, FOXP3−/CD8+, FOXP3−/CD3+/CAR+, FOXP3−/CD4+/CAR+, FOXP3−/CD8+/CAR+, FOXP3−/annexin V−, FOXP3−/annexin V−/CD3+, FOXP3−/annexin V−/CD4+, FOXP3−/annexin V−/CD8+, FOXP3−/annexin V/−CD3+/CAR+, FOXP3−/annexin V−/CD4+/CAR+, FOXP3−/annexin V−/CD8+/CAR+, FOXP3−/activated caspase 3−, FOXP3−/activated caspase 3−/CD3+, FOXP3−/activated caspase 3−/CD4+, FOXP3−/ activated caspase 3−/CD8+, FOXP3−/activated caspase 3−/CD3+/CAR+, FOXP3−/activated caspase 3−/CD4+/CAR+, FOXP3−/activated caspase 3−/CD8+/CAR+, or a combination thereof.

In certain embodiments, the phenotype is the negative expression of a specific molecule that is associated with T cell activation. In some embodiments, the phenotype is or includes the negative expression of one or more of a specific molecule that is an activation marker. T cell activation refers to the elicitation of an immune response by a T cell, upon stimulation of the latter by an antigen presenting cell (APC). This interactive pathway explains the main stimulatory signals that trigger T cell activation as well as their downstream pathways. In general, T cell activation requires two simultaneous signals. The first is binding of the T cell receptor complex (TCR) to a major histocompatibility complex (MHC) molecule carrying a peptide antigen. The second is provided by the binding of the co-stimulatory receptor CD28 to proteins in the surface of the APC, such as B7-2 or B7-1. In certain embodiments, the specific molecule is associated with TCR activation, e.g., is activated, altered, or expressed as a result of T cell activation. In some embodiments, the specific molecule is associated with activation of a CD28 receptor, e.g., a molecule that is activated, altered, or expressed as a result of T cell activation.

In particular embodiments, the phenotype is or includes the negative expression of one or more of a specific molecule that is an activation marker. In certain embodiments, the activation marker is one or more of CD25, CD26, CD27, CD28, CD30, CD71, CD154, CD40L, CD127, LAG3, Ki67, or a combination thereof. In certain embodiments, the phenotype is the negative or positive expression of one or more of CD25, CD26, CD27, CD28, CD30, CD71, CD154, CD40L, CD127, LAG3, or Ki67. In certain embodiments, the phenotype is or includes the expression of CD25, CD127, LAG3, Ki67, or a combination thereof.

In some embodiments, the phenotype is or includes positive or negative expression of an activation marker in a CD3+ cell that expresses a recombinant receptor or a CAR. In particular embodiments, the phenotype is or includes positive or negative expression of activation marker in a CD4+ cell that expresses a recombinant receptor or a CAR. In some embodiments, the phenotype is or includes positive or negative expression of activation marker in a CD8+ cell that expresses a recombinant receptor or a CAR. In particular embodiments, the activation marker is one or more of CD25, CD26, CD27, CD28, CD30, CD71, CD154, CD40L, CD127, LAG3, or Ki67. In particular embodiments, the activation marker is CD25, CD127, LAG3, Ki67, or a combination thereof.

In particular embodiments, the phenotype is or includes positive or negative expression of an activation marker and CD3+, CD4+, CD8+, CD3+/CAR+, CD4+/CAR+, CD8+/CAR+, annexin V−, annexin V−/CD3+, annexin V−/CD4+, annexin V−/CD8+, annexin V/−CD3+/CAR+, annexin V−/CD4+/CAR+, annexin V−/CD8+/CAR+, activated caspase 3−, activated caspase 3−/CD3+, activated caspase 3−/CD4+, activated caspase 3−/CD8+, activated caspase 3−/CD3+/CAR+, activated caspase 3−/CD4+/CAR+, activated caspase 3−/CD8+/CAR+, or a combination thereof.

In some embodiments, the phenotype is assessed by a response to a stimulus, for example a stimulus that stimulates triggers, induces, stimulates, or prolongs an immune cell function. In certain embodiments, the cells are incubated in the presence of stimulating conditions or a stimulatory agent, the phenotype is or includes the response to the stimulation. In particular embodiments, the phenotype is or includes the production or secretion of a soluble factor in response to one or more stimulations. In some embodiments, the phenotype is or includes a lack or production or secretion of s soluble factor in response to one or more stimulations. In certain embodiments, the soluble factor is a cytokine.

In some embodiments, the stimulatory conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the cells are stimulated and the phenotype is determined by whether or not a soluble factor, e.g., a cytokine or a chemokine, is produced or secreted. In some embodiments, the stimulation is nonspecific, i.e., is not an antigen-specific stimulation. In some embodiments, cells are incubated in the presence of stimulating conditions or a stimulatory agent for about 1 hour, about 2 hours, about 3 hours, about 4 hours, about 5 hours, about 6 hours, about 7 hours, about 8 hours, about 9 hours, about 10 hours, about 11 hours, about 12 hours, about 18 hours, about 24 hours, about 48 hours, or for a duration of time between 1 hour and 4 hours, between 1 hour and 12 hours, between 12 hours and 24 hours, each inclusive, or for more than 24 hours.

In some embodiments, the cells are stimulated with an agent that is an antigen or an epitope thereof that is specific to the recombinant receptor, or is an antibody or fragment thereof that binds to and/or recognizes the recombinant receptor, or a combination thereof. In some embodiments, the recombinant receptor is a CAR, and the agent is an antigen or an epitope thereof that is specific to the CAR, or is an antibody or fragment thereof that binds to and/or recognizes the CAR, or a combination thereof. In particular embodiments, the cells are stimulated by incubating the cells in the presence of target cells with surface expression of the antigen that is recognized by the CAR. In certain embodiments, the recombinant receptor is a CAR, and the agent is an antibody or an active fragment, variant, or portion thereof that binds to the CAR. In certain embodiments, the antibody or the active fragment, variant, or portion thereof that binds to the CAR is an anti-idiotypic (anti-ID) antibody.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. In some embodiments, the one or more agents are PMA and ionomycin.

In particular embodiments, the phenotype is or includes the production or secretion of a cytokine in response to one or more of stimulations. The production and/or the secretion of cytokines contributes to immune responses, and is involved in different processes including the induction of anti-viral proteins and the induction of T cell proliferation. Cytokines are not pre-formed factors but are rapidly produced and secreted in response to cellular activation. The production or secretion of cytokines may be measured, detected, and/or quantified by any suitable technique known in the art.

In certain embodiments, the phenotype is the production of one or more cytokines. In particular embodiments, the production of one or more cytokines is measured, detected, and/or quantified by intracellular cytokine staining. Intracellular cytokine staining (ICS) by flow cytometry is a technique well-suited for studying cytokine production at the single-cell level. It detects the production and accumulation of cytokines within the endoplasmic reticulum after cell stimulation, allowing for the identification of cell populations that are positive or negative for production of a particular cytokine or for the separation of high producing and low producing cells based on a threshold. ICS can also be used in combination with other flow cytometry protocols for immunephenotyping using cell surface markers or with MHC multimers to access cytokine production in a particular subgroup of cells, making it an extremely flexible and versatile method. Other single-cell techniques for measuring or detecting cytokine production include, but are not limited to ELISPOT, limiting dilution, and T cell cloning.

In some embodiments, the phenotype is the production of a cytokine. In particular embodiments, the phenotype is the lack of the production of the cytokine. In particular embodiments, the phenotype is positive for or is a high level of production of a cytokine. In certain embodiments, the phenotype is negative for or is a low level of production of a cytokine. Cytokines may include, but are not limited to, IL-1, IL-1B, IL-2, sIL-2Ra, IL-3, IL-5, IL-6, IL-7, IL-8, IL-10, IL-12, IL-13, IL 27, IL-33, IL-35, TNF, TNF alpha, CXCL2, CCL2, CCL3, CCL5, CCL17, CCL24, PGD2, LTB4, interferon gamma (IFN-γ), granulocyte macrophage colony stimulating factor (GM-CSF), macrophage inflammatory protein (MIP)-1a, MIP-1b, Flt-3L, fracktalkine, and/or IL-5.

In some embodiments, the phenotype is or includes the production of a cytokine. In certain embodiments, the phenotype is or includes the production of more than one cytokines. In certain embodiments, the phenotype is or includes a lack of a production of one or more cytokines. In certain embodiments, the phenotype is or includes the production, or lack thereof, of one or more of IL-2, IL-13, IFN-gamma, or TNF-alpha. In some embodiments, the phenotype is the presence of a production, and/or the presence of a high level of production of the cytokine. In some embodiments, the phenotype is a low, reduced, or absent production of a cytokine.

In some embodiments, the phenotype is or includes the internal (intracellular) production of a cytokine, for example, as assessed in the presence of a stimulatory agent or under stimulatory conditions when secretion is prevented or inhibited. In particular embodiments, the phenotype is or includes the lack or absence of an internal production of a cytokine. In certain embodiments, the phenotype is or includes the internal amount of one or more cytokines when the production of more than one cytokines as assessed with an ICS assay. In certain embodiments, the phenotype is or includes the internal amount of one or more of IL-2, IL-13, IFN-gamma, or TNF-alpha as assessed with an ICS assay. In some embodiments, the phenotype is or includes a low internal amount or a lack of a detectable amount of one or more cytokines as assessed with an ICS assay. In certain embodiments, phenotype is or includes a low internal amount or a lack of a detectable amount of IL-2, IL-13, IFN-gamma, or TNF-alpha as assessed with an ICS assay.

Particular embodiments contemplate that the phenotype may include the production of a cytokine or a lack of or a low amount of production for a cytokine. This may depend on several factors that include, but are not limited to, the identity of the cytokine, the assay performed to detect the cytokine, and the stimulatory agent or condition used with the assay. For example, in some embodiments it is contemplated that the phenotype is or includes a lack of, or a low level of IL-13 production as indicated by ICS while in some embodiments, the phenotype is or includes production of IFN-gamma as indicated by ICS.

In some embodiments, the phenotype is or includes production of one or more cytokines and either CD3+, CD4+, CD8+, CD3+/CAR+, CD4+/CAR+, CD8+/CAR+, annexin V−, annexin V−CD3+, annexin V−CD4+, annexin V−CD8+, annexin V−CD3+/CAR+, annexin V−CD4+/CAR+, annexin V−CD8+/CAR+, activated caspase 3−, activated caspase 3−/CD3+, activated caspase 3−/CD4+, activated caspase 3−/CD8+, activated caspase 3−/CD3+/CAR+, activated caspase 3−/CD4+/CAR+, or activated caspase 3−/CD8+/CAR+, or a combination thereof. In particular embodiments, the phenotype is or includes production of one or more cytokines in CD4+/CAR+ and/or CD8+/CAR+.

In some embodiments, the phenotype is or includes a lack of production of one or more cytokines. In certain embodiments, the phenotype is or includes a lack of a production of one or more cytokines and either CD3+, CD4+, CD8+, CD3+/CAR+, CD4+/CAR+, CD8+/CAR+, annexin V−, annexin V−CD3+, annexin V−CD4+, annexin V−CD8+, annexin V−CD3+/CAR+, annexin V−CD4+/CAR+, annexin V−CD8+/CAR+, activated caspase 3−, activated caspase 3−/CD3+, activated caspase 3−/CD4+, activated caspase 3−/CD8+, activated caspase 3−/CD3+/CAR+, activated caspase 3−/CD4+/CAR+, or activated caspase 3−/CD8+/CAR+, or a combination thereof.

In particular embodiments, the phenotype is or includes the presence or absence of an internal amount of one or more of IL-2, IL-13, IFN-gamma, or TNF-alpha as assessed with an ICS assay and one or more specific markers for a subset of cells or cells of a particular cell type. In some embodiments, the phenotype is or includes production, or lack thereof, of one or more of IL-2, IL-13, IFN-gamma, or TNF-alpha and CD4+/CAR+ and/or CD8+/CAR+. In certain embodiments, the phenotype is or includes production of IL-2 and CD4+/CAR+ and/or CD8+/CAR+. In some embodiments, the phenotype is or includes a lack of or low production of IL-2 and CD4+/CAR+ and/or CD8+/CAR+. In some embodiments, the phenotype is or includes production of IL-13 and CD4+/CAR+ and/or CD8+/CAR+. In some embodiments, the phenotype is or includes production of IL-13 and CD4+/CAR+ and/or CD8+/CAR+. In certain embodiments, the phenotype is or includes the lack of or low production of IL-13 and CD4+/CAR+ and/or CD8+/CAR+. In some embodiments, the phenotype is or includes production of IFN-gamma and CD4+/CAR+ and/or CD8+/CAR+. In certain embodiments, the phenotype is or includes production of TNF-alpha and CD4+/CAR+ and/or CD8+/CAR+. In certain embodiments, the phenotype is or includes a lack of or low production of TNF-alpha and CD4+/CAR+ and/or CD8+/CAR+.

Any one or more the phenotypes, alone or in combination, can be assessed or determined in accord with the provided methods. In some embodiments, the phenotype is CD3+, CD3+/CAR+, CD4+/CAR+, CD8+/CAR+, or a combination thereof.

In certain embodiments, the phenotype is or includes CD3+. In certain embodiments, the phenotype is or includes CD3+/CAR+. In some embodiments, the phenotype is or includes CD8+/CAR+. In certain embodiments, the phenotype is or includes In particular embodiments, the phenotype is or includes Annexin-/CD3+/CAR+. In some embodiments, the phenotype is or includes Annexin-/CD4+/CAR+ In particular embodiments, the phenotype is Annexin-/CD8+/CAR.

In particular embodiments, the phenotype is or includes a lack of or a low amount of intracellular IL-2 and CD4+/CAR+. In particular embodiments, the phenotype is a lack of or a low amount of intracellular IL-13 and CD4+/CAR+. In some embodiments, the phenotype is a lack of or a low amount of intracellular expression of IL-13 and CD8+/CAR+ cells. In particular embodiments, the phenotype is a lack of or a low amount of intracellular TNF-alpha CD4+/CAR+.

In certain embodiments, the phenotype is or includes CD8+/CAR+. In certain embodiments, the phenotype is or includes annexin-/CD8+/CAR+.

In certain embodiments, a number, multiple, or fraction of cells of a particular phenotype of a cell composition is determined, measured, obtained, detected, observed, and/or identified. In some embodiments, the cell composition is a T cell composition. In certain embodiments, the cell composition contains cells that express a recombinant receptor, e.g., a CAR. In particular embodiments, the cell composition is a therapeutic T composition containing cells that express a recombinant receptor that may be administered to a subject to treat a disease or condition. In certain embodiments, the number of cells of the phenotype is the total amount of cells of the phenotype of the cell composition. In certain embodiments, the number of cells of the phenotype is the total number of cells of the phenotype present in a dose of the cell composition. In particular embodiments, the number of cells of the phenotype is the number of cells of the phenotype present in a sample of the cell composition. In some embodiments, the number of the cells of the phenotype may be expressed as a frequency, ratio, and/or a percentage of cells of the phenotype present in the cell composition, or a dose or a sample thereof.

In some embodiments, the cell composition is obtained from a subject, and the number, multiple, or fraction of cells of the phenotype is the number of cells of the phenotype present in the cell composition normalized to the subject's body weight. In certain embodiments, the measurement of the phenotype is the number of cells of the phenotype per pound of subject's body weight. In particular embodiments, the measurement of the phenotype is the number of cells of the phenotype per 1 lb., 2 lbs., 3 lbs., 4 lbs., 5 lbs., 10 lbs., of 20 lbs. of subject's body weight. In some embodiments, the measurement of the phenotype is the number of cells of the phenotype per kg of subject's body weight. In particular embodiments, the measurement of the phenotype is the number of cells of the phenotype per 1 kg, 2 kg, 3 kg, 4 kg, 5 kg, 10 kg, or 20 kg or the subject's body weight.

In particular embodiments, the number, multiple, or fraction of the cells of a phenotype is transformed, for example to compress the range of relevant values of the number, multiple, or fraction. In some embodiments, the transformation is any application of a deterministic mathematical function to each point in a data set, such as, each data point x is replaced with the transformed value y=f(x), where f is a function. In general, transforms may be applied so that the data appear to more closely meet the assumptions of a statistical inference procedure that is to be applied, or to improve the interpretability or appearance of graphs. In most cases the function that is used to transform the data is invertible, and generally is continuous. The transformation is usually applied to a collection of comparable measurements. Examples of suitable transformations include, but are not limited to, logarithm and square root transformation, reciprocal transformations, and power transformations. In certain embodiments, the number, multiple, or fraction of the cells of a phenotype is transformed by a logarithmic transformation. In certain embodiments, the logarithmic transformation is a common log ($\log_{10}(x)$), a natural log(ln (x)) or a binary log($\log_2(x)$).

B. Antigen-Specific or Recombinant Receptor-Dependent Activity

Particular embodiments contemplate that a recombinant receptor dependent activity, e.g., a CAR dependent activity, or "B", is an activity that occurs in a cell that expresses a recombinant receptor which does not and/or cannot occur in a cell that does not express the recombinant receptor. In some embodiments, the recombinant receptor dependent activity is an activity that depends on an activity or presence of the recombinant receptor. The recombinant receptor dependent activity may be any cellular process that is directly or indirectly influenced by the expression and/or presence of the recombinant receptor or by a change in activity, such as receptor stimulation, of the recombinant receptor. In some embodiments, the recombinant receptor dependent activity may include, but is not limited to cellular processes such as cell division, DNA replication, transcription, protein synthesis, membrane transport, protein translocation, and/or secretion, or it may be an immune cell function, e.g., a cytolytic activity. In certain embodiments, recombinant receptor dependent activity may be measured by a change in the confirmation of the CAR receptor, the phosphorylation of an intracellular signaling molecule, degradation of a protein, transcription, translation, translocation of a protein, and/or production and secretion of a factor, such as a protein, or growth factor, cytokine. In certain embodiments, the recombinant receptor is a CAR.

In certain embodiments, the recombinant receptor dependent activity, e.g., a CAR dependent activity is a measurement of a factor, e.g., an amount or concentration, or a change in the amount or concentration following stimulation of the cell composition. In certain embodiments, the factor may be a protein, a phosphorylated protein, a cleaved protein, a translocated protein, a protein in an active confirmation, a polynucleotide, an RNA polynucleotide, an mRNA, and/or an shRNA. In certain embodiments, the measurement may include, but is not limited to, an increase or decrease of kinase activity, protease activity, phosphatase activity, cAMP production, ATP metabolism, translocation, e.g., a nuclear localization of a protein, an increase in transcriptional activity, an increase in translational activity, production and/or secretion of a soluble factor, cellular uptake, ubiquitination, and/or protein degradation.

In particular embodiments, the factor is a soluble factor that is secreted, such as a hormone, a growth factor, a chemokine, and/or a cytokine.

In some embodiments, the recombinant receptor activity, e.g., a CAR dependent activity is a response to stimulation. In certain embodiments, the cells are incubated in the presence of stimulating conditions or a stimulatory agent, and the activity is or includes at least one aspect of a response to the stimulation. A response may include, but is not limited to, an intracellular signaling event, such as an increased activity of a receptor molecule, an increased kinase activity of one or more kinases, an increase in the transcription of one or more genes, increased protein synthesis of one or more proteins, and/or an intracellular signaling molecule e.g., an increased kinase activity of a protein. In some embodiments, the response or activity is associated with an immune activity, and may include, but is not limited to, production and/or section of a soluble factor, e.g., a cytokine, an increase in antibody production, and/or an increase in cytolytic activity.

In particular embodiments, the response to a stimulation of a cell composition is assessed by measuring, detecting, or quantifying an response to a stimulus, i.e. at least one activity that is initiated, triggered, supported, prolonged, and/or caused by the stimulus. In certain embodiments, the cells are stimulated and the response to the stimulation is an activity that is specific to cells that express a recombinant receptor. In certain embodiments, the activity is a recombinant receptor specific activity and the activity occurs in cells that express the recombinant receptor, but does not occur, or only minimally occurs, in cells that do not express the receptor. In particular embodiments, the recombinant receptor is a CAR. In some embodiments, the activity is a CAR dependent activity.

The conditions used for stimulating cells, e.g., immune cells or T cells, can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the cells are stimulated and the activity is determined by whether or not a soluble factor, e.g., a cytokine or a chemokine, is produced or secreted. In some embodiments, the stimulation is nonspecific, i.e., is not an antigen-specific stimulation.

In some embodiments, the activity is specific to cells that express a recombinant receptor. In some embodiments, an activity that is specific to cells that express a recombinant receptor does not occur in cells that lack expression of the recombinant receptor. In certain embodiments, the recombinant receptor is a CAR, and the activity is a CAR dependent activity. In particular embodiments, the activity is not present in cells that lack expression of the recombinant receptor under the same conditions where the activity is present in cells that express the recombinant receptor. In certain embodiments, the CAR dependent activity is about 10%, about 20%, about 30%, about 40%, about 50%, about 60% about 70%, about 75%, about 80%, about 85%, about 90%, about 95%, about 97%, about 98%, about 99%, or about 99% less than the CAR dependent activity in CAR-cells under the same conditions.

In some embodiments, the activity is specific to cells that express a recombinant receptor, e.g., a CAR, and the activity is produced by stimulation with an agent or under stimulatory conditions that are specific to cells that express the recombinant receptor. In some embodiments, the recombinant receptor is a CAR, and a CAR specific stimulation stimulates, triggers, initiates, and/or prolongs an activity in CAR+ cells, but does not stimulate, trigger, initiate, and/or prolong the activity in CAR-cells. In some embodiments, the CAR dependent activity is about 10%, about 20%, about 30%, about 40%, about 50%, about 60% about 70%, about 75%, about 80%, about 85%, about 90%, about 95%, about 97%, about 98%, about 99%, or about 99% less in CAR-cells than in the CAR+ cells following stimulation by the CAR specific stimulus.

In certain embodiments, the activity is a recombinant receptor dependent, e.g., a CAR dependent activity that is stimulated by an agent that is specific for the recombinant receptor. In some embodiments, the recombinant receptor specific agent, e.g., a CAR specific agent, is an antigen or an epitope thereof that is bound by and/or recognized by the recombinant receptor, e.g., the CAR. In some embodiments, the recombinant receptor specific agent is an antibody or active fragment thereof that binds to and/or recognizes the recombinant receptor. In some embodiments, the agent is an anti-idiotypic antibody or an active fragment, variant, or portion thereof (anti-ID) that binds to the recombinant receptor. In certain embodiments, the recombinant receptor specific agent is a cell that expresses the antigen on its surface. In some embodiments, the recombinant receptor dependent activity is stimulated by an antigen or an epitope thereof that is bound by and/or recognized by the recombinant receptor. In certain embodiments, the recombinant receptor dependent activity is stimulated by an antibody or active fragment thereof that binds to and/or recognizes the recombinant receptor. In particular embodiments, the recombinant receptor dependent activity is stimulated by an anti-ID.

In some embodiments, the activity is measured in the cell composition containing cells expressing a recombinant receptor, e.g., a CAR, and the measurement is compared to one or more controls. In certain embodiments, the control is a similar or identical composition of cells that was not stimulated. For example, in some embodiments, the activity is measured in a cell composition following or during incubation with an agent, and the resulting measurement is compared to a control measurement of the activity from the similar or identical cell composition that is not incubated with the agent. In some embodiments, the activity is a recombinant receptor dependent activity, and both the cell composition and the control cell composition contain cells that express the recombinant receptor. In some embodiments, the activity is a recombinant receptor dependent activity, and the control is taken from a similar cell composition that does not contain cells that express the recombinant receptor, e.g., CAR+ cells. Thus in some embodiments, a cell composition that contains recombinant receptor expressing cells and a control cell composition that does not contain recombinant receptor expressing cells are contacted with a recombinant receptor expressing specific agent. In certain embodiments, the control is a measurement from the same cell composition that expresses a recombinant receptor that is taken prior to any stimulation. In certain embodiments, a control measurement is obtained to determine a background signal, and control measurement is subtracted from the measurement of the activity. In some embodiments, the measurement of the activity in the cell composition is divided by the control measurement, to obtain a value that is a ratio of the activity over a control level.

In particular embodiments, the activity is or includes the production and/or secretion of a soluble factor. In some embodiments, the activity is a recombinant receptor, e.g., a CAR, dependent activity that is or includes the production and/or secretion of a soluble factor. In certain embodiments, the soluble factor is a cytokine or a chemokine.

Suitable techniques for the measurement of the production or secretion of a soluble factor are known in the art. Production and/or secretion of a soluble factor can be measured by determining the concentration or amount of the extracellular amount of the factor, or determining the amount of transcriptional activity of the gene that encodes the factor. Suitable techniques include, but are not limited to assays such as an immunoassay, an aptamer-based assay, a histological or cytological assay, an mRNA expression level assay, an enzyme linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay or avidity assay, protein microarrays, high-performance liquid chromatography (HPLC), Meso Scale Discovery (MSD) electrochemiluminescence and bead based multiplex immunoassays (MIA).

In some embodiments, the suitable technique may employ a detectable binding reagent that specifically binds the soluble factor.

In particular embodiments, the measurement of the soluble factor is measured by ELISA (enzyme-linked immunosorbent assay). ELISA is a plate-based assay technique designed for detecting and quantifying substances such as peptides, cytokines, antibodies and hormones. In an ELISA, the soluble factor must be immobilized to a solid surface and then complexed with an antibody that is linked to an enzyme. Detection is accomplished by assessing the conjugated enzyme activity via incubation with a substrate to produce a detectable signal. In some embodiments, The CAR dependent activity is measured with an ELISA assay.

In some embodiments, the recombinant receptor dependent activity is a secretion or production of the soluble factor. In certain embodiments, production or secretion is stimulated in a cell composition that contains recombinant receptor expressing cells, e.g., CAR expressing cells, by a recombinant receptor specific agent, e.g., a CAR+ specific agent. In some embodiments, the recombinant receptor specific agent that is an antigen or an epitope thereof that is specific to the recombinant receptor; a cell, e.g., a target cell, that expresses the antigen; or an antibody or a portion or variant thereof that binds to and/or recognizes the recombinant receptor; or a combination thereof. In certain embodiments, the recombinant receptor specific agent is a recombinant protein that comprises the antigen or epitope thereof that is bound by or recognized by the recombinant receptor.

In certain embodiments, the recombinant receptor dependent soluble factor production and/or secretion is measured by incubating the cell composition that contains cells expressing the recombinant receptor, e.g., a CAR, with a recombinant receptor specific agent, e.g., CAR+ specific agent. In certain embodiments, the soluble factor is a cytokine or a chemokine. In some embodiments, cells of the cell composition that contain recombinant receptor expressing cells are incubated in the presence of recombinant receptor specific agent for an amount of time, and the production and/or secretion of the soluble factor is measured at one or more time points during the incubation. In some embodiments, the cells are incubated with the CAR specific agent for up to or about 1 hour, about 2 hours, about 3 hours, about 4 hours, about 5 hours, about 6 hours, about 7 hours, about 8 hours, about 9 hours, about 10 hours, about 11 hours, about 12 hours, about 18 hours, about 19 hours, about 20 hours, about 21 hours, about 22 hours, about 23 hours, about 24 hours, about 48 hours, or for a duration of time between 1 hour and 4 hours, between 1 hour and 12 hours, between 12 hours and 24 hours, each inclusive, or for more than 24 hours and the amount of a soluble factor, e.g., a cytokine is detected.

In some embodiments, the recombinant receptor specific agent is a target cell that expresses an antigen recognized by the recombinant receptor. In some embodiments, the recombinant receptor is a CAR, and the cells of the cell composition are incubated with the target cells at ratio of total cells, CAR+ cells, CAR+/CD8+ cells, or Annexin-/CAR+/CD8+ cells of the cell composition to target cells of about 10:1, about 5:1, about 4:1, about 3:1, about 2:1, about 1:1, about 1:2, about 1:3, about 1:4, about 1:5, about 1:6, about 1:7, about 1:8, about 1:9, or about 1:10, or a range between any of the foregoing, such as at a ratio between 10:1 and 1:1, 3:1 and 1:3, or 1:1 and 1:10, each inclusive.

In some embodiments, between about $1\times10^2$ and about $1\times10^4$, between about $1\times10^3$ and about $1\times10^5$, between about $1\times10^4$ and about $1\times10^6$, between about $1\times10^5$ and about $1\times10^7$, between about $1\times10^6$ and about $1\times10^8$, between about $1\times10^7$ and about $1\times10^9$, or between about $1\times10^8$ and about $1\times10^{10}$ cells of the cell composition, each inclusive, are incubated with the recombinant receptor specific agent, e.g., a CAR+ specific reagent. In some embodiments, between about $1\times10^6$ and about $1\times10^7$ cells of the cell composition, inclusive, are incubated with the recombinant receptor specific agent, e.g., a CAR+ specific reagent. In certain embodiments, about $2.5\times10^6$ cells of the composition are incubated with the recombinant receptor specific agent. In certain embodiments, between about $1\times10^2$ and about $1\times10^4$, between about $1\times10^3$ and about $1\times10^5$, between about $1\times10^4$ and about $1\times10^6$, between about $1\times10^5$ and about $1\times10^7$, between about $1\times10^6$ and about $1\times10^8$, between about $1\times10^7$ and about $1\times10^9$, or between about $1\times10^8$ and about $1\times10^{10}$ recombinant receptor expressing cells, CAR+ cells, CAR+/CD8+ cells, or Annexin−/CAR+/CD8+ cells of the cell composition, each inclusive, are incubated with the CAR+ specific agent.

In some embodiments, the cells of the cell composition are incubated with the recombinant receptor specific agent, e.g., a CAR+ specific agent, in a volume of cell media. In certain embodiments, the cells are incubated with the recombinant receptor specific agent in a volume of at least or about 1 μL, at least or about 10 μL, at least or about 25 μL, at least or about 50 μL, at least or about 100 μL, at least or about 500 μL, at least or about 1 mL, at least or about 1.5 mL, at least or about 2 mL, at least or about 2.5 mL, at least or about 5 mL, at least or about 10 mL, at least or about 20 mL, at least or about 25 mL, at least or about 50 mL, at least or about 100 mL, or greater than 100 mL. In certain embodiments, the cells are incubated with the CAR+ specific agent in a volume that falls between about 1 L and about 100 μL, between about 100 μL and about 500 μL, between about 500 L and about 1 mL, between about 500 μL and about 1 mL, between about 1 mL and about 10 mL, between about 10 mL and about 50 mL, or between about 10 mL and about 100 mL, each inclusive. In certain embodiments, the cells are incubated with the recombinant receptor specific agent in a volume of between about 100 μL and about 1 mL, inclusive. In particular embodiments, the cells are incubated with the recombinant receptor specific agent in a volume of about 500 L.

In some embodiments, the cells of the cell composition are incubated with the CAR+ specific agent at an amount of between about 1 fmol and about 1 μmol, between about 1 pmol and about 1 nmol, between about 1 nmol and about 1 μmol, between about 1 μmol and about 1 mmol, or between about 1 mmol and 1 mol, each inclusive. In particular embodiments, the cells of the cell composition are incubated with the CAR+ specific agent at a concentration of between about 1 fM and about 1 pM, between about 1 pM and about 1 nM, between about 1 nM and about 1 μM, between about 1 μM and about 1 mM, or between about 1 mM and 1 mol, each inclusive. Exemplary units include, but are not limited to pg/mL, pg/(mL/hr), pg (mL×cell), pg/(mL×hr×cell), and pg/(mL×hr×$10^6$ cells).

In certain embodiments, the measurement of the recombinant receptor specific activity, e.g., the CAR+ specific activity is the amount or concentration, or a relative amount or concentration, of the soluble factor in the T cell composition at a time point during or at the end of the incubation. In particular embodiments, the measurement is subtracted by or normalized to a control measurement. In some embodiments, the control measurement is a measurement from the same cell composition taken prior to the incubation. In particular embodiments the control measurement is a measurement taken from an identical control cell composition that was not incubated with the recombinant receptor specific stimulation agent. In certain embodiments, the control is a measurement taken at an identical time point during incubation with the recombinant receptor specific agent from a cell composition that does not contain recombinant receptor positive cells.

In some embodiments, the measurement is a normalized ratio of the amount or concentration as compared to the control. In particular embodiments, the measurement is the amount or concentration of the soluble factor per an amount of time, e.g., per minute or per hour. In some embodiments, the measurement is an amount or concentration of the soluble factor per cell or per a set or reference number of cells, e.g., per 100 cells, per $10^3$ cells, per $10^4$ cells, per $10^5$ cells, per $10^6$ cells, etc. In certain the measurement is the amount or concentration of the soluble factor per an amount of time, per cell or per reference number of cells. In some embodiments, the measurement is the amount or concentration of the soluble factor per cell that expresses the recombinant receptor, CAR+ cell, CAR+/CD8+ cell, or Annexin−/CAR+/CD8+ cell of the cell composition. In certain embodiments, the measurement is the amount or concentration of the soluble factor per amount of time (e.g., per minute or per hour) per cell that expresses the recombinant receptor, CAR+ cell, CAR+/CD8+ cell, or Annexin−/CAR+/CD8+ cell of the cell composition. In some embodiments, the measurement is the amount or concentration of the soluble factor per an amount of time per amount or concentration of the recombinant receptor or CAR+ specific agent. In some embodiments, the measurement is an amount or concentration of the soluble factor per cell or per a set or reference number of cells per amount or concentration of the CAR+ specific agent. In certain the measurement is the amount or concentration of the soluble factor per an amount of time, per amount or concentration of the recombinant receptor or CAR+ specific agent, per cell or per reference number of cells. In some embodiments, the measurement is the amount or concentration of the soluble factor per amount or concentration of the recombinant receptor or CAR+ specific agent, per cell that expresses the recombinant receptor, CAR+ cell, CAR+/CD8+ cells, or Annexin−/CAR+/CD8+ cell of the cell composition. In certain embodiments, the measurement is the amount or concentration of the soluble factor per amount of time, per amount or concentration of the recombinant receptor or CAR+ specific agent, per amount of CAR+ cells, CAR+/CD8+ cells, or Annexin−/CAR+/CD8+ cells of the cell composition.

In particular embodiments, the recombinant receptor or CAR dependent activity is the production or secretion of two or more soluble factors. In certain embodiments, the recombinant receptor or CAR dependent activity is the production or secretion of two, three, four, five, six, seven, eight, nine, ten, or more than ten soluble factors. In some embodiments, the measurements of the two, three, four, five, six, seven, eight, nine, ten, or more than ten soluble factors are combined into an arithmetic mean or a geometric mean. In certain measurements, measurement of the recombinant receptor activity is the secretion of are composites of two, three, four, five, six, seven, eight, nine, ten, or more than ten soluble factors.

In particular embodiments, the measurement of the recombinant receptor dependent activity is transformed, e.g., by a logarithmic transformation. In certain embodiments, the measurement of the recombinant receptor activity is transformed by a common log($\log_{10}(x)$), a natural log(ln (x)) or a binary log($\log_2(x)$). In some embodiments, the measurement of the recombinant receptor dependent activity is a composite of measurement of the production or secretion of two more soluble factors. In some embodiments, two or more measurements of production or secretion of soluble factors are transformed prior to being combined into a composite measurement. In particular embodiments, the measurement of the recombinant receptor dependent activity is transformed prior to normalization to a reference measurement. In certain embodiments, the measurement of the recombinant receptor dependent activity is transformed prior to normalization to a reference measurement.

In certain embodiments, the soluble factor is a cytokine. Cytokines are a large group of small signaling molecules that function extensively in cellular communication. Cytokines are most often associated with various immune modulating molecules that include interleukins, chemokines, and interferons. Alternatively cytokines may be characterized by their structure, which are categorized in four families, the four alpha helix family that includes the IL-2 subfamily, the IFN subfamily, and the IL-10 subfamily; the IL-1 family, the IL-17 family, and cysteine-knot cytokines that include members of the transforming growth factor beta family. In some embodiments, the CAR dependent activity is the production or secretion of one or more soluble factors that include interleukins, interferons, and chemokines. In particular embodiments, the CAR dependent activity is the production or secretion of one or more of an IL-2 family member, an IFN subfamily member, an IL-10 subfamily member; an IL-1 family member, an IL-17 family member, a cysteine-knot cytokine, and/or a member of the transforming growth factor beta family.

In particular embodiments, the recombinant receptor or CAR dependent activity is the production and/or secretion of one or more of IL-1, IL-1B, IL-2, sIL-2Ra, IL-3, IL-5, IL-6, IL-7, IL-8, IL-10, IL-12, IL-13, IL 27, IL-33, IL-35, TNF, TNF alpha, CXCL2, CCL2, CCL3, CCL5, CCL17, CCL24, PGD2, LTB4, interferon gamma (IFN-γ), granulocyte macrophage colony stimulating factor (GM-CSF), macrophage inflammatory protein (MIP)-1a, MIP-1b, Flt-3L, fracktalkine, and/or IL-5. In certain embodiments, the CAR dependent activity production or secretion of a Th17 cytokine. In some embodiments, the Th17 cytokine is GMCSF. In some embodiments, the CAR dependent activity comprises production or secretion of a Th2 cytokine, wherein the Th2 cytokine is IL-4, IL-5, IL-10, or IL-13.

In certain embodiments, the recombinant receptor or CAR dependent activity is the production or secretion of a proinflammatory cytokine. Proinflammatory cytokines play a role in initiating the inflammatory response and to regulate the host defense against pathogens mediating the innate immune response. Proinflammatory cytokines include, but are not limited to, interleukins (IL), interleukin-1-beta (IL-1), interleukin-3 (IL-3), interleukin-5 (IL-5), interleukin-6 (IL-6), interleukin-13 (IL-13), tumor necrosis factor (TNF), CXC-chemokine ligand 2 (CXCL2), CC-chemokine ligand 2 (CCL2), CC-chemokine ligand 3 (CCL3), CC-chemokine ligand 5 (CCL5), CC-chemokine ligand 17 (CCL17), CC-chemokine ligand 24 (CCL24), prostaglandin D2 (PGD2) and leukotriene B4 (LTB4) as well as IL-33.). In some embodiments, the CAR dependent activity is production and or secretion of an interleukin and/or a TNF family member. In particular embodiments, the CAR dependent activity is production and or secretion of IL-1, IL-6, IL-8, and IL-18, TNF-alpha or a combination thereof.

In particular embodiments the CAR specific activity is secretion of IL-2, IFN-gamma, TNF-alpha or a combination thereof.

In particular embodiments, the activity is cytolytic (cytotoxic) activity of the T cell composition. In particular embodiments, the activity is a recombinant receptor, e.g., a CAR, dependent cytolytic activity. In some embodiments, recombinant receptor dependent cytolytic activity is assessed by exposing, incubating, and/or contacting cells expressing the recombinant receptor, or a cell composition containing cells that express the recombinant receptor, with a target cell that expresses the antigen and/or an epitope that is bound by and/or recognized by the recombinant receptor. The cytolytic activity can be measured by directly or indirectly measuring the target cell number over time. For example, the target cells may be incubated with a detectable marker prior to being incubated with recombinant receptor expressing cells, such a marker that is detectable then the target cell is lysed, or a detectable marker that is detectable in viable target cells. These readouts provide direct or indirect of target cell number and/or target cell death, and can be measured at different time points during the assay. A reduction of target cell number and/or an increase of target cell death indicate the cytolytic activity of the cells. Suitable methods for performing cytolytic assays are known in the art, and include, but are not limited to chromium-51 release assays, non-radioactive chromium assays, flow cytometric assays that use fluorescent dyes such as carboxyfluorescein succinimidyl ester (CFSE), PKH-2, and PKH-26.

In certain embodiments, the recombinant receptor, e.g., CAR, dependent cytolytic activity is measured by incubating the cell composition that contains cells expressing the recombinant receptor with target cells that express an antigen or an epitope thereof the is bound by or recognized by the recombinant receptor. In certain embodiments, the recombinant receptor is a CAR. In some embodiments, the cells of the cell composition are incubated with the target cells at a ratio of about 10:1, about 5:1, about 4:1, about 3:1, about 2:1, about 1:1, about 1:2, about 1:3, about 1:4, about 1:5, about 1:6, about 1:7, about 1:8, about 1:9, or about 1:10, or at a ratio between 10:1 and 1:1, 3:1 and 1:3, or 1:1 and 1:10, each inclusive. In some embodiments, the cells of the cell composition are incubated with the target cells at ratio of CAR+ cells, CAR+/CD8+ cells, or Annexin−/CAR+/CD8+ cells of the cell composition to target cells of about 10:1, about 5:1, about 4:1, about 3:1, about 2:1, about 1:1, about 1:2, about 1:3, about 1:4, about 1:5, about 1:6, about 1:7, about 1:8, about 1:9, or about 1:10, or at a ratio between 10:1 and 1:1, 3:1 and 1:3, or 1:1 and 1:10, each inclusive.

In certain embodiments, cells of the cell composition are incubated with the target cells for up to or about 1 hour, about 2 hours, about 3 hours, about 4 hours, about 5 hours, about 6 hours, about 8 hours, about 12 hours, about 18 hours, about 24 hours, about 48 hours, or greater than 48 hours. In some embodiments, the cell compositions are incubated for about 18 hours, 19 hours, 20 hours, 21 hours, 22 hours, 23 hours, or 24 hours. In some embodiments, between about $1\times10^2$ and about $1\times10^4$, between about $1\times10^3$ and about $1\times10^5$, between about $1\times10^4$ and about $1\times10^6$, between about $1\times10^5$ and about $1\times10^7$, between about $1\times10^6$ and about $1\times10^8$, between about $1\times10^7$ and about $1\times10^9$, or between about $1\times10^8$ and about $1\times10^{10}$ cells of the cell composition, each inclusive, are incubated with the target cells. In certain embodiments, the between about $1\times10^2$ and about $1\times10^4$, between about $1\times10^3$ and about $1\times10^5$, between about $1\times10^4$ and about $1\times10^6$, between about $1\times10^5$ and about $1\times10^7$, between about $1\times10^6$ and about $1\times10^8$, between about $1\times10^7$ and about $1\times10^9$, or between about $1\times10^8$ and about $1\times10^{10}$ CAR+ cells, CAR+/CD8+ cells, or Annexin−/CAR+/CD8+ cells of the cell composition, each inclusive, are incubated with the target cells.

In some embodiments, the measurement of the activity is compared to a control. In certain embodiments, the control is a culture of target cells that are not incubated with the cell composition. In some embodiments, the control is a measurement from a control cell composition that does not contain CAR+ cells that are incubated with the target cells at the same ratio.

In certain embodiments, the measurement of the cytolytic activity assay is the number of target cells that are viable at a time point during or at the end of the incubation. In certain embodiments, the measurement is an amount of a marker of target cell death, e.g., chromium-51, that is released during the incubation. In some embodiments, the measurement is an amount of target cell death that is determined by subtracting the amount of target cells in the co-incubation at a given time point from the amount of target cells of the control that was incubated alone. In some embodiments, the measurement is the percentage of target cells that remain at a time point compared to the starting amount of target cells. In particular embodiments, the measurement is the amount of cells killed over an amount of time. In certain embodiments, the measurement is the amount of cells killed per each cell of the cell composition. In some embodiments, the measurement is the amount of cells killed per cell, or the amount of cells killed per a set number or reference of cells, for example but not limited to, the amount of target cells killed per 100 cells, per $10^3$ cells, per $10^4$ cells, per $10^5$ cells, per $10^6$ cells, per $10^7$ cells, per $10^8$ cells, per $10^9$ cells, or per $10^{10}$ cells of the composition. In particular embodiments, the measurement is the amount of cells killed per each CAR+ cell, CAR+/CD8+ cell, or Annexin−/CAR+/CD8+ cell, or a reference or set number thereof, of the cell composition. In certain embodiments, the measurement is the amount of cells killed over an amount of time per cell of the cell composition. In particular embodiments, the measurement is the amount of cells killed over an amount of time per CAR+ cells, CAR+/CD8+ cells, or Annexin−/CAR+/CD8+ cells of the cell composition.

In some embodiments, the recombinant receptor dependent activity is not cytolytic activity. In particular embodiments, the CAR+ dependent activity is not cytolytic activity.

Reference Standards

Particular embodiments contemplate that a measurement of a recombinant receptor dependent activity and/or a CAR+ dependent activity can be normalized to a reference measurement, (i.e. a reference measure). In particular embodiments, the reference measurement is a predetermined measurement, or value thereof, of the activity. In some embodiments, the reference measurement is a mean or mode of a plurality of cell compositions that are derived from different subjects. In some embodiments, the cell compositions of the plurality are derived from different subjects and contain cells expressing the same recombinant receptor. In certain embodiments, the reference standard is derived from measurements that were normalized or subtracted from control groups in the same manner as the measurement of the recombinant receptor dependent activity. In particular embodiments, the reference measurement is derived from measurements taken from different cell compositions taken under the same assay conditions as the measurement of the recombinant receptor activity. In particular embodiments, the measurement of the recombinant receptor dependent activity is normalized to a reference measurement.

In certain embodiments the reference measurement is a mean or a mode of measurements from a plurality of cell compositions. In certain embodiments, the reference measurement is taken from the cell composition that contains cells that express the same CAR that is expressed by at least a portion of the cells in the cell compositions of the plurality. In certain embodiments, the reference measurement is a mean or a median of measurements taken from two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, more than twenty five, more than thirty, more than forty, or more than fifty cell compositions.

In certain embodiments, a measurement of a recombinant receptor specific or CAR specific activity is taken from a cell composition that is derived from a human subject with a disease or a condition, and compared to a reference measurement. In certain embodiments, the reference measurement is taken from cell compositions that are therapeutic T cell compositions. In certain embodiments, the therapeutic T cell compositions are cell compositions that were administered therapeutically to human subjects, for example, in clinical trial. In some embodiments, the safety and efficacy outcomes following administration of the reference T cell compositions are known. In certain embodiments, the subject has a disease or condition expressing or associated with the antigen.

In some embodiments, each of the reference T cell compositions has been administered to a subject. In particular embodiments, administration of the reference T cell compositions to the subjects were observed and were determined to result in an acceptable safety profile following administration to a subject. In particular embodiments, administration of the reference T cell compositions did not result in any severe toxicity. In certain embodiments, administration of the reference T cell compositions did not result in any severe neurotoxicity. In particular embodiments, the reference T cell compositions are all compositions that were associated with grade 4 or lower, grade 3 or lower, grade 2 or lower, grade 1 or lower, or grade 0 score for neurotoxicity. In some embodiments, the reference cell compositions are associated with acceptable safety profiles. In particular embodiments, the acceptable safety profile is an absence of observed grade 1 or higher, observed grade 2 or higher, observed grade 3 or higher, or grade 4 or higher, neurotoxicity. In certain embodiments, the reference T cell compositions are associated with acceptable safety profiles of an absence of an observed grade 3 or higher neurotoxicity. In particular embodiments, the reference T cell compositions are associated with acceptable safety profiles of an absence an observed grade 3 or higher neurotoxicity.

In certain embodiments, each of the reference therapeutic T cell compositions has been observed or determined to result in a desired efficacy following administration to a subject. In certain embodiments, the subject has a disease or condition expressing or associated with the antigen as the subjects that were administered the reference T cell compositions. In particular embodiments, each of the reference therapeutic T cell compositions has been observed or determined to result in a complete response (CR).

In some embodiments, the measurement of a recombinant receptor dependent activity is a measurement of the production or secretion of one or more soluble factors. In certain embodiments, the soluble factors are one or more cytokines. In particular embodiments, the CAR specific activity is the secretion of two or more cytokines. In certain embodiments, the measurement of the recombinant receptor dependent secretion of two or more cytokines is taken from a cell composition and normalized to reference measurements of the corresponding cytokines. In some embodiments, the measurements of two or more normalized are normalized to reference measurements. In some embodiments, the normalized measurements are combined into a single composite value.

In particular embodiments, the CAR specific activity is the secretion of IL-2, IFN-gamma, TNF-alpha, or a combination thereof. In certain embodiments, the measurement of the CAR-dependent secretion of IL-2, IFN-gamma, TNF-alpha, or the combination thereof, is taken from a cell composition and normalized to reference measurements of the corresponding cytokines. In some embodiments, the measurements of two or more of IL-2, IFN-gamma, and TNF-alpha are normalized to a reference measurements. In some embodiments, the normalized measurements are combined into a single value.

Particular embodiments contemplate that when the reference measurement is derived from reference compositions that were associated with acceptable safety profiles and or a desired efficacy, a normalized measurement that is close to 1 will have a high probability of also being associated with an acceptable safety profiles and/or a desired efficacy. Certain embodiments contemplate that a measurement from a T cell composition will have a high probability of being associated with an acceptable safety profiles and/or a desired efficacy, if the ratio of the measurement to the reference measurement is near or approximately 1:1.

Particular embodiments contemplate that CAR+ dependent secretion of particular cytokines have been observed not to indicate or correlate, or significantly correlate, with an adverse event or toxicity outcome or likelihood. For these cytokines, a measurement of CAR dependent secretion does predict safety or efficacy of a therapeutic administration the T cell composition. In some embodiments, measurements of CAR dependent secretion of cytokines that do not correlate or indicate safety or efficacy are measured and compared to or normalized to a reference measurement derived from measurements of corresponding cytokines taken from cell compositions derived from other subjects. In some embodiments, the measurements of CAR dependent cytokine secretion of cytokines that do not correlate or indicate safety or efficacy are compared to corresponding reference measurements to determine if the cell composition produces variable responses to CAR dependent stimulation. In some embodiments, the secretion of is not considered to correlate or indicate safety or efficacy. Particular embodiments contemplate that the normalization of one or more measurements of CAR dependent cytokine secretion of IL-4, IL-5, IL-10, or IL-13, or a composite thereof, is useful to determine or confirm the variability and reliability of measurements taken from the cell composition.

III. METHODS OF ASSESSING A THERAPEUTIC T CELL COMPOSITION

Provided herein are methods involving characterizing or assessing potency and/or safety and/or activity and/or efficacy of a therapeutic composition, in some embodiments and therapeutic T cell composition prior to or concurrently with or subsequent to administration of one or more unit doses of a therapeutic T cell composition to a subject having a disease or condition. In some embodiments, the provided methods assess risk of developing an adverse event upon administration of a T cell composition described herein. In some embodiments, a T cell composition is not released for subsequent administration to a subject if it is determined that the composition is outside of a determined safety range. In some aspects, the provided methods provide a release assay that can assess cell compositions to determine, among other aspects, if the composition administered to a subject, whether it is likely to correlate with a risk of developing a toxicity, such as severe neurotoxicity and/or whether it is likely to be efficacious. In some embodiments, a T cell composition is recommended not to be administered to a subject and/or the unit dose to be administered to a subject is altered or adjusted if B is above the USL. If B is below the USL, a product may be released for treatment.

In some embodiments, a sample to be assessed using the methods described herein is taken or derived from a T cell composition comprising T cells derived from a subject having a disease or condition and transduced with a nucleic acid encoding a recombinant receptor, optionally a chimeric antigen receptor (CAR), that specifically binds to an antigen associated with a disease or condition. In some aspects, the assays described herein determine B for the cell composition, wherein B is the value of a parameter, or a multiple or transformation thereof, which indicates or correlates with the degree of a recombinant receptor-dependent activity in the given composition. Also provided herein are methods of assaying a therapeutic T composition comprising assessing a sample from a T cell composition comprising T cells comprising a recombinant receptor that specifically binds to an antigen associated with a disease or condition for potency of the cell composition based on B wherein B is the value of a parameter, or a multiple or transformation thereof, that indicates or correlates with the degree of activity in the given composition. In some embodiments, the provided methods further assess potency of a cell composition based on B and/or assess whether the composition is above a LSL and/or is below a USL for B.

In some embodiments if B is above the USL, the unit dose to be administered to a subject is altered or adjusted, wherein the adjusted unit dose contains a target number of cells or a target number of reference units (RUs) of the T cell composition, wherein RU in a given composition is defined by the formula: RU=A×B, wherein A is the number of cells, or multiple, fraction or transformation thereof, of cells of a phenotype present in the given composition or is the average or weighted average of the number of cells, or multiple, fraction or transformation thereof, of two or more phenotypes in the given composition; and B is the value of a parameter, or a fraction or multiple or transformation thereof, that indicates or correlates with the degree of a recombinant receptor-dependent, optionally CAR-dependent, activity in the given composition.

In some embodiments, the parameter is a measure of one or more factors or a normalized value thereof. In some embodiments, the indicator of production is measured in an intracellular cytokine staining assay, comprising incubating a sample of the T cell composition with a polyclonal agent, an antigen-specific agent or an agent that binds the recombinant receptor. In some embodiments, the measure is in an assay involving culture or incubation for a fixed time, optionally 24 hours, of a given composition or sample thereof in the presence of the antigen, cells expressing the antigen and/or agent that specifically binds to the recombinant receptor, optionally the CAR. In some aspects, the assay is an ELISA.

In some embodiments, the measure of the factor is a measure or level indicative of concentration, relative concentration, amount, or relative amount of the factor, the amount or relative amount of the factor per unit of input cells of the given composition, the amount or relative amount of the factor per unit of input cells of the given composition per unit of time, optionally one hour. In some embodiments, the one or more factors is one or a combination of soluble factors, optionally one or a combination of cytokines, chemokines or soluble receptors, optionally soluble costimulatory receptors.

In some embodiments, the parameter is a measure of one or more factors or a normalized value thereof. In some embodiments, the recombinant receptor-dependent activity is a measure of the production or accumulation of one or more of IL-1, IL-1B, IL-2, sIL-2Ra, IL-3, IL-5, IL-6, IL-7, IL-8, IL-10, IL-12, IL-13, IL 27, IL-33, IL-35, TNF, TNF alpha, CXCL2, CCL2, CCL3, CCL5, CCL17, CCL24, PGD2, LTB4, interferon gamma (IFN-γ), granulocyte macrophage colony stimulating factor (GM-CSF), macrophage inflammatory protein (MIP)-1a, MIP-1b, Flt-3L, fracktalkine, and/or IL-5. In certain embodiments, the CAR dependent activity production or secretion of a Th17 cytokine. In some embodiments, the Th17 cytokine is GMCSF. In some embodiments, the recombinant receptor-dependent activity is a measure of the production or accumulation of a Th2 cytokine, wherein the Th2 cytokine is IL-4, IL-5, IL-10, or IL-13. In certain embodiments, B is indicative of the production and/or secretion of a proinflammatory cytokine such as, interleukins (IL), interleukin-1-beta (IL-1), interleukin-3 (IL-3), interleukin-5 (IL-5), interleukin-6 (IL-6), interleukin-13 (IL-13), tumor necrosis factor (TNF), CXC-chemokine ligand 2 (CXCL2), CC-chemokine ligand 2 (CCL2), CC-chemokine ligand 3 (CCL3), CC-chemokine ligand 5 (CCL5), CC-chemokine ligand 17 (CCL17), CC-chemokine ligand 24 (CCL24), prostaglandin D2 (PGD2) and leukotriene B4 (LTB4) as well as IL-33. In some embodiments, the recombinant receptor-dependent activity is a measure of the production or accumulation of an interleukin and/or a TNF family member such as IL-1, IL-6, IL-8, and IL-18, TNF-alpha or a combination thereof. In particular embodiments the recombinant receptor-dependent activity is a measure of the production or accumulation of IL-2, IFN-gamma, TNF-alpha or a combination thereof. In some embodiments, the one or more factors are one of or a combination of a pro-inflammatory cytokines, Th2 cytokines and Th17 cytokines. In some embodiments, the one or more factors are one of or a combination of IL-2, IFN-gamma, TNF-alpha, IL4, IL-5, IL-10, IL-13, GM-CSF, sCD137, MIP1a and M1Pb. In some embodiments, the one or more factors are one of or a combination of IL-2, IFN-gamma, TNF-alpha and IL-10.

In some embodiments, the one or more factors is one or a combination of soluble factors, optionally one or a combination of cytokines, chemokines or soluble receptors, optionally soluble costimulatory receptors. In some embodiments, the parameter is an arithmetic mean or geometric mean of the measure of the two or more factors. In some embodiments, the parameter is an arithmetic mean or geometric mean of a measure, optionally amount or concentration, of at least two of TNF-alpha, IFN-gamma and IL-2 or of TNF-alpha, IFN-gamma and IL-2. In some embodiments, the parameter is the normalized value of the measure, wherein normalization is as compared to a reference measure of the factor.

In some embodiments, A is the number of cells, or multiple or fraction or transformation thereof, of a given phenotype present in the given composition. In some aspects, A is the average or weighted average of the number of cells, or multiple, fraction or transformation thereof, of two or more phenotypes in the give composition, where optionally the two or more phenotypes comprise a first phenotype comprising CD8+ and a second phenotype comprising CD4+.

In some embodiments, the target number of reference RUs is at or below a threshold number of RUs, wherein the adjusted unit dose does not contain greater than the threshold number of RUs. In some aspects, the target number of units is less than a threshold number of units, which optionally is a safety number of reference units, wherein, the safety number of reference units is, with respect to a group of subjects analyzed following treatment with a therapeutic T cell composition comprising the T cells expressing the recombinant receptor, optionally the CAR, the lowest number of reference units of the therapy administered to a subject among those subjects in the group that went on to develop an adverse event. In some aspects, the adverse event is a severe adverse event, optionally severe neurotoxicity, optionally at or above grade 4 or grade 5 or at least prolonged grade 3 neurotoxicity. In some aspects, the target number of reference units is less than the safety number of reference units by an amount corresponding to a safety factor and/or by an amount within a range of 1.5- to 3-fold, optionally about 2-fold, or by an amount that is a multiple of a standard deviation of a group of subjects that did not develop the adverse event, optionally grade 0-2 neurotoxicity, optionally wherein the multiple is within a range of 1.5- to 3-fold. In some embodiments, the target number of reference units is less than the safety number of reference units by an amount corresponding to a safety factor. In certain embodiments, the safety factor is within a range of 0.5-fold to 10-fold, 1.0-5.0-fold, or 1.5- to 3-fold, and/or at, about, or at least 1-fold, 1.5-fold, 2-fold, 2.5-fold, or 3-fold of the safety number. In particular embodiments, the safety factor is less than the safety number. In some embodiments, the safety factor is, with respect to a group of subjects analyzed following treatment with a therapeutic T cell composition comprising the T cells expressing the recombinant receptor, such as a CAR, a multiple of a standard deviation from the average, e.g., the mean, of the dose in reference units administered to the subjects in the group that did not develop the adverse event, e.g., subjects in the group that experienced grade 2 or less neurotoxicity. In some embodiments, the safety factor is within a range of 0.5-fold to 10-fold, 1.0-5.0-fold, or 1.5- to 3-fold, and/or at, about, or at least 1-fold, 1.5-fold, 2-fold, 2.5-fold, or 3-fold of the standard deviation. In some embodiments, the a number or dose of reference units that is below the safety number by an amount corresponding to the safety factor includes numbers or doses of reference units that are associated with a response, e.g., a CR, such as with respect to a group of subjects that went on to develop a response, e.g., a CR.

In some aspects, the target number of reference units is at or above a reference efficacy number of reference units, wherein the reference efficacy number is, with respect to a group of subjects analyzed following treatment with a therapeutic T cell composition comprising the recombinant receptor, optionally the CAR, a number of units of the therapy administered to one or more subjects among the group that exhibited a desired therapeutic outcome, optionally a partial response or a complete response (CR).

In some aspects, the adjusted unit dose is less than, optionally less than 1.5-fold, less than 2-fold, less than 3-fold, less than 4-fold, the average unit dose of a group of subjects treated with a therapeutic T cell composition comprising the T cells expressing the recombinant receptor, optionally the CAR.

In some embodiments, a sample of the T cell composition, optionally a cryopreserved sample, is assessed after administration of the T cell composition to the subject. In some embodiments, if B is above the USL, the subject is determined to be at risk of toxicity. In some embodiments, if B is above the USL, a subject administered the composition is monitored and/or is treated with an agent to ameliorate or reduce the likelihood of a toxicity outcome or cytokine release syndrome following administration of the cell composition and optionally prior to the development of a sign or symptom of the toxicity outcome.

Also provided herein is a method of assessing a risk of toxicity to a therapeutic T cell composition, the method comprising: (a) assessing a sample from a T cell composition having been administered to a subject for reference units (RU) within a given range, the T cell composition comprising T cells comprising a recombinant receptor that specifically binds to an antigen associated with a disease or condition, wherein RU in a given composition is defined by the formula: $RU=A\times B$, wherein: A is the number of cells, or multiple, fraction or transformation thereof, of cells of a phenotype present in the given composition or is the average or weighted average of the number of cells, or multiple, fraction or transformation thereof, of two or more phenotypes in the given composition; and B is the value of a parameter, or a fraction or multiple or transformation thereof, that indicates or correlates with the degree of a recombinant receptor-dependent, optionally CAR-dependent, activity in the given composition; and (b) comparing the RUs to a reference safety number of RUs, wherein the comparison indicates whether the subject is or is not at risk for developing an adverse event, optionally a severe adverse event, optionally severe neurotoxicity at or above grade 4 or grade 5 or at least prolonged grade 3 neurotoxicity. In some aspects, A is the number of cells, or multiple or fraction or transformation thereof, of a given phenotype present in the given composition. In some aspects, A is the average or weighted average of the number of cells, or multiple, fraction or transformation thereof, of two or more phenotypes in the given composition, where optionally the two or more phenotypes comprise a first phenotype comprising CD8+ and a second phenotype comprising CD4+. In some aspects, the reference safety number of RUs is, with respect to a group of subjects analyzed following treatment with a therapeutic T cell composition comprising the T cells expressing the recombinant receptor, optionally the CAR, the lowest number of reference units of the therapy administered to a subject among those subjects in the group that went on to develop the adverse event. In some aspects, if the comparison indicates the RU is above the reference safety RU, the subject administered the composition is monitored and/or is treated with an agent to ameliorate or reduce the likelihood of a toxicity outcome or cytokine release syndrome following administration of the cell composition and optionally prior to the development of a sign or symptom of the toxicity outcome.

Also provided herein is a method of producing a therapeutic composition comprising a unit dose of a T cell composition, the method comprising: (a) assaying a T cell composition comprising T cells derived from a subject having a disease or condition and transduced with a nucleic acid encoding a recombinant receptor, optionally a chimeric antigen receptor (CAR), that specifically binds to an antigen associated with a disease or condition, wherein the assay determines B for the cell composition, wherein B is the value of a parameter, or a multiple or transformation thereof, that indicates or correlates with the degree of a recombinant receptor-dependent, optionally CAR-dependent, activity in the given composition; and (b) filling a container, e.g., a vial, with all or a portion of the composition and optionally another solution to achieve a unit dose of the T cell composition, wherein the unit dose contains a target number of reference units (RU) of the T cell composition, wherein RU in a given composition is defined by the formula: RU=A×B, wherein A is the number of cells, or multiple, fraction or transformation thereof, of cells of a phenotype present in the given composition or is the average or weighted average of the number of cells, or multiple, fraction or transformation thereof, of two or more phenotypes in the given composition.

Also provided herein is a method of producing a therapeutic composition comprising a unit dose of a T cell composition, the method comprising filling a container, e.g., a vial, with all or a portion of a T cell composition comprising T cells comprising a recombinant receptor that specifically binds an antigen associated with a disease or condition, and optionally another solution, to achieve a unit dose of the T cell composition, wherein the unit dose contains a target number of reference units (RU) of the T cell composition, wherein RU in a given composition is defined by the formula: RU=A×B, wherein A is the number of cells, or multiple, fraction or transformation thereof, of a phenotype present in the given composition or is the average or weighted average of the number of cells, or multiple, fraction or transformation thereof, of two or more phenotypes in the given composition; and B is the value of a parameter, or a multiple or transformation thereof, that indicates or correlates with the degree of a recombinant receptor-dependent, optionally CAR-dependent, activity in the given composition. In some aspects, A is the number of cells, or multiple or fraction or transformation thereof, of a given phenotype present in the given composition. In some aspects, A is the average or weighted average of the number of cells, or multiple, fraction or transformation thereof, of two or more phenotypes in the given composition, where optionally the two or more phenotypes comprise a first phenotype comprising CD8+ and a second phenotype comprising CD4+.

In some embodiments, A is the number of cells of a phenotype present in the given composition and B is the value of a parameter that indicates or correlates with the degree of recombinant receptor-dependent activity in the given composition. In some embodiments, A and/or B is a transformation of the number or value, respectively, wherein the transformation comprises a logarithmic transformation, power transformation or logit transformation. In some embodiments, A is a number of cells of a phenotype present in the given composition and B is a multiple or transformation of the value of the parameter that indicates or correlates with the degree of CAR-dependent activity in the given T cell composition, optionally wherein B is a logarithmic transformation of the value. In some embodiments, the logarithmic transformation is a common log($\log_{10}(x)$), a natural log($\ln(x)$) or a binary log($\log_2(x)$).

In some embodiments, A is the number of viable cells in the composition and/or is the number of cells that are not apoptotic, do not exhibit a factor indicative of early apoptosis or of apoptosis, are not in the early stages of apoptosis, or are not in the late stages of apoptosis, and/or is the number of cells of a particular differentiation state, and/or is the number of cells having a memory/stem-like attribute or is a multiple or transformation thereof. In some embodiments, the phenotype comprises absence of a factor indicative of apoptosis or one or more steps in an apoptotic cascade or pathway, optionally expression of a marker of apoptosis. In some embodiments, the phenotype comprises negative expression of a marker of apoptosis, optionally a marker of early apoptosis or late apoptosis. In some embodiments, the marker of apoptosis is surface phosphatidylserine and/or is detected with Annexin V, or is an active or proform of a caspase, optionally an active or proform of caspase 3. In some embodiments, the phenotype comprises Annexin−. In some embodiments, A is the total number of T cells, total number of CD3+ cells, total number of CD4+ or CD8+ cells, total number of CD3+CAR+ cells, total number of CD8+ CAR+ cells, total number of CD4+CAR+, or total number of live or viable cells of any of the foregoing, or a multiple or transformed value thereof. In some embodiments, A is the total number of CD3+ cells, total number of CD8+, total number of CD3+CAR+ cells, total number of CD8+CAR+ cells, or total number of live or viable cells of any of the foregoing, or a multiple or transformed value thereof. In some embodiments, A is the total number of apoptotic marker negative (−) cells that are CD3+CAR+ cells, total number of apoptotic marker negative (−) cells that are CD4+CAR+, total number of apoptotic marker negative (−) cells that are CD8+CAR+ cells, or a multiple or transformed value thereof, wherein the apoptotic marker is Annexin V or Caspase. A is the total number of Annexin−CD3+CAR+ cells, total number of Annexin−CD4+CAR+, total number of Annexin−CD8+CAR+ cells, or a multiple or transformed value thereof. In some embodiments, A is the total number of Annexin−CD3+CAR+ cells or the total number of Annexin−CD8+CAR+ cells.

In some embodiments, the phenotype comprises positive expression of a surface marker that is one or more of CD3, CD4 or CD8 and/or comprises positive expression of the recombinant receptor, optionally the CAR, or a surrogate marker for expression of the recombinant receptor. In some aspects, the phenotype is CD3+ CAR, CD4+/CAR+, CD8+/CAR+. In some embodiments, the phenotype comprises an indicator of production of one or a combination of cytokines, optionally non-specific to the antigen or the recombinant receptor and/or that is polyclonally produced, wherein the one or more cytokines is IL-2, IL-13, IL-17, IFN-gamma or TNF-alpha. In some embodiments, the indicator of production is measured in an assay, optionally an intracellular cytokine staining assay, comprising incubating a sample of the T cell composition with a polyclonal agent, an antigen-specific agent or an agent that binds the recombinant receptor, optionally CAR. In some embodiments, the agent is or comprises PMA and ionomycin or is or comprises a T cell receptor or T cell receptor complex agonist. In some embodiments, the phenotype comprises negative expression of an activation marker, wherein the activation marker is selected from among CD25, CD127, LAG3, Ki67 and combinations thereof. In some embodiments, the phenotype comprises negative expression of an exhaustion marker, wherein the exhaustion maker is a PD1 or FOXP3 gene product or a combination thereof. In some embodiments, the phenotype comprises a naïve phenotype or a memory phenotype, optionally wherein the memory phenotype comprises a T effector memory phenotype, a T central memory phenotype, or a T effector memory phenotype expressing CD45RA (Temra).

In some embodiments, the recombinant receptor-dependent activity is a measure of the production or accumulation of a proinflammatory cytokine, optionally, one of or a combination of TNF-alpha, IFN-gamma, IL-2 and IL-10. In some embodiments, the reference measure is the average of the measure among a plurality, optionally at least 10, at least 15, at least 20, of reference therapeutic T cell compositions comprising the chimeric antigen receptor (CAR) in which: (i) each of the reference therapeutic T cell compositions has been observed or determined to result in an acceptable safety profile following administration to a subject, optionally wherein the subject has a disease or condition expressing or associated with the antigen; and/or (ii) each of the reference therapeutic T cell compositions has been observed or determined to result in a desired efficacy following administration to a subject, optionally wherein the subject has a disease or condition expressing or associated with the antigen.

In some particular embodiments, the parameter is the normalized value of the measure, wherein normalization is as compared to a reference measure of the factor. In some embodiments, the reference measure is the average of the measure among a plurality, optionally at least 10, at least 15, at least 20, of reference therapeutic T cell compositions comprising the chimeric antigen receptor (CAR) in which: (i) each of the reference therapeutic T cell compositions has been observed or determined to result in an acceptable safety profile following administration to a subject, optionally wherein the subject has a disease or condition expressing or associated with the antigen; and/or (ii) each of the reference therapeutic T cell compositions has been observed or determined to result in a desired efficacy following administration to a subject, optionally wherein the subject has a disease or condition expressing or associated with the antigen. In some embodiments, the acceptable safety profile is absence of observed grade 2 or higher or absence of grade 3 or higher, neurotoxicity.

In some embodiments, the acceptable safety profile is the absence of observed grade 3 or higher neurotoxicity. In some embodiments, the efficacy is a partial response or is a complete response (CR). In some embodiments, the reference measure is the measure, by the same assay, of the factor in a reference T cell composition produced by the same method as the therapeutic T cell composition but not expressing the recombinant receptor, optionally the CAR, not specifically recognizing the antigen and/or not expressing any recombinant receptor, optionally any CAR. In some embodiments, the parameter is normalized to control for patient-specific variation of the measure of the one or more factors. In some embodiments, the parameter is a normalized value of the measure of the factor, compared to the same measure in the same assay, of a control factor, wherein the level of the control factor in a therapeutic T cell composition is known not to, or has been observed not to, indicate or correlate or significantly correlate with an adverse event or toxicity outcome or likelihood or risk thereof, wherein the adverse event or toxicity outcome optionally is severe neurotoxicity. In some embodiments, the control factor is or comprises a factor that is not statistically correlated and/or does not correlate to development of the adverse event among a plurality of subjects that went on to develop the adverse event following administration of the T cell composition, optionally the control factor is one of or a combination of IL-5, IL-13, GM-CSF, and IL-6, optionally wherein the measure of the control factor is an arithmetic mean or geometric mean of two or more of the foregoing.

In some embodiments, the parameter does not comprise cytolytic activity or a measure thereof. In some embodiments, the parameter does not comprise recombinant receptor-dependent or antigen-specific cytolytic activity or a measure thereof.

In some particular embodiments, the phenotype is CD8+ CAR+ cells or Annexin−CD8+ CAR+ cells; and the parameter is a measure of a pro-inflammatory cytokine, which optionally is one of or a combination of TNF-alpha, IL-2, and IFN-gamma, or is a normalized value thereof.

In some embodiments, the adverse event is grade 4 or 5 neurotoxicity and the threshold value: is or is about $1.75\times10^7$ if A is apoptotic marker negative (−) and CD8+CAR+ and B is TNF-alpha or a normalized value thereof; is or is about $2.19\times10^7$ if A is CD8+CAR+ and B is TNF-alpha or a normalized value thereof; is or is about $1.25\times10^7$ if A is apoptotic marker negative (−) CD8+CAR+ and if B is IFN-gamma or a normalized value thereof; is or is about $1.56\times10^7$ if A is CD8+CAR+ and B is IFN-gamma or a normalized value thereof; is or is about $1.5\times10^7$ if A is apoptotic marker negative (−) CD8+CAR+ and if B is IL-2 or a normalized value thereof; is or is about $1.88\times10^7$ if A is CD8+CAR+ and B is IL-2 or a normalized value thereof; is or is about $1.5\times10^7$ if A is apoptotic marker negative (−) CD8+CAR+ and if B is TNF-alpha and IFN-gamma or a normalized value thereof; is or is about $1.88\times10^7$ if A is CD8+CAR+ and B is TNF-alpha and IFN-gamma or a normalized value thereof; is or is about $2.0\times10^7$ if A is apoptotic marker negative (−) CD8+CAR+ and if B is TNF-alpha and IL-2 or a normalized value thereof; is or is about $2.5\times10^7$ if A is CD8+CAR+ and B is TNF-alpha and IL-2 or a normalized value thereof; is or is about $1.25\times10^7$ if A is apoptotic marker negative (−) CD8+CAR+ and if B is IFN-gamma and IL-2 or a normalized value thereof; is or is about $1.56\times10^7$ if A is CD8+CAR+ and B is IFN-gamma and IL-2 or a normalized value thereof; is or is about $1.75\times10^7$ if A is apoptotic marker negative (−) CD8+CAR+ and if B is TNF-alpha, IFN-gamma and IL-2 or a normalized value thereof; is or is about $2.19\times10^7$ if A is CD8+CAR+ and B is TNF-alpha, IFN-gamma and IL-2 or a normalized value thereof, optionally wherein the apoptosis marker is Annexin V or active Caspase 3.

In some embodiments, the adverse event is grade 4 or 5 neurotoxicity and the given range of the target reference units: is between or about between $2.0\times10^5$ and $1.75\times10^7$, inclusive, if A is apoptotic marker negative (−) and CD8+ CAR+ and B is TNF-alpha or a normalized value thereof; is between or about between $2.5\times10^5$ and $2.19\times10^7$, inclusive, if A is CD8+CAR+ and B is TNF-alpha or a normalized value thereof; is between or about between $4\times10^5$ and $1.25\times10^7$, inclusive, if A is apoptotic marker negative (−) CD8+CAR+ and if B is IFN-gamma or a normalized value thereof; is between or about between $5\times10^6$ and $1.56\times10^7$, inclusive, if A is CD8+CAR+ and B is IFN-gamma or a normalized value thereof; is between or about between $2.0\times10^5$ and $1.5\times10^7$, inclusive, if A is apoptotic marker negative (−) CD8+CAR+ and if B is IL-2 or a normalized value thereof; is between or about between $2.5\times10^5$ and $1.88\times10^7$, inclusive, if A is CD8+CAR+ and B is IL-2 or a normalized value thereof; is between or about between $3.0\times10^5$ and $1.5\times10^7$, inclusive, if A is apoptotic marker negative (−) CD8+CAR+ and if B is TNF-alpha and IFN-gamma or a normalized value thereof; is between or about between $3.75\times10^5$ and $1.88\times10^7$, inclusive, if A is CD8+ CAR+ and B is TNF-alpha and IFN-gamma or a normalized value thereof; is between or about between $3.0\times10^5$ and $2.0\times10^7$, inclusive, if A is apoptotic marker negative (−) CD8+CAR+ and if B is TNF-alpha and IL-2 or a normalized value thereof; is between or about between $3.75\times10^5$ and $2.5\times10^7$, inclusive, if A is CD8+CAR+ and B is TNF-alpha and IL-2 or a normalized value thereof; is between or about between $4.0\times10^5$ and $1.25\times10^7$, inclusive, if A is apoptotic marker negative (−) CD8+CAR+ and if B is IFN-gamma and IL-2 or a normalized value thereof; is between or about between $5.0\times10^5$ and $1.56\times10^7$, inclusive, if A is CD8+

CAR+ and if B is IFN-gamma and IL-2 or a normalized value thereof; is between or about between $4.0\times10^5$ and $1.75\times10^7$, inclusive, if A is apoptotic marker negative (−) CD8+CAR+ and if B is TNF-alpha, IFN-gamma and IL-2 or a normalized value thereof; is between or about between $5.0\times10^5$ and $2.19\times10^7$, inclusive, if A is CD8+CAR+ and B is TNF-alpha, IFN-gamma and IL-2 or a normalized value thereof, optionally wherein the apoptosis marker is Annexin V or active Caspase 3.

In some embodiments, the adverse event is at least prolonged grade 3 neurotoxicity and the threshold value: is or is about $1.0\times10^6$ if A is apoptotic marker negative (−) and CD8+CAR+ and B is TNF-alpha or a normalized value thereof; is or is about $1.25\times10^6$ if A is CD8+CAR+ and B is TNF-alpha or a normalized value thereof; is or is about $2.0\times10^6$ if A is apoptotic marker negative (−) CD8+CAR+ and if B is IFN-gamma or a normalized value thereof; is or is about $2.5\times10^6$ if A is CD8+CAR+ and B is IFN-gamma or a normalized value thereof; is or is about $3.0\times10^6$ if A is apoptotic marker negative (−) CD8+CAR+ and if B is IL-2 or a normalized value thereof; is or is about $3.75\times10^6$ if A is CD8+CAR+ and B is IL-2 or a normalized value thereof; is or is about $1.5\times10^6$ if A is apoptotic marker negative (−) CD8+CAR+ and if B is TNF-alpha and IFN-gamma or a normalized value thereof; is or is about $1.88\times10^6$ if A is CD8+CAR+ and B is TNF-alpha and IFN-gamma or a normalized value thereof; is or is about $2.5\times10^6$ if A is apoptotic marker negative (−) CD8+CAR+ and if B is TNF-alpha and IL-2 or a normalized value thereof; is or is about $3.12\times10^6$ if A is CD8+CAR+ and B is TNF-alpha and IL-2; or a normalized value thereof is or is about $3.0\times10^6$ if A is apoptotic marker negative (−) CD8+CAR+ and if B is IFN-gamma and IL-2 or a normalized value thereof; is or is about $3.75\times10^6$ if A is CD8+CAR+ and B is IFN-gamma and IL-2 or a normalized value thereof; is or is about $2.0\times10^6$ if A is apoptotic marker negative (−) CD8+CAR+ and if B is TNF-alpha, IFN-gamma and IL-2 or a normalized value thereof; is or is about $2.5\times10^6$ if A is CD8+CAR+ and B is TNF-alpha, IFN-gamma and IL-2 or a normalized value thereof, optionally wherein the apoptosis marker is Annexin V or active Caspase 3.

In some embodiments, the adverse event is at least prolonged grade 3 and the given range of the target reference units: is between or about between $3.0\times10^5$ and $1.0\times10^6$, inclusive, if A is apoptotic marker negative (−) and CD8+ CAR+ and B is TNF-alpha or a normalized value thereof; is between or about between $3.75\times10^5$ and $1.25\times10^6$, inclusive, if A is CD8+CAR+ and B is TNF-alpha or a normalized value thereof; is between or about between $4\times10^5$ and $2.0\times10^6$, inclusive, if A is apoptotic marker negative (−) CD8+CAR+ and if B is IFN-gamma or a normalized value thereof; is between or about between $5\times10^6$ and $2.5\times10^6$, inclusive, if A is CD8+CAR+ and B is IFN-gamma or a normalized value thereof; is between or about between $2.0\times10^5$ and $3.0\times10^6$, inclusive, if A is apoptotic marker negative (−) CD8+CAR+ and if B is IL-2 or a normalized value thereof; is between or about between $2.5\times10^5$ and $3.75\times10^6$, inclusive, if A is CD8+CAR+ and B is IL-2 or a normalized value thereof; is between or about between $3.0\times10^5$ and $1.5\times10^6$, inclusive, if A is apoptotic marker negative (−) CD8+CAR+ and if B is TNF-alpha and IFN-gamma or a normalized value thereof; is between or about between $3.75\times10^5$ and $1.88\times10^6$, inclusive, if A is CD8+ CAR+ and B is TNF-alpha and IFN-gamma or a normalized value thereof; is between or about between $3.0\times10^5$ and $2.5\times10^6$, inclusive, if A is apoptotic marker negative (−) CD8+CAR+ and if B is TNF-alpha and IL-2 or a normalized value thereof; is between or about between $3.75\times10^5$ and $3.12\times10^6$, inclusive, if A is CD8+CAR+ and B is TNF-alpha and IL-2 or a normalized value thereof; is between or about between $4.0\times10^5$ and $3.0\times10^6$, inclusive, if A is apoptotic marker negative (−) CD8+CAR+ and if B is IFN-gamma and IL-2 or a normalized value thereof; is between or about between $5.0\times10^5$ and $3.75\times10^6$, inclusive, if A is CD8+ CAR+ and B is IFN-gamma and IL-2 or a normalized value thereof; is between or about between $4.0\times10^5$ and $2.0\times10^6$, inclusive, if A is apoptotic marker negative (−) CD8+CAR+ and if B is TNF-alpha, IFN-gamma and IL-2 or a normalized value thereof; is between or about between $5.0\times10^5$ and $2.5\times10^6$, inclusive, if A is CD8+CAR+ and B is TNF-alpha, IFN-gamma and IL-2 or a normalized value thereof, optionally wherein the apoptosis marker is Annexin V or active Caspase 3.

In some embodiments that may be combined with any other embodiment described herein, the recombinant receptor is a CAR. In some embodiments, the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3° C.) chain; and/or wherein the CAR further comprises a costimulatory signaling region, which optionally comprises a signaling domain of CD28 or 4-1BB. In some embodiments that may be combined with any other embodiment the T cells are CD4+ or CD8+. In some embodiments, the T cells are primary T cells, optionally autologous or allogenic to the subject.

IV. METHODS OF TREATMENT WITH A THERAPEUTIC T CELL COMPOSITION

Provided herein are methods involving administering to a subject having a disease or condition one or more unit doses of a therapeutic T cell composition. In some embodiments, the one or more unit doses contains a target reference number of units of the cell composition based on A (number of cells of a phenotype) and/or B (value of a parameter associated with the degree of recombinant receptor-dependent activity, such as CAR-dependent activity, e.g. antigen-specific activity).

A. Diseases and Conditions and Methods of Administration

In some embodiments, a dose of cells expressing a recombinant receptor are administered to a subject to treat or prevent diseases, conditions, and disorders, including cancers. In some embodiments, the cells, populations, and compositions are administered to a subject or patient having the particular disease or condition to be treated, e.g., via adoptive cell therapy, such as adoptive T cell therapy. In some embodiments, cells and compositions, such as engineered compositions and end-of-production compositions following incubation and/or other processing steps, are administered to a subject, such as a subject having or at risk for the disease or condition. In some aspects, the methods thereby treat, e.g., ameliorate one or more symptom of, the disease or condition, such as by lessening tumor burden in a cancer expressing an antigen recognized by an engineered T cell.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8 (10): 577-85). See, e.g., Themeli et al. (2013) Nat Biotechnol. 31 (10): 928-933; Tsukahara et al. (2013) Biochem Biophys Res Commun 438 (1): 84-9; Davila et al. (2013) PLoS ONE 8 (4): e61338.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the chimeric antigen receptor or transgenic TCR specifically binds to an antigen associated with the disease or condition.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, and parasitic disease, and autoimmune and inflammatory diseases. In some embodiments, the disease or condition is a tumor, cancer, malignancy, neoplasm, or other proliferative disease or disorder. Such diseases include but are not limited to leukemia, lymphoma, e.g., chronic lymphocytic leukemia (CLL), acute-lymphoblastic leukemia (ALL), non-Hodgkin's lymphoma, acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin, melanoma, bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, and/or mesothelioma. In some embodiments, the subject has acute-lymphoblastic leukemia (ALL). In some embodiments, the subject has non-Hodgkin's lymphoma.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is selected from the group consisting of orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, 0EPHa2, ErbB2, 3, or 4, FBP, fetal acetylcholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In some embodiments, the antigen is or includes avβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

The cells can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjunctival injection, subconjunctival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

In some embodiments, the methods comprise administration of a chemotherapeutic agent, e.g., a conditioning chemotherapeutic agent, for example, to reduce tumor burden prior to the administration.

Preconditioning subjects with immunodepleting (e.g., lymphodepleting) therapies in some aspects can improve the effects of adoptive cell therapy (ACT).

Thus, in some embodiments, the methods include administering a preconditioning agent, such as a lymphodepleting or chemotherapeutic agent, such as cyclophosphamide, fludarabine, or combinations thereof, to a subject prior to the initiation of the cell therapy. For example, the subject may be administered a preconditioning agent at least 2 days prior, such as at least 3, 4, 5, 6, or 7 days prior, to the initiation of the cell therapy. In some embodiments, the subject is administered a preconditioning agent no more than 7 days prior, such as no more than 6, 5, 4, 3, or 2 days prior, to the initiation of the cell therapy. Exemplary preconditioning dosing regimens are described in International Patent Application No. WO2016/191756.

In some embodiments, the subject is preconditioned with cyclophosphamide at a dose between or between about 20 mg/kg and 120 mg/kg, such as between or between about 40 mg/kg and 80 mg/kg, each inclusive. In some aspects, the subject is preconditioned with or with about 60 mg/kg of cyclophosphamide. In some embodiments, the subject is preconditioned with cyclophosphamide at a dose between or between about 200 mg/m2 and 4440 mg/m2, such as between or between about 200 mg/m2 and 500 mg/m2, each inclusive. In some instances, the subject is preconditioned with 300 mg/m2 of cyclophosphamide, in some cases daily for example 300 mg/m2/day. In some instances, the subject is preconditioned with or with about 500 mg/m2 of cyclophosphamide, in some cases daily for example 500 mg/m2/day. In some instances, the subject is preconditioned with or with about 2220-4440 mg/m2 of cyclophosphamide. In some aspects, the subject is preconditioned with or with about 200 mg/m2/day, about 250 mg/m2/day about 300 mg/m2/day, about 350 mg/m2/day, about 400 mg/m2/day, about 450 mg/m2/day, about 500 mg/m2/day, about 550 mg/m2/day, about 600 mg/m2/day, about 650 mg/m2/day, about 700 mg/m2/day, about 800 mg/m2/day, about 900 mg/m2/day, or about 1000 mg/m2/day. In some embodiments, the cyclophosphamide can be administered as a single dose or can be administered as a plurality of doses, such as given daily, every other day or every three days. In some embodiments, the cyclophosphamide is administered once daily for one or two or three or more days. In some embodiments, the doses described herein represent daily doses, for example mg/m2/day, administered daily for three consecutive days.

In some embodiments, where the lymphodepleting agent comprises fludarabine, the subject is administered fludarabine at a dose between or between about 1 $mg/m^2$ and 100 $mg/m^2$, such as between or between about 10 $mg/m^2$ and 75 $mg/m^2$, 15 $mg/m^2$ and 50 $mg/m^2$, 20 $mg/m^2$ and 30 $mg/m^2$, or 24 $mg/m^2$ and 26 $mg/m^2$, each inclusive. In some instances, the subject is preconditioned with or with about 10 $mg/m^2$/day, about 15 $mg/m^2$/day, about 20 $mg/m^2$/day, about 25 $mg/m^2$/day, about 30 $mg/m^2$/day, about 35 $mg/m^2$/day, about 40 $mg/m^2$/day, about 45 $mg/m^2$/day, about 50 $mg/m^2$/day, about 55 $mg/m^2$/day, about 60 $mg/m^2$/day, about 65 $mg/m^2$/day, about 70 $mg/m^2$/day, about 75 $mg/m^2$/day, about 80 $mg/m^2$/day, about 85 $mg/m^2$/day, about 90 $mg/m^2$/day, about 95 $mg/m^2$/day, about 100 $mg/m^2$/day, about 200 $mg/m^2$/day, or about 300 $mg/m^2$/day. In some instances, the subject is administered 25 $mg/m^2$ of fludarabine. In some instances, the subject is administered 30 $mg/m^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days. In some embodiments, the doses described herein represent daily doses, for example $mg/m^2$/day, administered daily for three consecutive days.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 $g/m^2$) of cyclophosphamide and 3 to 5 doses of 25 $mg/m^2$ fludarabine prior to the first or subsequent dose. Dosing The pharmaceutical composition in some embodiments contains the cells in amounts effective to treat or prevent the disease or condition, such as a therapeutically effective or prophylactically effective amount. In some embodiments, the composition includes the cells in an amount effective to reduce burden of the disease or condition.

In some embodiments, provided are methods involving administering to a subject one or more unit doses of a therapeutic T cell composition in which each unit dose contains either (i) a target number of total recombinant receptor-expressing (e.g. CAR-expressing) cells or a target number or total of recombinant receptor-expressing (e.g. CAR-expressing) cells of a certain phenotype; or (ii) a target number of reference units (RUs) of the T cell composition that is within a given or target range of RUs. In some embodiments, the unit dose does not contain greater than the threshold number of RUs, such as a greater than a safety number of reference units.

In some embodiments, provided are treatment methods involving administering to a subject having a disease or condition a unit dose of a T cell composition comprising cells comprising a recombinant receptor, such as a chimeric antigen receptor (CAR), that specifically binds to an antigen associated with the disease or condition, wherein the unit dose contains a target number of reference units (RU) within a given range. An RU in a given composition is defined by the formula RU=A×B, wherein A is the number of cells, or multiple, fraction or transformation thereof, of a phenotype present in the given composition or is the average or weighted average of the number of cells, or multiple, fraction or transformation thereof, of two or more phenotypes in the given composition; and B is the value of a parameter, or a multiple or transformation thereof, that indicates or correlates with the degree of a recombinant receptor-dependent, optionally CAR-dependent, activity in the given composition. Exemplary attributes associated with A and B are described herein with reference to determining or providing a unit dose of cells for administration.

In some embodiments, A is the number of cells, or multiple or fraction or transformation thereof, of a given phenotype present in the given composition, such as a phenotype that is or includes CD8+ cells or other phenotype as described herein. In some embodiments, A is the average or weighted average of the number of cells, or multiple, fraction or transformation thereof, of two or more phenotypes in the give composition. In one example, two or more phenotypes comprise a first phenotype comprising CD8+ and a second phenotype comprising CD4+.

In some embodiments, the target number of units contained in a unit dose for administration that is less than a threshold number of reference units, such as a predetermined threshold identified or known to indicate a risk of an adverse event, such as severe toxicity, such as a least prolonged grade 3 or higher toxicity or grade 4 or grade 5 toxicity. In some embodiments, the threshold number of RUs is a safety number of reference units that can be determined from a group or plurality of subjects similarly treated with a therapeutic T cell composition, and typically a therapeutic T cell composition produced, such as engineered, cultured, cultivated, activated, cryopreserved, using the same or similar methods. In some embodiments, the plurality of subjects includes at least 10 subjects, such as at least 15, at least 20, at least 25, at least 30, at least 40, at least 50, at least 60, at least 70, at least 80, at least 90, at least 100 or more subjects.

In some embodiments, the safety number of reference units is, with respect to a group of subjects analyzed following treatment with a therapeutic T cell composition comprising the T cells expressing the recombinant receptor, such as a CAR, the lowest number of reference units of the therapy administered to a subject among those subjects in the group that went on to develop an adverse event. In some embodiments, the adverse event is a severe adverse event, optionally severe neurotoxicity, optionally at or above grade 4 or grade 5 or at least prolonged grade 3 neurotoxicity.

In some embodiments, the target number of reference units is less than the safety number of reference units by an amount corresponding to a safety factor and/or by an amount within a range of 1.5- to 3-fold, optionally about 2-fold, or by an amount that is a multiple of a standard deviation of a group of subjects that did not develop the adverse event, optionally grade 0-2 neurotoxicity, optionally wherein the multiple is within a range of 1.5- to 3-fold.

In some embodiments, the target number of reference units is at or above a reference efficacy number of reference units that can be determined from a group or plurality of subjects similarly treated with a therapeutic T cell composition, and typically a therapeutic T cell composition produced, such as engineered, cultured, cultivated, activated, cryopreserved, using the same or similar methods. In some embodiments, the plurality of subjects includes at least 10 subjects, such as at least 15, at least 20, at least 25, at least 30, at least 40, at least 50, at least 60, at least 70, at least 80, at least 90, at least 100 or more subjects. In some embodiments, the efficacy number of reference units is, with respect to a group of subjects analyzed following treatment with a therapeutic T cell composition comprising the recombinant receptor, optionally the CAR, a number of units of the therapy administered to one or more subjects among the group that exhibited a desired therapeutic outcome, optionally a partial response or a complete response (CR).

In some embodiments, provided are methods involving administering to a subject having a disease or condition a unit dose of a T cell composition comprising cells comprising a recombinant receptor, such as a chimeric antigen receptor (CAR), that specifically binds to an antigen associated with the disease or condition, wherein either a target number of total CD8+ recombinant receptor-expressing cells of the therapeutic composition are administered and/or a unit dose of such cells is administered in which a target number of reference units within a given range is administered as described above. In some cases, the target number of reference units that is administered is at or below a threshold number of RUs, such that the unit dose does not contain greater than the threshold number of RUs. In some aspects, the target number of total CD8+ recombinant receptor cells that are administered are CD8+ that are apoptotic marker negative (−) and CD8+, optionally wherein the apoptotic marker is Annexin V or active Caspase 3.

In some embodiments, the provided methods involve administering a dose containing a number of cells, such as a dose providing a target number of cells. In some embodiments, the dose, such as the target number of cells is between or between about $5.0\times10^6$ and $2.25\times10^7$, $5.0\times10^6$ and $2.0\times10^7$, $5.0\times10^6$ and $1.5\times10^7$, $5.0\times10^6$ and $1.0\times10^7$, $5.0\times10^6$ and $7.5\times10^6$, $7.5\times10^6$ and $2.25\times10^7$, $7.5\times10^6$ and $2.0\times10^7$, $7.5\times10^6$ and $1.5\times10^7$, $7.5\times10^6$ and $1.0\times10^7$, $1.0\times10^7$ and $2.25\times10^7$, $1.0\times10^7$ and $2.0\times10^7$, $1.0\times10^7$ and $1.5\times10^7$, $1.5\times10^7$ and $2.25\times10^7$, $1.5\times10^7$ and $2.0\times10^7$, $2.0\times10^7$ and $2.25\times10^7$, each inclusive. In some embodiments, such dose, such as such target number of cells refers to the total recombinant-receptor expressing cells in the administered composition. In some embodiments, such dose, such as such target number of cells, refers to the total recombinant-receptor expressing cells that are CD8+ or that are apoptotic marker negative (−) and CD8+. In some embodiments, the apoptotic marker is Annexin V or active Caspase 3.

In some embodiments, the dose of cells of the unit dose contains a number of cells, such as a target number of cells, between at least or at least about $5\times10^6$, $6\times10^6$, $7\times10^6$, $8\times10^6$, $9\times10^6$, $10\times10^6$ and about $15\times10^6$ recombinant-receptor expressing cells, such as recombinant-receptor expressing cells that are CD8+ or that are apoptotic marker negative (−) and CD8+, optionally wherein the apoptotic marker is Annexin V or active Caspase 3.

In some embodiments, the dose of cells of the unit dose contains a number of cells, such as a target number of cells, between at least or at least about $5.55\times10^6$, $6.66\times10^6$, $7.77\times10^6$, $8.99\times10^6$, $1.0\times10^7$, $1.1\times10^7$ and about $1.67\times10^7$ recombinant-receptor expressing cells, optionally recombinant-receptor expressing cells that are CD8+ or that are apoptotic marker negative (−) and CD8+, such as wherein the apoptotic marker is Annexin V or active Caspase 3.

In some embodiments, the dose of cells of the unit dose contains a number of cells, such as a target number of cells, between at least or at least about $6.25\times10^6$, $7.5\times10^6$, $8.75\times10^6$, $1.0\times10^7$, $1.13\times10^7$, $1.25\times10^7$ and about $1.9\times10^7$ recombinant-receptor expressing cells, optionally recombinant-receptor expressing cells that are CD8+ or that are apoptotic marker negative (−) and CD8+, such as wherein the apoptotic marker is Annexin V or active Caspase 3.

In some embodiments, the dose of cells of the unit dose contains a number of cells, such as a target number of cells, between at least or at least about between at least or at least about $7.14\times10^6$, $8.5\times10^6$, $1.0\times10^7$, $1.14\times10^7$, $1.29\times10^7$, $1.42\times10^7$ and about $2.14\times10^7$ recombinant-receptor expressing cells, optionally recombinant-receptor expressing cells that are CD8+ or that are apoptotic marker negative (−) and CD8+, optionally wherein the apoptotic marker is Annexin V or active Caspase 3.

In some embodiments, the dose of cells of the unit dose contains a number of cells, such as a target number of cells, between at least or at least about $5\times10^6$, $6\times10^6$, $7\times10^6$, $8\times10^6$, $9\times10^6$, $10\times10^6$ and about $15\times10^6$ recombinant-receptor expressing cells that are apoptotic marker negative (−) and CD8+, optionally wherein the apoptotic marker is Annexin V or active Caspase 3.

In some embodiments, the dose of cells of the unit dose contains a number of cells, such as a target number of cells, between at least or at least about $6.25\times10^6$, $7.5\times10^6$, $8.75\times10^6$, $1.0\times10^7$, $1.13\times10^7$, $1.25\times10^7$ and about $1.9\times10^7$ recombinant-receptor expressing cells that are CD8+.

In some embodiments, the method includes administering to a subject having a disease or condition a unit dose of a T cell composition comprising cells comprising a recombinant receptor, such as a chimeric antigen receptor (CAR), that specifically binds to an antigen associated with the disease or condition, wherein the unit dose contains a target number of reference units (RU) within a given range. In some embodiments, the target number of reference units is less than a threshold value, such as less than a reference safety value. In some aspects, the adverse event is a severe adverse event, such as severe neurotoxicity at or above grade 4 or grade 5 or at least prolonged grade 3 neurotoxicity. In some embodiments, the threshold value is less than the reference safety value by an amount corresponding to a safety factor or by at least 2-fold.

In some embodiments, the adverse event is grade 4 or 5 neurotoxicity and the threshold value: is or is about $1.75\times10^7$ if A is apoptotic marker negative (−) and CD8+CAR+ and B is TNF-alpha or a normalized value thereof; is or is about $2.19\times10^7$ if A is CD8+CAR+ and B is TNF-alpha or a normalized value thereof; is or is about $1.25\times10^7$ if A is apoptotic marker negative (−) CD8+CAR+ and if B is IFN-gamma or a normalized value thereof; is or is about $1.56\times10^7$ if A is CD8+CAR+ and B is IFN-gamma or a normalized value thereof; is or is about $1.5\times10^7$ if A is apoptotic marker negative (−) CD8+CAR+ and if B is IL-2 or a normalized value thereof; is or is about $1.88\times10^7$ if A is CD8+CAR+ and B is IL-2 or a normalized value thereof; is or is about $1.5\times10^7$ if A is apoptotic marker negative (−) CD8+CAR+ and if B is TNF-alpha and IFN-gamma or a normalized value thereof; is or is about $1.88\times10^7$ if A is CD8+CAR+ and B is TNF-alpha and IFN-gamma or a normalized value thereof; is or is about $2.0\times10^7$ if A is apoptotic marker negative (−) CD8+CAR+ and if B is TNF-alpha and IL-2 or a normalized value thereof; is or is about $2.5\times10^7$ if A is CD8+CAR+ and B is TNF-alpha and IL-2 or a normalized value thereof; is or is about $1.25\times10^7$ if A is apoptotic marker negative (−) CD8+CAR+ and if B is IFN-gamma and IL-2 or a normalized value thereof; is or is about $1.56\times10^7$ if A is CD8+CAR+ and B is IFN-gamma and IL-2 or a normalized value thereof; is or is about $1.75\times10^7$ if A is apoptotic marker negative (−) CD8+CAR+ and if B is TNF-alpha, IFN-gamma and IL-2 or a normalized value thereof; is or is about $2.19\times10^7$ if A is CD8+CAR+ and B is TNF-alpha, IFN-gamma and IL-2 or a normalized value thereof. In some embodiments, the apoptosis marker is Annexin V or active Caspase 3.

In some embodiments, the adverse event is grade 4 or 5 neurotoxicity and the given range of the target reference units: is between or about between $2.0\times10^5$ and $1.75\times10^7$, inclusive, if A is apoptotic marker negative (−) and CD8+CAR+ and B is TNF-alpha or a normalized value thereof; is between or about between $2.5\times10^5$ and $2.19\times10^7$, inclusive, if A is CD8+CAR+ and B is TNF-alpha or a normalized value thereof; is between or about between $4\times10^5$ and $1.25\times10^7$, inclusive, if A is apoptotic marker negative (−) CD8+CAR+ and if B is IFN-gamma or a normalized value thereof; is between or about between $5\times10^6$ and $1.56\times10^7$ inclusive, if A is CD8+CAR+ and B is IFN-gamma or a normalized value thereof; is between or about between $2.0\times10^5$ and $1.5\times10^7$, inclusive, if A is apoptotic marker negative (−) CD8+CAR+ and if B is IL-2 or a normalized value thereof; is between or about between $2.5\times10^5$ and $1.88\times10^7$, inclusive, if A is CD8+CAR+ and B is IL-2 or a normalized value thereof; is between or about between $3.0\times10^5$ and $1.5\times10^7$, inclusive, if A is apoptotic marker negative (−) CD8+CAR+ and if B is TNF-alpha and IFN-gamma or a normalized value thereof; is between or about between $3.75\times10^5$ and $1.88\times10^7$, inclusive, if A is CD8+CAR+ and B is TNF-alpha and IFN-gamma or a normalized value thereof; is between or about between $3.0\times10^5$ and $2.0\times10^7$, inclusive, if A is apoptotic marker negative (−) CD8+CAR+ and if B is TNF-alpha and IL-2 or a normalized value thereof; is between or about between $3.75\times10^5$ and $2.5\times10^7$, inclusive, if A is CD8+CAR+ and B is TNF-alpha and IL-2 or a normalized value thereof; is between or about between $4.0\times10^5$ and $1.25\times10^7$, inclusive, if A is apoptotic marker negative (−) CD8+CAR+ and if B is IFN-gamma and IL-2 or a normalized value thereof; is between or about between $5.0\times10^5$ and $1.56\times10^7$, inclusive, if A is CD8+CAR+ and if B is IFN-gamma and IL-2 or a normalized value thereof; is between or about between $4.0\times10^5$ and $1.75\times10^7$, inclusive, if A is apoptotic marker negative (−) CD8+CAR+ and if B is TNF-alpha, IFN-gamma and IL-2 or a normalized value thereof; is between or about between $5.0\times10^5$ and $2.19\times10^7$, inclusive, if A is CD8+CAR+ and B is TNF-alpha, IFN-gamma and IL-2 or a normalized value thereof. In some embodiments, the apoptosis marker is Annexin V or active Caspase 3.

In some embodiments, the adverse event is at least prolonged grade 3 neurotoxicity and the threshold value: is or is about $1.0\times10^6$ if A is apoptotic marker negative (−) and CD8+CAR+ and B is TNF-alpha or a normalized value thereof; is or is about $1.25\times10^6$ if A is CD8+CAR+ and B is TNF-alpha or a normalized value thereof; is or is about $2.0\times10^6$ if A is apoptotic marker negative (−) CD8+CAR+ and if B is IFN-gamma or a normalized value thereof; is or is about $2.5\times10^6$ if A is CD8+CAR+ and B is IFN-gamma or a normalized value thereof; is or is about $3.0\times10^6$ if A is apoptotic marker negative (−) CD8+CAR+ and if B is IL-2 or a normalized value thereof; is or is about $3.75\times10^6$ if A is CD8+CAR+ and B is IL-2 or a normalized value thereof; is or is about $1.5\times10^6$ if A is apoptotic marker negative (−) CD8+CAR+ and if B is TNF-alpha and IFN-gamma or a normalized value thereof; is or is about $1.88\times10^6$ if A is CD8+CAR+ and B is TNF-alpha and IFN-gamma or a normalized value thereof; is or is about $2.5\times10^6$ if A is apoptotic marker negative (−) CD8+CAR+ and if B is TNF-alpha and IL-2 or a normalized value thereof; is or is about $3.12\times10^6$ if A is CD8+CAR+ and B is TNF-alpha and IL-2; or a normalized value thereof is or is about $3.0\times10^6$ if A is apoptotic marker negative (−) CD8+CAR+ and if B is IFN-gamma and IL-2 or a normalized value thereof; is or is about $3.75\times10^6$ if A is CD8+CAR+ and B is IFN-gamma and IL-2 or a normalized value thereof; is or is about $2.0\times10^6$ if A is apoptotic marker negative (−) CD8+CAR+ and if B is TNF-alpha, IFN-gamma and IL-2 or a normalized value thereof; is or is about $2.5\times10^6$ if A is CD8+CAR+ and B is TNF-alpha, IFN-gamma and IL-2 or a normalized value thereof. In some embodiments, the apoptosis marker is Annexin V or active Caspase 3.

In some embodiments, the adverse event is at least prolonged grade 3 and the given range of the target reference units: is between or about between $3.0\times10^5$ and $1.0\times10^6$, inclusive, if A is apoptotic marker negative (−) and CD8+CAR+ and B is TNF-alpha or a normalized value thereof; is between or about between $3.75\times10^5$ and $1.25\times10^6$, inclusive, if A is CD8+CAR+ and B is TNF-alpha or a normalized value thereof; is between or about between $4\times10^5$ and $2.0\times10^6$, inclusive, if A is apoptotic marker negative (−) CD8+CAR+ and if B is IFN-gamma or a normalized value thereof; is between or about between $5\times10^6$ and $2.5\times10^6$, inclusive, if A is CD8+CAR+ and B is IFN-gamma or a normalized value thereof; is between or about between $2.0\times10^5$ and $3.0\times10^6$, inclusive, if A is apoptotic marker negative (−) CD8+CAR+ and if B is IL-2 or a normalized value thereof; is between or about between $2.5\times10^5$ and $3.75\times10^6$, inclusive, if A is CD8+CAR+ and B is IL-2 or a normalized value thereof; is between or about between $3.0\times10^5$ and $1.5\times10^6$, inclusive, if A is apoptotic marker negative (−) CD8+CAR+ and if B is TNF-alpha and IFN-gamma or a normalized value thereof; is between or about between $3.75\times10^5$ and $1.88\times10^6$, inclusive, if A is CD8+CAR+ and B is TNF-alpha and IFN-gamma or a normalized value thereof; is between or about between $3.0\times10^5$ and $2.5\times10^6$, inclusive, if A is apoptotic marker negative (−) CD8+CAR+ and if B is TNF-alpha and IL-2 or a normalized value thereof; is between or about between $3.75\times10^5$ and $3.12\times10^6$, inclusive, if A is CD8+CAR+ and B is TNF-alpha and IL-2 or a normalized value thereof; is between or about between $4.0\times10^5$ and $3.0\times10^6$, inclusive, if A is apoptotic marker negative (−) CD8+CAR+ and if B is IFN-gamma and IL-2 or a normalized value thereof; is between or about between $5.0\times10^5$ and $3.75\times10^6$, inclusive, if A is CD8+CAR+ and B is IFN-gamma and IL-2 or a normalized value thereof; is between or about between $4.0\times10^5$ and $2.0\times10^6$, inclusive, if A is apoptotic marker negative (−) CD8+CAR+ and if B is TNF-alpha, IFN-gamma and IL-2 or a normalized value thereof; is between or about between $5.0\times10^5$ and $2.5\times10^6$, inclusive, if A is CD8+CAR+ and B is TNF-alpha, IFN-gamma and IL-2 or a normalized value thereof. In some embodiments, the apoptosis marker is Annexin V or active Caspase 3.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, for example, where the subject is a human, the dose includes fewer than about $5\times10^8$ total recombinant receptor (e.g., CAR)-expressing cells, T cells, or peripheral blood mononuclear cells (PBMCs), e.g., in the range of about $1\times10^6$ to $5\times10^8$ such cells, such as $2\times10^6$, $5\times10^6$, $1\times10^7$, $5\times10^7$, $1\times10^8$, or $5\times10^8$ or total such cells, or the range between any two of the foregoing values.

In some embodiments, the dose of genetically engineered cells comprises from or from about $1\times10^5$ to $5\times10^8$ total CAR-expressing T cells, $1\times10^5$ to $2.5\times10^8$ total CAR-expressing T cells, $1\times10^5$ to $1\times10^8$ total CAR-expressing T cells, $1\times10^5$ to $5\times10^7$ total CAR-expressing T cells, $1\times10^5$ to $2.5\times10^7$ total CAR-expressing T cells, $1\times10^5$ to $1\times10^7$ total CAR-expressing T cells, $1\times10^5$ to $5\times10^6$ total CAR-expressing T cells, $1\times10^5$ to $2.5\times10^6$ total CAR-expressing T cells, $1\times10^5$ to $1\times10^6$ total CAR-expressing T cells, $1\times10^6$ to $5\times10^8$ total CAR-expressing T cells, $1\times10^6$ to $2.5\times10^8$ total CAR-expressing T cells, $1\times10^6$ to $1\times10^8$ total CAR-expressing T cells, $1\times10^6$ to $5\times10^7$ total CAR-expressing T cells, $1\times10^6$ to $2.5\times10^7$ total CAR-expressing T cells, $1\times10^6$ to $1\times10^7$ total CAR-expressing T cells, $1\times10^6$ to $5\times10^6$ total CAR-expressing T cells, $1\times10^6$ to $2.5\times10^6$ total CAR-expressing T cells, $2.5\times10^6$ to $5\times10^8$ total CAR-expressing T cells, $2.5\times10^6$ to $2.5\times10^8$ total CAR-expressing T cells, $2.5\times10^6$ to $1\times10^8$ total CAR-expressing T cells, $2.5\times10^6$ to $5\times10^7$ total CAR-expressing T cells, $2.5\times10^6$ to $2.5\times10^7$ total CAR-expressing T cells, $2.5\times10^6$ to $1\times10^7$ total CAR-expressing T cells, $2.5\times10^6$ to $5\times10^6$ total CAR-expressing T cells, $5\times10^6$ to $5\times10^8$ total CAR-expressing T cells, $5\times10^6$ to $2.5\times10^8$ total CAR-expressing T cells, $5\times10^6$ to $1\times10^8$ total CAR-expressing T cells, $5\times10^6$ to $5\times10^7$ total CAR-expressing T cells, $5\times10^6$ to $2.5\times10^7$ total CAR-expressing T cells, $5\times10^6$ to $1\times10^7$ total CAR-expressing T cells, $1\times10^7$ to $5\times10^8$ total CAR-expressing T cells, $1\times10^7$ to $2.5\times10^8$ total CAR-expressing T cells, $1\times10^7$ to $1\times10^8$ total CAR-expressing T cells, $1\times10^7$ to $5\times10^7$ total CAR-expressing T cells, $1\times10^7$ to $2.5\times10^7$ total CAR-expressing T cells, $2.5\times10^7$ to $5\times10^8$ total CAR-expressing T cells, $2.5\times10^7$ to $2.5\times10^8$ total CAR-expressing T cells, $2.5\times10^7$ to $1\times10^8$ total CAR-expressing T cells, $2.5\times10^7$ to $5\times10^7$ total CAR-expressing T cells, $5\times10^7$ to $5\times10^8$ total CAR-expressing T cells, $5\times10^7$ to $2.5\times10^8$ total CAR-expressing T cells, $5\times10^7$ to $1\times10^8$ total CAR-expressing T cells, $1\times10^8$ to $5\times10^8$ total CAR-expressing T cells, $1\times10^8$ to $2.5\times10^8$ total CAR-expressing T cells, or $2.5\times10^8$ to $5\times10^8$ total CAR-expressing T cells.

In some embodiments, the dose of genetically engineered cells comprises at least or at least about $1\times10^5$ CAR-expressing cells, at least or at least about $2.5\times10^5$ CAR-expressing cells, at least or at least about $5\times10^5$ CAR-expressing cells, at least or at least about $1\times10^6$ CAR-expressing cells, at least or at least about $2.5\times10^6$ CAR-expressing cells, at least or at least about $5\times10^6$ CAR-expressing cells, at least or at least about $1\times10^7$ CAR-expressing cells, at least or at least about $2.5\times10^7$ CAR-expressing cells, at least or at least about $5\times10^7$ CAR-expressing cells, at least or at least about $1\times10^8$ CAR-expressing cells, at least or at least about $2.5\times10^8$ CAR-expressing cells, or at least or at least about $5\times10^8$ CAR-expressing cells.

In some embodiments, the cell therapy comprises administration of a dose comprising a number of cell from or from about $1\times10^5$ to $5\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive. In some embodiments, the cell therapy comprises administration of a dose of cells comprising a number of cells at least or about at least $1\times10^5$ total recombinant receptor-expressing cells, total T cells, or total peripheral blood mononuclear cells (PBMCs), such at least or at least $1\times10^6$, at least or about at least $1\times10^7$, at least or about at least $1\times10^8$ of such cells. In some embodiments, the number is with reference to the total number of CD3+ or CD8+, in some cases also recombinant receptor-expressing (e.g. CAR+) cells. In some embodiments, the cell therapy comprises administration of a dose comprising a number of cell from or from about $1\times10^5$ to $5\times10^8$ CD3+ or CD8+ total T cells or CD3+ or CD8+ recombinant receptor-expressing cells, from or from about $5\times10^5$ to $1\times10^7$ CD3+ or CD8+ total T cells or CD3+ or CD8+ recombinant receptor-expressing cells, or from or from about $1\times10^6$ to $1\times10^7$ CD3+ or CD8+ total T cells or CD3+ or CD8+ recombinant receptor-expressing cells, each inclusive. In some embodiments, the cell therapy comprises administration of a dose comprising a number of cell from or from about $1\times10^5$ to $5\times10^8$ total CD3+/CAR+ or CD8+/CAR+ cells, from or from about $5\times10^5$ to $1\times10^7$ total CD3+/CAR+ or CD8+/CAR+ cells, or from or from about $1\times10^6$ to $1\times10^7$ total CD3+/CAR+ or CD8+/CAR+ cells, each inclusive.

In some embodiments, the T cells of the dose include CD4+ T cells, CD8+ T cells or CD4+ and CD8+ T cells.

In some embodiments, for example, where the subject is human, the CD8+ T cells of the dose, including in a dose including CD4+ and CD8+ T cells, includes between about $1\times10^6$ and $5\times10^8$, inclusive, total recombinant receptor (e.g., CAR)-expressing CD8+ cells, e.g., in the range of about $5\times10^6$ to $1\times10^8$ such cells, such cells $1\times10^7$, $2.5\times10^7$, $5\times10^7$, $7.5\times10^7$, $1\times10^8$, or $5\times10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1\times10^7$ to $0.75\times10^8$ total recombinant receptor-expressing CD8+ T cells, $1\times10^7$ to $2.5\times10^7$ total recombinant receptor-expressing CD8+ T cells, from or from about $1\times10^7$ to $0.75\times10^8$ total recombinant receptor-expressing CD8+ T cells, each inclusive. In some embodiments, the dose of cells comprises the administration of or about $1\times10^7$, $2.5\times10^7$, $5\times10^7$ $7.5\times10^7$, $1\times10^8$, or $5\times10^8$ total recombinant receptor-expressing CD8+ T cells.

In some embodiments, the dose of cells, e.g., recombinant receptor-expressing T cells, is administered to the subject as a single dose or is administered only one time within a period of two weeks, one month, three months, six months, 1 year or more.

In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose, provided in multiple individual compositions or infusions, over a specified period of time, which is no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells of the dose are administered in a single pharmaceutical composition. In some embodiments, the cells of the dose are administered in a plurality of compositions, collectively containing the cells of the first dose.

The term "split dose" refers to a dose that is split so that it is administered over more than one day. This type of dosing is encompassed by the present methods and is considered to be a single dose.

Thus, the dose in some aspects may be administered as a split dose. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the first dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, the cells are administered at a desired dosage, which in some aspects includes a desired dose or number of cells or cell type(s) and/or a desired ratio of cell types. Thus, the dosage of cells in some embodiments is based on a target number of total cells or a target reference number of units and a desired ratio of the individual populations or sub-types, such as the CD4+ to CD8+ ratio. In some embodiments, the dosage of cells is based on a desired target number of total cells or a target reference number of units in the individual populations or of individual cell types. In some embodiments, the dosage is based on a combination of such features, such as a desired number of total cells, target reference units, desired ratio, and desired total number of cells in the individual populations.

In some embodiments, the populations or sub-types of cells, such as CD8+ and CD4+ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as CD4+ to CD8+ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed dose, which may be at or above a minimum dose of T cells and/or at or above a maximum dose, and in some aspects a desired ratio of CD4+ to CD8+ cells, and/or is based on a desired fixed dose of CD4+ and/or CD8+ cells.

In some embodiments, the target dose or dose includes at or about or is less than at or about $5\times10^6$ CD8+CAR+ cells, includes at or about or is less than at or about $7\times10^6$ CD8+CAR+ cells or CD3+CAR+ cells, includes at or about or is less than at or about $8\times10^6$ CD8+CAR+ cells or CD3+CAR+ cells, includes at or about or is less than at or about $8\times10^6$CD8+CAR+ cells or CD3+CAR+ cells, includes at or about or is less than at or about $9\times10^6$ CD8+CAR+ cells or CD3+CAR+ cells, includes at or about or is less than at or about $10\times10^6$ CD8+CAR+ cells, includes at or about or is less than at or about $11\times10^6$ CD8+ CAR+ cells or CD3+CAR+ cells, includes at or about or is less than at or about $12\times10^6$ CD8+ CAR+ cells, includes at or about or is less than at or about $13\times10^6$ CD8+ CAR+ cells or CD3+CAR+ cells, includes at or about or is less than at or about $14\times10^6$ CD8+CAR+ cells, includes at or about or is less than at or about $15\times10^6$ CD8+CAR+ cells or CD3+ CAR+ cells, includes at or about or is less than at or about $20\times10^6$ or $30\times10^6$ or $40\times10^6$ or $50\times10^6$ CD8+CAR+ cells or CD3+CAR+ cells. In some aspects of such embodiments, at or about or at least at or about 70, 75, 80, 85, or 90% CD8+CAR+ cells of such dose exhibit one or more properties or phenotypes indicative of cell health or biologically active CAR cell, such as absence of an apoptotic marker, and/or the process used to produce the cells achieves a percentage of such cells among the CD8+CAR+ cells in the dose within 70-90% or at an average of 80% of the time. In some aspects, variance of frequency of biologically active or functional or non-apoptotic cells among the dose is less than a threshold value, and/or the frequency does not vary outside the range of 70-80% more than 1, 5, 10 or 20% of the time.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios. for example, in some embodiments, the desired ratio (e.g., ratio of CD4+ to CD8+ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, each inclusive, or such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

B. Patient and/or Clinical Factors

In some of the provided embodiments, a dose of cells in accordance with the methods provided herein can be administered to a subject with a patient-specific and/or clinical risk factor such as any described herein. In some embodiments, among such subjects treated, the method results in no substantial difference, no significant difference, or no difference above a threshold level or degree, in the incidence or risk of a toxicity, e.g., severe adverse side effect, CRS, and/or neurotoxicity or grade thereof, as compared to the total group of subjects treated according to the method or subjects not having such patient-specific or clinical risk factor. In certain embodiments, the difference for subjects having such risk factor as compared to the total number of subjects or subjects without the risk factor is not greater than 1%, 5%, 10%, 15%, 20%, 25% or 30%, 35% or 40%. In some embodiments, the toxicity is CRS. In particular embodiments, the toxicity is CRS of grade 2 or higher, grade 3 or higher, grade 4 or higher, or grade 5. In certain embodiments, the toxicity is neurotoxicity. In particular embodiments, the toxicity is neurotoxicity of grade 2 or higher, grade 3 or higher, grade 4 or higher, or grade 5. In some embodiments, the toxicity is or is associated with cerebral edema.

In certain embodiments, a dose of cells in accordance with the methods provided herein is administered to a subject without a patient and/or clinical factor, such as any described herein. In some embodiments, a reduced and/or a lower dose of cells is administered to a subject with a patient and/or clinical factor. In certain embodiments, the reduced and/or lower dose is or is at least 5%, 10%, 15%, 20%, 25%, 30%, 35%, 40%, 45%, 50%, 60%, 70%, 80%, 90%, or 95% less than the dose that is administered to a subject without a patient and/or clinical factor. In certain embodiments, there is no substantial difference in the incidence of toxicity, e.g., severe adverse side effect, CRS, and/or neurotoxicity, between subjects without a patient and/or clinical factor that are administered the dose of cells and the subjects with a patient and/or clinical factor that are administered the lower dose of cells.

In some embodiments, the patient and/or clinical factor is an amount of prior therapies, e.g., one or more therapies prior to initiation of administration of the therapeutic T cell composition. In some embodiments, the prior therapies have been administered to treat the same disease and/or condition as the therapeutic T cell composition. In particular embodiments, the patient and/or clinical factor is fewer than ten prior therapies, nine prior therapies, eight prior therapies, seven prior therapies, six prior therapies, five prior therapies, four prior therapies, three prior therapies, two prior therapies, or fewer than one prior therapy. In some embodiments, the patient and/or clinical factor is fewer than three prior therapies. In certain embodiments, the patient and/or clinical factor is two or fewer prior therapies.

In certain embodiments, the patient and/or clinical factor is age, e.g., subject age at the initiation of administration of the therapeutic T cell composition. In certain embodiments, the patient and/or clinical factor is a young and/or a relatively young age. In some embodiments, the patient and/or clinical factor is an age of less than 65 years, 60 years, 55 years, 50 years, 45 years, 40 years, 35 years, 30 years, 25 years, or 20 years. In particular embodiments, the patient and/or clinical factor is an age of less than 30 years.

In particular embodiments, the patient and/or clinical factor is the ratio of CD4:CD8 T cells in an apheresis sample from the subject. In some embodiments, the patient and/or clinical factor is ratio of CD4:CD8 T cells in an apheresis sample below a certain threshold. In certain embodiments, the patient and/or clinical factor is ratio of CD4:CD8 T cells of below 3:1, 2:1, 1.5:1, 1:1, 0.9:1, 0.8:1, 0.7:1, 0.6:1, 0.5:1, 0.4:1, 0.3:1, 0.2:1, or 0.1:1. In certain embodiments, the ratio of CD4:CD8 T cells in an apheresis sample is a patient and/or clinical factor when the dose administered is based on total T cells or total T cells expressing a recombinant receptor. In particular embodiments, the patient and/or clinical factor is ratio of CD4:CD8 T cells in an apheresis sample below 1:5, below 1:1, or below 0.5:1.

In certain embodiments, the patient and/or clinical factor is subject weight, e.g., body weight. In certain embodiments, the subject weight is the weight of the subject at the time when the therapeutic T cell composition is administered. In certain embodiments, the patient and/or clinical factor is weight above 100 lbs., above 125 lbs., above 150 lbs., above 175 lbs., above 200 lbs., above 225 lbs., above 250 lbs., above 275 lbs., above 300 lbs., above 350 lbs., or above 400 lbs. In particular embodiments, the patient and/or clinical factor is weight above 50 kg, 60 kg, 70 kg, 80 kg, 90 kg, 100 kg, 125 kg, 150 kg, 175 kg, or 200 kg. In some embodiments, the patient and/or clinical factor is a weight greater than the average weight among a group of subjects. In particular embodiments, the patient and/or clinical factor is a weight greater than the mean, median, and/or mode weight among a group of subjects. In some embodiments, the group of subjects are treated with the same therapeutic cell composition.

In certain embodiments, the patient and/or clinical factor is platelet count. In some embodiments, the patient and/or clinical factor is platelet count of or of about less than 500,000, less than 450,000, less than 400,000, less than 350,000, less than 300,000, less than 250,000, less than 200,000, less than 180,000, less than 160,000, less than 140,000, less than 120,000, less than 100,000, less than 75,000, less than 50,000, or less than 25,000. In some embodiments, the patient and/or clinical factor is a platelet count of less than 120,000.

In particular embodiments, the patient and/or clinical factor is having a leukemia. In some embodiments, the patient or clinical factor is having a B cell leukemia. In certain embodiments, the leukemia is acute lymphoblastic leukemia (ALL), non-Hodgkin's lymphoma (NHL), chronic lymphocytic leukemia (CLL), diffuse large B-cell lymphoma (DLBCL), or acute myeloid leukemia (AML). In certain embodiments, the patient and/or clinical factor is having acute lymphocytic leukemia (ALL).

In particular embodiments, the patient and/or clinical factor is high disease burden, e.g., a high disease burden prior to initiation of administration of the therapeutic T cell composition. In certain embodiments, the patient and/or clinical factor is high disease burden immediately prior to, or within 1 week, 2 weeks, 3 weeks, 4 weeks, 5 weeks, 6 weeks, 7 weeks, 8 weeks, 9 weeks, one month, two months, three months, four months, five months, six months, or greater than six months prior to initiation of administration of the therapeutic T cell composition. In some embodiments, the high disease burden is determined based on percent of bone marrow blasts. In certain embodiments, the high disease burden is greater than or equal to 1%, 2%, 3%, 4%, 5%, 6%, 7%, 8%, 9%, or 10% blasts. In some embodiments, the patient and/or clinical factor is a disease burden of greater than 5% blasts immediately prior to or within one month prior to initiation of administration of the therapeutic T cell composition. In certain embodiments, the patient and/or clinical factor is high disease burden, such as the sum of product diameter (SPD) or levels of lactate dehydrogenase.

In particular embodiments, the patient and/or clinical factor is high tumor burden, e.g., a high disease burden prior to initiation of administration of the therapeutic T cell composition. In some embodiments, the factor indicative of tumor burden is a volumetric measure of tumor(s). In some embodiments, the volumetric measure is a measure of the lesion(s), such as the tumor size, tumor diameter, tumor volume, tumor mass, tumor load or bulk, tumor-related edema, tumor-related necrosis, and/or number or extent of metastases. In some embodiments, the volumetric measure of tumor is a bidimensional measure. For example, in some embodiments, the area of lesion(s) is calculated as the product of the longest diameter and the longest perpendicular diameter of all measurable tumors. In some cases, the volumetric measure of tumor is a unidimensional measure. In some cases, the size of measurable lesions is assessed as the longest diameter. In some embodiments, the sum of the products of diameters (SPD), longest tumor diameters (LD), sum of longest tumor diameters (SLD), necrosis, tumor volume, necrosis volume, necrosis-tumor ratio (NTR), peritumoral edema (PTE), and edema-tumor ratio (ETR) is measured.

Exemplary methods for measuring and assessing tumor burden include those described in, e.g., Carceller et al., Pediatr Blood Cancer. (2016) 63 (8): 1400-1406 and Eisenhauer et al., Eur J Cancer. (2009) 45 (2): 228-247. In some embodiments, the volumetric is a sum of the products of diameters (SPD) measured by determining the sum of the products of the largest perpendicular diameters of all measurable tumors. In some aspects, the tumor or lesion are measured in one dimension with the longest diameter (LD) and/or by determining the sum of longest tumor diameters (SLD) of all measurable lesions. In some embodiments, the volumetric measure of tumor is a volumetric quantification of tumor necrosis, such as necrosis volume and/or necrosis-tumor ratio (NTR), see Monsky et al., Anticancer Res. (2012) 32 (11): 4951-4961. In some aspects, the volumetric measure of tumor is a volumetric quantification of tumor-related edema, such as peritumoral edema (PTE) and/or edema-tumor ratio (ETR). In some embodiments, measuring can be performed using imaging techniques such as computed tomography (CT), positron emission tomography (PET), and/or magnetic resonance imaging (MRI) of the subject.

In some embodiments, the volumetric measure is SPD and in some cases, development of toxicity, e.g., CRS or NT, is correlated with the SPD value that is above a threshold value. In some embodiments, the volumetric measure is SPD, and the threshold value is or is about 30 per $cm^2$, is or is about 40 per $cm^2$, is or is about 50 per $cm^2$, is or is about 60 per $cm^2$, or is or is about 70 per $cm^2$. In some embodiments, the volumetric measure is SPD and the threshold value is or is about 30 per $cm^2$, is or is about 40 per $cm^2$, is or is about 50 per $cm^2$, is or is about 60 per $cm^2$, or is or is about 70 per $cm^2$. In certain embodiments, the patient and/or clinical factor is SPD greater than 30 per $cm^2$, greater than 40 per $cm^2$, greater than 50 per $cm^2$, greater than 60 per $cm^2$, or greater than 70 per $cm^2$.

In some embodiments, the volumetric measure of tumor is determined at a screening session, such as a routine assessment or blood draw to confirm and/or identify the condition or disease in the subject.

In particular embodiments, the patient and/or clinical factor is a level, amount, and/or a concentration of an inflammatory marker. In some embodiments, the inflammatory marker is or includes the level or presence of C-reactive protein (CRP), erythrocyte sedimentation rate (ESR), albumin, ferritin, β2 microglobulin (β2-M), or lactate dehydrogenase (LDH) is detected and assessed. In some embodiments, the inflammatory marker is assessed using an immune assay. For example, an enzyme-linked immunosorbent assay (ELISA), enzyme immunoassay (EIA), radioimmunoassay (RIA), surface plasmon resonance (SPR), Western Blot, Lateral flow assay, immunohistochemistry, protein array or immuno-PCR (iPCR) can be used to detect the inflammatory marker. In some embodiments, the presence, level, amount, and/or concentration of an inflammatory marker is indicative of tumor burden, e.g., a high tumor burden. In some cases, the assaying or assessing of an inflammatory marker is using flow cytometry. In some cases, the reagent is a soluble protein that binds the inflammatory marker. In some example, the reagent is a protein that binds C-reactive protein (CRP), erythrocyte sedimentation rate (ESR), albumin, ferritin, β2 microglobulin (β2-M), or lactate dehydrogenase (LDH).

In some embodiments, the patient and/or clinical factor is a level, amount or concentration of an inflammatory marker that is greater than or greater than about or is 5%, 10%, 15%, 20%, 25%, 30%, 40%, 50%, 75%, 100%, 150%, 1-fold, 2-fold, 3-fold, 4-fold, 5-fold of the average, median, or mean, and/or is 3, 2.5, 2, 1.5, 1, 0.8, 0.6, 0.5, 0.4, 0.3, 0.2, or 0.1 standard deviations greater than the median or mean, of the level, amount or concentration of the inflammatory marker measured in samples obtained from a group of subjects prior to receiving administration of a therapeutic T cell composition, wherein each of the subjects of the group did not go on to develop grade 2 or higher, grade 3 or higher, prolonged grade 3 or higher, grade 4 or higher, or grade 5 toxicity following administration of the therapeutic T cell composition. In some embodiments, the toxicity is neurotoxicity.

In some embodiments, the biomarker, e.g., inflammatory marker is or includes C-reactive protein (CRP). In some embodiments, CRP is assessed using an in vitro enzyme-linked immunosorbent assay to obtain a quantitative measurement of human CRP from a sample such as serum, plasma, or blood. In some examples, CRP is detected using a human Enzyme-Linked Immunosorbent Assay (ELISA). In some embodiments, the biomarker, e.g. inflammatory marker is or includes erythrocyte sedimentation rate (ESR). In some embodiments, ESR is assessed by measuring the distance (in millimeters per hour) that red cells have fallen after separating from the plasma in a vertical pipette or tube. In some embodiments the biomarker is or includes albumin. In some aspects, albumin is assessed using a colorimetric test or an in vitro enzyme-linked immunosorbent assay. In some examples, albumin is detected using a human Enzyme-Linked Immunosorbent Assay (ELISA). In some embodiments, the biomarker, e.g., inflammatory marker is or includes ferritin or β2 microglobulin. In some embodiments, ferritin or β2 microglobulin is assessed using an immunoassay or detected using an ELISA. In some aspects, the biomarker, e.g., inflammatory marker is or includes lactate dehydrogenase (LDH), and LDH is assessed using a colorimetric test or an in vitro enzyme-linked immunosorbent assay.

In some embodiments, the patient and/or clinical factor is a level, concentration, and/or amount of LDH. In some embodiments, development of toxicity, e.g., CRS or NT, is correlated with the LDH value that is above a threshold value. In some embodiments, the inflammatory marker is LDH and the threshold value is or is about 300 units per liter, is or is about 400 units per liter, is or is about 500 units per liter or is or is about 600 units per liter. In particular embodiments, the patient and/or clinical risk factor at least 300 units per liter, at least 400 units per liter, at least 500 units per liter, or at least 600 units per liter.

In some embodiments, the level, concentration and/or number of LDH is a surrogate for disease burden, e.g., for tumors or cancers, and may be useful for potential neurotoxicity risk assessment and/or risk-adapted dosing or adjustment of treatment of certain subjects. In some aspects, LDH levels may be assessed alone and/or in combination with another pre-treatment parameter, such as another measure or indicator of disease burden, such as a volumetric tumor measurement such as sum of product dimensions (SPD) or other CT-based or MRI-based volumetric measurement of disease burden, such as any described herein. In some aspects, one or more parameters indicative of disease burden are assessed, and in some contexts may indicate the presence, absence or degree of risk of developing neurotoxicity following the T cell therapy. In some aspects, the one or more parameters include LDH and/or a volumetric tumor measurement. In some embodiments, the parameter is SPD and/or LDH.

In some embodiments, the patient and/or clinical factor is receiving a bridging chemotherapy prior to initiation of administration of the therapeutic T cell composition.

In particular embodiments, the patient and/or clinical factor is preconditioning with a lymphodepleting therapy, e.g., prior to initiation of administration of the therapeutic T cell composition. In some embodiments, the lymphodepleting therapy is or includes the administration of a chemotherapy. In certain embodiments, the lymphodepleting therapy is or includes the administration of. In particular embodiments, the patient and/or clinical factor is preconditioning with fludarabine and/or cyclophosphamide prior to initiation of administration of the therapeutic T cell composition. In certain embodiments, the patient and/or clinical factor is preconditioning with cyclophosphamide prior to initiation of administration of the therapeutic T cell composition. In some embodiments, the patient and/or clinical factor is preconditioning with fludarabine and cyclophosphamide prior to initiation of administration of the therapeutic T cell composition.

In certain embodiments, the patient and/or clinical factor is a molecular subtype of a disease. In certain embodiments, the patient and/or clinical factor is a molecular subtype of a leukemia. In particular embodiments, the patient and/or clinical factor is a molecular subtype of ALL. In certain embodiments, the patient and/or clinical factor is a molecular subtype of ALL that is not Philadelphia chromosome positive (Ph+) or Philadelphia Chromosome (Ph)-like molecular subtype of ALL, such as a non-Ph molecular subtype. In particular embodiments, non-Ph molecular subtypes of ALL include, but are not limited to, subtypes associated with a TCF3-PBX1 fusion, a ETV6-RUNX1 fusion, a EP300-ZNF384 fusion, a KMT2A-AFF1 fusion, hyperploidy, or a dic(9; 20) chromosome abnormality, e.g., dic(9; 20)(p13.2; q11.2).

In certain embodiments, the Philadelphia chromosome is contains a translocation, t(9; 22) (q34; ql 1), that results in a novel chimeric gene and protein which fuses the BCR gene on chromosome 22 with the gene encoding the Abelson tyrosine kinase (ABL1) on chromosome 9. In particular embodiments, the Philadelphia-like (Ph-like) subtype of ALL is characterized by related gene expression signatures variously referred to as "cluster group R8," "Philadelphia Chromosome (Ph)-like, "Ph-like," "BCR-ABL1-like," or an "activated tyrosine kinase gene expression signature." These gene expression signatures have been shown to be highly similar to gene expression profiles measured in Ph+ ALL subjects, despite the fact that, in some embodiments, Ph-like subjects to not have the Philadelphia chromosome translocation or the BCR-ABL1 fusion transcript. Methods and techniques of identifying and/or determining a Ph+ and/or a Ph-like ALL subtypes have been described (see, e.g., Roberts et al., N Engl J Med (2014) 371 (11): 1005-1015; Roberts et al. Cancer Cell (2012) 14; 22 (2): 153-66; Perez-Andreu et al. Nature Genetics (2013) 45 (12): 1494-1498; Yap et al. Leuk Lymphoma (2017) 58 (4): 950-958; Roberts et al. J Clin Oncol (2017) 35 (4): 394-401; Harvey et al. Blood (2013) 122:826; Harvey et al., Blood (2010) 116 (23): 4874-4884; and Pct App. No. WO 2013/090419, hereby incorporated by reference in their entirety).

In some embodiments, the patient and/or clinical factor is a level, amount or concentration of a cytokine in a blood, serum, or plasma sample prior to initiation of administration of the therapeutic T cell composition. In some embodiments, the cytokine is an interleukin, e.g., interleukin-15 (IL-15). In particular embodiments, the patient and/or clinical factor is an elevated level, amount, or concentration of IL-15 in a blood sample prior to initiation of administration of the therapeutic T cell composition. In certain embodiments, the patient and/or clinical factor is a level, amount or concentration of IL-15 that is greater than or equal to 1 pg/mL, 5 pg/mL, 10 pg/mL, 15 pg/mL, 20 pg/mL, 25 pg/mL, 30 pg/mL, 35 pg/mL, 40 pg/mL, 45 pg/mL, 50 pg/mL, 100 pg/mL, 150 pg/mL, 200 pg/mL, 250 pg/mL, or 300 pg/mL in a blood, serum, or plasma sample prior to initiation of administration of the therapeutic T cell composition. In certain embodiments, the patient and/or clinical factor is a level, amount or concentration of IL-15 that is greater than or equal to 30 pg/mL in a blood, serum, or plasma sample prior to initiation of administration of the therapeutic T cell composition.

In particular embodiments, the patient and/or clinical factor is a level, amount, or concentration of IL-15 that is greater than or greater than about or is 5%, 10%, 15%, 20%, 25%, 30%, 40%, 50%, 75%, 100%, 150%, 1-fold, 2-fold, 3-fold, 4-fold, 5-fold of the average, median, or mean, and/or is 3, 2.5, 2, 1.5, 1, 0.8, 0.6, 0.5, 0.4, 0.3, 0.2, or 0.1 standard deviations greater than the median or mean, of the level, amount or concentration of IL-15 in blood samples obtained from a group of subjects prior to receiving administration of a therapeutic T cell composition comprising a dose of cells engineered with a recombinant receptor, wherein each of the subjects of the group did not go on to develop grade 2 or higher, grade 3 or higher, prolonged grade 3 or higher, grade 4 or higher, or grade 5 toxicity following administration of the therapeutic T cell composition. In some embodiments, the toxicity is neurotoxicity.

In certain embodiments, the patient and/or clinical factor is a pharmacokinetic property of the cell composition following its administration to a subject, such as is in vivo expansion of recombinant receptor-expressing cells, e.g., CAR T cells. In some embodiments, the pharmacokinetic parameter can include the exposure, number, concentration, persistence and proliferation. In some cases, pharmacokinetics can be assessed by measuring such parameters as the maximum (peak) plasma concentration ($C_{max}$), the peak time (i.e. when maximum plasma concentration ($C_{max}$) occurs; $T_{max}$), the minimum plasma concentration (i.e. the minimum plasma concentration between doses of a therapeutic agent, e.g., CAR+ T cells; $C_{min}$), the elimination half-life ($T_{1/2}$) and area under the curve (i.e. the area under the curve generated by plotting time versus plasma concentration of the therapeutic agent CAR+ T cells; AUC), following administration. The concentration of a particular therapeutic agent, e.g., CAR+ T cells, in the plasma following administration can be measured using any method known in the art suitable for assessing concentrations of the therapeutic agents, e.g., CAR+ T cells, in samples of blood, or any methods described herein. For example, nucleic acid-based methods, such as quantitative PCR (qPCR) or flow cytometry-based methods, or other assays, such as an immunoassay, ELISA, or chromatography/mass spectrometry-based assays can be used.

In some embodiments, the pharmacokinetics (PK) of administered cells, e.g., CAR+ T cell composition, are determined to assess the availability, e.g., bioavailability, of the administered cells. In some embodiments, the determined pharmacokinetic parameters of the administered cells include maximum (peak) plasma concentrations ($C_{max}$), such as $C_{max}$ of $CD3^+CAR^+$ cells, $CD4^+$ $CAR^+$ cells and or $CD8^+$ $CAR^+$ T cells; the time point at which $C_{max}$ is achieved ($T_{max}$), such as the $T_{max}$ of $CD3^+$ $CAR^+$ cells, $CD4^+$ $CAR^+$ cells and or $CD8^+$ $CAR^+$ T cells, and or area under the curve (AUC), such as the $AUC_{0-28}$ of $CD3^+$ $CAR^+$ cells, $CD4^+$ $CAR^+$ cells and or $CD8^+$ $CAR^+$ T cells. In some embodiments, the pharmacokinetic parameter is peak $CD3^+$ $CAR^+$ T cell concentration ($C_{max}$ $CD3^+$ $CAR^+$ T cells), or $CD8^+$ $CAR^+$ T cell concentration ($C_{max}$ $CD8^+$ $CAR^+$ T cells). In some embodiments, the pharmacokinetic parameter is $AUC_{0-28}$, of $CD3^+$ CAR+ T cells, ($AUC_{0-28}$ $CD3^+$ $CAR^+$ T cells), or $AUC_{0-28}$, of $CD8^+$ $CAR^+$ T cells, ($AUC_{0-28}$ $CD8^+$ $CAR^+$ T cells).

The exposure, e.g., number or concentration of cells, e.g. T cells administered for T cell therapy, indicative of expansion and/or persistence, may be stated in terms of maximum numbers or concentration of the cells to which the subject is exposed, duration of detectable cells or cells above a certain number or percentage, area under the curve (AUC) for number or concentration of cells over time, and/or combinations thereof and indicators thereof. Such outcomes may be assessed using known methods, such as qPCR to detect copy number of nucleic acid encoding the recombinant receptor compared to total amount of nucleic acid or DNA in the particular sample, e.g., blood, serum, plasma or tissue, such as a tumor sample, and/or flow cytometric assays detecting cells expressing the receptor generally using antibodies specific for the receptors. Cell-based assays may also be used to detect the number or percentage or concentration of functional cells, such as cells capable of binding to and/or neutralizing and/or inducing responses, e.g., cytotoxic responses, against cells of the disease or condition or expressing the antigen recognized by the receptor.

In some embodiments exposure can be set forth as the area under the therapeutic agent concentration-time curve (AUC) as determined by pharmacokinetic analysis after administration of a dose of the therapeutic agent, e.g., CAR+ T cells. In some cases, the AUC is expressed in cells*days/μL, for cells administered in cell therapy, or in corresponding units thereof. In some embodiments, the AUC is measured as an average AUC in a patient population, such as a sample patient population, e.g., the average AUC from one or more patient(s). In some embodiments, systemic exposure refers to the area under the curve (AUC) within a certain period of time, e.g., from day 0 to day 1, 2, 3, 4, 5, 6, 7, 8, 9, 10, 11, 12, 13, 14, 21, 28 days or more, or week 1, 2, 3, 4, 5, 6, 7, 8, 9, 10, 11, 12, 13, 14, 15 or more, or month 1, 2, 3, 4, 5, 6, 7, 8, 9, 10, 11, 12, 18, 24, 48 or more. In some embodiments, the AUC is measured as an AUC from day 0 to day 28 ($AUC_{0-28}$) after administration of the therapeutic agent, e.g., CAR+ T cells, including all measured data and data extrapolated from measured pharmacokinetic (PK) parameters, such as an average AUC from a patient population, such as a sample patient population. In some embodiments, to determine exposure over time, e.g., AUC for a certain period of time, such as $AUC_{0-28}$, a therapeutic agent concentration-time curve is generated, using multiple measurements or assessment of parameters, e.g., cell concentrations, over time, e.g., measurements taken every 1, 2, 3, 4, 5, 6, 7, 8, 9, 10, 11, 12, 13, 14, 21 or 28 days or more.

In some embodiments, the presence and/or amount of cells expressing the recombinant receptor (e.g., CAR-expressing cells administered for T cell based therapy) in the subject following the administration of the T cells is determined. In some aspects, nucleic acid-based methods, such as quantitative PCR (qPCR), is used to assess the quantity of cells expressing the recombinant receptor (e.g., CAR-expressing cells administered for T cell based therapy) in the blood or serum or organ or tissue sample (e.g., disease site, e.g., tumor sample) of the subject. In some aspects, persistence is quantified as copies of DNA or plasmid encoding the receptor, e.g., CAR, per microgram of DNA, or as the number of receptor-expressing, e.g., CAR-expressing, cells per microliter of the sample, e.g., of blood or serum, or per total number of peripheral blood mononuclear cells (PBMCs) or white blood cells or T cells per microliter of the sample. In some embodiments, the primers or probe used for qPCR or other nucleic acid-based methods are specific for binding, recognizing and/or amplifying nucleic acids encoding the recombinant receptor, and/or other components or elements of the plasmid and/or vector, including regulatory elements, e.g., promoters, transcriptional and/or post-transcriptional regulatory elements or response elements, or markers, e.g., surrogate markers. In some embodiments, the primers can be specific for regulatory elements, such as the woodchuck hepatitis virus post-transcriptional regulatory element (WPRE).

In some embodiments, the cells are detected in the subject at or at least at 2, 3, 4, 5, 6, 7, 14, 15, 27, or 28 days following the administration of the T cells, e.g., CAR-expressing T cells. In some aspects, the cells are detected at or at least at 2, 4, or 6 weeks following, or 3, 6, or 12, 18, or 24, or 30 or 36 months, or 1, 2, 3, 4, 5, or more years, following the administration of the T cells, e.g., CAR-expressing T cells. In some embodiments, cells expressing the receptor are detectable in the serum, plasma, blood or tissue, e.g., tumor sample, of the subject, e.g., by a specified method, such as qPCR or flow cytometry-based detection method.

In some embodiments, the receptor expressing cells, e.g. CAR-expressing cells, expand in the subject following administration of the T cells, e.g., CAR-expressing T cells. In some aspects, increased exposure of the subject to the cells includes increased expansion of the cells. As shown herein, increased expansion that happens early, e.g. within 7 days, such as 4-7 days, following administration of the cell therapy is associated, correlated and/or can be indicative of the risk of likely risk of developing a toxicity. In some embodiments, methods are provided in which subjects are monitored for pharmacokinetic properties of the administered recombinant receptor-expressed cells and, if early or fast expansion is detected, one or more agents to ameliorate toxicity or a risk of or likely risk of toxicity can be administered to a subject. Exemplary agents to ameliorate toxicity are known and are described, e.g. in Section IV.E.

In particular embodiments, the pharmakokinetic parameter is a number of recombinant receptor-expressing cells that is indicative of early or fast expansion of the cells in the subject. In some embodiments, such detectable expansion can be shown if at least, at, or about 2, 3, 4, 5, 10, 15, 20, 25, 30, 35, 40, 45, 50, 75, 100, 125, 150, or 200 recombinant receptor-expressing cells per microliter are detected in a blood or serum sample collected within four, five, six, seven, eight, nine, ten, eleven, twelve, thirteen, or fourteen or more than fourteen days after the initiation of the administration of the cell therapy. In some embodiments, the pharmacokinetic parameter is a number of recombinant receptor-expressing cells that is at least, at, or about 2 recombinant receptor-expressing cells per microliter in a blood or serum sample collected within four days after the initiation of the administration. In particular embodiments, the pharmacokinetic parameter is a number of recombinant receptor-expressing cells that is at least, at, or about 5 recombinant receptor-expressing cells per microliter in a blood or serum sample collected within five or six days after the initiation of the administration. In some embodiments, the pharmacokinetic parameter is a number of recombinant receptor-expressing cells that is at least, at, or about 10 recombinant receptor-expressing cells per microliter in a blood or serum sample collected within five or six days after the initiation of the administration. In particular embodiments, the pharmacokinetic parameter is a number of recombinant receptor-expressing cells that is at least, at, or about 15 recombinant receptor-expressing cells per microliter in a blood or serum sample collected within seven days after the initiation of the administration.

In particular embodiments, provided herein are methods of designing a trial for administering a therapeutic T cell composition. In some embodiments, the methods comprise allocating a subject to a treatment regimen based on the presence or absence of one or more patient and/or clinical risk factors, such as any as described. In some embodiments, a subject that does not have, or is not identified or considered to have, a patient and/or clinical factor and is allocated to receive a dose of a therapeutic T cell composition. In particular embodiments, a subject has, or is identified or considered to have, a patient and/or clinical factor, and allocated to be administered a reduced and/or lower dose of cells. In certain embodiments, the reduced and/or lower dose is or is at least 5%, 10%, 15%, 20%, 25%, 30%, 35%, 40%, 45%, 50%, 60%, 70%, 80%, 90%, or 95% less than the dose that is administered to a subject without a patient and/or clinical factor. In certain embodiments, there is no substantial difference in the incidence of toxicity, e.g., severe adverse side effects, CRS, and/or neurotoxicity, between subjects without a patient and/or clinical factor that are administered the dose of cells and the subjects with a patient and/or clinical factor that are administered the lower dose of cells.

In certain embodiments, the subject is allocated to be administered the low or reduced dose if the subject has one or more patient and/or clinical factors that may include, but are not limited to, (i) subjects having received fewer prior therapies, optionally less than two prior therapies, prior to initiation of administration of the therapeutic T cell composition, (ii) subjects of a young age, optionally less than 30 years, (iii) subjects in which the ratio of CD4:CD8 in an apheresis sample from the subject is below a certain threshold, optionally below 1:1 or below 1.5:1 or below 0.5:1 or lower, optionally wherein the dose administered is based on total T cells or total T cells expressing a recombinant receptor; (iv) subjects having a weight greater than the average weight among the group of subjects treated; (v) subjects with a platelet count less than or about less than 120,000; (vi) subjects having a B cell leukemia, optionally acute lymphocytic leukemia (ALL); (vii) subjects having a high disease burden prior to, such as immediately prior to or within one month prior to, initiation of administration of the therapeutic T cell composition, optionally as determined based on percent of bone marrow blasts greater than or equal to 5%, sum of product diameter (SPD), or levels of lactate dehydrogenase; (ix) subjects having received a bridging chemotherapy prior to initiation of administration of the therapeutic T cell composition; (x) subjects having been preconditioned with a lymphodepleting therapy, optionally comprising the administration of fludarabine and/or cyclophosphamide, prior to initiation of administration of the therapeutic T cell composition; (xi) subjects in which the level, amount or concentration of interleukin-15 (IL-15) in a blood sample prior to initiation of administration of the therapeutic T cell composition is greater than or equal to a threshold value, optionally wherein the threshold value is 30 pg/mL plasma, (xii) rapid, in vivo expansion of cells expressing the recombinant receptors, (xiii) subjects not exhibiting a Philadelphia chromosome (Ph+) and/or Ph chromosome-like (Ph-like) molecular subtype of acute lymphoblastic leukemia (ALL).

C. Response Outcome

In some embodiments, a response outcome in a subject following administration of the T cell composition can be monitored or assessed. In some embodiments, the response outcome is no response. In some embodiments, the response outcome is a partial response. In some embodiments, the response outcome is a complete response (CR). In some embodiments, response outcome is assessed by monitoring the disease burden in the subject. In some embodiments, the presence of no response, a partial response or a clinical or complete response can be assessed.

In some embodiments, a partial response or complete response is one in which the therapeutic agent reduces or prevents the expansion or burden of the disease or condition in the subject. For example, where the disease or condition is a tumor, reduced disease burden exists or is present if there is a reduction in the tumor size, bulk, metastasis, percentage of blasts in the bone marrow or molecularly detectable cancer and/or an improvement prognosis or survival or other symptom associated with tumor burden compared to prior to treatment with the therapeutic agent (e.g. CAR T cells).

In some embodiments, the disease or condition is a tumor and a reduction in disease burden is a reduction in tumor size. In some embodiments, the disease burden reduction is indicated by a reduction in one or more factors, such as load or number of disease cells in the subject or fluid or organ or tissue thereof, the mass or volume of a tumor, or the degree or extent of metastases. In some embodiments, disease burden, e.g. tumor burden, can be assessed or monitored for the extent of morphological disease and/or minimal residual disease.

In some embodiments, the burden of a disease or condition in the subject is detected, assessed, or measured. Disease burden may be detected in some aspects by detecting the total number of disease or disease-associated cells, e.g., tumor cells, in the subject, or in an organ, tissue, or bodily fluid of the subject, such as blood or serum. In some embodiments, disease burden, e.g. tumor burden, is assessed by measuring the mass of a solid tumor and/or the number or extent of metastases. In some aspects, survival of the subject, survival within a certain time period, extent of survival, presence or duration of event-free or symptom-free survival, or relapse-free survival, is assessed. In some embodiments, any symptom of the disease or condition is assessed. In some embodiments, the measure of disease or condition burden is specified.

In some embodiments, disease burden can encompass a total number of cells of the disease in the subject or in an organ, tissue, or bodily fluid of the subject, such as the organ or tissue of the tumor or another location, e.g., which would indicate metastasis. For example, tumor cells may be detected and/or quantified in the blood or bone marrow in the context of certain hematological malignancies. Disease burden can include, in some embodiments, the mass of a tumor, the number or extent of metastases and/or the percentage of blast cells present in the bone marrow.

In some embodiments, a subject has leukemia. The extent of disease burden can be determined by assessment of residual leukemia in blood or bone marrow.

In some embodiments, a response outcome exists if there is a reduction in the percent of blasts in the bone marrow compared to the percent of blasts in the bone marrow prior to treatment with the therapeutic agent. In some embodiments, reduction of disease burden exists if there is a decrease or reduction of at least or at least about 20%, 30%, 40%, 50%, 60%, 70%, 80%, 90%, 95% or more in the number or percentage of blasts in the bone marrow compared to the number or percent of blasts in the bone marrow prior to treatment.

In some embodiments, the subject exhibits a response if the subject does not exhibit morphologic disease (non-morphological disease) or does not exhibit substantial morphologic disease. In some embodiments, a subject exhibits morphologic disease if there are greater than or equal to 5% blasts in the bone marrow, for example, as detected by light microscopy. In some embodiments, a subject exhibits complete or clinical remission if there are less than 5% blasts in the bone marrow.

In some embodiments, a subject exhibits reduced or decreased disease burden if they exhibited morphological disease prior to treatment and exhibit complete remission (e.g., fewer than 5% blasts in bone marrow) with or without molecular disease (e.g., minimum residual disease (MRD) that is molecularly detectable, e.g., as detected by flow cytometry or quantitative PCR) after treatment. In some embodiments, a subject exhibits reduced or decreased disease burden if they exhibited molecular disease prior to treatment and do not exhibit molecular disease after treatment.

In some embodiments, a subject may exhibit complete remission, but a small proportion of morphologically undetectable (by light microscopy techniques) residual leukemic cells are present. A subject is said to exhibit minimum residual disease (MRD) if the subject exhibits less than 5% blasts in the bone marrow and exhibits molecularly detectable cancer. In some embodiments, molecularly detectable cancer can be assessed using any of a variety of molecular techniques that permit sensitive detection of a small number of cells. In some aspects, such techniques include PCR assays, which can determine unique Ig/T-cell receptor gene rearrangements or fusion transcripts produced by chromosome translocations. In some embodiments, flow cytometry can be used to identify cancer cell based on leukemia-specific immunophenotypes. In some embodiments, molecular detection of cancer can detect as few as 1 leukemia or blast cell in 100,000 normal cells or 1 leukemia or blast cell in 10,000 normal cells. In some embodiments, a subject exhibits MRD that is molecularly detectable if at least or greater than 1 leukemia cell in 100,000 cells is detected, such as by PCR or flow cytometry.

In some embodiments, the disease burden of a subject is molecularly undetectable or $MRD^-$, such that, in some cases, no leukemia cells are able to be detected in the subject using PCR or flow cytometry techniques.

In some embodiments the response outcome is the absence of a CR or the presence of a complete response in which the subject achieves or exhibits minimal residual disease or molecular detectable disease status. In some embodiments, the response outcome is the presence of a CR with molecularly detectable disease or the presence of a CR without molecularly detectable disease. In some embodiments, subjects are assessed for disease burden using methods as described herein, such as methods that assess blasts in bone marrow or molecular disease by flow cytometry or qPCR methods.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32 (7): 689-702 (2009), and Herman et al. J. Immunological Methods, 285 (1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

D. Agent to Ameliorate or Treat Toxicity

In some embodiments, methods provided herein relate to monitoring subjects for risk or likely risk of toxicity, and/or identifying subjects who are at risk or likely risk of developing a toxicity, e.g. a severe toxicity, such as severe CRS or severe neurotoxicity, following administration of the cell therapy comprising cells expressing a recombinant receptor (e.g. CAR). In some embodiments, the methods include administering one or more agents or therapies that treat a toxicity of the cell therapy, such as CRS or neurotoxicity, e.g. severe CRS or severe neurotoxicity). In some embodiments, the agent is administered at a time at which it is determined the subject is at risk for developing a toxicity, such as a severe toxicity, and/or at a time at which one or more signs or symptoms of the toxicity has manifested.

In some embodiments, the agent is a steroid. In some embodiments, the agent is an antagonist or inhibitor of a cytokine receptor, such as IL-6 receptor, CD122 receptor (IL-2Rbeta receptor), or CCR2, or is an inhibitor of a cytokine, such as IL-6, MCP-1, IL-10, IFN-γ, IL-8, or IL-18. In some embodiments, the agent is an agonist of a cytokine receptor and/or cytokine, such as TGF-β. In some embodiments, the agent, e.g., agonist, antagonist or inhibitor, is an antibody or antigen-binding fragment, a small molecule, a protein or peptide, or a nucleic acid.

In some embodiments, a fluid bolus can be employed as an intervention, such as to treat hypotension associated with CRS. In some embodiments, the target hematocrit levels are >24%. In some embodiments, the intervention includes the use of absorbent resin technology with blood or plasma filtration. In some cases, the intervention includes dialysis, plasmapheresis, or similar technologies. In some embodiments, vassopressors or acetaminophen can be employed.

1. Steroid

In some embodiments, the agent that treats and/or that prevents, delays, or attenuates the development of or risk for developing a toxicity to the cell therapy, such as grade 2 or higher or severe CRS or neurotoxicity, is a steroid, e.g., corticosteroid. Corticosteroids typically include glucocorticoids and mineralocorticoids.

Any corticosteroid, e.g., glucocorticoid, can be used in the methods provided herein. In some embodiments, glucocorticoids include synthetic and non-synthetic glucocorticoids. Exemplary glucocorticoids include, but are not limited to: alclomethasones, algestones, beclomethasones (e.g. beclomethasone dipropionate), betamethasones (e.g. betamethasone 17-valerate, betamethasone sodium acetate, betamethasone sodium phosphate, betamethasone valerate), budesonides, clobetasols (e.g. clobetasol propionate), clobetasones, clocortolones (e.g. clocortolone pivalate), cloprednols, corticosterones, cortisones and hydrocortisones (e.g. hydrocortisone acetate), cortivazols, deflazacorts, desonides, desoximethasones, dexamethasones (e.g. dexamethasone 21-phosphate, dexamethasone acetate, dexamethasone sodium phosphate), diflorasones (e.g. diflorasone diacetate), diflucortolones, difluprednates, enoxolones, fluazacorts, flucloronides, fludrocortisones (e.g., fludrocortisone acetate), flumethasones (e.g. flumethasone pivalate), flunisolides, fluocinolones (e.g. fluocinolone acetonide), fluocinonides, fluocortins, fluocortolones, fluorometholones (e.g. fluorometholone acetate), fluperolones (e.g., fluperolone acetate), fluprednidenes, fluprednisolones, flurandrenolides, fluticasones (e.g. fluticasone propionate), formocortals, halcinonides, halobetasols, halometasones, halopredones, hydrocortamates, hydrocortisones (e.g. hydrocortisone 21-butyrate, hydrocortisone aceponate, hydrocortisone acetate, hydrocortisone buteprate, hydrocortisone butyrate, hydrocortisone cypionate, hydrocortisone hemisuccinate, hydrocortisone probutate, hydrocortisone sodium phosphate, hydrocortisone sodium succinate, hydrocortisone valerate), loteprednol etabonate, mazipredones, medrysones, meprednisones, methylprednisolones (methylprednisolone aceponate, methylprednisolone acetate, methylprednisolone hemisuccinate, methylprednisolone sodium succinate), mometasones (e.g., mometasone furoate), paramethasones (e.g., paramethasone acetate), prednicarbates, prednisolones (e.g. prednisolone 25-diethylaminoacetate, prednisolone sodium phosphate, prednisolone 21-hemisuccinate, prednisolone acetate; prednisolone farnesylate, prednisolone hemisuccinate, prednisolone-21 (beta-D-glucuronide), prednisolone metasulphobenzoate, prednisolone steaglate, prednisolone tebutate, prednisolone tetrahydrophthalate), prednisones, prednivals, prednylidenes, rimexolones, tixocortols, triamcinolones (e.g. triamcinolone acetonide, triamcinolone benetonide, triamcinolone hexacetonide, triamcinolone acetonide 21-palmitate, triamcinolone diacetate). These glucocorticoids and the salts thereof are discussed in detail, for example, in Remington's Pharmaceutical Sciences, A. Osol, ed., Mack Pub. Co., Easton, Pa. (16th ed. 1980).

In some examples, the glucocorticoid is selected from among cortisones, dexamethasones, hydrocortisones, methylprednisolones, prednisolones and prednisones. In a particular example, the glucocorticoid is dexamethasone.

In some embodiments, the agent is a corticosteroid and is administered in an amount that is therapeutically effective to treat, ameliorate or reduce one or more symptoms of a toxicity to the cell therapy, such as CRS or neurotoxicity. In some embodiments, indicators of improvement or successful treatment include determination of the failure to manifest a relevant score on toxicity grading scale (e.g. CRS or neurotoxicity grading scale), such as a score of less than 3, or a change in grading or severity on the grading scale as discussed herein, such as a change from a score of 4 to a score of 3.

In some aspects, the corticosteroid is provided in a therapeutically effective dose. Therapeutically effective concentration can be determined empirically by testing in known in vitro or in vivo (e.g. animal model) systems. For example, the amount of a selected corticosteroid to be administered to ameliorate symptoms or adverse effects of a toxicity to a cell therapy, such as CRS or neurotoxicity, can be determined by standard clinical techniques. In addition, animal models can be employed to help identify optimal dosage ranges. The precise dosage, which can be determined empirically, can depend on the particular therapeutic preparation, the regime and dosing schedule, the route of administration and the seriousness of the disease.

The corticosteroid can be administered in any amount that is effective to ameliorate one or more symptoms associated with the toxicity, such as with the CRS or neurotoxicity. The corticosteroid, e.g., glucocorticoid, can be administered, for example, at an amount between at or about 0.1 and 100 mg, per dose, 0.1 to 80 mg, 0.1 to 60 mg, 0.1 to 40 mg, 0.1 to 30 mg, 0.1 to 20 mg, 0.1 to 15 mg, 0.1 to 10 mg, 0.1 to 5 mg, 0.2 to 40 mg, 0.2 to 30 mg, 0.2 to 20 mg, 0.2 to 15 mg, 0.2 to 10 mg, 0.2 to 5 mg, 0.4 to 40 mg, 0.4 to 30 mg, 0.4 to 20 mg, 0.4 to 15 mg, 0.4 to 10 mg, 0.4 to 5 mg, 0.4 to 4 mg, 1 to 20 mg, 1 to 15 mg or 1 to 10 mg, each inclusive, to a 70 kg adult human subject. Typically, the corticosteroid, such as a glucocorticoid is administered at an amount between at or about 0.4 and 20 mg, for example, at or about 0.4 mg, 0.5 mg, 0.6 mg, 0.7 mg, 0.75 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg per dose, to an average adult human subject.

In some embodiments, the corticosteroid can be administered, for example, at a dosage of at or about 0.001 mg/kg (of the subject), 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.025 mg/kg, 0.03 mg/kg, 0.035 mg/kg, 0.04 mg/kg, 0.045 mg/kg, 0.05 mg/kg, 0.055 mg/kg, 0.06 mg/kg, 0.065 mg/kg, 0.07 mg/kg, 0.075 mg/kg, 0.08 mg/kg, 0.085 mg/kg, 0.09 mg/kg, 0.095 mg/kg, 0.1 mg/kg, 0.15 mg/kg, 0.2 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, 0.70 mg/kg, 0.75 mg/kg, 0.80 mg/kg, 0.85 mg/kg, 0.90 mg/kg, 0.95 mg/kg, 1 mg/kg, 1.05 mg/kg, 1.1 mg/kg, 1.15 mg/kg, 1.20 mg/kg, 1.25 mg/kg, 1.3 mg/kg, 1.35 mg/kg or 1.4 mg/kg, to an average adult human subject, typically weighing about 70 kg to 75 kg.

The corticosteroid, or glucocorticoid, for example dexamethasone, can be administered orally (tablets, liquid or liquid concentrate), PO, intravenously (IV), intramuscularly or by any other known route or route described herein (e.g., with respect to pharmaceutical formulations). In some aspects, the corticosteroid is administered as a bolus, and in other aspects it may be administered over a period of time.

In some aspects, the glucocorticoid can be administered over a period of more than one day, such as over two days, over 3 days, or over 4 or more days. In some embodiments, the corticosteroid can be administered one per day, twice per day, or three times or more per day. For example, the corticosteroid, e.g., dexamethasone, may in some examples be administered at 10 mg (or equivalent) IV twice a day for three days.

In some embodiments, the dosage of corticosteroid, e.g., glucocorticoid, is administered in successively lower dosages per treatment. Hence, in some such treatment regimes, the dose of corticosteroid is tapered. For example, the corticosteroid may be administered at an initial dose (or equivalent dose, such as with reference to dexamethasone) of 4 mg, and upon each successive administration the dose may be lowered, such that the dose is 3 mg for the next administration, 2 mg for the next administration, and 1 mg for the next administration Generally, the dose of corticosteroid administered is dependent upon the specific corticosteroid, as a difference in potency exists between different corticosteroids. It is typically understood that drugs vary in potency, and that doses can therefore vary, in order to obtain equivalent effects. Table 4 shows equivalence in terms of potency for various glucocorticoids and routes of administration. Equivalent potency in clinical dosing is well known. Information relating to equivalent steroid dosing (in a non-chronotherapeutic manner) may be found in the British National Formulary (BNF), 37 March 1999.

TABLE 4

| Glucocorticoid administration | |
|---|---|
| Glucocorticoid (Route) | Equivalency Potency |
| Hydrocortisone (IV or PO) | 20 |
| Prednisone | 5 |
| Prednisolone (IV or PO) | 5 |
| Methylprednisolone sodium succinate (IV) | 4 |
| Dexamethasone (IV or PO) | 0.5-0.75 |

Thus, in some embodiments, the steroid is administered in an equivalent dosage amount of from or from about 1.0 mg to 20 mg dexamethasone per day, such as 1.0 mg to 15 mg dexamethasone per day, 1.0 mg to 10 mg dexamethasone per day, 2.0 mg to 8 mg dexamethasone per day, or 2.0 mg to 6.0 mg dexamethasone per day, each inclusive. In some cases, the steroid is administered in an equivalent dose of at or about 4 mg or at or about 8 mg dexamethasone per day.

In some embodiments, the steroid is administered if fever persists after treatment with tocilizumab. For example, in some embodiments, dexamethasone is administered orally or intravenously at a dosage of 5-10 mg up to every 6-12 hours with continued fevers. In some embodiments, tocilizumab is administered concurrently with or subsequent to oxygen supplementation.

2. Other Agents

In some embodiments, the agent that treats or ameliorates symptoms of a toxicity of a cell therapy, such as CRS or neurotoxicity, is one that targets a cytokine, e.g., is an antagonist or inhibitor of a cytokine, such as transforming growth factor beta (TGF-beta), interleukin 6 (IL-6), interleukin 10 (IL-10), IL-2, MIP1β (CCL4), TNF alpha, IL-1, interferon gamma (IFN-gamma), or monocyte chemoattractant protein-1 (MCP-1). In some embodiments, the agent that treats or ameliorates symptoms of a toxicity of a cell therapy, such as CRS or neurotoxicity, is one that targets (e.g. inhibits or is an antagonist of) a cytokine receptor, such as IL-6 receptor (IL-6R), IL-2 receptor (IL-2R/CD25), MCP-1 (CCL2) receptor (CCR2 or CCR4), a TGF-beta receptor (TGF-beta I, II, or III), IFN-gamma receptor (IFNGR), MIP1β receptor (e.g., CCR5), TNF alpha receptor (e.g., TNFR1), IL-1 receptor (IL1-Rα/IL-1Rβ), or IL-10 receptor (IL-10R).

The amount of a selected agent that treats or ameliorates symptoms of a toxicity of a cell therapy, such as CRS or neurotoxicity to be administered to ameliorate symptoms or adverse effects of a toxicity to a cell therapy, such as CRS or neurotoxicity, can be determined by standard clinical techniques. Exemplary adverse events include, but are not limited to, an increase in alanine aminotransferase, an increase in aspartate aminotransferase, chills, febrile neutropenia, headache, hypotension, left ventricular dysfunction, encephalopathy, hydrocephalus, seizure, and/or tremor.

In some embodiments, the agent is administered in a dosage amount of from or from about 30 mg to 5000 mg, such as 50 mg to 1000 mg, 50 mg to 500 mg, 50 mg to 200 mg, 50 mg to 100 mg, 100 mg to 1000 mg, 100 mg to 500 mg, 100 mg to 200 mg, 200 mg to 1000 mg, 200 mg to 500 mg or 500 mg to 1000 mg.

In some embodiments, the agent is administered from or from about 0.5 mg/kg to 100 mg/kg, such as from or from about 1 mg/kg to 50 mg/kg, 1 mg/kg to 25 mg/kg, 1 mg/kg to 10 mg/kg, 1 mg/kg to 5 mg/kg, 5 mg/kg to 100 mg/kg, 5 mg/kg to 50 mg/kg, 5 mg/kg to 25 mg/kg, 5 mg/kg to 10 mg/kg, 10 mg/kg to 100 mg/kg, 10 mg/kg to 50 mg/kg, 10 mg/kg to 25 mg/kg, 25 mg/kg to 100 mg/kg, 25 mg/kg to 50 mg/kg to 50 mg/kg to 100 mg/kg. In some embodiments, the agent is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive. In some aspects, the agent is administered in a dosage amount of at least or at least about or about 1 mg/kg, 2 mg/kg, 4 mg/kg, 6 mg/kg, 8 mg/kg, 10 mg/kg or more. In some embodiments, the agent is administered at a dose of 4 mg/kg or 8 mg/kg.

In some embodiments, the agent is administered by injection, e.g., intravenous or subcutaneous injections, intraocular injection, periocular injection, subretinal injection, intravitreal injection, trans-septal injection, subscleral injection, intrachoroidal injection, intracameral injection, subconjunctival injection, subconjunctival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration.

In some embodiments, the amount of the agent is administered about or approximately twice daily, daily, every other day, three times a week, weekly, every other week or once a month.

In some embodiments, the agent is administered as part of a composition or formulation, such as a pharmaceutical composition or formulation as described below. Thus, in some cases, the composition comprising the agent is administered as described below. In other aspects, the agent is administered alone and may be administered by any known acceptable route of administration or by one described herein, such as with respect to compositions and pharmaceutical formulations.

In some embodiments, the agent that treats or ameliorates symptoms of a toxicity of the cell therapy, such as CRS or neurotoxicity, is an antibody or antigen binding fragment. In some embodiments, the agent is tocilizumab, siltuximab, sarilumab, olokizumab (CDP6038), elsilimomab, ALD518/BMS-945429, sirukumab (CNTO 136), CPSI-2634, ARGX-109, FE301, or FM101.

In some embodiments, the agent is an antagonist or inhibitor of IL-6 or the IL-6 receptor (IL-6R). In some aspects, the agent is an antibody that neutralizes IL-6 activity, such as an antibody or antigen-binding fragment that binds to IL-6 or IL-6R. For example, in some embodiments, the agent is or comprises tocilizumab (atlizumab) or sarilumab, anti-IL-6R antibodies. In some embodiments, the agent is an anti-IL-6R antibody described in U.S. Pat. No. 8,562,991. In some cases, the agent that targets IL-6 is an anti-IL-6 antibody, such as siltuximab, elsilimomab, ALD518/BMS-945429, sirukumab (CNTO 136), CPSI-2634, ARGX-109, FE301, FM101, or olokizumab (CDP6038). In some aspects, the agent may neutralize IL-6 activity by inhibiting the ligand-receptor interactions. The feasibility of this general type of approach has been demonstrated with a natural occurring receptor antagonist for interleukin-1. See Harmurn, C. H. et al., Nature (1990) 343:336-340. In some aspects, the IL-6/IL-6R antagonist or inhibitor is an IL-6 mutein, such as one described in U.S. Pat. No. 5,591,827. In some embodiments, the agent that is an antagonist or inhibitor of IL-6/IL-6R is a small molecule, a protein or peptide, or a nucleic acid.

In some embodiments, the agent is tocilizumab. In some embodiments, tocilizumab is administered as an early intervention in accord with the provided methods a dosage of from or from about 1 mg/kg to 12 mg/kg, such as at or about 4 mg/kg, 8 mg/kg, or 10 mg/kg. In some embodiments, tocilizumab is administered by intravenous infusion. In some embodiments, tocilizumab is administered for a persistent fever of greater than 39° C. lasting 10 hours that is unresponsive to acetaminophen. In some embodiments, a second administration of tocilizumab is provided if symptoms recur after 48 hours of the initial dose.

In some embodiments, the agent is an agonist or stimulator of TGF-β or a TGF-β receptor (e.g., TGF-β receptor I, II, or III). In some aspects, the agent is an antibody that increases TGF-β activity, such as an antibody or antigen-binding fragment that binds to TGF-β or one of its receptors. In some embodiments, the agent that is an agonist or stimulator of TGF-β and/or its receptor is a small molecule, a protein or peptide, or a nucleic acid.

In some embodiments, the agent is an antagonist or inhibitor of MCP-1 (CCL2) or a MCP-1 receptor (e.g., MCP-1 receptor CCR2 or CCR4). In some aspects, the agent is an antibody that neutralizes MCP-1 activity, such as an antibody or antigen-binding fragment that binds to MCP-1 or one of its receptors (CCR2 or CCR4). In some embodiments, the MCP-1 antagonist or inhibitor is any described in Gong et al. J Exp Med. 1997 Jul. 7; 186 (1): 131-137 or Shahrara et al. J Immunol 2008; 180:3447-3456. In some embodiments, the agent that is an antagonist or inhibitor of MCP-1 and/or its receptor (CCR2 or CCR4) is a small molecule, a protein or peptide, or a nucleic acid.

In some embodiments, the agent is an antagonist or inhibitor of IFN-γ or an IFN-γ receptor (IFNGR). In some aspects, the agent is an antibody that neutralizes IFN-γ activity, such as an antibody or antigen-binding fragment that binds to IFN-γ or its receptor (IFNGR). In some aspects, the IFN-gamma neutralizing antibody is any described in Dobber et al. Cell Immunol. 1995 February; 160 (2): 185-92 or Ozmen et al. J Immunol. 1993 Apr. 1; 150 (7): 2698-705. In some embodiments, the agent that is an antagonist or inhibitor of IFN-γ/IFNGR is a small molecule, a protein or peptide, or a nucleic acid.

In some embodiments, the agent is an antagonist or inhibitor of IL-10 or the IL-10 receptor (IL-10R). In some aspects, the agent is an antibody that neutralizes IL-10 activity, such as an antibody or antigen-binding fragment that binds to IL-10 or IL-10R. In some aspects, the IL-10 neutralizing antibody is any described in Dobber et al. Cell Immunol. 1995 February; 160 (2): 185-92 or Hunter et al. J Immunol. 2005 Jun. 1; 174 (11): 7368-75. In some embodiments, the agent that is an antagonist or inhibitor of IL-10/IL-10R is a small molecule, a protein or peptide, or a nucleic acid.

V. ENGINEERED CELLS

Provided herein are engineered cells that express one or more recombinant antigen receptor. In some embodiments, the cells can include cells genetically engineered with a recombinant receptor, such as a chimeric antigen receptor.

A. Recombinant Antigen Receptors

Provided are engineered cells, such as T cells, that express a recombinant receptor, including chimeric receptors containing ligand-binding domains or binding fragments thereof, such as functional non-TCR antigen receptors, such as chimeric antigen receptors (CARs), and also including T cell receptors (TCRs), such as transgenic TCRs, and components thereof. The chimeric receptor, such as a CAR, generally includes the extracellular antigen (or ligand) binding domain linked to one or more intracellular signaling components, in some aspects via linkers and/or transmembrane domain(s).

1. Chimeric Antigen Receptors

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., *Cancer Discov.,* 3 (4): 388-398 (2013); Davila et al. *PLoS ONE* 8 (4): e61338 (2013); Turtle et al., *Curr. Opin. Immunol.,* 24 (5): 633-39 (2012); Wu et al., *Cancer,* 18 (2): 160-75 (2012). In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., *Nature Reviews Clinical Oncology,* 10, 267-276 (2013); Wang et al., *J. Immunother.* 35 (9): 689-701 (2012); and Brentjens et al., *Sci Transl Med,.* 5 (177) (2013). See also WO2014031687, U.S. Pat. Nos. 8,339,645, 7,446,179, US 2013/0149337, U.S. Pat. Nos. 7,446,190, and 8,389,282. The chimeric receptors, such as CARs, generally include an extracellular antigen binding domain, such as a portion of an antibody molecule, generally a variable heavy (VH) chain region and/or variable light (VL) chain region of the antibody, e.g., an scFv antibody fragment.

In some embodiments, the recombinant receptor, e.g., antigen receptor contains an extracellular antigen- or ligand-binding domain that binds, e.g., specifically binds, to an antigen, a ligand and/or a marker. Among the antigen receptors are functional non-TCR antigen receptors, such as chimeric antigen receptors (CARs). In some embodiments, the antigen receptor is a CAR that contains an extracellular antigen-recognition domain that specifically binds to an antigen. In some embodiments, the CAR is constructed with a specificity for a particular antigen, marker or ligand, such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more ligand—(e.g., antigen-) binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy ($V_H$) and variable light ($V_L$) chains of a monoclonal antibody (mAb), or a single domain antibody (sdAb), such as sdFv, nanobody, $V_H$H and $V_{NAR}$. In some embodiments, an antigen-binding fragment comprises antibody variable regions joined by a flexible linker.

In some embodiments, among the antigens targeted by the chimeric receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas. In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues, e.g., in healthy cells or tissues. In other embodiments, the antigen is expressed on normal cells and/or is expressed on the engineered cells.

Antigens targeted by the receptors in some embodiments include orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, 0EPHa2, ErbB2, 3, or 4, FBP, fetal acetylcholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In some embodiments, the antigen targeted by the receptors include avβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, fetal acetylcholine receptor, ganglioside GD2, O-acetylated GD2 (OGD2), ganglioside GD3, glycoprotein 100 (gp100), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-AIA1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen targeted by the receptor is or includes CD20, CD19, CD22, ROR1, CD45, CD21, CD5, CD33, Igkappa, Iglambda, CD79a, CD79b or CD30.

In some embodiments, the CAR binds a pathogen-specific antigen. In some embodiments, the CAR is specific for viral antigens (such as a viral antigen from HIV, HCV, HBV, etc.), bacterial antigens, and/or parasitic antigens.

In some embodiments, the antibody or an antigen-binding fragment (e.g. scFv or $V_H$ domain) specifically recognizes an antigen, such as CD19. In some embodiments, the antibody or antigen-binding fragment is derived from, or is a variant of, antibodies or antigen-binding fragment that specifically binds to CD19.

In some embodiments the scFv and/or $V_H$ domains is derived from FMC63. FMC63 generally refers to a mouse monoclonal IgG1 antibody raised against Nalm-1 and -16 cells expressing CD19 of human origin (Ling, N. R., et al. (1987). Leucocyte typing III. 302). The FMC63 antibody comprises CDR H1 set forth in SEQ ID NO: 38; CDR H2 set forth in SEQ ID NO: 39; CDR H3 set forth in SEQ ID NOS: 40 or 54; and CDR L1 set forth in SEQ ID NO: 35; CDR L2 set forth in SEQ ID NO:36 or 55; and CDR L3 set forth in SEQ ID NO:37 or 56. The FMC63 antibody comprises the heavy chain variable region ($V_H$) comprising the amino acid sequence of SEQ ID NO: 41 and the light chain variable region ($V_L$) comprising the amino acid sequence of SEQ ID NO: 42. In some embodiments, the scFv comprises a variable light chain containing a CDR L1 sequence of SEQ ID NO:35, a CDR L2 sequence of SEQ ID NO:36, and a CDR L3 sequence of SEQ ID NO:37 and/or a variable heavy chain containing a CDR H1 sequence of SEQ ID NO:38, a CDR H2 sequence of SEQ ID NO:39, and a CDR H3 sequence of SEQ ID NO:40, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the scFv comprises a variable heavy chain region of FMC63 set forth in SEQ ID NO:41 and a variable light chain region of FMC63 set forth in SEQ ID NO:42, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the variable heavy and variable light chains are connected by a linker. In some embodiments, the linker is set forth in SEQ ID NO:58. In some embodiments, the scFv comprises, in order, a $V_H$, a linker, and a $V_L$. In some embodiments, the scFv comprises, in order, a $V_L$, a linker, and a $V_H$. In some embodiments, the scFv is encoded by a sequence of nucleotides set forth in SEQ ID NO:57 or a sequence that exhibits at least 85%, 86%, 87%, 88%, 89%, 90%, 91%, 92%, 93%, 94%, 95%, 96%, 97%, 98%, or 99% sequence identity to SEQ ID NO: 57. In some embodiments, the scFv comprises the sequence of amino acids set forth in SEQ ID NO: 43 or a sequence that exhibits at least 85%, 86%, 87%, 88%, 89%, 90%, 91%, 92%, 93%, 94%, 95%, 96%, 97%, 98%, or 99% sequence identity to SEQ ID NO:43.

In some embodiments, the scFv and/or $V_H$ domain is derived from SJ25C1. SJ25C1 is a mouse monoclonal IgG1 antibody raised against Nalm-1 and -16 cells expressing CD19 of human origin (Ling, N. R., et al. (1987). Leucocyte typing III. 302). The SJ25C1 antibody comprises CDR H1, H2 and H3 set forth in SEQ ID NOS: 47-49, respectively, and CDR L1, L2 and L3 sequences set forth in SEQ ID NOS: 44-46, respectively. The SJ25C1 antibody comprises the heavy chain variable region ($V_H$) comprising the amino acid sequence of SEQ ID NO: 50 and the light chain variable region ($V_L$) comprising the amino acid sequence of SEQ ID NO: 51. In some embodiments, the svFv comprises a variable light chain containing a CDR L1 sequence set forth in SEQ ID NO:44; a CDR L2 set forth in SEQ ID NO: 45; and a CDR L3 set forth in SEQ ID NO:46; and/or a variable heavy chain containing a CDR H1 set forth in SEQ ID NO: 47, a CDR H2 set forth in SEQ ID NO:48, and a CDR H3 set forth in SEQ ID NO:49, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the scFv comprises a variable heavy chain region of SJ25C1 set forth in SEQ ID NO: 50 and a variable light chain region of SJ25C1 set forth in SEQ ID NO:51, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the variable heavy and variable light chains are connected by a linker. In some embodiments, the linker is set forth in SEQ ID NO:52. In some embodiments, the scFv comprises, in order, a $V_H$, a linker, and a $V_L$. In some embodiments, the scFv comprises, in order, a $V_L$, a linker, and a $V_H$. In some embodiments, the scFv comprises the sequence of amino acids set forth in SEQ ID NO: 53 or a sequence that exhibits at least 85%, 86%, 87%, 88%, 89%, 90%, 91%, 92%, 93%, 94%, 95%, 96%, 97%, 98%, or 99% sequence identity to SEQ ID NO:53.

In some aspects, the CAR contains a ligand—(e.g., antigen-) binding domain that binds or recognizes, e.g., specifically binds, a universal tag or a universal epitope. In some aspects, the binding domain can bind a molecule, a tag, a polypeptide and/or an epitope that can be linked to a different binding molecule (e.g., antibody or antigen-binding fragment) that recognizes an antigen associated with a disease or disorder. Exemplary tag or epitope includes a dye (e.g., fluorescein isothiocyanate) or a biotin. In some aspects, a binding molecule (e.g., antibody or antigen-binding fragment) linked to a tag that recognizes the antigen associated with a disease or disorder, e.g., tumor antigen, with an engineered cell expressing a CAR specific for the tag, to effect cytotoxicity or other effector function of the engineered cell. In some aspects, the specificity of the CAR to the antigen associated with a disease or disorder is provided by the tagged binding molecule (e.g., antibody), and different tagged binding molecule can be used to target different antigens. Exemplary CARs specific for a universal tag or a universal epitope include those described, e.g., in U.S. Pat. No. 9,233,125, WO 2016/030414, Urbanska et al., (2012) Cancer Res 72:1844-1852, and Tamada et al., (2012). Clin Cancer Res 18:6436-6445.

In some embodiments, the CAR contains a TCR-like antibody, such as an antibody or an antigen-binding fragment (e.g. scFv) that specifically recognizes an intracellular antigen, such as a tumor-associated antigen, presented on the cell surface as a major histocompatibility complex (MHC)-peptide complex. In some embodiments, an antibody or antigen-binding portion thereof that recognizes an MHC-peptide complex can be expressed on cells as part of a recombinant receptor, such as an antigen receptor. Among the antigen receptors are functional non-T cell receptor (TCR) antigen receptors, such as chimeric antigen receptors (CARs). In some embodiments, a CAR containing an antibody or antigen-binding fragment that exhibits TCR-like specificity directed against peptide-MHC complexes also may be referred to as a TCR-like CAR. In some embodiments, the CAR is a TCR-like CAR and the antigen is a processed peptide antigen, such as a peptide antigen of an intracellular protein, which, like a TCR, is recognized on the cell surface in the context of an MHC molecule. In some embodiments, the extracellular antigen-binding domain specific for an MHC-peptide complex of a TCR-like CAR is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

Reference to "Major histocompatibility complex" (MHC) refers to a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MHC class I molecules are heterodimers having a membrane spanning a chain, in some cases with three a domains, and a non-covalently associated β2 microglobulin. Generally, MHC class II molecules are composed of two transmembrane glycoproteins, α and β, both of which typically span the membrane. An MHC molecule can include an effective portion of an MHC that contains an antigen binding site or sites for binding a peptide and the sequences necessary for recognition by the appropriate antigen receptor. In some embodiments, MHC class I molecules deliver peptides originating in the cytosol to the cell surface, where a MHC-peptide complex is recognized by T cells, such as generally $CD8^+$ T cells, but in some cases $CD4^+$ T cells. In some embodiments, MHC class II molecules deliver peptides originating in the vesicular system to the cell surface, where they are typically recognized by $CD4^+$ T cells. Generally, MHC molecules are encoded by a group of linked loci, which are collectively termed H-2 in the mouse and human leukocyte antigen (HLA) in humans. Hence, typically human MHC can also be referred to as human leukocyte antigen (HLA).

The term "MHC-peptide complex" or "peptide-MHC complex" or variations thereof, refers to a complex or association of a peptide antigen and an MHC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

In some embodiments, a peptide, such as a peptide antigen or epitope, of a polypeptide can associate with an MHC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the MHC Class II complex. In some embodiments, a peptide has a length of from or from about 8 to 13 amino acids for recognition in the MHC Class I complex. In some embodiments, upon recognition of the peptide in the context of an MHC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, a TCR-like antibody or antigen-binding portion, are known or can be produced by known methods (see e.g. US Published Application Nos. US 2002/0150914; US 2003/0223994; US 2004/0191260; US 2006/0034850; US 2007/00992530; US20090226474; US20090304679; and International App. Pub. No. WO 03/068201).

In some embodiments, an antibody or antigen-binding portion thereof that specifically binds to a MHC-peptide complex can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described below. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFv or other antibody forms can be generated, for example, in which members of the library are mutated at one or more residues of a CDR or CDRs. See e.g. US Pat. App. Pub. No. US20020150914, US20140294841; and Cohen C J. et al. (2003) *J Mol. Recogn.* 16:324-332.

The term "antibody" herein is used in the broadest sense and includes polyclonal and monoclonal antibodies, including intact antibodies and functional (antigen-binding) antibody fragments, including fragment antigen binding (Fab) fragments, $F(ab')_2$ fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody, $V_H$H or $V_{NAR}$) or fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD. In some aspects, the CAR is a bispecific CAR, e.g., containing two antigen-binding domains with different specificities.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, $F(ab')_2$, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ Or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Single-domain antibodies (sdAb) are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known. Exemplary single-domain antibodies include sdFv, nanobody, $V_H$H or $V_{NAR}$.

Antibody fragments can be made by various techniques, including but not limited to proteolytic digestion of an intact antibody as well as production by recombinant host cells. In some embodiments, the antibodies are recombinantly produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Thus, in some embodiments, the chimeric antigen receptor, including TCR-like CARs, includes an extracellular portion containing an antibody or antibody fragment. In some embodiments, the antibody or fragment includes an scFv. In some aspects, the antibody or antigen-binding fragment can be obtained by screening a plurality, such as a library, of antigen-binding fragments or molecules, such as by screening an scFv library for binding to a specific antigen or ligand.

In some aspects, the recombinant receptor, e.g., a chimeric antigen receptor, includes an extracellular portion containing one or more ligand—(e.g., antigen-) binding domains, such as an antibody or fragment thereof, and one or more intracellular signaling region or domain (also interchangeably called a cytoplasmic signaling domain or region). In some aspects, the recombinant receptor, e.g., CAR, further includes a spacer and/or a transmembrane domain or portion. In some aspects, the spacer and/or transmembrane domain can link the extracellular portion containing the ligand—(e.g., antigen-) binding domain and the intracellular signaling region(s) or domain(s).

In some embodiments, the antibody portion of the recombinant receptor, e.g., CAR, further includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers, e.g., hinge regions, include those described in international patent application publication number WO2014031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. In some embodiments, the spacer is less than 250 amino acids in length, less than 200 amino acids in length, less than 150 amino acids in length, less than 100 amino acids in length, less than 75 amino acids in length, less than 50 amino acids in length, less than 25 amino acids in length, less than 20 amino acids in length, less than 15 amino acids in length, less than 12 amino acids in length, or less than 10 amino acids in length. In some embodiments, the spacer is from or from about 10 to 250 amino acids in length, 10 to 150 amino acids in length, 10 to 100 amino acids in length, 10 to 50 amino acids in length, 10 to 25 amino acids in length, 10 to 15 amino acids in length, 15 to 250 amino acids in length, 15 to 150 amino acids in length, 15 to 100 amino acids in length, 15 to 50 amino acids in length, 15 to 25 amino acids in length, 25 to 250 amino acids in length, 25 to 100 amino acids in length, 25 to 50 amino acids in length, 50 to 250 amino acids in length, 50 to 150 amino acids in length, 50 to 100 amino acids in length, 100 to 250 amino acids in length, 100 to 150 amino acids in length, or 150 to 250 amino acids in length. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. *Clin. Cancer Res.*, 19:3153 (2013), international patent application publication number WO2014031687, U.S. Pat. No. 8,822,647 or published app. No. US2014/0271635.

In some embodiments, the constant region or portion is of a human IgG, such as IgG4 or IgG1. In some aspects, the spacer is a polypeptide spacer such as one or more selected from: (a) comprises or consists of all or a portion of an immunoglobulin hinge or a modified version thereof or comprises about 15 amino acids or less, and does not comprise a CD28 extracellular region or a CD8 extracellular region, (b) comprises or consists of all or a portion of an immunoglobulin hinge, optionally an IgG4 hinge, or a modified version thereof and/or comprises about 15 amino acids or less, and does not comprise a CD28 extracellular region or a CD8 extracellular region, or (c) is at or about 12 amino acids in length and/or comprises or consists of all or a portion of an immunoglobulin hinge, optionally an IgG4, or a modified version thereof; or (d) comprises or consists of the formula $X_1PPX_2P$ (SEQ ID NO: 31), where $X_1$ is glycine, cysteine or arginine and $X_2$ is cysteine or threonine. In some embodiments, the spacer has the sequence ESKYGPPCPPCP (set forth in SEQ ID NO: 1), and is encoded by the sequence set forth in SEQ ID NO: 2. In some embodiments, the spacer has the sequence set forth in SEQ ID NO: 3. In some embodiments, the spacer has the sequence set forth in SEQ ID NO: 4. In some embodiments, the constant region or portion is of IgD. In some embodiments, the spacer has the sequence set forth in SEQ ID NO: 5. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4 or 5 or 27-34.

This antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen-binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137 (4-1BB), CD 154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s). In some aspects, the transmembrane domain contains a transmembrane portion of CD28 or a variant thereof. The extracellular domain and transmembrane can be linked directly or indirectly. In some embodiments, the extracellular domain and transmembrane are linked by a spacer, such as any described herein.

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-2) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal.

Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CD8, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., *Sci. Transl. Medicine,* 5 (215) (2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687.

For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 7 or 23 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 23. An exemplary T2A linker sequence comprises the sequence of amino acids set forth in SEQ ID NO: 6 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, third or fourth generation CARs. In some aspects, a first generation CAR is one that solely provides a primary stimulation or activation signal, e.g., via CD3-chain induced signal upon antigen binding; in some aspects, a second-generation CAR is one that provides such a signal and costimulatory signal, such as one including an intracellular signaling region(s) or domain(s) from one or more costimulatory receptor such as CD28, CD137 (4-1BB), OX40 (CD134), CD27, DAP10, DAP12, NKG2D, ICOS and/or other costimulatory receptors; in some aspects, a third generation CAR is one that includes multiple costimulatory domains of different costimulatory receptors, e.g., selected from CD28, CD137 (4-1BB), OX40 (CD134), CD27, DAP10, DAP12, NKG2D, ICOS and/or other costimulatory receptors; in some aspects, a fourth generation CAR is one that includes three or more costimulatory domains of different costimulatory receptors, e.g., selected from CD28, CD137 (4-1BB), OX40 (CD134), CD27, DAP10, DAP12, NKG2D, ICOS and/or other costimulatory receptors.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD35) chain. In some embodiments, the chimeric antigen receptor includes a transmembrane domain linking the extracellular domain and the intracellular signaling domain. In some aspects, the transmembrane domain contains a transmembrane portion of CD28. In some embodiments, the chimeric antigen receptor contains an intracellular domain of a T cell costimulatory molecule. The antigen-binding portion of the extracellular domain and transmembrane domain can be linked directly or indirectly. In some embodiments, the antigen-binding portion of the extracellular domain and the transmembrane domain are linked by a spacer, such as any described herein. In some embodiments, the receptor contains an extracellular portion of the molecule from which the transmembrane domain is derived, such as a CD28 extracellular portion. In some embodiments, the chimeric antigen receptor contains an intracellular domain derived from a T cell costimulatory molecule or a functional variant thereof, such as between the transmembrane domain and ITAM-containing, e.g., CD3zeta-derived, signaling domain. In some aspects, the T cell costimulatory molecule is CD28 or 41BB.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge or variant thereof, e.g. an IgG4 hinge or variant thereof, such as a hinge-only spacer.

In some embodiments, the transmembrane domain of the recombinant receptor, e.g., the CAR, is or includes a transmembrane domain of human CD28 (e.g. Accession No. P10747.1) or variant thereof, such as a transmembrane domain that comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8; in some embodiments, the transmembrane-domain containing portion of the recombinant receptor comprises the sequence of amino acids set forth in SEQ ID NO: 9 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 10 or 11 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular domain comprises an intracellular costimulatory signaling domain of 4-1BB (e.g. (Accession No. Q07011.1) or functional variant or portion thereof, such as the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD3ξ (Accession No.: P20963.2) or a CD3 zeta signaling domain as described in U.S. Pat. No. 7,446,190 or U.S. Pat. No. 8,911,993. For example, in some embodiments, the intracellular signaling domain comprises the sequence of amino acids as set forth in SEQ ID NO: 13, 14 or 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO: 1. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains, such as set forth in SEQ ID NO: 4. In some embodiments, the spacer is an Ig hinge, e.g., an IgG4 hinge, linked to a CH3 domain only, such as set forth in SEQ ID NO: 3. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, the sequence encodes a T2A ribosomal skip element set forth in SEQ ID NO: 6, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802,374). In some embodiments, the sequence encodes an tEGFR sequence set forth in SEQ ID NO: 7 or 23, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 23.

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition.

B. TCRs

In some embodiments, engineered cells, such as T cells, are provided that express a T cell receptor (TCR) or antigen-binding portion thereof that recognizes an peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., *Immunobiology: The Immune System in Health and Disease,* 3rd Ed., *Current Biology Publications*, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or Cβ, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ξ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) *Nat Immunol,* 4, 55-62; Holler et al. (2000) *Proc Natl Acad Sci USA,* 97, 5387-92), phage display (Li et al. (2005) *Nat Biotechnol,* 23, 349-54), or T cell display (Chervin et al. (2008) *J Immunol Methods,* 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified by a skilled artisan. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using computer prediction models known to those of skill in the art. In some embodiments, for predicting MHC class I binding sites, such models include, but are not limited to, ProPred 1 (Singh and Raghava (2001) *Bioinformatics* 17 (12): 1236-1237, and SYFPEITHI (see Schuler et al. (2007) *Immunoinformatics Methods in Molecular Biology,* 409 (1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known to those of skill in the art. For predicting MHC class I binding sites, such models include, but are not limited to, ProPred 1 (described in more detail in Singh and Raghava, ProPred: prediction of HLA-DR binding sites. *BIOINFORMATICS* 17 (12): 1236-1237 2001), and SYFPEITHI (see Schuler et al. SYFPEITHI, Database for Searching and T-Cell Epitope Prediction. in *Immunoinformatics Methods in Molecular Biology*, vol 409 (1): 75-93 2007)

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR a chain variable region sequence is fused to the N terminus of a sequence corresponding to a TCR a chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR a chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR a chain and TCR β chain together.

In some embodiments, the TCR is a scTCR. Typically, a scTCR can be generated using methods known to those of skill in the art, See e.g., Soo Hoo, W. F. et al. *PNAS* (*USA*) 89, 4759 (1992); Wülfing, C. and Plückthun, A., *J. Mol. Biol.* 242, 655 (1994); Kurucz, I. et al. *PNAS* (*USA*) 90 3830 (1993); International published PCT Nos. WO 96/13593, WO 96/18105, WO99/60120, WO99/18129, WO 03/020763, WO2011/044186; and Schlueter, C. J. et al. *J. Mol. Biol.* 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRß variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-(SGGGG) 5-P- wherein P is proline, G is glycine and S is serine (SEQ ID NO: 16). In some embodiments, the linker has the sequence GSADDAKKDAAKKDGKS (SEQ ID NO: 17)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about $10^{-5}$ and $10^{-12}$ M and all individual values and ranges therein. In some embodiments, the target antigen is an MHC-peptide complex or ligand.

In some embodiments, nucleic acid or nucleic acids encoding a TCR, such as α and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-C1, pMAM and pMAMneo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other promoters known to a skilled artisan also are contemplated.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

C. Multi-Targeting

In some embodiments, the cells and methods include multi-targeting strategies, such as expression of two or more genetically engineered receptors on the cell, each recognizing the same of a different antigen and typically each including a different intracellular signaling component. Such multi-targeting strategies are described, for example, in International Patent Application, Publication No.: WO 2014055668 A1 (describing combinations of activating and costimulatory CARs, e.g., targeting two different antigens present individually on off-target, e.g., normal cells, but present together only on cells of the disease or condition to be treated) and Fedorov et al., *Sci. Transl. Medicine,* 5 (215) (2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1 BB), OX40, CD27, DAP10, DAP12, NKG2D, ICOS and/or other costimulatory receptors. In some embodiments, the first and second receptor include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

D. Cells and Preparation of Cells for Engineering

Also provided are cells, such as cells that contain the engineered recombinant receptor, such as described herein. Also provided are populations of such cells, compositions containing such cells and/or enriched for such cells, such as in which cells expressing the recombinant receptor, e.g. chimeric receptor, make up at least 50, 60, 70, 80, 90, 91, 92, 93, 94, 95, 96, 97, 98, 99, or more percent of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients, such as in accord with the provided methods.

Thus, also provided are genetically engineered cells expressing the recombinant receptors e.g., CARs. The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, manufacturing, generating or producing a cell therapy, e.g., therapeutic cell compositions containing cells expressing a recombinant receptor, can be carried out via a process that includes one or more further processing steps, such as steps for the activation or stimulation, transduction, cultivation, expansion, washing, suspension, dilution, concentration, and/or formulation of the cells. In some embodiments, the methods of generating or producing a cell therapy include isolating cells from a subject, preparing, processing, culturing under one or more stimulating conditions. In some embodiments, the method includes processing steps carried out in an order in which: cells, e.g. primary cells, are first isolated, such as selected or separated, from a biological sample; selected cells are incubated with viral vector particles for transduction, optionally subsequent to a step of stimulating the isolated cells in the presence of a stimulation reagent; culturing the transduced cells, such as to expand the cells; formulating the transduced cells in a composition and introducing the composition into a provided biomedical material vessel. In some embodiments, the generated engineered cells are re-introduced into the same subject, before or after cryopreservation.

In some embodiments, the one or more processing steps can include one or more of (a) washing a biological sample containing cells (e.g., a whole blood sample, a buffy coat sample, a peripheral blood mononuclear cells (PBMC) sample, an unfractionated T cell sample, a lymphocyte sample, a white blood cell sample, an apheresis product, or a leukapheresis product), (b) isolating, e.g. selecting, from the sample a desired subset or population of cells (e.g., CD4+ and/or CD8+ T cells), for example, by incubation of cells with a selection or immunoaffinity reagent for immunoaffinity-based separation; (c) activating and/or stimulating cells by exposing cells to stimulating conditions and/or stimulatory reagents, which can be performed prior to, during and/or subsequent to the incubation of cells with viral vector particles, (d) incubating the isolated, such as selected cells, with viral vector particles, e.g., transducing the cells, (e) culturing, cultivating or expanding the cells such using methods as described and (f) formulating the transduced cells, such as in a pharmaceutically acceptable buffer, cryopreservative or other suitable medium. In some embodiments, the cells of the PBMC sample, unfractionated T cell sample, lymphocyte sample, white blood cell sample, apheresis product, or leukapheresis product are cryofrozen and then thawed prior to any steps for isolating, selecting, incubating, transducing, transfecting, cultivating, expanding, and/or formulating the cells.

In some embodiments, one or more further step of washing or suspending step, such as for dilution, concentration and/or buffer exchange of cells, can also be carried out prior to or subsequent to any of the above steps. In some aspects, the resulting engineered cell composition is introduced into one or more provided biomedical culture vessel.

In some embodiments, one, more, or all steps in the preparation of cells for clinical use, e.g., in adoptive cell therapy, are carried out without exposing the cells to non-sterile conditions and without the need to use a sterile room or cabinet. In some embodiments of such a process, the cells are isolated, separated or selected, transduced, washed, optionally activated or stimulated and formulated, all within a closed system. In some aspects of such a process, the cells are expressed from a closed system and introduced into one or more of the biomaterial vessels. In some embodiments, the methods are carried out in an automated fashion. In some embodiments, one or more of the steps is carried out apart from the closed system or device.

In some embodiments, a closed system is used for carrying out one or more of the other processing steps of a method for manufacturing, generating or producing a cell therapy. In some embodiments, one or more or all of the processing steps, e.g., isolation, selection and/or enrichment, processing, incubation in connection with transduction and engineering, and formulation steps is carried out using a system, device, or apparatus in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps. In one example, the system is a system as described in International Patent Application, Publication Number WO2009/072003, or US20110003380 A1. In one example, the system is a system as described in International Publication Number WO2016/073602.

In some embodiments, preparation of the engineered cells includes one or more culture and/or preparation steps. The cells for introduction of the recombinant receptor, e.g., CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished using a semi-automated "flow-through" centrifuge (for example, the Cobe 2991 cell processor, Baxter) according to the manufacturer's instructions. In some aspects, a washing step is performed in a centrifugal chamber, for example those produced and sold by Biosafe SA, including those for use with the Sepax® and Sepax® 2 system, including an A-200/F and A-200 centrifugal chambers according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, Ca++/Mg++ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques.

For example, CD3+, CD28+ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (markerhigh) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakuraet al. (2012) Blood. 1:72-82; Wang et al. (2012) J Immunother. 35 (9): 689-701. In some embodiments, combining $T_{CM}$-enriched CD8+ T cells and CD4+ T cells further enhances efficacy.

In embodiments, memory T cells are present in both CD62L+ and CD62L-subsets of CD8+ peripheral blood lymphocytes. PBMC can be enriched for or depleted of CD62L-CD8+ and/or CD62L+CD8+ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or ROR1, and positive selection based on a marker characteristic of central memory T cells, such as CD62L or CCR7, where the positive and negative selections are carried out in either order.

CD4+ T helper cells are sorted into naïve, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO−

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, NJ).

In some aspects, two or more selection steps may be performed sequentially. For example, the sample or composition of cells to be separated is subjected to selection of CD8+ cells, where both the negative and positive fractions are retained. The CD8 negative fraction may be further subjected to selection of CD4+ cells. In some aspects, the sample or composition of cells to be separated is subjected to selection of CD4+ cells, where both the negative and positive fractions are retained and the CD4 negative fraction may be subjected to selection of CD8+ cells. Exemplary methods for cell selection are described in International Patent Application Publication Numbers WO2015157384 and/or WO 2015/164675, which are incorporated by reference in their entirety, all or a portion of which could be used in connection with the methods described herein.

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1. In some aspects, the apheresis or leukapheresis product, or a sample derived therefrom, is processed and/or the isolation or selection is carried out using a system, device, apparatus, and/or method as described in International Patent Application Publication Number WO2016/073602 or US 2016/0122782 the contents of which are incorporated by reference in their entirety. In some embodiments, the isolation or separation is carried out according to methods described in International Patent Application Publication Number WO 2015/164675, the contents of which are incorporated by reference in their entirety.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotic), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) J Immunother. 35 (9): 651-660, Terakuraet al. (2012) Blood. 1:72-82, and Wang et al. (2012) J Immunother. 35 (9): 689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1 (5): 355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. In some embodiments, the cells are frozen by any method, and/or with any reagents, containers, freezing solutions, and/or cryoprotectants described herein. In some embodiments, the cells are then frozen to −80° C. at a rate of or of about 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some aspects, the cells are incubated in the presence of one or more cytokines and in some embodiments a cytokine cocktail can be employed, for example as described in International Patent Application Publication Number WO2015157384. In some embodiments, the cells are incubated with one or more cytokines and/or a cytokine cocktail prior to, concurrently with, or subsequent to transduction.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Exemplary stimulatory reagents are described herein, such as for example in Section V-D-1. Optionally, the expansion method may further comprise the step of adding anti-CD3 and/or anti CD28 antibody to the culture medium (e.g., at a concentration of at least about 0.5 ng/mL). In some embodiments, the stimulating agents include IL-2, IL-15 and/or IL-7. In some aspects, the IL-2 concentration is at least about 10 units/mL. In some embodiments, the stimulating agents include IL-2, IL-7 and/or IL-15, for example, at concentrations of, of at least, or of about 10 units/mL, 20 units/mL, 50 units/mL, 100 units/mL, 250 units/mL, 500 units/mL, 600 units/mL, 700 units/mL, 800 units/mL, 900 units/mL, or 1,000 units/mL.

In some aspects, incubation is carried out in accordance with techniques such as those described in U.S. Pat. No. 6,040,177 to Riddell et al., Klebanoff et al. (2012) J Immunother. 35 (9): 651-660, Terakuraet al. (2012) Blood. 1:72-82, and/or Wang et al. (2012) J Immunother. 35 (9): 689-701. In some aspects, incubation is carried out using a system, device, apparatus, and/or method as described in International Patent Application Publication Number WO2016/073602 or US 2016/0122782 the contents of which are incorporated by reference in their entirety. In some embodiments, the incubation and/or culturing is carried out according to methods described in International Patent Application Publication Number WO 2015/164675, the contents of which are incorporated by reference in their entirety. In some embodiments, at least a portion of the incubation performed in a centrifugal chamber includes mixing with a reagent or reagents to induce stimulation and/or activation. In some embodiments, cells, such as selected cells, are mixed with a stimulating condition or stimulatory agent in the centrifugal chamber. In some aspects of such processes, a volume of cells is mixed with an amount of one or more stimulating conditions or agents that is far less than is normally employed when performing similar stimulations in a cell culture plate or other system.

In some embodiments, the stimulating agent is added to cells in the cavity of the chamber in an amount that is substantially less than (e.g. is no more than 5%, 10%, 20%, 30%, 40%, 50%, 60%, 70% or 80% of the amount) as compared to the amount of the stimulating agent that is typically used or would be necessary to achieve about the same or similar efficiency of selection of the same number of cells or the same volume of cells when selection is performed without mixing in a centrifugal chamber, e.g. in a tube or bag with periodic shaking or rotation. In some embodiments, the incubation is performed with the addition of an incubation buffer to the cells and stimulating agent to achieve a target volume with incubation of the reagent of, for example, 10 mL to 200 mL, such as at least or about at least or about or 10 mL, 20 mL, 30 mL, 40 mL, 50 mL, 60 mL, 70 mL, 80 mL, 90 mL, 100 mL, 150 mL, or 200 mL. In some embodiments, the incubation buffer and stimulating agent are pre-mixed before addition to the cells. In some embodiments, the incubation buffer and stimulating agent are separately added to the cells. In some embodiments, the stimulating incubation is carried out with periodic gentle mixing condition, which can aid in promoting energetically favored interactions and thereby permit the use of less overall stimulating agent while achieving stimulating and activation of cells.

In some embodiments, the incubation generally is carried out under mixing conditions, such as in the presence of spinning, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, the total duration of the incubation, e.g. with the stimulating agent, is between or between about 1 hour and 96 hours, 1 hour and 72 hours, 1 hour and 48 hours, 4 hours and 36 hours, 8 hours and 30 hours or 12 hours and 24 hours, such as at least or about at least 6 hours, 12 hours, 18 hours, 24 hours, 36 hours or 72 hours, each inclusive. In some embodiments, the further incubation is for a time between or about between 1 hour and 48 hours, 4 hours and 36 hours, 8 hours and 30 hours or 12 hours and 24 hours, each inclusive.

In some embodiments, the processing steps include introduction of a nucleic acid molecule encoding a recombinant protein. Among such recombinant proteins are recombinant receptors, such as any described in Section V. Introduction of the nucleic acid molecules encoding the recombinant protein, such as recombinant receptor, in the cell may be carried out using any of a number of known vectors. Such vectors include viral and non-viral systems, including lentiviral and gammaretroviral systems, as well as transposon-based systems such as PiggyBac or Sleeping Beauty-based gene transfer systems. Exemplary methods include those for transfer of nucleic acids encoding the receptors, including via viral, e.g., retroviral or lentiviral, transduction, transposons, and electroporation.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some embodiments, recombinant nucleic acids are transferred into cells using recombinant infectious virus particles, such as, e.g., vectors derived from simian virus 40 (SV40), adenoviruses, adeno-associated virus (AAV), and human immunodeficiency virus (HIV). In some embodiments, recombinant nucleic acids are transferred into T cells using recombinant lentiviral vectors or retroviral vectors, such as gamma-retroviral vectors.

Methods of viral transduction, e.g., lentiviral transduction are known. Exemplary methods are described in, e.g., Wang et al. (2012) J. Immunother. 35 (9): 689-701; Cooper et al. (2003) Blood. 101:1637-1644; Verhoeyen et al. (2009) Methods Mol Biol. 506:97-114; and Cavalieri et al. (2003) Blood. 102 (2): 497-505.

In some embodiments, the introducing is carried out by contacting one or more cells of a composition with a nucleic acid molecule encoding the recombinant protein, e.g. recombinant receptor. In some embodiments, the contacting can be effected with centrifugation, such as spinoculation (e.g. centrifugal inoculation). Such methods include any of those as described in International Publication Number WO2016/073602. Exemplary centrifugal chambers include those produced and sold by Biosafe SA, including those for use with the Sepax® and Sepax® 2 system, including an A-200/F and A-200 centrifugal chambers and various kits for use with such systems. Exemplary chambers, systems, and processing instrumentation and cabinets are described, for example, in U.S. Pat. Nos. 6,123,655, 6,733,433 and Published U.S. Patent Application, Publication No.: US 2008/0171951, and published international patent application, publication no. WO 00/38762, the contents of each of which are incorporated herein by reference in their entirety. Exemplary kits for use with such systems include, but are not limited to, single-use kits sold by BioSafe SA under product names CS-430.1, CS-490.1, CS-600.1 or CS-900.2.

In some embodiments, the system is included with and/or placed into association with other instrumentation, including instrumentation to operate, automate, control and/or monitor aspects of the transduction step and one or more various other processing steps performed in the system, e.g. one or more processing steps that can be carried out with or in connection with the centrifugal chamber system as described herein or in International Publication Number WO2016/073602. This instrumentation in some embodiments is contained within a cabinet. In some embodiments, the instrumentation includes a cabinet, which includes a housing containing control circuitry, a centrifuge, a cover, motors, pumps, sensors, displays, and a user interface. An exemplary device is described in U.S. Pat. Nos. 6,123,655, 6,733,433 and US 2008/0171951.

In some embodiments, the system comprises a series of containers, e.g., bags, tubing, stopcocks, clamps, connectors, and a centrifuge chamber. In some embodiments, the containers, such as bags, include one or more containers, such as bags, containing the cells to be transduced and the viral vector particles, in the same container or separate containers, such as the same bag or separate bags. In some embodiments, the system further includes one or more containers, such as bags, containing medium, such as diluent and/or wash solution, which is pulled into the chamber and/or other components to dilute, resuspend, and/or wash components and/or compositions during the methods. The containers can be connected at one or more positions in the system, such as at a position corresponding to an input line, diluent line, wash line, waste line and/or output line.

In some embodiments, the chamber is associated with a centrifuge, which is capable of effecting rotation of the chamber, such as around its axis of rotation. Rotation may occur before, during, and/or after the incubation in connection with transduction of the cells and/or in one or more of the other processing steps. Thus, in some embodiments, one or more of the various processing steps is carried out under rotation, e.g., at a particular force. The chamber is typically capable of vertical or generally vertical rotation, such that the chamber sits vertically during centrifugation and the side wall and axis are vertical or generally vertical, with the end wall(s) horizontal or generally horizontal.

In some embodiments, the composition containing cells, viral particles and reagent can be rotated, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm). In some embodiments, the rotation is carried at a force, e.g., a relative centrifugal force, of from or from about 100 g to 3200 g (e.g. at or about or at least at or about 100 g, 200 g, 300 g, 400 g, 500 g, 1000 g, 1500 g, 2000 g, 2500 g, 3000 g or 3200 g), as measured for example at an internal or external wall of the chamber or cavity. The term "relative centrifugal force" or RCF is generally understood to be the effective force imparted on an object or substance (such as a cell, sample, or pellet and/or a point in the chamber or other container being rotated), relative to the earth's gravitational force, at a particular point in space as compared to the axis of rotation. The value may be determined using well-known formulas, taking into account the gravitational force, rotation speed and the radius of rotation (distance from the axis of rotation and the object, substance, or particle at which RCF is being measured).

In some embodiments, during at least a part of the genetic engineering, e.g. transduction, and/or subsequent to the genetic engineering the cells are transferred to a container such as a bag for culture of the genetically engineered cells, such as for cultivation or expansion of the cells, as described above. In some embodiments, the container for cultivation or expansion of the cells is a bioreactor bag, such as a perfusion bag.

In some embodiments, the provided methods include one or more steps for cultivating engineered cells, e.g., cultivating cells under conditions that promote proliferation and/or expansion. In some embodiments, engineered cells are cultivated under conditions that promote proliferation and/or expansion subsequent to a step of genetically engineering, e.g., introducing a recombinant polypeptide to the cells by transduction or transfection. In particular embodiments, the cells are cultivated after the cells have been incubated under stimulating conditions and transduced or transfected with a recombinant polynucleotide, e.g., a polynucleotide encoding a recombinant receptor. In some embodiments, the cultivation produces one or more cultivated compositions of enriched T cells.

In some aspects, the culture media is an adapted culture medium that supports that growth, cultivation, expansion or proliferation of the cells, such as T cells. In some aspects, the medium can be a liquid containing a mixture of salts, amino acids, vitamins, sugars or any combination thereof. In some embodiments, the culture media further contains one or more stimulating conditions or agents, such as to stimulate the cultivation, expansion or proliferation of cells during the incubation. In some embodiments, the stimulating condition is or includes one or more cytokine selected from IL-2, IL-7 or IL-15. In some embodiments, the cytokine is a recombinant cytokine. In some embodiments, the concentration of the one or more cytokine in the culture media during the culturing or incubation, independently, is from or from about 1 IU/mL to 1500 IU/mL, such as from or from about 1 IU/mL to 100 IU/mL, 2 IU/mL to 50 IU/mL, 5 IU/mL to 10 IU/mL, 10 IU/mL to 500 IU/mL, 50 IU/mL to 250 IU/mL or 100 IU/mL to 200 IU/mL, 50 IU/mL to 1500 IU/mL, 100 IU/mL to 1000 IU/mL or 200 IU/mL to 600 IU/mL. In some embodiments, the concentration of the one or more cytokine, independently, is at least or at least about 1 IU/mL, 5 IU/mL, 10 IU/mL, 50 IU/mL, 100 IU/mL, 200 IU/mL, 500 IU/mL, 1000 IU/mL or 1500 IU/mL.

In some aspects, the cells are incubated for at least a portion of time after transfer of the engineered cells and culture media. In some embodiments, the stimulating conditions generally include a temperature suitable for the growth of primary immune cells, such as human T lymphocytes, for example, at least about 25 degrees Celsius, generally at least about 30 degrees, and generally at or about 37 degrees Celsius. In some embodiments, the cells are incubated at a temperature of 25 to 38 degrees Celsius, such as 30 to 37 degrees Celsius, for example at or about 37 degrees Celsius±2 degrees Celsius. In some embodiments, the incubation is carried out for a time period until the culture, e.g. cultivation or expansion, results in a desired or threshold density, number or dose of cells. In some embodiments, the incubation is greater than or greater than about or is for about or 24 hours, 48 hours, 72 hours, 96 hours, 5 days, 6 days, 7 days, 8 days, 9 days or more.

In some embodiments, the cells are incubated under conditions to maintain a target amount of carbon dioxide in the cell culture. In some aspects, this ensures optimal cultivation, expansion and proliferation of the cells during the growth. In some aspects, the amount of carbon dioxide ($CO_2$) is between 10% and 0% (v/v) of said gas, such as between 8% and 2% (v/v) of said gas, for example an amount of or about 5% (v/v) $CO_2$.

In some embodiments, cells are incubated using containers, e.g., bags, which are used in connection with a bioreactor. In some cases, the bioreactor can be subject to motioning or rocking, which, in some aspects, can increase oxygen transfer. Motioning the bioreactor may include, but is not limited to rotating along a horizontal axis, rotating along a vertical axis, a rocking motion along a tilted or inclined horizontal axis of the bioreactor or any combination thereof. In some embodiments, at least a portion of the incubation is carried out with rocking. The rocking speed and rocking angle may be adjusted to achieve a desired agitation. In some embodiments the rock angle is or is about 20°, 19°, 18°, 17°, 16°, 15°, 14°, 13°, 12°, 11°, 10°, 9°, 8°, 7°, 6°, 5°, 4°, 3°, 2° or 1°. In certain embodiments, the rock angle is between 6-16°, inclusive. In other embodiments, the rock angle is between 7-16°. In other embodiments, the rock angle is between 8-12°, inclusive. In some embodiments, the rock rate is 1, 2, 3, 4, 5, 6, 7, 8, 9, 10, 11, 1 12, 13, 14 15, 16, 17, 18, 19, 20, 21, 22, 23, 24, 25, 26, 27, 28, 29, 30, 31, 32, 33, 34, 35, 36, 37, 38, 39, 40 rpm. In some embodiments, the rock rate is between 4 and 12 rpm, such as between 4 and 6 rpm, inclusive. At least a portion of the cell culture expansion is performed with a rocking motion, such as at an angle of between 5° and 10°, inclusive, such as 6°, at a constant rocking speed, such as a speed of between 5 and 15 RPM, inclusive, such as 6 RMP or 10 RPM. The CD4+ and CD8+ cells are each separately expanded until they each reach a threshold amount or cell density.

In some embodiments, at least a portion of the incubation is carried out under static conditions. In some embodiments, at least a portion of the incubation is carried out with perfusion, such as to perfuse out spent media and perfuse in fresh media during the culture. In some embodiments, the method includes a step of perfusing fresh culture medium into the cell culture, such as through a feed port. In some embodiments, the culture media added during perfusion contains the one or more stimulating agents, e.g. one or more recombinant cytokine, such as IL-2, IL-7 and/or IL-15. In some embodiments, the culture media added during perfusion is the same culture media used during a static incubation.

In some embodiments, subsequent to the incubation, the container, e.g., bag, is re-connected to a system for carrying out the one or more other processing steps of for manufacturing, generating or producing the cell therapy, such as is re-connected to the system containing the centrifugal chamber. In some aspects, cultured cells are transferred from the bag to the internal cavity of the chamber for formulation of the cultured cells.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

In some embodiments, the engineered cells are collected, e.g., harvested, for formulation after the cells have been transduced, transfected, cultivated, and/or expanded. In some embodiments, the cells are harvested within an amount of time, e.g., at or within 2 days, 3 days, 4 days, 5 days, 6 days, 7 days, 8 days, 9 days, 10 days, 11 days, 12 days, 13 days, or 14 days, after the start and/or initiation, or the end and/or completion of a processing step, such as the isolation, selection, incubation, stimulation, activation, transduction, transfection, cultivation, and/or expansion steps. In certain embodiments, the engineered cells are collected after cultivation, e.g., at or within 1 day, 2 days, 3 days, 4 days, 5 days, 6 days, 7 days, 8 days, 9 days, or 10 days of cultivation and/or after the engineered cells and/or cell compositions including the engineered cells have been expanded to a threshold cell density, cell number, and/or expansion. In some embodiments, the harvested cells are formulated by any method described herein, such as for example as described in Section VI.

1. Stimulatory Reagents

In some embodiments, the cells can be incubated and/or contacted with a stimulatory reagent that is capable of activating and/or expanding T cells. In certain embodiments, the stimulatory reagent comprises a particle, e.g., a bead, that is conjugated or linked to one or more agents, e.g., biomolecules, that are capable of activating and/or expanding cells, e.g., T cells. In some embodiments, the one or more agents are bound to a bead. In some embodiments, the bead is biocompatible, i.e., composed of a material that is suitable for biological use. In some embodiments, the beads are non-toxic to cultured cells, e.g., cultured T cells. In some embodiments, the beads may be any particles which are capable of attaching agents in a manner that permits an interaction between the agent and a cell.

In some embodiments, a stimulatory reagent comprises one or more agents that are capable of activating and/or expanding cells, e.g., T cells, that are bound to or otherwise attached to a bead, for example to the surface of the bead. In certain embodiments, the bead is a non-cell particle. In particular embodiments, the bead may include a colloidal particle, a microsphere, nanoparticle, a magnetic bead, or the like. In some embodiments the beads are agarose beads. In certain embodiments, the beads are sepharose beads.

In particular embodiments, the stimulatory reagent comprises beads that are monodisperse. In certain embodiments, beads that are monodisperse comprise size dispersions having a diameter standard deviation of less than 5% from each other.

In some embodiments, the bead contains one or more agents, such as an agent that is coupled, conjugated, or linked (directly or indirectly) to the surface of the bead. In some embodiments, an agent as contemplated herein can include, but is not limited to, RNA, DNA, proteins (e.g., enzymes), antigens, polyclonal antibodies, monoclonal antibodies, antibody fragments, carbohydrates, lipids lectins, or any other biomolecule with an affinity for a desired target. In some embodiments, the desired target is a T cell receptor and/or a component of a T cell receptor. In certain embodiments, the desired target is CD3. In certain embodiment, the desired target is a costimulatory molecule, e.g., CD28. The one or more agents may be attached directly or indirectly to the bead by a variety of methods known and available in the art. The attachment may be covalent, noncovalent, electrostatic, or hydrophobic and may be accomplished by a variety of attachment means, including for example, a chemical means, a mechanical means, or an enzymatic means. In some embodiments, a biomolecule (e.g., a biotinylated anti-CD3 antibody) may be attached indirectly to the bead via another biomolecule (e.g., anti-biotin antibody) that is directly attached to the bead.

In some embodiments, one or more of the agents attached to the bead is an antibody. The antibody can include a polyclonal antibody, monoclonal antibody (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, $F(ab')_2$, and Fv). In some embodiments, the stimulatory reagent is an antibody fragment (including antigen-binding fragment), e.g., a Fab, Fab'-SH, Fv, scFv, or $(Fab')_2$ fragment. It will be appreciated that constant regions of any isotype can be used for the antibodies contemplated herein, including IgG, IgM, IgA, IgD, and IgE constant regions, and that such constant regions can be obtained from any human or animal species (e.g., murine species). In some embodiments, the agent is an antibody that binds to and/or recognizes one or more components of a T cell receptor. In particular embodiments, the agent is an anti-CD3 antibody. In certain embodiments, the agent is an antibody that binds to and/or recognizes a co-receptor. In some embodiments, the stimulatory reagent comprises an anti-CD28 antibody.

In some embodiments, the bead has a diameter of greater than about 0.001 μm, greater than about 0.01 μm, greater than about 0.1 μm, greater than about 1.0 μm, greater than about 10 μm, greater than about 50 μm, greater than about 100 μm or greater than about 1000 μm and no more than about 1500 μm. In some embodiments, the bead has a diameter of about 1.0 μm to about 500 μm, about 1.0 μm to about 150 μm, about 1.0 μm to about 30 μm, about 1.0 μm to about 10 μm, about 1.0 μm to about 5.0 μm, about 2.0 μm to about 5.0 μm, or about 3.0 μm to about 5.0 μm. In some embodiments, the bead has a diameter of about 3 μm to about 5 μm. In some embodiments, the bead has a diameter of at least or at least about or about 0.001 μm, 0.01 μm, 0.1 μm, 0.5 μm, 1.0 μm, 1.5 μm, 2.0 μm, 2.5 μm, 3.0 μm, 3.5 μm, 4.0 μm, 4.5 μm, 5.0 μm, 5.5 μm, 6.0 μm, 6.5 μm, 7.0 μm, 7.5 μm, 8.0 μm, 8.5 μm, 9.0 μm, 9.5 μm, 10 μm, 12 μm, 14 μm, 16 μm, 18 μm or 20 μm. In certain embodiments, the bead has a diameter of or about 4.5 μm. In certain embodiments, the bead has a diameter of or about 2.8 μm.

In some embodiments, the beads have a density of greater than 0.001 $g/cm^3$, greater than 0.01 $g/cm^3$, greater than 0.05 $g/cm^3$, greater than 0.1 $g/cm^3$, greater than 0.5 $g/cm^3$, greater than 0.6 $g/cm^3$, greater than 0.7 $g/cm^3$, greater than 0.8 $g/cm^3$, greater than 0.9 $g/cm^3$, greater than 1 $g/cm^3$, greater than 1.1 $g/cm^3$, greater than 1.2 $g/cm^3$, greater than 1.3 $g/cm^3$, greater than 1.4 $g/cm^3$, greater than 1.5 $g/cm^3$, greater than 2 $g/cm^3$, greater than 3 $g/cm^3$, greater than 4 $g/cm^3$, or greater than 5 $g/cm^3$. In some embodiments, the beads have a density of between about 0.001 $g/cm^3$ and about 100 $g/cm^3$, about 0.01 $g/cm^3$ and about 50 $g/cm^3$, about 0.1 $g/cm^3$ and about 10 $g/cm^3$, about 0.1 $g/cm^3$ and about 0.5 $g/cm^3$, about 0.5 $g/cm^3$ and about 1 $g/cm^3$, about 0.5 $g/cm^3$ and about 1.5 $g/cm^3$, about 1 $g/cm^3$ and about 1.5 $g/cm^3$, about 1 $g/cm^3$ and about 2 $g/cm^3$, or about 1 $g/cm^3$ and about 5 $g/cm^3$, each inclusive. In some embodiments, the beads have a density of about 0.5 $g/cm^3$, about 0.5 $g/cm^3$, about 0.6 $g/cm^3$, about 0.7 $g/cm^3$, about 0.8 $g/cm^3$, about 0.9 $g/cm^3$, about 1.0 $g/cm^3$, about 1.1 $g/cm^3$, about 1.2 $g/cm^3$, about 1.3 $g/cm^3$, about 1.4 $g/cm^3$, about 1.5 $g/cm^3$, about 1.6 $g/cm^3$, about 1.7 $g/cm^3$, about 1.8 $g/cm^3$, about 1.9 $g/cm^3$, or about 2.0 $g/cm^3$. In certain embodiments, the beads have a density of about 1.6 $g/cm^3$. In particular embodiments, the beads or particles have a density of about 1.5 $g/cm^3$. In certain embodiments, the particles have a density of about 1.3 $g/cm^3$.

In certain embodiments, a plurality of the beads has a uniform density. In certain embodiments, a uniform density comprises a density standard deviation of less than 10%, less than 5%, or less than 1% of the mean bead density.

In some embodiments, the beads have a surface area of between about 0.001 $m^2$ per each gram of particles ($m^2/g$) and about 1,000 $m^2/g$, about 0.010 $m^2/g$ and about 100 $m^2/g$, about 0.1 $m^2/g$ and about 10 $m^2/g$, about 0.1 $m^2/g$ and about 1 $m^2/g$, about 1 $m^2/g$ and about 10 $m^2/g$, about 10 $m^2/g$ and about 100 $m^2/g$, about 0.5 $m^2/g$ and about 20 $m^2/g$, about 0.5 $m^2/g$ and about 5 $m^2/g$, or about 1 $m^2/g$ and about 4 $m^2/g$, each inclusive. In some embodiments, the particles or beads have a surface area from about 1 $m^2/g$ to about 4 $m^2/g$.

In some embodiments, the bead contains at least one material at or near the bead surface that can be coupled, linked, or conjugated to an agent. In some embodiments, the bead is surface functionalized, i.e. comprises functional groups that are capable of forming a covalent bond with a binding molecule, e.g., a polynucleotide or a polypeptide. In particular embodiments, the bead comprises surface-exposed carboxyl, amino, hydroxyl, tosyl, epoxy, and/or chloromethyl groups. In particular embodiments, the beads comprise surface exposed agarose and/or sepharose. In certain embodiments, the bead surface comprises attached stimulatory reagents that can bind or attach binding molecules. In particular embodiments, the biomolecules are polypeptides. In some embodiments, the beads comprise surface exposed protein A, protein G, or biotin.

In some embodiments, the bead reacts in a magnetic field. In some embodiments, the bead is a magnetic bead. In some embodiments, the magnetic bead is paramagnetic. In particular embodiments, the magnetic bead is superparamagnetic. In certain embodiments, the beads do not display any magnetic properties unless they are exposed to a magnetic field.

In particular embodiments, the bead comprises a magnetic core, a paramagnetic core, or a superparamagnetic core. In some embodiments, the magnetic core contains a metal. In some embodiments, the metal can be, but is not limited to, iron, nickel, copper, cobalt, gadolinium, manganese, tantalum, zinc, zirconium or any combinations thereof. In certain embodiments, the magnetic core comprises metal oxides (e.g., iron oxides), ferrites (e.g., manganese ferrites, cobalt ferrites, nickel ferrites, etc.), hematite and metal alloys (e.g., CoTaZn). In some embodiments, the magnetic core comprises one or more of a ferrite, a metal, a metal alloy, an iron oxide, or chromium dioxide. In some embodiments, the magnetic core comprises elemental iron or a compound thereof. In some embodiments, the magnetic core comprises one or more of magnetite ($Fe_3O_4$), maghemite (γFe2O3), or greigite (Fe3S4). In some embodiments, the inner core comprises an iron oxide (e.g., $Fe_3O_4$).

In certain embodiments, the bead contains a magnetic, paramagnetic, and/or superparamagnetic core that is covered by a surface functionalized coat or coating. In some embodiments, the coat can contain a material that can include, but is not limited to, a polymer, a polysaccharide, a silica, a fatty acid, a protein, a carbon, agarose, sepharose, or a combination thereof. In some embodiments, the polymer can be a polyethylene glycol, poly (lactic-co-glycolic acid), polyglutaraldehyde, polyurethane, polystyrene, or a polyvinyl alcohol. In certain embodiments, the outer coat or coating comprises polystyrene. In particular embodiments, the outer coating is surface functionalized.

In some embodiments, the stimulatory reagent comprises a bead that contains a metal oxide core (e.g., an iron oxide core) and a coat, wherein the metal oxide core comprises at least one polysaccharide (e.g., dextran), and wherein the coat comprises at least one polysaccharide (e.g., amino dextran), at least one polymer (e.g., polyurethane) and silica. In some embodiments the metal oxide core is a colloidal iron oxide core. In certain embodiments, the one or more agents include an antibody or antigen-binding fragment thereof. In particular embodiments, the one or more agents include an anti-CD3 antibody and an anti-CD28 antibody. In some embodiments, the stimulatory reagent comprises an anti-CD3 antibody, anti-CD28 antibody, and an anti-biotin antibody. In some embodiments, the stimulatory reagent comprises an anti-biotin antibody. In some embodiments, the bead has a diameter of about 3 μm to about 10 μm. In some embodiments, the bead has a diameter of about 3 μm to about 5 μm. In certain embodiments, the bead has a diameter of about 3.5 μm.

In some embodiments, the stimulatory reagent comprises one or more agents that are attached to a bead comprising a metal oxide core (e.g., an iron oxide inner core) and a coat (e.g., a protective coat), wherein the coat comprises polystyrene. In certain embodiments, the beads are monodisperse, superparamagnetic beads comprising a superparamagnetic iron core, e.g., a core comprising magnetite ($Fe_3O_4$) and/or maghemite ($\gamma Fe_2O_3$) c and a polystyrene coat or coating. In some embodiments, the bead is non-porous. In some embodiments, the beads contain a functionalized surface to which the one or more agents are attached. In certain embodiments, the one or more agents are covalently bound to the beads at the surface. In some embodiments, the one or more agents include an antibody or antigen-binding fragment thereof. In some embodiments, the one or more agents include an anti-CD3 antibody and an anti-CD28 antibody. In certain embodiments, the beads have a density of about 1.5 $g/cm^3$ and a surface area of about 1 $m^2/g$ to about 4 $m^2/g$. In particular embodiments; the beads are monodisperse superparamagnetic beads that have a diameter of about 4.5 μm and a density of about 1.5 $g/cm^3$. In some embodiments, the beads the beads are monodisperse superparamagnetic beads that have a mean diameter of about 2.8 μm and a density of about 1.3 $g/cm^3$.

E. Vectors and Methods for Genetic Engineering

Polynucleotides (nucleic acid molecules) encoding the recombinant receptors can be included in vectors for genetically engineering cells to express such receptors. In some embodiments, the vectors or constructs contain one or more promoters operatively linked to the nucleotide encoding the polypeptide or receptor to drive expression thereof. In some embodiments, the promoter is operatively linked to one or more than one nucleic acid molecule.

In some cases, the vector is a viral vector, such as a retroviral vector, e.g., a lentiviral vector or a gammaretroviral vector. In some embodiments, the polynucleotide, such as a vector, encoding the recombinant receptor is introduced into a composition containing cultured cells, such as by retroviral transduction, transfection, or transformation.

Various methods for the introduction of genetically engineered components, e.g., recombinant receptors, e.g., CARs or TCRs, are well known and may be used with the provided methods and compositions. Exemplary methods include those for transfer of nucleic acids encoding the polypeptides or receptors, including via viral vectors, e.g., retroviral or lentiviral, non-viral vectors or transposons, e.g. Sleeping Beauty transposon system. Methods of gene transfer can include transduction, electroporation or other method that results into gene transfer into the cell.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, it may be desired to safeguard against the potential that overexpression of a stimulatory factor (for example, a lymphokine or a cytokine) could potentially result in an unwanted outcome or lower efficacy in a subject, such as a factor associated with toxicity in a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II: 223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 April 3. doi: 10.1038/gt. 2014.25; Carlens et al. (2000) Exp Hematol 28 (10): 1137-46; Alonso-Camino et al. (2013) Mol Ther Nucl Acids 2, e93; Park et al., Trends Biotechnol. 2011 Nov. 29 (11): 550-557.

In some embodiments, the polynucleotide encoding the recombinant receptor and/or additional polypeptide is contained in a vector or can be cloned into one or more vector(s). In some embodiments, the one or more vector(s) can be used to transform or transfect a host cell, e.g., a cell for engineering. Exemplary vectors include vectors designed for introduction, propagation and expansion or for expression or both, such as plasmids and viral vectors. In some aspects, the vector is an expression vector, e.g., a recombinant expression vector. In some embodiments, the recombinant expression vectors can be prepared using standard recombinant DNA techniques.

In some embodiments, the vector can be a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-C1, pMAM and pMAMneo (Clontech).

In some embodiments, the vector is a viral vector, such as a retroviral vector. In some embodiments, the polynucleotide encoding the recombinant receptor and/or additional polypeptide(s) are introduced into the cell via retroviral or lentiviral vectors, or via transposons (see, e.g., Baum et al. (2006) Molecular Therapy: The Journal of the American Society of Gene Therapy. 13:1050-1063; Frecha et al. (2010) Molecular Therapy 18:1748-1757; and Hackett et al. (2010) Molecular Therapy 18:674-683).

In some embodiments, transcription units can be engineered as a bicistronic unit containing an IRES, which allows coexpression of gene products (e.g. encoding the recombinant receptor and the additional polypeptide) by a message from a single promoter. Alternatively, in some cases, a single promoter may direct expression of an RNA that contains, in a single open reading frame (ORF), two or three genes (e.g. encoding the marker and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as a T2A, can cause the ribosome to skip (ribosome skipping)

synthesis of a peptide bond at the C-terminus of a 2A element, leading to separation between the end of the 2A sequence and the next peptide downstream (see, e.g., de Felipe, Genetic Vaccines and Ther. 2:13 (2004) and de Felipe et al. Traffic 5:616-626 (2004)). Various 2A elements are known. Examples of 2A sequences that can be used in the methods and system disclosed herein, without limitation, 2A sequences from the foot-and-mouth disease virus (F2A, e.g., SEQ ID NO: 21), equine rhinitis A virus (E2A, e.g., SEQ ID NO: 20), Thosea asigna virus (T2A, e.g., SEQ ID NO: 6 or 17), and porcine teschovirus-1 (P2A, e.g., SEQ ID NO: 18 or 19) as described in U.S. Patent Pub. No. 20070116690.

In some embodiments, the recombinant receptor, e.g., a CAR, is under control of a promoter. In some embodiments, the vector includes a promoter. In some embodiments, the promoter is or comprises a constitutive promoter. Exemplary constitutive promoters include, e.g., simian virus 40 early promoter (SV40), cytomegalovirus immediate-early promoter (CMV), human Ubiquitin C promoter (UBC), human elongation factor 1α promoter (EF1α), mouse phosphoglycerate kinase 1 promoter (PGK), and chicken β-Actin promoter coupled with CMV early enhancer (CAGG). In some embodiments, the constitutive promoter is a synthetic or modified promoter. In some embodiments, the promoter is or comprises an MND promoter, a synthetic promoter that contains the U3 region of a modified MoMuLV LTR with myeloproliferative sarcoma virus enhancer (see Challita et al. (1995) J. Virol. 69 (2): 748-755). In some embodiments, the promoter is a tissue-specific promoter. In another embodiment, the promoter is a viral promoter. In another embodiment, the promoter is a non-viral promoter. In some embodiments, exemplary promoters can include, but are not limited to, human elongation factor 1 alpha (EF1α) promoter or a modified form thereof or the MND promoter.

In some embodiments, the promoter is a regulated promoter (e.g., inducible promoter). In some embodiments, the promoter is an inducible promoter or a repressible promoter. In some embodiments, the promoter comprises a Lac operator sequence, a tetracycline operator sequence, a galactose operator sequence or a doxycycline operator sequence, or is an analog thereof or is capable of being bound by or recognized by a Lac repressor or a tetracycline repressor, or an analog thereof. In some embodiments, the polynucleotide does not include a regulatory element, e.g. promoter.

In some cases, the nucleic acid sequence encoding the recombinant receptor contains a signal sequence that encodes a signal peptide. In some aspects, the signal sequence may encode a signal peptide derived from a native polypeptide. In other aspects, the signal sequence may encode a heterologous or non-native signal peptide, such as the exemplary signal peptide of the GMCSFR alpha chain set forth in SEQ ID NO:25 and encoded by the nucleotide sequence set forth in SEQ ID NO:24. In some cases, the nucleic acid sequence encoding the recombinant receptor, e.g., chimeric antigen receptor (CAR) contains a signal sequence that encodes a signal peptide. Non-limiting exemplary signal peptides include, for example, the GMCSFR alpha chain signal peptide set forth in SEQ ID NO: 25 and encoded by the nucleotide sequence set forth in SEQ ID NO:24, or the CD8 alpha signal peptide set forth in SEQ ID NO:26.

In some embodiments, the polynucleotide contains a nucleic acid sequence encoding one or more additional polypeptides, e.g., one or more marker(s) and/or one or more effector molecules. In some embodiments, the one or more marker(s) includes a transduction marker, a surrogate marker and/or a selection marker. Among additional nucleic acid sequences introduced, e.g., encoding for one or more additional polypeptide(s), include nucleic acid sequences that can improve the efficacy of therapy, such as by promoting viability and/or function of transferred cells; nucleic acid sequences to provide a genetic marker for selection and/or evaluation of the cells, such as to assess in vivo survival or localization; nucleic acid sequences to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also WO 1992008796 and WO 1994028143 describing the use of bifunctional selectable fusion genes derived from fusing a dominant positive selectable marker with a negative selectable marker, and U.S. Pat. No. 6,040,177.

In some embodiments, a single promoter may direct expression of an RNA that contains, in a single open reading frame (ORF), two or three genes (e.g. encoding the molecule involved in modulating a metabolic pathway and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known. Examples of 2A sequences that can be used in the methods and nucleic acids disclosed herein, without limitation, 2A sequences from the foot-and-mouth disease virus (F2A, e.g., SEQ ID NO: 22), equine rhinitis A virus (E2A, e.g., SEQ ID NO: 21), Thosea asigna virus (T2A, e.g., SEQ ID NO: 6 or 18), and porcine teschovirus-1 (P2A, e.g., SEQ ID NO: 19 or 20) as described in U.S. Patent Publication No. 20070116690.

In some embodiments, the vector contains a nucleic acid sequence encoding one or more marker(s). In some embodiments, the one or more marker(s) is a transduction marker, surrogate marker and/or a selection marker.

In some embodiments, the marker is a transduction marker or a surrogate marker. A transduction marker or a surrogate marker can be used to detect cells that have been introduced with the polynucleotide, e.g., a polynucleotide encoding a recombinant receptor. In some embodiments, the transduction marker can indicate or confirm modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same polynucleotide that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A, a P2A, an E2A or an F2A. Extrinsic marker genes may in some cases be utilized in connection with engineered cell to permit detection or selection of cells and, in some cases, also to promote cell suicide.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing. Exemplary truncated cell surface polypeptides including truncated forms of growth factors or other receptors such as a truncated human epidermal growth factor receptor 2 (tHER2), a truncated epidermal growth factor receptor (tEGFR, exemplary tEGFR sequence set forth in SEQ ID NO:7 or 23) or a prostate-specific membrane antigen (PSMA) or modified form thereof. tEGFR may contain an epitope recognized by the antibody cetuximab (Erbitux®) or other therapeutic anti-EGFR antibody or binding molecule, which can be used to identify or select cells that have been engineered with the tEGFR construct and an encoded exogenous protein, and/or to eliminate or separate cells expressing the encoded exogenous protein. See U.S. Pat. No. 8,802,374 and Liu et al., Nature Biotech. 2016 April; 34 (4): 430-434). In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR).

In some embodiments, the marker is or comprises a fluorescent protein, such as green fluorescent protein (GFP), enhanced green fluorescent protein (EGFP), such as super-fold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35 (9): 689-701; Cooper et al. (2003) *Blood.* 101: 1637-1644; Verhoeyen et al. (2009) *Methods Mol Biol.* 506:97-114; and Cavalieri et al. (2003) Blood. 102 (2): 497-505. In some embodiments, the polynucleotide encoding the recombinant receptor and/or one or more additional polypeptide(s) is introduced into a composition containing cultured cells, such as by retroviral transduction, transfection, or transformation.

In some embodiments, recombinant nucleic acids are transferred into T cells via electroporation (see, e.g., Chicaybam et al, (2013) *PLoS ONE* 8 (3): e60298 and Van Tedeloo et al. (2000) *Gene Therapy* 7 (16): 1431-1437). In some embodiments, recombinant nucleic acids are transferred into T cells via transposition (see, e.g., Manuri et al. (2010) Hum Gene Ther 21 (4): 427-437; Sharma et al. (2013) *Molec Ther Nucl Acids* 2, e74; and Huang et al. (2009) *Methods Mol Biol* 506:115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346:776-777 (1990)); and strontium phosphate DNA co-precipitation (Brash et al., Mol. Cell Biol., 7:2031-2034 (1987)). In some aspects, a washing step is performed in a centrifugal chamber, for example those produced and sold by Biosafe SA, including those for use with the Sepax® and Sepax® 2 system, including an A-200/F and A-200 centrifugal chambers according to the manufacturer's instructions.

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion, e.g. with a T cell receptor (TCR), or a chimeric antigen receptor (CAR). This transfection for the introduction of the gene of the desired polypeptide or receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65:333-347 (2014).

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. In some embodiments, one or more of the incubation steps may be carried out using a rocking bioreactor, such as the WAVE™ Bioreactor (GE Healthcare) or the BIOSTAT® RM (Sartorius). In some embodiments, one or more of the incubation steps may be carried out using a static bioreactor or incubation chamber. In specific embodiments, an anti-shear agent, for example a poloxamer, may be added to the composition if using a rocking bioreactor for one or more incubation steps.

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some aspects, the cells are incubated in the presence of one or more cytokines and in some embodiments a cytokine cocktail can be employed, for example as described in International Patent Application Publication Number WO2015157384. In some embodiments, the cells are incubated with one or more cytokines and/or a cytokine cocktail prior to, concurrently with, or subsequent to transduction.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/mL). In some embodiments, the stimulating agents include IL-2, and/or IL-15, for example, an IL-2 concentration of at least about 10 units/mL. In certain embodiments, the simulating conditions include incubation with any stimulatory reagents described herein, such as those described in Section V-D-1.

In some aspects, incubation is carried out in accordance with techniques such as those described in U.S. Pat. No. 6,040,177 to Riddell et al., Klebanoff et al. (2012) J Immunother. 35(9): 651-660, Terakuraet al. (2012) Blood. 1:72-82, and/or Wang et al. (2012) J Immunother. 35(9):689-701. In some aspects, the transduction is carried out using a system, device, apparatus, and/or method as described in International Patent Application Publication Number WO2016/073602 or US 2016/0122782 the contents of which are incorporated by reference in their entirety. In some embodiments, the transduction is carried out according to methods described in International Patent Application Publication Number WO 2015/164675, the contents of which are incorporated by reference in their entirety.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank. In some embodiments, the composition is enclosed in a bag suitable for cryopreservation (for example, CryoMacs® Freezing Bags, Miltenyi Biotec). In some embodiments, the composition is enclosed in a vial suitable for cryopreservation (for example, CellSeal® Vials, Cook Regentec). In some embodiments, the steps and/or reagents for freezing are or include any of the steps and/or reagents for freezing that are described herein.

In particular embodiments, the cells are frozen, e.g., following a washing step, e.g., to remove plasma and platelets. In some embodiments, the cells are frozen prior to, subsequent to, and/or during any of the steps associated with manufacturing and/or generating cells, e.g., CD4+ and/or CD8+ T cells, that express a recombinant receptor, e.g., a CAR. In certain embodiments, such steps may include any steps associated with the generation of engineered cells, including but not limited to, selection and/or isolation of a subset of cells, e.g., CD4+ and/or CD8+ T cells, the stimulation and/or expansion of cells, e.g. T cells or a subset thereof, or transfection or transduction of the cells. In some embodiments, the cells are cells of an apheresis sample collected from a subject, prior to the selection and/or isolation of cells, the stimulation and/or expansion of cells, or transfection or transduction of the cells. In particular embodiments, the cells are frozen after the completion of an engineering process, e.g., after a process involving one or more steps of isolation, selections, stimulation, activation, transduction, transfection, and/or expansion.

In some embodiments, the cells are suspended in a freezing solution, e.g., a cryoprotectant and/or a solution containing a cryoprotectant. Any of a variety of known freezing solutions and parameters in some aspects may be used, including freezing solutions containing cryopreservation or vitrification medium or solutions containing cryoprotectant. Suitable cryoprotectants include, but are not limited to, dimethyl sulfoxide (DMSO), glycerol, a glycol, a propylene glycol, an ethylene glycol, propanediol, polyethylene glycol (PEG), 1,2-propanediol (PROH) or a mixture thereof. In some examples, the cryopreservation solution can contain one or more non-cell permeating cryopreservative, including but not limited to, polyvinyl pyrrolidione, a hydroxyethyl starch, a polysaccharide, a monosaccharide, an alginate, trehalose, raffmose, dextran, human serum albumin, Ficoll, lipoproteins, polyvinyl pyrrolidone, hydroxyethyl starch, autologous plasma or a mixture thereof. In some embodiments, the cells are suspended in a freezing solution with a final concentration of cryoprotectant of between about 1% and about 20%, between about 3% and about 9%, or between about 6% and about 9% by volume, each inclusive. In certain embodiments, the final concentration of cryoprotectant in the freezing solution is about 3%, about 4%, about 5%, about 5.5%, about 6%, about 6.5%, about 7%, about 7.5%, about 8%, about 8.5%, about 9%, about 9.5%, or about 10% by volume.

In some embodiments, the cells, e.g., are frozen at particular cell density, e.g., a known or controlled cell density. In certain embodiments, the cell density during the freezing process may affect cell death and/or cell damage that occurs during and/or due to the freezing process.

For example, in particular embodiments, cell density affects equilibrium, e.g., osmotic equilibrium, with surroundings during the freezing process. In some embodiments, this equilibrium is, includes, and/or results in dehydration. In certain embodiments, the dehydration is or includes cellular dehydration that occurs with contact, combination, and/or incubation with a freezing solution, e.g., DMSO and/or a DMSO containing solution. In particular embodiments, the dehydration is or includes dehydration resulting from the nucleation and enlargement of ice crystals in extracellular space, such as by reducing the effective liquid water concentration exposed to the cells. In some embodiments, the cells are frozen at a cell density that results in slower and/or less rapid dehydration than cells that are frozen at a different, e.g., higher or lower, cell density. In some embodiments, the cells are frozen at a cell density that results in about, at least, or at 5%, 10%, 20%, 25%, 30%, 40%, 50%, 60%, 70%, 80%, 90%, 100%, 125%, 150%, 175%, 200%, 1-fold, 2-fold, 3-fold, 4-fold, 5-fold, 10-fold, 50-fold, or 100-fold slower dehydration that cells frozen at a different cell density, e.g., higher or lower, under the same or similar conditions.

In some embodiments, the cryoprotectant is DMSO. In particular embodiments, the cells are suspended in a freezing solution with a final concentration of DMSO of between about 1% and about 20%, between about 3% and about 9%, or between about 6% and about 9% by volume, each inclusive. In certain embodiments, the final concentration of DMSO in the freezing solution is about 3%, about 4%, about 5%, about 5.5%, about 6%, about 6.5%, about 7%, about 7.5%, about 8%, about 8.5%, about 9%, about 9.5%, or about 10% by volume.

In particular embodiments, the cells are suspended in a freezing solution at a density of between or between about $0.1\times10^6$ cells/mL and about $5{,}000\times10^6$ cells/mL, between or between about $1\times10^6$ cells/mL and about $500\times10^6$ cells/mL, between or between about $5\times10^6$ cells/mL and about $150\times10^6$ cells/mL, between or between about $10\times10^6$ cells/mL and about $70\times10^6$ cells/mL, or between or between about $15\times10^6$ cells/mL and about $60\times10^6$ cells/mL, each inclusive. In some embodiments, the cells are viable cells.

In certain embodiments, the cells are suspended in a freezing solution at a density of between or between about $1\times10^6$ cells/mL and about $1\times10^8$ cells/mL, between about $1\times10^6$ cells/mL and about $2\times10^7$ cells/mL, between about $1\times10^7$ cells/mL and about $5\times10^7$ cells/mL, or between about $1\times10^7$ cells/mL and $5\times10^7$ cells/mL, each inclusive. In certain embodiments, the cells are suspended in the freezing solution at a density of about $1\times10^6$ cells/mL, about $2\times10^6$ cells/mL, about $5\times10^6$ cells/mL, about $1\times10^7$ cells/mL, about $1.5\times10^7$ cells/mL, about $2\times10^7$ cells/mL, about $2.5\times10^7$ cells/mL, about $2.5\times10^7$ cells/mL, about $2.5\times10^7$ cells/mL, about $3\times10^7$ cells/mL, about $3.5\times10^7$ cells/mL, about $4\times10^7$ cells/mL, about $4.5\times10^7$ cells/mL, or about $5\times10^7$ cells/mL, each inclusive. In certain embodiments, the cells are suspended in the freezing solution at a density of between about $1.5\times10^7$ cells/mL and about $6\times10^7$ cells/mL, inclusive. In certain embodiments, the cells are suspended in a freezing solution at a density of at least about $1\times10^7$ cells/mL. In particular embodiments, the cells are suspended in a freezing solution at a density of at least about $1.5\times10^7$ cells/mL. In some embodiments, the cells are viable cells.

In some embodiments, the cells are frozen in a container. In certain embodiments, the container is a freezing container and/or a cryoprotectant container. Containers suitable for cryofreezing include, but are not limited to vials, bags, e.g., plastic bags, and canes. In particular embodiments, cells, e.g., cells of the same cell composition such as a cell composition containing CAR expressing cells, are frozen in 1, 2, 3, 4, 5, 6, 7, 8, 9 10, or more than 10 separate containers. For example, in some embodiments, the cells and/or a composition of cells are suspended in a volume, e.g., such as in a solution, a freezing solution, and/or a cryoprotectant, and that is larger than a volume suitable for a container, and so the volume is placed in two or more containers. In some embodiments, the volume is, is about, or less than 100 mL, 50 mL, 25 mL, 20 mL, 15 mL, 10 mL, 5 mL, or less than 5 mL, and the cells are frozen in two, three, four, five six, seven, eight, nine, ten, or more than ten separate vials. In particular embodiments, the same volume of cells is placed into each vial. In some embodiments, the vials are identical vials, e.g., vials of the same make, model, and/or manufacturing lot. In particular embodiments, the volume is, is about, or greater than 10 mL, 15 mL, 20 mL, 25 mL, 30 mL, 40 mL, 50 mL, 60 mL, 70 mL, 80 mL, 90 mL, 100 mL, 120 mL, 150 mL, 200 mL, or more than 200 mL and the cells are frozen in two, three, four, five six, seven, eight, nine, ten, or more than ten separate bags. In particular embodiments, the same volume of cells is placed into each bag. In some embodiments, the bags are identical bags, e.g., bags of the same make, model, and/or manufacturing lot.

In some embodiments, the container is a vial. In certain embodiments, the container is a vial with a fill volume of, of about, or of at least 0.5 mL, 1 mL, 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 45 mL, or 50 mL. In some embodiments, the vial has a fill volume of between 1 mL and 120 mL, 1 mL and 20 mL, 1 mL and 5 mL, 1 mL and 10 mL, 1 mL and 40 mL, or 20 mL and 40 mL, each inclusive. In some embodiments, the vial is a freezing vial, cryoprotectant vial, and/or a cryovial. Suitable vials are known, and include but are not limited to CellSeal® Vials (Cook Regentec), and vials described in U.S. Patent Nos: U.S. Pat. Nos. 8,936,905, 9,565,854 and 8,709,797, hereby incorporated by reference in their entirety.

In particular embodiments, the container is a bag. In certain embodiments, the container is a bag with a fill volume of, of about, or of at least 0.5 mL, 1 mL, 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 45 mL, or 50 mL. In some embodiments, the bag has a fill volume of between 1 mL and 120 mL, 1 mL and 20 mL, 1 mL and 5 mL, 1 mL and 40 mL, 20 mL and 40 mL, 1 mL and 70 mL, or 50 mL and 70 mL, each inclusive. In some embodiments, the bag is filled with a volume of, of about, or less than 100 mL, 75 mL, 70 mL, 50 mL, 25 mL, 20 mL, or 10 mL. Suitable bags are known, and include but are not limited to CryoMacs® Freezing Bags (Miltenyi Biotec). In certain embodiments, the volume is the volume at room temperature. In some embodiments, the volume is the volume between 37° C. and 4° C., 16° C. and 27° C., inclusive, or at, at about, or at least 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., or 37° C. In some embodiments, the volume is the volume at 25° C.

In some embodiments, cells in a volume of media or solution, e.g., freezing solution, of between 1 mL and 20 mL are frozen in one or more vials, inclusive. In some embodiments, the one or more vials have a fill volume of between 1 mL and 5 mL, inclusive. In certain embodiments, cells in a volume of media or solution, e.g., freezing solution, of between 20 mL and 120 mL, inclusive, are frozen in one or more bags. In particular embodiments, the one or more bags have a fill volume of between 20 mL and 40 mL, inclusive. In some embodiments, cells in a volume of media or solution, e.g., freezing solution, of 120 mL or greater are frozen in one or more bags. In certain embodiments, the one or more bags have a fill volume of between 50 mL and 70 mL, inclusive.

In certain embodiments, the cells are frozen in solution, e.g., freezing solution, that is placed in a container, e.g., a bag or a vial, at a surface area to volume ratio. In particular embodiments, the surface area to volume ratio is from or from about 0.1 $cm^{-1}$ to 100 $cm^{-1}$; 1 $cm^{-1}$ to 50 $cm^{-1}$, 1 $cm^{-1}$ to 20 $cm^{-1}$, 1 $cm^{-1}$ to 10 $cm^{-1}$, 2 $cm^{-1}$ to 10 $cm^{-1}$, 3 $cm^{-1}$ to 7 $cm^{-1}$, or 3 $cm^{-1}$ to 6 $cm^{-1}$, each inclusive. In particular embodiments, the surface area to volume ratio is between or between about 3 $cm^{-1}$ to 6 $cm^{-1}$. In some embodiments, the surface area to volume ratio is, is about, or is at least 3 $cm^{-1}$, 4 $cm^{-1}$, 5 $cm^{-1}$, 6 $cm^{-1}$, or 7 $cm^{-1}$.

In some embodiments, transfer to cryopreservation medium is associated with one or more processing steps that can involve washing of the sample, e.g., engineered cell composition, such as to remove the media and/or replacing the cells in an appropriate cryopreservation buffer or media for subsequent freezing. In certain embodiments, the transfer to the cryopreservation medium is fully automated on a clinical-scale level in a closed and sterile system. In certain embodiments the transfer to the cryopreservation medium carried out using CliniMACS system (Miltenyi Biotec).

In some embodiments, the cells are thawed. In particular embodiments, the cells are thawed rapidly, e.g., rapidly as possible without overheating the cells or exposing cells to high temperatures such as above 37° C. In some embodiments, rapid thawing reduces and/or prevents exposure of the cells to high concentrations of cryoprotectant and/or DMSO. In particular embodiments, the rate at which thawing occurs may be affected by properties of the container, e.g., the vial and/or the bag, that the cells are frozen and thawed in. In particular embodiments, the cells are thawed at a temperature of, of about, or less than 37° C., 35° C., 32° C., 30° C., 29° C., 28° C., 27° C., 26° C., 25° C., 24° C., 23° C., 22° C., 21° C., 20° C., or 15° C., or between 15° C. and 30° C., between 23° C. and 28° C., or between 24° C. and 26° C., each inclusive. In some embodiments, the cells are thawed on a heat block or in a water bath. In certain embodiments, the cells are not thawed on a heat block or water bath. In some embodiments, the cells are thawed at room temperature. In some embodiments, the thickness of container the walls effects the rate of cell thawing, such as for example cells in containers with thick walls thaw at a slower rate than in containers with thinner walls. In some embodiments, containers having a low ratio of surface area to volume have a slow and/or uneven rate of thawing. In some embodiments, cryofrozen cells are rapidly thawed in a containing having a surface area to volume ratio is, is about, or is at least 1 $cm^{-1}$, 2 $cm^{-1}$, 3 $cm^{-1}$, 4 $cm^{-1}$, 5 $cm^{-1}$, 6 $cm^{-1}$, or 7 $cm^{-1}$, 8 $cm^{-1}$, 9 $cm^{-1}$, or 10 $cm^{-1}$. In particular embodiments, the cells are thawed in, in about, or in less than 120 minutes, 90 minutes, 60 minutes, 45 minutes, 30 minutes, 25 minutes, 20 minutes, 15 minutes, or ten minutes. In some embodiments, the cells are thawed for between 10 minutes and 60 minutes, 15 minutes and 45 minutes, or 15 minutes and 25 minutes, each inclusive. In particular embodiments, the cells are thawed in, in about, or in less than 20 minutes.

In certain embodiments, the thawed cells are rested, e.g., incubated or cultured, prior to administration or prior to any subsequent engineering and/or processing steps. In some embodiments, the cells are rested in low and/or undetectable amounts of cryoprotectant, or in the absence of cryoprotectant, e.g., DMSO. In particular embodiments, the thawed cells are rested after or immediately after washing steps, e.g., to remove cryoprotectant and/or DMSO. In some embodiments, the resting is or includes culture and/or incubation at or at about 37° C. In some embodiments, the resting is performed in the absence of any reagents, e.g., stimulatory reagents, bead reagents, or recombinant cytokines, used with and/or associated with any processing or engineering step. In some embodiments, the cells are rested for, for about, or for at least 5 minutes, 10 minutes, 15 minutes, 30 minutes, 1 hour, 2 hours, 3 hours, 4 hours, 5 hours, 6 hours, 8 hours, 12 hours, 18 hours, or 24 hours. In certain embodiments, the cells are rested for, for about, or for at least 2 hours.

In some embodiments, the cells are frozen, e.g., cryopreserved, either before, during, or after said methods for processing and/or engineering the cells. In some embodiments, the freeze and subsequent thaw step removes granulocytes and, to some extent, monocytes in the cell population. The cells are generally then frozen to −80° C. at a rate of 1° per minute and stored in the vapor phase of a liquid nitrogen storage tank. In some embodiments, the cells are actively and/or effectively cooled at a rate of or of about 1° per minute using a controlled rate freezer. In some embodiments, cells can be frozen with a controlled rate freezer. In some aspects, the controlled rate freezers are used to freeze cells with programmed cooling profiles, e.g. profiles with multiple cooling and/or heating rates. Such freezing profiles may be programmed to control nucleation, e.g., ice formation, for example to reduce intracellular ice formation.

In some embodiments, features of the frozen cells including any of the cells and compositions as described, such as cell compositions at a particular concentration or cell density, frozen in the presence of a cryoprotectant and/or filled into a container at a particular volume or surface to volume ratio, include improved, increased, and/or faster expansion; improved increased, and/or enhanced cell survival and reduced instances of cell death, e.g., necrosis, programmed cell death, and/or apoptosis; improved, enhanced, and/or increased activity, e.g., cytolytic activity; and/or reduced instance of senescence or quiescence after thawing than cells frozen by alternate means.

In particular embodiments, the cells are frozen at a cell density and/or a surface area to volume ratio provided herein and have reduced cell death, e.g., necrosis and/or apoptosis, during and/or resulting from the freezing, cryofreezing, and/or cryopreservation, as compared to cells frozen at a different cell density and/or a different surface area to volume ratio under the same or similar conditions. In particular embodiments, the cells are frozen at a cell density and/or a surface area to volume ratio provided herein and have reduced delayed cell death, e.g., a reduction in the amount of cells that die, e.g., via necrosis, programmed cell death, or apoptosis, within 48 hours after freezing, cryofreezing, and/or cryopreservation, e.g. after the thawing of the frozen cells. In certain embodiments, at least or about 5%, 10%, 20%, 25%, 30%, 40%, 50%, 60%, 70%, 80%, 90%, or 99% less cells die during and/or resulting from freezing and/or cryopreservation as compared to cells that are frozen at a different cell density and/or a different surface area to volume ratio under the same or similar conditions. In certain embodiments, less than 40%, 30%, 25%, 20%, 15%, 10%, 5%, 1%, 0.1%, or 0.01% of the cells frozen at the provided cell density and/or a surface area to volume ratio die during or as a result from freezing, cryofreezing, and/or cryopreservation.

In some embodiments, the cells are frozen at a cell density and/or a surface area to volume ratio provided herein and have reduced instances of senescence or quiescence due to and/or resulting from the freezing, cryofreezing, and/or cryopreservation, as compared to cells frozen at a different a different cell density and/or a different surface area to volume ratio under the same or similar conditions. In particular embodiments, at least or about 5%, 10%, 20%, 25%, 30%, 40%, 50%, 60%, 70%, 80%, 90%, or 99% less cells are senescent and/or quiescent cells as compared to cells frozen at a different cell density and/or a different surface area to volume ratio under the same or similar conditions. In certain embodiments, the cells are frozen at the provided cell density and/or surface area to volume ratio and less than 40%, 30%, 25%, 20%, 15%, 10%, 5%, 1%, 0.1%, or 0.01% of the cells become senescent and/or quiescent as a result from freezing, cryofreezing, and/or cryopreservation.

In certain embodiments, the cells are frozen, e.g., cryofrozen, at a cell density and/or surface area to volume ratio provided herein and have improved, faster, and/or more rapid expansion, e.g., under stimulatory conditions such as by incubation with a stimulatory reagent described herein, after the cells are thawed, as compared to cells frozen at a different cell density and/or surface area to volume ratio under the same or similar conditions. In particular embodiments, the cells expand at a rate that is faster and/or more rapid by, by about, or by at least 5%, 10%, 20%, 25%, 30%, 40%, 50%, 60%, 70%, 80%, 90%, 100%, 150%, 200%, 1-fold, 1.5 fold, 2-fold, 3-fold, 4-fold, 5-fold, or 10-fold as compared to cells frozen at a different cell density and/or a different surface area to volume ratio under the same or similar conditions. For example, in some embodiments, the thawed cells reach a threshold expansion, e.g., a predetermined cell number, density, or factor such as a 2-fold expansion, in, in about, or in at least 5% 10%, 20%, 25%, 30%, 40%, 50%, 60%, 70%, 80%, 90%, 95%, or 99%, less time than thawed cells that were frozen at a different cell density and/or a different surface area to volume ratio under the same or similar conditions.

In some embodiments, the cells are frozen, e.g., cryofrozen, at the cell density and have improved, increased, and/or more cytolytic activity, e.g., such as measured by any assay for measuring cytolytic activity described herein, after the cells are thawed, as compared to cells frozen at a different cell density, e.g., a higher or lower density, under the same or similar conditions. In particular embodiments, the cytolytic activity is increased by, by about, or by at least 5%, 10%, 20%, 25%, 30%, 40%, 50%, 60%, 70%, 80%, 90%, 100%, 150%, 200%, 1-fold, 1.5 fold, 2-fold, 3-fold, 4-fold, 5-fold, or 10-fold as compared to cells frozen at a different density under the same or similar conditions.

VI. COMPOSITIONS AND FORMULATIONS

Also provided are compositions including the cells, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine.

In some embodiments, the composition includes the cells in an amount effective to reduce burden of the disease or condition, and/or in an amount that does not result in CRS or severe CRS in the subject and/or to effect any of the other outcomes of the methods as described herein.

The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

The cells and compositions may be administered using standard administration techniques, formulations, and/or devices. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

In some embodiments, the therapeutic T cell composition comprises between about 10 million cells per mL and about 70 million cells per mL or between about 10 million viable cells per mL and about 70 million viable cells per mL, each inclusive. In some embodiments, the therapeutic T cell composition comprises between about 15 million cells or viable cells per mL and about 60 million cells or viable cells per mL, each inclusive. In some embodiments, the T cell composition comprises greater than 10 million cells or viable cells per mL. In some embodiments, the therapeutic T cell composition comprises greater than 15 million cells or greater than 15 million cells per mL.

In some embodiments, the article further contains information indicating that the container, e.g., a vial or a bag, such as an IV bag, or a syringe, contains the target number of units.

In some embodiments, the article of manufacture, the container is a first container and the article further comprises additional containers, wherein each of the additional containers comprises a unit dose comprising the target number of units of the T cell composition. In some embodiments, the additional containers comprise between about 10 million cells or viable cells per mL and about 70 million cells or viable cells per mL, between about 15 million cells or viable cells and about 60 million cells or viable cells per mL, greater than 10 million cells or viable cells per mL, greater than 15 million cells or viable cells per mL, each inclusive, or a combination thereof. In some embodiments, the composition further comprises a cryoprotectant and/or the article further includes instructions for thawing the composition prior to administration to the subject.

In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively.

Any of a variety of known freezing solutions and parameters in some aspects may be used. In some embodiments, a cell sample can contain a cryopreservation or vitrification medium or solution containing the cryoprotectant. Suitable cryoprotectants include, but are not limited to, dimethy sulfoxide (DMSO), glycerol, a glycol, a propylene glycol, an ethylene glycol, propanediol, polyethylene glycol (PEG), 1,2-propanediol (PROH) or a mixture thereof. In some examples, the cryopreservation solution can contain one or more non-cell permeating cryopreservative, including but not limited to, polyvinyl pyrrolidione, a hydroxyethyl starch, a polysaccharide, a monosaccharide, an alginate, trehalose, raffmose, dextran, human serum albumin, Ficoll, lipoproteins, polyvinyl pyrrolidone, hydroxyethyl starch, autologous plasma or a mixture thereof. In some embodiments, the cells are suspended in a freezing solution with a final concentration of cryoprotectant of between about 1% and about 20%, between about 3% and about 9%, or between about 6% and about 9% by volume, each inclusive. In certain embodiments, the final concentration of cryoprotectant in the freezing solution is about 3%, about 4%, about 5%, about 5.5%, about 6%, about 6.5%, about 7%, about 7.5%, about 8%, about 8.5%, about 9%, about 9.5%, or about 10% by volume.

In some embodiments, the cryoprotectant is DMSO. In particular embodiments, the cells are suspended in a freezing solution with a final concentration of DMSO of between about 1% and about 20%, between about 3% and about 9%, or between about 6% and about 9% by volume, each inclusive. In certain embodiments, the final concentration of DMSO in the freezing solution is about 3%, about 4%, about 5%, about 5.5%, about 6%, about 6.5%, about 7%, about 7.5%, about 8%, about 8.5%, about 9%, about 9.5%, or about 10% by volume.

In certain embodiments, the cells are suspended in a freezing solution at a density of between about $1\times10^6$ cells/mL and about $1\times10^8$ cells/mL, between about $1\times10^6$ cells/mL and about $2\times10^7$ cells/mL, between about $1\times10^7$ cells/mL and about $5\times10^7$ cells/mL, or between about $1\times10^7$ cells/mL to $5\times10^7$ cells/mL, each inclusive. In certain embodiments, the cells are suspended in the freezing solution at a density of about $1\times10^6$ cells/mL, about $2\times10^6$ cells/mL, about $5\times10^6$ cells/mL, about $1\times10^7$ cells/mL, about $1.5\times10^7$ cells/mL, about $2\times10^7$ cells/mL, about $2.5\times10^7$ cells/mL, about $2.5\times10^7$ cells/mL, about $2.5\times10^7$ cells/mL, about $3\times10^7$ cells/mL, about $3.5\times10^7$ cells/mL, about $4\times10^7$ cells/mL, about $4.5\times10^7$ cells/mL, or about $5\times10^7$ cells/mL. In certain embodiments, the cells are suspended in the freezing solution at a density of between about $1.5\times10^7$ cells/mL and about $6\times10^7$ cells/mL, inclusive. In certain embodiments, the cells are suspended in a freezing solution at a density of at least about $1\times10^7$ cells/mL. In particular embodiments, the cells are suspended in a freezing solution at a density of at least about $1.5\times10^7$ cells/mL. In some embodiments, the cells are viable cells.

In some embodiments, transfer to cryopreservation medium is associated with one or more processing steps that can involve washing of the sample, e.g., engineered cell composition, such as to remove the media and/or replacing the cells in an appropriate cryopreservation buffer or media for subsequent freezing. In certain embodiments, the transfer to the cryopreservation medium is fully automated on a clinical-scale level in a closed and sterile system. In certain embodiments the transfer to the cryopreservation medium carried out using CliniMACS system (Miltenyi Biotec).

In some embodiments, the cells are frozen, e.g., cryopreserved, either before, during, or after said methods for processing and/or engineering the cells. In some embodiments, the freeze and subsequent thaw step removes granulocytes and, to some extent, monocytes in the cell population. The cells are generally then frozen to −80° C. at a rate of 1° per minute and stored in the vapor phase of a liquid nitrogen storage tank.

In some embodiments, the composition is enclosed in a bag suitable for cryopreservation (for example, CryoMacs® Freezing Bags, Miltenyi Biotec). In some embodiments, the composition is enclosed in a vial suitable for cryopreservation (for example, CellSeal® Vials, Cook Regentec).

VII. ARTICLES OF MANUFACTURE

Also provided are articles of manufacture, such as kits and devices, for the administration of the cells to subjects in according to the provided methods for adoptive cell therapy, and for storage and administration of the cells and compositions.

The articles of manufacture include one or more containers, typically a plurality of containers, packaging material, and a label or package insert on or associated with the container or containers and/or packaging, generally including instructions for administration of the cells to a subject.

The containers generally contain the cells to be administered, e.g., one or more unit doses thereof. The article of manufacture typically includes a plurality of containers, each containing a single unit dose of the cells. The unit dose may be an amount or number of the cells to be administered to the subject in the first dose or twice the number (or more)

the cells to be administered in the first or any one or more consecutive dose(s). It may be the lowest dose or lowest possible dose of the cells that would be administered to the subject in connection with the administration method. In some embodiments, the unit dose is the minimum number of cells or number of cells or the minimum number of reference units or the target reference units or reference units within a target range that would be administered in a single dose to any subject having a particular disease or condition or any subject, according to the methods herein. In some embodiments, the number of cells in the unit dose is the number of cells or number of recombinant receptor-expressing or CAR-expressing cells, or number of such cells of a certain phenotype, e.g. CD8+, apoptosis marker negative (e.g. Annexin V− or Caspase 3−) and CD8+, that it is desired to administer to a particular subject in a dose, such as a subject from which the cells have been derived. In some embodiments, the target number of reference units or the reference units with a target range in the unit dose is the reference units of the composition as a function of the number of cells or number of recombinant receptor-expressing or CAR-expressing cells, or number of such cells of a certain phenotype, e.g. CD8+, apoptosis marker negative (e.g. Annexin V− or Caspase 3−) and CD8+ and the recombinant-receptor dependent activity (e.g. antigen-specific activity) of the composition, and that it is desired to administer to a particular subject in a dose, such as a subject from which the cells have been derived. In some embodiments, the cells have been derived from the subject to be treated by methods as provided herein or in need thereof.

In some embodiments, the article of manufacture contain a unit dose of cells containing a target number of reference unit (RU) within a given range, such as according to the formula as described elsewhere herein. Exemplary unit doses of target number of reference units (RU) or target number of total cells include any as described throughout this disclosure.

In some embodiments, each of the containers individually comprises a unit dose of the cells, e.g., including the same or substantially the same number of cells or number of recombinant receptor-expressing or CAR-expressing cells, or number of such cells of a certain phenotype, e.g. CD8+, apoptosis marker negative (e.g. Annexin V− or Caspase 3−). In some embodiments, each of the containers individually comprises a unit dose of the cells, e.g., including the same or substantially the same number of target reference units or a number of reference units within a target range.

Suitable containers include, for example, bottles, vials, syringes, and flexible bags, such as infusion bags. In particular embodiments, the containers are bags, e.g., flexible bags, such as those suitable for infusion of cells to subjects, e.g., flexible plastic or PVC bags, and/or IV solution bags. The bags in some embodiments are sealable and/or able to be sterilized, so as to provide sterile solution and delivery of the cells and compositions. In some embodiments, the containers, e.g., bags, have a capacity of at or about or at least at or about 10, 20, 30, 40, 50, 60, 70, 80, 90, 100, 200, 300, 400, 500, or 1000 mL capacity, such as between at or about 10 and at or about 100 or between at or about 10 and at or about 500 mL capacity, each inclusive. In some embodiments, the containers, e.g., bags, are and/or are made from material which is stable and/or provide stable storage and/or maintenance of cells at one or more of various temperatures, such as in cold temperatures, e.g. below at or about or at or about −20° C., −80° C., −120° C., 135° C. and/or temperatures suitable for cryopreservation, and/or other temperatures, such as temperatures suitable for thawing the cells and body temperature such as at or about 37° C., for example, to permit thawing, e.g., at the subject's location or location of treatment, e.g., at bedside, immediately prior to treatment.

The containers may be formed from a variety of materials such as glass or plastic. In some embodiments, the container has one or more port, e.g., sterile access ports, for example, for connection of tubing or cannulation to one or more tubes, e.g., for intravenous or other infusion and/or for connection for purposes of transfer to and from other containers, such as cell culture and/or storage bags or other containers. Exemplary containers include infusion bags, intravenous solution bags, vials, including those with stoppers pierceable by a needle for injection.

The article of manufacture may further include a package insert or label with one or more pieces of identifying information and/or instructions for use. In some embodiments, the information or instructions indicates that the contents can or should be used to treat a particular condition or disease, and/or providing instructions therefor. The label or package insert may indicate that the contents of the article of manufacture are to be used for treating the disease or condition. In some embodiments, the label or package insert provides instructions to treat a subject, e.g., the subject from which the cells have been derived, via a method involving the administration of a first and one or more consecutive doses of the cells, e.g., according to any of the embodiments of the provided methods. In some embodiments, the instructions specify administration, in a first dose, of one unit dose, e.g., the contents of a single individual container in the article of manufacture, followed by one or more consecutive doses at a specified time point or within a specified time window and/or after the detection of the presence or absence or amount or degree of one or more factors or outcomes in the subject.

In some embodiments, the instructions specify administering one or more of the unit doses to the subject.

In some embodiments, the label or package insert or packaging comprises an identifier to indicate the specific identity of the subject from which the cells are derived and/or are to be administered. In the case of autologous transfer, the identity of the subject from which the cells are derived is the same as the identity of the subject to which the cells are to be administered. Thus, the identifying information may specify that the cells are to be administered to a particular patient, such as the one from which the cells were originally derived. Such information may be present in the packaging material and/or label in the form of a bar code or other coded identifier, or may indication the name and/or other identifying characteristics of the subject.

The article of manufacture in some embodiments includes one or more, typically a plurality, of containers containing compositions comprising the cells, e.g., individual unit dose forms thereof, and further include one or more additional containers with a composition contained therein which includes a further agent, such as a cytotoxic or otherwise therapeutic agent, for example, which is to be administered in combination, e.g., simultaneously or sequentially in any order, with the cells. Alternatively, or additionally, the article of manufacture may further include another or the same container comprising a pharmaceutically-acceptable buffer. It may further include other materials such as other buffers, diluents, filters, tubing, needles, and/or syringes.

The term "package insert" is used to refer to instructions customarily included in commercial packages of therapeutic products, that contain information about the indications, usage, dosage, administration, combination therapy, contraindications and/or warnings concerning the use of such therapeutic products.

VIII. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the described or claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

IX. EXEMPLARY EMBODIMENTS

1. An article of manufacture, comprising:

(a) a container comprising a unit dose of a therapeutic T cell composition comprising T cells comprising a recombinant receptor, which optionally is a chimeric antigen receptor (CAR), that specifically binds to an antigen, wherein the unit dose contains a target number of reference units (RU) within a given range, wherein RU in a given composition is defined by the formula $RU=A \times B$, wherein:

A is the number of cells, or multiple, fraction or transformation thereof, of a phenotype present in the given composition or is the average or weighted average of the number of cells, or multiple, fraction or transformation thereof, of two or more phenotypes in the given composition; and B is the value of a parameter, or a fraction or multiple or transformation thereof, that indicates or correlates with the degree of a recombinant receptor-dependent, optionally CAR-dependent, activity in the given composition; and (b) instructions for administering the composition, optionally one or more unit doses thereof, to a subject, optionally a subject having or suspected of having a disease or condition.

2. The article of manufacture of embodiment 1, wherein A is the number of cells, or multiple or fraction or transformation thereof, of a given phenotype present in the given composition.

3. The article of manufacture of embodiment 1, wherein A is the average or weighted average of the number of cells, or multiple, fraction or transformation thereof, of two or more phenotypes in the give composition.

4. The article of manufacture of any of embodiments 1-3, wherein the target number of units is less than a threshold number of units, which optionally is a safety number of reference units, wherein, the safety number of reference units is, with respect to a group of subjects analyzed following treatment with a therapeutic T cell composition comprising the T cells expressing the recombinant receptor, optionally the CAR, the lowest number of reference units of the therapy administered to a subject among those subjects in the group that went on to develop an adverse event.

5. The article of manufacture of embodiment 4, wherein the adverse event is a severe adverse event, optionally severe neurotoxicity, optionally at or above grade 4 or grade 5 or at least prolonged grade 3 neurotoxicity.

6 The article of manufacture of embodiment 4 or embodiment 5, wherein the target number of reference units is less than the safety number of reference units by an amount corresponding to a safety factor and/or by an amount within a range of 1.5- to 3-fold, optionally about 2-fold, or by an amount that is a multiple of a standard deviation of a group of subjects that did not develop the adverse event, optionally grade 0-2 neurotoxicity, optionally wherein the multiple is within a range of 1.5- to 3-fold.

7. The article of manufacture of any of embodiments 1-6, wherein the target number of reference units is at or above a reference efficacy number of reference units, wherein the reference efficacy number is, with respect to a group of subjects analyzed following treatment with a therapeutic T cell composition comprising the recombinant receptor, optionally the CAR, a number of units of the therapy administered to one or more subjects among the group that exhibited a desired therapeutic outcome, optionally a partial response or a complete response (CR).

8. An article of manufacture, comprising:

(a) a container comprising a unit dose of a therapeutic T cell composition, the therapeutic T cell composition comprising T cells comprising a recombinant receptor, which optionally is a chimeric antigen receptor (CAR), that specifically binds to an antigen, wherein:

the unit dose contains at or about (i) a target number of total recombinant receptor-expressing cells or a target number of total CD3+ recombinant receptor-expressing cells or a target number of total CD8+ recombinant receptor-expressing cells, or (ii) a target number of reference units (RU) within a given range, which target number of reference RUs is at or below a threshold number of RUs, wherein the unit dose does not contain greater than the threshold number of RUs, wherein the number of RU in a given composition is defined by the formula:

$RU=A\times B$, wherein

A is the number of cells, or multiple or transformation thereof, of a phenotype present in the given composition or is the average or weighted average of the number of cells, or multiple, fraction or transformation thereof, of two or more phenotypes in the given composition; and B is the value of a parameter, or a multiple, or transformation thereof, that indicates or correlates with the degree of a recombinant receptor-dependent, optionally CAR-dependent, activity in the given T cell composition; and (b) instructions for administering the composition, optionally one or more unit doses thereof, to a subject, optionally a subject having or suspected of having a disease or condition.

9. The article of manufacture of embodiment 8, wherein A is the number of cells, or multiple or fraction or transformation thereof, of a given phenotype present in the given composition.

10. The article of manufacture of embodiment 8, wherein A is the average or weighted average of the number of cells, or multiple, fraction or transformation thereof, of two or more phenotypes in the given composition.

11. The article of manufacture of any of embodiments 8-10, wherein:

the target number is the target number of recombinant-receptor expressing cells that are CD3+ that are apoptotic marker negative (−) and CD3+, optionally wherein the apoptotic marker is Annexin V or active Caspase 3; or the target number is the target number of recombinant-receptor expressing cells that are CD8+ that are apoptotic marker negative (−) and CD8+, optionally wherein the apoptotic marker is Annexin V or active Caspase 3.

12. The article of manufacture of any of embodiments 1-11, wherein the target number of cells in (i) is: between and between about $5.0\times10^6$ and $2.25\times10^7$, $5.0\times10^6$ and $2.0\times10^7$, $5.0\times10^6$ and $1.5\times10^7$, $5.0\times10^6$ and $1.0\times10^7$, $5.0\times10^6$ and $7.5\times10^6$, $7.5\times10^6$ and $2.25\times10^7$, $7.5\times10^6$ and $2.0\times10^7$, $7.5\times10^6$ and $1.5\times10^7$, $7.5\times10^6$ and $1.0\times10^7$, $1.0\times10^7$ and $2.25\times10^7$, $1.0\times10^7$ and $2.0\times10^7$, $1.0\times10^7$ and $1.5\times10^7$, $1.5\times10^7$ and $2.25\times10^7$, $1.5\times10^7$ and $2.0\times10^7$, $2.0\times10^7$ and $2.25\times10^7$ recombinant-receptor expressing cells, each inclusive, optionally recombinant-receptor expressing cells that are CD3+ or CD8+ or that are apoptotic marker negative (−) and CD8+, optionally wherein the apoptotic marker is Annexin V or active Caspase 3.

13. The article of manufacture of any of embodiments 1-12, wherein the target number of cells in (i) is:

between at least or at least about $5\times10^6$, $6\times10^6$, $7\times10^6$, $8\times10^6$, $9\times10^6$, $10\times10^6$ and about $15\times10^6$ recombinant-receptor expressing cells, each inclusive, optionally recombinant-receptor expressing cells that are CD8+ or that are apoptotic marker negative (−) and CD8+, optionally wherein the apoptotic marker is Annexin V or active Caspase 3;

between at least or at least about $5.55\times10^6$, $6.66\times10^6$, $7.77\times10^6$, $8.99\times10^6$, $1.0\times10^7$, $1.1\times10^7$ and about $1.67\times10^7$ recombinant-receptor expressing cells, each inclusive, optionally recombinant-receptor expressing cells that are CD8+ or that are apoptotic marker negative (−) and CD8+, optionally wherein the apoptotic marker is Annexin V or active Caspase 3;

between at least or at least about $6.25\times10^6$, $7.5\times10^6$, $8.75\times10^6$, $1.0\times10^7$, $1.13\times10^7$, $1.25\times10^7$ and about $1.9\times10^7$ recombinant-receptor expressing cells, each inclusive, optionally recombinant-receptor expressing cells that are CD8+ or that are apoptotic marker negative (−) and CD8+, optionally wherein the apoptotic marker is Annexin V or active Caspase 3; between at least or at least about $7.14\times10^6$, $8.5\times10^6$, $1.0\times10^7$, $1.14\times10^7$, $1.29\times10^7$, $1.42\times10^7$ and about $2.14\times10^7$ recombinant-receptor expressing cells, each inclusive, optionally recombinant-receptor expressing cells that are CD8+ or that are apoptotic marker negative (−) and CD8+, optionally wherein the apoptotic marker is Annexin V or active Caspase 3.

14. The article of manufacture of any of embodiments 1-13, wherein the target number of cells in (i) is between at least or at least about $5\times10^6$, $6\times10^6$, $7\times10^6$, $8\times10^6$, $9\times10^6$, $10\times10^6$ and about $15\times10^6$ recombinant-receptor expressing cells that are apoptotic marker negative (−) and CD8+, each inclusive, optionally wherein the apoptotic marker is Annexin V or active Caspase 3.

15. The article of manufacture of any of embodiments 1-13, wherein the target number of cells in (i) is between at least or at least about $6.25\times10^6$, $7.5\times10^6$, $8.75\times10^6$, $1.0\times10^7$, $1.13\times10^7$, $1.25\times10^7$ and about $1.9\times10^7$ recombinant-receptor expressing cells that are CD8+, each inclusive.

16. The article of manufacture of any of embodiments 8-15, wherein the target reference number of RUs is less than a threshold number of units or is less than a reference safety number of RUs, wherein the reference safety number of RUs is, with respect to a group of subjects analyzed following treatment with a therapeutic T cell composition comprising the T cells expressing the recombinant receptor, optionally the CAR, the lowest number of reference units of the therapy administered to a subject among those subjects in the group that went on to develop an adverse event.

17. The article of manufacture of embodiment 16, wherein the adverse event is a severe adverse event, optionally severe neurotoxicity at or above grade 4 or grade 5 or at least prolonged grade 3 neurotoxicity.

18. The article of manufacture of embodiment 16 or embodiment 17, wherein the target reference number of RUs is less than the reference safety number of units by an amount corresponding to a safety factor or by at least 2-fold.

19. The article of manufacture of an of embodiments 8-18, wherein the target number of reference units is at or above a reference efficacy number of reference units, wherein the reference efficacy number is, with respect to a group of subjects analyzed following treatment with a T cell composition comprising the recombinant receptor, optionally the CAR, a number of reference units of the therapy administered to one or more subjects among the group that exhibited a desired therapeutic outcome, optionally a complete response (CR).

20. The article of manufacture of any one of embodiments 1-19, wherein A is the number of cells of a phenotype present in the given composition and B is the value of a parameter that indicates or correlates with the degree of recombinant receptor-dependent activity in the given composition.

21. The article of manufacture of any one of embodiments 1-20, wherein A and/or B is a transformation of the number or value, respectively, wherein the transformation comprises a logarithmic transformation, power transformation or logit transformation.

22. The article of manufacture of any one of embodiments 1-21, wherein A is a number of cells of a phenotype present in the given composition and B is a multiple or transformation of the value of the parameter that indicates or correlates with the degree of CAR-dependent activity in the given T cell composition, optionally wherein B is a logarithmic transformation of the value.

23. The article of manufacture of embodiment 21 or embodiment 22, wherein the logarithmic transformation is a common log($\log_{10}(x)$), a natural log($\ln(x)$) or a binary log ($\log_2(x)$).

24. The article of manufacture of any of embodiments 1-23, wherein A is the number of viable cells in the composition and/or is the number of cells that are not apoptotic, do not exhibit a factor indicative of early apoptosis or of apoptosis, are not in the early stages of apoptosis, or are not in the late stages of apoptosis, and/or is the number of cells of a particular differentiation state, and/or is the number of cells having a memory/stem-like attribute or is a multiple or transformation thereof.

25. The article of manufacture of any of embodiments 1-24, wherein the phenotype comprises positive expression of a surface marker that is one or more of CD3, CD4 or CD8 and/or comprises positive expression of the recombinant receptor, optionally the CAR, or a surrogate marker for expression of the recombinant receptor.

26. The article of manufacture of embodiment 25, wherein the phenotype is CD3+CAR, CD4+/CAR+, CD8+/CAR+.

27. The article of manufacture of any of embodiments 1-26, wherein the phenotype comprises absence of a factor indicative of apoptosis or one or more steps in an apoptotic cascade or pathway, optionally expression of a marker of apoptosis.

28. The article of manufacture of any of embodiments 1-27, wherein the phenotype comprises negative expression of a marker of apoptosis, optionally a marker of early apoptosis or late apoptosis.

29. The article of manufacture of embodiment 28, wherein the marker of apoptosis is surface phosphatidylserine and/or is detected with Annexin V, or is an active or proform of a caspase, optionally an active or proform of Caspase 3.

30. The article of manufacture of any of embodiments 1-29, wherein the phenotype comprises Annexin-.

31. The article of manufacture of any of embodiments 1-30, wherein the phenotype comprises an indicator of production of one or a combination of cytokines, optionally non-specific to the antigen or the recombinant receptor and/or that is polyclonally produced, wherein the one or more cytokines is IL-2, IL-13, IL-17, IFN-gamma or TNF-alpha.

32. The article of manufacture of embodiment 31, wherein the indicator of production is measured in an assay, optionally an intracellular cytokine staining assay, comprising incubating a sample of the T cell composition with a polyclonal agent, an antigen-specific agent or an agent that binds the recombinant receptor, optionally CAR.

33. The article of manufacture of embodiment 31 or embodiment 32, wherein the agent is or comprises PMA and ionomycin or is or comprises a T cell receptor or T cell receptor complex agonist.

34. The article of manufacture of any of embodiments 1-33, wherein the phenotype comprises negative expression of an activation marker, wherein the activation marker is selected from among CD25, CD127, LAG3, Ki67 and combinations thereof.

35. The article of manufacture of any of embodiments 1-34, wherein the phenotype comprises negative expression of an exhaustion marker, wherein the exhaustion maker is a PD1 or FOXP3 gene product or a combination thereof.

36. The article of manufacture of any of embodiments 1-35, wherein the phenotype comprises a naïve phenotype or a memory phenotype, optionally wherein the memory phenotype comprises a T effector memory phenotype, a T central memory phenotype, or a T effector memory phenotype expressing CD45RA (Temra).

37. The article of manufacture of any of embodiments 1-36, wherein A is the total number of T cells, total number of CD3+ cells, total number of CD4+ or CD8+ cells, total number of CD3+CAR+ cells, total number of CD8+CAR+ cells, total number of CD4+ CAR+, or total number of live or viable cells of any of the foregoing, or a multiple or transformed value 38. The article of manufacture of any of embodiments 1-37, wherein A is the total number of CD3+ cells, total number of CD8+, total number of CD3+CAR+ cells, total number of CD8+CAR+ cells, or total number of live or viable cells of any of the foregoing, or a multiple or transformed value thereof.

39. The article of manufacture of any of embodiments 1-38, wherein A is the total number of apoptotic marker negative (−) cells that are CD3+CAR+ cells, total number of apoptotic marker negative (−) cells that are CD4+CAR+, total number of apoptotic marker negative (−) cells that are CD8+ CAR+ cells, or a multiple or transformed value thereof, wherein the apoptotic marker is Annexin V or active Caspase 3.

40. The article of manufacture of any of embodiments 1-39, wherein A is the total number of apoptotic marker-CD3+ CAR+ cells or the total number of apoptotic marker-CD8+CAR+ cells, optionally wherein the apoptotic marker is Annexin V or active Caspase 3.

41. An article of manufacture, comprising:

(a) a container comprising a unit dose of a therapeutic T cell composition comprising T cells expressing a chimeric antigen receptor (CAR) that specifically binds to an antigen, wherein the unit dose contains a target dose of the therapeutic T cell composition, wherein:

(i) if the value of a parameter that indicates or correlates with the degree of recombinant receptor-dependent activity of the composition is at or greater than a threshold value, the target dose is a first number (or is within a first range of numbers) of cells of a given phenotype of the composition;

(ii) if the value of the parameter is less than the threshold value, the target dose is a second number (or is within a second range of numbers) of cells of a given phenotype of the composition wherein the first number (or first range) is lower than the second number (or second range); and (b) instructions for administering the composition, optionally one or more unit doses thereof, to a subject, optionally a subject having or suspected of having a disease or condition.

42. The article of manufacture of embodiment 41, wherein the threshold value of the recombinant receptor-dependent activity is less than a reference safety value, wherein the reference safety value is, with respect to a group of subjects analyzed following treatment with a therapeutic T cell composition comprising T cells expressing the recombinant receptor, optionally the CAR, the lowest value of the CAR-dependent activity of the therapeutic composition administered to a subject among those subjects in the group that went on to develop an adverse event.

43. The article of manufacture of embodiment 42, wherein the adverse event is a severe adverse event, optionally severe neurotoxicity at or above grade 4 or grade 5 or at least prolonged grade 3 neurotoxicity.

44. The article of manufacture of embodiment 42 or embodiment 43, wherein the threshold value is less than the reference safety value by an amount corresponding to a safety factor or by at least 2-fold.

45. The article of manufacture of any of embodiments 41-44, wherein the first number is lower than the second number by greater than or greater than about 1.5-fold, 2.0-fold, 3.0-fold, 4.0-fold, 5.0-fold, 6.0-fold, 7.0-fold, 8.0-fold, 9.0-fold, 10.0-fold or more.

46. An article of manufacture, comprising:

(a) a container comprising a unit dose of a therapeutic T cell composition, the therapeutic T cell composition comprising T cells comprising a recombinant receptor, which optionally is a chimeric antigen receptor (CAR), that specifically binds to an antigen, wherein:

the unit dose contains a target dose of the therapeutic T cell composition; and the therapeutic T cell composition is above a lower specification limit (LSL) and below an upper specification limit (USL) for B, wherein B is the value of a parameter that indicates or correlates with the degree of recombinant receptor-dependent activity of the composition; and (b) instructions for administering the composition, optionally one or more unit doses thereof, to a subject, optionally a subject having or suspected of having a disease or condition.

47. The article of manufacture of embodiment 46, wherein the product is released for treatment of the subject only if the composition is below the USL for B.

48. The article of manufacture of any of embodiments 41-47, wherein the recombinant receptor-dependent activity is a measure of the production or accumulation of a proinflammatory cytokine, optionally, one of or a combination of TNF-alpha, IFN-gamma, IL-2 and IL-10.

49. The article of manufacture of any one of embodiments 1-48, wherein the parameter is a measure of one or more factors or a normalized value thereof.

50. The article of manufacture of embodiment 49, wherein the measure is in an assay involving culture or incubation for a fixed time, optionally 24 hours, of a given composition or sample thereof in the presence of the antigen, cells expressing the antigen and/or agent that specifically binds to the recombinant receptor, optionally the CAR.

51. The article of manufacture of embodiment 50, wherein the assay is an ELISA.

52. The article of manufacture of any of embodiments 49-51, wherein the measure of the factor is:

(i) concentration, relative concentration, amount, or relative amount of the factor; or (ii) amount or relative amount of the factor per unit of input cells of the given composition, or (iii) amount or relative amount of the factor per unit of input cells of the given composition per unit of time, optionally one hour; or (iv) a level indicative of any of (i)-(iii).

53. The article of manufacture of any of embodiments 49-52, wherein the one or more factors is one or a combination of soluble factors, optionally one or a combination of cytokines, chemokines or soluble receptors, optionally soluble costimulatory receptors.

54. The article of manufacture of any of embodiments 49-53, wherein the one or more factors is one of or a combination of a pro-inflammatory cytokines, Th2 cytokines and Th17 cytokines.

55. The article of manufacture of any of embodiments 49-54, wherein the one or more factors is one of or a combination of IL-2, IFN-gamma, TNF-alpha, IL4, IL-5, IL-10, IL-13, GM-CSF, sCD137, MIP1a and M1Pb.

56. The article of manufacture of any of embodiments 49-55, wherein the one or more factors is one of or a combination of IL-2, IFN-gamma, TNF-alpha and IL-10.

57. The article of manufacture of any of embodiments 53-56, wherein the one or more factors is a combination of any of two or more of the foregoing soluble factors and the parameter is an arithmetic mean or geometric mean of the measure of the two or more factors.

58. The article of manufacture of any embodiments 49-57, wherein the parameter is an arithmetic mean or geometric mean of a measure, optionally amount or concentration, of at least two of TNF-alpha, IFN-gamma and IL-2 or of TNF-alpha, IFN-gamma and IL-2.

59. The article of manufacture of any of embodiments 49-58, wherein the parameter is the normalized value of the measure, wherein normalization is as compared to a reference measure of the factor.

60. The article or manufacture of embodiment 59, wherein the reference measure is the average of the measure among a plurality, optionally at least 10, at least 15, at least 20, of reference therapeutic T cell compositions comprising the chimeric antigen receptor (CAR) in which:

(i) each of the reference therapeutic T cell compositions has been observed or determined to result in an acceptable safety profile following administration to a subject, optionally wherein the subject has a disease or condition expressing or associated with the antigen; and/or (ii) each of the reference therapeutic T cell compositions has been observed or determined to result in a desired efficacy following administration to a subject, optionally wherein the subject has a disease or condition expressing or associated with the antigen.

61. The article of manufacture of embodiment 60, wherein the acceptable safety profile is absence of observed grade 2 or higher or absence of grade 3 or higher, neurotoxicity.

62. The article of manufacture of embodiment 60 or embodiment 61, wherein the acceptable safety profile is the absence of observed grade 3 or higher neurotoxicity.

63. The article of manufacture of any of embodiments 60-62, wherein the efficacy is a partial response or is a complete response (CR).

64. The article of manufacture of embodiment 59, wherein the reference measure is the measure, by the same assay, of the factor in a reference T cell composition produced by the same method as the therapeutic T cell composition but not expressing the recombinant receptor, optionally the CAR, not specifically recognizing the antigen and/or not expressing any recombinant receptor, optionally any CAR.

65. The article of manufacture of embodiment 64, wherein the parameter is normalized to control for patient-specific variation of the measure of the one or more factors.

66. The article of manufacture of embodiment 64 or embodiment 65, wherein the parameter is a normalized value of the measure of the factor, compared to the same measure in the same assay, of a control factor, wherein the level of the control factor in a therapeutic T cell composition is known not to, or has been observed not to, indicate or correlate or significantly correlate with an adverse event or toxicity outcome or likelihood or risk thereof, wherein the adverse event or toxicity outcome optionally is severe neurotoxicity.

67. The article of manufacture of embodiment 66, wherein the control factor is a factor that is not statistically correlated and/or does not correlate to development of the adverse event among a plurality of subjects that went on to develop the adverse event following administration of the T cell composition, optionally the control factor is or comprises one of or a combination of IL-5, IL-13, GM-CSF, and IL-6, optionally wherein the measure of the control factor is an arithmetic mean or geometric mean of two or more of the foregoing.

68. The article of manufacture of any of embodiments 1-67, wherein the parameter does not comprise cytolytic activity or a measure thereof.

69. The article of manufacture of any of embodiments 1-68, wherein the parameter does not comprise recombinant receptor-dependent or antigen-specific cytolytic activity or a measure thereof.

70. The article of manufacture of any of embodiments 1-40 and 49-69, wherein:

the phenotype is CD8+ CAR+ cells or apoptotic marker -CD8+ CAR+ cells, optionally wherein the apoptotic marker is Annexin V or active Caspase 3; and the parameter is a measure of a pro-inflammatory cytokine, which optionally is one of or a combination of TNF-alpha, IL-2, and IFN-gamma, or is a normalized value thereof.

71. The article of manufacture of any of embodiments 1-70, wherein the adverse event is grade 4 or 5 neurotoxicity and the threshold number of units:

is or is about $1.75\times10^7$ if A is apoptotic marker negative (−) and CD8+ CAR+ and B is TNF-alpha or a normalized value thereof;

is or is about $2.19\times10^7$ if A is CD8+ CAR+ and B is TNF-alpha or a normalized value thereof;

is or is about $1.25\times10^7$ if A is apoptotic marker negative (−) CD8+ CAR+ and if B is IFN-gamma or a normalized value thereof;

is or is about $1.56\times10^7$ if A is CD8+CAR+ and B is IFN-gamma or a normalized value thereof;

is or is about $1.5\times10^7$ if A is apoptotic marker negative (−) CD8+CAR+ and if B is IL-2 or a normalized value thereof;

is or is about $1.88\times10^7$ if A is CD8+CAR+ and B is IL-2 or a normalized value thereof;

is or is about $1.5\times10^7$ if A is apoptotic marker negative (−) CD8+CAR+ and if B is TNF-alpha and IFN-gamma or a normalized value thereof;

is or is about $1.88\times10^7$ if A is CD8+CAR+ and B is TNF-alpha and IFN-gamma or a normalized value thereof;

is or is about $2.0\times10^7$ if A is apoptotic marker negative (−) CD8+CAR+ and if B is TNF-alpha and IL-2 or a normalized value thereof;

is or is about $2.5\times10^7$ if A is CD8+CAR+ and B is TNF-alpha and IL-2 or a normalized value thereof;

is or is about $1.25\times10^7$ if A is apoptotic marker negative (−) CD8+CAR+ and if B is IFN-gamma and IL-2 or a normalized value thereof;

is or is about $1.56\times10^7$ if A is CD8+CAR+ and B is IFN-gamma and IL-2 or a normalized value thereof;

is or is about $1.75\times10^7$ if A is apoptotic marker negative (−) CD8+CAR+ and if B is TNF-alpha, IFN-gamma and IL-2 or a normalized value thereof;

is or is about $2.19\times10^7$ if A is CD8+CAR+ and B is TNF-alpha, IFN-gamma and IL-2 or a normalized value thereof, optionally wherein the apoptotic marker is Annexin V or active Caspase 3.

72. The article of manufacture of any of embodiments 1-71, wherein the adverse event is grade 4 or 5 neurotoxicity and the given range of the target reference units:

is between or about between $2.0\times10^5$ and $1.75\times10^7$, inclusive, if A is apoptotic marker negative (−) and CD8+CAR+ and B is TNF-alpha or a normalized value thereof;

is between or about between $2.5\times10^5$ and $2.19\times10^7$, inclusive, if A is CD8+CAR+ and B is TNF-alpha or a normalized value thereof;

is between or about between $4 \times 10^5$ and $1.25 \times 10^7$, inclusive, if A is apoptotic marker negative (−) CD8+CAR+ and if B is IFN-gamma or a normalized value thereof;

is between or about between $5 \times 10^6$ and $1.56 \times 10^7$, inclusive, if A is CD8+CAR+ and B is IFN-gamma or a normalized value thereof;

is between or about between $2.0 \times 10^5$ and $1.5 \times 10^7$, inclusive, if A is apoptotic marker negative (−) CD8+CAR+ and if B is IL-2 or a normalized value thereof;

is between or about between $2.5 \times 10^5$ and $1.88 \times 10^7$, inclusive, if A is CD8+CAR+ and B is IL-2 or a normalized value thereof;

is between or about between $3.0 \times 10^5$ and $1.5 \times 10^7$, inclusive, if A is apoptotic marker negative (−) CD8+CAR+ and if B is TNF-alpha and IFN-gamma or a normalized value thereof;

is between or about between $3.75 \times 10^5$ and $1.88 \times 10^7$, inclusive, if A is CD8+CAR+ and B is TNF-alpha and IFN-gamma or a normalized value thereof;

is between or about between $3.0 \times 10^5$ and $2.0 \times 10^7$, inclusive, if A is apoptotic marker negative (−) CD8+CAR+ and if B is TNF-alpha and IL-2 or a normalized value thereof;

is between or about between $3.75 \times 10^5$ and $2.5 \times 10^7$, inclusive, if A is CD8+CAR+ and B is TNF-alpha and IL-2 or a normalized value thereof;

is between or about between $4.0 \times 10^5$ and $1.25 \times 10^7$, inclusive, if A is apoptotic marker negative (−) CD8+CAR+ and if B is IFN-gamma and IL-2 or a normalized value thereof;

is between or about between $5.0 \times 10^5$ and $1.56 \times 10^7$, inclusive, if A is CD8+CAR+ and if B is IFN-gamma and IL-2 or a normalized value thereof;

is between or about between $4.0 \times 10^5$ and $1.75 \times 10^7$, inclusive, if A is apoptotic marker negative (−) CD8+CAR+ and if B is TNF-alpha, IFN-gamma and IL-2 or a normalized value thereof;

is between or about between $5.0 \times 10^5$ and $2.19 \times 10^7$, inclusive, if A is CD8+CAR+ and B is TNF-alpha, IFN-gamma and IL-2 or a normalized value thereof, optionally wherein the apoptotic marker is Annexin V or active Caspase 3.

73. The article of manufacture of any of embodiments 1-70, wherein the adverse event is at least prolonged grade 3 neurotoxicity and the threshold number of units:

is or is about $1.0 \times 10^6$ if A is apoptotic marker negative (−) and CD8+CAR+ and B is TNF-alpha or a normalized value thereof;

is or is about $1.25 \times 10^6$ if A is CD8+CAR+ and B is TNF-alpha or a normalized value thereof;

is or is about $2.0 \times 10^6$ if A is apoptotic marker negative (−) CD8+CAR+ and if B is IFN-gamma or a normalized value thereof;

is or is about $2.5 \times 10^6$ if A is CD8+CAR+ and B is IFN-gamma or a normalized value thereof;

is or is about $3.0 \times 10^6$ if A is apoptotic marker negative (−) CD8+CAR+ and if B is IL-2 or a normalized value thereof;

is or is about $3.75 \times 10^6$ if A is CD8+CAR+ and B is IL-2 or a normalized value thereof;

is or is about $1.5 \times 10^6$ if A is apoptotic marker negative (−) CD8+CAR+ and if B is TNF-alpha and IFN-gamma or a normalized value thereof;

is or is about $1.88 \times 10^6$ if A is CD8+CAR+ and B is TNF-alpha and IFN-gamma or a normalized value thereof;

is or is about $2.5 \times 10^6$ if A is apoptotic marker negative (−) CD8+CAR+ and if B is TNF-alpha and IL-2 or a normalized value thereof;

is or is about $3.12 \times 10^6$ if A is CD8+CAR+ and B is TNF-alpha and IL-2; or a normalized value thereof is or is about $3.0 \times 10^6$ if A is apoptotic marker negative (−) CD8+CAR+ and if B is IFN-gamma and IL-2 or a normalized value thereof;

is or is about $3.75 \times 10^6$ if A is CD8+CAR+ and B is IFN-gamma and IL-2 or a normalized value thereof;

is or is about $2.0 \times 10^6$ if A is apoptotic marker negative (−) CD8+CAR+ and if B is TNF-alpha, IFN-gamma and IL-2 or a normalized value thereof;

is or is about $2.5 \times 10^6$ if A is CD8+CAR+ and B is TNF-alpha, IFN-gamma and IL-2 or a normalized value thereof, optionally wherein the apoptotic marker is Annexin V or active Caspase 3.

74. The article of manufacture of any of embodiments 1-70 and 73, wherein the adverse event is at least prolonged grade 3 and the given range of the target reference units:

is between or about between $3.0 \times 10^5$ and $1.0 \times 10^6$, inclusive, if A is apoptotic marker negative (−) and CD8+CAR+ and B is TNF-alpha or a normalized value thereof;

is between or about between $3.75 \times 10^5$ and $1.25 \times 10^6$, inclusive, if A is CD8+CAR+ and B is TNF-alpha or a normalized value thereof;

is between or about between $4 \times 10^5$ and $2.0 \times 10^6$, inclusive, if A is apoptotic marker negative (−) CD8+CAR+ and if B is IFN-gamma or a normalized value thereof;

is between or about between $5 \times 10^6$ and $2.5 \times 10^6$, inclusive, if A is CD8+CAR+ and B is IFN-gamma or a normalized value thereof;

is between or about between $2.0 \times 10^5$ and $3.0 \times 10^6$, inclusive, if A is apoptotic marker negative (−) CD8+CAR+ and if B is IL-2 or a normalized value thereof;

is between or about between $2.5 \times 10^5$ and $3.75 \times 10^6$, inclusive, if A is CD8+CAR+ and B is IL-2 or a normalized value thereof;

is between or about between $3.0 \times 10^5$ and $1.5 \times 10^6$, inclusive, if A is apoptotic marker negative (−) CD8+CAR+ and if B is TNF-alpha and IFN-gamma or a normalized value thereof;

is between or about between $3.75 \times 10^5$ and $1.88 \times 10^6$, inclusive, if A is CD8+CAR+ and B is TNF-alpha and IFN-gamma or a normalized value thereof;

is between or about between $3.0 \times 10^5$ and $2.5 \times 10^6$, inclusive, if A is apoptotic marker negative (−) CD8+CAR+ and if B is TNF-alpha and IL-2 or a normalized value thereof;

is between or about between $3.75 \times 10^5$ and $3.12 \times 10^6$, inclusive, if A is CD8+CAR+ and B is TNF-alpha and IL-2 or a normalized value thereof;

is between or about between $4.0 \times 10^5$ and $3.0 \times 10^6$, inclusive, if A is apoptotic marker negative (−) CD8+CAR+ and if B is IFN-gamma and IL-2 or a normalized value thereof;

is between or about between $5.0 \times 10^5$ and $3.75 \times 10^6$, inclusive, if A is CD8+CAR+ and B is IFN-gamma and IL-2 or a normalized value thereof;

is between or about between $4.0 \times 10^5$ and $2.0 \times 10^6$, inclusive, if A is apoptotic marker negative (−) CD8+CAR+ and if B is TNF-alpha, IFN-gamma and IL-2 or a normalized value thereof;

is between or about between $5.0 \times 10^5$ and $2.5 \times 10^6$, inclusive, if A is CD8+CAR+ and B is TNF-alpha, IFN-gamma and IL-2 or a normalized value thereof, optionally wherein the apoptotic marker is Annexin V or active Caspase 3.

75. The article of manufacture of any of embodiments 1-74, wherein the therapeutic T cell composition comprises between about 10 million cells per mL and about 70 million cells per mL or between about 10 million viable cells per mL and about 70 million viable cells permL, each inclusive.

76. The article of manufacture of any of embodiments 1-75, wherein the therapeutic T cell composition comprises between about 15 million cells or viable cells per mL and about 60 million cells or viable cells per mL, inclusive.

77. The article of manufacture of any of embodiments 1-76, wherein the T cell composition comprises greater than 10 million cells or viable cells per mL.

78. The article of manufacture of any of embodiments 1-77, wherein the therapeutic T cell composition comprises greater than 15 million cells or greater than 15 million cells per mL.

79. The article of manufacture of any of embodiments 1-78, wherein the composition further comprises a cryoprotectant and/or the article further includes instructions for thawing the composition prior to administration to the subject.

80. The article of manufacture of any of embodiments 1-79, wherein the disease or condition is a cancer, optionally a myeloma, lymphoma or leukemia.

81. The article of manufacture of embodiment 80, wherein the disease or condition is a B cell malignancy, optionally a B cell malignancy is selected from the group consisting of acute lymphoblastic leukemia (ALL), adult ALL, chronic lymphoblastic leukemia (CLL), non-Hodgkin lymphoma (NHL), and Diffuse Large B-Cell Lymphoma (DLBCL).

82. The article of manufacture of any of embodiments 1-81, wherein the antigen is CD19, CD22, ROR1, Igkappa, Her2, L1-CAM, CD20, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acetylcholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1), and cyclin A1 (CCNA1).

83. The article of manufacture of any of embodiments 1-82, wherein the recombinant receptor is a CAR.

84. The article of manufacture of embodiment 83, wherein the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3° C.) chain; and/or wherein the CAR further comprises a costimulatory signaling region, which optionally comprises a signaling domain of CD28 or 4-1BB.

85. The article of manufacture of any of embodiments 1-84, wherein the T cells are CD4+ or CD8+.

86. The article of manufacture of any of embodiments 1-85, wherein the T cells are primary T cells obtained from a subject.

87. The article of manufacture of any of embodiments 1-86, wherein the article further contains information indicating that the container contains the target number of units.

88. The article of manufacture of any of embodiments 1-87, wherein the container is a first container and the article further comprises additional containers, wherein each of the additional containers comprises a unit dose comprising the target number of units of the T cell composition.

89. The article of manufacture of embodiment 88, wherein the additional containers comprise between about 10 million cells or viable cells per mL and about 70 million cells or viable cells per mL, between about 15 million cells or viable cells and about 60 million cells or viable cells per mL, each inclusive, or greater than 10 million cells or viable cells per mL, greater than 15 million cells or viable cells per mL, or a combination thereof.

90. The article of manufacture of any of embodiments 1-89, wherein the unit dose contains no more than $15\times10^6$ number of CD8+CAR+ cells that are negative for detection with Annexin V or for the active or proform of Caspase 3.

91. The article of manufacture of any of embodiments 1-90, wherein the unit dose further comprises a number of CD4+ cells positive for the CAR, wherein the number is at a ratio of CD8+CAR+ cells of or about 1:1.

92. The article of manufacture composition of any of embodiments 1-91, wherein the T cell composition is produced by a process in which:

the frequency, (1) among CAR+ cells in the composition, (2) among CAR+CD3+ cells in the composition, and/or (3) among CAR+CD8+ cells in the composition, of a cell of a phenotype that indicates a features of biologically active cells and/or of the absence of apoptosis or early or late stages of apoptosis varies by no more than 40%, or no more than 30%, or no more than 20% or no more than 10% or no more than 5% from an average of said frequency in a plurality of T cell compositions produced by the process and/or varies from such average by no more than one standard deviation; or the frequency, (1) among CAR+ cells in the composition, (2) among CAR+CD3+ cells in the composition, and/or (3) among CAR+CD8+ cells in the composition, in the composition, of cell of a phenotype that indicates the absence of apoptosis or early or late stage of apoptosis, varies by no more than 40% or no more than 20% or no more than 10% among a plurality of T cell compositions produced by the process 93. The article of manufacture of embodiment 92, wherein the process comprises:

(a) incubating a population of cells comprising T cells with an agent comprising a nucleic acid molecule encoding the recombinant receptor under conditions to introduce the nucleic acid encoding the recombinant receptor into cells in the population; and (b) stimulating the cells, prior to, during and/or subsequent to said incubation, wherein stimulating comprises incubating the cells in the presence of a stimulating condition that induces a primary signal, signaling, stimulation, activation and/or expansion of the cells.

94. The article of manufacture of embodiment 93, wherein the process further comprises, prior to (a), isolating the population of cells from a biological sample.

95. The article of manufacture of embodiment 94, wherein the isolating comprises, selecting cells based on surface expression of CD3 or based on surface expression of one or both of CD4 and CD8, optionally by positive or negative selection.

96. The article of manufacture of embodiment 94 or embodiment 95, wherein the isolating comprises carrying out immunoaffinity-based selection.

97. The article of manufacture of embodiment 94-96, wherein the biological sample is or comprises a whole blood sample, a buffy coat sample, a peripheral blood mononuclear cells (PBMC) sample, an unfractionated T cell sample, a lymphocyte sample, a white blood cell sample, an apheresis product, or a leukapheresis product.

98. The article of manufacture of any of embodiments 93-97, wherein the stimulating condition comprises incubation with a stimulatory reagent capable of activating one or more intracellular signaling domains of one or more components of a TCR complex and/or one or more intracellular signaling domains of one or more costimulatory molecules.

99. The article of manufacture of embodiment 98, wherein the stimulatory reagent comprises a primary agent that specifically binds to a member of a TCR complex and a secondary agent that specifically binds to a T cell costimulatory molecule.

100. The article of manufacture of embodiment 98 or embodiment 99, wherein the primary agent specifically binds to CD3 and/or the costimulatory molecule is selected from the group consisting of CD28, CD137 (4-1-BB), OX40, or ICOS.

101. The article of manufacture of embodiment 99 or embodiment 100, wherein the primary and secondary agents comprise antibodies and/or are present on the surface of a solid support, optionally a bead.

102. The article of manufacture of any of embodiments 98-101, wherein:

- the stimulatory reagent is one in which it has been determined that a recombinant receptor-dependent activity or an antigen-specific activity, optionally recombinant receptor-dependent or antigen-specific dependent production or accumulation of a proinflammatory cytokine, varies by no more than 40%, or no more than 30%, or no more than 20% or no more than 10% or no more than 5% from an average of a measure of the production or accumulation of the proinflammatory cytokine among a plurality of T cell compositions produced by the process using the stimulatory reagent and/or varies from such average by no more than one standard deviation; and/or
- the stimulatory reagent is one in which it has been determined that a recombinant receptor-dependent activity or an antigen-specific activity, optionally recombinant receptor-dependent or antigen-specific dependent production or accumulation of a proinflammatory cytokine, varies by no more than 40%, or no more than 30%, or no more than 20% or no more than 10% or no more than 5% among a plurality of T cell compositions produced by the process; and/or
- the stimulatory reagent is one in which it has been determined that a recombinant receptor-dependent activity or an antigen-specific activity, optionally recombinant receptor-dependent or antigen-specific dependent production or accumulation of a proinflammatory cytokine, of a cell composition produced using the stimulatory reagent varies by no more than 40%, no more than 30%, no more than 20% or no more than 10% or no more than 5% from a control composition, wherein the control composition and cell composition are produced using the same process, including from the same population of cells, except the control composition is carried out in the presence of a control stimulatory reagent or standard unit for the recombinant receptor-dependent activity.

103. The article of manufacture of embodiment 102, wherein the control stimulatory reagent, when employed in the process, is known to produce a T cell composition in which the recombinant receptor-dependent activity or antigen-specific activity is within an acceptable range of variance.

104. The article of manufacture of any of embodiments 93-103, wherein the stimulating the cells is carried out or is initiated prior to the incubating, optionally for 18-24 hours at or about 37 deg.

105. The article of manufacture of any of embodiments 93-104, wherein the stimulating condition comprises a cytokine selected from among IL-2, IL-15 and IL-7.

106. The article of manufacture of any of embodiments 93-105, wherein the stimulating cells is carried out subsequent to the incubating, optionally for a period of time to achieve a threshold concentration.

107. The article of manufacture of any of embodiments 93-106, further comprising (c) filling a container with all or a portion of the T cell composition, and optionally another solution, to a concentration between about 10 million cells and about 70 million cells per mL, inclusive.

108. The article of manufacture of embodiment 107, wherein the container is filled with another solution and the solution comprises a cryoprotectant, optionally DMSO.

109. The article of manufacture of embodiment 107 or embodiment 108, wherein the concentration is between about 15 and about 60 million cells per mL, inclusive.

110. The article of manufacture of any of embodiments 107-109, wherein the concentration is greater than 10 million cells per mL.

111. The article of manufacture of any of embodiments 107-110, wherein the concentration is greater than 15 million cells per mL.

112. The article of manufacture of any of embodiments 107-111, wherein the concentration of DMSO is or is about or is no more than 7.5%.

113. The article of manufacture of embodiment 107 or embodiment 108, wherein the concentration is greater than 60 million cells per mL.

114. The article of manufacture of any of embodiments 107-108 and 113, wherein the concentration of DMSO is greater than 7.5%, optionally between or about between 7.5% and 9.0%, inclusive.

115. The article of manufacture of any of embodiments 93-114, wherein the agent comprising a nucleic acid molecule encoding the recombinant receptor is a viral vector, optionally a lentiviral vector or a gamma retroviral vector.

116. The article of manufacture of any of embodiments 107-115, wherein the filling is carried out in an automated fashion, optionally in a closed system.

117. The article of manufacture of any of embodiments 93-116, further comprising freezing the cells in the container or storing the container at a temperature less than or about less than 80° C.

118. A method of treatment, the method comprising administering to a subject having a disease or condition a unit dose of a T cell composition comprising cells comprising a recombinant receptor, optionally a chimeric antigen receptor (CAR), that specifically binds to an antigen associated with the disease or condition, wherein the unit dose contains a target number of reference units (RU) within a given range, wherein RU in a given composition is defined by the formula $$RU=A\times B, \text{ wherein:}$$

- A is the number of cells, or multiple, fraction or transformation thereof, of a phenotype present in the given composition or is the average or weighted average of the number of cells, or multiple, fraction or transformation thereof, of two or more phenotypes in the given composition; and B is the value of a parameter, or a multiple or transformation thereof, that indicates or correlates with the degree of a recombinant receptor-dependent, optionally CAR-dependent, activity in the given composition.

119. The method of embodiment 118, wherein A is the number of cells, or multiple or fraction or transformation thereof, of a given phenotype present in the given composition.

120. The method of embodiment 118, wherein A is the average or weighted average of the number of cells, or multiple, fraction or transformation thereof, of two or more phenotypes in the give composition.

121. The method of any of embodiments 118-120, wherein the target number of units is less than threshold number of RUs, which optionally is a safety number of reference units, wherein the safety number of reference units is, with respect to a group of subjects analyzed following treatment with a therapeutic T cell composition comprising the T cells expressing the recombinant receptor, optionally the CAR, the lowest number of reference units of the therapy administered to a subject among those subjects in the group that went on to develop an adverse event.

122. The method of embodiment 121, wherein the adverse event is a severe adverse event, optionally severe neurotoxicity, optionally at or above grade 4 or grade 5 or at least prolonged grade 3 neurotoxicity.

123. The method of embodiment 121 or embodiment 122, wherein the target number of reference units is less than the safety number of reference units by an amount corresponding to a safety factor and/or by an amount within a range of 1.5- to 3-fold, optionally about 2-fold, or by an amount that is a multiple of a standard deviation of a group of subjects that did not develop the adverse event, optionally grade 0-2 neurotoxicity, optionally wherein the multiple is within a range of 1.5- to 3-fold.

124. The method of any of embodiments 118-123, wherein the target number of reference units is at or above a reference efficacy number of reference units, wherein the reference efficacy number is, with respect to a group of subjects analyzed following treatment with a therapeutic T cell composition comprising the recombinant receptor, optionally the CAR, a number of units of the therapy administered to one or more subjects among the group that exhibited a desired therapeutic outcome, optionally a partial response or a complete response (CR).

125. A method of treatment, the method comprising administering to a subject having a disease or condition a unit dose of a T cell composition comprising cells comprising a recombinant receptor, optionally a chimeric antigen receptor (CAR), that specifically binds to an antigen associated with the disease or condition, wherein the unit dose contains at or about (i) a target number of total recombinant receptor-expressing cells or a target number of total CD8+ recombinant receptor-expressing cells or (ii) a target number of reference units (RU) within a given range, which target number is at or below a threshold number of RUs, wherein the unit dose does not contain greater than the threshold number of RUs, wherein the number of RU in a given composition is defined by the formula:

$$RU=A\times B, \text{ wherein}$$

A is the number of cells, or multiple or transformation thereof, of a phenotype present in the given composition or is the average or weighted average of the number of cells, or multiple, fraction or transformation thereof, of two or more phenotypes in the given composition; and B is the value of a parameter, or a multiple, or transformation thereof, that indicates or correlates with the degree of a recombinant receptor-dependent, optionally CAR-dependent, activity in the given T cell composition.

126. The method of embodiment 125, wherein A is the number of cells, or multiple or fraction or transformation thereof, of a given phenotype present in the given composition.

127. The method of embodiment 125, wherein A is the average or weighted average of the number of cells, or multiple, fraction or transformation thereof, of two or more phenotypes in the given composition.

128. The method of any of embodiments 118-127, wherein the target number is the target number of recombinant-receptor expressing cells that are CD3+ or CD8+ that are apoptotic marker negative (−) and CD3+ or CD8+, optionally wherein the apoptotic marker is Annexin V or active Caspase 3.

129. The method of any of embodiments 125-128, wherein the target number of cells in (i) is: between and between about $5.0\times10^6$ and $2.25\times10^7$, $5.0\times10^6$ and $2.0\times10^7$, $5.0\times10^6$ and $1.5\times10^7$, $5.0\times10^6$ and $1.0\times10^7$, $5.0\times10^6$ and $7.5\times10^6$, $7.5\times10^6$ and $2.25\times10^7$, $7.5\times10^6$ and $2.0\times10^7$, $7.5\times10^6$ and $1.5\times10^7$, $7.5\times10^6$ and $1.0\times10^7$, $1.0\times10^7$ and $2.25\times10^7$, $1.0\times10^7$ and $2.0\times10^7$, $1.0\times10^7$ and $1.5\times10^7$, $1.5\times10^7$ and $2.25\times10^7$, $1.5\times10^7$ and $2.0\times10^7$, $2.0\times10^7$ and $2.25\times10^7$ recombinant-receptor expressing cells, each inclusive, optionally recombinant-receptor expressing cells that are CD8+ or that are apoptotic marker negative (−) and CD8+, optionally wherein the apoptotic marker is Annexin V or active Caspase 3.

130. The method of any of embodiments 125-129, wherein the target number of cells in (i) is:

between at least or at least about $5\times10^6$, $6\times10^6$, $7\times10^6$, $8\times10^6$, $9\times10^6$, $10\times10^6$ and about $15\times10^6$ recombinant-receptor expressing cells, each inclusive, optionally recombinant-receptor expressing cells that are CD8+ or that are apoptotic marker negative (−) and CD8+, optionally wherein the apoptotic marker is Annexin V or active Caspase 3;

between at least or at least about $5.55\times10^6$, $6.66\times10^6$, $7.77\times10^6$, $8.99\times10^6$, $1.0\times10^7$, $1.1\times10^7$ and about $1.67\times10^7$ recombinant-receptor expressing cells, each inclusive, optionally recombinant-receptor expressing cells that are CD8+ or that are apoptotic marker negative (−) and CD8+, optionally wherein the apoptotic marker is Annexin V or active Caspase 3;

between at least or at least about $6.25\times10^6$, $7.5\times10^6$, $8.75\times10^6$, $1.0\times10^7$, $1.13\times10^7$, $1.25\times10^7$ and about $1.9\times10^7$ recombinant-receptor expressing cells, each inclusive, optionally recombinant-receptor expressing cells that are CD8+ or that are apoptotic marker negative (−) and CD8+, optionally wherein the apoptotic marker is Annexin V or active Caspase 3; between at least or at least about $7.14\times10^6$, $8.5\times10^6$, $1.0\times10^7$, $1.14\times10^7$, $1.29\times10^7$, $1.42\times10^7$ and about $2.14\times10^7$ recombinant-receptor expressing cells, each inclusive, optionally recombinant-receptor expressing cells that are CD8+ or that are apoptotic marker negative (−) and CD8+, optionally wherein the apoptotic marker is Annexin V or active Caspase 3;

131. The method of any of embodiments 125-130, wherein the target number of cells in (i) is between at least or at least about $5\times10^6$, $6\times10^6$, $7\times10^6$, $8\times10^6$, $9\times10^6$, $10\times10^6$ and about $15\times10^6$ recombinant-receptor expressing cells that are apoptotic marker negative (−) and CD8+, each inclusive, optionally wherein the apoptotic marker is Annexin V or active Caspase 3.

132. The method of any of embodiments 125-130, wherein the target number of cells in (i) is between at least or at least about $6.25\times10^6$, $7.5\times10^6$, $8.75\times10^6$, $1.0\times10^7$, $1.13\times10^7$, $1.25\times10^7$ and about $1.9\times10^7$ recombinant-receptor expressing cells that are CD8+, each inclusive.

133. The method of any of embodiments 118-132, wherein the target reference number of RUs is less than a reference safety number of RUs, wherein the reference safety number of RUs is, with respect to a group of subjects analyzed following treatment with a therapeutic T cell composition comprising the T cells expressing the recombinant receptor, optionally the CAR, the lowest number of reference units of the therapy administered to a subject among those subjects in the group that went on to develop an adverse event.

134. The method of embodiment 133, wherein the adverse event is a severe adverse event, optionally severe neurotoxicity at or above grade 4 or grade 5 or at least prolonged grade 3 neurotoxicity.

135. The method of embodiment 133 or embodiment 134, wherein the target reference number of RUs is less than the reference safety number of units by an amount corresponding to a safety factor or by at least 2-fold.

136. The method of any of embodiments 118-135, wherein the target number of reference units is at or above a reference efficacy number of reference units, wherein the reference efficacy number is, with respect to a group of subjects analyzed following treatment with a T cell composition comprising the recombinant receptor, optionally the CAR, a number of reference units of the therapy administered to one or more subjects among the group that exhibited a desired therapeutic outcome, optionally a complete response (CR).

137. The method of any one of embodiments 118-136, wherein A is the number of cells of a phenotype present in the given composition and B is the value of a parameter that indicates or correlates with the degree of recombinant receptor-dependent activity in the given composition.

138. The method of any one of embodiments 118-137, wherein A and/or B is a transformation of the number or value, respectively, wherein the transformation comprises a logarithmic transformation, power transformation or logit transformation.

139. The method of any one of embodiments 118-138, wherein A is a number of cells of a phenotype present in the given composition and B is a multiple or transformation of the value of the parameter that indicates or correlates with the degree of CAR-dependent activity in the given T cell composition, optionally wherein B is a logarithmic transformation of the value.

140. The method of embodiment 138 or embodiment 139, wherein the logarithmic transformation is a common log ($\log_{10}(x)$), a natural log ($\ln(x)$) or a binary log($\log_2(x)$).

141. The method of any of embodiments 118-140, wherein A is the number of viable cells in the composition and/or is the number of cells that are not apoptotic, do not exhibit a factor indicative of early apoptosis or of apoptosis, are not in the early stages of apoptosis, or are not in the late stages of apoptosis, and/or is the number of cells of a particular differentiation state, and/or is the number of cells having a memory/stem-like attribute or is a multiple or transformation thereof.

142. The method of any of embodiments 118-141, wherein the phenotype comprises positive expression of a surface marker that is one or more of CD3, CD4 or CD8 and/or comprises positive expression of the recombinant receptor, optionally the CAR, or a surrogate marker for expression of the recombinant receptor.

143. The method of embodiment 142, wherein the phenotype is CD3+CAR, CD4+/CAR+, CD8+/CAR+.

144. The method of any of embodiments 118-143, wherein the phenotype comprises absence of a factor indicative of apoptosis or one or more steps in an apoptotic cascade or pathway, optionally expression of a marker of apoptosis.

145. The method of any of embodiments 118-144, wherein the phenotype comprises negative expression of a marker of apoptosis, optionally a marker of early apoptosis or late apoptosis.

146. The method of embodiment 145, wherein the marker of apoptosis is surface phosphatidylserine and/or is detected with Annexin V, or is an active or proform of a caspase, optionally an active or proform of Caspase 3.

147. The method of any of embodiments 118-146, wherein the phenotype comprises Annexin-.

148. The method of any of embodiments 118-147, wherein the phenotype comprises an indicator of production of one or a combination of cytokines, optionally non-specific to the antigen or the recombinant receptor and/or that is polyclonally produced, wherein the one or more cytokines is IL-2, IL-13, IL-17, IFN-gamma or TNF-alpha.

149. The method of embodiment 148, wherein the indicator of production is measured in an assay, optionally an intracellular cytokine staining assay, comprising incubating a sample of the T cell composition with a polyclonal agent, an antigen-specific agent or an agent that binds the recombinant receptor, optionally CAR.

150. The method of embodiment 148 or embodiment 149, wherein the agent is or comprises PMA and ionomycin or is or comprises a T cell receptor or T cell receptor complex agonist.

151. The method of any of embodiments 118-150, wherein the phenotype comprises negative expression of an activation marker, wherein the activation marker is selected from among CD25, CD127, LAG3, Ki67 and combinations thereof.

152. The method of any of embodiments 118-151, wherein the phenotype comprises negative expression of an exhaustion marker, wherein the exhaustion maker is a PD1 or FOXP3 gene product or a combination thereof.

153. The method of any of embodiments 118-152, wherein the phenotype comprises a naïve phenotype or a memory phenotype, optionally wherein the memory phenotype comprises a T effector memory phenotype, a T central memory phenotype, or a T effector memory phenotype expressing CD45RA (Temra).

154. The method of any of embodiments 118-153, wherein A is the total number of T cells, total number of CD3+ cells, total number of CD4+ or CD8+ cells, total number of CD3+CAR+ cells, total number of CD8+CAR+ cells, total number of CD4+CAR+, or total number of live or viable cells of any of the foregoing, or a multiple or transformed value thereof.

155. The method of any of embodiments 118-154, wherein A is the total number of CD3+ cells, total number of CD8+, total number of CD3+CAR+ cells, total number of CD8+CAR+ cells, or total number of live or viable cells of any of the foregoing, or a multiple or transformed value thereof.

156.

The method of any of embodiments 118-155, wherein A is the total number of apoptotic marker negative (−) cells that are CD3+CAR+ cells, total number of apoptotic marker negative (−) cells that are CD4+CAR+, total number of apoptotic marker negative (−) cells that are CD8+CAR+ cells, or a multiple or transformed value thereof, wherein the apoptotic marker is Annexin V or Caspase.

157. The method of any of embodiments 118-156, wherein A is the total number of apoptotic marker—CD3+ CAR+ cells or the total number of apoptotic marker—CD8+ CAR+ cells, wherein the apoptotic marker is Annexin V or Caspase 3

158. A method of treatment, the method comprising administering to a subject having a disease or condition a unit dose of a T cell composition comprising cells comprising a recombinant receptor, optionally a chimeric antigen receptor (CAR), that specifically binds to an antigen associated with the disease or condition, wherein the unit dose contains target dose of the therapeutic T cell composition:

(i) if the value of a parameter that indicates or correlates with the degree of recombinant receptor-dependent, optionally CAR-dependent, activity of the composition is at or greater than a threshold value, the target dose is a first number (or is within a first range of numbers) of cells of a given phenotype of the composition;

(ii) if the value of the parameter is less than the threshold value, the target dose is a second number (or is within a second range of numbers) of cells of a given phenotype of the composition wherein the first number (or first range) is lower than the second number (or second range).

159. The method of embodiment 158, wherein the threshold value of the recombinant receptor-dependent activity is less than a reference safety value, wherein the reference safety value is, with respect to a group of subjects analyzed following treatment with a therapeutic T cell composition comprising T cells expressing the recombinant receptor, optionally the CAR, the lowest value of the CAR-dependent activity of the therapeutic composition administered to a subject among those subjects in the group that went on to develop an adverse event.

160. The method of embodiment 159, wherein the adverse event is a severe adverse event, optionally severe neurotoxicity at or above grade 4 or grade 5 or at least prolonged grade 3 neurotoxicity.

161. The method of embodiment 159 or embodiment 160, wherein the threshold value is less than the reference safety value by an amount corresponding to a safety factor or by at least 2-fold.

162. The method of any of embodiments 159-161, wherein the first number is lower than the second number by greater than or greater than about 1.5-fold, 2.0-fold, 3.0-fold, 4.0-fold, 5.0-fold, 6.0-fold, 7.0-fold, 8.0-fold, 9.0-fold, 10.0-fold or more.

163. The method of any of embodiments 118-162 wherein the recombinant receptor-dependent activity is a measure of the production or accumulation of a proinflammatory cytokine, optionally, one of or a combination of TNF-alpha, IFN-gamma, IL-2 and IL-10.

164. The method of any one of embodiments 118-163, wherein the parameter is a measure of one or more factors or a normalized value thereof.

165. The method of embodiment 164, wherein the measure is in an assay involving culture or incubation for a fixed time, optionally 24 hours, of a given composition or sample thereof in the presence of the antigen, cells expressing the antigen and/or agent that specifically binds to the recombinant receptor, optionally the CAR.

166. The method of embodiment 165, wherein the assay is an ELISA.

167. The method of any of embodiments 164-166, wherein the measure of the factor is:

(i) concentration, relative concentration, amount, or relative amount of the factor; or (ii) amount or relative amount of the factor per unit of input cells of the given composition, or (iii) amount or relative amount of the factor per unit of input cells of the given composition per unit of time, optionally one hour; or (iv) a level indicative of any of (i)-(iii).

168. The method of any of embodiments 164-167, wherein the one or more factors is one or a combination of soluble factors, optionally one or a combination of cytokines, chemokines or soluble receptors, optionally soluble costimulatory receptors.

169. The method of any of embodiments 164-168, wherein the one or more factors is one of or a combination of a pro-inflammatory cytokines, Th2 cytokines and Th17 cytokines.

170. The method of any of embodiments 164-169, wherein the one or more factors is one of or a combination of IL-2, IFN-gamma, TNF-alpha, IL4, IL-5, IL-10, IL-13, GM-CSF, sCD137, MIP1a and M1Pb.

171. The method of any of embodiments 164-170, wherein the one or more factors is one of or a combination of IL-2, IFN-gamma, TNF-alpha and IL-10.

172. The method of any of embodiments 168-171, wherein the one or more factors is a combination of any of two or more of the foregoing soluble factors and the parameter is an arithmetic mean or geometric mean of the measure of the two or more factors.

173. The method of any embodiments 168-172, wherein the parameter is an arithmetic mean or geometric mean of a measure, optionally amount or concentration, of at least two of TNF-alpha, IFN-gamma and IL-2 or of TNF-alpha, IFN-gamma and IL-2.

174. The method of any of embodiments 164-173, wherein the parameter is the normalized value of the measure, wherein normalization is as compared to a reference measure of the factor.

175. The article or manufacture of embodiment 174, wherein the reference measure is the average of the measure among a plurality, optionally at least 10, at least 15, at least 20, of reference therapeutic T cell compositions comprising the chimeric antigen receptor (CAR) in which:

(i) each of the reference therapeutic T cell compositions has been observed or determined to result in an acceptable safety profile following administration to a subject, optionally wherein the subject has a disease or condition expressing or associated with the antigen; and/or (ii) each of the reference therapeutic T cell compositions has been observed or determined to result in a desired efficacy following administration to a subject, optionally wherein the subject has a disease or condition expressing or associated with the antigen.

176. The method of embodiment 175, wherein the acceptable safety profile is absence of observed grade 2 or higher or absence of grade 3 or higher, neurotoxicity.

177. The method of embodiment 175 or embodiment 176, wherein the acceptable safety profile is the absence of observed grade 3 or higher neurotoxicity.

178. The method of any of embodiment 177, wherein the efficacy is a partial response or is a complete response (CR).

179. The method of embodiment 178, wherein the reference measure is the measure, by the same assay, of the factor in a reference T cell composition produced by the same method as the therapeutic T cell composition but not expressing the recombinant receptor, optionally the CAR, not specifically recognizing the antigen and/or not expressing any recombinant receptor, optionally any CAR.

180. The method of embodiment 179, wherein the parameter is normalized to control for patient-specific variation of the measure of the one or more factors.

181. The method of embodiment 179 or embodiment 180, wherein the parameter is a normalized value of the measure of the factor, compared to the same measure in the same assay, of a control factor, wherein the level of the control factor in a therapeutic T cell composition is known not to, or has been observed not to, indicate or correlate or significantly correlate with an adverse event or toxicity outcome or likelihood or risk thereof, wherein the adverse event or toxicity outcome optionally is severe neurotoxicity.

182. The method of embodiment 181, wherein the control factor is or comprises a factor that is not statistically correlated and/or does not correlate to development of the adverse event among a plurality of subjects that went on to develop the adverse event following administration of the T cell composition, optionally the control factor is one of or a combination of IL-5, IL-13, GM-CSF, and IL-6, optionally wherein the measure of the control factor is an arithmetic mean or geometric mean of two or more of the foregoing.

183. The method of any of embodiments 118-182, wherein the parameter does not comprise cytolytic activity or a measure thereof.

184. The method of any of embodiments 118-183, wherein the parameter does not comprise recombinant receptor-dependent or antigen-specific cytolytic activity or a measure thereof.

185. The method of any of embodiments 118-184, wherein:

the phenotype is CD8+ CAR+ cells or apoptotic marker -CD8+CAR+ cells, optionally wherein the apoptotic marker is Annexin V or active Caspase 3; and the parameter is a measure of a pro-inflammatory cytokine, which optionally is one of or a combination of TNF-alpha, IL-2, and IFN-gamma, or is a normalized value thereof.

186. The method of any of embodiments 118-185, wherein the adverse event is grade 4 or 5 neurotoxicity and the threshold value:

is or is about $1.75\times10^7$ if A is apoptotic marker negative (−) and CD8+CAR+ and B is TNF-alpha or a normalized value thereof;

is or is about $2.19\times10^7$ if A is CD8+CAR+ and B is TNF-alpha or a normalized value thereof;

is or is about $1.25\times10^7$ if A is apoptotic marker negative (−) CD8+CAR+ and if B is IFN-gamma or a normalized value thereof;

is or is about $1.56\times10^7$ if A is CD8+CAR+ and B is IFN-gamma or a normalized value thereof;

is or is about $1.5\times10^7$ if A is apoptotic marker negative (−) CD8+CAR+ and if B is IL-2 or a normalized value thereof;

is or is about $1.88\times10^7$ if A is CD8+CAR+ and B is IL-2 or a normalized value thereof;

is or is about $1.5\times10^7$ if A is apoptotic marker negative (−) CD8+CAR+ and if B is TNF-alpha and IFN-gamma or a normalized value thereof;

is or is about $1.88\times10^7$ if A is CD8+CAR+ and B is TNF-alpha and IFN-gamma or a normalized value thereof;

is or is about $2.0\times10^7$ if A is apoptotic marker negative (−) CD8+CAR+ and if B is TNF-alpha and IL-2 or a normalized value thereof;

is or is about $2.5\times10^7$ if A is CD8+CAR+ and B is TNF-alpha and IL-2 or a normalized value thereof;

is or is about $1.25\times10^7$ if A is apoptotic marker negative (−) CD8+CAR+ and if B is IFN-gamma and IL-2 or a normalized value thereof;

is or is about $1.56\times10^7$ if A is CD8+CAR+ and B is IFN-gamma and IL-2 or a normalized value thereof;

is or is about $1.75\times10^7$ if A is apoptotic marker negative (−) CD8+CAR+ and if B is TNF-alpha, IFN-gamma and IL-2 or a normalized value thereof;

is or is about $2.19\times10^7$ if A is CD8+CAR+ and B is TNF-alpha, IFN-gamma and IL-2 or a normalized value thereof, optionally wherein the apoptotic marker is Annexin V or active Caspase 3.

187. The method of any of embodiments 118-186, wherein the adverse event is grade 4 or 5 neurotoxicity and the given range of the target reference units:

is between or about between $2.0\times10^5$ and $1.75\times10^7$, inclusive, if A is apoptotic marker negative (−) and CD8+CAR+ and B is TNF-alpha or a normalized value thereof;

is between or about between $2.5\times10^5$ and $2.19\times10^7$, inclusive, if A is CD8+CAR+ and B is TNF-alpha or a normalized value thereof;

is between or about between $4\times10^5$ and $1.25\times10^7$, inclusive, if A is apoptotic marker negative (−) CD8+CAR+ and if B is IFN-gamma or a normalized value thereof;

is between or about between $5\times10^6$ and $1.56\times10^7$, inclusive, if A is CD8+CAR+ and B is IFN-gamma or a normalized value thereof;

is between or about between $2.0\times10^5$ and $1.5\times10^7$, inclusive, if A is apoptotic marker negative (−) CD8+CAR+ and if B is IL-2 or a normalized value thereof;

is between or about between $2.5\times10^5$ and $1.88\times10^7$, inclusive, if A is CD8+CAR+ and B is IL-2 or a normalized value thereof;

is between or about between $3.0\times10^5$ and $1.5\times10^7$, inclusive, if A is apoptotic marker negative (−) CD8+CAR+ and if B is TNF-alpha and IFN-gamma or a normalized value thereof;

is between or about between $3.75\times10^5$ and $1.88\times10^7$, inclusive, if A is CD8+CAR+ and B is TNF-alpha and IFN-gamma or a normalized value thereof;

is between or about between $3.0\times10^5$ and $2.0\times10^7$, inclusive, if A is apoptotic marker negative (−) CD8+CAR+ and if B is TNF-alpha and IL-2 or a normalized value thereof;

is between or about between $3.75\times10^5$ and $2.5\times10^7$, inclusive, if A is CD8+CAR+ and B is TNF-alpha and IL-2 or a normalized value thereof;

is between or about between $4.0\times10^5$ and $1.25\times10^7$, inclusive, if A is apoptotic marker negative (−) CD8+ CAR+ and if B is IFN-gamma and IL-2 or a normalized value thereof;

is between or about between $5.0\times10^5$ and $1.56\times10^7$, inclusive, if A is CD8+CAR+ and if B is IFN-gamma and IL-2 or a normalized value thereof;

is between or about between $4.0\times10^5$ and $1.75\times10^7$, inclusive, if A is apoptotic marker negative (−) CD8+CAR+ and if B is TNF-alpha, IFN-gamma and IL-2 or a normalized value thereof;

is between or about between $5.0\times10^5$ and $2.19\times10^7$, inclusive, if A is CD8+CAR+ and B is TNF-alpha, IFN-gamma and IL-2 or a normalized value thereof, optionally wherein the apoptotic marker is Annexin V or active Caspase 3.

188. The method of any of embodiments 118-185, wherein the adverse event is at least prolonged grade 3 neurotoxicity and the threshold value:

is or is about $1.0\times10^6$ if A is apoptotic marker negative (−) and CD8+CAR+ and B is TNF-alpha or a normalized value thereof;

is or is about $1.25\times10^6$ if A is CD8+CAR+ and B is TNF-alpha or a normalized value thereof;

is or is about $2.0\times10^6$ if A is apoptotic marker negative (−) CD8+CAR+ and if B is IFN-gamma or a normalized value thereof;

is or is about $2.5\times10^6$ if A is CD8+CAR+ and B is IFN-gamma or a normalized value thereof;

is or is about $3.0\times10^6$ if A is apoptotic marker negative (−) CD8+CAR+ and if B is IL-2 or a normalized value thereof;

is or is about $3.75\times10^6$ if A is CD8+CAR+ and B is IL-2 or a normalized value thereof;

is or is about $1.5\times10^6$ if A is apoptotic marker negative (−) CD8+CAR+ and if B is TNF-alpha and IFN-gamma or a normalized value thereof;

is or is about $1.88\times10^6$ if A is CD8+CAR+ and B is TNF-alpha and IFN-gamma or a normalized value thereof;

is or is about $2.5\times10^6$ if A is apoptotic marker negative (−) CD8+CAR+ and if B is TNF-alpha and IL-2 or a normalized value thereof;

is or is about $3.12\times10^6$ if A is CD8+CAR+ and B is TNF-alpha and IL-2; or a normalized value thereof is or is about $3.0\times10^6$ if A is apoptotic marker negative (−) CD8+CAR+ and if B is IFN-gamma and IL-2 or a normalized value thereof;

is or is about $3.75\times10^6$ if A is CD8+CAR+ and B is IFN-gamma and IL-2 or a normalized value thereof;

is or is about $2.0\times10^6$ if A is apoptotic marker negative (−) CD8+CAR+ and if B is TNF-alpha, IFN-gamma and IL-2 or a normalized value thereof;

is or is about $2.5\times10^6$ if A is CD8+CAR+ and B is TNF-alpha, IFN-gamma and IL-2 or a normalized value thereof, optionally wherein the apoptotic marker is Annexin V or active Caspase 3.

189. The method of any of embodiments 118-185 and 188, wherein the adverse event is at least prolonged grade 3 and the given range of the target reference units:

is between or about between $3.0\times10^5$ and $1.0\times10^6$, inclusive, if A is apoptotic marker negative (−) and CD8+CAR+ and B is TNF-alpha or a normalized value thereof;

is between or about between $3.75\times10^5$ and $1.25\times10^6$, inclusive, if A is CD8+CAR+ and B is TNF-alpha or a normalized value thereof;

is between or about between $4\times10^5$ and $2.0\times10^6$, inclusive, if A is apoptotic marker negative (−) CD8+CAR+ and if B is IFN-gamma or a normalized value thereof;

is between or about between $5\times10^6$ and $2.5\times10^6$, inclusive, if A is CD8+CAR+ and B is IFN-gamma or a normalized value thereof;

is between or about between $2.0\times10^5$ and $3.0\times10^6$, inclusive, if A is apoptotic marker negative (−) CD8+CAR+ and if B is IL-2 or a normalized value thereof;

is between or about between $2.5\times10^5$ and $3.75\times10^6$, inclusive, if A is CD8+CAR+ and B is IL-2 or a normalized value thereof;

is between or about between $3.0\times10^5$ and $1.5\times10^6$, inclusive, if A is apoptotic marker negative (−) CD8+CAR+ and if B is TNF-alpha and IFN-gamma or a normalized value thereof;

is between or about between $3.75\times10^5$ and $1.88\times10^6$, inclusive, if A is CD8+CAR+ and B is TNF-alpha and IFN-gamma or a normalized value thereof;

is between or about between $3.0\times10^5$ and $2.5\times10^6$, inclusive, if A is apoptotic marker negative (−) CD8+CAR+ and if B is TNF-alpha and IL-2 or a normalized value thereof;

is between or about between $3.75\times10^5$ and $3.12\times10^6$, inclusive, if A is CD8+CAR+ and B is TNF-alpha and IL-2 or a normalized value thereof;

is between or about between $4.0\times10^5$ and $3.0\times10^6$, inclusive, if A is apoptotic marker negative (−) CD8+CAR+ and if B is IFN-gamma and IL-2 or a normalized value thereof;

is between or about between $5.0\times10^5$ and $3.75\times10^6$, inclusive, if A is CD8+CAR+ and B is IFN-gamma and IL-2 or a normalized value thereof;

is between or about between $4.0\times10^5$ and $2.0\times10^6$, inclusive, if A is apoptotic marker negative (−) CD8+CAR+ and if B is TNF-alpha, IFN-gamma and IL-2 or a normalized value thereof;

is between or about between $5.0\times10^5$ and $2.5\times10^6$, inclusive, if A is CD8+CAR+ and B is TNF-alpha, IFN-gamma and IL-2 or a normalized value thereof, optionally wherein the apoptotic marker is Annexin V or active Caspase 3.

190. The method of any of embodiments 118-189, wherein the therapeutic T cell composition comprises between about 10 million cells per mL and about 70 million cells per mL or between about 10 million viable cells per mL and about 70 million viable cells per mL, each inclusive.

191. The method of any of embodiments 118-190, wherein the therapeutic T cell composition comprises between about 15 million cells or viable cells per mL and about 60 million cells or viable cells per mL, each inclusive.

192. The method of any of embodiments 118-191, wherein the T cell composition comprises greater than 10 million cells or viable cells per.

193. The method of any of embodiments 118-192, wherein the therapeutic T cell composition comprises greater than 15 million cells or greater than 15 million cells per mL.

194. The method of any of embodiments 118-193, wherein the disease or condition is a cancer, optionally a myeloma, lymphoma or leukemia.

195. The method of embodiment 194, wherein the disease or condition is a B cell malignancy, optionally a B cell malignancy selected from the group consisting of acute lymphoblastic leukemia (ALL), adult ALL, chronic lymphoblastic leukemia (CLL), non-Hodgkin lymphoma (NHL), and Diffuse Large B-Cell Lymphoma (DLBCL).

196. The method of any of embodiments 118-195, wherein the antigen is CD19, CD22, ROR1, Igkappa, Her2, L1-CAM, CD20, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acetylcholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1), and cyclin A1 (CCNA1).

197. The method of any of embodiments 118-196, wherein the recombinant receptor is a CAR.

198. The method of embodiment 197, wherein the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3) chain; and/or wherein the CAR further comprises a costimulatory signaling region, which optionally comprises a signaling domain of CD28 or 4-1BB.

199. The method of any of embodiments 118-198, wherein the T cells are CD4+ or CD8+.

200. The method of any of embodiments 118-199, wherein the T cells are primary T cells, optionally wherein the T cells are autologous to the subject or allogeneic to the subject.

201. The method of any of embodiments 118-200, wherein the unit dose contains no more than $15\times10^6$ number of CD8+CAR+ cells that are negative for detection with Annexin V or for the active or proform of Caspase 3.

202. The method of any of embodiments 118-201, wherein the unit dose further comprises a number of CD4+ cells positive for the CAR, wherein the number is at least or is at a ratio of CD8+CAR+ cells of or about 1:1.

203. The method of any of embodiments 118-202, wherein the method further comprises administering a lymphodepleting chemotherapy prior to administration of the T cell composition and/or wherein the subject has received a lymphodepleting chemotherapy prior to administration of the T cell composition.

204. The method of embodiment 203, wherein the lymphodepleting chemotherapy comprises administering fludarabine and/or cyclophosphamide to the subject.

205. The method of embodiment 204, wherein the cyclophosphamide is administered in an amount from or from 30 mg/kg to 60 mg/kg and/or the fludarabine is administered in an amount from or from about 25 mg/m2 to 30 mg/m2.

206. The method of embodiment 204, wherein:

the cyclophosphamide is administered in an amount from or from 900 to 1000 mg and/or the fludarabine is administered in an amount from or from about 25 mg/m2 to 30 mg/m2; or the cyclophosphamide is administered in an amount from or from about 300 mg/m2 and/or the fludarabine is administered in an amount from or from about 30 mg/m2.

207. The method of embodiment 204, wherein the cyclophosphamide is administered in an amount from or from about 500 mg/m2 and/or the fludarabine is administered in an amount from or from about 30 mg/m2.

208. The method of embodiment 204, wherein the cyclophosphamide is administered in an amount from or from about 500 mg/m2 and/or the fludarabine is administered in an amount from or from about 60 mg/m2.

209. The method of any of embodiments 203-208, wherein the lymphodepleting therapy is administered once per day for three consecutive days.

210. The method of any of embodiments 203-209, wherein the lymphodepleting therapy is administered on the 5th day prior to, the 4th day prior to, and the 3rd day prior to administration of the T cell composition.

211. The method of any of embodiments 203-210, wherein the lymphodepleting therapy is administered once daily for 3-5 days, optionally once daily for 3 days.

212. The method of any of embodiments 204-211, wherein the fludarabine and the cyclophosphamide are administered sequentially.

213. The method of any of embodiments 204-211, wherein the fludarabine and the cyclophosphamide are administered concurrently.

214. A method of assaying a therapeutic composition comprising a unit dose of a T cell composition, the method comprising:

(a) assaying a sample from a T cell composition comprising T cells derived from a subject having a disease or condition and transduced with a nucleic acid encoding a recombinant receptor, optionally a chimeric antigen receptor (CAR), that specifically binds to an antigen associated with a disease or condition, wherein the assay determines B for the cell composition, wherein B is the value of a parameter, or a multiple or transformation thereof, that indicates or correlates with the degree of a recombinant receptor-dependent activity in the given composition; and (b) assessing potency of the cell composition based on B and/or assessing whether the composition is above a lower specification limit (LSL) for B or below an upper specification limit (USL) for B.

215. A method of assaying a therapeutic T composition, the method comprising assessing a sample from a T cell composition comprising T cells comprising a recombinant receptor that specifically binds to an antigen associated with a disease or condition for potency of the cell composition based on B and/or assessing whether the composition is above a lower specification limit (LSL) for B or below an upper specification limit (USL) for B.

216. The method of embodiment 214 or embodiment 215, wherein the product is released for treatment of the subject only if the composition is below the USL for B.

217. The method of embodiment 214 or embodiment 215, wherein if B is above the USL, recommending not administering the composition to the subject or altering the number of cells administered to the subject to an adjusted unit dose, wherein the adjusted unit dose contains a target number of cells or a target number of reference units (RUs) of the T cell composition, wherein RU in a given composition is defined by the formula $RU=A\times B$, wherein:

A is the number of cells, or multiple, fraction or transformation thereof, of a phenotype present in the given composition or is the average or weighted average of the number of cells, or multiple, fraction or transformation thereof, of two or more phenotypes in the given composition; and B is the value of a parameter, or a fraction or multiple or transformation thereof, that indicates or correlates with the degree of a recombinant receptor-dependent, optionally CAR-dependent, activity in the given composition.

218. The method of any of embodiments 214-217, wherein A is the number of cells, or multiple or fraction or transformation thereof, of a given phenotype present in the given composition.

219. The method of any of embodiments 214-217, wherein A is the average or weighted average of the number of cells, or multiple, fraction or transformation thereof, of two or more phenotypes in the give composition.

220. The method of any of embodiments 214-219, wherein the target number of units is less than a threshold number of units, which optionally is a safety number of reference units, wherein, the safety number of reference units is, with respect to a group of subjects analyzed following treatment with a therapeutic T cell composition comprising the T cells expressing the recombinant receptor, optionally the CAR, the lowest number of reference units of the therapy administered to a subject among those subjects in the group that went on to develop an adverse event.

221. The method of embodiment 220, wherein the adverse event is a severe adverse event, optionally severe neurotoxicity, optionally at or above grade 4 or grade 5 or at least prolonged grade 3 neurotoxicity.

222. The method of embodiment 220 or embodiment 221, wherein the target number of reference units is less than the safety number of reference units by an amount corresponding to a safety factor and/or by an amount within a range of 1.5- to 3-fold, optionally about 2-fold, or by an amount that is a multiple of a standard deviation of a group of subjects that did not develop the adverse event, optionally grade 0-2 neurotoxicity, optionally wherein the multiple is within a range of 1.5- to 3-fold.

223. The method of any of embodiments 217-222, wherein the target number of reference units is at or above a reference efficacy number of reference units, wherein the reference efficacy number is, with respect to a group of subjects analyzed following treatment with a therapeutic T cell composition comprising the recombinant receptor, optionally the CAR, a number of units of the therapy administered to one or more subjects among the group that exhibited a desired therapeutic outcome, optionally a partial response or a complete response (CR).

224. The method of any of embodiments 217-223, wherein the adjusted unit dose is less than, optionally less than 1.5-fold, less than 2-fold, less than 3-fold, less than 4-fold, the average unit dose of a group of subjects treated with a therapeutic T cell composition comprising the T cells expressing the recombinant receptor, optionally the CAR.

225. The method of any of embodiments 214-224, wherein a sample of the T cell composition, optionally a cryopreserved sample, is assessed after administration of the T cell composition to the subject.

226. The method of any of embodiments 214-225, wherein if B is above the USL, the subject is determined to be at risk of toxicity.

227. The method of any of embodiments 214-225, wherein if B is above the USL, a subject administered the composition is monitored and/or is treated with an agent to ameliorate or reduce the likelihood of a toxicity outcome or cytokine release syndrome following administration of the cell composition and optionally prior to the development of a sign or symptom of the toxicity outcome.

228. A method of assessing a risk of toxicity to a therapeutic T cell composition, the method comprising:

(a) assessing a sample from a T cell composition having been administered to a subject for reference units (RU) within a given range, the T cell composition comprising T cells comprising a recombinant receptor that specifically binds to an antigen associated with a disease or condition, wherein RU in a given composition is defined by the formula:

$$RU = A \times B, \text{ wherein:}$$

A is the number of cells, or multiple, fraction or transformation thereof, of cells of a phenotype present in the given composition or is the average or weighted average of the number of cells, or multiple, fraction or transformation thereof, of two or more phenotypes in the given composition; and B is the value of a parameter, or a fraction or multiple or transformation thereof, that indicates or correlates with the degree of a recombinant receptor-dependent, optionally CAR-dependent, activity in the given composition; and (b) comparing the RUs to a reference safety number of RUs, wherein the comparison indicates whether the subject is or is not at risk for developing an adverse event, optionally a severe adverse event, optionally severe neurotoxicity at or above grade 4 or grade 5 or at least prolonged grade 3 neurotoxicity.

229. The method of embodiment 228, wherein A is the number of cells, or multiple or fraction or transformation thereof, of a given phenotype present in the given composition.

230. The method of embodiment 229, wherein A is the average or weighted average of the number of cells, or multiple, fraction or transformation thereof, of two or more phenotypes in the given composition.

231. The method of any of embodiments 228-230, wherein the reference safety number of RUs is, with respect to a group of subjects analyzed following treatment with a therapeutic T cell composition comprising the T cells expressing the recombinant receptor, optionally the CAR, the lowest number of reference units of the therapy administered to a subject among those subjects in the group that went on to develop the adverse event.

232. The method of any of embodiments 228-231, wherein if the comparison indicates the RU is above the reference safety RU, the subject administered the composition is monitored and/or is treated with an agent to ameliorate or reduce the likelihood of a toxicity outcome or cytokine release syndrome following administration of the cell composition and optionally prior to the development of a sign or symptom of the toxicity outcome.

233. A method of producing a therapeutic composition comprising a unit dose of a T cell composition, the method comprising:

(a) assaying a T cell composition comprising T cells derived from a subject having a disease or condition and transduced with a nucleic acid encoding a recombinant receptor, optionally a chimeric antigen receptor (CAR), that specifically binds to an antigen associated with a disease or condition, wherein the assay determines B for the cell composition, wherein B is the value of a parameter, or a multiple or transformation thereof, that indicates or correlates with the degree of a recombinant receptor-dependent, optionally CAR-dependent, activity in the given composition; and (b) filling a container with all or a portion of the composition and optionally another solution to achieve a unit dose of the T cell composition, wherein the unit dose contains a target number of reference units (RU) of the T cell composition, wherein RU in a given composition is defined by the formula:

RU=A×B, wherein A is the number of cells, or multiple, fraction or transformation thereof, of a phenotype present in the given composition or is the average or weighted average of the number of cells, or multiple, fraction or transformation thereof, of two or more phenotypes in the given composition.

234. A method of producing a therapeutic composition comprising a unit dose of a T cell composition, the method comprising filling a container with all or a portion of a T cell composition comprising T cells comprising a recombinant receptor that specifically binds an antigen associated with a disease or condition, and optionally another solution, to achieve a unit dose of the T cell composition, wherein the unit dose contains a target number of reference units (RU) of the T cell composition, wherein RU in a given composition is defined by the formula:

$RU=A\times B$, wherein

A is the number of cells, or multiple, fraction or transformation thereof, of a phenotype present in the given composition or is the average or weighted average of the number of cells, or multiple, fraction or transformation thereof, of two or more phenotypes in the given composition; and B is the value of a parameter, or a multiple or transformation thereof, that indicates or correlates with the degree of a recombinant receptor-dependent, optionally CAR-dependent, activity in the given composition.

235. The method of embodiment 233 or embodiment 234, wherein A is the number of cells, or multiple or fraction or transformation thereof, of a given phenotype present in the given composition.

236. The method of embodiment 233 or embodiment 234, wherein A is the average or weighted average of the number of cells, or multiple, fraction or transformation thereof, of two or more phenotypes in the given composition.

237. The method of any one of embodiments 217-236, wherein A is the number of cells of a phenotype present in the given composition and B is the value of a parameter that indicates or correlates with the degree of recombinant receptor-dependent activity in the given composition.

238. The method of any one of embodiments 217-237, wherein A and/or B is a transformation of the number or value, respectively, wherein the transformation comprises a logarithmic transformation, power transformation or logit transformation.

239. The method of any one of embodiments 217-238, wherein A is a number of cells of a phenotype present in the given composition and B is a multiple or transformation of the value of the parameter that indicates or correlates with the degree of CAR-dependent activity in the given T cell composition, optionally wherein B is a logarithmic transformation of the value.

240. The method of embodiment 238 or embodiment 239, wherein the logarithmic transformation is a common log ($\log_{10}(x)$), a natural log($\ln(x)$) or a binary log($\log_2(x)$).

241. The method of any of embodiments 217-240, wherein A is the number of viable cells in the composition and/or is the number of cells that are not apoptotic, do not exhibit a factor indicative of early apoptosis or of apoptosis, are not in the early stages of apoptosis, or are not in the late stages of apoptosis, and/or is the number of cells of a particular differentiation state, and/or is the number of cells having a memory/stem-like attribute or is a multiple or transformation thereof.

242. The method of any of embodiments 217-241, wherein the phenotype comprises positive expression of a surface marker that is one or more of CD3, CD4 or CD8 and/or comprises positive expression of the recombinant receptor, optionally the CAR, or a surrogate marker for expression of the recombinant receptor.

243. The method of embodiment 242, wherein the phenotype is CD3+ CAR, CD4+/CAR+, CD8+/CAR+.

244. The method of any of embodiments 217-243, wherein the phenotype comprises absence of a factor indicative of apoptosis or one or more steps in an apoptotic cascade or pathway, optionally expression of a marker of apoptosis.

245. The method of any of embodiments 217-244, wherein the phenotype comprises negative expression of a marker of apoptosis, optionally a marker of early apoptosis or late apoptosis.

246. The method of embodiment 245, wherein the marker of apoptosis is surface phosphatidylserine and/or is detected with Annexin V, or is an active or proform of a caspase, optionally an active or proform of Caspase 3.

247. The method of any of embodiments 217-246, wherein the phenotype comprises Annexin-.

248. The method of any of embodiments 217-247, wherein the phenotype comprises an indicator of production of one or a combination of cytokines, optionally non-specific to the antigen or the recombinant receptor and/or that is polyclonally produced, wherein the one or more cytokines is IL-2, IL-13, IL-17, IFN-gamma or TNF-alpha.

249. The method of embodiment 248, wherein the indicator of production is measured in an assay, optionally an intracellular cytokine staining assay, comprising incubating a sample of the T cell composition with a polyclonal agent, an antigen-specific agent or an agent that binds the recombinant receptor, optionally CAR.

250. The method of embodiment 248 or embodiment 249, wherein the agent is or comprises PMA and ionomycin or is or comprises a T cell receptor or T cell receptor complex agonist.

251. The method of any of embodiments 217-250, wherein the phenotype comprises negative expression of an activation marker, wherein the activation marker is selected from among CD25, CD127, LAG3, Ki67 and combinations thereof.

252. The method of any of embodiments 217-251, wherein the phenotype comprises negative expression of an exhaustion marker, wherein the exhaustion maker is a PD1 or FOXP3 gene product or a combination thereof.

253. The method of any of embodiments 217-252, wherein the phenotype comprises a naïve phenotype or a memory phenotype, optionally wherein the memory phenotype comprises a T effector memory phenotype, a T central memory phenotype, or a T effector memory phenotype expressing CD45RA (Temra).

254. The method of any of embodiments 217-253, wherein A is the total number of T cells, total number of CD3+ cells, total number of CD4+ or CD8+ cells, total number of CD3+CAR+ cells, total number of CD8+CAR+ cells, total number of CD4+CAR+, or total number of live or viable cells of any of the foregoing, or a multiple or transformed value thereof.

255. The method of any of embodiments 217-253, wherein A is the total number of CD3+ cells, total number of CD8+, total number of CD3+CAR+ cells, total number of CD8+CAR+ cells, or total number of live or viable cells of any of the foregoing, or a multiple or transformed value thereof.

256. The method of any of embodiments 217-253, wherein A is the total number of apoptotic marker negative (−) cells that are CD3+ CAR+ cells, total number of apoptotic marker negative (−) cells that are CD4+ CAR+, total number of apoptotic marker negative (−) cells that are CD8+ CAR+ cells, or a multiple or transformed value thereof, wherein the apoptotic marker is Annexin V or Caspase.

257. The method of any of embodiments 217-256, wherein A is the total number of Annexin− CD3+ CAR+ cells or the total number of Annexin− CD8+ CAR+ cells.

258. The method of any of embodiments 214-257, wherein the recombinant receptor-dependent activity is a measure of the production or accumulation of a proinflammatory cytokine, optionally, one of or a combination of TNF-alpha, IFN-gamma, IL-2 and IL-10.

259. The method of any one of embodiments 214-258, wherein the parameter is a measure of one or more factors or a normalized value thereof.

260. The method of embodiment 259, wherein the measure is in an assay involving culture or incubation for a fixed time, optionally 24 hours, of a given composition or sample thereof in the presence of the antigen, cells expressing the antigen and/or agent that specifically binds to the recombinant receptor, optionally the CAR.

261. The method of embodiment 260, wherein the assay is an ELISA. 262. The method of any of embodiments 259-261, wherein the measure of the factor is:

(i) concentration, relative concentration, amount, or relative amount of the factor; or (ii) amount or relative amount of the factor per unit of input cells of the given composition, or (iii) amount or relative amount of the factor per unit of input cells of the given composition per unit of time, optionally one hour; or (iv) a level indicative of any of (i)-(iii).

263. The method of any of embodiments 259-262, wherein the one or more factors is one or a combination of soluble factors, optionally one or a combination of cytokines, chemokines or soluble receptors, optionally soluble costimulatory receptors.

264. The method of any of embodiments 259-263, wherein the one or more factors is one of or a combination of a pro-inflammatory cytokines, Th2 cytokines and Th17 cytokines.

265. The method of any of embodiments 259-264, wherein the one or more factors is one of or a combination of IL-2, IFN-gamma, TNF-alpha, IL4, IL-5, IL-10, IL-13, GM-CSF, sCD137, MIP1a and M1Pb.

266. The method of any of embodiments 259-265, wherein the one or more factors is one of or a combination of IL-2, IFN-gamma, TNF-alpha and IL-10.

267. The method of any of embodiments 259-266, wherein the one or more factors is a combination of any of two or more of the foregoing soluble factors and the parameter is an arithmetic mean or geometric mean of the measure of the two or more factors.

268. The method of any embodiments 259-267, wherein the parameter is an arithmetic mean or geometric mean of a measure, optionally amount or concentration, of at least two of TNF-alpha, IFN-gamma and IL-2 or of TNF-alpha, IFN-gamma and IL-2.

269. The method of any of embodiments 259-268, wherein the parameter is the normalized value of the measure, wherein normalization is as compared to a reference measure of the factor.

270. The method of embodiment 269, wherein the reference measure is the average of the measure among a plurality, optionally at least 10, at least 15, at least 20, of reference therapeutic T cell compositions comprising the chimeric antigen receptor (CAR) in which:

(i) each of the reference therapeutic T cell compositions has been observed or determined to result in an acceptable safety profile following administration to a subject, optionally wherein the subject has a disease or condition expressing or associated with the antigen; and/or (ii) each of the reference therapeutic T cell compositions has been observed or determined to result in a desired efficacy following administration to a subject, optionally wherein the subject has a disease or condition expressing or associated with the antigen.

271. The method of embodiment 270, wherein the acceptable safety profile is absence of observed grade 2 or higher or absence of grade 3 or higher, neurotoxicity.

272. The method of embodiment 270 or embodiment 271, wherein the acceptable safety profile is the absence of observed grade 3 or higher neurotoxicity.

273. The method of any of embodiments 270-272, wherein the efficacy is a partial response or is a complete response (CR).

274. The method of embodiment 269, wherein the reference measure is the measure, by the same assay, of the factor in a reference T cell composition produced by the same method as the therapeutic T cell composition but not expressing the recombinant receptor, optionally the CAR, not specifically recognizing the antigen and/or not expressing any recombinant receptor, optionally any CAR.

275. The method of embodiment 274, wherein the parameter is normalized to control for patient-specific variation of the measure of the one or more factors.

276. The method of embodiment 274 or embodiment 275, wherein the parameter is a normalized value of the measure of the factor, compared to the same measure in the same assay, of a control factor, wherein the level of the control factor in a therapeutic T cell composition is known not to, or has been observed not to, indicate or correlate or significantly correlate with an adverse event or toxicity outcome or likelihood or risk thereof, wherein the adverse event or toxicity outcome optionally is severe neurotoxicity.

277. The method of embodiment 276, wherein the control factor is or comprises a factor that is not statistically correlated and/or does not correlate to development of the adverse event among a plurality of subjects that went on to develop the adverse event following administration of the T cell composition, optionally the control factor is one of or a combination of IL-5, IL-13, GM-CSF, and IL-6, optionally wherein the measure of the control factor is an arithmetic mean or geometric mean of two or more of the foregoing.

278. The method of any of embodiments 214-277, wherein the parameter does not comprise cytolytic activity or a measure thereof.

279. The method of any of embodiments 214-278, wherein the parameter does not comprise recombinant receptor-dependent or antigen-specific cytolytic activity or a measure thereof.

280. The method of any of embodiments 217-279, wherein:

the phenotype is CD8+CAR+ cells or apoptotic marker-CD8+CAR+ cells, optionally wherein the apoptotic marker is Annexin V or active Caspase 3; and the parameter is a measure of a pro-inflammatory cytokine, which optionally is one of or a combination of TNF-alpha, IL-2, and IFN-gamma, or is a normalized value thereof.

281. The method of any of embodiments 217-280, wherein:

the adverse event is grade 4 or 5 neurotoxicity and the threshold value:

is or is about $1.75 \times 10^7$ if A is apoptotic marker negative (−) and CD8+CAR+ and B is TNF-alpha or a normalized value thereof;

is or is about $2.19 \times 10^7$ if A is CD8+CAR+ and B is TNF-alpha or a normalized value thereof;

is or is about $1.25 \times 10^7$ if A is apoptotic marker negative (−) CD8+CAR+ and if B is IFN-gamma or a normalized value thereof;

is or is about $1.56 \times 10^7$ if A is CD8+CAR+ and B is IFN-gamma or a normalized value thereof;

is or is about $1.5 \times 10^7$ if A is apoptotic marker negative (−) CD8+CAR+ and if B is IL-2 or a normalized value thereof;

is or is about $1.88 \times 10^7$ if A is CD8+CAR+ and B is IL-2 or a normalized value thereof;

is or is about $1.5 \times 10^7$ if A is apoptotic marker negative (−) CD8+CAR+ and if B is TNF-alpha and IFN-gamma or a normalized value thereof;

is or is about $1.88 \times 10^7$ if A is CD8+CAR+ and B is TNF-alpha and IFN-gamma or a normalized value thereof;

is or is about $2.0 \times 10^7$ if A is apoptotic marker negative (−) CD8+CAR+ and if B is TNF-alpha and IL-2 or a normalized value thereof;

is or is about $2.5 \times 10^7$ if A is CD8+CAR+ and B is TNF-alpha and IL-2 or a normalized value thereof;

is or is about $1.25 \times 10^7$ if A is apoptotic marker negative (−) CD8+CAR+ and if B is IFN-gamma and IL-2 or a normalized value thereof;

is or is about $1.56 \times 10^7$ if A is CD8+CAR+ and B is IFN-gamma and IL-2 or a normalized value thereof;

is or is about $1.75 \times 10^7$ if A is apoptotic marker negative (−) CD8+CAR+ and if B is TNF-alpha, IFN-gamma and IL-2 or a normalized value thereof;

is or is about $2.19 \times 10^7$ if A is CD8+CAR+ and B is TNF-alpha, IFN-gamma and IL-2 or a normalized value thereof, optionally wherein the apoptotic marker is Annexin V or active Caspase 3.

282. The method of any of embodiments 217-281, wherein the adverse event is grade 4 or 5 neurotoxicity and the given range of the target reference units:

is between or about between $2.0 \times 10^5$ and $1.75 \times 10^7$, inclusive, if A is apoptotic marker negative (−) and CD8+CAR+ and B is TNF-alpha or a normalized value thereof;

is between or about between $2.5 \times 10^5$ and $2.19 \times 10^7$, inclusive, if A is CD8+CAR+ and B is TNF-alpha or a normalized value thereof;

is between or about between $4 \times 10^5$ and $1.25 \times 10^7$, inclusive, if A is apoptotic marker negative (−) CD8+CAR+ and if B is IFN-gamma or a normalized value thereof;

is between or about between $5 \times 10^6$ and $1.56 \times 10^7$, inclusive, if A is CD8+CAR+ and B is IFN-gamma or a normalized value thereof;

is between or about between $2.0 \times 10^5$ and $1.5 \times 10^7$, inclusive, if A is apoptotic marker negative (−) CD8+CAR+ and if B is IL-2 or a normalized value thereof;

is between or about between $2.5 \times 10^5$ and $1.88 \times 10^7$, inclusive, if A is CD8+CAR+ and B is IL-2 or a normalized value thereof;

is between or about between $3.0 \times 10^5$ and $1.5 \times 10^7$, inclusive, if A is apoptotic marker negative (−) CD8+CAR+ and if B is TNF-alpha and IFN-gamma or a normalized value thereof;

is between or about between $3.75 \times 10^5$ and $1.88 \times 10^7$, inclusive, if A is CD8+CAR+ and B is TNF-alpha and IFN-gamma or a normalized value thereof;

is between or about between $3.0 \times 10^5$ and $2.0 \times 10^7$, inclusive, if A is apoptotic marker negative (−) CD8+CAR+ and if B is TNF-alpha and IL-2 or a normalized value thereof;

is between or about between $3.75 \times 10^5$ and $2.5 \times 10^7$, inclusive, if A is CD8+CAR+ and B is TNF-alpha and IL-2 or a normalized value thereof;

is between or about between $4.0 \times 10^5$ and $1.25 \times 10^7$, inclusive, if A is apoptotic marker negative (−) CD8+CAR+ and if B is IFN-gamma and IL-2 or a normalized value thereof;

is between or about between $5.0 \times 10^5$ and $1.56 \times 10^7$, inclusive, if A is CD8+CAR+ and if B is IFN-gamma and IL-2 or a normalized value thereof;

is between or about between $4.0 \times 10^5$ and $1.75 \times 10^7$, inclusive, if A is apoptotic marker negative (−) CD8+CAR+ and if B is TNF-alpha, IFN-gamma and IL-2 or a normalized value thereof;

is between or about between $5.0 \times 10^5$ and $2.19 \times 10^7$, inclusive, if A is CD8+CAR+ and B is TNF-alpha, IFN-gamma and IL-2 or a normalized value thereof, optionally wherein the apoptotic marker is Annexin V or active Caspase 3.

283. The method of any of embodiments 217-280, wherein the adverse event is at least prolonged grade 3 neurotoxicity and the threshold value:

is or is about $1.0 \times 10^6$ if A is apoptotic marker negative (−) and CD8+CAR+ and B is TNF-alpha or a normalized value thereof;

is or is about $1.25 \times 10^6$ if A is CD8+CAR+ and B is TNF-alpha or a normalized value thereof;

is or is about $2.0 \times 10^6$ if A is apoptotic marker negative (−) CD8+CAR+ and if B is IFN-gamma or a normalized value thereof;

is or is about $2.5 \times 10^6$ if A is CD8+CAR+ and B is IFN-gamma or a normalized value thereof;

is or is about $3.0 \times 10^6$ if A is apoptotic marker negative (−) CD8+CAR+ and if B is IL-2 or a normalized value thereof;

is or is about $3.75 \times 10^6$ if A is CD8+CAR+ and B is IL-2 or a normalized value thereof;

is or is about $1.5 \times 10^6$ if A is apoptotic marker negative (−) CD8+CAR+ and if B is TNF-alpha and IFN-gamma or a normalized value thereof;

is or is about $1.88 \times 10^6$ if A is CD8+CAR+ and B is TNF-alpha and IFN-gamma or a normalized value thereof;

is or is about $2.5 \times 10^6$ if A is apoptotic marker negative (−) CD8+CAR+ and if B is TNF-alpha and IL-2 or a normalized value thereof;

is or is about $3.12 \times 10^6$ if A is CD8+CAR+ and B is TNF-alpha and IL-2; or a normalized value thereof is or is about $3.0 \times 10^6$ if A is apoptotic marker negative (−) CD8+CAR+ and if B is IFN-gamma and IL-2 or a normalized value thereof;

is or is about $3.75 \times 10^6$ if A is CD8+CAR+ and B is IFN-gamma and IL-2 or a normalized value thereof;

is or is about $2.0 \times 10^6$ if A is apoptotic marker negative (−) CD8+CAR+ and if B is TNF-alpha, IFN-gamma and IL-2 or a normalized value thereof;

is or is about $2.5 \times 10^6$ if A is CD8+CAR+ and B is TNF-alpha, IFN-gamma and IL-2 or a normalized value thereof, optionally wherein the apoptotic marker is Annexin V or active Caspase 3.

284. The method of any of embodiments 217-280 and 283, wherein the adverse event is at least prolonged grade 3 and the given range of the target reference units:

- is between or about between $3.0\times10^5$ and $1.0\times10^6$, inclusive, if A is apoptotic marker negative (−) and CD8+ CAR+ and B is TNF-alpha or a normalized value thereof;
- is between or about between $3.75\times10^5$ and $1.25\times10^6$, inclusive, if A is CD8+CAR+ and B is TNF-alpha or a normalized value thereof;
- is between or about between $4\times10^5$ and $2.0\times10^6$, inclusive, if A is apoptotic marker negative (−) CD8+CAR+ and if B is IFN-gamma or a normalized value thereof;
- is between or about between $5\times10^6$ and $2.5\times10^6$, inclusive, if A is CD8+CAR+ and B is IFN-gamma or a normalized value thereof;
- is between or about between $2.0\times10^5$ and $3.0\times10^6$, inclusive, if A is apoptotic marker negative (−) CD8+CAR+ and if B is IL-2 or a normalized value thereof;
- is between or about between $2.5\times10^5$ and $3.75\times10^6$, inclusive, if A is CD8+CAR+ and B is IL-2 or a normalized value thereof;
- is between or about between $3.0\times10^5$ and $1.5\times10^6$, inclusive, if A is apoptotic marker negative (−) CD8+CAR+ and if B is TNF-alpha and IFN-gamma or a normalized value thereof;
- is between or about between $3.75\times10^5$ and $1.88\times10^6$, inclusive, if A is CD8+CAR+ and B is TNF-alpha and IFN-gamma or a normalized value thereof;
- is between or about between $3.0\times10^5$ and $2.5\times10^6$, inclusive, if A is apoptotic marker negative (−) CD8+CAR+ and if B is TNF-alpha and IL-2 or a normalized value thereof;
- is between or about between $3.75\times10^5$ and $3.12\times10^6$, inclusive, if A is CD8+CAR+ and B is TNF-alpha and IL-2 or a normalized value thereof;
- is between or about between $4.0\times10^5$ and $3.0\times10^6$, inclusive, if A is apoptotic marker negative (−) CD8+CAR+ and if B is IFN-gamma and IL-2 or a normalized value thereof;
- is between or about between $5.0\times10^5$ and $3.75\times10^6$, inclusive, if A is CD8+CAR+ and B is IFN-gamma and IL-2 or a normalized value thereof;
- is between or about between $4.0\times10^5$ and $2.0\times10^6$, inclusive, if A is apoptotic marker negative (−) CD8+CAR+ and if B is TNF-alpha, IFN-gamma and IL-2 or a normalized value thereof;
- is between or about between $5.0\times10^5$ and $2.5\times10^6$, inclusive, if A is CD8+CAR+ and B is TNF-alpha, IFN-gamma and IL-2 or a normalized value thereof, optionally wherein the apoptotic marker is Annexin V or active Caspase 3.

285. The method of any of embodiments 214-284, wherein the recombinant receptor is a CAR.

286. The method of embodiment 285, wherein the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD35) chain; and/or wherein the CAR further comprises a costimulatory signaling region, which optionally comprises a signaling domain of CD28 or 4-1BB.

287. The method of any of embodiments 214-286, wherein the T cells are CD4+ or CD8+.

288. The method of any of embodiments 214-287, wherein the T cells are primary T cells, optionally autologous or allogenic to the subject.

289. A method of producing a therapeutic T cell composition for cell therapy, the method comprising filling a container with all or a portion of a composition comprising T cells to a concentration of between about 10 million cells and about 70 million cells per mL, inclusive, and optionally another solution.

290. The method of embodiment 289, wherein the T cells are derived from a subject having a disease or condition and transduced with a nucleic acid encoding a recombinant receptor, optionally a chimeric antigen receptor (CAR), specific for an antigen associated with or expressed by a disease or condition and/or the T cells comprise a recombinant receptor, optionally a CAR.

291. The method of any of embodiments 233-290, wherein the container is filled with between about 15 and about 60 million cells per mL, inclusive.

292. The method of any of embodiments 233-291, wherein the container is filled with greater than 10 million cells per mL.

293. The method of any of embodiments 233-292, wherein the container is filled with greater than 15 million cells per mL.

294. The method of any of embodiments 233-293, wherein the filling is carried out in an automated fashion.

295. The method of any of embodiments 233-295, wherein the filling is carried out in a closed system.

296. The method of any of embodiments 233-295, wherein the container is filled with another solution and the solution comprises a cryoprotectant, optionally DMSO.

297. The method of any of embodiments 233-295, further comprising freezing the cells in the container or storing the container at a temperature less than or about less than 80° C.

298. The method of any of embodiments 233-298, wherein the recombinant receptor is a CAR.

299. The method of embodiment 298, wherein the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD35) chain; and/or wherein the CAR further comprises a costimulatory signaling region, which optionally comprises a signaling domain of CD28 or 4-1BB.

300. The method of any of embodiments 233-299, wherein the T cells are CD4+ or CD8+.

301. The method of any of embodiments 233-301, wherein the T cells are primary T cells, optionally autologous or allogenic to the subject.

302. The method of any of embodiments 118-301, wherein the T cell composition is produced by a process in which:

- the frequency, (1) among CAR+ cells in the composition, (2) among CAR+CD3+ cells in the composition, and/or (3) among CAR+CD8+ cells in the composition, of a cell of a phenotype that indicates a features of biologically active cells and/or of the absence of apoptosis or early or late stages of apoptosis varies by no more than 40%, or no more than 30%, or no more than 20% or no more than 10% or no more than 5% from an average of said frequency in a plurality of T cell compositions produced by the process and/or varies from such average by no more than one standard deviation; or
- the frequency, (1) among CAR+ cells in the composition, (2) among CAR+CD3+ cells in the composition, and/or (3) among CAR+CD8+ cells in the composition, in the composition, of cell of a phenotype that indicates the absence of apoptosis or early or late stage of apoptosis, varies by no more than 40% or no more than 20% or no more than 10% among a plurality of T cell compositions produced by the process 303. The method of embodiment 302, wherein the process comprises:

(a) incubating a population of cells comprising T cells with an agent comprising a nucleic acid molecule encoding the recombinant receptor under conditions to introduce the nucleic acid encoding the recombinant receptor into cells in the population; and (b) stimulating the cells, prior to, during and/or subsequent to said incubation, wherein stimulating comprises incubating the cells in the presence of a stimulating condition that induces a primary signal, signaling, stimulation, activation and/or expansion of the cells.

304. The method of embodiment 303, wherein the process further comprises, prior to (a), isolating the population of cells from a biological sample.

305. The method of embodiment 304, wherein the isolating comprises, selecting cells based on surface expression of CD3 or based on surface expression of one or both of CD4 and CD8, optionally by positive or negative selection.

306. The method of embodiment 304 or embodiment 305, wherein the isolating comprises carrying out immunoaffinity-based selection.

307. The method of embodiment 304-306, wherein the biological sample is or comprises a whole blood sample, a buffy coat sample, a peripheral blood mononuclear cells (PBMC) sample, an unfractionated T cell sample, a lymphocyte sample, a white blood cell sample, an apheresis product, or a leukapheresis product.

308. The method of any of embodiments 303-307, wherein the stimulating condition comprises incubation with a stimulatory reagent capable of activating one or more intracellular signaling domains of one or more components of a TCR complex and/or one or more intracellular signaling domains of one or more costimulatory molecules.

309. The method of embodiment 308, wherein the stimulatory reagent comprises a primary agent that specifically binds to a member of a TCR complex and a secondary agent that specifically binds to a T cell costimulatory molecule.

310. The method of embodiment 308 or embodiment 309, wherein the primary agent specifically binds to CD3 and/or the costimulatory molecule is selected from the group consisting of CD28, CD137 (4-1-BB), OX40, or ICOS.

311. The method of embodiment 306 or embodiment 310, wherein the primary and secondary agents comprise antibodies and/or are present on the surface of a solid support, optionally a bead.

312. The method of any of embodiments 308-311, wherein:

the stimulatory reagent is one in which it has been determined that a recombinant receptor-dependent activity or an antigen-specific activity, optionally recombinant receptor-dependent or antigen-specific dependent production or accumulation of a proinflammatory cytokine, varies by no more than 40%, or no more than 30%, or no more than 20% or no more than 10% or no more than 5% from an average of a measure of the production or accumulation of the proinflammatory cytokine among a plurality of T cell compositions produced by the process using the stimulatory reagent and/or varies from such average by no more than one standard deviation; and/or the stimulatory reagent is one in which it has been determined that a recombinant receptor-dependent activity or an antigen-specific activity, optionally recombinant receptor-dependent or antigen-specific dependent production or accumulation of a proinflammatory cytokine, varies by no more than 40%, or no more than 30%, or no more than 20% or no more than 10% or no more than 5% among a plurality of T cell compositions produced by the process; and/or the stimulatory reagent is one in which it has been determined that a recombinant receptor-dependent activity or an antigen-specific activity, optionally recombinant receptor-dependent or antigen-specific dependent production or accumulation of a proinflammatory cytokine, of a cell composition produced using the stimulatory reagent varies by no more than 40%, or no more than 30%, or no more than 20% or no more than 10% or no more than 5% from a control composition, wherein the control composition and cell composition are produced using the same process, including from the same population of cells, except the control composition is carried out in the presence of a control stimulatory reagent or standard unit for the recombinant receptor-dependent activity.

313. The method of embodiment 312, wherein the control stimulatory reagent, when employed in the process, is known to produce a T cell composition in which the recombinant receptor-dependent activity or antigen-specific activity is within an acceptable range of variance.

314. The method of any of embodiments 303-313, wherein the stimulating the cells is carried out or is initiated prior to the incubating, optionally for 18-24 hours at or about 37 deg.

315. The method of any of embodiments 303-314, wherein the stimulating condition comprises a cytokine selected from among IL-2, IL-15 and IL-7.

316. The method of any of embodiments 303-315, wherein the stimulating cells is carried out subsequent to the incubating, optionally for a period of time to achieve a threshold concentration.

317. The method of any of embodiments 303-316, further comprising (c) filling a container with all or a portion of the T cell composition, and optionally another solution, to a concentration between about 10 million cells and about 70 million cells per ml, inclusive.

318. The method of embodiment 317, wherein the container is filled with another solution and the solution comprises a cryoprotectant, optionally DMSO.

319. The method of embodiment 317 or embodiment 318, wherein the concentration is between about 15 and about 60 million cells per ml, inclusive.

320. The method of any of embodiments 317-319, wherein the concentration is greater than 10 million cells per ml.

321. The method of any of embodiments 317-320, wherein the concentration is greater than 15 million cells per ml.

322. The method of any of embodiments 317-321, wherein the concentration of DMSO is or is about or is no more than 7.5%.

323. The method of embodiment 317 or embodiment 318, wherein the concentration is greater than 60 million cells per mL.

324. The method of any of embodiments 317-320 and 323, wherein the concentration of DMSO is greater than 7.5%, optionally between or about between 7.5% and 9.0%, inclusive.

325. The method of any of embodiments 303-324, wherein the agent comprising a nucleic acid molecule encoding the recombinant receptor is a viral vector, optionally a lentiviral vector or a gamma retroviral vector.

326. The method of any of embodiments 317-325, wherein the filling is carried out in an automated fashion, optionally in a closed system.

327. The method of any of embodiments 303-326, further comprising freezing the cells in the container or storing the container at a temperature less than or about less than 80° C.

328. A unit dose of a therapeutic T cell composition comprising a number of cells comprising a recombinant receptor, optionally a chimeric antigen receptor (CAR), specific for an antigen associated with or expressed by a disease or condition, wherein the number of cells is between and between about $5.0\times10^6$ and $2.25\times10^7$, $5.0\times10^6$ and $2.0\times10^7$, $5.0\times10^6$ and $1.5\times10^7$, $5.0\times10^6$ and $1.0\times10^7$, $5.0\times10^6$ and $7.5\times10^6$, $7.5\times10^6$ and $2.25\times10^7$, $7.5\times10^6$ and $2.0\times10^7$, $7.5\times10^6$ and $1.5\times10^7$, $7.5\times10^6$ and $1.0\times10^7$, $1.0\times10^7$ and $2.25\times10^7$, $1.0\times10^7$ and $2.0\times10^7$, $1.0\times10^7$ and $1.5\times10^7$, $1.5\times10^7$ and $2.25\times10^7$, $1.5\times10^7$ and $2.0\times10^7$, $2.0\times10^7$ and $2.25\times10^7$ recombinant-receptor expressing cells, optionally recombinant-receptor expressing cells that are CD8+ or that are apoptotic marker negative (−) and CD8+, each inclusive, optionally wherein the apoptotic marker is Annexin V or active Caspase 3.

329. The unit dose of embodiment 328, wherein the number of cells is:

between at least or at least about $5\times10^6$, $6\times10^6$, $7\times10^6$, $8\times10^6$, $9\times10^6$, $10\times10^6$ and about $15\times10^6$ recombinant-receptor expressing cells, each inclusive, optionally recombinant-receptor expressing cells that are CD8+ or that are apoptotic marker negative (−) and CD8+, optionally wherein the apoptotic marker is Annexin V or active Caspase 3;

between at least or at least about $5.55\times10^6$, $6.66\times10^6$, $7.77\times10^6$, $8.99\times10^6$, $1.0\times10^7$, $1.1\times10^7$ and about $1.67\times10^7$ recombinant-receptor expressing cells, optionally recombinant-receptor expressing cells that are CD8+ or that are apoptotic marker negative (−) and CD8+, each inclusive, optionally wherein the apoptotic marker is Annexin V or active Caspase 3;

between at least or at least about $6.25\times10^6$, $7.5\times10^6$, $8.75\times10^6$, $1.0\times10^7$, $1.13\times10^7$, $1.25\times10^7$ and about $1.9\times10^7$ recombinant-receptor expressing cells, optionally recombinant-receptor expressing cells that are CD8+ or that are apoptotic marker negative (−) and CD8+, each inclusive, optionally wherein the apoptotic marker is Annexin V or active Caspase 3;

between at least or at least about $7.14\times10^6$, $8.5\times10^6$, $1.0\times10^7$, $1.14\times10^7$, $1.29\times10^7$, $1.42\times10^7$ and about $2.14\times10^7$ recombinant-receptor expressing cells, optionally recombinant-receptor expressing cells that are CD8+ or that are apoptotic marker negative (−) and CD8+, each inclusive, optionally wherein the apoptotic marker is Annexin V or active Caspase 3.

330. The unit dose of embodiment 328 or embodiment 329, wherein the number of cells is between at least or at least about $5\times10^6$, $6\times10^6$, $7\times10^6$, $8\times10^6$, $9\times10^6$, $10\times10^6$ and about $15\times10^6$ recombinant-receptor expressing cells that are CD8+ each inclusive.

331. The unit dose of embodiment 328 or embodiment 329, wherein the number of cells is between at least or at least about $6.25\times10^6$, $7.5\times10^6$, $8.75\times10^6$, $1.0\times10^7$, $1.13\times10^7$, $1.25\times10^7$ and about $1.9\times10^7$ recombinant-receptor expressing cells that are apoptotic marker negative (−) and CD8+, optionally wherein the apoptotic marker is Annexin V or active Caspase 3 each inclusive.

332. The unit dose of any of embodiments 328-332, wherein the unit dose does not contain greater than a threshold number of reference units (RU), wherein the number of RU in a given composition is defined by the formula:

$RU=A\times B$, wherein

A is the number of cells, or multiple or transformation thereof, of cells of a phenotype present in the given composition or is the average or weighted average of the number of cells, or multiple, fraction or transformation thereof, of two or more phenotypes in the given composition; and B is the value of a parameter, or a multiple, or transformation thereof, that indicates or correlates with the degree of a recombinant receptor-dependent, optionally CAR-dependent, activity in the given T cell composition.

333. The unit dose of embodiment 332, wherein the threshold number of reference units is less than a reference safety number of units, wherein the reference safety number of units is, with respect to a group of subjects analyzed following treatment with a therapeutic T cell composition comprising the T cells expressing the recombinant receptor, optionally the CAR, the lowest number of units of the therapy administered to a subject among those subjects in the group that went on to develop an adverse event.

334. The unit dose of embodiment 333, wherein the adverse event is a severe adverse event, optionally severe neurotoxicity at or above grade 4 or grade 5 or at least prolonged grade 3 neurotoxicity.

335. The unit dose of embodiment 333 or embodiment 334, wherein the threshold number of units is less than the reference safety number of units by an amount corresponding to a safety factor or by at least 2-fold.

336. The unit dose of any of embodiments 332-335, wherein the threshold number of units is at or above a reference efficacy number of units, wherein the reference efficacy number is, with respect to a group of subjects analyzed following treatment with a T cell composition comprising the recombinant receptor, optionally the CAR, a number of units of the therapy administered to one or more subjects among the group that exhibited a desired therapeutic outcome, optionally a complete response (CR).

337. The unit dose of any of embodiments 121-127, wherein at least 50%, at least 60%, at least 75%, at least 80%, or at least 90% of the CD8+ cells and/or the CD8+ CAR+ cells in the composition are not positive for an apoptotic marker, are not apoptotic or are not in the early stages of apoptosis, or are not in the late stages of apoptosis.

338. The unit dose of any of embodiments 328-337, comprising no more than $1.88\times10^7$ of CD8+ CAR+ T cells, optionally CD8+CAR+ T cells that are not apoptotic or are not in the early stages of apoptosis or are not in the late stages of apoptosis.

339. The unit dose composition of any of embodiments 328-338, wherein the dose comprises at least $5\times10^6$ Annexin− CD8+ CAR+ cells but no more than $1.5\times10^7$ Annexin-CD8+CAR+ cells.

340. The unit dose composition of any of embodiments 328-339, wherein the T cell composition is produced by a process in which:

the frequency, (1) among CAR+ cells in the composition, (2) among CAR+CD3+ cells in the composition, and/or (3) among CAR+CD8+ cells in the composition, of a cell of a phenotype that indicates a features of biologically active cells and/or of the absence of apoptosis or early or late stages of apoptosis varies by no more than 40% or no more than 30% or no more than 20% or no more than 10% or no more than 5% from an average of said frequency in a plurality of T cell compositions produced by the process and/or varies from such average by no more than one standard deviation; or the frequency, (1) among CAR+ cells in the composition, (2) among CAR+CD3+ cells in the composition, and/or (3) among CAR+CD8+ cells in the composition, in the composition, of cell of a phenotype that indicates the absence of apoptosis or early or late stage of apoptosis, varies by no more than 40% or no more than 20% or no more than 10% among a plurality of T cell compositions produced by the process.

341. The unit dose of embodiment 340, wherein the process comprises:

(a) incubating a population of cells comprising T cells with an agent comprising a nucleic acid molecule encoding the recombinant receptor under conditions to introduce the nucleic acid encoding the recombinant receptor into cells in the population; and (b) stimulating the cells, prior to, during and/or subsequent to said incubation, wherein stimulating comprises incubating the cells in the presence of a stimulating condition that induces a primary signal, signaling, stimulation, activation and/or expansion of the cells.

342. The unit dose of embodiment 341, wherein the process further comprises, prior to (a), isolating the population of cells from a biological sample.

343. The unit dose of embodiment 342, wherein the isolating comprises, selecting cells based on surface expression of CD3 or based on surface expression of one or both of CD4 and CD8, optionally by positive or negative selection.

344. The unit dose of embodiment 342 or embodiment 343, wherein the isolating comprises carrying out immunoaffinity-based selection.

345. The unit dose of embodiment 342-344, wherein the biological sample is or comprises a whole blood sample, a buffy coat sample, a peripheral blood mononuclear cells (PBMC) sample, an unfractionated T cell sample, a lymphocyte sample, a white blood cell sample, an apheresis product, or a leukapheresis product.

346. The unit dose of any of embodiments 341-345, wherein the stimulating condition comprises incubation with a stimulatory reagent capable of activating one or more intracellular signaling domains of one or more components of a TCR complex and/or one or more intracellular signaling domains of one or more costimulatory molecules.

347. The unit dose of embodiment 346, wherein the stimulatory reagent comprises a primary agent that specifically binds to a member of a TCR complex and a secondary agent that specifically binds to a T cell costimulatory molecule.

348. The unit dose of embodiment 346 or embodiment 347, wherein the primary agent specifically binds to CD3 and/or the costimulatory molecule is selected from the group consisting of CD28, CD137 (4-1-BB), OX40, or ICOS.

349. The unit dose of embodiment 347 or embodiment 348, wherein the primary and secondary agents comprise antibodies and/or are present on the surface of a solid support, optionally a bead.

350. The unit dose of any of embodiments 346-349, wherein:

the stimulatory reagent is one in which it has been determined that a recombinant receptor-dependent activity or an antigen-specific activity, optionally recombinant receptor-dependent or antigen-specific dependent production or accumulation of a proinflammatory cytokine, varies by no more than 40% or no more than 30%, or no more than 20% or no more than 10% or no more than 5% from an average of a measure of the production or accumulation of the proinflammatory cytokine among a plurality of T cell compositions produced by the process using the stimulatory reagent and/or varies from such average by no more than one standard deviation; and/or the stimulatory reagent is one in which it has been determined that a recombinant receptor-dependent activity or an antigen-specific activity, optionally recombinant receptor-dependent or antigen-specific dependent production or accumulation of a proinflammatory cytokine, varies by no more than 40% no more than 30% or no more than 20% or no more than 10% or no more than 5% among a plurality of T cell compositions produced by the process; and/or the stimulatory reagent is one in which it has been determined that a recombinant receptor-dependent activity or an antigen-specific activity, optionally recombinant receptor-dependent or antigen-specific dependent production or accumulation of a proinflammatory cytokine, of a cell composition produced using the stimulatory reagent varies by no more than 40%, or no more than 30%, or no more than 20% or no more than 10% or no more than 5% from a control composition, wherein the control composition and cell composition are produced using the same process, including from the same population of cells, except the control composition is carried out in the presence of a control stimulatory reagent or standard unit for the recombinant receptor-dependent activity.

351. The unit dose of embodiment 350, wherein the control stimulatory reagent, when employed in the process, is known to produce a T cell composition in which the recombinant receptor-dependent activity or antigen-specific activity is within an acceptable range of variance.

352. The unit dose of any of embodiments 341-351, wherein the stimulating the cells is carried out or is initiated prior to the incubating, optionally for 18-24 hours at or about 37 deg.

353. The unit dose of any of embodiments 341-352, wherein the stimulating condition comprises a cytokine selected from among IL-2, IL-15 and IL-7.

354. The unit dose of any of embodiments 341-353, wherein the stimulating cells is carried out subsequent to the incubating, optionally for a period of time to achieve a threshold concentration.

355. The unit dose of any of embodiments 341-354, further comprising (c) filling a container with all or a portion of the T cell composition, and optionally another solution, to a concentration between about 10 million cells and about 70 million cells per ml, inclusive.

356. The unit dose of embodiment 355, wherein the container is filled with another solution and the solution comprises a cryoprotectant, optionally DMSO.

357. The unit dose of embodiment 355 or embodiment 356, wherein the concentration is between about 15 and about 60 million cells per ml, inclusive.

358. The unit dose of any of embodiments 355-357, wherein the concentration is greater than 10 million cells per ml.

359. The unit dose of any of embodiments 355-358, wherein the concentration is greater than 15 million cells per ml.

360. The unit dose of any of embodiments 355-359, wherein the concentration of DMSO is or is about or is no more than 7.5%.

361. The unit dose of embodiment 355 or embodiment 356, wherein the concentration is greater than 60 million cells per mL.

362. The unit dose of any of embodiments 355-358 and 361, wherein the concentration of DMSO is greater than 7.5%, optionally between or about between 7.5% and 9.0%, inclusive.

363. The unit dose of any of embodiments 341-362, wherein the agent comprising a nucleic acid molecule encoding the recombinant receptor is a viral vector, optionally a lentiviral vector or a gamma retroviral vector.

364. The unit dose of any of embodiments 355-363, wherein the filling is carried out in an automated fashion, optionally in a closed system.

365. The unit dose of any of embodiments 341-364, further comprising freezing the cells in the container or storing the container at a temperature less than or about less than 80° C.

366. A method of determining if a subject is at risk of toxicity, comprising assaying the number of recombinant receptor-expressing cells in the blood of a subject, said subject having been previously administered a dose of the recombinant receptor-expressing cells, wherein the subject is at risk of development of a toxicity if:

(i) no more than four days after initiation of the administration the number of recombinant receptor-expressing cells in the blood of the subject is at least at or about 2 recombinant receptor-expressing cells per microliter;

(ii) no more than five or six days after initiation of the administration the number of recombinant receptor-expressing cells in the blood of the subject is at least at or about 5 recombinant receptor-expressing cells per microliter or is at least at or about 10 recombinant receptor-expressing cells per microliter; or (iii) no more than seven days after initiation of the administration the number of recombinant receptor-expressing cells in the blood of the subject is at least at or about 15 recombinant receptor-expressing cells per microliter.

367. A method of determining if a subject is at risk of toxicity, comprising:

(a) administering to a subject having a disease or condition a dose of cells expressing a recombinant receptor; and (b) after administering the cells, assaying the number of recombinant receptor-expressing cells in the blood of a subject, wherein the subject is at risk of development of a toxicity if:

(i) no more than four days after initiation of the administration the number of recombinant receptor-expressing cells in the blood of the subject is at least at or about 2 recombinant receptor-expressing cells per microliter;

(ii) no more than five or six days after initiation of the administration the number of recombinant receptor-expressing cells in the blood of the subject is at least at or about 5 recombinant receptor-expressing cells per microliter or is at least at or about 10 recombinant receptor-expressing cells per microliter; or (iii) no more than seven days after initiation of the administration the number of recombinant receptor-expressing cells in the blood of the subject is at least at or about 15 recombinant receptor-expressing cells per microliter.

368. The method of embodiment 366 or embodiment 367, wherein if the subject is determined to be at risk of developing a toxicity; discontinuing administration of the recombinant receptor-expressing cells, administering to the subject lower dose of the dose of recombinant receptor-expressing cells; administering to the subject cells expressing a different recombinant receptor; and/or administering to the subject an agent capable of treating, preventing, delaying or attenuating the development of the toxicity.

369. The method of any of embodiments 366-368, wherein if the subject is determined to be at risk of developing a toxicity, administering to the subject an agent capable of treating, preventing, delaying or attenuating the development of the toxicity.

370. A method for assessing a stimulatory reagent for use in producing a therapeutic T cell composition, the method comprising:

(i) assessing a T cell composition produced using a stimulatory reagent for a recombinant receptor-dependent activity or a phenotype; and (ii) comparing the recombinant receptor-dependent activity or the phenotype, to the same activity or phenotype produced from a control composition or compared to a standard unit for the recombinant receptor-dependent activity or phenotype, wherein the stimulatory agent is determined suitable for release for use in a method for producing a therapeutic T cell composition if the recombinant receptor-dependent activity or phenotype of the cell composition produced using the stimulatory reagent varies by no more than 40% or no more than 30% or no more than 20% or no more than 10% or no more than 5% from the same activity produced by the control composition or from the standard unit.

371. The method of embodiment 370, wherein the recombinant receptor-dependent activity is an antigen-specific activity.

372. The method of embodiment 370 or embodiment 371, wherein the control composition and T cell composition are produced using the same process, including from the same population of cells, except the control composition is carried out in the presence of a control stimulatory reagent.

373. The method of any of embodiments 370-372, wherein a recombinant receptor-dependent activity is assessed and compared to the same activity produced from a control composition or compared to a standard unit for the recombinant receptor-dependent activity.

374. The method of any of embodiments 370-373, wherein the recombinant receptor-dependent activity is recombinant receptor-dependent or antigen-specific dependent production or accumulation of a proinflammatory cytokine.

375. The method of embodiment 364, wherein the proinflammatory cytokine is IL-2, TNF-alpha, IFNgamma or IL-10.

376. The method of any of embodiments 370-372, wherein a phenotype is assessed and compared to the same phenotype produced from a control composition or compared to a standard unit for the phenotype.

377. The method of any of embodiments 370-372 and 376, wherein the phenotype comprises a particular differentiation state and/or a memory/stem-like phenotype.

378. The method of any of embodiments 370-372, 376 and 377, wherein the phenotype comprises positive expression of a surface marker that is CD3, CD8, CD27, CD28 and/or comprises positive expression of the recombinant receptor, optionally the CAR, or a surrogate marker for expression of the recombinant receptor.

379. The method of any of embodiments 370-372 and 376-378, wherein the phenotype comprises CD27+/CD28+/CD8+.

380. The method of any of embodiments 370-379, wherein the stimulatory reagent is capable of activating one or more intracellular signaling domains of one or more components of a TCR complex and/or one or more intracellular signaling domains of one or more costimulatory molecules.

381. The method of any of embodiments 370-380, wherein the stimulatory reagent comprises a primary agent that specifically binds to a member of a TCR complex and a secondary agent that specifically binds to a T cell costimulatory molecule.

382. The method of embodiment 380 or embodiment 381, wherein the primary agent specifically binds to CD3 and/or the costimulatory molecule is selected from the group consisting of CD28, CD137 (4-1-BB), OX40, or ICOS.

383. The method of embodiment 381 or embodiment 382, wherein the primary and secondary agents comprise antibodies and/or are present on the surface of a solid support, optionally a bead.

384. A container comprising a therapeutic T cell composition at a concentration of between about 10 million cells and about 70 million cells per mL, and optionally another solution, wherein the therapeutic T cell composition comprises T cells comprising a recombinant receptor.

385. The container of embodiment 384, wherein the concentration is between about 15 and about 60 million cells per mL.

386. The container of embodiment 384 or 385, wherein the concentration is or is about 15 million cells per mL.

387. The container of embodiment 384 or 385 wherein the container is filled with another solution and the solution comprises a cryoprotectant, optionally DMSO.

388. The container of any of embodiments 384-386, wherein the container is a vial or is a bag.

389. The container of any of embodiments 384-387, wherein the container is a vial, optionally a cryogenic vial, and the volume of the composition is no more than 20 mL, optionally 1 mL to 20 mL, 1 mL to 15 mL, 1 mL to 10 mL, 1 mL to 5 mL, 1 mL to 2.5 mL, 2.5 mL to 20 mL, 2.5 mL to 15 mL, 2.5 mL to 10 mL, 2.5 mL to 5 mL, 5 mL to 20 mL, 5 mL to 15 mL, 5 mL to 10 mL, 10 mL to 20 mL, 10 mL to 15 mL or 15 mL to 20 mL.

390. The container of any of embodiments 384-388, wherein the container is a bag, optionally a freezing bag, and the volume of the composition:

is between or between about 15 mL and 150 mL, 20 mL and 100 mL, 20 mL and 80 mL, 20 mL and 60 mL, 20 mL and 40 mL, 40 mL and 100 mL, 40 mL and 80 mL, 40 mL and 60 mL, 60 mL and 100 mL, 60 mL and 80 mL or 80 mL and 100 mL, each inclusive; or is at least or at least about 15 mL, at least or at least about 20 mL, at least or at least about 30 mL, at least or at least about 40 mL, at least or at least about 50 mL, at least or at least about 60 mL, at least or at least about 70 mL, at least or at least about 80 mL or at least or at least about 90 mL; and/or is no more than 100 mL.

391. The container of any of embodiments 384-390, wherein the surface area to volume ratio of the composition in the container:

is between or between about 0.1 $cm^{-1}$ and 100 $cm^{-1}$; 1 $cm^{-1}$ and 50 $cm^{-1}$, 1 $cm^{-1}$ and 20 $cm^{-1}$, 1 $cm^{-1}$ and 10 $cm^{-1}$, 1 $cm^{-1}$ and 7 $cm^{-1}$, 1 $cm^{-1}$ and 6 $cm^{-1}$, 1 $cm^{-1}$ and 3 $cm^{-1}$, 1 $cm^{-1}$ and 2 $cm^{-1}$, 2 $cm^{-1}$ and 20 $cm^{-1}$, 2 $cm^{-1}$ and 10 $cm^{-1}$, 2 $cm^{-1}$ and 7 $cm^{-1}$, 2 $cm^{-1}$ and 6 $cm^{-1}$, 2 $cm^{-1}$ and 3 $cm^{-1}$, 3 $cm^{-1}$ and 20 $cm^{-1}$, 3 $cm^{-1}$ and 10 $cm^{-1}$, 3 $cm^{-1}$ and 7 $cm^{-1}$, 3 $cm^{-1}$ and 6 $cm^{-1}$, 6 $cm^{-1}$ and 20 $cm^{-1}$, 6 $cm^{-1}$ and 10 $cm^{-1}$, 6 $cm^{-1}$ and 7 $cm^{-1}$, 7 $cm^{-1}$ and 20 $cm^{-1}$, 7 $cm^{-1}$ and 10 $cm^{-1}$, or 7 $cm^{-1}$ and 20 $cm^{-1}$, each inclusive; or is, is about, or is at least 3 $cm^{-1}$, 4 $cm^{-1}$, 5 $cm^{-1}$, 6 $cm^{-1}$, 7 $cm^{-1}$, 10 $cm^{-1}$, 15 $cm^{-1}$, or 20 $cm^{-1}$.

392. The container of any of embodiments 384-3391, wherein the T cells are derived from a subject having a disease or condition and transduced with a nucleic acid encoding a recombinant receptor, optionally a chimeric antigen receptor (CAR), specific for an antigen associated with or expressed by a disease or condition and/or the T cells comprise a recombinant receptor, optionally a CAR.

393. The container of any of embodiments 97-105, wherein the recombinant receptor is a CAR.

394. The container of embodiment 106, wherein the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD35) chain; and/or wherein the CAR further comprises a costimulatory signaling region, which optionally comprises a signaling domain of 4-1BB.

395. The container of any of embodiments 97-107, wherein the T cells are CD4+ or CD8+.

396. The method of any of embodiments 97-108, wherein the T cells are primary T cells.

397. The container of any of embodiments 97-109, wherein the T cell composition is produced by a process in which:

the frequency, (1) among CAR+ cells in the composition, (2) among CAR+CD3+ cells in the composition, and/or (3) among CAR+CD8+ cells in the composition, of a cell of a phenotype that indicates a features of biologically active cells and/or of the absence of apoptosis or early or late stages of apoptosis varies by no more than 40%, or no more than 30%, or no more than 20% or no more than 10% or no more than 5% from an average of said frequency in a plurality of T cell compositions produced by the process and/or varies from such average by no more than one standard deviation; or the frequency, (1) among CAR+ cells in the composition, (2) among CAR+CD3+ cells in the composition, and/or (3) among CAR+CD8+ cells in the composition, in the composition, of cell of a phenotype that indicates the absence of apoptosis or early or late stage of apoptosis, varies by no more than 40% or no more than 20% or no more than 10% among a plurality of T cell compositions produced by the process.

X. EXAMPLES

The following examples are included for illustrative purposes only and are not intended to limit the scope of the invention.

Example 1: Determination of Parameters of CAR+ T Cell Compositions that are Predictive of Severe Neurotoxicity Various parameters were assessed following the treatment of subjects having relapsed or refractory Acute Lymphoblastic Leukemia (ALL) with therapeutic compositions containing autologous T cells engineered to express an anti-CD19 chimeric antigen receptor (CAR). Parameters assessed included parameters of the therapeutic cell compositions and doses (including functional features and numbers and frequencies of cells of various phenotypes), patient characteristics, and clinical and treatment parameters, including those indicative of response- and toxicity-related outcomes.

Parameters were analyzed for individual subjects, post facto, and compared among subjects using a number of statistical analyses, including descriptive, graphical, non-parametric and model-based analyses. Relationships between different parameters were assessed. In particular, the study assessed the degree to which various parameters of individual patients and of the cell compositions or doses, correlated (directly or inversely) with the likelihood of exhibiting a therapeutic response and/or with the risk of an adverse outcome such as neurotoxicity, e.g., severe or grade 5 neurotoxicity and cerebral edema.

A. CAR+ T Cell Therapy

The subjects (N=38) assessed had been administered a T cell composition containing autologous T cells expressing an anti-CD19 chimeric antigen receptor (CAR) for treatment of adult ALL. At the start of treatment, of the 38 subjects, thirty-two (32) had exhibited morphologic evidence of disease in bone marrow (at least 5% blasts) and six (6) had exhibited molecularly detectable disease by PCR. Subjects were 18 years or older, with relapsed or refractory morphological CD19 positive disease (as defined by greater than 5% blasts in bone marrow) including extramedullary and Philadelphia chromosome-positive (Ph+) disease, with first salvage therapy or greater (including post allogenic hematopoietic stem cell treatment), and had Eastern Cooperative Oncology Group (ECOG) scores of 0-2. Subjects had adequate organ function as indicated by values of serum creatinine ≤1.5×upper limit of normal [ULN] or creatinine clearance of >30 mL/min/1.73 m2, alanine aminotransferase <5×ULN, biliruvin<2.0 mg/dL, ≤grade 1 dyspnea and saturated oxygen of ≥92% on room air, and left ventricular ejection fraction of ≥40%. Subjects included those with prior blinatumomab treatment. Exclusion criteria included isolated extramedullary disease or Burkett's disease, active CNS involvement with the disease (CNS3) or CNS pathology, active acute (grade II-IV) or extensive chronic graft versus host disease (GvHD), active infection, and prior gene therapy. Subjects included those treated with alemtuzumab within the past 6 months, clofarabine or cladribine in the past 3 months, GvHD medications with in the past 4 weeks, or salvage chemo and therapeutic corticosteroids within the past week were also excluded.

The demographics and baseline characteristics of the subjects included in the study are shown in Table E1A.

TABLE E1-A

| Demographics and baseline characteristics | All Subjects (N = 38) | Morphological Subjects (n = 32) | MRD+ Subjects (n = 6) |
|---|---|---|---|
| Male, n(%) | 28 (74) | 25 (78) | 3 (50) |
| Age, median (range), yrs | 39 (19-69) | 28 (74) | 34 (24-47) |
| Age > 30 yrs, n(%) | 22 (58) | 19 (59) | 3 (50) |
| White, n (%) | 34 (89) | 28 (88) | 6 (100) |
| Time since primary diagnosis (range), yrs | 1.8 (0.5-21.5) | 1.7 (0.5-10.6) | 2.2 (0.6-21.5) |
| Prior regimens, median (range) | 2 (1-7) | 2 (1-7) | 2 (1-3) |
| Ph+, n (%) | 4 (11) | 4 (13) | 0 (0) |
| Prior blinatumomab, n (%) | 4 (11) | 16 (50) | 3 (50) |
| Prior HSCT, n (%) | 14 (37) | 11 (34) | 3 (50) |
| Prior CNS disease, n (%) | 8 (21) | 7 (22) | 1 (17) |
| Prior CNS radiation, n (%) | 12 (32) | 11 (34) | 1 (17) |
| Prior IT chemotherapy, n (%) | 30 (79) | 26 (81) | 4 (67) |
| Pre-LD BM blasts, median (range), % | 48 (0-98) | 66 (6-98) | 2 (0-4) |
| Aggressive bridging treatment, n (%)[a] | 19 (50) | 17 (53) | 2 (33) |

IT, intrathecal; LD, lymphodepletion.
[a]Hyper CVAD parts A or B, regimens containing fludarabine and/or cytarabine.

The therapeutic T cell compositions administered had been generated by a process including immunoaffinity-based selection of T cells (including CD4+ and CD8+ cells) from leukapheresis samples from the individual subjects, followed by activation and transduction with a viral vector encoding the anti-CD19 CAR, expansion and cryopreservation. The CAR contained an anti-CD19 scFv derived from a murine antibody, a region of CD28 including an extracellular region, a transmembrane domain and a costimulatory region, and a CD3-zeta intracellular signaling domain. The cryopreserved cell compositions were thawed at bedside prior to intravenous administration. Entire volumes of cell compositions that had been filled and cryopreserved were administered.

Cells had been administered at a first target dose of approximately $1\times10^6$ CD3+CAR+ cells/kg (subject body weight). The target dose and range of doses for administration had been assessed in part based on comparing toxicity outcomes for a group of subjects with morphologic disease having been administered similar compositions, at a range of different numbers of CD3+CAR+ cells per dose administered. In particular, relationship of CD3+CAR+/kg dose and whether or not including whether or not a subject went on to developed grade 3 neurotoxicity was assessed, and target dose and dose range was below the lowest number of CD3+CAR+ cells/kg administered to any of such subjects having demonstrated grade 3 or higher neurotoxicity, less a safety margin of at least $1.5\times10^6$ CD3+CAR+ cells/kg. See FIG. 22. Dose did not consider numbers or frequencies of CD4+ versus CD8+ cells, or of other T cell subsets. Cytotoxic activity against CAR antigen+ cells was assessed as a measure of potency. Some subjects received a second dose, at approximately between 14 and 28 days following the initial dose. Before administration of autologous CAR-expressing cells, subjects had been administered a preconditioning lymphodepleting chemotherapy containing either a single dose of cyclophosphamide (about 1-3 $g/m^2$) only or cyclophosphamide (30-60 mg/kg) and fludarabine (25 $mg/m^2$-30 $mg/m^2$, administered daily over three days).

Subjects were monitored for response and other outcomes, including by examination of bone marrow, peripheral blood and cerebrospinal fluid (CSF). Subjects also were assessed and monitored for neurotoxicity (neurological complications including symptoms of confusion, aphasia, encephalopathy, myoclonus seizures, convulsions, lethargy, and/or altered mental status), graded on a 1-5 scale, according to the National Cancer Institute-Common Toxicity Criteria (CTCAE) scale, version 4.03 (NCI-CTCAE v4.03). Common Toxicity Criteria (CTCAE) scale, version 4.03 (NCI-CTCAE v4.03). See Common Terminology for Adverse Events (CTCAE) Version 4, U.S. Department of Health and Human Services, Published: May 28, 2009 (v4.03: Jun. 14, 2010); and Guido Cavaletti & Paola Marmiroli *Nature Reviews Neurology* 6, 657-666 (December 2010). Cytokine release syndrome (CRS) also was determined and monitored, graded based on severity.

Response (percentage of subjects who showed a complete response (CR) or complete response with incomplete marrow recovery (CRi) (CR/CRi rate) (at a median 4 months follow-up)), and toxicity outcomes are summarized in table E1-B and E1-C for the subjects who had exhibited morphologic disease at the start of treatment. (NE=non-evaluable). As shown, 56% of the subjects developed grade 3-5 neurotoxicity. Five (5) subjects developed grade 5 neurotoxicity and, in particular, grade 5 cerebral edema.

TABLE E1-B

| Summary of Treated Subjects | | |
|---|---|---|
| Morphologic | Cy | Flu/Cy |
| CR/CRi rate | 50%<br>NE 8% | 100%<br>NE: 37% |
| Severe (grade 3 or higher) CRS | 17% | 38% |
| Grade 3-5 neurotoxicity | 46%<br>Grade 5: 8% | 88%<br>Grade 5: 38% |

TABLE E1-C

Outcomes for 32 subjects treated with Morphological disease (total treated = 38 subjects)

| | CY | Flu/Cy | CY | Total Morphological | Total MRD |
|---|---|---|---|---|---|
| Time Period | Time period 1 | Time period 2 | Time period 3 | | |
| Subjects, N | 14 | 8 | 10 | 32 | 6 |
| CR/CRi rate # Non-Evaluable | 6/14 (43%) | 5/5 (100%); 3 NE | 4/8 (50%) | | |
| Severe CRS Grade 3/4 | 1/14 (7%) | 3/8 (38%) | 3/10 (30%) | 7 (22%) | 2 (33%) |
| Severe NTX Grade 3-5 | 3/14 (21%) | 7/8 (88%) | 8/10 (80%) | 18 (56%) | 2 (33%) |
| Treatment Related Morality | Grade 5 events: 0 | Grade 5 events: 3 (all NTX events) | Grade 5 events: 2 (both NTX events) | Grade 5 events: 5 (16%) | Grade 5 events: 0 |

Additional 6 subjects treated were positive for minimal residual disease (MRD+) at time of treatment.

At least 15 instances of grade 5 neurotoxicity and at least 13 cases of cerebral edema associated with CAR-T cell therapy have been reported in several different clinical trials, as reported from publicly available information, including in trials involving CAR-T cells expressing different CARs with different antigen binding domains and different costimulatory domains, produced with different manufacturing protocols, and for the treatment of different diseases or indications.

B. Pharmacokinetic (PK) of CAR+ T cells in Blood

Analysis was carried out on samples derived from blood from subjects at various time points following administration of the first and, where applicable, second dose of the cell compositions. Samples were analyzed by flow cytometry for the presence and number of CAR-expressing cells in the blood.

Figure 1:
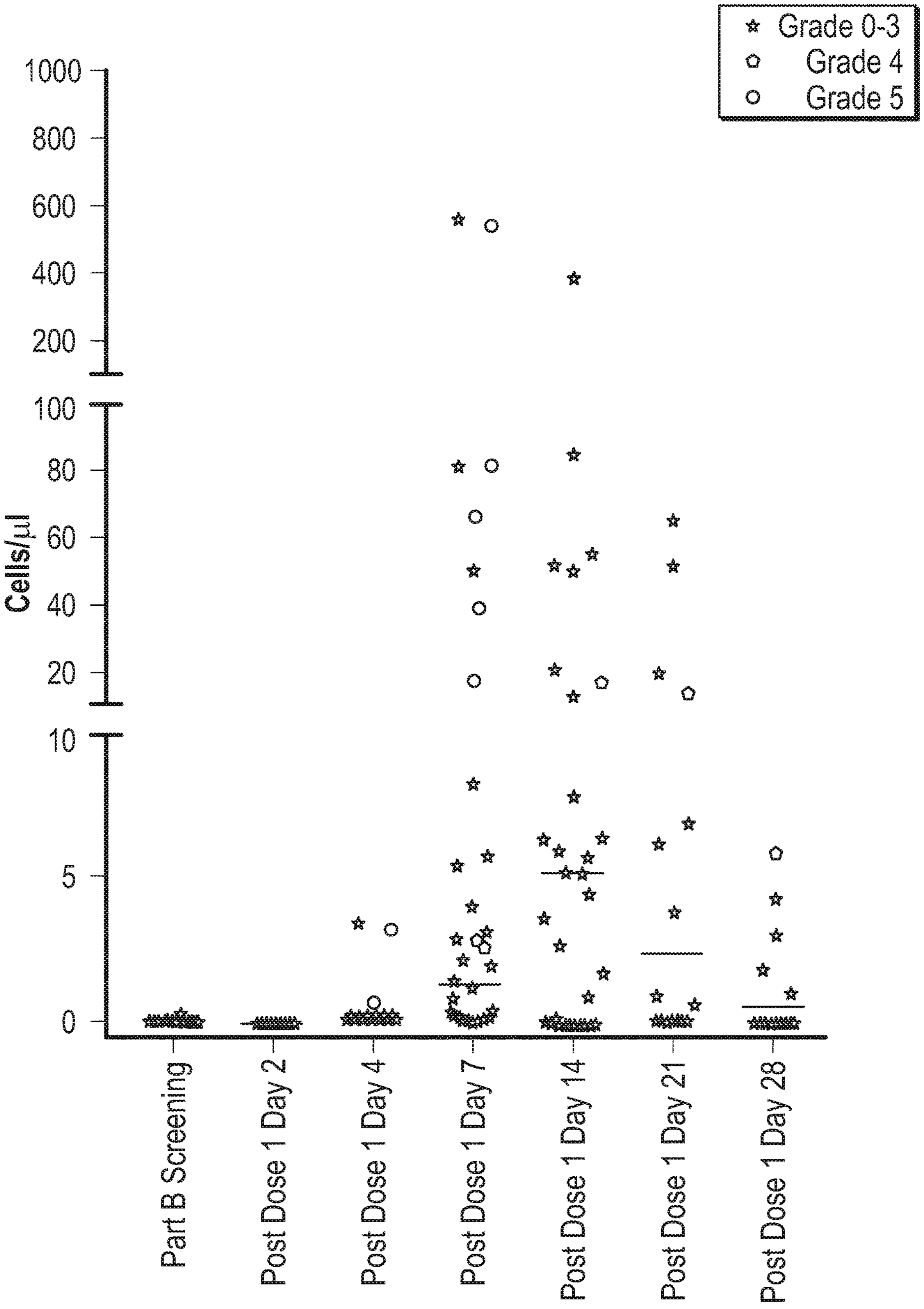
FIG. 1 shows a graph displaying the concentrations of CAR+ cells/μL of blood at different time points after administration of T cell compositions containing anti-CD19 CAR expressing cells. Data is shown for subjects who developed grade 3 or less (stars), grade 4 (pentagon), or grade 5 (circles) neurotoxicity.
Figure 2:
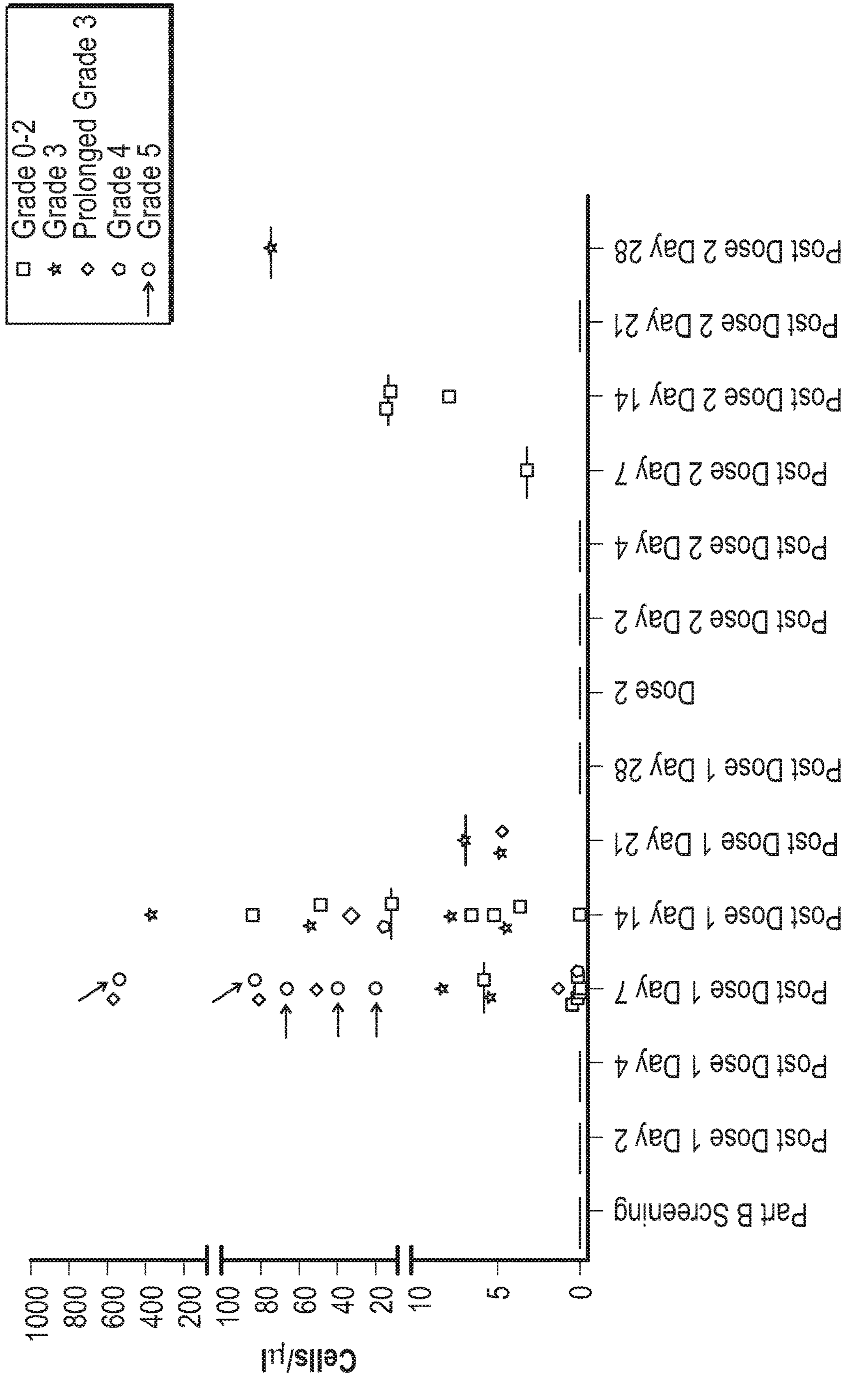
FIG. 2 shows a graph displaying the concentrations of CAR+ cells/μL of blood at different time points after administration of T cell compositions containing anti-CD19 CAR expressing cells. Data is shown for subjects who developed grade 2 or less (squares), grade 3 (stars), prolonged grade 3 (diamond), grade 4 (pentagon), or grade 5 (circles with arrow) neurotoxicity.

As shown in FIGS. 1 and 2, more rapid peak expansions of CAR-expressing T cells were observed in the blood of subjects that went on to develop more severe neurotoxicity, and in particular those who developed grade 5 neurotoxicity and cerebral edema. For example, results indicated that these subjects had exhibited a detectable level of CAR+ cells per μL of blood within 4-7 days after the first dose of cells, with greater than 20 CAR+ cells per μL of blood observed in blood of all such subjects within seven days after cells were administered. In subjects with grade 3 or 4 neurotoxicity, peak expansion of CAR+ T cells generally was observed later and with a lower peak number of CAR+ T cells per microliter (FIG. 2).

C. Assessment and Comparison of Clinical, Patient, Translational and CMC Parameters in Different Subjects Various parameters were assessed for different groups of the patients, according to severity of disease at start of treatment and treatment outcomes or development of toxicity, including varying degrees of neurotoxicity. Presence or absence of correlations and significance were assessed by descriptive, graphical, nonparametric and model-based analyses as described in this Example and in Example 2. Approximately 500 clinical and translational parameters were analyzed using univariate and multivariate logistic regression. Approximately 140 Chemistry, Manufacturing, and Control (CMC) parameters were examined in univariate and multivariate analyses using nonparametric tests and partition-based (decision tree) methods.

Various CMC attributes were assessed in samples from the T cell compositions that had been administered to the subjects (thawed from samples of cryopreserved therapeutic compositions that had been administered to subjects (CDP)). Samples were analyzed for the presence, absence, level, normalized level, amount, and/or normalized amount of various parameters. Among the exemplary clinical and patient attributes assessed were patient age, prior treatment history and whether a patient had received a lymphodepleting and/or holding chemotherapy prior to treatment, development and grade of neurotoxicity and other toxic outcomes. Cell composition-specific and/or dose-related parameters included amounts and frequencies (or normalized values thereof) of various cell populations (in the dose administered and/or administered per subject weight), cytokine production, cytotoxic activity in response to CAR antigen stimulation, and other parameters indicative of function such as of activation or stimulation and/or effector function in response to various conditions. The degree of correlation of the various parameters (individually and in some cases combinations thereof) in the therapeutic compositions to neurotoxicity and other outcomes observed in individual subjects following infusion of the CAR+ T cells was assessed.

Results of exemplary statistical analyses for certain parameters for a subset of subjects that exhibited morphologic disease at start of treatment were consistent with a finding that patient age, prior treatment history and lymphodepleting and/or holding chemotherapy correlated (directly or inversely) with the development of grade 5 neurotoxicity. For example, in this group of subjects, younger patients less than 30 years of age, those having received a lower number (equal to two or fewer) of prior therapies and those having received fludarabine within 3 months or an aggressive holding chemotherapy were more likely to have developed grade 5 neurotoxicity in this study. Calculated odds ratio estimates for experiencing cerebral edema following treatment with the cell therapy for exemplary clinical factors are shown in Table E1-D. The odds ratio was calculated by dividing the odds of developing a grade 5 neurotoxicity associated with the demographic or treatment history by the odds associated with the absence of the demographic or treatment history. An odds ratio over 1 indicated an increased probability or likelihood of developing grade 5 neurotoxicity.

TABLE E1-D

Exemplary Clinical Factors Associated with Cerebral Edema

| Demographics/ Treatment History | Odds Ratio | 95% CI | p-value |
|---|---|---|---|
| Received Flu/CY LD | 7.25 | 1.14, 53.96 | 0.045 |
| Received high intensity bridging chemo | 4.68 | 0.63, 32.64 | 0.133 |
| Age < 30 years | 5.16 | 0.83, 55.93 | 0.112 |
| ≤2 prior lines of therapy | 7.24 | 0.72, 980.23 | 0.208 |

No association for higher risk was observed for prior CNS irradiation, prior treatment with intrathecal (IT) chemotherapy, prior CNS disease, prior allogenic cell therapy, higher ECOG performance status, or prior treatment with blinatumomab.

In this study, certain of such parameters (e.g., young (≤30 y) patient age and fewer prior treatments) also were observed to correlate to certain therapeutic composition-specific or dose-related attributes (including total number of CD8+CAR+AnnV negative cells a subject had received in a dose of cells and the level of antigen-specific accumulation of the pro-inflammatory cytokine, IL-2, as measured in cultures of the thawed therapeutic cell composition in the presence of cells expressing CD19, the CAR antigen, indicative of CAR-induced cell activity). Also among the exemplary attributes assessed were numbers or frequencies of (or numbers/kg of) viable cells, and/or cells of various phenotypes, in individual doses administered to individual subjects. Exemplary such phenotypes included expression of one or more surface markers, as assessed by flow cytometry. For example, phenotypes included CD3+, CD8+, CD4+, and/or CAR+. Also among the phenotypes were viability, and those associated with or indicative of or considered to indicate functional, healthy or biologically active cells. In some aspects, such phenotypes included negative or low presence or expression of markers indicative of apoptosis, of apoptotic cells or of various, e.g., early or late, stages of one or more death or apoptotic pathway entry (e.g. Annexin V, Caspase 3). In some aspects, such markers included the ability of cells to produce cytokines or other factors in a non-CAR antigen-specific manner, such as in an intracellular cytokine staining (ICS) in response to PMA/ionomycin and/or FOXP3. In some aspects, markers and phenotypes included those associated with T cell activation, exhaustion, stem-like properties, naïve T cells, longevity, T cells subsets, memory phenotype(s) and phenotypes of T-memory subsets such as $T_{CM}$, $T_{EM}$, $T_{SCM}$.

For example, therapeutic cell composition-related attributes included total number of CD8+CAR+ T cells in the dose administered, total number or frequency (e.g., among CD8+CAR+ T cells) of CD8+CAR+ T cells in the dose administered that were observed to be negative for a factor indicative of apoptosis, such as surface staining with Annexin V (Annexin V−) or caspase 3 cleavage (indicating non-apoptotic cells). In some examples, therapeutic cell composition-related attributes included total number of CD3+CAR+ T cells in the dose administered, total number or frequency (e.g., among CD3+CAR+ T cells) of CD3+CAR+ T cells in the dose administered that were observed to be negative for a factor indicative of apoptosis, such as surface staining with Annexin V (Annexin V−) or caspase 3 cleavage (indicating non-apoptotic cells).

Also among the exemplary parameters were properties particular to the therapeutic compositions and/or the production thereof, including viable cell concentration (VCC), fold expansion of the cells between inoculation and harvest of the drug product; and vector copy number (VCN) in the administered dose.

Also among the exemplary parameters were those generally associated with or indicative of function or activity or other features or capabilities of cells in the compositions. Among these were various attributes associated with outcomes of cell stimulation, including various indications of proliferation and activation or activity, including those induced in a TCR and/or CAR-induced or dependent manner. Exemplary such parameters related to function or activity were measures or levels (such as amount or concentration or level thereof per cell) of production of one or more factors (such as various cytokines) by cells in the composition, in response to CAR antigen-specific or other stimulation.

In intracellular cytokine staining (ICS) assays, flow-based methods were used to assess the ability of cells in the composition to produce various cytokines in response to non-antigen-specific stimulus. Cells were stimulated for with PMA/ionomycin in the presence of Golgi inhibitor. FoxP3 expression was assessed by a qPCR assay targeting the Treg Specific Demethylation Region (TSDR) of the FOXP3 gene. Levels of FOXP3 indicative of Treg phenotype were not observed.

Several parameters indicative of CAR-targeted antigen-specific activities and functions (such as CAR-antigen-dependent cytokine secretion and cytotoxicity) of the compositions were assessed in co-culture assays. Cells of the therapeutic composition being assessed were incubated in the presence of CD19-expressing target cells. For cytokine assays, accumulated amounts (pg/mL) of the cytokine(s) (e.g. IL-2, IFN-gamma, TNF-alpha, IL-6, sCD137, MIP1b, MIP1a, IL-10, IL-4, IL-13, IL-5 or GM-CSF) were assessed following incubation of target cells and an amount of the various compositions including the same number of transduced or CAR+ cells, in the same volume, for a period of approximately 22-24 hours. Such assays provided a measure of antigen-specific cytokine secretion per CAR+ cell in the dose. In other assays, cytolytic activity against CD19-expressing target cells was assessed after incubation with the T cells.

In some cases, measures of activity or functional effect in response to a non-CAR antigen-specific stimulus, were assessed, such as cytokine or other factor production following stimulation with anti-CD3/anti-CD28, e.g., coated on magnetic beads. In such assays, cultures including fewer CAR+ cells among the T cells in the culture may exhibit a higher relative level of the measure.

Table E2 sets forth a list of a plurality of attributes selected in an unbiased manner from among attributes that had been assessed for therapeutic cell compositions and/or doses thereof administered to the subjects in the studies. These attributes were assessed via univariate analysis for a subset (22) of the subjects that had exhibited morphologic disease at the start of treatment. Table E2 lists p-values indicating the degree to which each attribute was observed to correlate (directly (+) or inversely (−)), based on univariate analysis, to neurotoxicity grade and/or cerebral edema (comparing grade 5 neurotoxicity/cerebral edema vs. other subjects). Among 15 of the subjects, the degree to which each attribute did or did not correlate with response outcome (as assessed by comparing subjects that achieved a complete response (CR) or no response (NR)) also was assessed; Table E2 also lists p-values for this comparison.

The parameters listed in Table E2 are arranged by lowest p value to highest p value, in descending order, based on the univariate statistical comparison between a given attribute and neurotoxicity/cerebral edema (Grade 5 neurotoxicity/CE vs. Grade 4 or lower neurotoxicity). For the parameters for which the p values with respect to grade of neurotoxicity were less than or equal to 0.2, Table E2 further indicates whether the observed relationship to neurotoxicity was direct ((+), indicating that the average level or measure for the parameter was observed to be greater in subjects with grade 5 neurotoxicity and cerebral edema, as compared to those with grade 4 or lower neurotoxicity) or was inverse ((−), indicating that the average level or measure for the parameter was observed to be lower in grade 5 subjects).

FIG. 3A through FIG. 3U show plots for a subset of parameters in which relationships (direct or inverse) were observed between the parameter and grade 5 neurotoxicity, depicting results for individual subjects in different neurotoxicity or response groups. Observed p values for these plots with respect to neurotoxicity were 0.05 or lower.

FIG. 3V shows a plot comparing a measure of number of CD3+CAR+ cells/kg (dose) administered to subjects and whether a subject developed grade 5 neurotoxicity (right-hand side) and/or achieved a complete response (left-hand side). Whereas a relationship between the two variables was observed, CD3+CAR+ cells/kg was not a strong predictor of grade 5 neurotoxicity, and no clear safety margin was observed. The results are consistent with an interpretation that defining dose based upon numbers or frequencies of CD3+CAR+ dose alone, without taking into account other parameters such as representation of biologically active (e.g., non-apoptotic) cells and/or CD8 vs CD4 cells, may not be adequate to prevent risk of severe neurotoxicity, and that with the advantage of developing dosing strategies that take into account one or more predictive parameters as observed herein.

FIGS. 4, 5A and 5B show plots and p values for measures of antigen-specific secretion of individual cytokines (TNFalpha, IFNgamma, IL-2), for individual subjects in the different neurotoxicity or response groups.

As shown, a number of the parameters assessed in the therapeutic cell compositions and doses were observed to significantly correlate (directly or inversely) to the development of grade 5 neurotoxicity following administration of the composition to the subject.

TABLE E2

Assessment of parameters of therapeutic cell compositions and/or dose and correlations to neurotoxicity and response outcomes

| | | Neurotoxicity Grade (Gr. 5 vs. Gr. 4 or lower) | | Response (CR or CRi) |
|---|---|---|---|---|
| Number of Annexin- CD8+CAR-expressing cells administered | p-value | 0 | (+) p-value | 0.164 |
| ICS:IL13 of CD8+CAR+ | p-value | 0.001 | (−) p-value | 0.912 |
| Number of Annexin- CD8+CAR-expressing cells/kg | p-value | 0.001 | (+) p-value | 0.13 |
| Frequency of CD127+ cells among CD4+CAR+ | p-value | 0.004 | (−) p-value | 0.426 |
| Total Cells Infused per KG | p-value | 0.007 | (+) p-value | 0.824 |
| Number of Active Caspase-negative CD8+CAR-expressing cells administered | p-value | 0.007 | (+) p-value | 0.498 |
| ICS: IL13 of CD4+CAR+ | p-value | 0.011 | (−) p-value | 0.654 |
| Frequency of Annexin V+ cells among CD8+CAR+ cells | p-value | 0.012 | (−) p-value | 0.056 |
| FOXP3 by QPCR | p-value | 0.012 | (+) p-value | |
| Number of Annexin V− CD3+CAR-expressing cells administered | p-value | 0.012 | (+) p-value | 0.056 |
| Number of Annexin V− CD3+CAR cells administered/KG | p-value | 0.015 | (+) p-value | 0.1 |
| Viable Cell Concentration (VCC) | p-value | 0.017 | (+) p-value | 0.859 |
| Total Cells Infused | p-value | 0.017 | (+) p-value | 0.859 |
| ICS:IL2 of CD4+CAR+ | p-value | 0.019 | (−) p-value | 0.738 |
| Frequency of Annexin V+ cells among CD3+CAR+ | p-value | 0.024 | (−) p-value | 0.164 |
| Frequency of FOXP3+ among CD4+CAR+ | p-value | 0.03 | (+) p-value | 0.912 |
| CD3+ Frequency | p-value | 0.033 | (+) p-value | 0.806 |
| Total CD8+CAR-expressing cells administered/KG | p-value | 0.037 | (+) p-value | 0.738 |
| Non-antigen/CAR-specific IL-10 production per total cell (CD3/28 stim) | p-value | 0.04 | (+) p-value | 1 |
| ICS:TNFA of CD4+CAR+ | p-value | 0.044 | (−) p-value | 0.953 |
| ICS:TNFA of CD8+CAR+ | p-value | 0.044 | (−) p-value | 0.498 |
| Non-antigen/CAR-specific IL-6 production per total cell (CD3/28 stim) | p-value | 0.045 | (+) p-value | NaN |
| Non-antigen/CAR-specific IFNgamma production per total cell (CD3/28 stim) | p-value | 0.055 | (+) p-value | 0.25 |
| Frequency of PD1-expressing cells among CD4+CAR+ cells | p-value | 0.055 | (+) p-value | 0.076 |
| Measure of IL10 production following CAR antigen-specific culture | p-value | 0.057 | (+) p-value | 0.722 |
| Frequency of Annexin V+ among CD4+CAR+ | p-value | 0.067 | (−) p-value | 0.164 |
| Frequency of PD1+ cells among CD8+CAR+ | p-value | 0.067 | (+) p-value | 0.36 |
| CD3+CAR+ Frequency among cells in dose | p-value | 0.08 | (−) p-value | 0.738 |
| CD3+CAR+ cells administered/KG | p-value | 0.08 | (+) p-value | 0.574 |
| Total CD8CAR cells in dose | p-value | 0.08 | (+) p-value | 0.654 |
| Non-antigen/CAR-specific sCD137 production per total cell (CD3/28 stim) | p-value | 0.085 | (+) p-value | 0.592 |
| Frequency of effector memory T cells among CD8+CAR+ | p-value | 0.094 | (+) p-value | 0.912 |
| Number of active Caspase 3 cleavage negative CD3+CAR+ cells administered | p-value | 0.094 | (+) p-value | 0.738 |
| Frequency of Naïve phenotype cells among CD8+CAR+ cells | p-value | 0.094 | (+) p-value | 0.654 |
| Frequency of CD27+ CD28+ cells among CD8+CAR+ cells | p-value | 0.111 | (+) p-value | 0.203 |
| CD4+CAR+ Frequency per cell in dose | p-value | 0.126 | (−) p-value | 0.906 |
| Frequency of effector memory phenotype among CD3+CAR+ | p-value | 0.13 | (+) p-value | 1 |
| Number of Annexin V− CD4+CAR+ cells administered/KG | p-value | 0.13 | (+) p-value | 0.13 |
| Measure of TNFalpha Production following CAR antigen-specific culture | p-value | 0.15 | (+) p-value | 0.654 |
| Number of Annexin V− CD4+CAR+ cells administered | p-value | 0.15 | (+) p-value | 0.1 |
| Measure of sCD137 production following CAR antigen-specific culture | p-value | 0.168 | (+) p-value | 0.635 |
| Measure of IFNG production following CAR antigen-specific culture | p-value | 0.174 | (+) p-value | 1 |
| Non-antigen/CAR-specific IL-4 production per total cell (CD3/CD28 stim) | p-value | 0.174 | (+) p-value | 0.912 |
| Total CD3+CAR+ cells administered | p-value | 0.174 | (+) p-value | 0.824 |
| Vector Copy Number (Per Genome) | p-value | 0.177 | (−) p-value | 0.498 |
| Measure of MIP1B production following CAR antigen-specific culture | p-value | 0.199 | (+) p-value | 0.824 |

TABLE E2-continued

Assessment of parameters of therapeutic cell compositions and/or dose and correlations to neurotoxicity and response outcomes

| | Neurotoxicity Grade (Gr. 5 vs. Gr. 4 or lower) | | Response (CR or CRi) | |
|---|---|---|---|---|
| Non-antigen/CAR-specific MIP1b production per total cell (CD3/CD28 stim) | p-value | 0.199 (+) | p-value | 0.824 |
| ICS: IL2 of CD8+CAR+ | p-value | 0.199 (−) | p-value | 0.426 |
| Measure of IL-2 Production following CAR antigen-specific culture | p-value | 0.199 (+) | p-value | 0.824 |
| CD27+ CD28+ frequency among CD3+CAR+ cells | p-value | 0.199 (+) | p-value | 0.25 |
| CD4/CD8 Ratio | p-value | 0.199 (−) | p-value | 0.824 |
| Fold Expansion: INOC 0 to Pre-Harvest | p-value | 0.199 (−) | p-value | 0.498 |
| Endotoxin | p-value | 0.217 | p-value | 0.192 |
| Non-antigen/CAR-specific TNFa production per total cell (CD3/CD28 stim) | p-value | 0.227 | p-value | 0.738 |
| ICS:IFNG of CD8+CAR+ | p-value | 0.227 | p-value | 0.301 |
| CD8+ Frequency in dose | p-value | 0.227 | p-value | 0.824 |
| Non-antigen/CAR-specific IL-2 production per total cell (CD3/CD28 stim) | p-value | 0.257 | p-value | 0.738 |
| CD127+ frequency among CD8+CAR+ cells | p-value | 0.257 | p-value | 0.1 |
| Naïve phenotype frequency among CD3+CAR+ | p-value | 0.257 | p-value | 0.574 |
| LAG3+ frequency among CD4+CAR+ | p-value | 0.263 | p-value | 0.301 |
| CD4+ Frequency in dose | p-value | 0.263 | p-value | 0.824 |
| Non-antigen/CAR-specific MIP1a production per total cell (CD3/CD28 stim) | p-value | 0.29 | p-value | 0.738 |
| CD27− CD28+ cell frequency among CD8+CAR+ | p-value | 0.29 | p-value | 0.426 |
| Measure of MIP1a production in CAR antigen-specific culture | p-value | 0.325 | p-value | 1 |
| ICS:IFNG of CD4+CAR+ | p-value | 0.325 | p-value | 0.426 |
| Temra frequency of CD4+CAR+ | p-value | 0.325 | p-value | 0.824 |
| CD27− CD28− frequency of CD4+CAR+ | p-value | 0.325 | p-value | 0.301 |
| Cytolytic Activity measure | p-value | 0.351 | p-value | 0.906 |
| Measure of IL-4 production in CAR antigen-specific culture | p-value | 0.363 | p-value | 0.912 |
| Measure of IL-6 production in CAR antigen-specific culture | p-value | 0.391 | p-value | 0.514 |
| CD27− CD28− frequency among CD8+CAR+ | p-value | 0.403 | p-value | 0.426 |
| CD27+ CD28− frequency among CD3+CAR+ | p-value | 0.403 | p-value | 1 |
| ICS:IL17 of CD4+CAR+ | p-value | 0.446 | p-value | 0.498 |
| CD27− CD28+ among CD3+CAR+ | p-value | 0.446 | p-value | 0.912 |
| CD25+ frequency among CD4+CAR+ | p-value | 0.456 | p-value | 0.514 |
| Measure of GMCSF production in CAR antigen-specific culture | p-value | 0.491 | p-value | 1 |
| Naïve cell frequency among CD4+CAR+ | p-value | 0.491 | p-value | 0.738 |
| CD25+ frequency among CD8+CAR+ | p-value | 0.502 | p-value | 0.738 |
| Vector Copy Number (Per CAR+ Genome) | p-value | 0.531 | p-value | 0.941 |
| CD27−CD28− among CD3+CAR+ | p-value | 0.538 | p-value | 0.574 |
| Number of CD4CAR cells administered/Kg | p-value | 0.538 | p-value | 0.498 |
| Number of CD4CAR cells administered | p-value | 0.538 | p-value | 0.25 |
| Tem phenotype frequency among CD8+CAR+ cells | p-value | 0.587 | p-value | 0.426 |
| CD27+ CD28− phenotype frequency among CD8+CAR+ | p-value | 0.602 | p-value | 0.824 |
| Cell viability in therapeutic composition | p-value | 0.628 | p-value | 0.813 |
| Tcm phenotype frequency among CD8+CAR+ cells | p-value | 0.638 | p-value | 0.426 |
| CD8+CAR+ Frequency in dose | p-value | 0.682 | p-value | 0.953 |
| Ki67+ phenotype among CD8+CAR+ cells | p-value | 0.709 | p-value | 1 |
| Tem phenotype among CD4+CAR+ | p-value | 0.794 | p-value | 0.906 |
| Non-antigen/CAR-specific GMCSF production per total cell (CD3/CD28 stim) | p-value | 0.801 | p-value | 0.654 |
| ICS:IL17 of CD8+CAR+ | p-value | 0.801 | p-value | 0.912 |
| Ki67+ frequency among CD4+CAR+ cells | p-value | 0.881 | p-value | 0.407 |
| LAG3+ frequency among CD8+CAR+ cells | p-value | 0.911 | p-value | 0.813 |
| Measure of IL-13 production in CAR antigen-specific culture | p-value | 0.914 | p-value | 1 |
| Tcm phenotype frequency among CD4+CAR+ | p-value | 0.914 | p-value | 0.574 |
| CD27+ CD28− phenotype among CD4+CAR+ | p-value | 0.914 | p-value | 0.301 |
| CD27− CD28+ phenotype among CD4+CAR+ | p-value | 0.914 | p-value | 0.912 |
| FOXP3+ phenotype among CD8+CAR+ | p-value | 0.97 | p-value | 0.594 |
| CD27+ CD28+ phenotype among CD4+CAR+ | p-value | 0.97 | p-value | 0.953 |

TABLE E2-continued

Assessment of parameters of therapeutic cell compositions and/or dose and correlations to neurotoxicity and response outcomes

| | Neurotoxicity Grade (Gr. 5 vs. Gr. 4 or lower) | | Response (CR or CRi) | |
|---|---|---|---|---|
| Non-antigen/CAR-specific IL-13 production per total cell (CD3/CD28 stim) | p-value | 0.971 | p-value | 0.574 |
| Tcm phenotype frequency among CD3+CAR+ | p-value | 0.971 | p-value | 0.25 |
| Tem frequency among CD3+CAR+ | p-value | 0.971 | p-value | 0.426 |
| Measure of IL-5 production in CAR antigen-specific culture | p-value | 1 | p-value | 0.906 |
| Non-antigen/CAR-specific IL-5 production per total cell (CD3/CD28 stim) | p-value | 1 | p-value | 0.553 |

It was observed that relationships observed in this study with respect to vector copy number (per cell or per genome) were considered surrogate indicators of cell fitness and/or multiple variables that associated with relative representation of engineered or not engineered cells in the composition and/or density of total cells in the composition. For example, in some embodiments, cells from blood samples that were generally less healthy at the start of the process had a lower likelihood of survival during the transduction phase and/or cell death during transduction can improve transduction efficiency. Thus, in some aspects, in some cases, higher copy numbers of a viral vector per composition, such as one introduced via lentiviral or gammaretroviral vector transduction, may indicate compositions in which a larger percentage of cells were unhealthy at the start of the process and in some aspects may have had properties that correlated, e.g., inversely, with neurotoxicity. In some embodiments, higher frequency of transduction can result in a composition that has a higher frequency of engineered (e.g., CAR+) cells during cryopreservation, storage and thaw. In some aspects, when dose is based on numbers of engineered cells (or subtype thereof, e.g., CAR+CD3+), such compositions with higher frequency of engineered cells can include lower overall cell densities, which in some embodiments correlates with reduced levels or frequency of biologically active or non-apoptotic cells.

The results of this univariate analysis identified several parameters of dose and/or the therapeutic cell composition that were observed to significantly correlate (directly or inversely) with the development of grade 5 neurotoxicity/cerebral edema. Among such parameters were those indicative of the number, number per patient weight, and/or frequency of cells having a phenotype generally indicative of biologically active cells, such as non-apoptotic CAR+ T cells or non-apoptotic CAR+CD8+ T cells administered in the dose. A number of parameters that correlated with grade 5 neurotoxicity, were observed not to significantly correlate with treatment response outcome (here, whether or not the subject achieved a complete response or no response). In various cases, a number of subjects achieving CRs were observed to have levels of these parameters that were below (for direct correlation) a threshold level corresponding to the lowest number (for direct correlation) observed among subjects that developed the unwanted effect such as grade 5 neurotoxicity. For example, the results indicated that numbers of biologically active or non-apoptotic CD3+ and/or CD8+ cells expressing the CAR could be used to determine a dose within safety and efficacy boundaries to reduce risk of neurotoxicity and be within range at which responses had been observed. No association was identified between fatal neurotoxicity and T cell differentiation state or other phenotypes.

Various measures of number(s) or normalized numbers of cells that were negative for surface staining for markers of apoptosis (including Annexin V), in the doses administered to the subject (or frequency of such apoptotic marker-negative cells among cells of the product such as among CAR+CD3+ or CAR+CD8+) were observed to correlate with neurotoxicity. Results for Annexin V and caspase 3 were generally observed to be similar. Whereas such parameters may also be considered to relate to function or potency of a CAR-T cell composition, and thus may be expected to relate to efficacy, these variables generally were not observed to significantly correlate with treatment response outcome, in this case whether or not the subject achieved a complete response or no response (see, e.g., FIGS. 2-5).

Results were consistent with the use of frequency or number of non-apoptotic (and/or biologically active) T cells or CAR+ cells or subset(s) thereof (as indicated by various measures) as a parameter predictive of grade 5 neurotoxicity or cerebral edema and/or of severity of neurotoxicity, and the use of such parameter(s) to determine appropriate dosage and/or appropriate safety limits for CAR-T therapy.

Example 2: Multivariate Analysis of Parameters of CAR+ T Cell Compositions that are Predictive of Severe Neurotoxicity and/or Cerebral Edema Univariate analyses generally consider one covariate at a time. Multivariate analyses consider multiple covariates at a time and/or in combination, and generally are able to take into account the covariance, i.e. the interaction between the covariates.

Multivariate analyses were performed to identify combinations of parameters (among those individually assessed in the univariate analysis) that strongly correlated with and/or had high predictive value for clinical and/or toxicity outcomes.

Recursive, two factor partition tree analysis was performed to analyze different combinations of attributes. Specifically, the combined dataset from the univariate analysis, including approximately 250 covariates (parameters), were examined using a partition (algorithmic, decision tree) based approach for binary classification. In general, classical regression methods generate functional (linear and non-linear) relationships typically more suitable for physicochemical data and/or hypothesis testing. Partition methods generally generate algorithmic ("tree") models which can in some embodiments be more suitable for biological data and exploratory analysis. Compared to data mining techniques such as Support Vector Machines (SVM) and Artificial Neural Networks (ANN), partition models can be advantageous in ease of interpretation.

Partition models generally include nested "if-then-else" bins/buckets, e.g., that predict average responses. In some embodiments, because partition methods do not assume an α priori model, they are more useful in assessing noisy or subjective measurements, non-linearities and data-sets with mixed data types (i.e. predictor and response variables that are categorical and/or continuous).

In general, tree-based approaches are non-parametric and, compared to other multivariate methods, better equipped to handle noisy and subjective measurements, combination of continuous and categorical variables and nonlinear relationships.

In the approach in this study, data for the total group of 38 subjects and, separately, for a group of 24 morphologic subjects were considered. Correlations to neurotoxicity were assessed by grouping patients in three different ways: according to whether or not subjects developed grade 5 neurotoxicity, whether or not they developed grade 4 or 5 neurotoxicity, and whether they developed grade 4, 5 or prolonged (10 days or greater) grade 3 neurotoxicity (3p). Model complexity was minimized by using combinations of, at most, two covariates (one primary predictor and one secondary predictor) at a time and keeping the size of the splits at a minimum of five observations.

An iterative search was conducted, in which several alternative models were generated using the (same) best primary predictor and several secondary predictors, as long as the number of false positives and false negatives were satisfactorily small. The search then considered the next best primary predictor and the steps were repeated. Several alternative models were evaluated and it was found that the better models (the ones with fewest number of false positives and false negatives) consistently used similar covariates.

Particular pairs of parameters observed by this method to have strong predictive power for severity of neurotoxicity (e.g., grade 5 neurotoxicity). Among such pairs were combinations of numbers, or normalized numbers, of particular cell populations (such as CAR+CD3+non-apoptotic or CAR+CD8+ non-apoptotic) in the dose administered and an indicator of CAR antigen-specific activity in the therapeutic composition, such as pro-inflammatory cytokines. Among such pairs was the combination of number of apoptotic marker-negative CD8+ CAR expressing cells administered to the subject, in combination with a parameter indicative of TNF-alpha production as measured by accumulation in supernatant following an 18 hour co-culture of a sample of the therapeutic cell composition containing $0.25\times10^6$ CD3+ CAR+ cells in co-culture with CD19 expressing cells at a ratio 1:1 (see FIGS. 6A and 6B). Similar findings were observed for other pro-inflammatory cytokines such as IFN-gamma and IL-2 in place of TNF-alpha.

These combinations of variables were not observed to strongly predict response (as measured by CR vs. no CR) in this study, either inversely or directly (see, e.g., FIGS. 9, 11, 13). Additionally, several of the subjects who achieved CR or CRi in the study described in Example 1 had received doses of the cell product containing numbers (or normalized numbers) of apoptotic marker-CD8+CAR+ cells that were below the lowest number (or normalized number) in any dose administered among subjects who went on to develop grade 5 neurotoxicity/cerebral edema. Similarly, several subjects who went on to achieve CRs had been administered cell compositions determined via the assay to have levels for CAR antigen-specific cytokine (e.g., TNF-a, IFN-g, IL-2) production that were below the lowest observed among compositions administered to any of the subjects who developed grade 5 neurotoxicity/cerebral edema (see, e.g., FIGS. 4 and 5).

Results from post-facto analysis from another trial were consistent with the utility of the identified covariate pairs for determining dose and predicting neurotoxicity. Results following a similar anti-CD19 CAR-expressing cell compositions administered in another clinical study to a subset (11 of 31) of subjects (selected for representation over a range of different responses) with relapsed or refractory adult ALL were analyzed for measures of certain parameters deemed to correlate or inversely correlate with neurotoxicity outcomes in the study above. Of the 31 subjects, 77% had experienced CR or CRi, with rates of 61% relapse and 27% stem cell transplant (SCT) among CR/CRi subjects. 42% experienced grade 3 or higher CRS and 35% exhibited grade 3 or 4 neurotoxicity; none of the 31 subjects experienced Grade 5 neurotoxicity or cerebral edema.

Certain parameters were assessed and compared for subjects and cell compositions in this other study, generally as described above, including number of apoptotic marker-negative CD8+CAR expressing cells administered and the same parameter of antigen-specific activity (same measure of TNF-alpha accumulation in an assay involving co-culture with CD19 expressing cells as used above). Results are shown in FIG. 7 and FIG. 6B. For the dose administered to each of the 11 subjects evaluated from the other similar clinical study—none of whom exhibited grade 5 neurotoxicity or cerebral edema-: (i) the number of apoptotic marker-negative, CAR-expressing CD8+ cells, was below the lowest number of such cells in a dose administered to any grade 5 neurotoxicity subject in the study above and/or (ii) the level of the parameter indicative of CAR-induced activity (e.g., measure of TNF-alpha production) (B) was below the lowest level observed in doses for grade 5 subjects in the study above. As shown in FIG. 6B, the general product profile range for this assay among a majority of subjects in the other study assessed was below such level indicative of CAR-induced activity, as indicated by the shaded oval.

Thus, among subjects in another study with a similar CAR-expressing cell composition, none of whom had developed grade 5 neurotoxicity, one or both of the covariates in the pair predictive of neurotoxicity was below the level observed for any patient experiencing the toxicity. Similar results were observed when IFNg or IL-2 was assessed in place of TNF-alpha. The results are consistent with the interpretation of use of a combination of a functional attribute (degree of CAR antigen-specific activity as assessed by the secretion of pro-inflammatory cytokines following co-culture with antigen-expressing cells) and number (or number per weight) of non-apoptotic CAR+CD8+ cells to determine or assess appropriate dose to minimize risk or severity of neurotoxicity.

The results of the studies were consistent with advantages of using a composite approach to defining an appropriate unit dose for administration of CAR-T compositions. For example, the results are consistent with the utility of an approach in which unit dose is based on two or more parameters and/or in which the release of the unit dose to be administered occurs only after accounting for any variability that could potentially be contributed by each of such two or more parameters. For example, the results are consistent with advantages of administering unit dose and/or identifying appropriate dose, in which dose (A) relates to the number or amount of cells of a particular phenotype (such as CD3+CAR+, CD8+CAR+, or CD8+CAR+apoptotic marker-negative) and the other of or composite number of cells of multiple phenotypes, which (B) indicates a CAR-induced/dependent and/or antigen-specific activity such as CAR-induced production of pro-inflammatory cytokine. The results were consistent with the utility of a composite approach in which (1) a target number of cells (A) is administered, provided that the measure of activity (B) is below a certain threshold number (based on correlations with toxicity), (2) a different target dose (A) is administered depending on whether B is above or below a given one or more threshold values (and optionally where cells are not administered if B is above an upper limit safety threshold) and/or (3) dose is defined as a target number of reference units, the number of reference units being determined based on a function of A and B (e.g., A×B or function of transformed value(s) or multiple(s) of A and B).

Moreover, it was observed that in some cases, changes of storage or handling conditions or lot of raw material(s) or reagent(s) used in a process for producing an engineered T cell composition—in an otherwise similar cell engineering process—appeared to correlate, in the final therapeutic composition, with certain parameters that were observed herein to have a relationship with severity of neurotoxicity and/or cerebral edema, e.g., in the study described above, e.g., in combination with another covariate. For example, differences in such storage or handling conditions or lots of such materials or reagents were observed to correlate with changes in certain measures of antigen-specific activity in the therapeutic composition produced by the methods, such as such as the measure of pro-inflammatory cytokine (e.g., TNFalpha) production in response to co-culture with cells expressing the CAR antigen.

Levels observed for measures of exemplary parameters (measure of CAR antigen-specific TNF alpha production and frequency of CD27+/CD28+ phenotype among CAR+ cells) were compared for two groups of therapeutic cell compositions, generated by a process using two different lots of raw material.

The results are shown in FIGS. 23A and 23B. As shown, the levels of these parameters varied among samples. A higher average level of each parameter was observed in cell compositions generated using the process using one lot (lot 2) of the raw material, as compared to those generated using a comparable process using another lot (lot 1) of the same reagent (TNFα: $p=0.066$); (CD27+/CD28+frequency: $p=0.018$). FIG. 23B further indicates grade of neurotoxicity/cerebral edema developed by the subject to which each individual cell composition was administered. Among the 15 subjects, higher grades of neurotoxicity/cerebral edema had been observed among subjects that had been administered cell compositions produced using lot 2 of the reagent.

In another example, the storage and/or handling of reagents was also observed to affect the parameters among two groups of therapeutic cell compositions, generated by a process using the same cell culture media, used with two different storage and/or handling conditions in an otherwise similar cell engineering process. Two groups of therapeutic cell compositions generated from the same media stored under each condition were assessed for TNF-alpha production in response to co-culture with cells expressing the CAR antigen. As shown in FIG. 23C, the levels of TNF-alpha production varied among samples. A trend of lower TNF-alpha production was observed in cell compositions generated using media stored under the first storage condition as compared to those generated using the same media stored under the second storage condition.

The observations were consistent with the interpretation that it can be advantageous—e.g., in identifying a safe and effective cell composition dose—to consider (e.g., assay for prior to release of product and/or factor into the dosing strategy) the degree of variability in factors that may contribute to certain cell/antigen-specific activities in a composition, from the perspective of compositions produced from cells derived from different subjects, and/or in the presence of one or more different storage or handling conditions of raw material or reagents, e.g. using different lots of reagents or other raw materials. The results highlight certain advantages of embodiments provided herein. In some aspects, it is advantageous to reduce the variability in such parameters and/or confirm acceptable range of variability among such different conditions/lots such as when introducing a new lot or reagent stored or handled under different conditions, such as using a release assay testing one or more parameters of cell compositions made using a process incorporating such changes, such as those parameters observed herein to be associated with risk of neurotoxicity, so as to avoid variability in such parameters, e.g., in different dosages or cell products.

In some embodiments, the provided methods, articles of manufacture, compositions, doses and dosing strategies are advantageous in that they take into account and, where relevant, adjust or correct for, potential sources of variability, including those deriving from change in reagents and/or patient-to-patient variability. For example, in some embodiments, it can be advantageous to produce engineered T cells by a process that involves the use of a T cell stimulation/expansion reagent (or lot thereof) that has been verified by a release assay to be below or within an acceptable range of variance as compared to a threshold level of a parameter, e.g., specific activity with respect to such a parameter of the therapeutic composition (such as measure of the amount or relative amount of the reagent necessary to induce a particular degree of the antigen-specific activity in the final T cell composition produced by T cell engineering process, for example, as compared to a control reagent or standard unit with respect to such assay). In some embodiments, the provided embodiments involve cell doses in which the cells have been produced by a process involving a release assay to confirm that any variability in such a specific activity parameter (e.g., antigen-specific inflammatory cytokine measure) is within an acceptable range and/or below an upper specification limit. In some embodiments, the provided processes include such a release assay. In some embodiments, the production of the cell compositions is carried out using reagents and/or processes in which variance of such parameters is within an acceptable range. In some embodiments, the provided methods, compositions and articles of manufacture are advantageous in that they use dosing and/or cell production strategies that mitigate risk associated with potential variance in such specific activity parameters, e.g., by minimizing variability in a second parameter that, together with the specific activity parameter, correlate with risk of toxicity. For example, by minimizing the variance in frequency of biologically active or healthy cells (e.g., non-apoptotic cells) produced by a process, impacts in changes of specific activity-related parameters on safety can be minimized. In some embodiments, a dose or dosing strategy that includes feature(s) related to the number or frequency of biologically active or non-apoptotic cells, such as biologically active or non-apoptotic engineered cells or engineered CD8+ cells, reduces risk associated with variance in antigen-specific activity parameters. In some aspects, this is achieved by doses that include an upper limit of such cells and/or that define dose based upon reference units, e.g., based on a formula taking into account the number of biologically active cells.

Compositions administered to subjects in the study in Example 1 were compared to compositions produced by an alternative process for producing engineered T cells, from blood samples derived from subjects having relapsed or refractory NHL. The process involved separately generating and then mixing, at approximately a target ratio, CD4+ and CD8+ populations of engineered T cells derived from the same subject. Each population was generated via a similar process that involved the use of different factors and reagents, including cytokines, e.g., during activation, transduction (which involved the use of a lentiviral vector), and/or expansion of the cells. The process further involved filling product containers, cryopreserving and thawing cells at a cell density that was comparably higher than densities used in the process in the above study, and was consistent across samples (see Example 4). In general, the process allowed for an enhanced degree of control over the phenotype, function and metabolic profile of engineered cells in the final composition. The CAR included a 41BB-derived costimulatory domain as opposed to a CD28 domain.

It was observed that among samples produced using a process (e.g., one using controlled ratios of T cell subsets, cytokines and reagents to allow for control of phenotype, function and metabolic state) and controlled and higher cell density during cryopreservation), there was less subject-to-subject variability, as compared to among samples analyzed in Example 1, in attributes of therapeutic cell compositions observed herein to be strongly predictive (alone and/or in combination) of risk of severe neurotoxicity.

For example, the alternative process (B) led to higher frequencies of biologically active or healthy cells among CD8+CAR+ cells, as measured by negativity for various apoptotic markers among samples generated using the process, as compared to samples administered as described in Example 1 (see, e.g., FIG. 21A). Additionally, there was a lower degree of variance in this parameter among samples produced by the process from different subjects. As observed herein, number of such cells was observed to correlate with grade 5 neurotoxicity and cerebral edema, whereas CD3+ CAR+ viable cells (not accounting for apoptotic state vs biologically active cells) was a poorer predictor and did not clearly define a safety boundary. In some embodiments, the use of a process with reduced variability in frequency of such biologically active cells among engineered cells, reduces the risk that certain patients (e.g., those having cells less prone to apoptosis or that are more healthy) will inadvertently be given a higher dose than intended of biologically active cells, when dosing based on engineered T cell numbers as a whole. Processes such as this one with a greater degree of control over phenotype and function further have been observed to reduce the degree of variability in the ability of cells produced by the process to make inflammatory cytokines in an antigen-specific manner (see, e.g., FIG. 21B). The results in the study above are consistent with an interpretation that, particularly when combined with numbers of biologically active engineered cells, a dosing strategy taking into account such cell-specific activity parameters (e.g., such that a specific target range of such activity—or no more than a threshold—is represented in a given dose), can be used to provide a dose capable of achieving a desired clinical or therapeutic outcome, while still within a safety margin or reducing the risk of unwanted toxicity, e.g., neurotoxicity.

In some embodiments, the use of a process that yields consistently higher frequencies of biologically active engineered cells, permits the use of cell doses that are far lower (from the perspective of numbers of engineered, e.g., CAR+, cells), as compared to other dosing strategies, in which a higher frequency of engineered cells are positive for apoptotic markers or otherwise are less healthy. For example, based on observations herein, and considering the observation that available dosing strategies generally have not taken to account frequency of apoptotic cells, in some embodiments, numbers of engineered (e.g., CAR+) T cells (e.g., engineered CD8+ and/or CD4+ cells), are as low as 5, 10, 11, 12, 13, 14, 15, 16, 17, 18, 19, 20, 30, 40 or 50 million cells.

Example 3: Determination and Formula for Target Dose Unit

Exemplary doses, dose ranges, and methods and formulas for dosing and dose determination, were identified and developed based on combinations of parameters identified in the multivariate analyses deemed to be predictive of neurotoxicity grade.

Data for all thirty-eight subjects or the morphologic subjects only were assessed. Dose data was available for 37/38 subjects; correlation to response (CR vs. no CR) was considered only for morphologic disease burden patients and was not considered for subjects who had developed grade 5 neurotoxicity and were not evaluable for CR. For individual subjects, the number of reference units (RU) in the dose administered was determined, where:

$$RU=A\times B,$$

A was equal to the number of apoptotic marker-negative, CD8+, CAR-expressing cells, and B was a parameter indicative of CAR-antigen-specific activity among cells in the composition. In some analyses (see FIGS. 8-13), B was a measure indicative of level of antigen-specific production of an individual cytokine (e.g., concentration per hour per input cell number), or geometric or arithmetic mean of such measure, for multiple cytokines.

In other analyses (see FIGS. 14-20), B was a corrected value indicative of one or more cytokine levels, based on such measure or composite measure, normalized to a central tendency of such measure among the subjects with grade 0-2 neurotoxicity.

Results were plotted on a logarithmic scale for subsets of subjects grouped according to neurotoxicity grade (with subjects grouped either by whether or not they developed grade 4 or 5 neurotoxicity or whether they developed prolonged grade 3 (3p), 4 or 5 neurotoxicity) and/or response rate (CR/no CR).

Results are shown in FIGS. 8-20. Specifically, FIGS. 8-13 show results among 38 subjects.

FIGS. 14, 15 and 16 show RU results among 32 morphologic disease subjects where A was equal to the number of apoptotic marker-negative, CD8+, CAR-expressing cells B was a corrected measure of antigen-specific production of an individual cytokine (TNF-alpha, IFN-gamma, and IL-2, respectively) normalized to a central tendency of the measure of the individual cytokine among subjects with grade 0-2 neurotoxicity (with FIGS. 14A, 15A, and 16A showing the results with subjects grouped according to neurotoxicity grade and FIGS. 14B, 15B and 16B showing results with subjects grouped according to response (CR vs no CR)).

Separations in various RU numbers were observed between groupings of subjects exhibiting different grades of toxicities. Results were used to identify exemplary upper or threshold numbers of reference units (based on the formula RU=A×B) and exemplary target RUs and target doses. In some example, the threshold or target RU was identified to be below the RU determined among subjects having developed a particular grade of neurotoxicity, in some aspects, less a number of RU corresponding to a safety window, such as resulting in a 1.5-fold or 2-fold decrease in RU. Plots grouping patients according to response were consistent with the finding that the target RU values and target doses would be within acceptable response windows.

Example 4: Correlation of Total Cell Density in Cryopreserved Composition and Parameters of Composition Indicative of Cell Function and Other Attributes Impacts of cell density, e.g., viable cell concentration (VCC), during cryopreservation and storage of therapeutic T cell compositions were examined. Increasing cell density in certain compositions is known to reduce cell survival. It was observed herein, however, that for some cryopreserved cell compositions for therapeutic use, particularly those that are cryopreserved at relatively low cell densities (such as below 10% cell volume to total freezing volume), that increasing cell density during cryopreservation, storage and/or thaw, of the composition, e.g., the therapeutic product, can be advantageous, e.g., with respect to cell health and/or biological activity and/or function.

The cryopreserved therapeutic cell compositions administered to subjects in the clinical study described in Example 1 had been cryofrozen at different densities at approximately below 1% (cell volume as a percentage of total freezing volume), with DMSO. In the studies assessing various parameters above, samples from the cell compositions, cryopreserved, maintained and thawed under conditions mimicking those under which administered cell compositions were maintained, shipped and thawed, including similar time periods.

To assess impacts of cell density during cryopreservation storage and thaw, cell compositions from different subjects that had been cryofrozen at different cell densities ($1\times10^6$ cells per mL, $8\times10^6$ cells per mL, and $15\times10^6$ cells per mL) and with different concentrations of DMSO (between approximately 3% and 9% DMSO by volume) were assessed. Cryopreserved cell compositions were then thawed, and cell potency (as assessed by measure of antigen-specific cytotoxicity) in the compositions was assessed.

The results showed that an increase in cellular potency generally was observed to be associated with the higher cell concentrations and/or DMSO concentrations during cryopreservation. The results were consistent with an interpretation that cryopreservation conditions can influence biological activity of therapeutic T cell compositions.

In an additional study, cell compositions containing cells expressing an anti-CD19 CAR were cryofrozen at different concentrations (e.g., of $1\times10^6$ cells/mL, $2\times10^6$ cells/mL, $5\times10^6$ cells/mL $10\times10^6$ cells/mL, $20\times10^6$ cells/mL, $50\times10^6$ cells/mL, and $100\times10^6$ cells/mL) and 7.5% DMSO and stored at 80 degrees for approximately 15 hours, thawed, and then analyzed for viability (viable cell concentration (VCC) and diameter, and for markers of apoptosis (e.g., Annexin V and activated caspase 3) by flow cytometry.

The observed loss of viable cell concentration (% Difference VCC) in this study, over the period of cryofreezing and thaw, ranged from 10-45%. No overall trend was observed across the concentrations for these attributes.

Results assessing the apoptotic markers demonstrated an overall trend in both CD4+ CAR expressing cells and CD8+ CAR expressing cells, with higher levels of cell apoptotic markers+ cells observed post-thaw for compositions in which cells had been frozen and stored at lower cell concentrations. In particular, results indicated that at the tested range of DMSO concentrations, such as 7.5% DMSO, in some embodiments, overall cell densities between at or about 10 and at or about 60 million or at or about 15 and at or about 60 or 70 million cells per mL during cryopreservation, storage and thaw, are particularly advantageous for increasing cell health and/or frequency of biologically active cells in a composition following cryopreservation and thaw.

The results are consistent with the utility of higher cell densities or cell concentrations of CD8+ cells and/or CD4+ cells in cryopreservation of therapeutic T cell products.

Example 5: Assessment and Comparison of Neuropathology in Different Subjects Autopsy assessments for neuropathology were performed in four subjects having Acute Lymphoblastic Leukemia (ALL) who developed severe neurotoxicity, including grade 4 or 5 neurotoxicity, and/or cerebral edema following the treatment with therapeutic compositions containing T cells engineered to express a chimeric antigen receptor (CAR). Specifically, the autopsy studies were carried out on 2 subjects who had experienced grade 5 cerebral edema (n=2) and in 2 subjects who had experienced severe neurotoxicity without cerebral edema (n=2). The results generally support the conclusion that brain involvement by B-ALL was not observed to be a factor in cerebral edema. In the two subjects with cerebral edema, no innate immune cells, no B-ALL cancer cells, and no CD19+ cancer cells were observed in CNS. Further, in patients with cerebral edema, edema tended to be observed to be vasogenic, not cytotoxic. In patients with cerebral edema, perivascular fibrin and red blood cell extravasation suggested complete blood brain barrier breakdown (BBB). BBB was observed in these subjects. Endothelial damage was also observed. There appeared, however, to be an absence of any remarkable T-cell infiltration, consistent with a conclusion that cerebral edema had not developed as a result of CAR T cell infiltration and/or activation within the brain or CNS.

Further, perivascular and more diffuse patterns of astrocytic and microglial damage/activation was observed in brains of subjects who had developed cerebral edema, indicative of BBB. The observation was consistent with a conclusion that microglia activation was a contributor to the development of cerebral edema in subjects administered a CAR-T cell therapy. In addition, irreversible damage to astrocytes (clasmatodendrosis) was observed in subjects who developed cerebral edema, contrasted by astrocytic proliferation observed in subjects who developed Grade 4 neurotoxicity. No significant edema was observed in peripheral tissues in subjects who exhibited cerebral edema such as lung, liver, or kidney. Complete breakdown of the BBB and resulting vasogenic edema was not observed in subjects who developed grade 4 neurotoxicity.

In autopsies for subjects who did not develop cerebral edema (n=2), diffuse CD8+ T-cell infiltration that was not consistent with simple reaction to focal injury was observed. T cells were present in CNS in these subjects. No evidence of blood brain barrier pathology was observed in these subjects without cerebral edema.

Example 6: Administration of Anti-CD19 CAR-Expressing Cells to Subjects with Relapsed and Refractory Non-Hodgkin's Lymphoma (NHL)

Therapeutic CAR+ T cell compositions containing autologous T cells expressing a chimeric antigen-receptor (CAR) specific for CD19 were administered to subjects with B cell malignancies. The therapeutic T cell compositions administered had been generated by a process including immunoaffinity-based enrichment of CD4+ and CD8+ cells from leukapheresis samples from the individual subjects to be treated. Isolated CD4+ and CD8+ T cells were separately activated and independently transduced with a lentiviral vector encoding an anti-CD19 CAR. The engineered CD4+ and CD8+ T cells were independently expanded in the presence of cytokines to a threshold number of cells. Following expansion, the cells were formulated and cryopreserved in a low-volume. The CAR contained an anti-CD19 scFv derived from a murine antibody, an immunoglobulin-derived spacer, a transmembrane domain derived from CD28, a costimulatory region derived from 4-1BB, and a CD3-zeta intracellular signaling domain. The cryopreserved cell compositions were thawed prior to intravenous administration. The therapeutic T cell dose was administered as a defined cell composition by administering a formulated CD4+CAR+ cell population and a formulated CD8+CAR+ population administered at a target ratio of approximately 1:1.

A. Subjects and Treatment

Example 6.A.1

Studies in described in this Example 6.A.1 describe treatment and evaluation of subjects through a particular time-point (6.A.1) in an ongoing clinical study administering such therapy to patients with B cell Malignancies. Specifically, a cohort (full cohort) of (at this time-point, fifty-five (55)) adult human subjects with relapsed or refractory (R/R) aggressive non-Hodgkin's lymphoma (NHL), including diffuse large B-cell lymphoma (DLBCL), de novo or transformed from indolent lymphoma (NOS), primary mediastinal large b-cell lymphoma (PMBCL), and follicular lymphoma grade 3b (FLG3B) after failure of 2 lines of therapy. Among the subjects treated were those having Eastern Cooperative Oncology Group (ECOG) scores of between 0 and 2 (median follow-up 3.2 months). The full cohort did not include subjects with mantle cell lymphoma (MCL). No subjects were excluded based on prior allogenic stem cell transplantation (SCT), secondary central nervous system (CNS) involvement or an ECOG score of 2, and there was no minimum absolute lymphocyte count (ALC) for apheresis required.

Outcomes were separately assessed for a core subset of subjects within the full cohort (subjects within the full cohort excluding those subjects with a poor performance status (ECOG 2), DLBCL transformed from marginal zone lymphomas (MZL) and/or chronic lymphocytic leukemia (CLL, Richter's) (core cohort)). At the time point in Example 1.A.1, outcomes for 44 subjects within this core cohort were assessed.

The demographics and baseline characteristics of the full and core cohort subjects at the time point in Example 6.A.1 are set forth in Table E3.

TABLE E3

Demographics and Baseline Characteristics

| Characteristic | FULL N = 55 | CORE N = 44 |
|---|---|---|
| Median Age, years (range) | 61 (29-82) | 61 (29-82) |
| ≥65 years, n (%) | 22 (40) | 17 (39) |
| Male/Female, n (%) | 38/17 (69/31) | 28/16 (64/36) |
| Months from diagnosis, median (range) | 17 (3-259) | 20 (8-259) |
| B-NHL Subtype, n (%) | | |
| DLBCL, NOS | 40 (73) | 35 (80) |
| Transformed DLBCL | 14 (26) | 8 (18) |
| Follicular, Grade 3B | 1 (2) | 1 (2) |
| Molecular Subtype, n (%) | | |
| Double/triple hit | 15 (27) | 12 (27) |
| Double expressor | 6 (11) | 4 (9) |
| Patient Characteristics, n (%) | | |
| Chemorefractory† | 42 (76) | 34 (77) |
| ECOG 0-1 | 48 (87) | 44 (100) |
| ECOG 2 | 7 (13) | 0 |
| Prior lines of therapy, median (range) | 3 (1-11) | 3 (1-8) |
| <5 lines of therapy | 44 (80) | 37 (84) |
| Any HSCT | 27 (49) | 22 (50) |
| Allogeneic | 4 (7) | 3 (7) |
| Autologous | 24 (44) | 20 (45) |

*SD or PD to last chemo-containing regimen or relapse <12 months after autologous SCT As shown in Table E4, subjects were administered a single or double dose of CAR-expressing T cells (each single dose via separate infusions of CD4+ CAR-expressing T cells and CD8+ CAR-expressing T cells, respectively) as follows: a single dose of dose level 1 (DL-1) containing $5\times10^7$ total CAR-expressing T cells (n=30 for subjects assessed in Example 6.A.1), a double dose of DL1 in which each dose was administered approximately fourteen (14) days part (n=6 for subjects assessed in Example 6.A.1, including one subject that inadvertently received two DL2 doses via the two-dose schedule, due to a dosing error), or a single dose of dose level 2 (DL-2) containing $1\times10^8$ (DL-2) total CAR-expressing T cells (n=18 for subjects assessed in Example 6.A.1). Beginning at three (3) days prior to CAR+ T cell infusion, subjects received a lymphodepleting chemotherapy with flurabine (flu, 30 mg/$m^2$) and cyclophosphamide (Cy, 300 mg/$m^2$).

TABLE E4

Dose levels and number of T cell subsets for cell compositions containing anti-CD19 CAR T cells

| Dose level (DL) | Helper T cell ($T_H$) Dose (CD4+CAR+) | Cytotoxic T Cell ($T_C$) Dose (CD8+CAR+) | Total T Cell Dose (CD3+CAR+) |
|---|---|---|---|
| DL1 | $25\times10^6$ | $25\times10^6$ | $50\times10^6$ |
| DL2 | $50\times10^6$ | $50\times10^6$ | $100\times10^6$ |

Example 6.A.2

For Example 6.A.2, at a subsequent point in time in the clinical study described in this Example above, results were analyzed at a second time point. At this analysis time point in Example 6.A.2, 74 patients had been treated (51 male, 23 female). The subjects included sixty-nine (69) subjects in the full DLBCL cohort (including 67 DLBCL NOS (45 de novo, 14 transformed from FL, 8 transformed from CLL or MZL), 1 FL grade 3B, and 1 PMBCL), and 5 subjects in the MCL cohort. Among subjects in the full (DLBCL) cohort, median age was 61 yrs (range 26, 82), median prior therapies was 3 (range 1, 12), 46 (67%) were chemorefractory, 32 (46%) had any prior transplant, and at least 16 (23%) patients had double/triple hit lymphoma. Forty-nine (49) subjects in the core cohort were assessed at this time point in 6.A.2.

B. Safety

The presence or absence of treatment-emergent adverse events (TEAE) following administration of the CAR-T cell therapy was assessed. Subjects also were assessed and monitored for neurotoxicity (neurological complications including symptoms of confusion, aphasia, encephalopathy, myoclonus seizures, convulsions, lethargy, and/or altered mental status), graded on a 1-5 scale, according to the National Cancer Institute-Common Toxicity Criteria (CTCAE) scale, version 4.03 (NCI-CTCAE v4.03). Common Toxicity Criteria (CTCAE) scale, version 4.03 (NCI-CTCAE v4.03). See Common Terminology for Adverse Events (CTCAE) Version 4, U.S. Department of Health and Human Services, Published: May 28, 2009 (v4.03: Jun. 14, 2010); and Guido Cavaletti & Paola Marmiroli *Nature Reviews Neurology* 6, 657-666 (December 2010). Cytokine release syndrome (CRS) also was determined and monitored, graded based on severity. See Lee et al, Blood. 2014; 124 (2): 188-95.

Example 6.B.1

Example 6.B.1 describes results based on the analysis time-point in Example 6.B.1.

In 84% of the full cohort subjects in Example 6.B.1 analysis, severe (grade 3 or higher) cytokine release syndrome (CRS) and severe neurotoxicity were not observed. Additionally, it was observed that 60% of the full cohort subjects did not develop any grade of CRS or neurotoxicity. No differences in incidence of CRS, neurotoxicity (NT), sCRS, or severe neurotoxicity (sNT) were observed between dose levels. Table E5 summarizes the incidence of cytokine release syndrome (CRS) and neurotoxicity adverse events in patients 28 days after receiving at least one dose of CAR-T cells. As shown in Table E5, no sCRS (Grade 3-4) was observed in any subjects that received a single dose of DL2 or double dose of DL1. Severe neurotoxicity or severe CRS (grade 3-4) was observed in 16% (9/55) of the full cohort of subjects and in 18% (8/44) of the subjects in the core subset. 11% (n=6) of subjects received tocilizumab, 24% (n=13) of subjects received dexamethasone. Among the ECOG2 subjects within the full cohort, observed rates of CRS and neurotoxicity were 71% and 29%, respectively.

TABLE E5

Assessment of Presence or Absence of CRS and Neurotoxicity Adverse Events for Example 6.B.1

| | FULL | | | | |
|---|---|---|---|---|---|
| | All Dose Levels | DL1S | DL2S | DL1D[†] | CORE |
| Safety, N | 55 | 30 | 19 | 6 | 44 |
| sCRS or sNT, n (%) | 9 (16) | 6 (20) | 2 (11) | 1 (17) | 8 (18) |
| CRS or NT, n (%) | 22 (40) | 12 (40) | 7 (37) | 3 (50) | 15 (34) |
| CRS | | | | | |
| Grade 1-2, n (%) | 18 (33) | 10 (33) | 5 (26) | 3 (50) | 12 (27) |
| Grade 3-4, n (%) | 1 (2) | 1 (3) | 0 | 0 | 1 (2) |
| Neurotoxicity | | | | | |
| Grade 1-2, n (%) | 3 (6) | 1 (3) | 2 (11) | 0 | 2 (5) |
| Grade 3-4, n (%) | 9 (16) | 6 (20) | 2 (11) | 1 (17) | 8 (18) |

[†]Includes one patient treated at DL2 2-dose schedule due to dosing error

Example 6.B.2

Example 6.B.2 describes assessment at the time-point in Example 6.B.2. Up to this time point, adverse event (AE) data were collected from lymphodepletion (LD) to 90 days post administration of CAR-expressing T cells. At the second time point, 69 subjects in the DLBCL cohort (full cohort) were evaluated for safety, 38 that had received DL1 single dose, 25 having received DL2 single dose, and 6 having received DL1 double dose schedule. The most common TEAEs other than CRS or NT included neutropenia (41%, 28/69), fatigue (30%, 21/69), thrombocytopenia (30%, 21/69), and anemia (26%, 18/69). One Grade 5 TEAE of diffuse alveolar damage was observed.

No acute infusional toxicity was observed, and the majority of subjects in the full cohort, 64% (44/69), were observed to have no CRS or NT, indicating that outpatient delivery of CAR-expressing T cells may be possible. Rates of CAR T cell-associated toxicities, including CRS and NT, did not differ between dose levels. Safety profile was observed to be similar across cohorts and dose levels. Among the 25 subjects in the full cohort (36%) who experienced any grade CRS or NT, 21 (30%) had CRS and 14 (20%) had NT. No subjects had Grade 3 CRS and only one (1%, 1/69) had Grade 4 CRS and required ICU care; the other 29% (20/69) had Grade 1-2 CRS. Of the 20% of subjects with NT, 6% (4/69) had Grade 1-2 and 14% (10/69) had Grade 3-4; 2 (3%) had seizure. No Grade 5 CRS or grade 5 NT was observed. No incidences of cerebral edema were observed. All CRS and NT events were resolved except one case of Grade 1 tremor, which was ongoing at the time of analysis. Median time to onset of first CRS and NT was 5 days (range 2, 12) and 10 days (range 5, 23), respectively. In the first 72 hours post infusion, no subjects were observed to have NT, and only 10% (7/69) were observed to have CRS (all Grade 1); NT was preceded by CRS in >70% of subjects. Overall, thirteen (13) subjects (19%) required intervention for CRS or NT with anti-cytokine therapy (tocilizumab alone 1 (1%), dexamethasone alone 6 (9%), or both 6 (9%)) and only one required any vasopressor support. Median doses of tocilizumab and dexamethasone were 1 and 6, respectively. Median CRS and NT duration was 5 days and 11 days, respectively. Analysis of the core cohort (n=49) also showed similar rates of CRS and NT.

In this assessment, low incidences and late onsets of CRS and/or NT were observed, at doses. supported the feasibility of outpatient infusion, such as with hospital admission at the first sign of fever or fever lasting beyond a certain period of time, in view of the. At the time of assessment in 6.B.2, four subjects had been treated in the outpatient setting.

C. Response Outcomes Following Treatment

Subjects were monitored for response, including by assessing tumor burden at 1, 3, 6, 7, 12, 18, and 24 months after administration of the CAR+ T cells.

Example 6.C.1

Example 6.C.1 describes results based on the analysis time-point in Example 6.A.1 and 6.B.1.

Response rates are listed in Table E6. High durable response rates were observed in the cohort of subjects, which included subjects heavily pretreated or, with poor prognosis and/or with relapsed or refractory disease. For subjects across all doses in the Core (n=44) cohort, the observed overall response rate (ORR) was 86% and the observed complete response (CR) rate was 59%. At three months for the core cohort, the overall response rate (ORR) was 66%; the three-month CR rate was 50% among the core cohort. In the core cohort, the 3 month ORR was 58% (11/19) at dose level 1 and 78% at dose level 2; the 3 month CR rate was 42% (8/19) for dose level 1 and 56% (5/9) for dose level 2, consistent with a suggested dose response effect on treatment outcome. Additionally, the results were consistent with a relationship between dose and durability of response.

TABLE E6

| | Response | | | | | | | |
|---|---|---|---|---|---|---|---|---|
| | FULL | | | | CORE | | | |
| | All Dose Levels | DL1S | DL2S | DL1D[c] | All Dose Levels | DL1S | DL2S | DL1D[a] |
| Best Overall Response, N[a] | 54 | 30 | 18 | 6 | 44 | 25 | 15 | 4 |
| ORR, % | 76 | 80 | 72 | 67 | 86 | 84 | 87 | 100 |
| (95% CI) | (62, 87) | (61, 92) | (47, 90) | (23, 96) | (73, 95) | (64, 95) | (60, 98) | (40, 100) |
| CR, % | 52 | 53 | 50 | 50 | 59 | 56 | 60 | 75 |
| (95% CI) | (38, 66) | (34, 72) | (26, 74) | (12, 88) | (43, 74) | (35, 76) | (32, 84) | (19, 99) |
| ≥3 mos f/u n[b] | 41 | 24 | 11 | 6 | 32 | 19 | 9 | 4 |
| 3 mo ORR, % | 51 | 46 | 64 | 50 | 66 | 58 | 78 | 75 |
| (95% CI) | (35, 67) | (26, 67) | (31, 89) | (12, 88) | (47, 81) | (34, 80) | (40, 97) | (19, 99) |
| 3 mo CR, % | 39 | 33 | 46 | 50 | 50 | 42 | 56 | 75 |
| (95% CI) | (24, 56) | (16, 55) | (17, 77) | (12, 88) | (32, 68) | (20, 67) | (21, 86) | (19, 99) |

DL1S: DL1 1-dose schedule;
DL2S: DL2 1-dose schedule;
DL1D: DL1 2-dose schedule;
[a]Included patients with event of PD, death, or 28 day restaging scans. Treated patients <28 days prior to data snapshot were not included.
[b]The denominator is number of patients who received the CAR T-cell therapy ≥3 months a snapshot date with an efficacy assessment at Month 3 or prior assessment of PD or death.
[c]Includes one patient treated at DL2 2-dose schedule due to dosing error Among the subjects treated six months or greater prior to the particular time-point of the evaluation, of the ten (10) patients that had been in response at three months, 9 (90%) remained in response at six months. At the evaluation time-point, 97% of subjects in the core subset who had responded were alive and in follow-up, median follow-up time 3.2 months. Prolonged survival was observed in responders, with increased durability of response in subjects with CRs. All patients in response at three months remained alive at the time of evaluation, although 5/6 subjects with poor performance status (ECOG 2) had expired.

Example 6.C.2

Example 6.C.2 describes results based on the analysis time-point in Example 6.A.2 and 6. B.2.

Up to the time point in Example 6.C.2, 68 subjects in the full DLBCL cohort was evaluated for response. Overall or objective response (OR), 3-month, and 6-month objective response rates were 75% (51/68), 49% (27/55), and 40% (14/35), respectively. Complete response (CR) rate, 3-month CR rate, and 6-month CR rate were 56% (38/68), 40% (22/55), and 37% (13/35), respectively. A trend toward improved response rate at 3 months was observed in subjects treated at DL2 compared to DL1: 63% (12/19; 95% CI 38, 84) vs 40% (12/30; 95% CI 23, 59) for ORR with p=0.148, and 58% (11/19; 95% CI 34, 80) vs 27% (8/30; 95% CI: 12, 46) for CR with p=0.0385. Among 16 double/triple hit lymphoma subjects, ORR was 81%, and 3-month CR rate was 60%.

In the core cohort (n=49 for the time-point in Example 1.C.2), OR, 3-month, and 6-month OR rates were 84% (41/49), 65% (26/40), and 57% (13/23), respectively. CR rate, 3-month CR rate, and 6-month CR rate were 61% (30/49), 53% (21/40), and 52% (12/23), respectively. A similar trend in improved durable ORR and CR at 3 months at higher doses was observed. Specifically, for patients in the CORE cohort administered DL2, 3-month ORR was 80% (12/15; 95% CI 52, 96) and 3-month CR was 73% (11/15; 95% CI 45, 92), compared to 3-month ORR and CR rates of 52% (11/21; 95% CI 30, 74) and 33% (7/21; 95% CI 15, 57) in CORE cohort subjects administered DL1, with p=0.159 and p=0.0409 respectively. Among subjects in the CORE cohort having received DL2 and with 3-month follow-up (n=15), 3-month ORR was 80% and 3-month CR was 73%.

Median DOR in the full cohort and core cohorts at this time-point in 1.C.2 was 5.0 and 9.2 months, respectively; median duration of CR was 9.2 months in the full cohort. Median duration of CR had not been reached in the core cohort. Median overall survival (OS) was 13.7 months in the full cohort and had not been reached in the core cohort. 6-month OS was 75% in the full cohort, with median follow-up of 5.8 months. 6-month OS was 88% in the core cohort, with median follow up of 5.6 months.

D. Assessment of CAR+ T cells in Blood

Based on data from the time-point described in Example 6.A.1, 6.B.1 and 6.C.1, pharmacokinetic analysis was carried out to assess numbers of CAR+ T cells in peripheral blood at various time points post-treatment. Results from the fifty-five (55) subjects assessed at the time-point in Example 6.A.1 in the DLBCL cohort and four (4) subjects (assessed at that same time-point) in the mantle cell lymphoma (MCL) cohort, as described in Example 7 below were analyzed. Pharmacokinetics (PK) measurements were carried out using validated flow cytometry to detect a marker expressed in the CAR construct and quantitative PCR-based assays to detect the integration of the CAR construct. B cell aplasia was assessed by flow cytometry using anti-CD19 antibodies. CD4+ and CD8+CAR-expressing cells, as measured by the number of cells/μL blood (median±quartiles) plotted on a log scale, were detected throughout the course of assessment at both administered dose levels. Subjects receiving DL2 relative to DL1 had higher median $C_{max}$ and median $AUC_{0-28}$ for $CD3^+/CAR^+$, $CD4^+/CAR^+$, and $CD8^+/CAR^+$ T cell subsets in peripheral blood ($AUC_{0-28}$: DL2 vs. DL1 was 1836 vs. 461, 350 vs. 182, and 1628 vs. 114, for $CD3^+$, $CD4^+$, and $CD8^+$, respectively; $p<0.05$ for CD8+; $C_{max}$: DL2 vs. DL1 was 99.8 vs. 27.9, 15.1 vs. 5.2, and 73.1 vs. 5.5 cells/μL, respectively). Median time to maximum $CD3^+$ $CAR^+$ T cell expansion was 15 days (range 8-29) and did not differ between dose levels. $CD4^+$ and $CD8^+$CAR-expressing T cells homed to the bone marrow at relatively similar levels.

An increased median area under the curve (AUC) ($CD8^+$ $CAR^+$ T cell numbers over time in the blood) was observed among subjects administered the higher dose level, as compared to the lower dose level, without an observed increase in toxicity. Higher peak $CD8^+/CAR^+$ T cell exposure was observed in responders (CR/PR) than non-responders (PD); persistence of cells over the time of assessment, including out to 3 and 6 months, was observed even in subjects whose disease had progressed. Median $C_{max}$ and median $AUC_{0-28}$ of $CD8^+$ $CAR^+$ T cells were higher in responding subjects and with durable response at month 3 ($CD8^+C_{max}$ median=20.8 vs. 5.5; $CD8^+AUC_{0-28}$ median=235 vs. 55 in CR/PR at Month 3 vs. PD at Month 3). Among subjects that were evaluated for CAR T cell persistence, 90% and 93% of 29 subjects had detectable $CD8^+$ and $CD4^+$ $CAR^+$ T cells, respectively, at month 3; 63% and 58% of 19 subjects had detectable $CD8^+$ and $CD4^+$ $CAR^+$ T cells, respectively, at month 6. At months 3 and 6, no statistically significant differences in the persistence of $CAR^+$ T cells were observed between subjects with durable response or relapse. $CAR^+$ T cells were detectable at time of relapse in 89% of 11 subjects with PK, even though B cell aplasia (<1 cell/μl) was demonstrated in nearly all subjects 97% (34/35) at month 3, and 100% (24/24) at month 6.

Higher $C_{max}$ and $AUC_{0-28}$ at DL2 as compared to DL1 was not observed to be associated with increased CRS or NT. For any NT or for >Grade 2 CRS, median AUCs of $CD4^+/CAR^+$ and $CD8^+/CAR^+$ T cells were 5 to 10 fold and 3 to 5 fold higher, respectively, than the median AUC for DL2. Higher disease burden and baseline levels of inflammatory cytokines was observed to be associated with higher peak levels of $CAR^+$ T cells, higher cytokine peak levels, and higher incidences of CRS and NT. The results were consistent with a conclusion that the higher $C_{max}$ and median AUC0-28 at DL2 did not increase CRS or NT.

Example 7: Administration of Anti-CD19 CAR-Expressing Cells to Subjects with Mantle Cell Lymphoma (MCL)

Therapeutic CAR+ T cell compositions containing autologous T cells expressing a chimeric antigen-receptor (CAR) specific for CD19, generated as described in Example 1, were administered to four (4) human subjects with mantle cell lymphoma (MCL) that had failed 1 line of therapy. The cryopreserved cell compositions were thawed prior to intravenous administration. The therapeutic T cell composition was administered as a defined composition cell product with formulated CD4+ and CD8+ populations of CAR+ engineered T cells derived from the same subject administered at a target ratio of approximately 1:1. Subjects were administered a dose of CAR-expressing T cells (as a split dose of the CD4+ and CD8+CAR-expressing T cells) at a single dose of dose level 1 (DL1) containing $5\times10^7$ CAR-expressing T cells. Beginning at three (3) days prior to CAR+ T cell infusion, subjects received a lymphodepleting chemotherapy with flurabine (flu, 30 $mg/m^2$) and cyclophosphamide (Cy, 300 $mg/m^2$).

Subjects were monitored for response and toxicities as described in Example 1. No CRS or neurotoxicity was observed in any of the subjects. Of the 4 subjects that were treated, two (2) subjects achieved PR (not durable) and two (2) patients had progressive disease.

Example 8: Attributes of Therapeutic T Cell Composition for Administration and Process for Generation of Composition Exemplary therapeutic T cell compositions containing autologous T cells expressing a chimeric antigen-receptor (CAR) specific for CD19, used for administration in Example 2 above were assessed for greater than one hundred phenotypic, functional, and cell health related attributes, using flow cytometry and in vitro assays. The therapeutic cell compositions were from subjects enrolled in a clinical study evaluating anti-CD19 CAR-T cell therapy for treatment of relapsed/refractory B-cell non-Hodgkin lymphoma were examined (N=63; core cohort). Cells were assessed before and after engineering, for various attributes. Attributes that were assessed include those described in Example 1, and exemplary assessed attributes are set forth in Table E7. Phenotypic markers associated with cell health and memory and other phenotypes of the cell products were examined using flow cytometry. T cell functionality was assessed using in vitro antigen-specific bioassays. Characterization and release testing was conducted on samples from the formulated therapeutic T cell compositions that had undergone a representative number of freeze-thaw cycles corresponding to those of the administered cell compositions.

TABLE E7

Representative characterization attributes measured in therapeutic cell compositions containing anti-CD19 CAR T cells

| Cell Composition Characterization Class | Representative Attribute |
|---|---|
| Cell Health | Viability<br>Active intracellular caspase-3<br>Annexin V |
| Memory phenotype | CCR7 (C-C chemokine receptor type 7) |
| Cell function | Inflammatory cytokines such as TNF-α (tumor necrosis factor α) |

For generation of cell compositions for administration, autologous cells were isolated from the subjects via leukapheresis. Leukapheresis samples were subjected to a process for generation of CAR-expressing cells. The process involved washing of cells using an automated wash and immunoaffinity based selection for purification of CD4+ and CD8+ T cells, resulting in two compositions, enriched for CD8+ (in which a median of 99%, Inter Quartile Range (IQR) 98-100%, of cells were CD8+) and $CD4^+$ (in which a median of 99%, IQR 99-100%, cells were CD4+) cells, respectively.

As shown in FIG. 24 and summarized in Table E8, the automated T cell purification resulted in the indicated purity of CD8+ and CD4+ T cell populations. In some embodiments, such purification aspects may lower the probability of transducing non-T cells in transduction steps in the process and/or result in high T cell purities in therapeutic cell composition, in a manner that is independent of expansion duration or other aspects of expansion or incubation with T cell-specific reagents.

TABLE E8

| T cell purity (% of total leukocytes) by process step | | | | | |
|---|---|---|---|---|---|
| | | Leuka-pheresis | Post-Purifi-cation | Mid-Process | Drug Composition |
| CD4+ T Cell frequency | Median | 17.6 | 95.3 | 98.9 | 99.2 |
| | IQR | 11.7-24.7 | 92.1-98.5 | 98.1-99.2 | 98.7-99.6 |
| CD8+ T Cell frequency | Median | 19.2 | 96.0 | 98.9 | 99.3 |
| | IQR | 13.2-30.9 | 93.4-98.6 | 98.0-99.2 | 98.4-99.7 |

Cells of the enriched $CD4^+$ and $CD8^+$ compositions were separately subjected to lentiviral transduction with a vector encoding an anti-CD19 CAR with a 41BB costimulatory domain. Transduced populations then were separately incubated in the presence of stimulating reagents for cell expansion. Expanded CD8+ and CD4+ cells were formulated and cryopreserved separately and stored prior to administration. To minimize variations, between lots and/or cell compositions derived from different patients, such as those having different patient attributes, in parameters indicative of cell health, cells were held at constant volumes across lots. Cell products exhibited a tight range of viable cell concentrations (based on an assessment of cell compositions for one group of subjects, $CD8^+$: median $31\times10^6$ cells/mL, IQR $28\text{-}40\times10^6$ cells/mL, N=38; $CD4^+$: median $35\times10^6$ cells/mL, IQR $31\text{-}40\times10^6$, N=36).

At the site of administration, cells were thawed and administered, according to a target volume of each composition corresponding to the number of CD8+CAR+ and CD4+CAR+ cells in the appropriate dose (such as for DL1 or DL2). To minimize variations in cell health between lots, for formulation, cryopreservation and storage were held at a constant volume, with a tight range of viable cell concentrations ($CD8^+$: median $31\times10^6$ cells/mL, IQR $28\text{-}40\times10^6$ cells/mL, N=38; $CD4^+$: median $35\times10^6$ cells/mL, IQR $31\text{-}40\times10^6$, N=36).

During the clinical trial there was a process change from a high-volume formulation to low-volume formulation. The post change therapeutic cell composition was formulated at a constant low volume, with a tightly controlled range of viable cell concentrations. In some cases, a low-volume formulation was used instead of a high-volume formulation. Parameters indicative of health of the CAR-expressing T cells in the compositions for administration were assessed, such as by measuring, post-thaw, viability, cell surface Annexin V expression and levels of active intracellular Caspase 3 Cell compositions that were formulated with high volume and those formulated with a low volume were compared.

The process change from the high-volume formulation to the low-volume formulation resulted in increased process robustness and decreased variability of the cell health attributes. Values for concentration, percentage of viable cells, and percentage of active caspase-3 negative cells among CD4+ and CD8+ T cells from individual cell compositions are shown in FIG. 25 and are summarized in Table E9. The median percentage of Annexin V− expressing cells was 11% (IQR 9-18%; N=33) of $CD8^+CAR^+$ T cells and 10% (IQR 8-17%; N=31) of $CD4^+CAR^+$ T cells. Caspase 3 expression was observed to be similar to Annexin V expression. The shift to low-volume formulation resulted in increased robustness of the process and reduced the variance of cell health attributes.

TABLE E9

| Cell Health Attributes | | | | | |
|---|---|---|---|---|---|
| | | CD4+ | | CD8+ | |
| | | High Formu-lation Volume | Low Formu-lation Volume | High Formu-lation Volume | Low Formu-lation Volume |
| Cell Concen-tration × $10^6$ cells/mL | Median | 17.1 | 37.2 | 12.1 | 30.8 |
| | IQR | 15.9-19.3 | 31.7-40.4 | 10.9-15.3 | 28.5-38.0 |
| Cell viability % | Median | 82.8 | 82.5 | 72.0 | 80.3 |
| | IQR | 79.5-84.7 | 80.4-84.3 | 69.3-76.6 | 76.4-83.3 |
| % Caspase-3 negative cells | Median | | 82.8 | | 82.5 |
| | IQR | | 79.5-84.7 | | 80.4-84.3 |

The quantities of CAR+CD4+ and CAR+CD8+ T cells in the composition for administration were precisely controlled. The number of cells actually administered to an exemplary set of subjects was observed to be within 8% or less of the target number of cells for a given dose:

2.4-2.7×$10^7$ (target ±8%) $CD4^+CAR^+$ T cells and 2.4-2.7×$10^7$ (target ±8%) $CD8^+CAR^+$ T cells for subjects administered cells at DL1 (n=48)

4.6-5.1×$10^7$ (target ±8%) $CD4^+CAR^+$ T cells or 4.6-5.1×$10^7$ (target ±8%) $CD8^+CAR^+$T cells for subjects administered cells at DL2 (n=20).

The range of administered dose was found to have low variability in a different exemplary set of subjects:

48-52×$10^6$ CD3+CAR+ T cell at DL1 (n=34)

96-101×$10^6$ CD3+CAR+ T cells at DL2 (n=29)

24-27×$10^6$ CD4+CAR+ or CD8+CAR+ T cells at DL1 (n=34)

46-51×$10^6$ CD4+CAR+ or CD8+CAR+ T cells at DL2 (n=29).

As shown in FIG. 26, CAR-expressing T cell compositions administered to subjects were observed to exhibit high T cell purity and low variance between lots. The process and product controls resulted in therapeutic cell compositions containing CAR T cells with low lot-to-lot variability in cell-specific T cell function.

In vitro antigen-specific cytokine accumulation and intracellular cytokine staining (ICS) showed a similar low variance between lots for cytokine production for multiple cytokines (IL-2, TNF-α and IFN-γ). In an exemplary ICS experiment, cells from compositions were stimulated with CD19, stained for cytokines, including TNF-α, and surface proteins, including C-C chemokine receptor type 7 (CCR7) as a memory phenotype marker, and analyzed by flow cytometry. The number of cells in the composition for administration that were positive for the cytokines or surface proteins were determined. FIG. 27 shows the number of CD4+CAR+ and CD8+CAR+ cells, CD4+CAR+TNF-α+ and CD8+CAR+TNF-α+ cells, CD4+CAR+CCR7+ and CD8+CAR+CCR7+ and present in CAR T cell compositions for administration at DL1 and DL2. These results are summarized in Table E10. The results show low variability in the number of CD4+CAR+ and CD8+CAR+ cells, CD4+CAR+TNF-α+ and CD8+CAR+TNF-α+ cells, CD4+CAR+CCR7+ and CD8+CAR+CCR7+ cells. For example, a tight range for the number of cells positive for TNF-α production was observed (n=61).

ing a different anti-CD19 CAR (Trial 3)). Subjects were administered anti-CD19 CAR-T cell compositions and monitored for clinical response and adverse outcomes. Neurotoxicity was graded on a 0-5 scale as described in Example 1.

Baseline factors were analyzed, post facto, and compared among subjects using a number of statistical analyses. Exemplary baseline factors that were observed to be associated with grade 3 or greater neurotoxicity in the subjects are listed in Tables E11-A and E11-B below, including levels

TABLE E10

| Controlled dose, T cell phenotypes, and cell specific function ($\times 10^6$ cells) | | | | | | | | | | | | |
|---|---|---|---|---|---|---|---|---|---|---|---|---|
| | $CD4^+CAR^+$ | | $CD8^+CAR^+$ | | $CD4^+CAR^+$ $TNF\text{-}\alpha^+$ | | $CD8^+CAR^+$ $TNF\text{-}\alpha^+$ | | $CD4^+CAR^+$ $CCR7^+$ | | $CD8^+CAR^+$ $CCR7^+$ | |
| | DL1 | DL2 | DL1 | DL2 | DL1 | DL2 | DL1 | DL2 | DL1 | DL2 | DL1 | DL2 |
| Median | 25.1 | 50.1 | 25.0 | 50.0 | 23.0 | 47.4 | 19.9 | 41.7 | 11.1 | 15.8 | 8.9 | 15.0 |
| IQR | 24.7-25.3 | 49.6-50.0 | 24.8-25.2 | 49.6-50.4 | 21.3-23.5 | 46.6-48.5 | 18.3-21.8 | 39.9-46.0 | 5.5-14.1 | 11.0-26.0 | 3.0-14.8 | 8.6-25.3 |

A parameter indicative of production by CAR+ cells of tumor necrosis factor alpha (TNFα) after stimulation with CD19 showed a narrow range among different lots, with relative standard deviation (RSD) of 37% for $CD4^+CAR^+$ T cells (N=59) and 51% for $CD8^+CAR^+$ T cells (N=61).

The results were consistent with an observation that a composition that contains a precise and consistent dose of $CD4^+$ and $CD8^+$CAR T cells, control and optimization of CD4+ and $CD8^+$ T cell culture conditions, low variability of cytokine production, and/or constant formulation and volume of the composition for administration can lead to consistent cell health in the composition. In provided embodiments, aspects of such manufacturing and control process contribute to low variability in attributes of such cell compositions engineered using cells from, and generated for administration to, a number of different subjects. Such aspects in some aspects include the use of a precise, consistent flat dose of administered CD4+ and CD8+ cells among subjects; control and optimization of CD4+ and CD8+ T cell culture conditions such as those that result in low between-drug product lot variability of phenotypes (e.g., CCR7) and in vitro function (e.g., IL-2, TNF-α and IFN-γ production after antigen stimulation) such as among different subjects; and the use of constant formulation and volume of drug product which can result in or contribute to consistency among therapeutic cell compositions generated by the method in attributes indicative of cell health.

Example 9: Additional Baseline Factors Associated with Development of Neurotoxicity Following CAR+ T Cell Therapy Various baseline factors, measured prior to treatment with CAR-T cell compositions in a number of different clinical studies for B cell malignancies such as ALL and NHL, were assessed and compared among subjects that had and that had not developed grade 3 or higher neurotoxicity. Data from 3 clinical trials were analyzed (including the study described in Example 1 that involved anti-CD19 CAR-T treatment in subjects with ALL (Trial 1), the clinical study described in Example 2 involving a similar anti-CD19 CAR treatment administered to subjects with relapsed or refractory adult ALL (Trial 2), and an additional clinical trial in which subjects with B-cell malignancies, including ALL and non-Hodgkin lymphoma (NHL), were treated with cells expressof serum IL-15 and platelet cell counts prior to administration of CAR-T cells, disease type (non-Hodgkin lymphoma (NHL) as compared to ALL), and disease burden as defined by percentages of blasts in the bone marrow. Gene expression signatures were also among the identified parameters: subjects positive for the Philadelphia chromosome (Ph+) or having a gene expression profile resembling the Ph+ gene expression profile (Ph-like), had significantly less instances of grade 3 or higher neurotoxicity that subjects who did not (non-Ph). Exemplary baseline factors associated with grade 3 or higher neurotoxicity in Trial 1 is shown in Table E11-A. Exemplary baseline factors associated with grade 3 or higher neurotoxicity across the three clinical trials are shown in Table E11-B.

TABLE E11-A

| Exemplary baseline parameters associated with Grade 3 or greater neurotoxicity in Trial 1 | | | | |
|---|---|---|---|---|
| Baseline Factor | Indication | Criterion | Gr ≥ 3 NTX | P value[a] |
| Inflammatory marker: Plasma IL-15 | B-Cell malignancies | High IL-15[b] | 10/11 (91%) | .01 |
| | | Low IL-15 | 10/24 (42%) | |
| Gene Expression Signature | ALL | non-Ph | 12/15 (80%) Grade 4 or 5: 7 events | .03 |
| | | Ph+/Ph-like | 6/16 (38%) Grade 4 or 5: 0 events | |

TABLE E11-B

| Exemplary baseline parameters associated with Grade 3 or greater neurotoxicity | | | | | |
|---|---|---|---|---|---|
| Baseline Factor | Indication | Criterion | Gr ≥ 3 NTX | P value[a] | Source |
| Inflammatory marker: Serum IL-15 | B-Cell malignancies | High IL-15[b] | 26/45 (58%) | <.0001 | Trial 1 Trial 3 |
| | | Low IL-15 | 19/109 (17%) | | |
| Platelet Count | ALL | <120K | 60/162 (37%) | .002 | Trial 1 Trial 2 Trial 3 |
| | | >120K | 9/60 (15%) | | |

TABLE E11-B-continued

Exemplary baseline parameters associated with Grade 3 or greater neurotoxicity

| Baseline Factor | Indi-cation | Crite-rion | Gr ≥ 3 NTX | P value[a] | Source |
|---|---|---|---|---|---|
| Disease Type | B-Cell malig-nancies | ALL | 14/47 (30%) | .003 | Trial 3 |
| | | NHL | 8/62 (13%) | | |
| Disease Burden | ALL | ≥5% BM blasts | 40/94 (43%) | .02 | Trail 1 Trial 2 |
| | | <5% BM blasts | 9/42 (21%) | | Trial 3 |
| Gene Expression Signature | ALL | non-Ph | 12/15 (80%) Grade 5: 5 events | .03 | Trial 1 |
| | | Ph+/ Ph-like | 6/16 (38%) Grade 5: none | | |

[a]Two sided Fisher's exact test

[b]High IL-15 ≥ 30 pg/mL.

Blood samples collected from subjects at various time points after administration of CAR-T cells in Trial 1 were analyzed for CAR+-T cell counts. Serum levels of cytokines, e.g., IL-15 from the subjects were assessed at pre-treatment (screening) and various post-treatment time-points (day 2, day 4, and day 7). The results demonstrated that prolonged and fatal neurotoxicity correlated with early and rapid rise in levels of IL-15, a T cell promoting cytokine, and CAR T cell expansion.

As discussed in Example 1, more rapid CAR-T cell expansion and earlier peak expansion of CAR-expressing T cells was observed in the blood of subjects that went on to develop more severe neurotoxicity, and in particular those who developed grade 5 neurotoxicity and cerebral edema. For example, results indicated that these subjects had exhibited a detectable level of CAR+ cells per μL of blood within 4-7 days after the first dose of cells, with greater than 20 CAR+ cells per μL of blood observed in blood of all such subjects within seven days after cells were administered (see FIGS. 1 and 2). In subjects with less severe neurotoxicity, peak expansion of CAR+ T cells generally was observed later and with a lower peak number of CAR+ T cells per microliter (FIGS. 2, 28).

Among the cytokines whose median levels peaked several fold over baseline levels following CAR-T cell infusion were IL-2 (14-fold), IL-6 (2.7-fold), IL-10 (3.5-fold), IL-15 (2.5 fold) and IFN-gamma (3.3-fold). For the group of subjects that had experienced earlier peak CAR-T cell expansion (peak CAR+-T numbers by day 7), higher medium baseline serum IL-15 levels and a steeper increase in serum through day 4 post-administration were observed as compared to subjects with later peak CAR-T cell expansion (FIG. 28). By the next time-point (day 7) at which serum IL-15 levels were measured, serum IL-15 levels in these subjects with rapid peak expansion had declined and were approximately comparable to or below levels in subjects with later peak expansion. The results were consistent with a conclusion that baseline serum IL-15 levels and/or higher or rapid increases in IL-15 levels, may indicate or correlate with potential risk for neurotoxicity or cerebral edema or severity thereof, following CAR-T cell treatment. Lymphodepleting and bridging chemotherapies are also observed to be associated with an increase in T cell proliferation-promoting cytokines such as IL-15.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO. | SEQUENCE | DESCRIPTION |
|---|---|---|
| 1 | ESKYGPPCPPCP | spacer (IgG4hinge) (aa) *Homo sapiens* |
| 2 | GAATCTAAGTACGGACCGCCCTGCCCCCCTTGCCCT | spacer (IgG4hinge) (nt) *homo sapiens* |
| 3 | ESKYGPPCPPCPGQPREPQVYTLPPSQEEMTKNQVSLTCLVKGFYPSDI AVEWESNGQPENNYKTTPPVLDSDGSFFLYSRLTVDKSRWQEGNVFSCS VMHEALHNHYTQKSLSLSLGK | Hinge-CH3 spacer *Homo sapiens* |
| 4 | ESKYGPPCPPCPAPEFLGGPSVFLFPPKPKDTLMISRTPEVTCVVVDVS QEDPEVQFNWYVDGVEVHNAKTKPREEQFNSTYRVVSVLTVLHQDWLNG KEYKCKVSNKGLPSSIEKTISKAKGQPREPQVYTLPPSQEEMTKNQVSL TCLVKGFYPSDIAVEWESNGQPENNYKTTPPVLDSDGSFFLYSRLTVDK SRWQEGNVFSCSVMHEALHNHYTQKSLSLSLGK | Hinge-CH2—CH3 spacer *Homo sapiens* |
| 5 | RWPESPKAQASSVPTAQPQAEGSLAKATTAPATTRNTGRGGEEKKKEKE KEEQEERETKTPECPSHTQPLGVYLLTPAVQDLWLRDKATFTCFVVGSD LKDAHLTWEVAGKVPTGGVEEGLLERHSNGSQSQHSRLTLPRSLWNAGT SVTCTLNHPSLPPQRLMALREPAAQAPVKLSLNLLASSDPPEAASWLLC EVSGFSPPNILLMWLEDQREVNTSGFAPARPPPQPGSTTFWAWSVLRVP APPSPQPATYTCVVSHEDSRTLLNASRSLEVSYVTDH | IgD-hinge-Fc *Homo sapiens* |
| 6 | LEGGGEGRGSLLTCGDVEENPGPR | T2A artificial |

-continued

SEQUENCES

| SEQ ID NO. | SEQUENCE | DESCRIPTION |
|---|---|---|
| 7 | RKVCNGIGIGEFKDSLSINATNIKHFKNCTSISGDLHILPVAFRGDSFT HTPPLDPQELDILKTVKEITGFLLIQAWPENRTDLHAFENLEIIRGRTK QHGQFSLAVVSLNITSLGLRSLKEISDGDVIISGNKNLCYANTINWKKL FGTSGQKTKIISNRGENSCKATGQVCHALCSPEGCWGPEPRDCVSCRNV SRGRECVDKCNLLEGEPREFVENSECIQCHPECLPQAMNITCTGRGPDN CIQCAHYIDGPHCVKTCPAGVMGENNTLVWKYADAGHVCHLCHPNCTYG CTGPGLEGCPTNGPKIPSIATGMVGALLLLLVVALGIGLFM | tEGFR artificial |
| 8 | FWVLVVVGGVLACYSLLVTVAFIIFWV | CD28 (amino acids 153-179 of Accession No. P10747) *Homo sapiens* |
| 9 | IEVMYPPPYLDNEKSNGTIIHVKGKHLCPSPLFPGPSKPFWVLVVVGGV LACYSLLVTVAFIIFWV | CD28 (amino acids 114-179 of Accession No. P10747) *Homo sapiens* |
| 10 | RSKRSRLLHSDYMNMTPRRPGPTRKHYQPYAPPRDFAAYRS | CD28 (amino acids 180-220 of P10747) *Homo sapiens* |
| 11 | RSKRSRGGHSDYMNMTPRRPGPTRKHYQPYAPPRDFAAYRS | CD28 (LL to GG) *Homo sapiens* |
| 12 | KRGRKKLLYIFKQPFMRPVQTTQEEDGCSCRFPEEEEGGCEL | 4-1BB (amino acids 214-255 of Q07011.1) *Homo sapiens* |
| 13 | RVKFSRSADAPAYQQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR | CD3 zeta *Homo sapiens* |
| 14 | RVKFSRSAEPPAYQQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR | CD3 zeta *Homo sapiens* |
| 15 | RVKFSRSADAPAYKQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR | CD3 zeta *Homo sapiens* |
| 16 | PGGG-(SGGGG)5-P- | linker |
| 17 | GSADDAKKDAAKKDGKS | linker |
| 18 | EGRGSLLTCGDVEENPGP | T2A |
| 19 | GSGATNFSLLKQAGDVEENPGP | P2A |
| 20 | ATNFSLLKQAGDVEENPGP | P2A |
| 21 | QCTNYALLKLAGDVESNPGP | E2A |
| 22 | VKQTLNFDLLKLAGDVESNPGP | F2A |
| 23 | MLLLVTSLLLCELPHPAFLLIPRKVCNGIGIGEFKDSLSINATNIKHFK NCTSISGDLHILPVAFRGDSFTHTPPLDPQELDILKTVKEITGFLLIQA WPENRTDLHAFENLEIIRGRTKQHGQFSLAVVSLNITSLGLRSLKEISD GDVIISGNKNLCYANTINWKKLFGTSGQKTKIISNRGENSCKATGQVCH ALCSPEGCWGPEPRDCVSCRNVSRGRECVDKCNLLEGEPREFVENSECI QCHPECLPQAMNITCTGRGPDNCIQCAHYIDGPHCVKTCPAGVMGENNT LVWKYADAGHVCHLCHPNCTYGCTGPGLEGCPTNGPKIPSIATGMVGAL LLLLVVALGIGLFM | EGFRt artificial |
| 24 | atgcttctcctggtgacaagccttctgctctgtgagttaccacacccag cattcctcctgatccca | GMCSFR alpha chain signal sequence |

-continued

SEQUENCES

| SEQ ID NO. | SEQUENCE | DESCRIPTION |
|---|---|---|
| 25 | MLLLVTSLLLCELPHPAFLLIP | GMCSFR alpha chain signal sequence |
| 26 | MALPVTALLLPLALLLHA | CD8 alpha signal peptide |
| 27 | EPKSCDKTHTCPPCP | Hinge |
| 28 | ERKCCVECPPCP | Hinge |
| 29 | ELKTPLGDTHTCPRCPEPKSCDTPPPCPRCPEPKSCDTPPPCPRCPEPK SCDTPPPCPRCP | Hinge |
| 30 | ESKYGPPCPSCP | Hinge |
| 31 | $X_1PPX_2P$<br>X1 is glycine, cysteine or arginine<br>X2 is cysteine or threonine | Hinge |
| 32 | Tyr Gly Pro Pro Cys Pro Pro Cys Pro | Hinge |
| 33 | Lys Tyr Gly Pro Pro Cys Pro Pro Cys Pro | Hinge |
| 34 | Glu Val Val Val Lys Tyr Gly Pro Pro Cys Pro Pro Cys Pro | Hinge |
| 35 | RASQDISKYLN | FMC63 CDR L1 |
| 36 | SRLHSGV | FMC63 CDR L2 |
| 37 | GNTLPYTFG | FMC63 CDR L3 |
| 38 | DYGVS | FMC63 CDR H1 |
| 39 | VIWGSETTYYNSALKS | FMC63 CDR H2 |
| 40 | YAMDYWG | FMC63 CDR H3 |
| 41 | EVKLQESGPGLVAPSQSLSVTCTVSGVSLPDYGVSWIRQPPRKGLEWLG VIWGSETTYYNSALKSRLTIIKDNSKSQVFLKMNSLQTDDTAIYYCAKH YYYGGSYAMDYWGQGTSVTVSS | FMC63 VH |
| 42 | DIQMTQTTSSLSASLGDRVTISCRASQDISKYLNWYQQKPDGTVKLLIY HTSRLHSGVPSRFSGSGSGTDYSLTISNLEQEDIATYFCQQGNTLPYTF GGGTKLEIT | FMC63 VL |
| 43 | DIQMTQTTSSLSASLGDRVTISCRASQDISKYLNWYQQKPDGTVKLLIY HTSRLHSGVPSRFSGSGSGTDYSLTISNLEQEDIATYFCQQGNTLPYTF GGGTKLEITGSTSGSGKPGSGEGSTKGEVKLQESGPGLVAPSQSLSVTC TVSGVSLPDYGVSWIRQPPRKGLEWLGVIWGSETTYYNSALKSRLTIIK DNSKSQVFLKMNSLQTDDTAIYYCAKHYYYGGSYAMDYWGQGTSVTVSS | FMC63 scFv |
| 44 | KASQNVGTNVA | SJ25C1 CDR L1 |
| 45 | SATYRNS | SJ25C1 CDR L2 |
| 46 | QQYNRYPYT | SJ25C1 CDR L3 |
| 47 | SYWMN | SJ25C1 CDR H1 |
| 48 | QIYPGDGDTNYNGKFKG | SJ25C1 CDR H2 |
| 49 | KTISSVVDFYFDY | SJ25C1 CDR H3 |
| 50 | EVKLQQSGAELVRPGSSVKISCKASGYAFSSYWMNWVKQRPGQGLEWIG QIYPGDGDTNYNGKFKGQATLTADKSSSTAYMQLSGLTSEDSAVYFCAR KTISSVVDFYFDYWGQGTTVTVSS | SJ25C1 VH |
| 51 | DIELTQSPKFMSTSVGDRVSVTCKASQNVGTNVAWYQQKPGQSPKPLIY SATYRNSGVPDRFTGSGSGTDFTLTITNVQSKDLADYFCQQYNRYPYTS GGGTKLEIKR | SJ25C1 VL |

-continued

SEQUENCES

| SEQ ID NO. | SEQUENCE | DESCRIPTION |
|---|---|---|
| 52 | GGGGSGGGGSGGGGS | Linker |
| 53 | EVKLQQSGAELVRPGSSVKISCKASGYAFSSYWMNWVKQRPGQGLEWIG<br>QIYPGDGDTNYNGKFKGQATLTADKSSSTAYMQLSGLTSEDSAVYFCAR<br>KTISSVVDFYFDYWGQGTTVTVSSGGGGSGGGGSGGGGSDIELTQSPKF<br>MSTSVGDRVSVTCKASQNVGTNVAWYQQKPGQSPKPLIYSATYRNSGVP<br>DRFTGSGSGTDFTLTITNVQSKDLADYFCQQYNRYPYTSGGGTKLEIKR | SJ25C1 scFv |
| 54 | HYYYGGSYAMDY | FMC63 HC-CDR3 |
| 55 | HTSRLHS | FMC63 LC-CDR2 |
| 56 | QQGNTLPYT | FMC63 LC-CDR3 |
| 57 | gacatccagatgacccagaccacctccagcctgagcgccagcctgggcg<br>accgggtgaccatcagctgccgggccagccaggacatcagcaagtacct<br>gaactggtatcagcagaagcccgacggcaccgtcaagctgctgatctac<br>cacaccagccggctgcacagcggcgtgcccagccggtttagcggcagcg<br>gctccggcaccgactacagcctgaccatctccaacctggaacaggaaga<br>tatcgccacctacttttgccagcagggcaacacactgccctacaccttt<br>ggcggcggaacaaagctggaaatcaccggcagcacctccggcagcggca<br>agcctggcagcggcgagggcagcaccaagggcgaggtgaagctgcagga<br>aagcggccctggcctggtggcccccagccagagcctgagcgtgacctgc<br>accgtgagcggcgtgagcctgcccgactacggcgtgagctggatccggc<br>agcccccaggaagggcctggaatggctgggcgtgatctggggcagcga<br>gaccacctactacaacagcgccctgaagagccggctgaccatcatcaag<br>gacaacagcaagagccaggtgttcctgaagatgaacagcctgcagaccg<br>acgacaccgccatctactactgcgccaagcactactactacggcggcag<br>ctacgccatggactactggggccagggcaccagcgtgaccgtgagcagc | Sequence encoding scFv |
| 58 | GSTSGSGKPGSGEGSTKG | Linker |

The invention claimed is:

1. A method of ameliorating the development of a toxicity in a subject, the method comprising administering to the subject an agent capable of treating the development of a toxicity that is severe cytokine release syndrome (CRS) or severe neurotoxicity, wherein the subject has been administered a dose of about $1.0 \times 10^7$ to about $1 \times 10^8$ total CAR-expressing T cells expressing a recombinant receptor that is a chimeric antigen receptor (CAR), wherein the subject is treated, following assessment of the number of recombinant-receptor expressing T cells in a blood sample of the subject, when:
   assessment of the subject determines that a peak expansion of the recombinant receptor-expressing T cells occurs within or within about seven days of administration of the dose, wherein the peak expansion of the recombinant receptor-expressing T cells occurring within or within about seven days of administration of the dose indicates the subject is at risk of developing a toxicity; and wherein the agent is a steroid or an IL-6 or IL-6 receptor inhibitor, or a combination thereof.

2. The method of claim 1, wherein the subject is at risk of developing the toxicity if, further, the level, amount or concentration of interleukin-15 (IL-15) detected in a blood or serum sample from the subject is at or above a threshold value.

3. The method of claim 2, wherein the threshold value is 30 pg/mL.

4. The method of claim 2, wherein the sample is obtained from the subject at or about no more than 5 days following initiation of administration of the cell therapy.

5. The method of claim 1, wherein the severe neurotoxicity is at least a prolonged grade 3 neurotoxicity, a grade 4 neurotoxicity, or a grade 5 neurotoxicity.

6. The method of claim 1, wherein the toxicity is or is associated with cerebral edema.

7. The method of claim 1, wherein the steroid is a corticosteroid.

8. The method of claim 7, wherein the corticosteroid is a glucocorticoid.

9. The method of claim 8, wherein the glucocorticoid is dexamethasone.

10. The method of claim 1, wherein the agent is tocilizumab, siltuximab, sarilumab, olokizumab (CDP6038), elsilimomab, ALD518/BMS-945429, sirukumab (CNTO 136), CPSI-2634, ARGX-109, FE301 or FM101.

11. The method of claim 1, wherein the dose is about $2.5 \times 10^7$ to about $1 \times 10^8$ total CAR-expressing T cells.

12. The method of claim 1, wherein the dose is a fixed dose.

13. The method of claim 1, wherein the CAR targets an antigen associated with a B cell malignancy.

14. The method of claim 13, wherein the B cell malignancy is selected from the group consisting of acute lymphoblastic leukemia (ALL), adult ALL, chronic lymphocytic leukemia (CLL), non-Hodgkin lymphoma (NHL) and diffuse large B-cell lymphoma (DLBCL).

15. The method of claim 1, wherein the CAR targets an antigen that is CD20, CD19, CD22, ROR1, CD45, CD21, CD5, CD33, Igkappa, Iglambda, CD79a, CD79b or CD30.

16. A method of ameliorating the development of a toxicity in a subject, the method comprising administering to the subject an agent capable of treating the development of a toxicity that is severe cytokine release syndrome (CRS) or severe neurotoxicity, wherein the subject has been administered a dose of about $1.0 \times 10^7$ to about $1 \times 10^8$ total CAR-expressing T cells expressing a recombinant receptor that is a chimeric antigen receptor (CAR), wherein the subject is treated, following assessment of the number of recombinant receptor-expressing cells in a blood sample of the subject, when:

(a) no more than four days after initiation of the dose of the recombinant receptor-expressing T cells, the number of recombinant receptor-expressing cells in the blood sample of the subject is at least at or about 2 recombinant receptor-expressing cells per microliter;

(b) no more than five or six days after initiation of the dose of the recombinant receptor-expressing T cells, the number of recombinant receptor-expressing cells in the blood sample of the subject is at least at or about 5 recombinant receptor-expressing cells per microliter; or (c) no more than seven days after initiation of the administration the number of recombinant receptor-expressing cells in the blood sample of the subject is at least at or about 15 recombinant receptor-expressing cells per microliter; and wherein the agent is a steroid or an IL-6 or IL-6 receptor inhibitor, or a combination thereof.

17. The method of claim 16, wherein the subject is at risk of developing the toxicity if, further, the level, amount or concentration of interleukin-15 (IL-15) detected in a blood or serum sample from the subject is at or above a threshold value.

18. The method of claim 17, wherein the threshold value is 30 pg/mL.

19. The method of claim 17, wherein the sample is obtained from the subject at or about no more than 5 days following initiation of administration of the cell therapy.

20. The method of claim 16, wherein the severe neurotoxicity is at least a prolonged grade 3 neurotoxicity, a grade 4 neurotoxicity, or a grade 5 neurotoxicity.

21. The method of claim 16, wherein the assessment of the subject determines that no more than five or six days after initiation of the administration the number of recombinant receptor-expressing T cells in the blood sample of the subject is at least at or about 10 recombinant receptor-expressing cells per microliter.

22. The method of claim 16, wherein the assessment comprises use of a nucleic acid- or flow cytometry-based detection method.

23. The method of claim 22, wherein nucleic acid-based detection method comprises use a quantitative polymerase chain reaction (qPCR)-based detection method.

24. The method of claim 16, wherein the toxicity is or is associated with cerebral edema.

25. The method of claim 16, wherein the steroid is a corticosteroid.

26. The method of claim 25, wherein the corticosteroid is a glucocorticoid.

27. The method of claim 26, wherein the glucocorticoid is dexamethasone.

28. The method of claim 16, wherein the agent is tocilizumab, siltuximab, sarilumab, olokizumab (CDP6038), elsilimomab, ALD518.

* * * * *

SEQUENCE LISTING

<160> NUMBER OF SEQ ID NOS: 58

<210> SEQ ID NO 1
<211> LENGTH: 12
<212> TYPE: PRT
<213> ORGANISM: Homo sapiens
<220> FEATURE:
<221> NAME/KEY: misc_feature
<223> OTHER INFORMATION: spacer (IgG4hinge)

<400> SEQUENCE: 1

```
Glu Ser Lys Tyr Gly Pro Pro Cys Pro Pro Cys Pro
1               5                   10
```

<210> SEQ ID NO 2
<211> LENGTH: 36
<212> TYPE: DNA
<213> ORGANISM: Homo sapiens
<220> FEATURE:
<221> NAME/KEY: misc_feature
<223> OTHER INFORMATION: spacer (IgG4hinge)

<400> SEQUENCE: 2

```
gaatctaagt acggaccgcc ctgccccct tgccct                                36
```

<210> SEQ ID NO 3
<211> LENGTH: 119
<212> TYPE: PRT
<213> ORGANISM: Homo sapiens
<220> FEATURE:

<221> NAME/KEY: misc_feature
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1 5 10 15

Glu Pro Gln Val Tyr Thr Leu Pro Pro Ser Gln Glu Glu Met Thr Lys
20 25 30

Asn Gln Val Ser Leu Thr Cys Leu Val Lys Gly Phe Tyr Pro Ser Asp
35 40 45

Ile Ala Val Glu Trp Glu Ser Asn Gly Gln Pro Glu Asn Asn Tyr Lys
50 55 60

Thr Thr Pro Pro Val Leu Asp Ser Asp Gly Ser Phe Phe Leu Tyr Ser
65 70 75 80

Arg Leu Thr Val Asp Lys Ser Arg Trp Gln Glu Gly Asn Val Phe Ser
85 90 95

Cys Ser Val Met His Glu Ala Leu His Asn His Tyr Thr Gln Lys Ser
100 105 110

Leu Ser Leu Ser Leu Gly Lys
115

<210> SEQ ID NO 4
<211> LENGTH: 229
<212> TYPE: PRT
<213> ORGANISM: Homo sapiens
<220> FEATURE:
<221> NAME/KEY: misc_feature
<223> OTHER INFORMATION: Hinge-CH2-CH3 spacer

<400> SEQUENCE: 4

Glu Ser Lys Tyr Gly Pro Pro Cys Pro Pro Cys Pro Ala Pro Glu Phe
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

```
Val Met His Glu Ala Leu His Asn His Tyr Thr Gln Lys Ser Leu Ser
    210                 215                 220

Leu Ser Leu Gly Lys
225


<210> SEQ ID NO 5
<211> LENGTH: 282
<212> TYPE: PRT
<213> ORGANISM: Homo sapiens
<220> FEATURE:
<221> NAME/KEY: misc_feature
<223> OTHER INFORMATION: IgD-hinge-Fc

<400> SEQUENCE: 5

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280


<210> SEQ ID NO 6
<211> LENGTH: 24
<212> TYPE: PRT
<213> ORGANISM: Artificial Sequence
<220> FEATURE:
<223> OTHER INFORMATION: T2A
```

<400> SEQUENCE: 6

Leu Glu Gly Gly Gly Glu Gly Arg Gly Ser Leu Leu Thr Cys Gly Asp
1 5 10 15

Val Glu Glu Asn Pro Gly Pro Arg
20

<210> SEQ ID NO 7
<211> LENGTH: 335
<212> TYPE: PRT
<213> ORGANISM: Artificial Sequence
<220> FEATURE:
<223> OTHER INFORMATION: tEGFR

<400> SEQUENCE: 7

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

Cys Ser Pro Glu Gly Cys Trp Gly Pro Glu Pro Arg Asp Cys Val Ser
180 185 190

Cys Arg Asn Val Ser Arg Gly Arg Glu Cys Val Asp Lys Cys Asn Leu
195 200 205

Leu Glu Gly Glu Pro Arg Glu Phe Val Glu Asn Ser Glu Cys Ile Gln
210 215 220

Cys His Pro Glu Cys Leu Pro Gln Ala Met Asn Ile Thr Cys Thr Gly
225 230 235 240

Arg Gly Pro Asp Asn Cys Ile Gln Cys Ala His Tyr Ile Asp Gly Pro
245 250 255

His Cys Val Lys Thr Cys Pro Ala Gly Val Met Gly Glu Asn Asn Thr
260 265 270

Leu Val Trp Lys Tyr Ala Asp Ala Gly His Val Cys His Leu Cys His
275 280 285

Pro Asn Cys Thr Tyr Gly Cys Thr Gly Pro Gly Leu Glu Gly Cys Pro
290 295 300

Thr Asn Gly Pro Lys Ile Pro Ser Ile Ala Thr Gly Met Val Gly Ala
305 310 315 320

Leu Leu Leu Leu Leu Val Val Ala Leu Gly Ile Gly Leu Phe Met

```
            325                 330                 335


<210> SEQ ID NO 8
<211> LENGTH: 27
<212> TYPE: PRT
<213> ORGANISM: Homo sapiens
<220> FEATURE:
<221> NAME/KEY: misc_feature
<223> OTHER INFORMATION: CD28

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 9
<211> LENGTH: 66
<212> TYPE: PRT
<213> ORGANISM: Homo sapiens
<220> FEATURE:
<221> NAME/KEY: misc_feature
<223> OTHER INFORMATION: CD28

<400> SEQUENCE: 9

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65


<210> SEQ ID NO 10
<211> LENGTH: 41
<212> TYPE: PRT
<213> ORGANISM: Homo sapiens
<220> FEATURE:
<221> NAME/KEY: misc_feature
<223> OTHER INFORMATION: CD28

<400> SEQUENCE: 10

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 11
<211> LENGTH: 41
<212> TYPE: PRT
<213> ORGANISM: Homo sapiens
<220> FEATURE:
<221> NAME/KEY: misc_feature
<223> OTHER INFORMATION: CD28

<400> SEQUENCE: 11

Arg Ser Lys Arg Ser Arg Gly Gly His Ser Asp Tyr Met Asn Met Thr
1               5                   10                  15
```

```
Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 12
<211> LENGTH: 42
<212> TYPE: PRT
<213> ORGANISM: Homo sapiens
<220> FEATURE:
<221> NAME/KEY: misc_feature
<223> OTHER INFORMATION: 4-1BB

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 13
<211> LENGTH: 112
<212> TYPE: PRT
<213> ORGANISM: Homo sapiens
<220> FEATURE:
<221> NAME/KEY: misc_feature
<223> OTHER INFORMATION: CD3 zeta

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 14
<211> LENGTH: 112
<212> TYPE: PRT
<213> ORGANISM: Homo sapiens
<220> FEATURE:
<221> NAME/KEY: misc_feature
<223> OTHER INFORMATION: CD3 zeta

<400> SEQUENCE: 14

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
```

```
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 15
<211> LENGTH: 112
<212> TYPE: PRT
<213> ORGANISM: Homo sapiens
<220> FEATURE:
<221> NAME/KEY: misc_feature
<223> OTHER INFORMATION: CD3 zeta

<400> SEQUENCE: 15

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 16
<211> LENGTH: 30
<212> TYPE: PRT
<213> ORGANISM: Artificial Sequence
<220> FEATURE:
<223> OTHER INFORMATION: Linker sequence

<400> SEQUENCE: 16

Pro Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Pro
            20                  25                  30


<210> SEQ ID NO 17
<211> LENGTH: 17
<212> TYPE: PRT
<213> ORGANISM: Artificial Sequence
<220> FEATURE:
<223> OTHER INFORMATION: linker sequence

<400> SEQUENCE: 17

Gly Ser Ala Asp Asp Ala Lys Lys Asp Ala Ala Lys Lys Asp Gly Lys
1               5                   10                  15

Ser


<210> SEQ ID NO 18
<211> LENGTH: 18
<212> TYPE: PRT
<213> ORGANISM: Artificial Sequence
```

<220> FEATURE:
<223> OTHER INFORMATION: T2A

<400> SEQUENCE: 18

Glu Gly Arg Gly Ser Leu Leu Thr Cys Gly Asp Val Glu Glu Asn Pro
1 5 10 15

Gly Pro

<210> SEQ ID NO 19
<211> LENGTH: 22
<212> TYPE: PRT
<213> ORGANISM: Artificial Sequence
<220> FEATURE:
<223> OTHER INFORMATION: P2A

<400> SEQUENCE: 19

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 20
<211> LENGTH: 19
<212> TYPE: PRT
<213> ORGANISM: Artificial Sequence
<220> FEATURE:
<223> OTHER INFORMATION: P2A

<400> SEQUENCE: 20

Ala Thr Asn Phe Ser Leu Leu Lys Gln Ala Gly Asp Val Glu Glu Asn
1 5 10 15

Pro Gly Pro

<210> SEQ ID NO 21
<211> LENGTH: 20
<212> TYPE: PRT
<213> ORGANISM: Artificial Sequence
<220> FEATURE:
<223> OTHER INFORMATION: E2A

<400> SEQUENCE: 21

Gln Cys Thr Asn Tyr Ala Leu Leu Lys Leu Ala Gly Asp Val Glu Ser
1 5 10 15

Asn Pro Gly Pro
20

<210> SEQ ID NO 22
<211> LENGTH: 22
<212> TYPE: PRT
<213> ORGANISM: Artificial Sequence
<220> FEATURE:
<223> OTHER INFORMATION: F2A

<400> SEQUENCE: 22

Val Lys Gln Thr Leu Asn Phe Asp Leu Leu Lys Leu Ala Gly Asp Val
1 5 10 15

Glu Ser Asn Pro Gly Pro
20

<210> SEQ ID NO 23
<211> LENGTH: 357
<212> TYPE: PRT
<213> ORGANISM: Artificial Sequence
<220> FEATURE:

<223> OTHER INFORMATION: tEGFR

<400> SEQUENCE: 23

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355
```

<210> SEQ ID NO 24
<211> LENGTH: 66
<212> TYPE: DNA
<213> ORGANISM: Homo sapiens
<220> FEATURE:

<221> NAME/KEY: misc_feature
<223> OTHER INFORMATION: GMCSFR alpha chain signal sequence

<400> SEQUENCE: 24
atgcttctcc tggtgacaag ccttctgctc tgtgagttac cacacccagc attcctcctg 60
atccca 66

<210> SEQ ID NO 25
<211> LENGTH: 22
<212> TYPE: PRT
<213> ORGANISM: Homo sapiens
<220> FEATURE:
<221> NAME/KEY: misc_feature
<223> OTHER INFORMATION: GMCSFR alpha chain signal sequence

<400> SEQUENCE: 25

Met Leu Leu Leu Val Thr Ser Leu Leu Leu Cys Glu Leu Pro His Pro
1 5 10 15

Ala Phe Leu Leu Ile Pro
20

<210> SEQ ID NO 26
<211> LENGTH: 18
<212> TYPE: PRT
<213> ORGANISM: Homo sapiens
<220> FEATURE:
<221> NAME/KEY: misc_feature
<223> OTHER INFORMATION: CD8 alpha signal peptide

<400> SEQUENCE: 26

Met Ala Leu Pro Val Thr Ala Leu Leu Leu Pro Leu Ala Leu Leu Leu
1 5 10 15

His Ala

<210> SEQ ID NO 27
<211> LENGTH: 15
<212> TYPE: PRT
<213> ORGANISM: Artificial Sequence
<220> FEATURE:
<223> OTHER INFORMATION: Hinge sequence

<400> SEQUENCE: 27

Glu Pro Lys Ser Cys Asp Lys Thr His Thr Cys Pro Pro Cys Pro
1 5 10 15

<210> SEQ ID NO 28
<211> LENGTH: 12
<212> TYPE: PRT
<213> ORGANISM: Artificial Sequence
<220> FEATURE:
<223> OTHER INFORMATION: Hinge sequence

<400> SEQUENCE: 28

Glu Arg Lys Cys Cys Val Glu Cys Pro Pro Cys Pro
1 5 10

<210> SEQ ID NO 29
<211> LENGTH: 61
<212> TYPE: PRT
<213> ORGANISM: Artificial Sequence
<220> FEATURE:
<223> OTHER INFORMATION: Hinge sequence

<400> SEQUENCE: 29

Glu Leu Lys Thr Pro Leu Gly Asp Thr His Thr Cys Pro Arg Cys Pro

-continued

```
1               5                   10                  15

Glu Pro Lys Ser Cys Asp Thr Pro Pro Pro Cys Pro Arg Cys Pro Glu
            20                  25                  30

Pro Lys Ser Cys Asp Thr Pro Pro Pro Cys Pro Arg Cys Pro Glu Pro
        35                  40                  45

Lys Ser Cys Asp Thr Pro Pro Pro Cys Pro Arg Cys Pro
    50                  55                  60


<210> SEQ ID NO 30
<211> LENGTH: 12
<212> TYPE: PRT
<213> ORGANISM: Artificial Sequence
<220> FEATURE:
<223> OTHER INFORMATION: Hinge Sequence

<400> SEQUENCE: 30

Glu Ser Lys Tyr Gly Pro Pro Cys Pro Ser Cys Pro
1               5                   10


<210> SEQ ID NO 31
<211> LENGTH: 5
<212> TYPE: PRT
<213> ORGANISM: Artificial Sequence
<220> FEATURE:
<223> OTHER INFORMATION: Hinge sequence
<220> FEATURE:
<221> NAME/KEY: misc_feature
<222> LOCATION: (1)..(1)
<223> OTHER INFORMATION: glycine, cysteine, or arginine
<220> FEATURE:
<221> NAME/KEY: misc_feature
<222> LOCATION: (4)..(4)
<223> OTHER INFORMATION: Xaa is cysteine or threonine

<400> SEQUENCE: 31

Xaa Pro Pro Xaa Pro
1               5


<210> SEQ ID NO 32
<211> LENGTH: 9
<212> TYPE: PRT
<213> ORGANISM: Artificial Sequence
<220> FEATURE:
<223> OTHER INFORMATION: Hinge sequence

<400> SEQUENCE: 32

Tyr Gly Pro Pro Cys Pro Pro Cys Pro
1               5


<210> SEQ ID NO 33
<211> LENGTH: 10
<212> TYPE: PRT
<213> ORGANISM: Artificial Sequence
<220> FEATURE:
<223> OTHER INFORMATION: Hinge sequence

<400> SEQUENCE: 33

Lys Tyr Gly Pro Pro Cys Pro Pro Cys Pro
1               5                   10


<210> SEQ ID NO 34
<211> LENGTH: 14
<212> TYPE: PRT
<213> ORGANISM: Artificial Sequence
<220> FEATURE:
<223> OTHER INFORMATION: Hinge sequence
```

<400> SEQUENCE: 34

Glu Val Val Val Lys Tyr Gly Pro Pro Cys Pro Pro Cys Pro
1               5                   10

<210> SEQ ID NO 35
<211> LENGTH: 11
<212> TYPE: PRT
<213> ORGANISM: Artificial Sequence
<220> FEATURE:
<223> OTHER INFORMATION: FMC63 CDR L1

<400> SEQUENCE: 35

Arg Ala Ser Gln Asp Ile Ser Lys Tyr Leu Asn
1               5                   10

<210> SEQ ID NO 36
<211> LENGTH: 7
<212> TYPE: PRT
<213> ORGANISM: Artificial Sequence
<220> FEATURE:
<223> OTHER INFORMATION: FMC63 CDR L2

<400> SEQUENCE: 36

Ser Arg Leu His Ser Gly Val
1               5

<210> SEQ ID NO 37
<211> LENGTH: 9
<212> TYPE: PRT
<213> ORGANISM: Artificial Sequence
<220> FEATURE:
<223> OTHER INFORMATION: FMC63 CDR L3

<400> SEQUENCE: 37

Gly Asn Thr Leu Pro Tyr Thr Phe Gly
1               5

<210> SEQ ID NO 38
<211> LENGTH: 5
<212> TYPE: PRT
<213> ORGANISM: Artificial Sequence
<220> FEATURE:
<223> OTHER INFORMATION: FMC63 CDR H1

<400> SEQUENCE: 38

Asp Tyr Gly Val Ser
1               5

<210> SEQ ID NO 39
<211> LENGTH: 16
<212> TYPE: PRT
<213> ORGANISM: Artificial Sequence
<220> FEATURE:
<223> OTHER INFORMATION: FMC63 CDR H2

<400> SEQUENCE: 39

Val Ile Trp Gly Ser Glu Thr Thr Tyr Tyr Asn Ser Ala Leu Lys Ser
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: FMC63 CDR H3

<400> SEQUENCE: 40

Tyr Ala Met Asp Tyr Trp Gly
1 5

<210> SEQ ID NO 41
<211> LENGTH: 120
<212> TYPE: PRT
<213> ORGANISM: Artificial Sequence
<220> FEATURE:
<223> OTHER INFORMATION: FMC63 VH

<400> SEQUENCE: 41

Glu Val Lys Leu Gln Glu Ser Gly Pro Gly Leu Val Ala Pro Ser Gln
1 5 10 15

Ser Leu Ser Val Thr Cys Thr Val Ser Gly Val Ser Leu Pro Asp Tyr
20 25 30

Gly Val Ser Trp Ile Arg Gln Pro Pro Arg Lys Gly Leu Glu Trp Leu
35 40 45

Gly Val Ile Trp Gly Ser Glu Thr Thr Tyr Tyr Asn Ser Ala Leu Lys
50 55 60

Ser Arg Leu Thr Ile Ile Lys Asp Asn Ser Lys Ser Gln Val Phe Leu
65 70 75 80

Lys Met Asn Ser Leu Gln Thr Asp Asp Thr Ala Ile Tyr Tyr Cys Ala
85 90 95

Lys His Tyr Tyr Tyr Gly Gly Ser Tyr Ala Met Asp Tyr Trp Gly Gln
100 105 110

Gly Thr Ser Val Thr Val Ser Ser
115 120

<210> SEQ ID NO 42
<211> LENGTH: 107
<212> TYPE: PRT
<213> ORGANISM: Artificial Sequence
<220> FEATURE:
<223> OTHER INFORMATION: FMC63 VL

<400> SEQUENCE: 42

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr
100 105

<210> SEQ ID NO 43
<211> LENGTH: 245
<212> TYPE: PRT
<213> ORGANISM: Artificial Sequence
<220> FEATURE:
<223> OTHER INFORMATION: FMC63 scFv

<400> SEQUENCE: 43

-continued

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245


<210> SEQ ID NO 44
<211> LENGTH: 11
<212> TYPE: PRT
<213> ORGANISM: Artificial Sequence
<220> FEATURE:
<223> OTHER INFORMATION: SJ25C1 CDR L1

<400> SEQUENCE: 44

Lys Ala Ser Gln Asn Val Gly Thr Asn Val Ala
1               5                   10


<210> SEQ ID NO 45
<211> LENGTH: 7
<212> TYPE: PRT
<213> ORGANISM: Artificial Sequence
<220> FEATURE:
<223> OTHER INFORMATION: SJ25C1 CDR L2

<400> SEQUENCE: 45

Ser Ala Thr Tyr Arg Asn Ser
1               5


<210> SEQ ID NO 46
<211> LENGTH: 9
<212> TYPE: PRT
<213> ORGANISM: Artificial Sequence
```

<220> FEATURE:
<223> OTHER INFORMATION: SJ25C1 CDR L3

<400> SEQUENCE: 46

Gln Gln Tyr Asn Arg Tyr Pro Tyr Thr
1               5

<210> SEQ ID NO 47
<211> LENGTH: 5
<212> TYPE: PRT
<213> ORGANISM: Artificial Sequence
<220> FEATURE:
<223> OTHER INFORMATION: SJ25C1 CDR H1

<400> SEQUENCE: 47

Ser Tyr Trp Met Asn
1               5

<210> SEQ ID NO 48
<211> LENGTH: 17
<212> TYPE: PRT
<213> ORGANISM: Artificial Sequence
<220> FEATURE:
<223> OTHER INFORMATION: SJ25C1 CDR H2

<400> SEQUENCE: 48

Gln Ile Tyr Pro Gly Asp Gly Asp Thr Asn Tyr Asn Gly Lys Phe Lys
1               5                   10                  15

Gly

<210> SEQ ID NO 49
<211> LENGTH: 13
<212> TYPE: PRT
<213> ORGANISM: Artificial Sequence
<220> FEATURE:
<223> OTHER INFORMATION: SJ25C1 CDR H3

<400> SEQUENCE: 49

Lys Thr Ile Ser Ser Val Val Asp Phe Tyr Phe Asp Tyr
1               5                   10

<210> SEQ ID NO 50
<211> LENGTH: 122
<212> TYPE: PRT
<213> ORGANISM: Artificial Sequence
<220> FEATURE:
<223> OTHER INFORMATION: SJ25C1 VH

<400> SEQUENCE: 50

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

```
Gly Gln Gly Thr Thr Val Thr Val Ser Ser
        115                 120


<210> SEQ ID NO 51
<211> LENGTH: 108
<212> TYPE: PRT
<213> ORGANISM: Artificial Sequence
<220> FEATURE:
<223> OTHER INFORMATION: SJ25C1 VL

<400> SEQUENCE: 51

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Thr Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Tyr Pro Tyr
                85                  90                  95

Thr Ser Gly Gly Gly Thr Lys Leu Glu Ile Lys Arg
            100                 105


<210> SEQ ID NO 52
<211> LENGTH: 15
<212> TYPE: PRT
<213> ORGANISM: Artificial Sequence
<220> FEATURE:
<223> OTHER INFORMATION: Linker sequence

<400> SEQUENCE: 52

Gly Gly Gly Gly Ser Gly Gly Gly Gly Ser Gly Gly Gly Gly Ser
1               5                   10                  15


<210> SEQ ID NO 53
<211> LENGTH: 245
<212> TYPE: PRT
<213> ORGANISM: Artificial Sequence
<220> FEATURE:
<223> OTHER INFORMATION: SJ25C1 scFv

<400> SEQUENCE: 53

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110
```

```
Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Glu Leu Thr Gln Ser
    130                 135                 140

Pro Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys
                165                 170                 175

Pro Gly Gln Ser Pro Lys Pro Leu Ile Tyr Ser Ala Thr Tyr Arg Asn
            180                 185                 190

Ser Gly Val Pro Asp Arg Phe Thr Gly Ser Gly Ser Gly Thr Asp Phe
        195                 200                 205

Thr Leu Thr Ile Thr Asn Val Gln Ser Lys Asp Leu Ala Asp Tyr Phe
    210                 215                 220

Cys Gln Gln Tyr Asn Arg Tyr Pro Tyr Thr Ser Gly Gly Gly Thr Lys
225                 230                 235                 240

Leu Glu Ile Lys Arg
                245


<210> SEQ ID NO 54
<211> LENGTH: 12
<212> TYPE: PRT
<213> ORGANISM: Artificial Sequence
<220> FEATURE:
<223> OTHER INFORMATION: FMC63 HC-CDR3

<400> SEQUENCE: 54

His Tyr Tyr Tyr Gly Gly Ser Tyr Ala Met Asp Tyr
1               5                   10


<210> SEQ ID NO 55
<211> LENGTH: 7
<212> TYPE: PRT
<213> ORGANISM: Artificial Sequence
<220> FEATURE:
<223> OTHER INFORMATION: FMC63 LC-CDR2

<400> SEQUENCE: 55

His Thr Ser Arg Leu His Ser
1               5


<210> SEQ ID NO 56
<211> LENGTH: 9
<212> TYPE: PRT
<213> ORGANISM: Artificial Sequence
<220> FEATURE:
<223> OTHER INFORMATION: FMC63 LC-CDR3

<400> SEQUENCE: 56

Gln Gln Gly Asn Thr Leu Pro Tyr Thr
1               5


<210> SEQ ID NO 57
<211> LENGTH: 735
<212> TYPE: DNA
<213> ORGANISM: Artificial Sequence
<220> FEATURE:
<223> OTHER INFORMATION: sequence encoding scFv

<400> SEQUENCE: 57

gacatccaga tgacccagac cacctccagc ctgagcgcca gcctgggcga ccgggtgacc      60

atcagctgcc gggccagcca ggacatcagc aagtacctga actggtatca gcagaagccc     120
```

```
gacggcaccg tcaagctgct gatctaccac accagccggc tgcacagcgg cgtgcccagc    180

cggtttagcg gcagcggctc cggcaccgac tacagcctga ccatctccaa cctggaacag    240

gaagatatcg ccacctactt ttgccagcag ggcaacacac tgccctacac ctttggcggc    300

ggaacaaagc tggaaatcac cggcagcacc tccggcagcg gcaagcctgg cagcggcgag    360

ggcagcacca agggcgaggt gaagctgcag gaaagcggcc ctggcctggt ggcccccagc    420

cagagcctga gcgtgacctg caccgtgagc ggcgtgagcc tgcccgacta cggcgtgagc    480

tggatccggc agccccccag gaagggcctg gaatggctgg gcgtgatctg gggcagcgag    540

accacctact acaacagcgc cctgaagagc cggctgacca tcatcaagga caacagcaag    600

agccaggtgt tcctgaagat gaacagcctg cagaccgacg acaccgccat ctactactgc    660

gccaagcact actactacgg cggcagctac gccatggact actggggcca gggcaccagc    720

gtgaccgtga gcagc                                                    735

<210> SEQ ID NO 58
<211> LENGTH: 18
<212> TYPE: PRT
<213> ORGANISM: Artificial Sequence
<220> FEATURE:
<223> OTHER INFORMATION: Linker sequence

<400> SEQUENCE: 58

Gly Ser Thr Ser Gly Ser Gly Lys Pro Gly Ser Gly Glu Gly Ser Thr
1               5                   10                  15

Lys Gly
```